US010609930B2

(12) United States Patent
Tao

(10) Patent No.: US 10,609,930 B2
(45) Date of Patent: Apr. 7, 2020

(54) METHODS AND COMPOSITIONS FOR WEED CONTROL

(71) Applicant: Monsanto Technology LLC, St. Louis, MO (US)

(72) Inventor: Nengbing Tao, O'Fallon, MO (US)

(73) Assignee: Monsanto Technology LLC, St. Louis, MO (US)

( * ) Notice: Subject to any disclaimer, the term of this patent is extended or adjusted under 35 U.S.C. 154(b) by 508 days.

(21) Appl. No.: 14/774,413

(22) PCT Filed: Mar. 11, 2014

(86) PCT No.: PCT/US2014/023409
§ 371 (c)(1),
(2) Date: Sep. 10, 2015

(87) PCT Pub. No.: WO2014/164761
PCT Pub. Date: Oct. 9, 2014

(65) Prior Publication Data
US 2016/0029644 A1 Feb. 4, 2016

Related U.S. Application Data

(60) Provisional application No. 61/779,476, filed on Mar. 13, 2013.

(51) Int. Cl.
*C12N 15/82* (2006.01)
*A01N 65/44* (2009.01)
*C12N 15/113* (2010.01)
*A01N 57/16* (2006.01)

(52) U.S. Cl.
CPC ............. *A01N 65/44* (2013.01); *A01N 57/16* (2013.01); *C12N 15/113* (2013.01); *C12N 15/8218* (2013.01); *C12N 15/8274* (2013.01)

(58) Field of Classification Search
CPC ............ C12N 15/8218; C12N 15/8274; C12N 15/9275; C12N 15/8278
See application file for complete search history.

(56) References Cited

U.S. PATENT DOCUMENTS

| | | | |
|---|---|---|---|
| 3,687,808 | A | 8/1972 | Merigan et al. |
| 3,791,932 | A | 2/1974 | Schuurs et al. |
| 3,839,153 | A | 10/1974 | Schuurs et al. |
| 3,850,578 | A | 11/1974 | McConnell |
| 3,850,752 | A | 11/1974 | Schuurs et al. |
| 3,853,987 | A | 12/1974 | Dreyer |
| 3,867,517 | A | 2/1975 | Ling |
| 3,879,262 | A | 4/1975 | Schuurs et al. |
| 3,901,654 | A | 8/1975 | Gross |
| 3,935,074 | A | 1/1976 | Rubenstein et al. |
| 3,984,533 | A | 10/1976 | Uzgiris |
| 3,996,345 | A | 12/1976 | Ullman et al. |
| 4,034,074 | A | 7/1977 | Miles |
| 4,098,876 | A | 7/1978 | Piasio et al. |
| 4,469,863 | A | 9/1984 | Ts'o et al. |
| 4,476,301 | A | 10/1984 | Imbach et al. |
| 4,535,060 | A | 8/1985 | Comai |
| 4,581,847 | A | 4/1986 | Hibberd et al. |
| 4,666,828 | A | 5/1987 | Gusella |
| 4,683,202 | A | 7/1987 | Mullis |
| 4,761,373 | A | 8/1988 | Anderson et al. |
| 4,769,061 | A | 9/1988 | Comai |
| 4,801,531 | A | 1/1989 | Frossard |
| 4,810,648 | A | 3/1989 | Stalker |
| 4,879,219 | A | 11/1989 | Wands et al. |
| 4,940,835 | A | 7/1990 | Shah et al. |
| 4,971,908 | A | 11/1990 | Kishore et al. |
| 5,004,863 | A | 4/1991 | Umbeck |
| 5,011,771 | A | 4/1991 | Bellet et al. |
| 5,013,659 | A | 5/1991 | Bedbrook et al. |
| 5,015,580 | A | 5/1991 | Christou et al. |

(Continued)

FOREIGN PATENT DOCUMENTS

| | | |
|---|---|---|
| AU | 2008258254 B2 | 7/2014 |
| CN | 101279950 A | 10/2008 |

(Continued)

OTHER PUBLICATIONS

Vila-Aiub, M. M., et al. "Glyphosate resistance in perennial *Sorghum halepense* (Johnsongrass), endowed by reduced glyphosate translocation and leaf uptake." Pest management science 68.3 (2012): 430-436. First published: Sep. 23, 2011 (Year: 2011).*
Riar, Dilpreet S., et al. "Glyphosate resistance in a johnsongrass (*Sorghum halepense*) biotype from Arkansas." Weed Science 59.3 (2011): 299-304. (Year: 2011).*
Pratt, Lee H., et al. "Sorghum expressed sequence tags identify signature genes for drought, pathogenesis, and skotomorphogenesis from a milestone set of 16,801 unique transcripts." Plant physiology 139.2 (2005): 869-884. (Year: 2005).*
Vila-Aiub, Martin M., et al. "Glyphosate resistance in perennial *Sorghum halepense* (Johnsongrass), endowed by reduced glyphosate translocation and leaf uptake." Pest management science 68.3 (2012): 430-436. (Year: 2012).*
Agrios, *Plant Pathology* (Second Edition), 2:466-470 (1978).
Alarcón-Reverte et al., "Resistance to ACCase-inhibiting herbicides in the weed *Lolium multiflorum*," *Comm. Appl. Biol. Sci.*, 73(4):899-902 (2008).

(Continued)

*Primary Examiner* — Weihua Fan
(74) *Attorney, Agent, or Firm* — Amanda Carmany-Rampey; Arnold & Porter Kaye Scholer LLP

(57) ABSTRACT

The present invention provides novel compositions for use to enhance weed control. Specifically, the present invention provides for methods and compositions that modulate gene expression in johnsongrass. The present invention also provides for combinations of compositions and methods that enhance johnsongrass control. The invention comprises a method of *Sorghum* species weed control, in particular johnsongrass (*Sorghum halepense*) plant control comprising an external application of a herbicidal composition to a *Sorghum halepense* plant or a part of the *Sorghum halepense* plant in need of control, said herbicidal composition comprising a polynucleotide, an organosilicone surfactant concentration of about 0.2 percent or greater, and an effective dose of a nonpolynucleotide herbicide.

12 Claims, No Drawings

Specification includes a Sequence Listing.

(56) References Cited

U.S. PATENT DOCUMENTS

| | | | |
|---|---|---|---|
| 5,023,243 | A | 6/1991 | Tullis |
| 5,034,506 | A | 7/1991 | Summerton et al. |
| 5,094,945 | A | 3/1992 | Comai |
| 5,141,870 | A | 8/1992 | Bedbrook et al. |
| 5,145,783 | A | 9/1992 | Kishore et al. |
| 5,159,135 | A | 10/1992 | Umbeck |
| 5,166,315 | A | 11/1992 | Summerton et al. |
| 5,177,196 | A | 1/1993 | Meyer, Jr. et al. |
| 5,185,444 | A | 2/1993 | Summerton et al. |
| 5,188,642 | A | 2/1993 | Shah et al. |
| 5,188,897 | A | 2/1993 | Suhadolnik et al. |
| 5,192,659 | A | 3/1993 | Simons |
| 5,214,134 | A | 5/1993 | Weis et al. |
| 5,216,141 | A | 6/1993 | Benner |
| 5,235,033 | A | 8/1993 | Summerton et al. |
| 5,264,423 | A | 11/1993 | Cohen et al. |
| 5,264,562 | A | 11/1993 | Matteucci |
| 5,264,564 | A | 11/1993 | Matteucci |
| 5,272,057 | A | 12/1993 | Smulson et al. |
| 5,276,019 | A | 1/1994 | Cohen et al. |
| 5,281,521 | A | 1/1994 | Trojanowski et al. |
| 5,286,634 | A | 2/1994 | Stadler et al. |
| 5,286,717 | A | 2/1994 | Cohen et al. |
| 5,304,732 | A | 4/1994 | Anderson et al. |
| 5,310,667 | A | 5/1994 | Eichholtz et al. |
| 5,312,910 | A | 5/1994 | Kishore et al. |
| 5,321,131 | A | 6/1994 | Agrawal et al. |
| 5,331,107 | A | 7/1994 | Anderson et al. |
| 5,339,107 | A | 8/1994 | Henry et al. |
| 5,346,107 | A | 9/1994 | Bouix et al. |
| 5,378,824 | A | 1/1995 | Bedbrook et al. |
| 5,384,253 | A | 1/1995 | Krzyzek et al. |
| 5,390,667 | A | 2/1995 | Kumakura et al. |
| 5,392,910 | A | 2/1995 | Bell et al. |
| 5,393,175 | A | 2/1995 | Courville |
| 5,399,676 | A | 3/1995 | Froehler |
| 5,405,938 | A | 4/1995 | Summerton et al. |
| 5,405,939 | A | 4/1995 | Suhadolnik et al. |
| 5,416,011 | A | 5/1995 | Hinchee et al. |
| 5,453,496 | A | 9/1995 | Caruthers et al. |
| 5,455,233 | A | 10/1995 | Spielvogel et al. |
| 5,459,127 | A | 10/1995 | Felgner et al. |
| 5,460,667 | A | 10/1995 | Moriyuki et al. |
| 5,462,910 | A | 10/1995 | Ito et al. |
| 5,463,174 | A | 10/1995 | Moloney et al. |
| 5,463,175 | A | 10/1995 | Barry et al. |
| 5,466,677 | A | 11/1995 | Baxter et al. |
| 5,470,967 | A | 11/1995 | Huie et al. |
| 5,476,925 | A | 12/1995 | Letsinger et al. |
| 5,489,520 | A | 2/1996 | Adams et al. |
| 5,489,677 | A | 2/1996 | Sanghvi et al. |
| 5,491,288 | A | 2/1996 | Chaubet et al. |
| 5,510,471 | A | 4/1996 | Lebrun et al. |
| 5,518,908 | A | 5/1996 | Corbin et al. |
| 5,519,126 | A | 5/1996 | Hecht |
| 5,536,821 | A | 7/1996 | Agrawal et al. |
| 5,538,880 | A | 7/1996 | Lundquist et al. |
| 5,541,306 | A | 7/1996 | Agrawal et al. |
| 5,541,307 | A | 7/1996 | Cook et al. |
| 5,550,111 | A | 8/1996 | Suhadolnik et al. |
| 5,550,318 | A | 8/1996 | Adams et al. |
| 5,550,398 | A | 8/1996 | Kocian et al. |
| 5,550,468 | A | 8/1996 | Häberlein et al. |
| 5,558,071 | A | 9/1996 | Ward et al. |
| 5,561,225 | A | 10/1996 | Maddry et al. |
| 5,561,236 | A | 10/1996 | Leemans et al. |
| 5,563,253 | A | 10/1996 | Agrawal et al. |
| 5,569,834 | A | 10/1996 | Hinchee et al. |
| 5,571,799 | A | 11/1996 | Tkachuk et al. |
| 5,587,361 | A | 12/1996 | Cook et al. |
| 5,591,616 | A | 1/1997 | Hiei et al. |
| 5,593,874 | A | 1/1997 | Brown et al. |
| 5,596,086 | A | 1/1997 | Matteucci et al. |
| 5,597,717 | A | 1/1997 | Guerineau et al. |
| 5,602,240 | A | 2/1997 | De Mesmaeker et al. |
| 5,605,011 | A | 2/1997 | Bedbrook et al. |
| 5,608,046 | A | 3/1997 | Cook et al. |
| 5,610,289 | A | 3/1997 | Cook et al. |
| 5,618,704 | A | 4/1997 | Sanghvi et al. |
| 5,623,070 | A | 4/1997 | Cook et al. |
| 5,625,050 | A | 4/1997 | Beaton et al. |
| 5,627,061 | A | 5/1997 | Barry et al. |
| 5,633,360 | A | 5/1997 | Bischofberger et al. |
| 5,633,435 | A | 5/1997 | Barry et al. |
| 5,633,448 | A | 5/1997 | Lebrun et al. |
| 5,639,024 | A | 6/1997 | Mueller et al. |
| 5,646,024 | A | 7/1997 | Leemans et al. |
| 5,648,477 | A | 7/1997 | Leemans et al. |
| 5,663,312 | A | 9/1997 | Chaturvedula |
| 5,677,437 | A | 10/1997 | Teng et al. |
| 5,677,439 | A | 10/1997 | Weis et al. |
| 5,719,046 | A | 2/1998 | Guerineau et al. |
| 5,721,138 | A | 2/1998 | Lawn |
| 5,731,180 | A | 3/1998 | Dietrich |
| 5,739,180 | A | 4/1998 | Taylor-Smith |
| 5,746,180 | A | 5/1998 | Jefferson et al. |
| 5,767,361 | A | 6/1998 | Dietrich |
| 5,767,373 | A | 6/1998 | Ward et al. |
| 5,780,708 | A | 7/1998 | Lundquist et al. |
| 5,804,425 | A | 9/1998 | Barry et al. |
| 5,824,877 | A | 10/1998 | Hinchee et al. |
| 5,837,848 | A | 11/1998 | Ely et al. |
| 5,859,347 | A | 1/1999 | Brown et al. |
| 5,866,775 | A | 2/1999 | Eichholtz et al. |
| 5,874,265 | A | 2/1999 | Adams et al. |
| 5,879,903 | A | 3/1999 | Strauch et al. |
| 5,914,451 | A | 6/1999 | Martinell et al. |
| 5,919,675 | A | 7/1999 | Adams et al. |
| 5,928,937 | A | 7/1999 | Kakefuda et al. |
| 5,939,602 | A | 8/1999 | Volrath et al. |
| 5,969,213 | A | 10/1999 | Adams et al. |
| 5,981,840 | A | 11/1999 | Zhao et al. |
| 5,985,793 | A | 11/1999 | Sandbrink et al. |
| RE36,449 | E | 12/1999 | Lebrun et al. |
| 6,040,497 | A | 3/2000 | Spencer et al. |
| 6,056,938 | A | 5/2000 | Unger et al. |
| 6,069,115 | A | 5/2000 | Pallett et al. |
| 6,084,089 | A | 7/2000 | Mine et al. |
| 6,084,155 | A | 7/2000 | Volrath et al. |
| 6,118,047 | A | 9/2000 | Anderson et al. |
| 6,121,513 | A | 9/2000 | Zhang et al. |
| 6,130,366 | A | 10/2000 | Herrera-Estrella et al. |
| 6,140,078 | A | 10/2000 | Sanders et al. |
| 6,153,812 | A | 11/2000 | Fry et al. |
| 6,160,208 | A | 12/2000 | Lundquist et al. |
| 6,177,616 | B1 | 1/2001 | Bartsch et al. |
| 6,194,636 | B1 | 2/2001 | McElroy et al. |
| 6,225,105 | B1 | 5/2001 | Sathasivan et al. |
| 6,225,114 | B1 | 5/2001 | Eichholtz et al. |
| 6,232,526 | B1 | 5/2001 | McElroy et al. |
| 6,245,968 | B1 | 6/2001 | Boudec et al. |
| 6,248,876 | B1 | 6/2001 | Barry et al. |
| 6,252,138 | B1 | 6/2001 | Karimi et al. |
| RE37,287 | E | 7/2001 | Lebrun et al. |
| 6,268,549 | B1 | 7/2001 | Sailland et al. |
| 6,271,359 | B1 | 8/2001 | Norris et al. |
| 6,282,837 | B1 | 9/2001 | Ward et al. |
| 6,288,306 | B1 | 9/2001 | Ward et al. |
| 6,288,312 | B1 | 9/2001 | Christou et al. |
| 6,294,714 | B1 | 9/2001 | Matsunaga et al. |
| 6,326,193 | B1 | 12/2001 | Liu et al. |
| 6,329,571 | B1 | 12/2001 | Hiei |
| 6,348,185 | B1 | 2/2002 | Piwnica-Worms |
| 6,365,807 | B1 | 4/2002 | Christou et al. |
| 6,384,301 | B1 | 5/2002 | Martinell et al. |
| 6,385,902 | B1 | 5/2002 | Schipper et al. |
| 6,399,861 | B1 | 6/2002 | Anderson et al. |
| 6,403,865 | B1 | 6/2002 | Koziel et al. |
| 6,414,222 | B1 | 7/2002 | Gengenbach et al. |
| 6,421,956 | B1 | 7/2002 | Boukens et al. |
| 6,426,446 | B1 | 7/2002 | McElroy et al. |
| 6,433,252 | B1 | 7/2002 | McElroy et al. |
| 6,437,217 | B1 | 8/2002 | McElroy et al. |
| 6,453,609 | B1 | 9/2002 | Soll et al. |

(56) References Cited

U.S. PATENT DOCUMENTS 6,479,291 B2 11/2002 Kumagai et al.
6,506,559 B1 1/2003 Fire et al.
6,642,435 B1 11/2003 Antoni et al.
6,644,341 B1 11/2003 Chemo et al.
6,645,914 B1 11/2003 Woznica et al.
6,768,044 B1 7/2004 Boudec et al.
6,992,237 B1 1/2006 Habben et al.
7,022,896 B1 4/2006 Weeks et al.
7,026,528 B2 4/2006 Cheng et al.
RE39,247 E 8/2006 Barry et al.
7,105,724 B2 9/2006 Weeks et al.
7,119,256 B2 10/2006 Shimizu et al.
7,138,564 B2 11/2006 Tian et al.
7,297,541 B2 11/2007 Moshiri et al.
7,304,209 B2 12/2007 Zink et al.
7,312,379 B2 12/2007 Andrews et al.
7,323,310 B2 1/2008 Peters et al.
7,371,927 B2 5/2008 Yao et al.
7,392,379 B2 6/2008 Le Pennec et al.
7,405,347 B2 7/2008 Hammer et al.
7,406,981 B2 8/2008 Hemo et al.
7,462,379 B2 12/2008 Fukuda et al.
7,485,777 B2 2/2009 Nakajima et al.
7,525,013 B2 4/2009 Hildebrand et al.
7,550,578 B2 6/2009 Budworth et al.
7,622,301 B2 11/2009 Ren et al.
7,657,299 B2 2/2010 Huizenga et al.
7,671,254 B2 3/2010 Tranel et al.
7,714,188 B2 5/2010 Castle et al.
7,738,626 B2 6/2010 Weese et al.
7,807,791 B2 10/2010 Sekar et al.
7,838,263 B2 11/2010 Dam et al.
7,838,733 B2 11/2010 Wright et al.
7,842,856 B2 11/2010 Tranel et al.
7,884,262 B2 2/2011 Clemente et al.
7,910,805 B2 3/2011 Duck et al.
7,935,869 B2 5/2011 Pallett et al.
7,943,819 B2 5/2011 Baum et al.
7,973,218 B2 7/2011 McCutchen et al.
8,090,164 B2 1/2012 Bullitt et al.
8,143,480 B2 3/2012 Axtell et al.
8,548,778 B1 10/2013 Hart et al.
8,554,490 B2 10/2013 Tang et al.
9,121,022 B2 9/2015 Sammons et al.
9,422,557 B2 8/2016 Ader
9,445,603 B2 9/2016 Baum et al.
2001/0006797 A1 7/2001 Kumagai et al.
2001/0042257 A1 11/2001 Connor-Ward et al.
2002/0069430 A1 6/2002 Kisaka et al.
2002/0114784 A1 8/2002 Li et al.
2003/0150017 A1 8/2003 Mesa et al.
2003/0154508 A1 8/2003 Stevens et al.
2003/0167537 A1 9/2003 Jiang
2003/0221211 A1 11/2003 Rottmann et al.
2004/0029275 A1 2/2004 Brown et al.
2004/0053289 A1 3/2004 Allen et al.
2004/0055041 A1 3/2004 Labate et al.
2004/0072692 A1 4/2004 Hoffman et al.
2004/0082475 A1 4/2004 Hoffman et al.
2004/0123347 A1 6/2004 Hinchey et al.
2004/0126845 A1 7/2004 Eenennaam et al.
2004/0133944 A1 7/2004 Hake et al.
2004/0147475 A1 7/2004 Li et al.
2004/0177399 A1 9/2004 Hammer et al.
2004/0216189 A1 10/2004 Houmard et al.
2004/0244075 A1 12/2004 Cai et al.
2004/0250310 A1 12/2004 Shukla et al.
2005/0005319 A1 1/2005 della-Cioppa et al.
2005/0215435 A1 9/2005 Menges et al.
2005/0223425 A1* 10/2005 Clinton .................. A01N 57/20
800/279
2005/0246784 A1 11/2005 Plesch et al.
2005/0250647 A1 11/2005 Hills et al.
2006/0009358 A1 1/2006 Kibler et al.
2006/0021087 A1 1/2006 Baum et al.
2006/0040826 A1 2/2006 Eaton et al.
2006/0111241 A1 5/2006 Gerwick, III et al.
2006/0130172 A1 6/2006 Whaley et al.
2006/0135758 A1 6/2006 Wu
2006/0200878 A1 9/2006 Lutfiyya et al.
2006/0223708 A1 10/2006 Hoffman et al.
2006/0223709 A1 10/2006 Helmke et al.
2006/0247197 A1 11/2006 Van De Craen et al.
2006/0272049 A1 11/2006 Waterhouse et al.
2006/0276339 A1 12/2006 Windsor et al.
2007/0011775 A1 1/2007 Allen et al.
2007/0021360 A1 1/2007 Nyce et al.
2007/0050863 A1 3/2007 Tranel et al.
2007/0124836 A1 5/2007 Baum et al.
2007/0199095 A1 8/2007 Allen et al.
2007/0250947 A1 10/2007 Boukharov et al.
2007/0259785 A1 11/2007 Heck et al.
2007/0269815 A1 11/2007 Rivory et al.
2007/0281900 A1 12/2007 Cui et al.
2007/0300329 A1 12/2007 Allen et al.
2008/0022423 A1 1/2008 Roberts et al.
2008/0050342 A1 2/2008 Fire et al.
2008/0092256 A1 4/2008 Kohn
2008/0113351 A1 5/2008 Naito et al.
2008/0155716 A1 6/2008 Sonnewald et al.
2008/0214443 A1 9/2008 Baum et al.
2008/0216187 A1* 9/2008 Tuinstra ......... C12Y 202/01006
800/260
2009/0011934 A1 1/2009 Zawierucha et al.
2009/0018016 A1 1/2009 Duck et al.
2009/0036311 A1 2/2009 Witschel et al.
2009/0054240 A1 2/2009 Witschel et al.
2009/0075921 A1 3/2009 Ikegawa et al.
2009/0098614 A1 4/2009 Zamore et al.
2009/0118214 A1 5/2009 Paldi et al.
2009/0137395 A1 5/2009 Chicoine et al.
2009/0165153 A1 6/2009 Wang et al.
2009/0165166 A1 6/2009 Feng et al.
2009/0188005 A1 7/2009 Boukharov et al.
2009/0205079 A1 8/2009 Kumar et al.
2009/0215628 A1 8/2009 Witschel et al.
2009/0285784 A1 11/2009 Raemaekers et al.
2009/0293148 A1 11/2009 Ren et al.
2009/0298787 A1 12/2009 Raemaekers et al.
2009/0306189 A1 12/2009 Raemaekers et al.
2009/0307803 A1 12/2009 Baum et al.
2010/0005551 A1 1/2010 Roberts et al.
2010/0048670 A1 2/2010 Biard et al.
2010/0068172 A1 3/2010 Van De Craen
2010/0071088 A1 3/2010 Sela et al.
2010/0099561 A1 4/2010 Selby et al.
2010/0100988 A1 4/2010 Tranel et al.
2010/0152443 A1 6/2010 Hirai et al.
2010/0154083 A1 6/2010 Ross et al.
2010/0192237 A1 7/2010 Ren et al.
2010/0247578 A1 9/2010 Salama
2010/0248373 A1 9/2010 Baba et al.
2011/0015084 A1 1/2011 Christian et al.
2011/0015284 A1 1/2011 Dees et al.
2011/0028412 A1 2/2011 Cappello et al.
2011/0035836 A1 2/2011 Eudes et al.
2011/0041400 A1 2/2011 Trias Vila et al.
2011/0053226 A1 3/2011 Rohayem
2011/0098180 A1 4/2011 Michel et al.
2011/0105327 A1 5/2011 Nelson
2011/0105329 A1 5/2011 Song et al.
2011/0112570 A1 5/2011 Mannava et al.
2011/0126310 A1 5/2011 Feng et al.
2011/0126311 A1 5/2011 Velcheva et al.
2011/0152339 A1 6/2011 Brown et al.
2011/0152346 A1 6/2011 Karleson et al.
2011/0152353 A1 6/2011 Koizumi et al.
2011/0160082 A1 6/2011 Woo et al.
2011/0166022 A1 7/2011 Israels et al.
2011/0166023 A1 7/2011 Nettleton-Hammond et al.
2011/0171176 A1 7/2011 Baas et al.
2011/0171287 A1 7/2011 Saarma et al.
2011/0177949 A1 7/2011 Krapp et al.
2011/0185444 A1 7/2011 Li et al.

(56) References Cited

U.S. PATENT DOCUMENTS

| | | | |
|---|---|---|---|
| 2011/0185445 A1 | 7/2011 | Bogner et al. | |
| 2011/0191897 A1 | 8/2011 | Poree et al. | |
| 2011/0201501 A1 | 8/2011 | Song et al. | |
| 2011/0203013 A1 | 8/2011 | Peterson et al. | |
| 2011/0296555 A1 | 12/2011 | Ivashuta et al. | |
| 2011/0296556 A1* | 12/2011 | Sammons | A01N 57/16 800/298 |
| 2012/0036594 A1 | 2/2012 | Cardoza et al. | |
| 2012/0107355 A1 | 5/2012 | Harris et al. | |
| 2012/0108497 A1 | 5/2012 | Paldi et al. | |
| 2012/0137387 A1 | 5/2012 | Baum et al. | |
| 2012/0150048 A1 | 6/2012 | Kang et al. | |
| 2012/0156784 A1 | 6/2012 | Adams, Jr. et al. | |
| 2012/0157512 A1 | 6/2012 | Ben-Chanoch et al. | |
| 2012/0164205 A1 | 6/2012 | Baum et al. | |
| 2012/0174262 A1 | 7/2012 | Azhakanandam et al. | |
| 2012/0185967 A1 | 7/2012 | Sela et al. | |
| 2012/0198586 A1 | 8/2012 | Narva et al. | |
| 2012/0230565 A1 | 9/2012 | Steinberg et al. | |
| 2012/0258646 A1 | 10/2012 | Sela et al. | |
| 2013/0003213 A1 | 1/2013 | Kabelac et al. | |
| 2013/0041004 A1 | 2/2013 | Drager et al. | |
| 2013/0047297 A1 | 2/2013 | Sammons et al. | |
| 2013/0047298 A1 | 2/2013 | Tang | |
| 2013/0060133 A1 | 3/2013 | Kassab et al. | |
| 2013/0067618 A1 | 3/2013 | Ader et al. | |
| 2013/0084243 A1 | 4/2013 | Goetsch et al. | |
| 2013/0096073 A1 | 4/2013 | Sidelman | |
| 2013/0097726 A1 | 4/2013 | Ader et al. | |
| 2013/0212739 A1 | 8/2013 | Giritch et al. | |
| 2013/0226003 A1 | 8/2013 | Edic et al. | |
| 2013/0247247 A1 | 9/2013 | Ader et al. | |
| 2013/0254940 A1 | 9/2013 | Ader et al. | |
| 2013/0254941 A1 | 9/2013 | Ader et al. | |
| 2013/0288895 A1 | 10/2013 | Ader et al. | |
| 2013/0318657 A1 | 11/2013 | Avniel et al. | |
| 2013/0318658 A1 | 11/2013 | Ader et al. | |
| 2013/0324842 A1 | 12/2013 | Mittal et al. | |
| 2013/0326731 A1 | 12/2013 | Ader et al. | |
| 2014/0018241 A1 | 1/2014 | Sammons et al. | |
| 2014/0057789 A1 | 2/2014 | Sammons et al. | |
| 2014/0109258 A1 | 4/2014 | Van De Craen et al. | |
| 2014/0230090 A1 | 8/2014 | Avniel et al. | |
| 2014/0274712 A1 | 9/2014 | Finnessy et al. | |
| 2014/0275208 A1 | 9/2014 | Hu et al. | |
| 2014/0296503 A1 | 10/2014 | Avniel et al. | |
| 2015/0096079 A1 | 4/2015 | Avniel et al. | |
| 2015/0143580 A1 | 5/2015 | Beattie et al. | |
| 2015/0159156 A1 | 6/2015 | Inberg et al. | |
| 2015/0203867 A1 | 7/2015 | Beattie et al. | |
| 2015/0240258 A1 | 8/2015 | Beattie et al. | |
| 2016/0015035 A1 | 1/2016 | Tao | |
| 2016/0029644 A1 | 2/2016 | Tao | |

FOREIGN PATENT DOCUMENTS

| | | | |
|---|---|---|---|
| CN | 101279951 | A | 10/2008 |
| CN | 101892247 | A | 11/2010 |
| CN | 101914540 | A | 12/2010 |
| CN | 102154364 | A | 8/2011 |
| CN | 102481311 | A | 5/2012 |
| CN | 102906263 | A | 1/2013 |
| DE | 288618 | A5 | 4/1991 |
| DE | 10000600 | A1 | 7/2001 |
| DE | 10116399 | A1 | 10/2002 |
| DE | 10256353 | A1 | 6/2003 |
| DE | 10256354 | A1 | 6/2003 |
| DE | 10256367 | A1 | 6/2003 |
| DE | 10204951 | A1 | 8/2003 |
| DE | 10234875 | A1 | 2/2004 |
| DE | 10234876 | A1 | 2/2004 |
| DE | 102004054666 | A1 | 5/2006 |
| DE | 102005014638 | A1 | 10/2006 |
| DE | 102005014906 | A1 | 10/2006 |
| DE | 102007012168 | A1 | 9/2008 |
| DE | 102010042866 | A1 | 5/2011 |
| EP | 0 804 600 | A1 | 11/1997 |
| EP | 1 155 615 | A1 | 11/2001 |
| EP | 1 157 991 | A2 | 11/2001 |
| EP | 1 238 586 | A1 | 9/2002 |
| EP | 1 416 049 | A1 | 5/2004 |
| EP | 1 496 123 | A1 | 1/2005 |
| EP | 1 889 902 | A1 | 2/2008 |
| EP | 1 964 919 | A1 | 9/2008 |
| EP | 2 147 919 | A1 | 1/2010 |
| EP | 2 160 098 | B1 | 11/2010 |
| EP | 2 530 159 | A1 | 3/2011 |
| EP | 2 305 813 | A2 | 4/2011 |
| EP | 2 545 182 | | 1/2013 |
| EP | 2545182 | A1 | 1/2013 |
| JP | 2001253874 | A | 9/2001 |
| JP | 2002080454 | A | 3/2002 |
| JP | 2002138075 | A | 5/2002 |
| JP | 2002145707 | A | 5/2002 |
| JP | 2002220389 | A | 8/2002 |
| JP | 2003064059 | A | 3/2003 |
| JP | 2003096059 | A | 4/2003 |
| JP | 2004051628 | A | 2/2004 |
| JP | 2004107228 | A | 4/2004 |
| JP | 2005008583 | A | 1/2005 |
| JP | 2005239675 | A | 9/2005 |
| JP | 2005314407 | A | 11/2005 |
| JP | 2006232824 | A | 9/2006 |
| JP | 2006282552 | A | 10/2006 |
| JP | 2007153847 | A | 6/2007 |
| JP | 2007161701 | A | 6/2007 |
| JP | 2007182404 | A | 7/2007 |
| JP | 2008074840 | A | 4/2008 |
| JP | 2008074841 | A | 4/2008 |
| JP | 2008133207 | A | 6/2008 |
| JP | 2008133218 | A | 6/2008 |
| JP | 2008169121 | A | 7/2008 |
| JP | 2009-508481 | A | 3/2009 |
| JP | 2009067739 | A | 4/2009 |
| JP | 2009114128 | A | 5/2009 |
| JP | 2009126792 | A | 6/2009 |
| JP | 2009137851 | A | 6/2009 |
| WO | WO 89/11789 | A1 | 12/1989 |
| WO | WO 95/34659 | A1 | 12/1995 |
| WO | WO 95/34668 | A2 | 12/1995 |
| WO | WO 96/005721 | A1 | 2/1996 |
| WO | WO 96/033270 | A1 | 10/1996 |
| WO | WO 96/038567 | A2 | 12/1996 |
| WO | WO 96/040964 | A2 | 12/1996 |
| WO | WO 1997/049816 | A1 | 12/1997 |
| WO | WO 99/024585 | A1 | 5/1999 |
| WO | WO 99/26467 | A1 | 6/1999 |
| WO | WO 99/27116 | A2 | 6/1999 |
| WO | WO 99/32619 | A1 | 7/1999 |
| WO | WO 99/61631 | A1 | 12/1999 |
| WO | WO 99/67367 | A1 | 12/1999 |
| WO | WO 00/32757 | A2 | 6/2000 |
| WO | WO 00/044914 | A1 | 8/2000 |
| WO | WO 2001/07601 | A2 | 2/2001 |
| WO | WO 2001/085970 | A2 | 11/2001 |
| WO | WO 02/14472 | A2 | 2/2002 |
| WO | WO 02/066660 | A2 | 8/2002 |
| WO | WO 03/000679 | A2 | 1/2003 |
| WO | WO 03/006422 | A1 | 1/2003 |
| WO | WO 2003/004649 | A1 | 1/2003 |
| WO | WO 03/012052 | A2 | 2/2003 |
| WO | WO 03/013247 | A1 | 2/2003 |
| WO | WO 03/016308 | A1 | 2/2003 |
| WO | WO 2003/014357 | A1 | 2/2003 |
| WO | WO 03/020704 | A1 | 3/2003 |
| WO | WO 03/022051 | A1 | 3/2003 |
| WO | WO 03/022831 | A1 | 3/2003 |
| WO | WO 03/022843 | A1 | 3/2003 |
| WO | WO 03/029243 | A2 | 4/2003 |
| WO | WO 03/037085 | A1 | 5/2003 |
| WO | WO 03/037878 | A1 | 5/2003 |
| WO | WO 03/045878 | A2 | 6/2003 |
| WO | WO 03/050087 | A2 | 6/2003 |

(56) References Cited

FOREIGN PATENT DOCUMENTS

| | | | |
|---|---|---|---|
| WO | WO 03/051823 | A1 | 6/2003 |
| WO | WO 03/051824 | A1 | 6/2003 |
| WO | WO 03/051846 | A2 | 6/2003 |
| WO | WO 03/064625 | A2 | 8/2003 |
| WO | WO 03/076409 | A1 | 9/2003 |
| WO | WO 03/077648 | A2 | 9/2003 |
| WO | WO 03/087067 | A1 | 10/2003 |
| WO | WO 03/090539 | A1 | 11/2003 |
| WO | WO 03/091217 | A1 | 11/2003 |
| WO | WO 03/093269 | A2 | 11/2003 |
| WO | WO 03/104206 | A2 | 12/2003 |
| WO | WO 2004/002947 | A1 | 1/2004 |
| WO | WO 2004/002981 | A2 | 1/2004 |
| WO | WO 2004/005485 | A2 | 1/2004 |
| WO | WO 2004/009761 | A2 | 1/2004 |
| WO | WO 2004/011429 | A1 | 2/2004 |
| WO | WO 2004/022771 | A2 | 3/2004 |
| WO | WO 2004/029060 | A1 | 4/2004 |
| WO | WO 2004/035545 | A2 | 4/2004 |
| WO | WO 2004/035563 | A1 | 4/2004 |
| WO | WO 2004/035564 | A1 | 4/2004 |
| WO | WO 2004/037787 | A1 | 5/2004 |
| WO | WO 2004/049806 | A1 | 6/2004 |
| WO | WO 2004/062351 | A2 | 7/2004 |
| WO | WO 2004/067518 | A1 | 8/2004 |
| WO | WO 2004/067527 | A1 | 8/2004 |
| WO | WO 2004/074443 | A2 | 9/2004 |
| WO | WO 2004/077950 | A1 | 9/2004 |
| WO | WO 2005/000824 | A1 | 1/2005 |
| WO | WO 2005/003362 | A2 | 1/2005 |
| WO | WO 2005/007627 | A1 | 1/2005 |
| WO | WO 2005/007860 | A1 | 1/2005 |
| WO | WO 2005/040152 | A1 | 5/2005 |
| WO | WO 2005/047233 | A1 | 5/2005 |
| WO | WO 2005/047281 | A1 | 5/2005 |
| WO | WO 2005/061443 | A2 | 7/2005 |
| WO | WO 2005/061464 | A1 | 7/2005 |
| WO | WO 2005/068434 | A1 | 7/2005 |
| WO | WO 2005/070889 | A1 | 8/2005 |
| WO | WO 2005/089551 | A1 | 9/2005 |
| WO | WO 2005/095335 | A1 | 10/2005 |
| WO | WO 2005/107437 | A2 | 11/2005 |
| WO | WO 2005/110068 | A2 | 11/2005 |
| WO | WO 2006/006569 | A1 | 1/2006 |
| WO | WO 2006/024820 | A1 | 3/2006 |
| WO | WO 2006/029828 | A1 | 3/2006 |
| WO | WO 2006/029829 | A1 | 3/2006 |
| WO | WO 2006/037945 | A1 | 4/2006 |
| WO | WO 2006/050803 | A1 | 5/2006 |
| WO | WO 2006/074400 | A2 | 7/2006 |
| WO | WO 2006/090792 | A1 | 8/2006 |
| WO | WO 2006/123088 | A2 | 11/2006 |
| WO | WO 2006/125687 | A1 | 11/2006 |
| WO | WO 2006/125688 | A1 | 11/2006 |
| WO | WO 2006/132270 | A1 | 12/2006 |
| WO | WO 2006/138638 | A1 | 12/2006 |
| WO | WO 2007/003294 | A1 | 1/2007 |
| WO | WO 2007/007316 | A1 | 1/2007 |
| WO | WO 2007/024783 | | 3/2007 |
| WO | WO 2007/026834 | A1 | 3/2007 |
| WO | WO 2007/035650 | A2 | 3/2007 |
| WO | WO 2007/038788 | A2 | 4/2007 |
| WO | WO 2007/039454 | A1 | 4/2007 |
| WO | WO 2007/050715 | A2 | 5/2007 |
| WO | WO 2007/070389 | A2 | 6/2007 |
| WO | WO 2007/071900 | A1 | 6/2007 |
| WO | WO 2007/074405 | A2 | 7/2007 |
| WO | WO 2007/077201 | A1 | 7/2007 |
| WO | WO 2007/077247 | A1 | 7/2007 |
| WO | WO 2007/080126 | A2 | 7/2007 |
| WO | WO 2007/080127 | A2 | 7/2007 |
| WO | WO 2007/083193 | A2 | 7/2007 |
| WO | WO 2007/096576 | A1 | 8/2007 |
| WO | WO 2007/051462 | A2 | 10/2007 |
| WO | WO 2007/051462 | A3 | 10/2007 |
| WO | WO 2007/119434 | A1 | 10/2007 |
| WO | WO 2007/134984 | A1 | 11/2007 |
| WO | WO 2008/007100 | A2 | 1/2008 |
| WO | WO 2008/009908 | A1 | 1/2008 |
| WO | WO 2008/029084 | A1 | 3/2008 |
| WO | WO 2008/042231 | A2 | 4/2008 |
| WO | WO 2008/059948 | A1 | 5/2008 |
| WO | WO 2008/063203 | A2 | 5/2008 |
| WO | WO 2008/071918 | A1 | 6/2008 |
| WO | WO 2008/074991 | A1 | 6/2008 |
| WO | WO 2008/084073 | A1 | 7/2008 |
| WO | WO 2008/100426 | A2 | 8/2008 |
| WO | WO 2008/102908 | A1 | 8/2008 |
| WO | WO 2008/148223 | A1 | 12/2008 |
| WO | WO 2008/152072 | A2 | 12/2008 |
| WO | WO 2008/152073 | A2 | 12/2008 |
| WO | WO 2009/000757 | A1 | 12/2008 |
| WO | WO 2009/005297 | A2 | 1/2009 |
| WO | WO 2009/029690 | A1 | 3/2009 |
| WO | WO 2009/035150 | A2 | 3/2009 |
| WO | WO 2009/037329 | A2 | 3/2009 |
| WO | WO 2009/046384 | A1 | 4/2009 |
| WO | WO 2009/063180 | A1 | 5/2009 |
| WO | WO 2009/068170 | A2 | 6/2009 |
| WO | WO 2009/068171 | A2 | 6/2009 |
| WO | WO 2009/086041 | A1 | 7/2009 |
| WO | WO 2009/090401 | A2 | 7/2009 |
| WO | WO 2009/090402 | A2 | 7/2009 |
| WO | WO 2009/115788 | A1 | 9/2009 |
| WO | WO 2009/116558 | A1 | 9/2009 |
| WO | WO 2009/125401 | A2 | 10/2009 |
| WO | WO 2009/144079 | A1 | 12/2009 |
| WO | WO 2009/152995 | A1 | 12/2009 |
| WO | WO 2009/158258 | A1 | 12/2009 |
| WO | WO 2010/012649 | A1 | 2/2010 |
| WO | WO 2010/026989 | A1 | 3/2010 |
| WO | WO 2010/034153 | A1 | 4/2010 |
| WO | WO 2010/049270 | A1 | 5/2010 |
| WO | WO 2010/049369 | A1 | 5/2010 |
| WO | WO 2010/049405 | A1 | 5/2010 |
| WO | WO 2010/049414 | A1 | 5/2010 |
| WO | WO 2010/056519 | A1 | 5/2010 |
| WO | WO 2010/063422 | A1 | 6/2010 |
| WO | WO 2010/069802 | A1 | 6/2010 |
| WO | WO 2010/078906 | A2 | 7/2010 |
| WO | WO 2010/078912 | A1 | 7/2010 |
| WO | WO 2010/093788 | A2 | 8/2010 |
| WO | WO 2010/104217 | A1 | 9/2010 |
| WO | WO 2010/108611 | A1 | 9/2010 |
| WO | WO 2010/112826 | A2 | 10/2010 |
| WO | WO 2010/116122 | A2 | 10/2010 |
| WO | WO 2010/119906 | A1 | 10/2010 |
| WO | WO 2010/130970 | A1 | 11/2010 |
| WO | WO 2011/001434 | A1 | 1/2011 |
| WO | WO 2011/003776 | A2 | 1/2011 |
| WO | WO 2011/035874 | A1 | 3/2011 |
| WO | WO 2011/045796 | A1 | 4/2011 |
| WO | WO 2011/065451 | A1 | 6/2011 |
| WO | WO 2011/067745 | A2 | 6/2011 |
| WO | WO 2011/075188 | A1 | 6/2011 |
| WO | WO 2011/080674 | A2 | 7/2011 |
| WO | WO 2011/112570 | A1 | 9/2011 |
| WO | WO 2011/132127 | A1 | 10/2011 |
| WO | WO 2012/001626 | A1 | 1/2012 |
| WO | WO 2012/056401 | A1 | 5/2012 |
| WO | WO 2012/092580 | A2 | 7/2012 |
| WO | WO 2012/164100 | A2 | 12/2012 |
| WO | WO 2013/010691 | A1 | 1/2013 |
| WO | WO 2013/025670 | A1 | 2/2013 |
| WO | WO 2013/039990 | A1 | 3/2013 |
| WO | WO 2013/040005 | A1 | 3/2013 |
| WO | WO 2013/040021 | A1 | 3/2013 |
| WO | WO 2013/040033 | A1 | 3/2013 |
| WO | WO 2013/040049 | A1 | 3/2013 |
| WO | WO 2013/040057 | A1 | 3/2013 |
| WO | WO 2013/040116 | A9 | 3/2013 |
| WO | WO 2013/040117 | A9 | 3/2013 |
| WO | WO 2013/153553 | A2 | 10/2013 |
| WO | WO 2013/175480 | A1 | 11/2013 |

(56) References Cited

FOREIGN PATENT DOCUMENTS

WO WO 2014/022739 A2 2/2014
WO WO 2014/106837 A2 7/2014
WO WO 2014/106838 A2 7/2014
WO WO 2014/151255 A1 9/2014
WO WO 2014/164761 A1 10/2014
WO WO 2014/164797 A2 10/2014
WO WO 2015/010026 A2 1/2015

OTHER PUBLICATIONS

Amarzguioui et al., "An algorithm for selection of functional siRNA sequences," *Biochemical and Biophysical Research Communications*, 316:1050-1058 (2004).
Ambrus et al., "The Diverse Roles of RNA Helicases in RNAi," *Cell Cycle*, 8(21):3500-3505 (2009).
An et al., "Transient RNAi Induction against Endogenous Genes in *Arabidopsis* Protoplasts Using in Vitro-Prepared Double-Stranded RNA," *Biosci Biotechnol Biochem*, 69(2):415-418 (2005).
Andersson et al., "A novel selection system for potato transformation using a mutated AHAS gene," *Plant Cell Reports*, 22(4):261-267 (2003).
Anonymous, "A handbook for high-level expression and purification of 6xHis-tagged proteins," *The QiaExpressionist*, (2003).
Anonymous, "Agronomy Facts 37: Adjuvants for enhancing herbicide performance," n. p., 1-8, (Jan. 26, 2000), *Web*, (Jan. 21, 2014).
Anonymous, "Devgen, The mini-Monsanto," KBC Securities (2006).
Anonymous, "Do Monsanto have the next big thing?," *Austalian Herbicide Resistance Initiative* (*AHRI*), (Apr. 23, 2013) Web. (Jan. 19, 2015).
Aoki et al., "In Vivo Transfer Efficiency of Antisense Oligonucleotides into the Myocardium Using HVJ—Liposome Method," *Biochem Biophys Res Commun*, 231:540-545 (1997).
Arpaia et al., "Production of transgenic eggplant (*Solanum melongena* L.) resistant to Colorado Potato Beetle (*Leptinotarsa decemlineata* Say)," (1997) *Theor. Appl. Genet.*, 95:329-334 (1997).
Artymovich, "Using RNA interference to increase crop yield and decrease pest damage," *MMG 445 Basic Biotech.*, 5(1):7-12 (2009).
Australian Patent Examination report No. 1 dated Nov. 11, 2013, in Australian Application No. 2011224570.
Axtell et al., "A Two-Hit Trigger for siRNA Biogenesis in Plants," *Cell*, 127:565-577 (2006).
Baerson et al., "Glyphosate-Resistant Goosegrass. Identification of a Mutation in the Target Enzyme 5-Enolpyruvylshikimate-3-Phosphate Synthase," *Plant Physiol.*, 129(3):1265-1275 (2002).
Bai et al., "Naturally Occurring Broad-Spectrum Powdery Mildew Resistance in a Central American Tomato Accession Is Caused by Loss of *Mlo* Function," *MPMI*, 21(1):30-39 (2008).
Bannerjee et al., "Efficient production of transgenic potato (S. *tuberosum* L. ssp. *andigena*) plants via *Agrobacterium tumefaciens*-mediated transformation," *Plant Sci.*, 170:732 738 (2006).
Baulcombe, "RNA silencing and heritable epigenetic effects in tomato and Arabidopsis," Abstract $13^{th}$ Annual Fall Symposium, Plant Genomes to Phenomes, Donald Danforth Plant Science Center, 28-30 (2011).
Bayer et al., "Programmable ligand-controlled riboregulators of eukaryotic gene expression," *Nature Biotechnol.*, 23(3):337-343 (2005).
Beal, et al., "Second Structural Motif for Recognition of DNA by Oligonucleotide-Directed Triple-Helix Formation," *Science*, 251:1360-1363 (1992).
Becker et al., "Fertile transgenic wheat from microprojectile bombardment of scutellar tissue," *The Plant Journal*, 5(2):299-307 (1994).
Bhargava et al., "Long double-stranded RNA-mediated RNA interference as a tool to achieve site-specific silencing of hypothalamic neuropeptides," *Brain Research Protocols*, 13:115-125 (2004).
Boletta et al., "High Efficient Non-Viral Gene Delivery to the Rat Kidney by Novel Polycationic Vectors," *J. Am Soc. Nephrol.*, 7:1728 (1996).
Bolognesi et al., "Characterizing the Mechanism of Action of Double-Stranded RNA Activity against Western Corn Rootworm(*Diabrotica virgifera virgifera* LeConte)," PLoS ONE 7(10):e47534 (2012).
Bolter et al., "A chloroplastic inner envelope membrane protease is essential for plant development," *FEBS Letters*, 580:789-794 (2006).
Bourgeois et al., "Field and producer survey of ACCase resistant wild oat in Manitoba," *Canadian Journal of Plant Science*, 709-715 (1997).
Breaker et al., "A DNA enzyme with $Mg2^+$-dependent RNA phosphoesterase activity," *Chemistry and Biology*, 2:655-660 (1995).
Brodersen et al., "The diversity of RNA silencing pathways in plants," *Trends in Genetics*, 22(5):268-280 (2006).
Brugière et al., "Glutamine Synthetase in the Phloem Plays a Major Role in Controlling Proline Production," *The Plant Cell*, 11:1995-2011 (1999).
Busi et al., "Gene flow increases the initial frequency of herbicide resistance alleles in unselectedpopulations," *Agriculture, Ecosystems and Environments*, Elsevier, Amsterdam, NL, 142(3):403-409 (2011).
Butler et al., "Priming and re-drying improve the survival of mature seeds of *Digitalis purpurea* during storage," *Annals of Botany*, 103:1261-1270 (2009).
Bytebier et al., "T-DNA organization in tumor cultures and transgenic plants of the monocotyledon *Asparagus officinalis*," *Proc. Natl. Acad. Sci. U.S.A.*, 84:5345-5349 (1987).
Campbell et al., "Gene-knockdown in the honey bee mite *Varroa destructor* by a non-invasive approach: studies on a glutathione 5-transferase," *Parasites & Vectors*, 3(1):73, pp. 1-10 (2010).
Chabbouh et al., "Cucumber mosaic virus in artichoke," *FAO Plant Protection Bulletin*, 38:52-53 (1990).
Chakravarty et al., "Genetic Transformation in Potato: Approaches and Strategies," *Amer J Potato Res*, 84:301 311 (2007).
Chang et al., "Cellular Internalization of Fluorescent Proteins via Arginine-rich Intracellular Delivery Peptide in Plant Cells," *Plant Cell Physiol.*, 46(3):482-488 (2005).
Chee et al., "Transformation of Soybean (*Glycine max*) by Infecting Germinating Seeds with *Agrobacterium tumefaciens*," *Plant Physiol.*, 91:1212-1218 (1989).
Chen et al., "In Vivo Analysis of the Role of atTic20 in Protein Import into Chloroplasts," *The Plant Cell*, 14:641-654 (2002).
Cheng et al., "Production of fertile transgenic peanut (*Arachis hypogaea* L.) plants using *Agrobacterium tumefaciens*," *Plant Cell Reports*, 15:653-657 (1996).
Chi et al., "The Function of RH22, a DEAD RNA Helicase, in the Biogenesis of the 50S Ribosomal Subunits of Arabidopsis Chloroplasts," *Plant Physiology*, 158:693-707 (2012).
Chinese Office Action dated Aug. 28, 2013 in Chinese Application No. 201180012795.2.
Chupp et al., "Chapter 8: White Rust," *Vegetable Diseases and Their Control*, The Ronald Press Company, New York, pp. 267-269 (1960).
Clough et al., "Floral dip: a simplified method for Agrobacterium-mediated transformation of *Arabidopsis thaliana*," *The Plant Journal*, 16(6):735-743 (1998).
CN101914540 Patent Diclosure, "Introduction of RNA into plant by interference," (2010).
Colbourne et al., "The Ecoresponsive Genome of *Daphnia pulex*," *Science*, 331(6017):555-561 (2011).
Colombian Office Action dated Aug. 2, 2013 in Application No. 12 152898.
Colombian Office Action dated Feb. 21, 2014 in Application No. 12 152898.
Communication pursuant to Article 94(3) EPC dated Jun. 26, 2015, as received in European Patent Application No. 11 753 916.3.
Communication pursuant to Article 94(3) EPC dated Oct. 23, 2015, as received in European Patent Application No. 12 831 945.6.
Cooney et al., "Site-Specific Oligonucleotide Binding Represses Transcription of the Human c-myc Gene in Vitro," *Science* ,241:456-459 (1988).
COST Action FA0806 progress report "Plant virus control employing RNA-based vaccines: A novel non-transgenic strategy" (2010).

(56) References Cited

OTHER PUBLICATIONS

Coticchia et al., "Calmodulin modulates Akt activity in human breast cancer cell lines," *Breast Cancer Res. Treat*, 115:545-560 (2009).
Dalmay et al., "An RNA-Depenedent RNA Polymerase Gene in *Arabidopsis* Is Required for Posttranscriptional Gene Silencing Mediated by a Transgene but Not by a Virus," *Cell*, 101:543-553 (2000).
Database EMBL CBIB Daphnia—XP-002732239 (2011).
Davidson et al., "Engineering regulatory RNAs," *TRENDS in Biotechnology*, 23(3):109-112 (2005).
De Block, et al. "Engineering herbicide resistance in plants by expression of a detoxifying enzyme," *EMBO J.* 6(9):2513-2519 (1987).
De Framond, "MINI-Ti: A New Vector Strategy for Plant Genetic Engineering," *Nature Biotechnology*, 1:262-269 (1983).
Della-Cioppa et al., "Import of a precursor protein into chloroplasts is inhibited by the herbicide glyphosate," *The EMBO Journal*, 7(5):1299-1305 (1988).
Desai et al., "Reduction in deformed wing virus infection in larval and adult honey bees (*Apis mellifera* L.) by double-stranded RNA ingestion," *Insect Molecular Biology*, 21(4):446-455 (2012).
Diallo et al., "Long Endogenous dsRNAs Can Induce Complete Gene Silencing in Mammalian Cells and Primary Cultures," *Oligonucleotides*, 13:381-392 (2003).
Dietemann et al.,"*Varroa destructor*: research avenues towards sustainable control," *Journal of Apicultural Research*, 51(1):125-132 (2012).
Du et al., "A systematic analysis of the silencing effects of an active siRNA at all single-nucleotide mismatched target sites," *Nucleic Acids Research*, 33(5):1671-1677 (2005).
Dunoyer et al., "Small RNA Duplexes Function as Mobile Silencing Signals Between Plant Cells," *Science*, 328:912-916 (2010).
Ellington et al., "In vitro selection of RNA molecules that bind specific ligands," *Nature*, 346:818-822 (1990).
Emery et al., "Radial Patterning of *Arabidopsis* Shoots by Class III HD-ZIP and Kanadi Genes," *Current Biology*, 13:1768-1774 (2003).
Eurasian Office Action dated Feb. 24, 2014, in Application No. 201201264.
European Cooperation in the field of Scientific and Technical Research—Memorandum of Understanding for COST Action FA0806 (2008).
European Supplemental Search Report dated Oct. 8, 2013 in Application No. 11753916.3.
Extended European Search Report dated Feb. 2, 2015, in European Patent Application No. 12 830 932.5.
Extended European Search Report dated Feb. 27, 2015, in European Patent Application No. 12 832 160.1.
Extended European Search Report dated Feb. 3, 2015, in European Patent Application No. 12 831 945.6.
Extended European Search Report dated Jan. 21, 2015, in European Patent Application No. 12 832 415.9.
Extended European Search Report dated Jan. 29, 2015, in European Patent Application No. 12 831 567.8.
Extended European Search Report dated Jun. 29, 2015, in European Patent Application No. 12 831 494.5.
Extended European Search Report dated Mar. 17, 2015, in European Patent Application No. 12 831 684.1.
Extended European Search Report dated Mar. 3, 2015, in European Patent Application No. 12 831 166.9.
Farooq et al., "Rice seed priming," *IPRN*, 30(2):45-48 (2005).
Final Office Action dated Nov. 10, 2015, in U.S. Appl. No. 13/612,985.
Final Office Action dated Nov. 7, 2013, in U.S. Appl. No. 13/042,856.
Final Office Action dated Nov. 30, 2015, in U.S. Appl. No. 13/612,948.
Fire et al., "Potent and specific genetic interference by double-stranded RNA in *Caenorhabditis elegans*," *Nature*, 391:806-811 (1998).
First Examination Report dated Apr. 23, 2013, in New Zealand Patent Application No. 601784.
First Examination Report dated Jul. 28, 2014, in New Zealand Patent Application No. 627060.
First Office Action dated Sep. 9, 2015, in Chinese Patent Application No. 201280055409.2.
First Office Action dated Mar. 12, 2015, in Chinese Patent Application No. 201280053984.9.
First Office Action dated Mar. 2, 2015, in Chinese Patent Application No. 201280054819.5.
First Office Action dated May 27, 2015, in Chinese Patent Application No. 201280054179.8.
First Office Action dated Jul. 7, 2015, in Chinese Patent Application No. 201280054820.8.
First Office Action dated Aug. 31, 2015, in Chinese Patent Application No. 201280053985.3.
Fukuhara et al., "Enigmatic Double-Stranded RNA in Japonica Rice," *Plant Molecular Biology*, 21:1121-1130 (1993).
Fukuhara et al., "The Unusual Structure of a Novel RNA Replicon in Rice," *The Journal of Biological Chemistry*, 270(30):18147-18149 (1995).
Fukuhara et al., "The wide distribution of endornaviruses, large double-stranded RNA replicons with plasmid-like properties," *Archives of Virology*, 151:995-1002 (2006).
Further Examination Report issued in New Zealand Patent Application No. 601784 dated May 16, 2014.
Gaines et al., "Gene amplification confers glyphosate resistance in *Amaranthus palmeri*," *Proc. Natl. Acad. Sci. USA*, 107(3):1029-1034 (2010).
Gan et al., "Bacterially expressed dsRNA protects maize against SCMV infection," *Plant Cell Rep*, 11:1261-1268 (2010).
Gao et al., "Down-regulation of acetolactate synthase compromises 01-1-mediated resistance to powdery mildew in tomato," *BMC Plant Biology*, 14 (2014).
Garbian et al., "Bidirectional Transfer of RNAi between Honey Bee and *Varroa destructor*: *Varroa* Gene Silencing Reduces *Varroa* Population," 8(12):1-9:e1003035 (2012).
Ge et al., "Rapid vacuolar sequestration: the horseweed glyphosate resistance mechanism," *Pest Management Sci.*, 66:345-348 (2010).
GenBank Accession No. AY545657.1, published 2004.
GenBank Accession No. DY640489, PU2_plate27_F03 PU2 Prunus persica cDNA similar to expressed mRNA inferred from Prunus persica hypothetical domain/motif containing IPR011005:Dihydropteroate synthase-like, MRNA sequence (2006) [Retrieved on Feb. 4, 2013]. Retrieved from the internet <URL: http://www.ncbi.nlm.nih.gov/nucest/DY640489>.
GenBank Accession No. EU24568—"Amaranthus hypochondriacus acetolactate synthase (ALS) gene," (2007).
GenBank Accession No. FJ972198, Solanum lycopersicum cultivar Ailsa Craig dihydropterin pyrophosphokinase-dihydropteroate synthase (HPPK-DHPS) gene, complete cds (2010) [Retrieved on Nov. 26, 2012]. Retrieved from the internet ,URL: http://www.ncbi.nlm.nih.gov/nuccore/FJ972198>.
GenBank Accession No. GI:186478573, published Jan. 22, 2014.
GenEmbl FJ861243, published Feb. 3, 2010.
Gong et al., "Silencing of Rieske iron-sulfur protein using chemically synthesised siRNA as a potential biopesticide against Plutella xylostella," *Pest Manag Sci*, 67:514-520 (2011).
Gressel et al., "A strategy to provide long-term control of weedy rice while mitigating herbicide resistance transgene flow, and its potential use for other crops with related weeds," *Pest Manag Sci*, 65(7):723-731 (2009).
Gutensohn et al., "Functional analysis of the two *Arabidopsis* homologues of Toc34, a component of the chloroplast protein import apparatus," *The Plant Journal*, 23(6):771-783 (2000).
Haigh, "The Priming of Seeds: Investigation into a method of priming large quantities of seeds using salt solutions," Thesis submitted to Macquarie University (1983).
Hamilton et al., "Guidelines for the Identification and Characterization of Plant Viruses," *J. gen. Virol.*, 54:223-241 (1981).
Hamilton et al., "Two classes of short interfering RNA in RNA silencing," *EMBO J.*, 21(17):4671-4679 (2002).
Han et al., "Molecular Basis for the Recognition of Primary microRNAs by the Drosha-DGCR8 Complex," *Cell*, 125(5):887-901 (2006).

(56) References Cited

OTHER PUBLICATIONS

Hannon, "RNA interference," *Nature*,481:244-251 (2002).
Hardegree, "Drying and storage effects on germination of primed grass seeds," *Journal of Range Management*, 47(3):196-199 (1994).
Harrison et al., "Does Lowering Glutamine Synthetase Activity in Nodules Modigy Nitrogen Metabolism and Growth of *Lotus japonicus*?," *Plant Physiology*, 133:253-262 (2003).
Herman et al., "A three-component dicamba O-demethylase from *Pseudomonas maltophilia*, strain DI-6: gene isolation, characterization, and heterologous expression," *J. Biol. Chem.*, 280: 24759-24767 (2005).
Hewezi et al., "Local infiltration of high- and low-molecular-weight RNA from silenced sunflower (*Helianthus annuus* L.) plants triggers post-transcriptional gene silencing in non-silenced plants," *Plant Biotechnology Journal*, 3:81-89 (2005).
Hidayat et al., "Enhanced Metabolism of Fluazifop Acid in a Biotype of *Digitaria sanguinalis* Resistant to the Herbicide Fluazifop-P-Butyl," *Pesticide Biochem. Physiol.*, 57:137-146 (1997).
Himber et al., "Transitivity-dependant and -independent cell-to-cell movement of RNA silencing," *The EMBO Journal*, 22(17):4523-4533 (2003).
Hirschberg et al., "Molecular Basis of Herbicide Resistance in *Amaranthus hybridus*," *Science*, 222:1346-1349 (1983).
Hoekema et al., "A binary plant vector strategy based on separation of vir- and T-region of the *Agrobacterium tumefaciens* Ti-plasmid," *Nature*, 303:179-180 (1983).
Hofgen et al., "Repression of Acetolactate Synthase Activity through Antisense Inhibition: Molecular and Biochemical Analysis of Transgenic Potato (*Solanum tuberosum* L. cv Desiree) Plants," *Plant Physiol.*, 107(2):469-477 (1995).
Hsieh et al., "A library of siRNA duplexes targeting the phosphoinositide 3-kinase pathway: determinants of gene silencing for use in cell-based screens," *Nucleic Acids Res.*, 32(3):893-901 (2004).
Huesken et al., "Design of a genome-wide siRNA library using an artificial neural network," *Nature Biotechnology*, 23(8): 995-1001 (2005).
Hunter et al., "RNA Interference Strategy to suppress Psyllids & Leafhoppers," *International Plant and Animal Genome XIX*, 15-19 (2011).
Ichihara et al., "Thermodynamic instability of siRNA duplex is a prerequisite for dependable prediction of siRNA activities," *Nucleic Acids Res.*, 35(18):e123 (2007).
International Preliminary Report on Patentability (Chapter II) dated Jul. 24, 2015, in International Application No. PCT/US2014/047204.
International Preliminary Report on Patentability dated Sep. 11, 2014, in International Application No. PCT/IL2013/050447.
International Search Report and the Written Opinion dated Feb. 25, 2013, in International Application No. PCT/US12/054883.
International Search Report and the Written Opinion dated Feb. 27, 2013, in International Application No. PCT/US12/054814.
International Search Report and the Written Opinion dated Feb. 27, 2013, in International Application No. PCT/US12/054842.
International Search Report and the Written Opinion dated Feb. 27, 2013, in International Application No. PCT/US12/054862.
International Search Report and the Written Opinion dated Feb. 27, 2013, in International Application No. PCT/US12/054894.
International Search Report and the Written Opinion dated Feb. 27, 2013, in International Application No. PCT/US12/054974.
International Search Report and the Written Opinion dated Feb. 27, 2013, in International Application No. PCT/US12/054980.
International Search Report and the Written Opinion dated Jul. 15 2014, in International Application No. PCT/US2014/025305.
International Search Report and the Written Opinion dated Jul. 22 2014, in International Application No. PCT/IL2013/051083.
International Search Report and the Written Opinion dated Jul. 22 2014, in International Application No. PCT/IL2013/051085.
International Search Report and the Written Opinion dated Jul. 24 2014, in International Application No. PCT/US2014/026036.
International Search Report and the Written Opinion dated May 10, 2011, in International Application No. PCT/US11/027528.
International Search Report and the Written Opinion dated Oct. 1, 2013, in International Application No. PCT/IL2013/050447.
International Search Report and Written Opinion dated Aug. 25, 2014, in International Application No. PCT/US2014/023503.
International Search Report and Written Opinion dated Aug. 27, 2014, in International Application No. PCT/US2014/023409.
International Search Report and Written Opinion dated Feb. 23, 2015, in International Application No. PCT/US2014/063832.
International Search Report and Written Opinion dated Jul. 8, 2015, in International Application No. PCT/US2015/011408.
International Search Report and Written Opinion dated Mar. 26, 2015, in International Application No. PCT/US2014/069353.
International Search Report and Written Opinion dated Nov. 24, 2015, in International Application No. PCT/US2015/037522.
International Search Report dated Mar. 12, 2013, in International Application No. PCT/US2012/054789.
Invitation to Pay Additional Fees dated May 6, 2014, in International Application No. PCT/IL2013/051083.
Invitation to Pay Additional Fees dated May 6, 2014, in International Application No. PCT/IL2013/051085.
Invitation to Pay Additional Fees dated Nov. 25, 2014, in International Application No. PCT/US2014/047204.
Invitation to Pay Additional Fees dated Sep. 8, 2015, in International Application No. PCT/US2015/037015.
Invitation to Pay Additional Fees dated Sep. 9, 2015, in International Application No. PCT/US2015/037522.
Isaacs et al., "Engineered riboregulators enable post-transcriptional control of gene expression," *Nature Biotechnology*, 22(7):841-847 (2004).
Ji et al., "Regulation of small RNA stability: methylation and beyond," *Cell Research*, 22:624-636 (2012).
Jofre-Garfias et al., "*Agrobacterium*-mediated transformation of Amaranthus *hypochondriacus*: light- and tissue-specific expression of a pea chlorophyll a/b-binding protein promoter," *Plant Cell Reports*, 16:847-852 (1997).
Jones-Rhoades et al., "MicroRNAs and Their Regulatory Roles in Plants," *Annu. Rev. Plant Biol.*, 57:19-53 (2006).
Josse et al., "A DELLA in Disguise: SPATULA Restrains the Growth of the Developing *Arabidopsis* Seedling," *Plant Cell*, 23:1337-1351 (2011).
Kam et al., "Nanotube Molecular Transporters: Internalization of Carbon Nanotube—Protein Conjugates into Mammalian Cells," *J. Am. Chem. Soc.*, 126(22):6850-6851 (2004).
Katoh et al., "Specific residues at every third position of siRNA shape its efficient RNAi activity," *Nucleic Acids Res.*, 35(4): e27 (2007).
Kertbundit et al., "In vivo random β-glucuronidase gene fusions in *Arabidopsis thaliana*," *Proc. Natl. Acad. Sci. U S A.*, 88:5212-5216 (1991).
Khachigian, "DNAzymes: Cutting a path to a new class of therapeutics," *Curr Opin Mol Ther* 4(2):119-121 (2002).
Khan et al., "Matriconditioning of Vegetable Seeds to Improve Stand Establishment in Early Field Plantings," *J. Amer. Soc. Hort. Sci.*, 117(1):41-47 (1992).
Khodakovskaya et al., "Carbon Nanotubes Are Able to Penetrate Plant Seed Coat and Dramatically Affect Seed Germination and Plant Growth," *ACS Nano*, 3(10):3221-3227 (2009).
Kim et al., "Synthetic dsRNA Dicer substrates enhance RNAi potency and efficacy," *Nature Biotechnology*, 23(2):222-226 (2005).
Kirkwood, "Use and Mode of Action of Adjuvants for Herbicides: A Review of some Current Work," *Pestic Sci.*, 38:93-102 (1993).
Klahre et al., "High molecular weight RNAs and small interfering RNAs induce systemic posttranscriptional gene silencing in plants," *Proc. Natl. Acad. Sci. USA*, PNAS, 99(18):11981-11986 (2002).
Kronenwett et al., "Oligodeoxyribonucleotide Uptake in Primary Human Hematopoietic Cells Is Enhanced by Cationic Lipids and Depends on the Hematopoietic Cell Subset," *Blood*, 91(3):852-862 (1998).
Kusaba et al., "Low glutelin content1: A Dominant Mutation That Suppresses the Glutelin Multigene Family via RNA Silencing ni Rice," *The Plant Cell*, 15(6):1455-1467 (2003).

(56) References Cited

OTHER PUBLICATIONS

Kusaba, "RNA interference in crop plants," *Curr Opin Biotechnol*, 15(2):139-143 (2004).
Lavigne et al., "Enhanced antisense inhibition of human immunodeficiency virus type 1 in cell cultures by DLS delivery system," *Biochem Biophys Res Commun*, 237:566-571 (1997).
Lee et al., "Aptamer Database," *Nucleic Acids Research*, 32:D95-D100 (2004).
Lein et al., "Target-based discovery of novel herbicides," *Current Opinion in Plant Biology*, 7:219-225 (2004).
Leopold et al., "Chapter 4: Moisture as a Regulator of Physiological Reaction in Seeds," *Seed Moisture, CSSA Special Publication No. 14*, pp. 51-69 (1989).
Lermontova et al., "Reduced activity of plastid protoporphyrinogen oxidase causes attenuated photodynamic damage during high-light compared to low-light exposure," *The Plant Journal*, 48(4):499-510 (2006).
Lesnik et al., "Prediction of rho-independent transcriptional terminators in *Escherichia coli*," *Nucleic Acids Research*, 29(17):3583-3594 (2001).
Li et al., "Establishment of a highly efficient transformation system for pepper (*Capsicum annuum* L.)," *Plant Cell Reports*, 21: 785-788 (2003).
Li et al., "The FAST technique: a simplified Agrobacterium-based transformation method for transient gene expression analysis in seedlings of *Arabidopsis* and other plant species," *Plant Methods*, 5(6):1-15 (2009).
Liu et al., "Carbon Nanotubes as Molecular Transporters for Walled Plant Cells," *Nano Letters*, 9(3):1007-1010 (2009).
Liu et al., "Comparative study on the interaction of DNA with three different kinds of surfactants and the formation of multilayer films," *Bioelectrochemistry*, 70:301-307 (2007).
Liu et al., "DNAzyme-mediated recovery of small recombinant RNAs from a 5S rRNA-derived chimera expressed in *Escherichia coli*," *BMC Biotechnology*, 10:85 (2010).
Llave et al., "Endogenous and Silencing-Associated Small RNAs in Plants," *The Plant Cell*, 14:1605-1619 (2002).
Lu et al., "OligoWalk: an online siRNA design tool utilizing hybridization thermodynamics," *Nucleic Acids Research*, 36:W104-W108 (2008).
Lu et al., "RNA silencing in plants by the expression of siRNA duplexes," *Nucleic Acids Res.*, 32(21):e171 (2004).
Luft, "Making sense out of antisense oligodeoxynucleotide delivery: getting there is half the fun," *J Mol Med*, 76:75-76 (1998).
Maas et al., "Mechanism and optimized conditions for PEG mediated DNA transfection into plant protoplasts," *Plant Cell Reports*, 8:148-149 (1989).
MacKenzie et al., "Transgenic *Nicotiana debneyii* expressing viral coat protein are resistant to potato virus S infection," *Journal of General Virology*, 71:2167-2170 (1990).
Maher III et al., "Inhibition of DNA binding proteins by oligonucleotide-directed triple helix formation," *Science*, 245(4919):725-730 (1989).
Makkouk et al., "Virus Diseases of Peas, Beans, and Faba Bean in the Mediterranean region," *Adv Virus Res*, 84:367-402 (2012).
Mandal et al., "Adenine riboswitches and gene activation by disruption of a transcription terminator," *Nature Struct. Mol. Biol.*, 11(1):29-35 (2004).
Mandal et al., "Gene Regulation by Riboswitches," *Nature Reviews | Molecular Cell Biology*, 5:451-463 (2004).
Manoharan, "Oligonucleotide Conjugates as Potential Antisense Drugs with Improved Uptake, Biodistribution, Targeted Delivery, and Mechanism of Action," *Antisense & Nucleic Acid Drug Development*, 12:103-128 (2002).
Maori et al., "IAPV, a bee-affecting virus associated with Colony Collapse Disorder can be silenced by dsRNA ingestion," *Insect Molecular Biology*, 18(1):55-60 (2009).
Masoud et al., "Constitutive expression of an inducible ß-1,3-glucanase in alfalfa reduces disease severity caused by the oomycete pathogen *Phytophthora megasperma* f. sp *medicaginis*, but does not reduce disease severity of chitincontaining fungi," *Transgenic Research*, 5:313-323 (1996).
Matveeva et al., "Prediction of antisense oligonucleotide efficacy by in vitro methods," *Nature Biotechnology*, 16:1374-1375 (1998).
Meinke, et al., "Identifying essential genes in *Arabidopsis thaliana*," *Trends Plant Sci.*, 13(9):483-491 (2008).
Meins et al., "RNA Silencing Systems and Their Relevance to Plant Development," *Annu. Rev. Cell Dev. Biol.*, 21:297-318 (2005).
Melnyk et al., "Intercellular and systemic movement of RNA silencing signals," *The EMBO Journal*, 30:3553-3563 (2011).
Misawa et al., "Expression of an *Erwinia* phytoene desaturase gene not only confers multiple resistance to herbicides interfering with carotenoid biosynthesis but also alters xanthophyll metabolism in transgenic plants," *The Plant Journal*, 6(4):481-489 (1994).
Misawa et al., "Functional expression of the *Erwinia uredovora* carotenoid biosynthesis gene crtl in transgenic plants showing an increase of β-carotene biosynthesis activity and resistance to the bleaching herbicide norflurazon," *The Plant Journal*, 4(5):833-840 (1993).
Miura et al., "The Balance between Protein Synthesis and Degradation in Chloroplasts Determines Leaf Variegation in *Arabidopsis yellow variegated* Mutants," *The Plant Cell*, 19:1313-1328 (2007).
Molina et al., "Inhibition of protoporphyrinogen oxidase expression in *Arabidopsis* causes a lesion-mimic phenotype that induces systemic acquired resistance," *The Plant Journal*, 17(6):667-678 (1999).
Molnar et al., "Plant Virus-Derived Small Interfering RNAs Originate redominantly from Highly Structured Single-Stranded Viral RNAs," *Journal of Virology*, 79(12):7812-7818 (2005).
Molnar et al., "Small Silencing RNAs in Plants Are Mobile and Direct Epigenetic Modification in Recipient Cells," *Science*, 328:872-875 (2010).
Moriyama et al., "Double-stranded RNA in rice: a novel RNA replicon in plants," *Molecular & General Genetics*, 248(3):364-369 (1995).
Moriyama et al., "Stringently and developmentally regulated levels of a cytoplasmic double-stranded RNA and its high-efficiency transmission via egg and pollen in rice," *Plant Molecular Biology*, 31:713-719 (1996).
Morrissey et al., "Potent and persistent in vivo anti-HBV activity of chemically modified siRNAs," *Nat Biotechnol.* 23(8):1002-1007 (2005).
Moser et al., "Sequence-Specific Cleavage of Double Helical DNA by Triple Helix Formation," *Science*, 238:645-646 (1987).
Non-Final Office Action dated Apr. 11, 2013, in U.S. Appl. No. 13/042,856.
Non-Final Office Action dated Aug. 12, 2015, in U.S. Appl. No. 13/612,936.
Non-Final Office Action dated Aug. 13, 2015, in U.S. Appl. No. 13/612,929.
Non-Final Office Action dated Jul. 23, 2015, in U.S. Appl. No. 14/335,135.
Non-Final Office Action dated Jul. 30, 2014, in U.S. Appl. No. 13/042,856.
Non-Final Office Action dated Jun. 5, 2015, in U.S. Appl. No. 13/612,948.
Non-Final Office Action dated Jun. 8, 2015, in U.S. Appl. No. 13/612,941.
Non-Final Office Action dated Mar. 30, 2015, in U.S. Appl. No. 13/583,302.
Non-Final Office Action dated May 15, 2015, in U.S. Appl. No. 14/608,951.
Non-Final Office Action dated May 22, 2015, in U.S. Appl. No. 13/612,985.
Nord-Larsen et al., "Cloning, characterization and expression analysis of tonoplast intrinsic proteins and glutamine synthetase in ryegrass (*Lolium perenne* L.)," *Plant Cell Reports*, 28(10):1549-1562 (2009).
Notice of Allowance dated Oct. 5, 2015, in U.S. Appl. No. 13/583,302.
Nowak et al., "A new and efficient method for inhibition of RNA viruses by DNA interference," *The FEBS Journal*, 276:4372-4380 (2009).

(56) References Cited

OTHER PUBLICATIONS

Office Action dated Feb. 17, 2014, in Mexican Patent Application No. MX/a/2012/010479.
Office Action dated Jul. 23, 2015, in Ukrainian Patent Application No. 201211548.
Office Action dated Nov. 3, 2014, in Chinese Patent Application No. 201180012795.2.
Office Action dated Jan. 6, 2015, in Japanese Patent Application No. 2012-557165.
Office Action dated Nov. 19, 2014, in Eurasian Patent Application No. 201201264/28.
Office Action dated Oct. 5, 2015, in Eurasian Patent Application No. 201201264/28.
Office Action dated Sep. 9, 2015, in Chinese Patent Application No. 201280055409.2.
Ongvarrasopone et al., "A Simple and Cost Effective Method to Generate dsRNA for RNAi Studies in Invertebrates," *Science Asia*, 33:35-39 (2007).
Orbović et al., "Foliar-Applied Surfactants and Urea Temporarily Reduce Carbon Assimilation of Grapefruit Leaves," *J. Amer. Soc. Hort. Sci.*, 126(4):486-490 (2001).
Ouellet et al., "Members of the Acetohydroxyacid Synthase Muligene Family of *Brassica napus* Have Divergent Patterns of Expression," *The Plant Journal*, Blackwell Scientific Publications, Oxford, GB, 2(3):321-330 (1992).
Paddison et al., "Stable suppression of gene expression by RNAi in mammalian cells," *Proc. Natl Acad. Sci. USA*, 99(3):1443-1448 (2002).
Palauqui et al., "Activation of systemic acquired silencing by localised introduction of DNA," *Current Biology*, 9:59-66 (1999).
Parera et al., "Dehydration Rate after Solid Matrix Priming Alters Seed Performance of Shrunken-2 Corn," *J. Amer. Soc. Hort. Sci.*, 119(3):629-635 (1994).
Partial Supplementary European Search Report dated Mar. 2, 2015, in European Patent Application No. 12 831 494.5.
Paungfoo-Lonhienne et al., "DNA is Taken up by Root Hairs and Pollen, and Stimulates Root and Pollen Tube Growth," *Plant Physiology*, 153:799-805 (2010).
Paungfoo-Lonhienne et al., "DNA uptake by *Arabidopsis* induces changes in the expression of CLE peptides which control root morphology," *Plant Signaling & Behavior*, 5(9):1112-1114 (2010).
Pei et al., "On the art of identifying effective and specific siRNAs," *Nature Methods*, 3(9):670-676 (2006).
Peretz et al., "A Universal Expression/Silencing Vector in Plants," *Plant Physiology*, 145:1251-1263 (2007).
Pornprom et al., "Glutamine synthetase mutation conferring target-site-based resistance to glufosinate in soybean cell selections," *Pest Manag Sci*, 2009; 65(2):216-222 (2009).
Pratt et al., "*Amaranthus rudis* and *A. tuberculatus*, One Species or Two?," *Journal of the Torrey Botanical Society*, 128(3):282-296 (2001).
Preston et al., "Multiple effects of a naturally occurring proline to threonine substitution within acetolactate synthase in two herbicide-resistant populations of *Lactuca serriola*," *Pesticide Biochem. Physiol.*, 84(3):227-235 (2006).
Qiwei,"Advance in DNA interference," *Progress in Veterinary Medicine*, 30(1):71-75 (2009).
Rajur et al., "Covalent Protein—Oligonucleotide Conjugates for Efficient Delivery of Antisense Molecules," *Bioconjug Chem.*, 8:935-940 (1997).
Reddy et al "Organosilicone Adjuvants Increased the Efficacy of Glyphosate for Control of Weeds in Citrus (*Citrus* spp.)" *HortScience* 27(9):1003-1005 (1992).
Reddy et al., "Aminomethylphosphonic Acid Accumulation in Plant Species Treated with Glyphosate," *J. Agric. Food Chem.*, 56(6):2125-2130 (2008).
Reither et al., "Specificity of DNA triple helix formation analyzed by a FRET assay," *BMC Biochemistry*, 3:27 (2002).
Restriction Requirement dated Apr. 21, 2015, in U.S. Appl. No. 13/612,954.
Restriction Requirement dated Feb. 12, 2015, in U.S. Appl. No. 13/612,985.
Restriction Requirement dated Mar. 12, 2015, in U.S. Appl. No. 13/612,948.
Restriction Requirement dated Mar. 4, 2015, in U.S. Appl. No. 13/612,941.
Restriction Requirement dated May 4, 2015, in U.S. Appl. No. 13/612,929.
Restriction Requirement dated May 5, 2015, in U.S. Appl. No. 13/612,936.
Restriction Requirement dated May 7, 2015, in U.S. Appl. No. 13/612,925.
Restriction Requirement dated May 7, 2015, in U.S. Appl. No. 13/612,995.
Restriction Requirement dated Oct. 2, 2012, in U.S. Appl. No. 13/042,856.
Restriction Requirement dated Oct. 21, 2014, in U.S. Appl. No. 13/583,302.
Rey et al., "Diversity of Dicotyledenous-Infecting Geminiviruses and Their Associated DNA Molecules in Southern Africa, Including the South-West Indian Ocean Islands," *Viruses*, 4:1753-1791 (2012).
Reynolds et al., "Rational siRNA design for RNA interference," *Nature Biotechnology*, 22:326-330 (2004).
Riggins et al., "Characterization of de novo transcriptome for waterhemp (*Amaranthus tuberculatus*) using GS-FLX 454 pyrosequencing and its application for studies of herbicide target-site genes," *Pest Manag. Sci.*, 66:1042-1052 (2010).
Rose et al., "Functional polarity is introduced by Dicer processing of short substrate RNAs," *Nucleic Acids Research*, 33(13):4140-4156 (2005).
Rothnie et al., Pararetroviruses and Retroviruses: A Comparative Review of Viral Structure and Gene Expression Strategies, *Advances in Virus Research*, 44:1-67 (1994).
Ryabov et al., "Cell-to-Cell, but Not Long-Distance, Spread of RNA Silencing That Is Induced in Individual Epidermal Cells," *Journal of Virology*, 78(6):3149-3154 (2004).
Ryan, "Human endogenous retroviruses in health and disease: a symbiotic perspective," *Journal of the Royal Society of Medicine*, 97:560-565 (2004).
Santoro et al., "A general purpose RNA-cleaving DNA enzyme," *Proc. Natl. Acad. Sci. USA*, 94:4262-4266 (1997).
Sathasivan et al., "Nucleotide sequence of a mutant acetolactate synthase gene from an imidazolinone-resistant *Arabidopsis thaliana* var. Columbia," *Nucleic Acids Research*, 18(8):2188-2193 (1990).
Schwab et al., "RNA silencing amplification in plants: Size matters," *PNAS*, 107(34):14945-14946 (2010).
Schweizer et al., "Double-stranded RNA interferes with gene function at the single-cell level in cereals," *The Plant Journal*, 24(6):895-903 (2000).
Schwember et al., "Drying Rates following Priming Affect Temperature Sensitivity of Germination and Longevity of Lettuce Seeds," *HortScience*, 40(3):778-781 (2005).
Second Chinese Office Action issued in Chinese Patent Application No. 201180012795.2, dated Jun. 10, 2014.
Seidman et al., "The potential for gene repair via triple helix formation," *J Clin Invest.*, 112(4):487-494 (2003).
Selvarani et al., "Evaluation of seed priming methods to improve seed vigour of onion (*Allium cepa* cv. *Aggregatum*) and carrot (*Daucus carota*)," *Journal of Agricultural Technology*, 7(3):857-867 (2011).
Senthil-Kumar et al., "A systematic study to determine the extent of gene silencing in Nicotiana benthamiana and other Solanaceae species when heterologous gene sequences are used for virus-induced gene silencing," *New Phytologist*, 176:782-791 (2007).
Sharma et al., "A simple and efficient *Agrobacterium*-mediated procedure for transformation of tomato," *J. Biosci.*, 34(3):423 433 (2009).
Sijen et al., "On the Role of RNA Amplification in dsRNA-Triggered Gene Silencing," *Cell*, 107:465-476 (2001).
Silwet L-77 Spray Adjuvant for agricultural applications, product description from Momentive Performance Materials, Inc. (2003).

(56) References Cited

OTHER PUBLICATIONS

Singh et al., "Absorption and translocation of glyphosate with conventional and organosilicone adjuvants," *Weed Biology and Management*, 8:104-111 (2008).
Snead et al., "Molecular basis for improved gene silencing by Dicer substrate interfering RNA compared with other siRNA variants," *Nucleic Acids Research*, 41(12):6209-6221 (2013).
Steeves et al., "Transgenic soybeans expressing siRNAs specific to a major sperm protein gene suppress *Heterodera glycines* reproduction," *Funct. Plant Biol.*, 33:991-999 (2006).
Stevens et al., "New Formulation Technology—Silwet® Organosilicone Surfactants Have Physical and Physiological Properties Which Enhance the Performance of Sprays," *Proceedings of the 9th Australian Weeds Conference*, pp. 327-331 (1990).
Stock et al., "Possible Mechanisms for Surfactant-Induced Foliar Uptake of Agrochemicals," *Pestic. Sci.*, 38:165-177 (1993).
Strat et al., "Specific and nontoxic silencing in mammalian cells with expressed long dsRNAs," *Nucleic Acids Research*, 34(13):3803-3810 (2006).
Street, "Why is DNA (and not RNA) a stable storage form for genetic information?," *Biochemistry Revisited*, pp. 1-4 (2008).
Sudarsan et al., "Metabolite-binding RNA domains are present in the genes of eukaryotes," *RNA*, 9:644-647 (2003).
Sun et al., "A Highly efficient Transformation Protocol for Micro-Tom, a Model Cultivar for Tomato Functional Genomics," *Plant Cell Physiol.*, 47(3):426-431 (2006).
Sun et al., "Sweet delivery—sugar translocators as ports of entry for antisense oligodeoxynucleotides in plant cells," *The Plant Journal*, 52:1192-1198 (2007).
Sutton et al., "Activity of mesotrione on resistant weeds in maize," *Pest Manag. Sci.*, 58:981-984 (2002).
Takasaki et al., "An Effective Method for Selecting siRNA Target Sequences in Mammalian Cells," *Cell Cycle*, 3:790-795 (2004).
Tank Mixing Chemicals Applied to Peanut Crops: Are the Chemicals Compatible?, College of Agriculture & Life Sciences, NC State University, AGW-653, pp. 1-11 (2004).
Taylor, "Seed Storage, Germination and Quality," *The Physiology of Vegetable Crops*, pp. 1-36 (1997).
Temple et al., "Can glutamine synthetase activity levels be modulated in transgenic plants by the use of recombinant DNA technology?" *Transgenic Plants and Plant Biochemistry*, 22(4):915-920 (1994).
Temple et al., "Down-regulation of specific members of the glutamine synthetase gene family in Alfalfa by antisense RNA technology," *Plant Molecular Biology*, 37:535-547 (1998).
Templeton et al., "Improved DNA: liposome complexes for increased systemic delivery and gene expression," *Nature Biotechnology*, 15:647-652 (1997).
Tenllado et al., "Crude extracts of bacterially expressed dsRNA can be used to protect plants against virus infection," *BMC Biotechnology*, 3(3):1-11 (2003).
Tenllado et al., "RNA interference as a new biotechnological tool for the control of virus diseases in plants," *Virus Research*, 102:85-96 (2004).
Tepfer, "Risk assessment of virus resistant transgenic plants," *Annual Review of Phytopathology*, 40:467-491 (2002).
The Seed Biology Place, Website Gerhard Leubner Lab Royal Holloway, University of London, <http://www.seedbiology.de/seedtechnology.asp.
Third Party Submission filed on Nov. 29, 2012 in U.S. Appl. No. 13/042,856.
Thompson, et al., "CLUSTAL W: improving the sensitivity of progressive multiple sequence alignment through sequence weighting, position-specific gap penalties and weight matrix choice," *Nucl. Acids Res.*, 22(22):4673-4680 (1994).
Timmons et al., "Specific interference by ingested dsRNA," *Nature*, 395:854 (1998).
Tomari et al., "Perspective: machines for RNAi," *Genes & Dev.*, 19:517-529 (2005).
Töpfer et al., "Uptake and Transient Expression of Chimeric Genes in Seed-Derived Embryos," *Plant Cell*, 1:133-139 (1989).
Toriyama et al., "Transgenic Rice Plants After Direct Gene Transfer Into Protoplasts," *Bio/Technology*, 6:1072-1074 (1988).
Tran et al., "Control of specific gene expression in mammalian cells by co-expression of long complementary RNAs," *FEBS Lett.*;573(1-3):127-134 (2004).
Tranel et al., "Resistance of weeds to ALS-inhibiting herbicides: what have we learned?," *Weed Science*, 50:700-712 (2002).
Tsugawa et al., "Efficient transformation of rice protoplasts mediated by a synthetic polycationic amino polymer," *Theor Appl Genet*, 97:1019-1026 (1998).
Turina et al., "Tospoviruses in the Mediterranean Area," *Advances in Virus Research*, 84:403-437 (2012).
Tuschl, "Expanding small RNA interference," *Nature Biotechnol.*, 20: 446-448 (2002).
Tuschl, "RNA Interference and Small Interfering RNAs," *ChemBiochem*. 2(4):239-245 (2001).
Ui-Tei et al., "Guidelines for the selection of highly effective siRNA sequences for mammalian and chick RNA interference," *Nucleic Acids Res.*, 32(3): 936-948 (2004).
Unnamalai et al., "Cationic oligopeptide-mediated delivery of dsRNA for post-transcriptional gene silencing in plant cells," *FEBS Letters*, 566:307-310 (2004).
Unniraman et al., "Alternate Paradigm for Intrinsic Transcription Termination in Eubacteria," *The Journal of Biological Chemistry*, 276(45)(9):41850-41855 (2001).
Urayama et al., "Knock-down of OsDCL2 in Rice Negatively Affects Maintenance of the Endogenous dsRNA Virus, *Oryza sativa* Endornavirus," *Plant and Cell Physiology*, 51(1):58-67 (2010).
Van de Wetering et al., "Specific inhibition of gene expression using a stably integrated, inducible small-interfering-RNA vector," *EMBO Rep.*, 4(6):609-615 (2003).
Vasil et al., "Herbicide Resistant Fertile Transgenic Wheat Plants Obtained by Microprojectile Bombardment of Regenerable Embryogenic Callus," *Bio/Technology*,10:667-674 (1992).
Vaucheret, "Post-transcriptional small RNA pathways in plants: mechanisms and regulations," *Genes Dev.*, 20:759-771 (2006).
Vencill et al., "Resistance of Weeds to Herbicides," *Herbicides and Environment*, 29:585-594 (2011).
Verma et al., "Modified oligonucleotides: synthesis and strategy for users," *Annu. Rev. Biochem.*, 67:99-134 (1998).
Vermeulen et al., "The contributions of dsRNA structure to Dicer specificity and efficiency," *RNA*, 11(5):674-682 (2005).
Vert et al., "An accurate and interpretable model for siRNA efficacy prediction," *BMC Bioinformatics*, 7:520 (2006).
Voinnet et al., "Systemic Spread of Sequence-Specific Transgene RNA Degradation in Plants Is Initiated by Localized Introduction of Ectopic Promoterless DNA," *Cell*, 95:177-187 (1998).
Wakelin et al., "A target-site mutation is present in a glyphosate-resistant *Lolium rigidum* population," *Weed Res.* (*Oxford*), 46(5):432-440 (2006).
Walton et al., "Prediction of antisense oligonucleotide binding affinity to a structured RNA target," *Biotechnol Bioeng* 65(1):1-9 (1999).
Wan et al., "Generation of Large Numbers of Independently Transformed Fertile Barley Plants," *Plant Physiol.*, 104:37-48 (1994).
Wang et al., "Foliar uptake of pesticides-Present status and future challenge," ScienceDirect, 87:1-8 (2007).
Wardell, "Floral Induction of Vegetative Plants Supplied a Purified Fraction of Deoxyribonucleic Acid from Stems of Flowering Plants," *Plant Physiol*, 60:885-891 (1977).
Wardell,"Floral Activity in Solutions of Deoxyribonucleic Acid Extracted from Tobacco Stems," *Plant Physiol*, 57:855-861 (1976).
Waterhouse et al., "Virus resistance and gene silencing in plants can be induced by simultaneous expression of sense and antisense RNA," *Proc Natl Acad Sci USA*, 95 13959-13964 (1998).
Welch et al., "Expression of ribozymes in gene transfer systems to modulate target RNA levels," *Curr Opin Biotechnol.* 9(5):486-496 (1998).
Wilson, et al., "Transcription termination at intrinsic terminators: The role of the RNA hairpin," *Proc. Natl. Acad. Sci. USA*, 92:8793-8797 (1995).

(56) References Cited

OTHER PUBLICATIONS

Winkler et al., "Thiamine derivatives bind messenger RNAs directly to regulate bacterial gene expression," *Nature*, 419:952-956 (2002).
Written Opinion dated May 8, 2014, in International Application No. PCT/IL2013/050447.
Written Opinion dated Sep. 1, 2014, in Singapore Patent Application No. 201206152-9.
Xu et al., Characterization and Functional Analysis of the Calmodulin-Binding Domain of Rac1 GTPase, *Plos One*, 7(8)1-12:e42975 (2012).
Yin et al., "Production of double-stranded RNA for interference with TMV infection utilizing a bacterial prokaryotic expression system," *Appl. Microbiol. Biotechnol.*, 84(2):323-333 (2009).
YouTube video by General Electric Company "Silwet Surfactants," screen shot taken on Jan. 11, 2012 of video of www.youtube.com/watch?v=WBw7nXMqHk8 (uploaded Jul. 13, 2009).
Zagnitko, "Lolium regidum clone LS1 acetyl-CoA carboxylase mRNA, partial cds; nuclear gene for plastid product," GenBank: AF359516.1, 2 pages (2001).
Zagnitko, et al., "An isoleucine/leucine residue in the carboxyltransferase domain of acetyl-CoA carboxylase is critical for interaction with aryloxyphenoxypropionate and cyclohexanedione inhibitors," *PNAS*, 98(12):6617-6622 (2001).
Zhang et al., "A novel rice gene, NRR responds to macronutrient deficiency and regulates root growth," *Mol Plant*, 5(1):63-72 (2012).
Zhang et al., "*Agrobacterium*-mediated transformation of *Arabidopsis thaliana* using the floral dip method," *Nature Protocols*, 1(2):1-6 (2006).
Zhang et al., "Cationic lipids and polymers mediated vectors for delivery of siRNA," *Journal of Controlled Release*, 123:1-10 (2007).
Zhang et al., "DEG: a database of essential genes," *Nucleic Acids Res.*, 32:D271-D272 (2004).
Zhang et al., "Transgenic rice plants produced by electroporation-mediated plasmid uptake into protoplasts," *The Plant Cell Rep.*, 7:379-384 (1988).
Zhao et al.,"*Phyllotreta striolata* (Coleoptera: Chrysomelidae):Arginine kinase cloning and RNAi-based pest control," *European Journal of Entomology*, 105(5):815-822 (2008).
Zhu et al., "Ingested RNA interference for managing the populations of the Colorado potato beetle, *Leptinotarsa decemlineata*," *Pest Manag Sci*, 67:175-182 (2010).
Communication pursuant to Article 94(3) EPC dated Mar. 24, 2016, in European Patent Application No. 12 831 684.1.
Communication pursuant to Article 94(3) EPC dated Mar. 4, 2016, in European Patent Application No. 12 830 932.5.
Communication pursuant to Article 94(3) EPC dated Mar. 9, 2016, in European Patent Application No. 12 831 166.9.
Communication pursuant to Article 94(3) EPC dated Mar. 18, 2016, in European Patent Application No. 12 832 160.1.
Communication pursuant to Article 94(3) EPC dated Jan. 14, 2016, in European Patent Application No. 12 832 415.9.
Extended European Search Report dated Jan. 20, 2016, in European Patent Application No. 13 794 339.5.
Extended European Search Report dated Oct. 8, 2013, in European Patent Application No. 11753916.3.
First Office Action dated Feb. 2, 2016, in Chinese Patent Application No. 201380039346.6.
Fukunaga et al., "dsRNA with 5' overhangs contributes to endogenous and antiviral RNA silencing pathways in plants," *The EMBO Journal*, 28(5):545-555 (2009).
GenBank Accession No. GU120406, "Chrysomela tremulae ribosomal protein L7 (RpL7) mRNA, complete cds" (2009).
GenBank Accession No. Q4GXM3_BIPLU, "Ribosomal protein L7e" (2006).
GenBank Accession No. FE348695, "CBIB7954.fwd CBIB_Daphnia_pulex_Chosen_One_Library_2 Daphnia pulex cDNA clone CBIB7954 5', mRNA sequence" (2011).
GenBank Accession No. HD315444, "Sequence 192160 from Patent EP2213738" (2010).
GenBank Accession No. EW765249, "ST020010B10C12 Normalized and subtracted western corn rootworm female head cDNA library Diabrotica virgifera virgifera cDNA clone STO20010B10C12 5-, mRNA sequence," (2007).
GenBank Accession No. EW771198, "ST020010B10C12 Normalized and subtracted western corn rootworm female head cDNA library Diabrotica virgifera virgifera cDNA clone ST020010B10C12 5-, mRNA sequence," (2007).
GenBank Accession No. CB377464, "CmaE1_37_J02_T3 Cowpea weevil larvae Lambda Zap Express Library Callosobruchus maculatus cDNA, mRNA sequence," (2007).
GenBank Accession No. Y08611.1, "P.sativum mRNA for dihydropterin pyrophosphokinase/dihydropteroate synthase " (2006).
Gudkov, "Minireview: The L7/L12 ribosomal domain of the ribosome: structural and functional studies," *FEBS Letters*, 407:253-256 (1997).
Heffer et al., "Rapid isolation of gene homologs across taxa: Efficient identification and isolation of gene orthologs from non-model organism genomes, a technical report," *EvoDevo Journal*, 2(7):1-5 (2011).
International Search Report and Written Opinion dated Nov. 27, 2015, in International Application No. PCT/US2015/037015.
International Search Report and Written Opinion dated May 26, 2016, in International Application No. PCT/US2016/014344.
Knudsen, "Promoter2.0: for the recognition of PolI promoter sequences," *Bioniformatics*, 15(5):356-361 (1999).
Migge et al., "Greenhouse-grown conditionally lethal tobacco plants obtained by expression of plastidic glutamine synthetase antisense RNA may contribute to biological safety," *Plant Science* 153:107-112 (2000).
Office Action dated Aug. 28, 2013, in Chinese Patent Application No. 201180012795.2.
Office Action dated Feb. 24, 2014, in Eurasian Patent Application No. 201201264.
Office Action dated Apr. 13, 2016, in Chinese Patent Application No. 201280053985.3.
Patent Examination Report No. 1 dated Feb. 8, 2016, in Australian Patent Application No. 2014262189.
Patent Examination Report No. 1 dated Nov. 11, 2013, in Australian Patent Application No. 2011224570.
Promoter Prediction for SEQ ID No. 1702 from 13/612929/MK/, Promoter 2.0 Prediction Results, pp. 1-4 (2016).
Salanenka et al.,"Seedcoat Permeability: Uptake and Post-germination Transport of Applied Model Tracer Compounds," *HortScience*, 46(4):622-626 (2011).
Scott et al., Botanical Insecticides for Controlling Agricultural Pests: Piperamides and the Colorado Potato Beetle *Leptinotarsa decemlineata* Say (Coleoptera: Chrysomelidae), *Archives of Insect Biochemistry and Physiology*, 54:212-225 (2003).
Second Office Action dated Mar. 4, 2016, in Chinese Patent Application No. 201280054820.8.
Second Office Action dated Feb. 25, 2016, in Chinese Patent Application No. 201280054179.8.
Shintani et al., "Antisense Expression and Overexpression of Biotin Carboxylase in Tobacco Leaves," *Plant Physiol.*, 114:881-886 (1997).
Written Opinion dated Apr. 7, 2016, in Singapore Patent Application No. 201206152-9.
Bachman et al., "Characterization of the spectrum of insecticidal activity of a double-stranded RNA with targeted activity against Western Corn Rootworm (*Diabrotica virgifera virgifera* LeConte)," Transgenic Res., pp. 1-16 (2013).
Colliver et al., "Differential modification of flavonoid and isoflavonoid biosynthesis with an antisense chalcone synthase construct in transgenic Lotus corniculatus," Plant Molecular Biology, 35:509-522 (1997).
Communication pursuant to Article 94(3) EPC dated Jun. 26, 2015, in European Patent Application No. 11 753 916.3.
Communication pursuant to Article 94(3) EPC dated Oct. 23, 2015, in European Patent Application No. 12 831 945.6.
Concise Descriptions of Relevance filed by a third party on Nov. 29, 2012, in U.S. Appl. No. 13/042,856.

(56) References Cited

OTHER PUBLICATIONS

Dalakouras et al., "Induction of Silencing in Plants by High-Pressure Spraying of In vitro-Synthesized Small RNAs," Frontiers in Plant Science, 7(1327):1-5 (2016).
Dawson et al., "cDNA cloning of the complete genome of tobacco mosaic virus and production of infectious transcripts," Proc. Natl. Acad. Sci. USA, 83:1832-1836 (1986).
Extended European Search Report dated Sep. 29, 2016, in European Patent Application No. 14778840.0.
Final Office Action dated Apr. 7, 2016, in U.S. Appl. No. 13/619,980.
Final Office Action dated Dec. 17, 2015, in U.S. Appl. No. 14/335,135.
Final Office Action dated Feb. 17, 2016, in U.S. Appl. No. 13/612,929.
Final Office Action dated Feb. 4, 2016, in U.S. Appl. No. 13/612,936.
Final Office Action dated Jun. 30, 2016, in U.S. Appl. No. 13/901,326.
Final Office Action dated Mar. 2, 2016, in U.S. Appl. No. 13/612,995.
Final Office Action dated Mar. 21, 2016, in U.S. Appl. No. 13/612,925.
Final Office Action dated May 26, 2016, in U.S. Appl. No. 14/532,596.
Final Office Action dated Sep. 9, 2016, in U.S. Appl. No. 13/612,954.
Final Office Action dated Nov. 19, 2015, in U.S. Appl. No. 13/612,941.
Final Office Action dated Nov. 10, 2016, in U.S. Appl. No. 13/583,302.
Final Office Action dated Sep. 9, 2016, in U.S. Appl. No. 14/608,951.
Final Office Action dated Sep. 9, 2016, in U.S. Appl. No. 14/603,347.
Final Office Action dated Oct. 20, 2016, in U.S. Appl. No. 14/480,199.
Final Office Action dated Oct. 22, 2015, in U.S. Appl. No. 14/608,951.
Fraley et al., "Liposome-mediated delivery of tobacco mosaic virus RNA into tobacco protoplasts: A sensitive assay for monitoring liposome-protoplast interactions," Proc Natl Acad Sci U S A., 79(6):1859-1863 (1982).
Fukunaga et al., "dsRNA with 5' overhangs v contributes to endogenous and antiviral RNA silencing pathways in plants," The EMBO Journal, 28(5):545-555 (2009).
Further Examination Report dated May 16, 2014, in New Zealand Patent Application No. 601784.
Gan et al., "Inhibition of Leaf Senescence by Autoregulated Production of Cytokinin," Science, 270:1986-1988 (1995).
Gao et al., "Nonviral Methods for siRNA Delivery," Molecular Pharmaceutics, 6(3):651-658 (2008).
GenBank Accession No. AY545657.1 (2004).
GenBank Accession No. DY640489, "PU2_plate27_F03 PU2 Prunus persica cDNA similar to expressed mRNA inferred from Prunus persica hypothetical domain/motif cont aining IPR011005:Dihydropteroate synthase-like, MRNA sequence" (2006).
GenBank Accession No. EU024568, "Amaranthus hypochondriacus acetolactate synthase (ALS) gene" (2007).
GenBank Accession No. FJ972198, "Solanum lycopersicum cultivar Ailsa Craig dihydropterin pyrophosphokinase-dihydropteroate synthase (HPPK-DHPS) gene, complete cds" (2010).
GenBank Accession No. GI:186478573 (2014).
GenBank Accession No. U87257.1, "Daucus carota 4-hydroxyphenylpyruvate dioxygenase mRNA, complete cds" (1997).
GenBank Accession No. XM_ 014456745.1, PREDICTED: Myotis lucifugus ribonucleoprotein, PTB-binding 2 (RAVER2), transcript variant X3, mRNA,: (2015).
GenEmbl Accession No. FJ861243 (2010).
Hajirezaei et al., "Impact of elevated cytosolic and apoplastic invertase activity on carbon metabolism during potato tuber development," Journal of Experimental Botany, 51:439-445 (2000).
Holtra et al., "Assessment of the Physiological Condition of Salvinia Natans L. Exposed to Copper(II) Ions," Environ. Protect. Eng., 41:147-158 (2015).
International Preliminary Report on Patentability dated Sep. 11, 2012, in International Application No. PCT/US2011/027528.
International Rice Genome Sequencing Project, The map-based sequence of the rice genome, Nature, 436(11):793-800 (2005).
International Search Report and the Written Opinion dated Feb. 25, 2013, in International Application No. PCT/US2012/054883.
International Search Report and the Written Opinion dated Feb. 27, 2013, in International Application No. PCT/US2012/054814.
International Search Report and the Written Opinion dated Feb. 27, 2013, in International Application No. PCT/US2012/054842.
International Search Report and the Written Opinion dated Feb. 27, 2013, in International Application No. PCT/US2012/054862.
International Search Report and the Written Opinion dated Feb. 27, 2013, in International Application No. PCT/US2012/054894.
International Search Report and the Written Opinion dated Feb. 27, 2013, in International Application No. PCT/US2012/054974.
International Search Report and the Written Opinion dated Feb. 27, 2013, in International Application No. PCT/US2012/054980.
International Search Report and the Written Opinion dated May 10, 2011, in International Application No. PCT/US2011/027528.
Jin et al., "Posttranslational Elevation of Cell Wall Invertase Activity by Silencing its Inhibitor in Tomato Delays Leaf Senescence and Increases Seed Weight and Fruit Hexose Level," The Plant Cell, 21:2072-2089 (2009).
Kaloumenos et al., "Identification of a Johnsongrass (*Sorghum halepense*) Biotype Resistant to ACCase-Inhibiting Herbicides in Northern Greece," Weed Technol, 23:470-476 (2009).
Kambiranda et al., "Relationship Between Acid Invertase Activity and Sugar Content in Grape Species," Journal of Food Biochemistry, 35:1646-1652 (2011).
Kim et al., "Optimization of Conditions for Transient Agrobacterium-Mediated Gene Expression Assays in *Arabidopsis*," Plant Cell Reports, 28:1159-1167 (2009).
Kirkwood, "Herbicides and Plants," Botanical Journal of Scotland, 46(3):447-462 (1993).
Liu, "Influence of Sugars on the Foliar Uptake of Bentazone and Glyphosate," New Zealand Plant Protection, 55:159-162 (2002).
Luque et al., "Water Permeability of Isolated Cuticular Membranes: A Structural Analysis," Archives of Biochemistry and Biophysics, 317(2):417-422 (1995).
Mora et al., "How Many Species Are There on Earth and in the Ocean?," PLOS Biol., 9(8):e100127, p. 1-8 (2011).
Mount et al., "Gene and Metabolite Regulatory Network Analysis of Early Developing Fruit Tissues Highlights New Candidate Genes for the Control of Tomato Fruit Composition and Development," Plant Physiology, 149:1505-1528 (2009).
Non-Final Office Action dated Aug. 19, 2016, in U.S. Appl. No. 13/612,925.
Non-Final Office Action dated Aug. 19, 2016, in U.S. Appl. No. 13/612,929.
Non-Final Office Action dated Apr. 29, 2016, in U.S. Appl. No. 13/583,302.
Non-Final Office Action dated Aug. 10, 2016, in U.S. Appl. No. 13/612,995.
Non-Final Office Action dated Nov. 9, 2016, in U.S. Appl. No. 14/901,003.
Non-Final Office Action dated Aug. 3, 2016, in U.S. Appl. No. 14/015,715.
Non-Final Office Action dated Aug. 5, 2016, in U.S. Appl. No. 14/015,785.
Non-Final Office Action dated Aug. 8, 2016, in U.S. Appl. No. 13/612,936.
Non-Final Office Action dated Dec. 17, 2015, in U.S. Appl. No. 14/532,596.
Non-Final Office Action dated Feb. 10, 2016, in U.S. Appl. No. 13/901,326.
Non-Final Office Action dated Feb. 23, 2016, in U.S. Appl. No. 14/603,347.
Non-Final Office Action dated Feb. 23, 2016, in U.S. Appl. No. 14/608,951.
Non-Final Office Action dated Sep. 6, 2016, in U.S. Appl. No. 14/335,135.
Non-Final Office Action dated Mar. 1, 2016, in U.S. Appl. No. 13/612,954.
Non-Final Office Action dated Oct. 3, 2016, in U.S. Appl. No. 14/403,491.
Non-Final Office Action dated Sep. 1, 2015, in U.S. Appl. No. 13/612,954.
Non-Final Office Action dated Sep. 11, 2015, in U.S. Appl. No. 13/612,925.
Non-Final Office Action dated Sep. 4, 2015, in U.S. Appl. No. 13/612,995.

(56) References Cited

OTHER PUBLICATIONS

Nookaraju et al., "Molecular approaches for enhancing sweetness in fruits and vegetables," Scientia Horticulture, 127:1-15 (2010).
Notice of Allowance dated Apr. 11, 2016, in U.S. Appl. No. 13/612,985.
Notice of Allowance dated Apr. 19, 2016, in U.S. Appl. No. 13/612,941.
Notice of Allowance dated Apr. 20, 2016, in U.S. Appl. No. 13/612,948.
Notice of Allowance dated Feb. 23, 2015, in U.S. Appl. No. 13/042,856.
Notice of Allowance dated Jun. 2, 2015, in U.S. Appl. No. 13/042,856.
Office Action dated Jul. 18, 2016, in Indonesian Patent Application No. W00201203610.
Office Action dated Sep. 5, 2016, in Ukrainian Patent Application No. a 2014 03846.
Office Action dated Aug. 25, 2016, in Eurasian Patent Application No. 201201264.
Office Action dated Jun. 20, 2016, in Chinese Patent Application No. 201280054819.5.
Office Action dated Jun. 24, 2016, in Chinese Patent Application No. 201280053984.9.
Office Action dated Nov. 15, 2016, in Mexican Patent Application. No. MX/a/2014/003068.
Office Action dated Dec. 15, 2016, in Ukrainian Patent Application No. a 2014 03845.
Office Action dated Dec. 15, 2016, in Ukrainian Patent Application No. a 2014 03852.
Office Action dated Dec. 13, 2016, in Ukrainian Patent Application No. a 2014 03843.
Office Action dated Dec. 15, 2016, in Ukrainian Patent Application No. a 2014 03849.
Office Action dated Dec. 14, 2016, in Ukrainian Patent Application No. a 2014 03850.
Office Action dated Dec. 27, 2016, in Ukrainian Patent Application No. a 2012 11548.
Office Action dated Mar. 16, 2017, in Chinese Patent Application No. 201280054819.5.
Patent Examination Report No. 1 dated Jun. 17, 2016, in Australian Patent Application No. 2012308659.
Patent Examination Report No. 1 dated Jun. 17, 2016, in Australian Patent Application No. 2012308660.
Promoter Prediction for SEQ ID No. 4 from 13/612995/MK/, Promoter 2.0 Prediction Results, pp. 1-3 (2016).
Promoter Prediction for SEQ ID No. 7 from 13/612936/MK/, Promoter 2.0 Prediction Results, pp. 1-2 (2016).
Promoter Prediction for SEQ ID No. 8 from 13/612,925/MK/, Promoter 2.0 Prediction Results, pp. 1-6 (2016).
Regalado, "The Next Great GMO Debate," MIT Technology Review, pp. 1-19 (2015).
Restriction Requirement dated Jul. 18, 2016, in U.S. Appl. No. 14/143,836.
Restriction Requirement dated Oct. 13, 2016, in U.S. Appl. No. 14/206,707.
Restriction Requirement dated Oct. 28, 2015, in U.S. Appl. No. 14/603,347.
Restriction Requirement dated Sep. 2, 2015, in U.S. Appl. No. 14/532,596.
Robson et al., "Leaf senescence is delayed in maize expressing the Agrobacterium IPT gene under the control of a novel maize senescence-enhanced promoter," Plant Biotechnology Journal, 2:101-112 (2004).
Roitsch et al., "Function and regulation of plant invertases: sweet sensations," Trades in Plant Science, 9(12):606-613 (2004).
Ruan et al., "Suppression of Sucrose Synthase Gene Expression Represses Cotton Fiber Cell Initiation, Elongation, and Seed Development," The Plant Cell, 15:952-964 (2003).
Schönherr, "Water Permeability of Isolated Cuticular Membranes: The Effect of pH and Cations on Diffusion, Hydrodynamic Permeability and Size of Polar Pores in the Cutin Matrix," Planta, 128:113-126 (1976).
Second Chinese Office Action dated Jun. 10, 2014, in Chinese Patent Application No. 201180012795.2.
Shaoquan, "The action target of herbicide and the innovation of a new variety," Chemical Industry Press, pp. 23-24 (2001).
Showalter, "Structure and Function of Plant Cell Wall Proteins," The Plant Cell, 5:9-23 (1993).
Song et al., "Herbicide," New Heterocyclic Pesticide, Chemical Industry Press, 354-356 (2011).
Stevens, "Organosilicone Surfactants as Adjuvants for Agrochemicals," Journal of Pesticide Science, 38:103-122 (1993).
Tang et al., "Efficient delivery of small interfering RNA to plant cells by a nanosecond pulsed laser-induced stress wave for post-transcriptional gene silencing," Plant Science, 171:375-381 (2006).
Tenllado et al., "Double-Stranded RNA-Mediated Interference with Plant Virus Infection," Journal of Virology, 75(24):12288-12297 (2001).
Thomas et al., "Size constraints for targeting post-transcriptional gene silencing and for RNA-directed methylation in Nicotiana bentharniana using a potato virus X vector," The Plant Journal, 25(4):417-425 (2001).
Tomlinson et al., "Evidence that the hexose-to-sucrose ratio does not control the switch to storage product accumulation in oilseeds: analysis of tobacco seed development and effects of overexpressing apoplastic invertase," Journal of Experimental Botany.
Unniraman et al., "Conserved Economics of Transcription Termination in Eubacteria," Nucleic Acids Research, 30(3):675-684 (2002).
Widholm et al., "Glyphosate selection of gene amplification in suspension cultures of 3 plant species," Phyisologia Plantarum, 112:540-545 (2001).
Wiesman et al., "Novel cationic vesicle platform derived from vernonia oil for efficient delivery of DNA through plant cuticle membranes," Journal of Biotechnology, 130:85-94 (2007).
Written Opinion dated Mar. 6, 2017, in Singaporean Patent Application No. 2012061529.
Zhang et al., "Chapter 10: New Characteristics of Pesticide Research & Development," New Progress of the world agriculture chemicals, p. 209 (2010).
Agricultural Chemical Usage 2006 Vegetables Summary, Agricultural Statistics Board, NASS, USDA, pp. 1-372 (2007).
Al-Kaff et al., "Plants rendered herbicide-susceptible by cauliflower mosaic virus—elicited suppression of a 35S promoter-regulated transgene," *Nature Biotechnology*, 18:995-999 (2000).
Andersen et al., "Delivery of siRNA from lyophilized polymeric surfaces," *Biomaterials*, 29:506-512 (2008).
Anonymous, "Resistant Weeds Spur Research Into New Technologies," Grains Research & Development Corporation, 2013.
Bachman et al., "Characterization of the spectrum of insecticidal activity of a double-stranded RNA with targeted activity against Western Corn Rootworm (*Diabrotica virgifera virgifera* LeConte)," *Transgenic Res.*, pp. 1-16 (2013) Herewith.
Balibrea et al., "Extracellular Invertase is an Essential Component of Cytokinin-Mediated Delay of Senescence," *The Plant Cell*, 16(5):1276-1287 (2004).
Bart et al., "A novel system for gene silencing using siRNAs in rice leaf and stem-derived protoplasts," *Plant Methods*, 2(13):1-9 (2006).
Basu et al., "Weed genomics: new tools to understand weed biology," *TRENDS in Plant Science*, 9(8):391-398 (2004).
Bauer et al., "The major protein import receptor of plastids is essential for chloroplast biogenesis," *Nature*, 403:203-207 (2000).
Busch et al., "RNAi for discovery of novel crop protection products," Pflanzenschutz-Nachrichten Bayer, 58(1):34-50 (2005).
Chabannes et al., "In situ analysis of lignins in transgenic tobacco reveals a differential impact of individual transformations on the spatial patterns of lignin deposition at the cellular and subcellular levels," *The Plant Journal*, 28(3):271-282 (2001).
Chang et al., "Dual-target gene silencing by using long, sythetic siRNA duplexes without triggering antiviral responses," *Molecules and Cells*, 27(6):689-695 (2009).

(56) References Cited

OTHER PUBLICATIONS

Chen et al., "Transfection and Expression of Plasmid DNA in Plant Cells by an Arginine-Rich Intracellular Delivery Peptide without Protoplast Preparation," *FEBS Letters*, 581, pp. 1891-1897 (2007).
Cheng et al., "Transient Expression of Minimum Linear Gene Cassettes in Onion Epidermal Cells Via Direct Transformation," *Appl Biochem Biotechnol*, 159:739-749 (2009).
Christiaens et al., "The challenge of RNAi-mediated control of hemipterans," *Current Opinion in Insect Science*, 6:15-21 (2014).
Database EMBL XP-002781749(BG442539) dated Mar. 20, 2001.
Egli et al., "A Maize Acetyl-Coenzyme A Carboxylase cDNA Sequence," *Plant Physiol.*, 108: 1299-1300 (1995).
Eudes et al., "Cell-penetrating peptides," *Plant Signaling & Behavior*, 3(8):549-5550 (2008).
European Search Report dated Sep. 7, 2017, in European Patent Application No. 17152830.0.
Examination Report dated Mar. 1, 2018, in Australian Patent Application No. 2013264742.
Examination Report No. 2, dated Mar. 23, 2018, in Australian Patent Application No. 2014248958.
Examination Report dated Jun. 29, 2017, in Australian Patent Application No. 2012308818.
Extended European Search Report dated Nov. 7, 2017, in European Patent Application No. 15811092.4.
Extended European Search Report dated Nov. 8, 2017, in European Patent Application No. 15737282.2.
Extended European Search Report dated Apr. 13, 2018, in European Patent Application No. 15812530.0.
Extended European Search Report dated Mar. 15, 2018, in European Patent Application No. 17181861.0.
Gallie et al., "Identification of the motifs within the tobacco mosaic virus 5'-leader responsible for enhancing translation," *Nucleic Acids Res.*, 20(17):4631-4638 (1992).
Gan et al., "Bacterially expressed dsRNA protects maize against SCMV infection," *Plant Cell Rep*, 29(11):1261-1268 (2010).
Gasser et al., "Structure, Expression, and Evolution of the 5-Enolpyruvylshikimate-3-phosphate Synthase Genes of Petunia and Tomato," *J. Biol. Chem.*, 263: 4280-4287 (1988).
Gomez-Zurita et al., "Recalibrated Tree of Leaf Beetles (Chrysomelidae) Indicates Independent Diversification of Angiosperms and Their Insect Herbivores," *PLoS One*, 4(e360):1-8 (2007).
Hoermann et al., "Tic32, as Essential Component in Chloroplast Biogenesis," *The Journal of Biological Chemistry*, 279(33):34756-34762 (2004).
Hu et al., "High efficiency transport of quantum dots into plant roots with the aid of silwet L-77," *Plant Physiology and Biochemistry*, 48:703-709 (2010).
Inaba et al., "*Arabidopsis* Tic110 Is Essential for the Assembly and Function of the Protein Import Machinery of Plastids," *The Plant Cell*, 17:1482-1496 (2005).
Jarvis et al, "An *Arabidopsis* mutant defective in the plastid general protein import apparatus," *Science*, 282:100-103 (1998).
Kovacheva et al., "Further in vivo studies on the role of the molecular chaperone, Hsp93, in plastid protein import," *The Plant Journal*, 50:364-379 (2007).
Kovacheva et al., "In vivo studies on the roles of Tic100, Tic40 and Hsp93 during chloroplast protein import," *The Plant Journal*, 41:412-428 (2005).
Li et al., "Long dsRNA but not siRNA initiates RNAi in western corn rootworm larvae and adults," *Journal of Applied Entomology*, 139(6):432-445 (2015).
Liu, "The Transformation of Nucleic Acid Degradants in Plants," China Organic Fertilizers, Agriculture Press, ISBN: 7-1091634 (with English translation).
Non-Final Office Action dated Mar. 21, 2018, in U.S. Appl. No. 13/619,980.
Office Action dated Dec. 5, 2017, in Japanese Patent Application No. 2016-502033.
Office Action dated Feb. 21, 2018, in Mexican Patent Application No. MX/a/2015/012632 (with English translation).
Office Action dated Mar. 8, 2018 (with English translation), in Chilean Patent Application No. 201403192.
Partial European Search Report dated Dec. 6, 2017, in European Patent Application No. 17181861.0.
Partial European Search Report dated Jun. 29, 2018, in European Patent Application No. 18157745.3.
Partial Supplementary European Search Report dated Jan. 11, 2018, in European Patent Application No. 15812530.0.
Qichuan et al., Seed Science, China Agriculture Press, pp. 101-103, Tables 2-37 (2001).
Regalado, The Next Great GMO Debate, MIT Technology Review, pp. 1-19 (2015) <https://www.technologyreview.com/s/540136/the-next-great-gmo-debate/>.
Roberts, "Fast-track applications: The potential for direct delivery of proteins and nucleic acids to plant cells for the discovery of gene function," *Plant Methods*, 1(12):1-3 (2005).
Roitsch et al., "Extracellular invertase: key metabolic enzyme and PR protein," *Journal of Experimental Botany*, 54(382):513-524 (2003).
Search Report dated Oct. 20, 2017, in Chinese Patent Application No. 201380039346.6.
Stevens, "Organosilicone Surfactants as Adjuvants for Agrochemicals," *New Zealand Journal of Forestry Science*, 24:27-34 (1994).
Summons to Attend Oral Proceedings Pursuant to Rule 115(1) EPC, dated Aug. 7, 2017, in European Patent Application No. 12832160.1.
Sun et al.,"Antisense oligodeoxynucleotide inhibition as a potentstrategy in plant biology: identification of SUSIBA2 as atranscriptional activator in plant sugar signalling," *The Plant Journal*, 44:128-138 (2005).
Sun, "Characterization of Organosilicone Surfactants and Their Effects on Sulfonylurea Herbicide Activity," Thesis Submitted to the Faculty of the Virginia Polytechnic Institute and State University dated Apr. 5, 1996.
Teng et al., "Tic21 Is an Essential Translocon Component for Protein Translocation across the Chloroplast Inner Envelope Membrane," *The Plant Cell*, 18:2247-2257 (2006).
Ulrich et al., "Large scale RNAi screen in Tribolium reveals novel target genes for pest control and the proteasome as prime target," *BMC genomics*, 16(1):671 (2015).
Wild Carrot, Noxious Weed Control Board (NWCB) of Washington State (2010).
Zaimin et al., Chapter III Seeds and Seedlings, Botany, Northwest A&F University Press, pp. 87-92 (2009).
Zhang et al., "Development and Validation of Endogenous Reference Genes for Expression Profiling of Medaka (*Oryzias latipes*) Exposed to Endocrine Disrupting Chemicals by Quantitative Real-Time RT-PCR," *Toxicological Sciences*, 95(2):356-368 (2007).
Zhang, Chapter 10: New Characteristics of Pesticide Research & Development, p. 209 (2010).
Zhong et al., "A pea antisense gene for the chloroplast stromal processing peptidase yields seedling lethals in *Arabidopsis*: survivors show defective GFP import in vivo," *The Plant Journal*, 34:802-812 (2003).
Zotti et al., "RNAi technology for insect management and protection of beneficial insects from diseases: lessons, challenges and risk assessments," *Neotropical Entomology*, 44(3):197-213 (2015).
Wang et al., "Principle and technology of genetic engineering in plants," in Plant genetic engineering principles and techniques, Beijing: Science Press, pp. 313-315 (1998).
Asad et al., "Silicon Carbide Whisker-mediated Plant Transformation," Properties and Applicants of Silicon Carbide, pp. 345-358 (2011).
Ascencio-Ibanez et al., "DNA Abrasion onto Plants is an Effective Method for Geminivirus Infection and Virus-Induced Gene Silencing," *Journal of Virological Methods*, 142:198-203 (2007).
Baker, "Chlorophyll Fluorescence: A Probe of Photosynthesis In Vivo," *Annu. Rev. Plant Biol.*, 59:89-113 (2008).
Baum et al., "Progress Towards RNAi-Mediated Insect Pest Management" *Advances in Insect Physiology*, 47:249-295 (2014).
Bedell et al., "Sorghum Genome Sequencing by Methylation Filtration," *PLOS Biology*, 3(1):E13/104-115 (2005).

(56) References Cited

OTHER PUBLICATIONS

Belhadj et al., "Methyl Jasmonate Induces Defense Responses in Grapevine and Triggers Protection Against Erysiphe Necator," *J. Agric Food Chem.*, 54:9119-9125 (2006).
Burgos et al., "Review: Confirmation of Resistance to Herbicides and Evaluation of Resistance Levels," *Weed Science*, 61(1):4-20 (2013).
Burleigh, "Relative quantitative RT-PCR to Study the Expression of Plant Nutrient Transporters in Arbuscular Mycorrhizas," *Plant Science*, 160:899-904 (2001).
Chang et al., "Dual-Target Gene Silencing by Using Long, Synthetic siRNA duplexes without triggering antiviral responses," *Molecules and Cells*, 27(6)689-695 (2009).
Chen et al., "Exploring MicroRNA-Like Small RNAs in the Filamentous Fungus *Fusarium oxysporum*," *PLoS One*, 9(8):e104956:1-10 (2014).
Communication Pursuant to Article 94(3) EPC dated Sep. 5, 2018, in European Patent Application No. 17152830.0.
Constan et al., "An Outer Envelope Membrane Component of the Plastid Protein Import Apparatus Plays an Essential Role in *Arabidopsis*," The Plant Journal, 38:93-106 (2004).
Declaration of Jerzy Zabkiewicz executed Nov. 28, 2017, as filed by Opponent in Australian Patent Application No. 2014262189, pp. 1-73.
Declaration of Jerzy Zabkiewicz executed Nov. 28, 2017, as filed by Opponent in Australian Patent Application No. 2014262189, pp. 1-4.
Declaration of Neena Mitter executed Nov. 30, 2017, as filed by Opponent in Australian Patent Application No. 2014262189, pp. 1-114.
Declaration of Neena Mitter executed Nov. 30, 2017, as filed by Opponent in Australian Patent Application No. 2014262189, pp. 1-25.
Delye et al., "PCR-based detection of resistance to acetyl-CoA carboxylase-inhibiting herbicides in black-grass (*Alopecurus myosuroides* Huds) and ryegrass (*Lolium rigidum* Gaud)," *Pest Management Science*, 58:474-478 (2002).
Delye et al., "Variation in the Gene Encoding Acetolactate-Synthase in Lolium Aspecies and Proactive Detection of Mutant, Herbicide-Resistant Alleles," *Weed Research*, 49:326-336 (2009).
Desveaux et al., "PBF-2 Is a Novel Single-Stranded DNA Binding Factor Implicated in PR-10a Gene Activation in Potato," *The Plant Cell*, 12:1477-1489 (2000).
Di Stilio et al., "Virus-Induced Gene Silencing as a Tool for Comparative Functional Studies in Thalictrum," *PLoS One*, 5(8):e12064 (2010).
Dietzgen et al., "Transgenic Gene Silencing Strategies for Virus Control," *Australasian Plant Pathology*, 35:605-618 (2006).
Dilpreet et al., "Glyphosate Resistance in a Johnsongrass (*Sorghum halepense*) Biotype from Arkansas," *Weed Science*, 59(3):299-304 (2011).
Duhoux et al., "Reference Genes to Study Herbicide Stress Response in Lolium sp.: Up-Regulation of P3450 Genes in Plants Resistant to Acetolactate-Synthase Inhibitors," *PLoS One*, 8(5):e63576 (2013).
Eamens et al., "RNA Silencing in Plants: Yesterday, Today, and Tomorrow," *Plant Physiology*, 147(2):456-468 (2008).
Extended European Search Report dated Dec. 19, 2018, in European Patent Application No. 16804395.8.
Extended European Search Report dated Nov. 16, 2018, in European Patent Application No. 18182238.8.
Extended European Search Report dated Nov. 21, 2018, in European Patent Application No. 18175809.5.
Extended European Search Report dated Sep. 28, 2018, in European Patent Application No. 16740770.9.
Fassler, BLAST Glossary, National Center for Biotechnology Information (2011).
Fernandez et al., "Uptake of Hydrophilic Solutes Through Plant Leaves: Current State of Knowledge and Perspectives of Foliar Fertilization," *Critical Reviews in Plant Sciences*, 28:36-38 (2009).
Feuillet et al., "Crop Genome Sequencing: Lessons and Rationales," *Trends Plant Sci.*, 16:77-88 (2011).
Friedberg, "Automated Protein Function Prediction—the Genomic Challenge," *Briefings in Bioinformatics*, 7(3):225-242 (2006).
Funke et al., "Molecular Basis for herbicide Resistance in Roundup Ready Crops," *PNAS*, 103:13010-13015 (2006).
Gaskin et al., "Novel Organosillicone Adjuvants to Reduce Agrochemical spray volumes on row crops," *New Zealand Plant Protection*, 53:350-354 (2000).
GenBank Accession No. EF143582 (2007).
Gilmer et al., "Latent Viruses of Apple I. Detection with Woody Indicators," *Plant Pathology*, 1(10):1-9 (1971).
Gossamer Threads, Compendium of Herbicide Adjuvants: Organo-Silicone Surfactant, p. 1-4 (1998).
Guttieri et al., "DNA Sequence Variation in Domain A of the Acetolactate Synthase Genes of Herbicide-Resistant and -Susceptible Weed Biotypes," *Weed Science*, 40:670-679 (1992).
Hagio, "Chapter 25: Direct Gene Transfer into Plant Mature Seeds via Electroporation After Vacuum Treatment," *Electroporation and Sonoporation in Developmental Biology*, p. 285-293 (2009).
Hess, "Surfactants and Additives," 1999 Proceedings of the California *Weed Science Society*, 51:156-172 (1999).
Huang et al., "In Vivo Analyses of the Roles of Essential Omp85-Related Proteins in the Chloroplast Outer Envelope Membrane," *Plant Physiol.*, 157:147-159 (2011).
Huggett et al., "Real-time RT-PCR Normalisation; Strategies and Considerations," *Genes and Immunity*, 6:279-284 (2005).
Ivanova et al., "Members of the Toc159 Import Receptor Family Represent Distinct Pathways for Protein Targeting to Plastids," *Molecular Biology of the Cell*, 15:3379-3392 (2004).
Jacque et al., "Modulation of HIV-1 replication by RNA interference," *Nature*, 418, 435-438 (2002).
Jang et al., "Resistance to herbicides caused by Single Amino Acid Mutations in Acetyl-CoA Carboxylase in resistant Populations of Grassy Weeds," *New Phytologist*, 197(4):1110-1116 (2013).
Jiang et al., Chapter III Seeds and Seedlings, Botany, Northwest A&F University Press, pp. 87-92 (2009).
Kikkert et al., "Stable Transformation of Plant Cells by Particle Bombardment/Biolistics," *Methods in Molecular Biology*, 286:61-78 (2005).
Kim et al., "Synthesis and Characterization of Mannosylated Pegylated Polyethylenimine as a Carrier for siRNA," *International Journal of Pharmaceutics*, 427:123-133 (2012).
Kirkwood, "Recent developments in our understanding of the plant cuticle as a barrier to the foliar uptake of pesticides," *Pestic Sci*, 55:69-77 (1999).
Kumar et al., "Sequencing, De Novo Assembly and Annotation of the Colorado Potato Beetle, *Leptinotarsa decemlineata*, Transcriptome," *PLoS One*, 9(1):e86012 (2014).
Liu et al., "Identification and Application of a Rice Senescence-Associated Promoter," *Plant Physiology*, 153:1239-1249 (2010).
Liu, "Confocal laser scanning microscopy—an attractive tool for studying the uptake of xenobiotics into plant foliage," *Journal of Microscopy*, 213(Pt 2):87-93 (2004).
Liu et al., "The Helicase and RNaseIIIa Domains of *Arabidopsis* Dicer-Like1 Modulate Catalytic Parameters during MicroRNA Biogenesis," *Plant Physiology*, 159:748-758 (2012).
Liu, "Calmodulin and Cell Cycle," *Foreign Medical Sciences Section of Pathophysiology and Clinical Medicine*, 18(4):322-324 (1998).
Lodish et al., Molecular Cell Biology, Fourth Edition, p. 210 (2000).
Lucas et al., "Plasmodesmata—Bridging the Gap Between Neighboring Plant Cells," *Trends in Cell Biology*, 19:495-503 (2009).
Morozov et al., "Evaluation of Preemergence Herbicides for Control of Diclofop-Resistant Italian Ryegrass (*Lolium multiflorum*) in Virginia," Virginia Polytechnic Institute and State University, pp. 43-71 (2004).
Nemeth, "Virus, Mycoplasma and Rickettsia Diseases of Fruit Trees," Martinus Nijhoff Publishers, 197-204 (1986).
N-TER Nanoparticle siRNA, Sigma Aldrich TM website, Web. Nov. 20, 2018 <https://www.sigmaaldrich.com/life-science/custom-oligos/sirna-oligos/n-ter-nanoparticle.html>.

(56) References Cited

OTHER PUBLICATIONS

Office Action dated Aug. 1, 2017, in European Patent Application No. 12 830 932.5.
Office Action dated Aug. 14, 2017, in Israeli Patent Application No. 235878.
Office Action dated Aug. 22, 2017, in Korean Patent Application No. 10-2012-7023415.
Office Action dated Aug. 3, 2017, in Chinese Patent Application No. 201480014392.5 (with English translation).
Office Action dated Aug. 3, 2017, in European Patent Application No. 12 831 684.1.
Office Action dated Aug. 8, 2017, in Chilean Patent Application No. 201501874.
Office Action dated Aug. 9, 2018, in Canadian Patent Application No. 2,848,371.
Office Action dated Jul. 11, 2017, in Mexican Patent Application No. MX/a/2015/013118 (with English translation).
Office Action dated Jul. 3, 2017, in Mexican Patent Application No. MX/a/2015/012632 (with English translation).
Office Action dated Jul. 30, 2018, in Canadian Patent Application No. 2,848,576.
Office Action dated Jul. 6, 2017, in Mexican Patent Application No. MX/a/2015/013103 (with English translation).
Office Action dated May 3, 2016, in Chilean Patent Application No. 201601057.
Office Action dated Nov. 15, 2016, in Mexican Patent Application No. MX/a/2014/003068 (with English translation).
Office Action dated Sep. 20, 2018, in Chilean Patent Application No. 201601440 (with English translation).
Office Action dated Sep. 6, 2017, in Chinese Patent Application No. 2014800154012 (with English translation).
Patent Examination Report No. 1 dated Jun. 8, 2017, in Australian Patent Application No. 2012308686.
Powles et al., "Evolution in Action: Plants Resistant to Herbicides," *Annual Review of Plant Biology*, 61(1):317-347 (2010).
Pratt et al., "Sorghum Expressed Sequence Tags Identify Signature Genes for Drought, Pathogenesis, and Skotomorphogenesis from a Milestone Set of 16,801 Unique Transcripts," *Plant Physiology*, 139:869-884 (2005).
Rakoczy-Trojanowska, "Alternative Methods of Plant Transformation—A Short Review," *Cellular & Molecular Biology Letters*, 7:849-858 (2002).
Restriction Requirement dated Jul. 15, 2016, in U.S. Appl. No. 14/143,748.
Reverdatto et al., "A Multisubunit Acetyl Coenzyme A Carboxylase from Soybean," *Plant Physiol.*, 119: 961-978 (1999).
Richardson et al., "Targeting and assembly of components of the TOC protein import complex at the chloroplast outer envelope membrane," *Frontiers in Plant Science*, 5:1-14 (2014).
Schöinherr et al.,"Size selectivity of aqueous pores in astomatous cuticular membranes isolated from *Populus canescens* (Aiton) Sm. Leaves," *Planta*, 219:405-411 (2004).
Search Report dated Jul. 24, 2017, in Chinese Patent Application No. 201480014392.5 (with English translation).
Simeoni et al., "Insight into the mechanism of the peptide-based gene delivery system MPG: implications for delivery of siRNA into mammalian cells," *Nucleic Acids Research*, 31(11):2717-2724 (2003).
Small, "RNAi for revealing and Engineering Plant Gene Functions," *Current Opinion in Biotechnology*, 18:148-153 (2007).
Statement of Grounds and Particulars dated Sep. 1, 2017, in Australian Patent No. 2014262189.
Stevens, "Formulation of Sprays to Improve the Efficacy of Foliar Fertilisers," *New Zealand Journal of Forestry Science*, 24(1):27-34 (1994).
Tice, "Selecting the right compounds for screening: does Lipinski's Rule of 5 for pharmaceuticals apply to agrochemicals?" *Pest Management Science*, 57(1):3-16 (2001).
Tomlinson, "Evidence that the Hexose-to-Sucrose Ratio Does Not Control the Switch to Storage Product Accumulation in Oilseeds: Analysis of Tobacco Seed Development and Effects..," *Jrnl. of Exper. Bot.*, 55(406):2291-2303 (2004).
Trucco et al., "Amaranthus Hybridus can be Pollinated Frequently by A. Tuberculatus Under Filed Conditions," *Heredity*, 94:64-70 (2005).
Voinnet, "Origin, Biogenesis, and Activity of Plant MicroRNAs," *Cell*, 136:669-687 (2009).
Watson et al., "RNA silencing platforms in plants," *FEBS Letters*, 579:5982-5987 (2005).
Wool et al., "Structure and Evolution of Mammalian Ribosomal Proteins," *Biochem. Cell Biol.*, 73:933-947 (1995).
Yan et al., Seed Science, China Agriculture Press, pp. 101-103, Tables 2-37 (2001).
Yu et al., "Diversity of Acetyl-Coenzyme A Carboxylase Mutations in Resistant Lolium Populations: Evaluation Using Clethodim," *Plant Physiology*, 145:547-558 (2007).
Yu et al., "Glyphosate, paraquat and ACCase Multiple Herbicide Resistance Evolved in a Lolium rigidum biotype," *Planta*, 225:499-513 (2007).
Zabkiewicz, "Adjuvants and Herbicidal Efficacy—Present Status and Future Prospects," *Weed Research*, 40:139-149 (2000).
Zhang, "Artificial Trans-Acting Small Interfering RNA: A Tool for Plant Biology Study and Crop Improvements," *Planta*, 239:1139-1146 (2014).
Zhao et al., "Ps0r1, a Potential Target for RNA Interference-Based Pest Management," *Insect Molecular Biology*, 20(1):97-104 (2011).
Zhao et al., "Vegetable Standardized Production Technology," Hangzhou: Zhejiang Science and Technology Press, p. 19 (2008).
Zhong et al., "A Forward Genetic Screen to Explore Chloroplast Protein Import in vivo Identifies Moco Sulfurase, Pivotal for ABA and IAA Biosynthesis and Purine Turnover," *The Plant Journal*, 63:44-59 (2010).

* cited by examiner

SEQUENCE LISTING

```
<160> NUMBER OF SEQ ID NOS: 386

<210> SEQ ID NO 1
<211> LENGTH: 6748
<212> TYPE: DNA
<213> ORGANISM: Sorghum halepense

<400> SEQUENCE: 1

ccgacgattt tccaggaatt ttcctctctt tttatggcac tgtgcttttg agaagatctt      60

taattgtgct gtctgggcca cggaacgaca atgtcgcagc ttggattagc tgcagctgcc     120
```

-continued

```
tcaaaggcac tgccgctact ccctaatcgc cagcgaagtc ctgctgggac tacattctca    180
tcatctgcat tgtcgaggcc ctcaaaccga aggaaaagcc gtacccgttc actccgtgat    240
ggtggagatg gggtatcaga tgtcaaaaag cacagccagt ctgttcgtca aggtcttgct    300
ggcattattg acctcccaag cgaggcagct tcggaagtgg acatttcaca tggatctgag    360
gatcctaggg gtccaccaga ttcctatcaa atgaatggga ttatcaatga aacacataat    420
ggaagacatg cttcagtgtc caaggttgtt gaattttgtg cggcactagg tggcaaaaca    480
ccaattcaca gtatattagt ggccaataat ggaatggcag cagcaaagtt catgaggagt    540
gtccggacat gggctaatga tacttttgga tctgagaagg caattcagct catagctatg    600
gcaactccgg aagacatgag gataaatgca gagcacatta gaattgctga tcaatttgta    660
gaggtgcctg gtggaacaaa caataataac tacgccaacg ttcaactcat agtggaggta    720
gcagaaagag taggtgtttc tgctgtttgg cctggttggg gtcatgcttc tgagaatcct    780
gaactgccgg atgcattgac cgcaaaagga atcgttttcc ttgggccacc tgcatcatca    840
atgaatgcat tgggagataa ggtcggttca gctctcattg ctcaagcagc tggggtccca    900
actcttgctt ggagtggatc acatgttgaa gttccattag agtgctgctt agacgctata    960
cctgaggaga tgtatagaaa agcttgtgtt actaccacag aggaagcagt tgcaagttgt   1020
caagtgattg gttatcctgc catgattaag gcatcctggg gaggtggtgg taaaggaata   1080
agaaaggttc ataatgatga tgaggttaga gcactgttta agcaagtaca aggtgaagtc   1140
cctggctccc caatatttat catgaggctt gcagcccaga gtcggcatct tgaagttcag   1200
ttgctttgtg atcaatatgg caatgtagca gcacttcaca gtcgtgattg cagtgtgcaa   1260
cggcgacacc agaagattat tgaagaaggc ccagttactg ttgctcctcg tgagacagtt   1320
aaagcacttg agcaggcagc aaggaggctt gctaaggctg tgggttatgt tggtgctgct   1380
actgttgagt atctttacag catggaaact ggagaatact attttctgga gcttaatccc   1440
cgactacagg tcgagcatcc agtcaccgaa tggatagctg aagtaaatct gcctgcagct   1500
caagttgctg ttggaatggg catacctctt tggcaaattc cagaaatcag acgtttctat   1560
ggaatggact atggaggagg gtatgatatt tggaggaaaa cagcagctct tgctacacca   1620
tttaattttg atgaagtaga ttctcaatgg ccaaagggcc attgtgtagc agttagaatt   1680
actagtgagg acccagatga tggtttcaaa cctactggtg ggaaagtgaa ggagataact   1740
tttaaagcca agcctaatgt ttgggcctac ttctcagtaa agtctggtgg aggcattcac   1800
gaatttgctg attctcagtt tggacatgtt tttgcatatg gactctctag atcagcagca   1860
ataacaaaca tggctcttgc attaaaagag attcaaattc gtggagaaat tcattcaaat   1920
gttgattaca ctgttgacct cttaaacgct tcagacttca gagaaaacaa gattcatact   1980
ggttggctgg ataccagaat agctatgcgt gttcaagctg agaggccccc atggtatatt   2040
tcagtggttg gaggcgcttt atataaaaca gtaaccacca atgcagccac tgtttctgac   2100
tatgttagtt atctcaccaa gggccagatt ccaccaaagc atatatccct tgtcaattct   2160
acagttagct tgaatataga agggagcaaa tacacaattg aaactgtcag gactggacat   2220
ggtagctaca ggttgcgaat gaatgaatcg acagttgaag cgaatgtaca atctttatgt   2280
gatggtggac tcttaatgca gttggatgga aacagccatg taatttatgc agaagaagaa   2340
gctggtggta cacggcttca gattgatgga aagacatgct tgttgcagaa tgaccatgat   2400
ccatcaaagt tattagctga gacaccctgc aaacttcttc gtttcttggt tgctgatggt   2460
```

-continued

```
gctcatgttg atgcggatgt accatacgct gaagttgagg ttatgaagat gtgcatgcct   2520
ctcctgtcac ctgcttctgg tgtcgttcat tgtatgatgt ctgagggcca ggcgttgcag   2580
gctggtgatc ttatagcaag gctggatctt gatgaccctt ctgctgtgaa aagggctgaa   2640
ccatttgatg gaatatttcc acaaatggcg ctccctgttg ctgcctctag tcaagtacac   2700
aaaagatatg ctgcaagttt gaatgctgct cgaatggttc ttgcaggata tgagcacaat   2760
atcaatgaag tcgttcaaga tttgatatgc tgcctggaca accctgagct tcctttccta   2820
cagtgggatg aacttatgtc tgttctagca acgaggcttc caagaaatct caagagtgag   2880
ttagaggata aatacaagga atacaagttg aatttttacc gtggaaaaaa cgtggacttc   2940
ccttccaagt tgctaagaga catcattgag gaaaatcttg catatggttc agagaaggaa   3000
aaggctacaa atgagaggct tgttgagcct cttacgaacc tactgaagtc atatgagggt   3060
gggagagaaa gtcatgcaca ttttattgcc aagtcccttt tcgaggagta tcttatggtg   3120
gaagaacttt tcagtgatgg aattcagtct gacgttattg aaaccttgcg tcatcagcac   3180
agtaaagacc tgcagaaggt tgtagacatt gtgttgtctc accagggtgt gagaaacaaa   3240
gctaagcttg taacagcact catggaaaag ctggtttatc caaatccggt tgcttacagg   3300
gatctgttgg ttcgcttttc ttccctcaat cataaaagat attataagtt ggcccttaaa   3360
gcaagtgaac ttcttgaaca aaccaaacta agtgaactcc gtgcaagcat tgcaagaagc   3420
ctttcagatc tggggatgca taagggagac atgactatta aggatagcat ggaagattta   3480
gtctctgccc cattgcctgt tgaagatgct cttatttctt tgtttgatta cagtgatgca   3540
actgttcagc agaaagtgat tgagacatac atatcacgat tgtaccagcc tcatcttgtg   3600
aaggatagca tccaaatgaa attcaaggaa tatggtgcta ttgctttttg ggaattttct   3660
gaagggcatg ttgatacttc aaatggacat gggactattc ttggtaggaa gagatggggt   3720
tccatggtca tcctcaaatc acttgaatct gcatcaacag ccattgtggc tgcattaaag   3780
gattcagcac agtacaacag ctctgagggc aacacgatgc acattgcatt attgagtgct   3840
gaaaatgaaa gtaatatgag tggaacaagt gatgatcaag ctcaacatag gatggaaaag   3900
cttaccaaga tactgaagga tactaatgtt gcaagtgatc tccgagctgc tggtttgaag   3960
gttataagtt gcattgttca aagagatgaa gctcgcatgc caatgcgcca cacattcctc   4020
tggttggatg aaaagagttg ttatgaagaa gagcaaattc tccggcatgt ggagcctccc   4080
ctctctgcac ttcttgaatt gggtaagttg aaagtgaaag gatacaatga aatgaagtat   4140
actccgtcac gtgatcgtca atggcatatc tacacactaa gaaatactga aaaccccaaa   4200
atgttgcata gggtattttt ccgaactatt gtcaggcaac ccaatgcagg caacaagttt   4260
acatcagctc aggtcagtga cactgaagta ggaggtcctg aagattctct gtcattcaca   4320
tcgaatagca tcctaagatc attgatgact gctatagaag aattagagct tcatgcgatt   4380
aggacaggtc attctcacat gtatttgtgc atattgaaag agcaaaagct tcttgatctc   4440
attccatttt cagggagtac aattgttgat gttggccaag atgaagctac tgcttgttca   4500
cttttaaaat caatggcttt gaagatacat gaccttgttg gtgcaaggat gcatcatctg   4560
tctgtatgcc agtgggaggt gaaactcaag ttggattgtg atgggcctgc aagtggtacc   4620
tggagagttg tgactacaaa tgttactagt cacacctgca ccattgatat ctaccgagaa   4680
gtggaagata cagaatcgca gaagttagta taccattcaa ccacttcggc agctggtcct   4740
ggtccgttgc atggtgttgc actgaataat ccatatcaac ctttaagtgt gattgatcta   4800
aagcgctgct ctgctaggaa caacagaaca acatattgct acgattttcc gctggcattt   4860
```

-continued

```
gaaactgcac tgcagaagtc atggcagtcc aacggctcta gtgtttctgt aggcagtaga   4920
aatagtaaat cctacgtgaa ggcaactgag ctggtgtttg ctgaaaaaca tgggtcctgg   4980
ggcactccta tagttcccat ggaacgtcct gctgggctca atgacattgg tatggtcgct   5040
tggatcttgg agatgtcaac acctgaattt cccaatggca ggcagattat tgttatagca   5100
aatgatatta ctttcagagc tggatcattc ggcccaaggg aagatgcatt ttttgaagct   5160
gtcaccaacc tggcttgtga aaggaaactt ccccttatat acttggcagc aaactctggt   5220
gctaggattg gcatagctga tgaagtaaaa tcttgcttcc gtgttgggtg gtctgacgaa   5280
ggcagccctg agcgagggtt tcagtacatc tatcttactg aagaagacta tgcccgtatt   5340
agctcttctg ttatagcaca taagctgcag ctagatagcg gtgaaattag gtggattatt   5400
gactctgttg tgggcaagga ggatgggctt ggtgttgaga acatacatgg aagtgctgct   5460
atcgccagtg cttattctag ggcatatgag gagacattta cacttacatt tgtgaccgga   5520
cggactgtag gaataggagc ttatcttgct agacttggta tacggtgcat acagcgtctt   5580
gaccagccga ttattttaac agggttttct gccctgaaca agctccttgg gcgggaagtg   5640
tacagctccc acatgcagct tggtggtcct aagatcatgg cgaccaatgg tgttgtccac   5700
ctgactgttc cagatgacct tgaaggtgtt tccaatatat tgaggtggct cagctatgtt   5760
cctgcaaaca ttggtggacc tcttcctatt accaaacctt tggaccctcc agacagacct   5820
gttgcataca tccctgagaa cacatgcgat ccacgtgcag ccatccgtgg tgtagatgac   5880
agccaaggga aatggttggg tggtatgttt gacaaagaca gctttgtgga gacatttgaa   5940
ggatgggcaa aaacagtggt tactggcaga gcaaagcttg gaggaattcc tgtgggtgtc   6000
atagctgtgg agacacagac catgatgcag cttgtccctg ctgatccagg tcagcttgat   6060
tcccatgagc gatccgttcc tcgggctgga caagtgtggt tcccagattc tgcaaccaag   6120
acagctcagg cattattaga cttcaaccgt gaaggattgc ctctgtttat cctggctaac   6180
tggagaggtt tctctggtgg acagagagat ctctttgaag gaattcttca ggctgggtca   6240
acaattgtcg agaaccttag gacatataat cagcctgcgt ttgtctacat tcctatggct   6300
ggagagcttc gtggaggagc ttgggttgtg gtcgatagca aaataaatcc agaccgcatt   6360
gagtgttatg ctgagaggac tgccaaaggt aatgttctcg aacctcaagg gttaattgaa   6420
atcaagttca ggtcagagga actccaagac tgtatgggta ggcttgaccc ggagttgata   6480
aatctgaaag caaaactcca agatgtaaag catggaaatg gaagtctacc agacatagaa   6540
tcccttcaga agagtataga agcacgtacg aaacagttgc tgcctttata tacccagatt   6600
gcaatacggt ttgctgaatt gcatgatact tccctaagaa tggcagctaa aggcgtgatt   6660
aagaaagttg tagactggga agaatcacgc tctttcttct ataaaaggct acggagaagg   6720
atctctgaag atgttcttat acacatct                                      6748
```

<210> SEQ ID NO 2
<211> LENGTH: 828
<212> TYPE: DNA
<213> ORGANISM: Sorghum halepense

<400> SEQUENCE: 2

```
gttaaagaag ctgctggtga gcagctttcc cacagatcag cactagactc tatcaagaaa     60
tggtatctag tgtccaaagg aactgaaggt ggtagtgaaa tgtggaatga tgatgaatct    120
ttctttgctt ggaaggatga ttccaagaac tatgaaaatt atcttgagga gttgaaggct    180
```

```
gaaagagtat cgaactggtt ctcgcatctt gctgaaagtt ccgacgtgaa agctctgcca    240

aacggtcttt cactcctcct taacaagatg aatcctctga agagggagca ggtcattgat    300

ggcctcaggc agcttcttgg ttgatcgatg gtggtatcgc attccaaccg gaaaatgtcc    360

tcacttttttg cacataaact atgtgttctt gcaagatcga agtggagcat gaagccctgc    420

ttagttggga acgaattgtt gtttgtagtc atgtatttag ctgtttatcc tgtaattagt    480

tggatgtcgt ttctcgatgt catatgatac atcagcaatc ctgatcaagt aattatttac    540

ttttcaatcc aaataataca tgattttcat cagtacgctt tgtgcttgta atatactctc    600

tcatttcaaa ttataagacg tttgaggttt cctagataca ttacttttac tatgcttaga    660

catagtagat atctaagttc atagtaaaaa aactatgtat ttagaaaagc taaaatgtct    720

tataatttaa aattattaga catgtattgt agacatgtag acatattgta attcaagccc    780

cgttagaatg actctgcaat ttatcaaggc tgtctcttat acacatct                  828
```

```
<210> SEQ ID NO 3
<211> LENGTH: 728
<212> TYPE: DNA
<213> ORGANISM: Sorghum halepense

<400> SEQUENCE: 3

atagattgca gagagaactc gtgtatctgc agtttggcct ggctggggtc atgcgtctga     60

gaacccagaa cttccagatg ctctaaacga gaaaggaatc atttttcttg ggccaccatc    120

agctgcaatg gctgcacttg gtgataagat tggttcttct ctcattgcac aagcagcagg    180

agttccaact cttccatgga gtggatcaca tgtatgccgt ctcctatttc tgtgtggttt    240

tactcctatt ttcctctgct acttttgtgt tcacttaata ttaaatcaaa ctctctgcag    300

gtaaaagttc caccagaaag ctgccattca attcccgagg agatatataa gaatgcttgt    360

gtttccacca cagaggaagc agtggctagt tgtcaggtgg ttgggtaccc tgccatgatc    420

aaggcatctt ggggaggtgg tggtaaagga ataagaaagg ttggttttct ttttcatttg    480

aactgtggga aagagaagag accagtattc agaaaaggaa aatgaagtta aagtttcagt    540

aaacaattta gattgattat cactaatttt gttgtcatct gcatggatct gtaggttcat    600

aacgatgatg aggtgagggc actgttcaag caagttcaag gagaagtccc tggctcgcct    660

atatttatta tgaaagtggc atctcaggtg agaactgatt caaagatttt gtttcccttg    720

ttaccaac                                                            728
```

```
<210> SEQ ID NO 4
<211> LENGTH: 2312
<212> TYPE: DNA
<213> ORGANISM: Sorghum halepense

<400> SEQUENCE: 4

ttgacttgaa ggaataagca gtttggattg tttcaactac tgactatatt ctgacatcat     60

ttggaaatac ataatttcat ttttgttctc ttaattgtac tttgcagaaa gaacatgatc    120

cttcaaagtt gttggctgat acaccttgca aacttcttcg gttcttggtt gccgatggct    180

ctcatgtgga tgctgataca ccatatgctg aggtggaagt catgaagatg tgcatgccac    240

tgttactgcc tgcctctggt gtcattcact ttgttatgcc tgagggtcag gccatgcagg    300

tatttcattc ctctatattt ccctccccct ctgcttgcac atccatgctc tctctctctc    360

tcatgaaatc agtatgaacg cttcatctat aacaaacttc atgaaattag catggttact    420

acatttataa caaacttgaa tgtatgtttt cctttttttca ggcgagtgac ctgatagcaa    480
```

-continued

```
gattggacct tgatgacccc tcttctgtga ggagagctga accatttcat ggttcctttc    540
ccaaactggg acctcctacc gctatctctg gcaaagttca tcaaaaattt gctgcaagtg    600
tgaattctgc acacatgatc cttgcaggat atgaacataa tataaatgac gtaagacatt    660
aatttttaca atgatttgta atttcaattt gctttcattt ttctctcctc ttccttatct    720
tcatctacaa agaaaaacca agttcgtagt ttacggcaca cactgtgaca ttttcttgga    780
aataatctgt tcctttttttt aaaaaatagt ctttatgtaa tatttaatca acattttcct    840
atctatacgt gcttttgcag gttgtacaag atttgctgaa ctgcctagac agccctgagc    900
tccctttttct acagtggcaa gaacttatgt ctgttttagc aacacggctt ccaaaagatc    960
ttaggaatga ggtgattagc ttttgactag ttttctgtca aatcaattgt ggtattcttt   1020
ctgtattact tctctcctct tttgggtgca catgagatgt ctgactagtt tggatgcatt   1080
cagttggatg gtaagtacaa ggagtatgaa ttgaatcctg acttctgcaa gagtaaggat   1140
ttccctgcaa agcagctgag gtgtgttatt gaggtcagtt tgagactgct acttagtgtt   1200
aactcctgtt tgagtattta tattgcttac ttacaaaatt actactatag gcaaatcttg   1260
catactgttc ggagaaagat aggattacta atgagaggct tgtggaacca cttatgagcc   1320
tggtcaagtc atatgagggt ggaagagaaa gccatgctcg tgttgttgtc aaatctctat   1380
ttgaggagta tctgtctgtt gaagagctct tcaatgataa ccttcaggca agtttttgaa   1440
gaggttgctc aatgctcatt tgctcaccaa atgtcctaac tattgttgtg ttttctgttt   1500
ttcttttttt ttctttttca gtctgatgtt atagagcgtc tacgccttca acatgcaaaa   1560
gaccttgaga aggttgtata cattgtgttc tcacaccagg taatttctgt gaactgtgat   1620
tttttatttt tattttggta catctagaga ttcgagggcc tttttttttc tgacaatttg   1680
tttttgtttg aagggtgtga ggagaaaaaa taaattaata ctacggctta tggaagcatt   1740
ggtatatcca aacccatctg cttacaggga tcagctgatt cgcttctctg ctttgaacca   1800
ttcatcatat tccaaggtaa aattgaggat ttttgaagat tgaggttcga tttattttgc   1860
tcatgtagtc atgtgatagt tgataaaaaa tgtgtaatat attgttattg atgcagctgg   1920
cacttaaagc aagccaactt cttgagcaca ctaaattgag tgaacttcgc acaagcatag   1980
caagaagcct ttcagagctg gaaatgttta ctgaggaagg agagcgtttg tcaacaccta   2040
ggagaaagat ggcgataaat gagagaatgg aagatttagt ttgtgctcca ctggcagttg   2100
aagatgctct tgtagcgttg ttcgatcaca gtgatcctac tcttcaacgg agagtggttg   2160
agacatatgt acgcagattg tatcaggtat cagcgacttt gtccactact ttgcttgtct   2220
tgatacagct taaatcttga caaaatttat atgaactaac acaaatcata ttacagcctt   2280
atcttgtaag tggaagtatc cggatgcaat gg                                 2312
```

<210> SEQ ID NO 5
<211> LENGTH: 1454
<212> TYPE: DNA
<213> ORGANISM: Sorghum halepense

<400> SEQUENCE: 5

```
ttttcagtct gatgttatag agcgtctacg ccttcaacat gcaaaagacc ttgagaaggt     60
tgtatacatt gtgttctcac accaggtaat ttctgtgaac tgtgattttt tatttttatt    120
ttggtacatc tagagattcg agggcctttt ttttctgaca atttgttttt gtttgaaggg    180
tgtgaggagc aaaaataaat taatactacg gcttatggaa gcattggtat atccaaaccc    240
```

atctgcttac agggatcagc tgattcgctt ctctgctttg aaccattcat catattccaa 300
ggtaaaattg aggatttttg aagattgagg ttcgatttat tttgctcatg tagtcatgtg 360
atagttgata aaaaatgtgt aatatattgt tattgatgca gctggcactt aaagcaagcc 420
aacttcttga gcacactaaa ttgagtgaac ttcgcacaag catagcaaga agcctttcag 480
agctggaaat gtttactgag gaaggagagc gtttgtcaac acctaggaga aagatagcga 540
taaatgagag aatggaagat ttagtttgtg ctccactggc agttgaagat gctcttgtag 600
cgttgttcga tcacagtgat cctactcttc aacggagagt ggttgagaca tatatacgca 660
gattgtatca ggtagcagcg actttgtcca ctactttgct tgtcttggta cagcttaaat 720
cttgacaaaa tttatatgaa ctaacacaaa tcatattaca gccttatctt gtaagtggaa 780
gtatccggat gcaatggcac cgagctggcc taattgccat atgggagttc tctgaagagc 840
atcttaagca aagaattggg caagatgtgc ccctacagca agtagagaat tccactgaga 900
agagatgggg cgtcatggtt gtaattaagt ctctccagtt tttagcaact gcaattgatg 960
ttgcactgaa ggagacttca cagtacagag tgggtgtcgg aagtgtctcg aacggtgacc 1020
atgtaaattc taatcaaagc aatatgcttc atattgcttt ggttggtatc aataatcaga 1080
tgagtactct ccaagacagg tttgtttgct ctccatatcc ttatgtggct atttgtttca 1140
tgaaaatttt caagagtgat tccattggat gtcatcaatt tcttatttta cctatttttt 1200
gtctgtttgt agtggtgatg aggatcaagc acaagaaagg gtcaacaaac tatccaagat 1260
tttgaaggat aacactatta catcacatct taatggcgct agtgttaagg ttgtcagctg 1320
tattatccaa agagatgaag ggcgtccacc aatgcgacac tccttccaat ggtctgttga 1380
caagctttat tatgaggagg atccaatgct tcgccatgtg gaaccgccgt tgtctacatt 1440
ccttgagctg gtat 1454

<210> SEQ ID NO 6
<211> LENGTH: 666
<212> TYPE: DNA
<213> ORGANISM: Sorghum halepense

<400> SEQUENCE: 6
ttatgcctga gggtcaggcc atgcaggtat ttcattcctc tatatttccc tccccctctg 60
cttgcacatc catgctctct ctctctctca tgaaatcagt atgaacgctt catctataac 120
aaacttcatg aaattagcat ggttactaca tttgtaacaa acttgaatgt atgttttcct 180
tttttcaggc gaatgacctg atagcaagat tggaccttga tgacccatct tctgtgagga 240
aagctgaacc atttcatggt tcctttccca aactgggacc tcctactgct atctctggca 300
aagttcatca aaaatttgct gcaagtgtga attctgcaca catgatcctt gcaggatatg 360
aacataatat aaatgacgta agacattaat ttttacaatg atttgtaatt tcaatttgct 420
ttcatttttc tctcctcttc cttatcttca tctacaaaga aaaaccaagt tcgtagttta 480
cggcacacac tgtgacattt tcttggaaat aatctgttcc ttttttaaaa aaatagtctt 540
tatgtaatat ttaatcaaca ttttcctatc tatacgtgct tttgcaggtt gtacaagatt 600
tgctgaactg cctagacagc cctgagctcc cttttctaca gtggcaagaa cttatgtctg 660
ttttag 666

<210> SEQ ID NO 7
<211> LENGTH: 323
<212> TYPE: DNA
<213> ORGANISM: Sorghum halepense

<400> SEQUENCE: 7
cagagtaccg cgaaaataag atccatactg gttggcttga cagcagaata gctatgcgtg 60
ttagagcaga gaggccccca tggtacctct cagttgttgg aggagctcta tatgtatgcc 120
tgtttgactg cagaaccatg atttcttacc tgcttgtgag cttggaagtc agctatcttt 180
gttgacatca aacatttatc tcttatttca caggaagcat caagcaggag ctcaagcgct 240
gttactgatt atgttggtta tctcagcaaa ggtcagatac caccaaaggt ataatataat 300
gctgaaatgc ccttgttgca gat 323

<210> SEQ ID NO 8
<211> LENGTH: 633
<212> TYPE: DNA
<213> ORGANISM: Sorghum halepense

<400> SEQUENCE: 8
acagtggatc tcttgaatgt atgatgacct ccatagtaaa tgatcttctg tacatgatac 60
tctttatatg tctttgtgta atttagtttt caattttgca tctgtacagg ccgcagagta 120
ccgcgaaaat aagatccata ctggttggct tgacagcaga atagctatgc gtgttagagc 180
agagaggccc ccatggtacc tctcagttgt tggaggagct ctatatgtat gcctgtttga 240
ctgcagaacc atgatttctt acctgcttgt gagcttggaa gtcagctatc tttgttgaca 300
tcagacattt atctcttatt tcacaggaag catcaagcag gagctcaagc gttgttactg 360
attatgttgg ttatctcagc aaaggtcaga taccaccaaa ggtataatat atgctgaaat 420
gcccttgttg cagattatac ttgttgctgt tggacttaaa acagcttggt aactgtgtaa 480
cttctttctt cattgcagca catctcgctt gtcaatttaa gtgttactct gaacatagag 540
gggaacaaat acacggtact catctatagt tttctcttta catttctgtg cttacaactc 600
agtgactcac ttacatgatt aaactctgct gta 633

<210> SEQ ID NO 9
<211> LENGTH: 1285
<212> TYPE: DNA
<213> ORGANISM: Sorghum halepense

<400> SEQUENCE: 9
tgaaattagc atggttacta catttataac aaacttgaat gtatgttttc cttttttcag 60
gcgagtgacc tgatagcaag attggacctt gatgacccct cttctgtgag gagagctgaa 120
ccatttcatg gttcctttcc caaactggga cctcctaccg ctatctctgg caaagttcat 180
caaaaatttg ctgcaagtgt gaattctgca cacatgatcc ttgcaggata tgaacataat 240
atcaatgacg taagacatta atttttgcaa tgatttgtaa tttcaatttg ctttcatttt 300
tctctcctct tccttatctt catctacaaa gaaaaaccaa gtttgtagtt tacggcacac 360
attggcggac tcaaggggga gcccccctct tggactcaaa atttttaaac agattttctc 420
tttagcaaaa gattctatgt atttggtatt tttctatatt tattctatga atctttgctt 480
ttgagcactt tgaatcaata ttaaattatt aattttaact atatctatta gtgtattgga 540
ttgaacgaga attttttttt ttaactatgt tatttagccc ccctcttggt ccgtttctaa 600
gtccgccact gacggcacac actgtgccat tttcttggaa ataatctgtt cctttttttt 660
aaatagtctt tatgtaatat ttaatcaaca ttttcctttc tgtacgtgct tttgcaggtt 720
gtacaagatt tgctaaactg cctagacagc cctgagctcc cttttctaca atggcaagaa 780

-continued

```
cttatgtctg ttttagcaac acggcttcca aaagatctta ggaatgaggt gattagcttt    840

tgactagttt tctgtcaaat caattgtggt cttatttctg tattacttct cttttgggtg    900

cacatgagat gtctgactaa tttggatgca ttcagttgga tggtaagtac aaggagtatg    960

aatttaatcc tgacttctgc aagagtaagg atttccctgc aaagttgctg aggggggtta   1020

ttgaggtcag tttgagactg ctacttagtg ttaactcctg tttgagtatt tatattgctt   1080

acttacaaaa ttactactat aggcaaatct tgcatactgt tcggagaaag atagggttac   1140

taatgagagg cttgtggaac cacttatgag cctggtcaag tcatatgagg gtggaagaga   1200

aagccatgct cgtgttgttg tcaaatctct atttgaggag tatctgtctg ttgaagagct   1260

cttcaatgat aaccttcagg caagt                                         1285


<210> SEQ ID NO 10
<211> LENGTH: 453
<212> TYPE: DNA
<213> ORGANISM: Sorghum halepense

<400> SEQUENCE: 10

aataatcata acaataattt agtaatgact gtgaagaact aaagatttct accacctgtc     60

tgatatgcat aaaacttgac agtaatagca atctcatcaa ctatcataca tgtttcttta    120

gctaatagaa aatgctccgt atgctaagta tttttgacca tttactttta ggtagaagga    180

tatcatttgc actttttgat gtgcttatgt tcaaattctt tgcttatgtt caaattcttt    240

ctcccagatt taccgagaag tggaagaccc cagcacacat cagcttctct accactctgc    300

cacagccacg gctggtcctt tgcatggtgt tgcattgaat gaaccataca agcctttgga    360

cgctattgac ctcaaacgtt atgctgctag gaaaaatgaa accacatact gctacgattt    420

ccccttggta agttgcttgc agctccttgt ttt                                 453


<210> SEQ ID NO 11
<211> LENGTH: 540
<212> TYPE: DNA
<213> ORGANISM: Sorghum halepense

<400> SEQUENCE: 11

cagtgtcttt ctattaaact gaaaggtctc tagctgagtt ggttgggtgg cttgagtatc     60

ccctcaggtc tcagggctta aaaacctcgt ctatcccacg ccaaatcata ggtctaaggt    120

ctggcctgtg gtcgttctca catgggctac agtgcctgta tgggtggggc aggggttcaa    180

gggtttttctt gacctatgtg agaagatctt cttaatgtaa tgtccagggg ctgtcctaat    240

ccctgcaggt tgagtttttt tttctgttag acaagttctg atacatcttt gttgtaattt    300

cttcagttgg atggaaacag tcatgtaatt tatgcagaga cggaggctgc tggtacacgc    360

cttctcatta atggtagaac atgcttacta caggtaaaga tggctacatt ttcatatttt    420

aactctttca tgttacgtac taaaccacag tacttttaca tataattact tgaaactgaa    480

ggtattggat ctggcaattt cttgtgaatc ttgcattcgt acgaagatca taaaacttta    540


<210> SEQ ID NO 12
<211> LENGTH: 7197
<212> TYPE: DNA
<213> ORGANISM: Sorghum halepense

<400> SEQUENCE: 12

tatgaagaaa atttgattta ctttcttcag agggaatatt tcaaaccaac aattttctta     60

ctgtccaagc cactgaaatt ttatcatgat cttacacgca caagccacat gaaaccttat    120
```

-continued

```
caccccctga taaaaaaaag aaaggatcaa tttggtgatt catagaatgg ggaaaaacaa    180
cctgttgcca tttggggaag gttgaggtcc gtgtccctgc tcccgtccta tgcaaccatc    240
tccattgaaa agattttgca ctacatttgg gctttgtatg ataaaaaaaa ctaaacagca    300
gaaacatagt agaattgtag aaaaaaggtg ctggcaagtt ttagtggcag agacctttgt    360
atgtttggac atagcttact agtatatagt tttctgtaat cttcatgaaa ggtggccaat    420
aaacctgata agatctcaac atggtaggtt ccttcaaaat gagaggaaaa ctggaaacat    480
cacaaatatt tttctagcaa ctggcctata aaccataatg ttgcttttca tttctttgat    540
attcgaaact tcctaagagt attctgctag agttctgatg gtattatttg cctctgtcag    600
attttccagg aaatttcctc tctttttatg gcactgtgct tttgagaaga tctttaattg    660
tgctgtctgg gccacggaac gacaatgtcg cagcttggat tagctgcagc tgcctcaaag    720
gcactgccac tactccctaa tcgccagcga agtcctgctg ggactacatt ctcatcatct    780
gcattgtcga ggccctcaaa ccgaaggaaa agccgtaccc gttcactccg tgatggtgga    840
gatggggtat cagatgtcaa aaagcacagc cagtctgttc gtcaaggtac tgtgaatatc    900
tttcgataca agctaaaatt ttgtttcaaa atatatatgg agttctttat tggctggcat    960
tgttcatttg ttttaacatc gtaatgtttg atgcctcatt ctaggtatca acgtagatat   1020
gctcactgct cagtttcaaa tgtttgtctg catgtaggtc ttgctggcat tattgacctc   1080
ccaagcgagg cagcttcgga agtggacatt tcacagtaag cggctatagt attttgcgta   1140
ttatatgttt gttttggaaa aagaaaatat tctgcagctt atttatacta gtttccctga   1200
tactgaaatg ctgtcttaat gtcctagtgc tgtatactca atatttcata gtaaatgctg   1260
caaaatatgt gatataaatg ttgcaacaca gccaggggcc tgcttctgta cctgctattg   1320
agcatgatga atactttgct cacttatatg atgtggttat atctcatgta gaagaattag   1380
ttgcagtatt gctggacaat ggttacttat tatgaaatca tgtctgctac aaattttctg   1440
acttctgttg ctgtaaatgc ctgttttttt ttggaaaaga ttaaatgttt gacctaaatt   1500
ggacatatac tccctccgtc cctgaatatc cgtcgttctc gcttccctag aaatgacttt   1560
tattaatttt atataaaaac atattaatat tttttataca attgacatca ttagataggt   1620
cttttaatct agttttttaa taaatttatt tggagatata aatgttgtac gcatgtgcta   1680
caaatctagt taaacttgtg gcaggaaacc cagaaacgac acttaaaaag gggcggaggg   1740
agtatgatag acacaatgct cattttgaac ttttttgatt tgtgacaacc atgcatattg   1800
ttagtgttgt gaacaaaatg gtaatccttt ccttttgtat ttttccagtg gatctgagga   1860
tcctaggggt ccaccagatt cctatcaaat gaatgggatt atcaatgaaa cacataatgg   1920
aagacatgct tcagtgtcca aggttgttga attttgtgcg gcactaggtg gcaaaacacc   1980
aattcacagt atattagtgg ccaataatgg aatggcagca gcaaagttca tgaggagtgt   2040
ccggacatgg gctaatgata cttttggatc tgagaaggca attcagctca tagctatggc   2100
aactccggaa gacatgagga taaatgcaga gcacattaga attgctgatc aatttgtaga   2160
ggtgcctggt ggaacaaaca ataataacta cgccaacgtt caactcatag tggaggttag   2220
cactgctaat ctgttagttt actactgatc ggctgttccc tttatttctt ctataaccat   2280
tgtcatattt aagtagagaa gtttatattt ctcctctgct gttgttgtgg aagtctaatt   2340
gtcaccattt attaactatg aaatattgca ggtagcagaa agagtaggtg tttctgctgt   2400
ttggcctggt tggggtcatg cttctgagaa tcctgaactg ccggatgcat tgaccgcaaa   2460
```

-continued

```
aggaatcgtt ttccttgggc cacctgcgtc atcaatgaat gcattgggag ataaggtcgg   2520
ttcagctctc attgctcaag cagctggggt cccaactctt gcttggagtg gatcacatgt   2580
gagtctctct ctctctctct ctctgattac tatctgccgg tttcattgct ctaacttcaa   2640
tattctaata atgacactaa atttaggttg aagttccatt agagtgctgc ttagatgcta   2700
tacctgagga gatgtataga aaagcttgtg ttactaccac agaggaagca gttgcaagtt   2760
gtcaagtgat tggttatcct gccatgatta aggcatcctg gggaggtggt ggtaaaggaa   2820
taagaaaggt gtgttttatt tatgtgacta aactatctgt gaagaactgt gcacattggg   2880
gagtatggtg tagggagcta ccccccctctc ctgtgatgtg attaaatcaa tttccctggc   2940
aggttcataa tgatgatgag gttagagcac tgtttaagca agtacaaggt gaagtccctg   3000
gctccccaat atttatcatg aggcttgcag cccaggttag ttttttttctt tctgaaatct   3060
atattccatc cctttttgtt cttttaaagt tatccttgta ttttctggaa gcttcatctg   3120
atgcattatt gacaagtgca ctgatgatca tcatatttgg agattaacat atttatgaaa   3180
ggttaattga tgggaactct tgaaagagaa cggttgagcg gataccattc tatttttaga   3240
atttagaaat cgcggttttt gcgcacaaaa ttgcatttcc aggaactgga ctaagctttt   3300
cttagtattg agtggcatgt tatacatgga ccatttttgt caacttacag ggctgtgata   3360
atggctggag agaaataata catcttgttt ctcaacactt atgtggagaa gatgttttac   3420
ctttttctaa aattactttt tggattaaat tgtataagtt ttcaatattc tcactattat   3480
tgaactgtgc tatgtcaaac agccaaaaca tgtttcattc tttacacctt tatttttcaa   3540
gatggaagcc tggaattgtg ctctgttatc tatagtcaat tagtcataca tttatttgat   3600
tttaaatctt tttctctact gtagagtcgg catcttgaag ttcagttgct ttgtgatcaa   3660
tatggcaatg tagcagcact tcacagtcgt gattgcagtg tgcaacggcg acaccagaag   3720
gtctgccccc acccactcag ccataaacac caaattatag aaccatgcat tttgttatgc   3780
gatctatttc tcaactgtag ttccattcgc atttttctac aacagattat tgaagaaggc   3840
ccagttactg ttgctcctcg tgagacagtt aaagcacttg agcaggcagc aaggaggctt   3900
gctaaggctg tgggttatgt tggtgctgct actgttgagt atctttacag catggaaact   3960
ggagaatact attttctgga gcttaatccc cgactacagg tttgctatac gtgaacatca   4020
ttgactaatt aacctgtcgg ggaatccttc acataaaatt atctccatgc aggtcgagca   4080
tccagtcacc gaatggatag ctgaagtaaa tctgcctgca gctcaagttg ctgttggaat   4140
gggcatacct ctttggcaaa ttccaggtaa ttaccaattt accaacttat ttagttcctt   4200
attagtttat tctctaatct gtctacttat gtagaaatca gacgtttcta tggaatggac   4260
tatggaggag ggtatgatat ttggaggaaa acagcagctc ttgctacacc atttaatttt   4320
gatgaagtag attctcaatg gccaaagggc cattgtgtag cagttagaat tactagtgag   4380
gacccagatg atggtttcaa acctactggt gggaaagtga aggtaagatt ttgagatgac   4440
agatgtatta tgtatagttc aaacagatta agtttggtta agtgaccaga tcttgatttt   4500
ttatctttta ggagataact tttaaagcca agcctaatgt ttgggcctac ttctcagtaa   4560
aggtaacttg ttaactttgt tacactgtta cattattctt cattgtgcag ataatttgga   4620
tgggactaag tttttaacca ttcatcgtct catttagctg agcaaatgtt tgcactgact   4680
ccccttttta tctgctttca gtctggtgga ggcattcacg aatttgctga ttctcagttt   4740
ggtatgtgta aatcaagaat attcttcttt gtaatttgta ttggtcctca ttttctaaat   4800
atcgctcttt ctgttacagg acatgttttt gcatatggac tctctagatc agcagcaata   4860
```

```
acaaacatgg ctcttgcatt aaaagagatt caaattcgtg gagaaattca ttcaaatgtt   4920
gattacactg ttgacctctt aaacgtatga aatattaacc accttttgaa tccctgtttt   4980
cattatgctg attcatatca ttatgtttga ttttccatta tggctaaacc tgtggtgcta   5040
tttccctatt attccaggct tcagacttca gagaaaacaa gattcatact ggttggctgg   5100
ataccagaat agctatgcgt gttcaagctg agaggccccc atggtatatt tcagtggttg   5160
gaggtgcttt atatgtaaga taaagaaatc atgctaacat cttttgtcaa actactgtga   5220
aaaacatacg atgtaaggtc taatttaaat aattgtcaca tgctacagaa aacagtaacc   5280
accaatgcag ccactgtttc tgactatgtt agttatctca ccaagggcca gattccacca   5340
aaggtatgtt ttgtgggatt aactctggat atttttaagg tgaaaaatgg ttgatgaata   5400
atatttttat gcagcatata tcccttgtca attctacagt tagcttgaat atagaaggga   5460
gcaaatacac agtaagtttg acattccaca agggaattta ttttagttgt aacaataaag   5520
ttagacatca ttctgagttc cgtttgcatt gtgttgtaga ttgaaactgt aaggactgga   5580
catggtagct acaggttgcg aatgaatgaa tcgacagttg aagcgaatgt acaatcttta   5640
tgtgatggtg gactcttaat gcaggtaact tgttctttct tttgtgcatt attattaatt   5700
agttggataa atggttttga tttcatggcg gttctgattg ttgaactgca atggctccag   5760
ttggatggaa acagccatgt aatttatgca gaagaagaag ctggtggtac acggcttcag   5820
attgatggaa agacatgctt gttgcaggta aatactccct tccttcttta tattcttggt   5880
gtctgattgg gcaacttctg ccagatttat ctgtatcatt tattattgca ttttgctcca   5940
ctaccttatc tttaaaagat gggttctgtt gtttgcttct gcaggagaca tcacataaga   6000
aaattgttac taatccttgt tttcttgcag aatgaccatg atccatcaaa gttattagct   6060
gagacaccct gcaaacttct tcgtttcttg gttgctgatg gtgctcatgt tgatgcggat   6120
gtaccatacg ctgaagttga ggttatgaag atgtgcatgc ctctcctgtc acctgcttct   6180
ggtgtcgttc attgtatgat gtctgagggc caggcgttgc aggttatatt cttagtttta   6240
catgtccatt ccttgcattg tgctttcatc ccataatatt tcatgtaaca tttgtcaaat   6300
tacatttgtt ttaggctggt gatcttatag caaggctgga tcttgatgac ccttctgctg   6360
tgaaaagggc tgaaccattt gatggaatat ttccacaaat ggcgctccct gttgctgcct   6420
ctagtcaagt acacaaaaga tatgctgcaa gtttgaatgc tgctcgaatg gttcttgcag   6480
gatatgagca caatatcaat gaagtaaaca ttccatctta ttgtgaccac atcctgttta   6540
ttttctttgt ttatcttgtg tttcctttac ttagatagtt tctacaaaaa tgatcttttg   6600
tccagtcaca tgtcttctcc ctcactcatc tacctatcat atctcttcat gtcttggttt   6660
ccgtgtatac atggtttctt attaagaaac cattgccccc tcttctttaa ttgtagtgcc   6720
acatcatcat ttctgtttag ttcaccctaa ttaatgaaca tagaaaccat gtagtttctg   6780
ggttgggagt gcccttagca cttggttatc cattatcaac tgattcatgt taagctattc   6840
ttcttttcag gtcgttcaag atttgatatg ctgcctggac aaccctgagc ttcctttcct   6900
acagtgggat gaacttatgt ctgttctagc aacgaggctt ccaagaaatc tcaagagtga   6960
ggtatgagac agttggcaag atatagccaa tctggattaa aggaaagatg attcatttta   7020
gtagatatat tatcttaatt ttacatttta catattggct tatgttgatg gcagaaaaag   7080
ccatcagaga aactgtgata ttttataaca ttagtttgca ccgtgttatg ttcataaata   7140
aacctgacaa tggtttgggc cggaaccagt ttccatggtt tgatttcctt gttgggc      7197
```

<210> SEQ ID NO 13
<211> LENGTH: 810
<212> TYPE: DNA
<213> ORGANISM: Sorghum halepense

<400> SEQUENCE: 13
tttgtatcct gagcgcttct gtgtaatata tatttgtttc tgaaagcatt cattcttttc 60
tttctttgta gagccgacat ctggaggttc aattgctctg tgataaacat ggcaatgtgg 120
cagcactaca cagtcgagat tgcagtgttc aaagaaggca ccaaaaggtt agctcttcaa 180
attctattaa acacctgatt cccattgcga gttcatgcct tcgctgaatt tgtcccattc 240
ttggattgtg tattttgttc tgtagaagtt tatatctttc ttgaataact tttatagttg 300
aacaagtgca cgacaatttt ttccctattt gtattttatt gaaaaaaata ttatttttca 360
ccatttacct ctgcaacaga ttattgaaga ggggccaatc acagttgctg ctccagacac 420
tgttaaagag cttgagcagg cagcaaggtg gcttgctaag tgtgttcaat acgttggtgc 480
tgctaccgta gaatatctgt acagcatgga aacgggcgaa tactattttt tggagcttaa 540
tccacggttg caggtctgtt ctaaacttcc aatgcaggga ttttgcagag gcattcttct 600
atggttcttg catttgagt ttttgactgg cttcctttca ggtagaacat cctgtgactg 660
aatggatagc tcaagtaaac ttgccagcag cccaagttgc agtcggaatg ggcatacccc 720
tctataactc caggtatttc attttctcga ctccatgatt gatgatattt tgttctcttg 780
ttctgatgaa tgaattaatc actgcagaga 810

<210> SEQ ID NO 14
<211> LENGTH: 263
<212> TYPE: DNA
<213> ORGANISM: Sorghum halepense

<400> SEQUENCE: 14
ttctgataca tctttgttgt aatttcttca gttggatgga aacagtcatg taatttatgc 60
agagacagaa gctgctggta cgcgccttct cattaatggt agaacatgct tactacaggt 120
aaagctggct acattttcat attttaactc tttcatgtta cgtactaaac cacagtactt 180
ttacatgtaa ttacttgaaa ctgaaggtat tggatctggc aaattcttgt gaatcttgcg 240
ttcgtacgaa gatcataaaa ctt 263

<210> SEQ ID NO 15
<211> LENGTH: 1231
<212> TYPE: DNA
<213> ORGANISM: Sorghum halepense

<400> SEQUENCE: 15
caaatcatat tacagcctta tcttgtaagt ggaagtatcc ggatgcaatg gcaccgagct 60
ggcctaattg ccatatggga gttctctgaa gagcatctta agcaaagaat tgggcaagat 120
gtgcccctac agcaagtaga gaattccact gagaagagat ggggcgtcat ggttgtaatt 180
aagtctctcc agtttttagc aactgcaatt gatgttgcac tgaaggagac ttcacagtac 240
agagtgggtg tcggaagtgt ctcgaacggt gaccatgtaa attctaatca aagcaatatg 300
cttcatattg ctttggttgg tatcaataat cagatgagta ctctccaaga caggtttgtt 360
tgctctccat atccttatgt ggctatttgt ttcatgaaaa ttttcaagag tgattccatt 420
ggatgtcatc aatttcttat tttacctatt ttttgtctgt ttgtagtggt gatgaggatc 480
aagcacaaga aagggtcaac aaactatcca agattttgaa ggataacact attacatcac 540

```
atcttaatgg cgctagtgtt aaggttgtca gctgtattat ccaaagagat gaagggcgtc    600

caccaatgcg acactccttc caatggtctg ttgacaagct ttattatgag gaggatccaa    660

tgcttcgcca tgtggaaccg ccgttgtcta cattccttga gctggtatgt agctatattc    720

atactttcat attcttttaa tatcctcttt gactataact gcacctcttt aacatttttc    780

tgtaaataca ggagaaagta aatttggaag gttacaatga agtaaaatac accccatcac    840

gtgatcgtca gtggcatatt tatacactta tcaagaacaa gaaagatcag agattaaacg    900

accagagaat gttccttcgt accatagtca gacaaccaag tgcaacaaat ggtttcctgt    960

caggtaatat tgacaatgaa gtaggacgcg ccaagcttca tcatcgttca catcaaacag   1020

cattctcaga tcattgatgg gagcactaga agaaatagag ctacatgctc atagtgagac   1080

tgtgagatca ggccactcac agatgtatct gtgcttactg agagaacaac aattgcatga   1140

actaattcca ttttcaaggt cagtcaatgc aacttgtctt tttatgttgc ggatatgaag   1200

gataggttgt taatttgctt gaagttatcc a                                  1231
```

<210> SEQ ID NO 16
<211> LENGTH: 6576
<212> TYPE: DNA
<213> ORGANISM: Sorghum halepense
<220> FEATURE:
<221> NAME/KEY: unsure
<222> LOCATION: (1)..(6576)
<223> OTHER INFORMATION: unsure at all n locations

<400> SEQUENCE: 16

```
tactccctcc gtccctgaat atccgtcgtt ctcgcttccc tagaaatgac ttttattaat     60

tttatataaa aacatattaa tattttttat acaattgaca tcattagata ggtcttttaa    120

tctagttttt taataaatnn ntttggagat ataaatgttg tacgcatgtg ctacaaatct    180

agtcaaactt gtggcaggaa acccagaaac gacacttaaa aaggggcgga gggagtatga    240

tagacacaaa gctcattttg aacttttttg atttgtgaca accatgcata ttgttagtgt    300

tgtgaacaaa atggtaatcc tttccttttg ttttttttcca gtggatctga ggatcctagg    360

ggtccaccag attcctatca aatgaatggg attatcaatg aaacacataa tggaagacat    420

gcttcagtgt ccaaggttgt tgaattttgt gcggcactag gtggcaaaac accaattcac    480

agtatattag tggccaataa tggaatggca gcagcaaagt tcatgaggag tgtccggaca    540

tgggctaatg atacttttgg atctgagaag gcaattcagc tcatagctat ggcaactccg    600

gaagacatga ggataaatgc agagcacatt agaattgctg atcaatttgt agaggtgcct    660

ggtggaacaa acaataataa ctacgccaac gttcaactca tagtggaggt tagcactgct    720

aatctgttag tttactactg atcggctgtt ccctttattt cttctataac cattgtcata    780

tttaagtaga gaagtttata tttctccctt gctgttgttg tggaagtcta attgtcacca    840

tttattaact atgaaatatt gcaggtagca gaaagagtag gtgtttctgc tgtttggcct    900

ggttggggtc atgcttctga gaatcctgaa ctgccggatg cattgaccgc aaaaggaatc    960

gttttccttg ggccacctgc atcatcaatg aatgcattgg gagataaggt cggttcagct   1020

ctcattgctc aagcagctgg ggtcccaact cttgcttgga gtggatcaca tgtgagtctc   1080

tctctctctc tctctctctg attactatct gccggtctca ttgctctaac tttcatattc   1140

taataatgac actaaattta ggttgaagtt ccattagagt gctgcttaga cgctatacct   1200

gaggagatgt atagaaaagc ttgtgttact accacagagg aagcagttgc aagttgtcaa   1260
```

-continued

```
gtgattggtt atcctgccat gattaaggca tcctggggag gtggtggtaa aggaataaga   1320
aaggtgtgtt ttatttatgt gactaaacta tctgtgaaga actgtgcaca ttggggagta   1380
tggtgtaggg agctaccccc tctcctgtga tgtgattaaa tcaatttccc tggcaggttc   1440
ataatgatga tgaggttaga gcactgttta agcaagtaca aggtgaagtc cctggctccc   1500
caatatttat catgaggctt gcagcccagg ttagtttttt ttctttctga aatctatatt   1560
ccatcccttt ttgttctttt aaagttatcc ttgtattttc tggaagcttc atctgatgca   1620
ttattgacaa gtgcactgat gatcatcata tttggagatt aatatattta tgaaaggtta   1680
attgatggga actcttgaaa gagaacggtt gagcggatac cattctattt ttagaattta   1740
gaaatcgcgg tttttgcgta caaaattgca tttccaggaa ctggactaag cttttcttag   1800
tattgagtgg catgttatac atggaccatt tttgtcaact tacaggactg tgataattgc   1860
tggagagaaa taatacatct tgtttctcaa cacttatgtg gagaagatgt tttacctttt   1920
tctaaaatta ctttttggat taaattgtat aagttttcaa tattctcact attattgaac   1980
tgtactatgt caaacagcca aaacatgttt cattctttac acctttattt ttcaagatgg   2040
aagcctggaa ttgtgctctg ttatctatag tcaattagtc atacatttat ttgattttaa   2100
atctttttct ctattgtaga gtcggcatct tgaagttcag ttgctttgtg atcaatatgg   2160
caatgtagca gcacttcaca gtcgtgattg cagtgtgcaa cggcgacacc agaaggtctg   2220
cccccaccca ctcagccata aacaccaaat tatagaacca tgcattttgt tatgcgatct   2280
atttctcaac tgtagttcca ttcgcatttt tctacaacag attattgaag aaggcccagt   2340
tactgttgct cctcgtgaga cagttaaagc acttgagcag gcagcaagga ggcttgctaa   2400
ggctgtgggt tatgttggtg ctgctactgt tgagtatctt tacagcatgg aaactggaga   2460
atactatttt ctggagctta atccccgact acaggtttgc tatacgtgaa catcattgac   2520
taattaacct gtcggggaat ccttcacata aaattatctc catgcaggtc gagcatccag   2580
tcaccgaatg gatagctgaa gtaaatctgc ctgcagctca agttgctgtt ggaatgggca   2640
tacctctttg gcaaattcca ggtaattacc aatttaccaa cttatttagt tccttattag   2700
tttattctct aatctgtcta cttatgtaga aatcagacgt ttctatggaa tggactatgg   2760
aggagggtat gatatttgga ggaaaacagc agctcttgct acaccattta attttgatga   2820
agtagattct caatggccaa agggccattg tgtagcagtt agaattacta gtgaggaccc   2880
agatgatggt ttcaaaccta ctggtgggaa agtgaaggta agattttgag atgacagatg   2940
tattatgtat agttcaaaca gattaagttt ggttaagtga ccagatcttg atttttttatc   3000
ttttaggaga taacttttaa agccaagcct aatgtttggg cctacttctc agtaaaggta   3060
acttgttaac tttgttacac tgttacatta ttcttcattg tgcagataat ttggatggga   3120
ctaagttttt aaccattcat cgtctcattt agctgagcaa atgtttgcac tgactcccct   3180
ttttatctgc tttcagtctg gtggaggcat tcacgaattt gctgattctc agtttggtat   3240
gtgtaaatca agaatattct tctttgtaat ttgtattggt cctcattttc taaatatcgc   3300
tctttctgtt acaggacatg tttttgcata tggactctct agatcagcag caataacaaa   3360
catggctctt gcattaaaag agattcaaat tcgtggagaa attcattcaa atgttgatta   3420
cactgttgac ctcttaaacg tatgaaatat taaccacctt ttgaatccct gttttcatta   3480
tgctgattca tatcattatg tttgattttc cattatggct aaacctgtgg tgctatttcc   3540
ctattattcc aggcttcaga cttcagagaa aacaagattc atactggttg gctggatacc   3600
agaatagcta tgcgtgttca agctgagagg cccccatggt atatttcagt ggttggaggc   3660
```

-continued

```
gctttatatg taagataaag aaatcatgct aacatctttt gtcaaactac tgtgaaaaac   3720
atacgatgta aggtctaatt taaataattg tcacatgcta cagaaaacag taaccaccaa   3780
tgcagccact gtttctgact atgttagtta tctcaccaag ggccagattc caccaaaggt   3840
atgttttgtg ggattaactc tggatatttt taaggtgaaa aatggttgac gaataatatt   3900
tttatgcagc atatatccct tgtcaattct acagttagct tgaatataga agggagcaaa   3960
tacacagtaa gtttgacatt ccacaaggga atttatttta gttgtaacaa taaagttaaa   4020
catcattctg agtttcgtct gcattgtgtt gtagattgaa actgtcagga ctggacatgg   4080
tagctacagg ttgcgaatga atgaatcgac agttgaagcg aatgtacaat ctttatgtga   4140
tggtggactc ttaatgcagg taacttgttc tttcttttgt gcattattat taattagttg   4200
gataaatggt tttgatttca tggcggttct gattgttgaa ctgcaatggc tccagttgga   4260
tggaaacagc catgtaattt atgcagaaga agaagctggt ggtacacggc ttcagattga   4320
tggaaagaca tgcttgttgc aggtaaatac tcccttcctc ctttatattc ttggtgtctg   4380
attgggcaac ttctgccaga tttatctgta tcatttatta ttgcattttg ctccactacc   4440
ttatctttaa aagatgggtt ctgttgtttg cgtctgcagg agacatcaca taagaaaatt   4500
gttactaatc cttgttttct tgcagaatga ccatgatcca tcaaagttat tagctgagac   4560
accctgcaaa cttcttcgtt tcttggttgc tgatggtgct catgttgatg cggatgtacc   4620
atacgctgaa gttgaggtta tgaagatgtg catgcctctc ctgtcacctg cttctggtgt   4680
cgttcattgt atgatgtctg agggccaggc gttgcaggtt atattcttag ttttacatgt   4740
ccattccttg cattgtgctt tcatcccata atatttcatg taacatttgt caaattacat   4800
ttgttttagg ctggtgatct tatagcaagg ctggatcttg atgacccttc tgctgtgaaa   4860
agggctgaac catttgatgg aatatttcca caaatggcgc tccctgttgc tgcctctagt   4920
caagtacaca aaagatatgc tgcaagtttg aatgctgctc gaatggttct tgcaggatat   4980
gagcacaata tcaatgaagt aaacattcca tcttattgtg accacatcct gtttattttc   5040
tttgtttatc ttgtgtttcc tttacttaga tagtttctac aaaaatgatc ttttgtccag   5100
tcacatgtct tctccctcac tcatctacct aacatatctc ttcatgtctt ggtttccgtg   5160
tatacatggt ttcttattaa gaaaccattt ccccctcttc tttaattgta gtgccacatc   5220
atcatttctg tttagtttgc accctaatta atgaacatag aagccatgta gtttctgggt   5280
tgggagtgcc cttagcactt ggttatccat tatcaactga ttcatgttaa gctattcttc   5340
ttttcaggtc gttcaagatt tgatatgctg cctggacaac cctgagcttc ctttcctaca   5400
gtgggatgaa cttatgtctg ttctagcaac gaggcttcca agaaatctca agagtgaggt   5460
atgagacagt tggcaagata tagccaatct ggattaaagg aaagatgatt catttttagta   5520
gatatattat cttaatttta cattttacat attggcttat gttgatggca gaaaaagcca   5580
tcagagaaac tgtgatattt tataacatta gtttgcaccg tgttatgctc ataaataaac   5640
ctgacaatgg tttgggccgg aaccagtttc catggtttga tttccttgtt gggccaattc   5700
aatttgggtg aaaacgggct gagcaagcta gtgggctggt tcagtctgag ttattactta   5760
gagtagttta gtttggtttt ggactgagtg ttttggcttg ctaacgggct gaagctgtgg   5820
ttccaaccca gcatcacacc acggtacagc agaagcccca tccgcgtcca ctagtattcc   5880
tattgtatta ctggatttgt ttttctatag gaaaacggcc ataaagtgta gcatgacgtc   5940
atgctgatgt tgacaagcta ggaacgaagc agagcacaca caacactcag ccggctactc   6000
```

gctccgcgcc gcgcagcagc gcatgtcacg catgcacatg tgggaggacg ttcacagacg 6060
tccgtgctca gctcggccac gctcgggacc tcgtggttgc cggagctgcc gggagcggtg 6120
cgaatggcgg cgcatggccg gacggaggag aggctcgcgc tgcactgctt gggctttgcc 6180
agcctcaaga cctccggggc cgtcaagctc gtggatgccg cggtgctggc gcgctccctg 6240
cccaggctct gctctctctt acctgctctc catcctctcc accttcagtg acctgcggga 6300
gttcatcatt tcagcgcccg gagctgtatc ggcttctata acaaggacga ggaggtgctc 6360
aggcaagggg ccaggatcca gcggttcgac gtcagagggt ccaagttggt ggacgagcta 6420
gagaatgagt tcgccggtgg tgaagttttc tgcgactcgt cctacgttga agtgatgtga 6480
tctctgtctg aaccattcca cgatgacagt tcgaagtcgg tttcgaatcc cggttgtagg 6540
ctgtggactg gtcttgtttg gatttaggaa cactac 6576

<210> SEQ ID NO 17
<211> LENGTH: 1053
<212> TYPE: DNA
<213> ORGANISM: Sorghum halepense

<400> SEQUENCE: 17 ttttttaat tgaggccatt tctttcagca gtgatgatca agctcaacat aggatggaaa 60
agcttaccaa gatactgaag gatactaatg ttgcaagtga tctccgagct gctggtttga 120
aggttataag ttgcattgtt caaagagatg aagctcgcat gccaatgcgc cacacattcc 180
tctggttgga tgaaaagagt tgttatgaag aagagcaaat tctccggcat gtggagcctc 240
ccctctctgc acttcttgaa ttggtctgtt tatcaaaatg attgcatgct tgtttgctac 300
attctgttat tatgctttgc ttatttttctt cactatactt attttgccta ttatgaatac 360
aggataagtt gaaagtgaaa ggatacaatg aaatgaagta tactccgtca cgtgatcgcc 420
aatggcatat ctacacacta agaaatactg aaaaccccaa aatgttgcat agggtatttt 480
tccgaactat tgtcaggcaa cccaatgcag gcaacaagtt tacatcagct caggtcagtg 540
acactgaagt aggaggtcct gaagattctc tgtcattcac atcgaatagc atcctaagat 600
cattgatgac tgctatagaa gaattagagc ttcatgcgat taggacaggt cattctcaca 660
tgtatttgtg catactgaaa gagcaaaagc ttcttgatct cattccattt tcagggtaag 720
tgtgcacata atcctattga aggaaatgtt tatgcattga ctattatatc ggtctcctta 780
acaagctttt catattattc aggagtacaa ttgttgatgt tggccaagat gaagctactg 840
cttgttcact tttaaaatca atggctttga agatacatga ccttgttggt gcaaggatgc 900
atcatctgtc tgtatgccag tgggaggtga aactcaagtt ggattgtgat gggcctgcaa 960
gtggtacctg gagagttgtg actacaaatg ttactagtca cacctgcacc attgatgtaa 1020
gttgtcccta ctgttttagt attctgtata tca 1053

<210> SEQ ID NO 18
<211> LENGTH: 635
<212> TYPE: DNA
<213> ORGANISM: Sorghum halepense

<400> SEQUENCE: 18
gcattattga gtgctgaaaa tgaaagtaat atgagtggaa caaggtttgt tcatgtgcaa 60
tattaggtcg aaaggggttt ttgtttaagt tttgtaactc tttttttttt taattgaggc 120
catttctttc agcagtgatg atcaagctca acataggatg gaaaagctta acaagatact 180
gaaggatact aatgttgcaa gtgatctccg agctgctggt ttgaaggtta taagttgcat 240
tgttcaaaga gatgaagctc gcatgccaat gcgccacaca ttcctctggt tggatgaaaa 300
gagttgttat gaagaagagc aaattctccg gcatgtggag cctcccctct ctgcacttct 360
tgaattggtc tgtttatcaa aatgattgca tgcttgtttg ctacattctg ttattatgct 420
ttgcttattt tcttcactat acttattttg cctattatga atacagggta agttgaaagt 480
gaaaggatac aatgaaatga agtatactcc gtcacgtgat cgtcaatggc atatctacac 540
actaagaaat actgaaaacc ccaaaatgtt gcatagggta tttttccgaa ctattgtcag 600
gcaacccaat gcaggcaaca agtttacatc agctt 635

<210> SEQ ID NO 19
<211> LENGTH: 1771
<212> TYPE: DNA
<213> ORGANISM: Sorghum halepense

<400> SEQUENCE: 19
cctgtctgat atgcgtaaaa cttgacagta atagcaatct catcaactat catacatgtt 60
tctttagcta atagaaaatg ctccgtatgc ttagtatttt tgaccattta cttttaggta 120
gaaggatatc atttgcactt tttgatgtgc ttatgttcaa attctttgct tatgttcaaa 180
ttctttctcc cagatttacc gagaagtgga agaccccagc acacatcagc ttctctacca 240
ctctgccaca gccacggctg gtcctttgca tggtgttgca ttgaatgaac catacaagcc 300
tttggacgct attgacctca aacgttatgc tgctaggaaa aatgaaacca catactgcta 360
cgatttcccc ttggtaagtt gcttgcagct ccttgttttt cctaacttta gttatggcat 420
gcttaaagag accaattcat ctcagtaata ttgtttatgc aggcatttga aacagcgctg 480
aagagattat ggaaatcaag tagctatggt gttagtgaag ctaatgagcg caatcaactc 540
tatgctgaag tgaaagagct tatatttgtt gattcggatg gagcatgggg cactccattg 600
gtttcatttg aacgccctcc aggcatcaat gatattggca ttgttgcttg gaacatgaag 660
ctgtccacgc cagaattccc aagtggccgg gagattatag ttgttgccaa tgatgtgaca 720
tttaaagctg ggtcctttgg tccaagagaa gatgcatttt ttgatgctgt taccaatctt 780
gcctgtgaga ggaaacttcc tcttatctat ctggcagcaa ctgctggtgc caggcttggt 840
gtagctgagg aaataaagtc atgcttccat gtcggctggt ctgatgatga gagccctgaa 900
cgtggttttc agtacattta cctcactaca caagattact cacgtctaag cttcaataat 960
agctcacgag ctgcaactag aaaatggaga aaccagatgg gtggttgata ccattgttgg 1020
taaagaggat ggacttggtt gtgagaatct ccatggaagt ggtgcgattg ccagtgcata 1080
ttccaaggca tacaaagaga cctttactct gacatttgtg actggaagag ctgttggcat 1140
tggggcttat ctggctcgtt taggtatgag gtgtatacaa cgtcttgatc aaccaattat 1200
tctgactggg ttttctgcac taaacaagct tctggggcgg gaggtgtaca gttctcatat 1260
gcaattgggt ggccccaaaa tcatggctac aaatggtgtt gtccaccaaa ctgtgtcaga 1320
tgaccttgaa ggtgtttctg ctatcctgaa atggctcagt tatgttcctc catatgttgg 1380
tggtcctctt cccattatga aaccccctgga cccacccgaa agaccagtag catacttccc 1440
tgagaatgct tgtgatgctc gtgcagccat ctgtggcatt caagacggtg aagggaagtg 1500
gttaggtggt atgtttgata gggaaacctt cgtggaaaca ttggaaggtt gggcaaaaac 1560
agttatcacc ggaagagcaa agcttggtgg aataccagtt ggtgtcatag ctgtggaaac 1620
ccagactgtg atgcaagtca tcccagctga tccaggtcag cttgattccg ctgagcgtgt 1680

-continued agtccctcaa gcaggtcagg tgtggttccc agattctgca gccaaaacag ctcaggcatt 1740
aatggatttc aaccgtgagg agcttccact g 1771

<210> SEQ ID NO 20
<211> LENGTH: 1931
<212> TYPE: DNA
<213> ORGANISM: Sorghum halepense

<400> SEQUENCE: 20
cgttatagcg aagcagatgt ttacaatcct attatagcga aacccacacg tttgggatcc 60
tataatagca aatttctcca tctggtctcg atttttctct catcacatat atggtcaacc 120
tacttgcctt tgcgattttg ctttaggaaa taaaaaaact gtgtccttgc tcttcctatt 180
ctgctggctg gttatgctct attacgatta cgatacaacc agttggtgct gaaccatttg 240
atctgcttaa atagttgctt ctctgctatt aacttgctat catttcctca cggtatttca 300
gaaactattg cttgtctgtt tgaatttcga ctattctgat gatgaatggg aatagcatcg 360
tggtagtgat ttgttgacat tcatctaagt accgcctctc atgaatcgtg attaatatac 420
taacaatctg tttcttttgc tcctaccagg agatctgaac tgaaaagggt gaaataatgg 480
cggagcccta ccaaatgaac ggcatactga atgggatgcc taatttgagg catccatcct 540
ctccatcaga gaggtcgacg aattctgtaa agcgcttgat ggtgactcgc caatacacag 600
gtgtgctggt cgctaacaat gggatggccg cggtcaagtt catgggcagc atccggatat 660
gggccctgga gagctttggg acagagaagg ccattctttt ggttgctatg gcaactccgg 720
aggacttgag gataaacgct gagcacataa gaatcgctga tcagttcgta gaagttcctg 780
gaggaacaaa caataacaac tatgcgaatg tacggcttat agtggaggtt agcacaattc 840
atcatctgga gttctgtaaa ttttcacaag attgtgttta attttacatg tatttttcac 900
tgtactttgg taatttacat ttcaagttca atttcataga ttgcagagag aactcgtgta 960
tctgcagttt ggcctggctg gggtcatgcg tctgagaacc cagaacttcc agatgctcta 1020
aacgagaaag gaatcatttt tcttgggcca ccatcagctg caatggctgc acttggtgat 1080
aagattggtt cttctctcat tgcacaagca gcaggagttc caactcttcc atggagtgga 1140
tcacatgtat gccgtctcct atttctgtgt ggttttactc ctattttcct ctgctacttt 1200
tgtgttcact taatattaaa tcaaactctc tgcaggtaaa agttccacca gaaagctgcc 1260
attcaattcc cgaggagata tataagaatg cttgtgtttc caccacagag gaagcagtgg 1320
ctagttgtca ggtggtcggg taccctgcca tgatcaaggc atcttgggga gaagaaaggt 1380
tggttttctt gttcatctga actgtgggaa aaagaaggga ccactattca gaaaaaaaat 1440
gaagttaaaa tttcagtaaa aaatttagat tgattatcac taattttgtt gtcatctgca 1500
tggatctgta ggttcataac gatgatgagg tgaggacact gttcaagcaa gttcaaggag 1560
aagtccctgg ctcgcctata tttattatga aagtggcatc tcaggtgaga actgattcaa 1620
agattttgtt tcccttgtta ccaacctggg gatttgagag aatgatctac ccatctccat 1680
cagtggagat aaccatatag agagagcctc atgggccata tgggcctata atagatgggc 1740
ttttataaac ttaacaattt tcatgttggc tttgagcctt tcaccctgcc tttgttcttt 1800
gtatcctgag cacttctgtg taatctttac tatacgaatc cagcaccagg cactcttgcg 1860
tctcatttgg ccacgtggct tcatattctc catcgaaccg tcaacagcgg gcactgcagc 1920
tataatttct a 1931

<210> SEQ ID NO 21
<211> LENGTH: 3184
<212> TYPE: DNA
<213> ORGANISM: Sorghum halepense

<400> SEQUENCE: 21

```
tggttcttat attccgaact gccatccatg tcattatgtt ctgaagcaca tagtacttct     60
aatggtttta gatctaccga gaagtggaag atacagaatc gcagaagtta gtataccatt    120
caaccacttc ggcagctggt cctggtccgt tgcatggtgt tgcactgaat aatccatatc    180
aacctttaag tgtgattgat ctaaagcgct gctctgctag gaacaacaga acaacatatt    240
gctacgattt tccgctggtg agttgacccc cgccccaccc ctcagtgaat acacatctgt    300
agttattttg aacctaggct gataatgaca aaaaaaaatg taggcatttg aaactgcact    360
gcagaagtca tggcagtcca acggctctag tgtttctgta ggcagtggaa atagtaaatc    420
ctacgtgaag gcaactgagc tggtgtttgc tgaaaagcat gggtcctggg gcactcctat    480
agttcccatg gaacgtcctg ctgggctcaa tgacattggt atggtcgctt ggatcttgga    540
gatgtcaaca cctgaatttc ccaatggcag gcagattatt gttgtagcaa atgatattac    600
tttcagagct ggatcattcg gcccaaggga agatgcattt tttgaagctg tcaccaacct    660
ggcttgtgaa aggaaacttc cccttatata cttggcagca aactctggtg ctaggattgg    720
catagctgat gaagtaaaat cttgcttccg tgttgggtgg tctgacgaag gcagccctga    780
gcgagggttt cagtacatct atcttactga agaagactat gcccgtatta gctcttctgt    840
tatagcacat aagctgcagc tagatagcgg tgaaattagg tggattattg actctgttgt    900
gggcaaggag gatgggcttg gtgttgagaa catacatgga agtgctgcta tcgccagtgc    960
ttattctagg gcatatgagg agacatttac acttacattt gtgaccggac ggactgtagg   1020
aataggagct tatcttgcta gacttggtat acggtgcata cagcgtcttg accagccgat   1080
tattttaaca gggttttctg ccctgaacaa gctccttggg cgggaagtgt acagctccca   1140
catgcagctt ggtggtccta agatcatggc gaccaatggt gttgtccacc tgactgttcc   1200
agatgacctt gaaggtgttt ccaatatatt gaggtggctc agctatgttc ctgcaaacat   1260
tggtggacct cttcctatta ccaaaccttt ggaccctcca gacagacctg ttgcatacat   1320
ccctgagaac acatgcgatc cacgtgcagc catccgtggt gtagatgaca gccaagggaa   1380
atggttgggt ggtatgtttg acaaagacag ctttgtggag acatttgaag gatgggcaaa   1440
aacagtggtt actggcagag caaagcttgg aggaattcct gtgggtgtca tagctgtgga   1500
gacacagacc atgatgcagc ttgtccctgc tgatccaggt cagcttgatt cccatgagcg   1560
atccgttcct cgggctggac aagtgtggtt cccagattct gcaaccaaga cagctcaggc   1620
attattagac ttcaaccgtg aaggattgcc tctgtttatc ctggctaact ggagaggttt   1680
ctctggtgga cagagagatc tctttgaagg aattcttcag gctgggtcaa caattgtcga   1740
gaaccttagg acatataatc agcctgcgtt tgtctacatt cctatggctg gagagcttcg   1800
tggaggagct tgggttgtgg tcgatagcaa aataaatcca gaccgcatcg agtgttatgc   1860
tgagaggact gccaaaggta atgttctcga acctcaaggg ttaattgaaa tcaagttcag   1920
gtcagaggaa ctccaagact gtatgggtag gcttgacccg gagttgataa atctgaaagc   1980
aaaactccaa gatgtaaagc atggaaatgg aagtctacca gacatagaat cccttcagaa   2040
gagtatagaa gcacgtacga aacagttgct gcctttatat acccagattg caatacggtt   2100
tgctgaattg catgatactt ccctaagaat ggcagctaaa ggcgtgatta agaaagttgt   2160
```

agactgggaa gaatcacgct ctttcttcta taaaaggcta cggagaagga tctctgaaga 2220
tgttcttgca aaagaaataa gacatatagt cggtgacaac ttcactcacc aatcagcaat 2280
ggagctcatc aaggaatggt acctggcttc tccagccaca acaggaagca ctggatggga 2340
tgacgatgat gcatttgttg cctggaagga cagtcctgaa aactacaatg gatatatcca 2400
agagctaagg gctcaaaaag tgtctcagtc gctctctgat ctcactgact ccagttcaga 2460
tctacaagca ttctcgcagg gtctttctac gctattagat aaggtaaatt tgcttacagt 2520
ttcaccttat tttttatttg caattaacct gtgggctaca actggttgta tctgttgcgt 2580
gttacttttt aagagctcct atttcaattg cattgcatac atggcatctt atcaattcat 2640
gattctaata catacccatt gccttctcac gtattccgtc tttggatgct gattcagatg 2700
gatccctctc aaagagcgaa gtttgttcag gaagtcaaga aggtccttgg ttgatgatat 2760
gataccaaca catccaacac tatgtgcatg ctacatgttt ttgttcaagt acatacatag 2820
aaggatattg cttggcctcg tttgcttggc cgtttgatca tgtctgatct aagtcgacca 2880
ttatttgttg aaacttcctt tttggacctg gtgctatggt tgatgaatgt atattggatg 2940
tgtgcgactg tgcgttctgc caggtgtaag ctcaaatgtt tagacagacc gagttatggt 3000
taggaagagc acgagtgaac ttgttggttt tgcagtggtt caggaaggca gaaagttgtt 3060
tcactgtagt tctgagatgt attaccagcg gccccctgct gtaattttag ggtgtataat 3120
gcggatacta gtaaaacaat tgagtggttc attaaatttt gaactcgaat aatgtttttc 3180
tagg 3184

<210> SEQ ID NO 22
<211> LENGTH: 6249
<212> TYPE: DNA
<213> ORGANISM: Sorghum halepense

<400> SEQUENCE: 22
ggttggatcc aacccaaccc acccaacccc caaccaaaca cacggtacag tttggcgtga 60
actggttttg gagggggaac gagtggggtg gattggggat ttgaaggcag acgtgattag 120
tttggtttgg ttatggtctg gatcacggac cattaacagg tttactcata aaaatcgtgt 180
agtttttcct gcagtttgtt ttgtaaaatt tgatgaaaac ttagaatttt tcactctagc 240
attttaccgg aaggtgaatc cttcagtaag tttgttttga ttctgtgatt gtagttctgg 300
tatgtcctta cataatcgat ttttattcta gcttctgatg tttttatctt ttatgcatgc 360
agttagagga taaatacaag gaatacaagt tgaattttta ccgtggaaaa aacgtggact 420
tcccttccaa gttgctaaga gacatcattg aggtcagtta tgtttctttt gtggtatctc 480
ttaaactgtt tgctattgtc ttaatcttaa ctagtgtttt ctctgtagga aaatcttgca 540
tatggttcag agaaggaaaa ggctacaaat gagaggcttg ttgagcctct tacgaaccta 600
ctgaagtcat atgagggtgg gagagaaagt catgcacatt ttattgccaa gtcccttttc 660
gaggagtatc ttatggtgga agaacttttc agtgatggaa ttcaggttat tgtacatgac 720
aagactaaac agatcagtat tagaaaaagc acacaaaatg ttcactcctt ttcactctct 780
tagttgggag aaactttttg catggctagc tgtatttatt cgaacaatct gacttgttat 840
ttttctctaa ttatgtcatg gcagtctgac gttattgaaa ccttgcgtca tcagcacagt 900
aaagacctgc agaaggttgt agacattgtg ttgtctcacc aggtaaattt gtttatggct 960
gatgactttt atgcaaatga ttagtgaaac aatctttgtt attgatagtg tgattttatt 1020
cacagggtgt gagaaacaaa gctaagcttg taacagcact catggaaaag ctggtttatc 1080

-continued

```
caaatccggt tgcttacagg gatctgttgg ttcgcttttc ttccctcaat cataaaagat   1140
attataaggt gcaatgatta gaataaccta gacatccccc ttataattta ttttgatgtt   1200
ttacctaatg aattccatgc atcttaataa acacagttgg cccttaaagc aagtgaactt   1260
cttgaacaaa ccaaactaag tgaactccgt gcaagcattg caagaagcct ttcagatctg   1320
gggatgcata agggagacat gactattaag gatagcatgg aagatttagt ctctgcccca   1380
ttgcctgttg aagatgctct tatttctttg tttgattaca gtgatgcaac tgttcagcag   1440
aaagtgattg agacatacat atcacgattg taccaggtat tatatcaact aagttgatgt   1500
ctttatagtc ccactaagca tatctgatat gttagatgcc ctaatgacat ggaatgctca   1560
tctcttcatt tcacatgaag aaatattgag aaatgagatg ctgatgtttg gctgcattaa   1620
ctgggtgtga aaaattgtga tctcccaact tgttaatgca caatgtgctg gctaacttgc   1680
caatatatat ttttttcag cctcatcttg tgaaggatag catccaaatg aaattcaagg   1740
aatctggtgc tattgctttt tgggaatttt ctgaagggca tgttgatact tcaaatggac   1800
atgggactat tcttggtagg aagagatggg gttccatggt catcctcaaa tcacttgaat   1860
ctgcatcaac agccattgtg gctgcattaa aggattcagc acagtacaac agctctgagg   1920
gcaacacgat gcacattgca ttattgagtg ctgaaaatga aagtaatatg agtggaacaa   1980
ggtttgttca tgtgcaatat taggtcgaaa ggggttttg tttaagtttt gtaactcttt   2040
tttttttaa ttgaggccat ttctttcagc agtgatgatc aagctcaaca taggatggaa   2100
aagcttacca agatactgaa ggatactaat gttgcaagtg atctccgagc tgctggtttg   2160
aaggttataa gttgcattgt tcaaagagat gaagctcgca tgccaatgcg ccacacattc   2220
ctctggttgg atgaaaagag ttgttatgaa gaagagcaaa ttctccggca tgtggagcct   2280
cccctctctg cacttcttga attggtctgt ttatcaaaat gattgcatgc ttgtttgcta   2340
cattctgtta ttatgctttg cttattttct tcactatact tattttgcct attatgaata   2400
cagggtaagt tgaaagtgaa aggatacaat gaaatgaagt atactccgtc acgtgatcgt   2460
caatggcata tctacacact aagaaatact gaaaacccca aaatgttgca tagggtattt   2520
ttccgaacta ttgtcaggca acccaatgca ggcaacaagt ttacatcagc tcaggtcagt   2580
gacactgaag taggaggtcc tgaagattct ctgtcattca catcgaatag catcctaaga   2640
tcattgatga ctgctataga agaattagag cttcatgcga ttaggacagg tcattctcac   2700
atgtatttgt gcatattgaa agagcaaaag cttcttgatc tcattccatt ttcagggtaa   2760
gtgtgtacat aatcctattc aaggaaatgt ttatgcattg actattatat cggtctcctt   2820
aacaagcttt tcatattatt caggagtaca attgttgatg ttggccaaga tgaagctact   2880
gcttgttcac ttttaaaatc aatggctttg aagatacatg accttgttgg tgcaaggatg   2940
catcatctgt ctgtatgcca gtgggaggtg aaactcaagt tggattgtga tgggcctgca   3000
agtggtacct ggagagttgt gactacaaat gttactagtc acacctgcac cattgatgta   3060
agttgtccct actgttttag tattctgtat atcacacaca tgaaagtata agtcaacgtg   3120
tggttcttat attccgaact gccatccatg tcattatgtt ctgaagcaca tagtacttct   3180
aatggtttta gatctaccga gaagtggaag atacagaatc gcagaagtta gtataccatt   3240
caaccacttc ggcagctggt cctggtccgt tgcatggtgt tgcactgaat aatccatatc   3300
aacctttaag tgtgattgat ctaaagcgct gctctgctag gaacaacaga acaacatatt   3360
gctacgattt tccgctggtg agttgacccc cgccccacgt gaatacacat ctgtagttat   3420
```

-continued

```
tttgaaccta agctgataat gacaaaaaaa atgtaggcat ttgaaactgc actgcagaag   3480
tcatggcagt ccaacggctc tagtgtttct gtaggcagta gaaatagtaa atcctacgtg   3540
aaggcaactg agctggtgtt tgctgaaaaa catgggtcct ggggcactcc tatagttccc   3600
atggaacgtc ctgctgggct caatgacatt ggtatggtcg cttggatctt ggagatgtca   3660
acacctgaat ttcccaatgg caggcagatt attgttatag caaatgatat tactttcaga   3720
gctggatcat tcggcccaag ggaagatgca ttttttgaag ctgtcaccaa cctggcttgt   3780
gaaaggaaac ttccccttat atacttggca gcaaactctg gtgctaggat tggcatagct   3840
gatgaagtaa aatcttgctt ccgtgttggg tggtctgacg aaggcagccc tgagcgaggg   3900
tttcagtaca tctatcttac tgaagaagac tatgcccgta ttagctcttc tgttatagca   3960
cataagctgc agctagatag cggtgaaatt aggtggatta ttgactctgt tgtgggcaag   4020
gaggatgggc ttggtgttga gaacatacat ggaagtgctg ctatcgccag tgcttattct   4080
agggcatatg aggagacatt tacacttaca tttgtgaccg gacggactgt aggaatagga   4140
gcttatcttg ctagacttgg tatacggtgc atacagcgtc ttgaccagcc gattatttta   4200
acagggtttt ctgccctgaa caagctcctt gggcgggaag tgtacagctc ccacatgcag   4260
cttggtggtc ctaagatcat ggcgaccaat ggtgttgtcc acctgactgt tccagatgac   4320
cttgaaggtg tttccaatat attgaggtgg ctcagctatg ttcctgcaaa cattggtgga   4380
cctcttccta ttaccaaacc tttggaccct ccagacagac ctgttgcata catccctgag   4440
aacacatgcg atccacgtgc agccatccgt ggtgtagatg acagccaagg gaaatggttg   4500
ggtggtatgt ttgacaaaga cagctttgtg gagacatttg aaggatgggc aaaaacagtg   4560
gttactggca gagcaaagct tggaggaatt cctgtgggtg tcatagctgt ggagacacag   4620
accatgatgc agcttgtccc tgctgatcca ggtcagcttg attcccatga gcgatccgtt   4680
cctcgggctg gacaagtgtg gttcccagat tctgcaacca agacagctca ggcattatta   4740
gacttcaacc gtgaaggatt gcctctgttt atcctggcta actggagagg tttctctggt   4800
ggacagagag atctctttga aggaattctt caggctgggt caacaattgt cgagaacctt   4860
aggacatata atcagcctgc gtttgtctac attcctatgg ctggagagct tcgtggagga   4920
gcttgggttg tggtcgatag caaaataaat ccagaccgca ttgagtgtta tgctgagagg   4980
actgccaaag gtaatgttct cgaacctcaa gggttaattg aaatcaagtt caggtcagag   5040
gaactccaag actgtatggg taggcttgac ccggagttga taaatctgaa agcaaaactc   5100
caagatgtaa agcatggaaa tggaagtcta ccagacatag aatcccttca gaagagtata   5160
gaagcacgta cgaaacagtt gctgccttta tatacccaga ttgcaatacg gtttgctgaa   5220
ttgcatgata cttccctaag aatggcagct aaaggcgtga ttaagaaagt tgtagactgg   5280
gaagaatcac gctctttctt ctataaaagg ctacggagaa ggatctctga agatgttctt   5340
gcaaaagaaa taagacatat agtcggtgac aacttcactc accaatcagc aatggagctc   5400
atcaaggaat ggtacctggc ttctccagcc acaacaggaa gcactggatg ggatgacgat   5460
gatgcatttg ttgcctggaa ggacagtcct gaaaactaca atggatatat ccaagagcta   5520
agggctcaaa aagtgtctca gtcgctctct gatctcactg actccagttc agatctacaa   5580
gcattctcgc agggtctttc tacgctatta gataaggtaa atttgcttac agtttcacct   5640
tattttttat ttgcaattaa cctgtgggct acaactggtt gtatctgttg cgtgttactt   5700
tttaagagct cctatttcaa ttgcattgca tacatggcat gttataaatt catgattcta   5760
atacataccc attgccttct cacgtattcc gtctttggat gctgattcag atggatccct   5820
```

```
ctcaaagagc gaagtttgtt caggaagtca agaaggtcct tggttgatga tatgatacca   5880

acacatccaa cactatgtgc atgctacatg tttttgttca agtacataca tagaaggata   5940

ttgcttggcc tcgtttgctt ggccgtttga tcatgtctga tctaagtcga ccattatttg   6000

ttgaaacttc ctttttggac ctggtgctat ggttgatgaa tgtatattgg atgtgtgcga   6060

ctgtgcgttc tgccaggtgt aagctcaaat gtttagacag accgagttat ggttaggaag   6120

agcacgagtg aacatgttct ggttttgcag tggttcagga aggcagaaaa ttgtttcact   6180

gtagttctga gatgtactac cagcggcccc ctgctgtaat tttagggtgt ataatgcgga   6240

tactagtaa                                                           6249
```

<210> SEQ ID NO 23
<211> LENGTH: 987
<212> TYPE: DNA
<213> ORGANISM: Sorghum halepense

<400> SEQUENCE: 23

```
cttcagtaag tttgttttga ttctgtgatt gtagttctgg tatgtcctta cataatcgat     60

ttttattcta gcttctgatg tttttatctt ttatgcatgc agttagagga taaatacaag    120

gaatacaagt tgaattttta ccgtggaaaa aacgtggact tcccttccaa gttgctaaga    180

gacatcattg aggtcagtta tgtttctttt gtggtatctc ttaaactgtt tgctattgtc    240

ttaatcttaa ctagtgtttt ctctgtagga aaatcttgca tatggttcag agaaggaaaa    300

ggctacaaat gagaggcttg ttgagcctct tacgaaccta ctgaagtcat atgagggtgg    360

gagagaaagt catgcacatt ttattgccaa gtccctttc gaggagtatc ttatggtgga    420

agaacttttc agtgatggaa ttcaggttat tgtacatgac aagactaaac agatcagtat    480

tagaaaaagc acacaaaatg ttcactcctt ttcactctct tagttgggag aaactttttg    540

catggctagc tgtatttatt cgaacaatct gacttgttat ttttctctaa ttatgtcatg    600

gcagtctgac gttattgaaa ccttgcgtca tcagcacagt aaagacctgc agaaggttgt    660

agacattgtg ttgtctcacc aggtaaattt gtttatggct gatgactttt atgcaaatga    720

ttagtgaaac aatctttgtt attgatagtg tgattttatt cacagggtgt gagaaacaaa    780

gctaagcttg taacagcact catggaaaag ctggtttatc caaatccggt tgcttacagg    840

gatctgttgg ttcgcttttc ttccctcaat cataaaagat attataaggt gcaatgatta    900

gaataaccta gacatccccc ttataattta ttttgatgtt ttacctaatg aattccatgc    960

atcttaataa acacagttgg cccttaa                                        987
```

<210> SEQ ID NO 24
<211> LENGTH: 6644
<212> TYPE: DNA
<213> ORGANISM: Sorghum halepense

<400> SEQUENCE: 24

```
ctaatttgag gcatccatcc tctccatcag agaggtcgac gaattctgta aagcgcttga     60

tggtgactcg ccaatacaca ggtgtgctgg tcgctaacaa tgggatggcc gcggtcaagt    120

tcatgggcag catccggata tgggccctgg agagctttgg gacagagaag gccattcttt    180

tggttgctat ggcaactccg gaggacttga ggataaacgc tgagcacata agaatcgctg    240

atcagttcgt agaagttcct ggaggaacaa acaataacaa ctatgcgaat gtacggctta    300

tagtggaggt tagcacaatt catcatctgg agttctgtaa attttcacaa gattgtgttt    360
```

-continued

```
aattttacat gtatttttca ctgtactttg gtaatttaca tttcaagttc aatttcatag    420
attgcagaga gaactcgtgt atctgcagtt tggcctggct ggggtcatgc gtctgagaac    480
ccagaacttc cagatgctct aaacgagaaa ggaatcattt ttcttgggcc accatcagct    540
gcaatggctg cacttggtga taagattggt tcttctctca ttgcacaagc agccagcaga    600
ataggaagag caaggacaca gtttttttat ttcctaaagc aaaatcgcaa aggcaagtag    660
gttgaccata tatgtgatga gagaaaaatc gagaccagat ggagaaattt gctattatag    720
gatcccaaac gtgtgggttt cgctataata ggattgtaaa catctgcttc gctataacga    780
ctctagaaac attgacactt tgctattata acatcatagc cttcaaatag acaaattgaa    840
ctcaaatatc ttcaaattca aatattatca tttaatcaca gaactgcgct tagggcggcg    900
gctgctgctg catggctgct ggctggcgct gctgcctggc cggctggctc agccttgccg    960
gctgcttgct gcagcaagat tcaaccatga tccaagccat gataacaaac aaaaatatag   1020
atccaagcca tagattcaac catgattata agttataaca caaacaagat catctcataa   1080
gaccaagatt gtgctggtgg ctggccatgg tcgggcagca gtcggcgcgt gcgaaggagg   1140
gagggcgtcg gtctctcgca tcggggaacc aatagtcgcg gctagcaact gaaaggtccc   1200
gtggtgaagg ggtatagcag tgattaaatg aaaatattga atttgaagag atttgagatc   1260
aatttgccta tttgaaggcc atgatgttat aatagcaaag tgttaatgtt tcgagagtca   1320
ttatagcgaa gcagatattt gggatcctat tatagcgaaa cccacacgtt tgggatgcta   1380
taatagcaaa tttctatatg agtccaaaca cgaaaaaggt gaataaagtc gaaataaagg   1440
ggaccaaccc catacaaaac aacaagctcc cctaaccaaa atgaaaagaa aacctactac   1500
ttcctgcata cttgacaaat tccgatcgtc cgcaacacgc aggatctctc ccttccccaa   1560
tcccacttga cacgccacaa cctgctcgac agaataccaa accgagtgcc aatcgccacc   1620
gaggaagcag gagcgatctt gtaccggcgg cgctgccaga aatcgcattt tggagctgga   1680
ttggactggg gacgcccccc agcggccgct tgcgcatgga gcgatgcaaa attccaacac   1740
cctgagcgga acagagctga gctactatgt tagcggctcc ccatctccag gcccagatgc   1800
tatggagcag gccggcccaa ggaggagtac cagaagccga aggcccaaca ggaatatctc   1860
tggggaagat tgggcgtgag cgcctgcgtg cgcgagtcta ggctaaggct tgtaagcgac   1920
tatatgagag gaaacctgag agagagaggc atcgaataat tgatgtaaac tcaactcatc   1980
ccctaagcac tcttggttgc tctatcccct tgctgttctt cctctcctga tccccaattc   2040
tctaatcctt tcccaaattg ctgtaacctg tttctgatgc taacaattgg tatcggagac   2100
actgttcctc agtgattctt ttcgcctgca cttactccat cgattgattg agcaaatgga   2160
tctggttggc ttgattgggt ttctagcagt gagctgctta aatagttgct tctctgctat   2220
taacttgcta tcatttcctc acggtatttc agaaactatt gcttgtctgt ttgaatttcg   2280
actattctga tgatgaatgg gaatagcatc gtggtagtga tttgttgaca ttcatctaag   2340
taccgcctct catgaatcgt gattaatata ctaacaatct gtttcttttg ctcctaccag   2400
gagatctgaa ctgaaaaggg tgaaataatg gcggagccct accaaatgaa cggcatactg   2460
aatgggatgc ctaatttgag gcatccatcc tctccatcag agaggtcgac gaattctgta   2520
aagcgcttga tggtgactcg ccaatacaca ggtgtgctgg tcgctaacaa tgggatggcc   2580
gcggtcaagt tcatgggcag catccggata tgggccctgg agagctttgg gacagagaag   2640
gccattcttt tggttgctat ggcaactccg gaggacttga ggataaacgc tgagcacata   2700
agaatcgctg atcagttcgt agaagttcct ggaggaacaa acaataacaa ctatgcgaat   2760
```

gtacggctta tagtggaggt tagcacaatt catcatctgg agttctgtaa attttcacaa 2820
gattgtgttt aattttacat gtatttttca ctgtactttg gtaatttaca tttcaagttc 2880
aatttcatag attgcagaga gaactcgtgt atctgcagtt tggcctggct ggggtcatgc 2940
gtctgagaac ccagaacttc cagatgctct aaacgagaaa ggaatcattt ttcttgggcc 3000
accatcagct gcaatggctg cacttggtga taagattggt tcttctctca ttgcacaagc 3060
agcaggagtt ccaactcttc catggagtgg atcacatgta tgccgtctcc tatttctgtg 3120
tggttttact cctattttcc tctgctactt ttgtgttcac ttaatattaa atcaaactct 3180
ctgcaggtaa aagttccacc agaaagctgc cattcaattc ccgaggagat atataagaat 3240
gcttgtgttt ccaccacaga ggaagcagtg gctagttgtc aggtggtcgg gtaccctgcc 3300
atgatcaagg catcttgggg agaagaaagg ttggttttct tgttcatctg aactgtggga 3360
aaaagaaggg accactattc agaaaaaaaa tgaagttaaa atttcagtaa aaaatttaga 3420
ttgattatca ctaattttgt tgtcatctgc atggatctgt aggttcataa cgatgatgag 3480
gtacttagat gaatgtcaac aaatcactac cacgatgcta ttcccattca tcatcagaat 3540
agtcgaaatt caaacagaca agcaatagtt tctgaaatac cgtgaggaaa tgatagcaag 3600
ttaatagcag agaagcaact atttaagcag atcaaatggt tcagcaccaa ctggttgtat 3660
cgtaatcgta atagagcata accagccagc agaataggaa gagcaaggac acagtttttt 3720
tatttcctaa agcaaaatcg caaaggcaag taggttgacc atatatgtga tgagagaaaa 3780
atcgagacca gatggagaaa tttgctatta taggatccca aacgtgtggg tttcgctata 3840
ataggattgt aaacatctgc ttcgctataa cgactctaga aacattgaca ctttgctatt 3900
ataacatcat agccttcaaa tagacaaatt gaactcaaat atcttcaaat tcaaatatta 3960
tcatttaatc acagaactgc gcttagggcg gcggctgctg ctgcatggct gctggctggc 4020
gctgctgcct ggccggctgg ctcagccttg ccggctgctt gctgcagcaa gattcaacca 4080
tgatccaagc catgataaca aacaaaaata tagatccaag ccatagattc aaccatgatt 4140
ataagttata acacaaacaa gatcatctca taagaccaag attgtgctgg tggctggcca 4200
tggtcgggca gcagtcggcg cgtgcgaagg agggagggcg tcggtctctc gcatcgggga 4260
accaatagtc gcggctagca actgaaaggt cccgtggtga aggggtatag cagtgattaa 4320
atgaaaatat tgaatttgaa gagatttgag atcaatttgc ctatttgaag gccatgatgt 4380
tataatagca aagtgttaat gtttcgagag tcattatagc gaagcagata tttgggatcc 4440
tattatagcg aaacccacac gtttgggatg ctataatagc aaatttctat atgagtccaa 4500
acacgaaaaa ggtgaataaa gtcgaaataa aggggaccaa ccccatacaa aacaacaagc 4560
tcccctaacc aaaatgaaaa gaaaacctac tacttcctgc atacttgaca aattccgatc 4620
gtccgcaaca cgcaggatct ctcccttccc caatcccact tgacacgcca caacctgctc 4680
gacagaatac caaaccgagt gccaatcgcc accgaggaag caggagcgat cttgtaccgg 4740
cggcgctgcc agaaatcgca ttttggagct ggattggact ggggacgccc cccagcggcc 4800
gcttgcgcat ggagcgatgc aaaattccaa caccctgagc ggaacagagc tgagctacta 4860
tgttagcggc tccccatctc caggcccaga tgctatggag caggccggcc caaggaggag 4920
taccagaagc cgaaggccca acaggaatat ctctggggaa gattgggcgt gagcgcctgc 4980
gtgcgcgagt ctaggctaag gcttgtaagc gactatatga gaggaaacct gagagagaga 5040
ggcatcgaat aattgatgta aactcaactc atcccctaag cactcttggt tgctctatcc 5100

```
ccttgctgtt cttcctctcc tgatccccaa ttctctaatc ctttcccaaa ttgctgtaac   5160

ctgtttctga tgctaacaat tggtatcgga gacactgttc ctcagtgatt cttttcgcct   5220

gcacttactc catcgattga ttgagcaaat ggatctggtt ggcttgattg ggtttctagc   5280

agtgagctgc tggtagaaat ctggtcgcta taattccact ccccgcttga acaatttgtg   5340

gcgtgcagac ggtctggatc ccgatccgcc ccttccccac caccacttca cccgtcgcaa   5400

gcgcaaattg gggtcatga gtcctcaaac caagcttatc atcgacgaaa tctcccgccg   5460

cttcaccgag cacgatctca agtgggattc ccgcttttcg gagcaggaat ctcgcttggt   5520

tcgccagatc caggatctgg agaagacgca tggcgaccgc gttgctatgc tggagggcgt   5580

ctccaagtcg cttgacgagt ggaagtcgtc catcgaggaa accattgatg gtacccaact   5640

ggaggtgaag aagctatctc gcacctgggc acgcaaggtc gtcgacaacc cgggcgactc   5700

aagtggcgtg tacgccgcat ctccatcgat ggttgggcgt ccgccttccg ccaagcctcc   5760

agaccctgcc gctattccgc agcctgtgtt tgggcaccat ggtgaacccc atcaacggga   5820

gagtggattt ggggttgttt caaccctggt tcattccccg gtcaagggtg agcatccact   5880

tcctaaacct ccctttccgc attcttttgg atttcctaaa cctgtgggtc tgtcgtctga   5940

taatcagtct tgggaggagg gtcgtaaatc tggctttaac aaattcccta aggttaattt   6000

tcctgtgttt gatggggaac aacctaaagt ttggttgcgt gattgcttag attactttga   6060

gctctatgcg gtagaaccaa gttcatgggt tagaattgct cgcatgcatt tagttgctgc   6120

tgctaagcgt tggtatagct ctgttgagtc ccaggttcag gataccaatt gaaaactttt   6180

gctgccttag tgcttaatcg ctttgcacag gagcatcatg aattgttgtt gcgccagctt   6240

ttccaaattc accaaacggc catggtggct gagtatattg atcagttttt agccattgtt   6300

gaccaactgg gggcttataa cagaaccact gatcccacgt tttataccat gcgtttcatt   6360

gatggattac aagagcatat ttgtgctgtt gttgctcttc atcgtccgcc aaatttggat   6420

attgcttgcc tccttgctaa attgtaggaa gagatggctg atcccgcgct caaacaggat   6480

gtccggaggg ataatcaggc tggtcaccgg ccatatcaca agaatgcttt cccatttgtc   6540

ggtctccctc atcacaactg atgccctatc atgtcccttg tatatgtact tgaacaaata   6600

ctttactgat ttaatgctcc cacaagcctc aacgtttata tggc                     6644
```

<210> SEQ ID NO 25
<211> LENGTH: 1743
<212> TYPE: DNA
<213> ORGANISM: Sorghum halepense
<220> FEATURE:
<221> NAME/KEY: unsure
<222> LOCATION: (1)..(1743)
<223> OTHER INFORMATION: unsure at all n locations

<400> SEQUENCE: 25

```
ctgcatgtgg gagcttgggt tgtggtcgat agcaaaataa atccagaccg cattgagtgt     60

tatgctgaga ggactgccaa aggtaatgtt ctcgaacctc aagggttaat tgaaatcaag    120

ttcaggtcag aggaactcca agactgtatg ggtaggcttg acccggagtt gataaatctg    180

aaagcaaaac tccaagatgt aaagcatgga aatggaagtc taccagacat agaatccctt    240

cagaagagta tagaagcacg tacgaaacag ttgctgcctt tatataccca gattgcaata    300

cggtttgctg aattgcatga tacttcccta agaatggcag ctaaaggcgt gattaagaaa    360

gttgtagact gggaagaatc acgctctttc ttctataaaa ggctacggag aaggatctct    420

gaagatgttc ttgcaaaaga aataagacat atagtcggtg acaacttcac tcaccaatca    480
```

gcaatggagc tcatcaagga atggtacctg gcttctccag ccacaacagg aagcactgga 540
tgggatgacg atgatgcatt tgttgcctgg aaggacagtc ctgaaaacta caatggatat 600
atccaagagc taagggctca aaaagtgtct cagtcgctct ctgatctcac tgactccagt 660
tcagatctac aagcattctc gcagggtctt tctacgctat tagataaggt aaatttgctt 720
acagtttcac cttatttttc atttgcaatt aacctgtggg ctacaactag ttgtatctgt 780
tgcatgttac tttttaagag ctcctatttc aattgcattg catacatggc atgttataaa 840
ttcatgattc taatacatac ccattgcctt ctcacgtatt ccgtctttgg atgctgattc 900
agatggatcc ctctcaaaga gcgaagtttg ttcaggaagt caagaaggtc cttggttgat 960
gatatgatac caacacatcc aacactatgt gcatgctaca tgtttttgtt caagtacata 1020
catagaagga tattgcttgg cctcgtttgc ttggccgttt gatcatgtct gatctaagtc 1080
gaccattatt tgttgaaact tcctttttgg acctggtgct atggttgatg aatgtatatt 1140
ggatgtgtgc gactgtgcgt tctgccaggt gtaagctcaa atgtttagac agaccgagtt 1200
atggttagga agagcacgag tgaacatgtt ctggttttgc agtggttcag gaaggcagaa 1260
aattgtttca ctgtagttct gagatgtact accagcggcc ccctgctgta attttagggt 1320
gtataatgcg gatactagta agactatctc caacaatcgt cacccaaaat acaagaccca 1380
tttgtccttt gggtagcgct acaggtaaaa ggttccatac ctatttttag tcttcnnnnn 1440
nnnnngagag aggataccca aatttgggtt atgtctctcc tgatacccaa aatgagtttt 1500
ctgtttgggt actctgttgg aggctatagg tattgtgttg gagacccatt ttgggtttgg 1560
gttcccaaat gggtctccta ttggagacag cctaaaacaa ttgagtggtt cattaaattt 1620
tgaactcgaa taatgttttt ctaggcatat gtaccttacc tctacgtgaa ataaatgctg 1680
ttgaaatagc attcgacacc agaatatatg taccttacct aagagcaagt attataatac 1740
agc 1743

<210> SEQ ID NO 26
<211> LENGTH: 1984
<212> TYPE: DNA
<213> ORGANISM: Sorghum halepense

<400> SEQUENCE: 26
gctcttgagc gctgcggcgt ccgcgacgtc ttcgcctacc ccggcggcgc gtccatggag 60
atccaccagg cactcacccg ttccccgtc atcgccaacc acctcttccg ccacgagcaa 120
ggggaggcct tcgccgcctc tggcttcgcg cgctcctcgg gccgcgtcgg cgtctgcgtc 180
gccacctccg gccccggcgc caccaaccta gtctccgcgc ttgccgacgc gctgctcgac 240
tccgtcccca tggtcgccat cacgggacag gtgccgcgac gcatgattgg caccgacgcc 300
ttccaggaga cgcccatcgt cgaggtcacc cgctccatca ccaaacataa ctacctggtc 360
ctcgacgtcg acgacatccc ccgcgtcgtg caggaggctt tcttcctcgc ctcttctggt 420
cgcccgggac cggtgcttgt cgacatcccc aaggacatcc agcagcagat ggccgtgccg 480
gtctgggaca cgcccatgag tctgcctggg tacattgcgc gccttcccaa gcctcctgcg 540
actgaattgc ttgagcaggt gctgcgtctt gttggtgaat caaggcgccc tgttctttat 600
gttggtggtg gctgcgcagc atctggcgag gagttgcgcc gctttgtgga gatgactgga 660
atcccagtca caactactct tatgggcctt ggcaacttcc ccggcgacga cccactgtct 720
ctgcgcatgc ttggtatgca tggcacggtg tatgcaaatt atgcagtgga taaggcggat 780
ctgttgcttg catttggtgt gcggtttgat gatcgtgtga cagggaagat tgaggctttt 840
gcaagcaggg ctaagattgt gcacattgat attgatcccg ctgagattgg caagaacaag 900
cagccacatg tgtccatctg tgcagacgtt aagcttgctt tgcagggcat gaatgctctt 960
ctggaaggaa gcacatcaaa gaagagcttt gactttggct catggcaagc tgagttggat 1020
cagcagaaga gagagttccc ccttgggtat aaaacttttg atgacgagat ccagccacaa 1080
tatgctattc aggttcttga tgagctgaca aaaggggagg ccatcattgc cacaggtgtt 1140
gggcagcacc agatgtgggc ggcacagtac tacacttaca agcggccaag gcagtggttg 1200
tcttcagctg gtcttggggc tatgggattt ggtttgccgg ctgctgctgg cgctgctgtg 1260
gccaacccag gtatcactgt tgttgacatc gacggagatg gtagcttcct catgaacatt 1320
caggagctag ctatgatccg aattgagaac ctcccagtga aggtctttgt gctaaacaac 1380
cagcacctgg ggatggtggt gcagtgggag gacaggttct ataaggccaa tagagcacac 1440
acatacttgg gaaacccaga gaatgaaagt gagatatatc cagatttcgt gacaattgcc 1500
aaagggttca acattccagc agtccgtgtg acaaagaaga gcgaagtcca tgcagcaatc 1560
aagaagatgc ttgagactcc agggccatac ctcttggata taatcgtccc gcaccaggag 1620
catgtgttgc ctatgatccc tagtggtggg gctttcaagg atatgatcct ggatggtgat 1680
ggcaggactg tgtattgatc taaatttcag catgcacatc tccctgcctt tctttgacat 1740
gcatatgagc tggtacaagg gtgatgtgtt atttatgtga tgttctcctg tgttctatct 1800
ttttgtaagc cgtcagctat ctatagtgtg cttgtttgat gtactctgtt atggtaatct 1860
taagtagttt cctaccttgt agtggtgtag tctgttgttt cgtgctggca tatctgtcat 1920
cagaggtcat gtaagtgcct tttgctacag ataaataagg aaataagcat tgctatgcag 1980
tggt 1984

<210> SEQ ID NO 27
<211> LENGTH: 1361
<212> TYPE: DNA
<213> ORGANISM: Sorghum halepense

<400> SEQUENCE: 27
atagagccat aggaaatatg gaaattaaca acaggggaca ttacagatca ggtctgtgga 60
cctggcacta ctaaactttg ttgcttggct gacatctcta gttgtgaata cagataatgg 120
gtttggttcg cattttcaaa gcagaagtgg ttgatctttc agaccataca ctaactattg 180
aggtaatatc tgtggtgtgt cttcgctcga agattactga tgttgtcttt cttatggttc 240
tttgtggtta tgttaaaggt aactggagat cctggaaaga tggttgcaat acagaagact 300
ctgagcaaat atgggatcag agaaattgct agaactggca agatagcttt acgccgtgaa 360
agaatgggag aaactgctcc attttggagg ttctctgcag cttcttatcc tgatctcgaa 420
atggcaatac cttcaaattt ccagcaaaac actggtgcga gggcaatcga tcagaataca 480
gaaggatctt caggggggtga tgtttatcca gtggaatctt atgaaagctt ctcatcaagt 540
caaattctgg atgctcattg ggtgttatg actgatggtg atccaacagg gttttgttca 600
catactctat caattcttgt gaatgatgtc cctggagttc tcaatgttgt aacaggtgtt 660
ttctccagaa ggggctacaa tattcagagt cttgctgttg gtccagctgc aaaagaagga 720
acttctcgca tcactactgt tgttcctgga actgatgaat ccattgccaa gctagtacat 780
caactgtaca agctcattga tgttcatgag gtccaggatt ttactcactt accatttgtt 840
ggtagagagt taatgatcat aaaggttgct gcaaatgcta cagcccgaag ggatgtctta 900

```
gatattgctc agatttttga ggcacagaaa gttgacatat ctgatcacac aattacacta    960
ctgctcaccg gagacattga cagaatggtt agattgcaaa agatgctgga gcaatatggt   1020
atctgtgagg ttgcacgaac aggacgggtt gctctgctcc gtgagtctgg agttgactcc   1080
aaataccttc gtgggttttc cctccctctg taattctcca tctgcggatc gacatagcac   1140
tccacaattc aggtcgcacg gccattttga ggaatcattc aaatattcta gggtgagaac   1200
tgtagacaca ctatattgtt ggggttgcta cgttctatgc tattaagctt cttgcttatg   1260
caagtatata tcacgcagca cctgggcaga aaccatatcc ggtccaatat tttcattgca   1320
caggtagtat acgtgtccta gttgaaggaa aggcagtata t                       1361
```

<210> SEQ ID NO 28
<211> LENGTH: 2080
<212> TYPE: DNA
<213> ORGANISM: Sorghum halepense

<400> SEQUENCE: 28

```
atattattca attataaact aattagattt aaaaattcat cttgtgattt atggataaac     60
tgtgtaatta gtttttattt tcgtccatat ctaatgtttc atgcatatgc tctatgattt    120
aatgtgacaa agttttttttg tttcgggaga aaaaggtgat gcggagccgc cagtcctaga    180
ttgggaaatc aaccacctca tccgtccgcg tgtgcgcgtt gacacaaaag tccctctctc    240
cctccgaaaa cccccgccgc ggcgttccgt tccccctccg gcatctccgg tatccatcct    300
ttcgccatga acgctgctgc aatcatctcc cgacttggcc tcgccacctc agggcctggg    360
gccgggtccc acgcggactg ccggccgccg acgccggcgg tgggtttcac ggcggggccg    420
agagcgcgcc cagttgccgt cgccgccgcc gcctcctcct cttctccggc gaccgatggc    480
gtggcgccgg tgccaccccg ctccaatcac tcggtcataa agcgtcacac actatcagtt    540
tttgttggtg atgaaagtgg gatgatcaat cgaattgctg ggtttttgc tagaagagga    600
tataacatcg agtcattggc tgttgggttg aacaaggata aagcattatt tacaatagtt    660
gtgtcaggaa cagacaaaat attgaaccag gttgtagagc aactaaacaa acttgttaat    720
gtaataaagg ttgatgactt atcaatggaa ccacaagttg aaagagaact tatgcttata    780
aaagtaaatg cagagcggga aaagctacct gagataatgg gtttggttcg cattttcaaa    840
gcagaagtgg ttgatctttc agaccataca ctaactattg aggtaatatc tgtggtgtgt    900
cttcgctcga agattactga tgttgtcttt cttatggttc tttgtggtta tgttaaaggt    960
aactggagat cctggaaaga tggttgcaat acagaagact ctgagcaaat atgggatcag   1020
agaaattgct agaactggca agatagcttt acgccgtgaa agaatgggag aaactgctcc   1080
attttggagg ttctctgcag cttcttatcc tgatctcgaa atggcaatac cttcaaattt   1140
ccagcaaaac actggtgcga gggcaatcga tcagaataca gaaggatctt caggggggtga   1200
tgtttatcca gtggaatctt atgaaagctt ctcatcaagt caaattctgg atgctcattg   1260
gggtgttatg actgatggtg atccaacagg gttttgttca catactctat caattcttgt   1320
gaatgatgtc cctggagttc tcaatgttgt aacaggtgtt ttctccagaa ggggctacaa   1380
tattcagagt cttgctgttg gtccagctgc aaaagaagga acttctcgca tcactactgt   1440
tgttcctgga actgatgaat ccattgccaa gctagtacat caactgtaca agctcattga   1500
tgttcatgag gtccaggatt ttactcactt accatttgtt ggtagagagt taatgatcat   1560
aaaggttgct gcaaatgcta cagcccgaag ggatgtctta gatattgctc agatttttga   1620
```

```
ggcacagaaa gttgacatat ctgatcacac aattacacta ctgctcaccg gagacattga   1680
cagaatggtt agattgcaaa agatgctgga gcaatatggt atctgtgagg ttgcacgaac   1740
aggacgggtt gctctgctcc gtgagtctgg agttgactcc aaataccttc gtgggttttc   1800
cctccctctg taattctcca tctgcggatc gacatagcac tccacaattc aggtcgcacg   1860
gccattttga ggaatcattc aaatattcta gggtgagaac tgtagacaca ctatattgtt   1920
ggggttgcta cgttctatgc tattaagctt cttgcttatg caagtatata tcacgcagca   1980
cctgggcaga aaccatatcc ggtccaatat tttcattgca caggtagtat acgtgtccta   2040
gttgaaggaa aggcagtata tctgtctctt atacacatct                         2080
```

<210> SEQ ID NO 29
<211> LENGTH: 2080
<212> TYPE: DNA
<213> ORGANISM: Sorghum halepense

<400> SEQUENCE: 29

```
atattattca attataaact aattagattt aaaaattcat cttgtgattt atggataaac     60
tgtgtaatta gtttttattt tcgtccatat ctaatgtttc atgcatatgc tctatgattt    120
aatgtgacaa agttttttttg tttcgggaga aaaaggtgat gcggagccgc cagtcctaga   180
ttgggaaatc aaccacctca tccgtccgcg tgtgcgcgtt gacacaaaag tccctctctc    240
cctccgaaaa cccccgccgc ggcgttccgt tccccctccg gcatctccgg tatccatcct    300
ttcgccatga acgctgctgc aatcatctcc cgacttggcc tcgccacctc agggcctggg    360
gccgggtccc acgcggactg ccggccgccg acgccggcgg tgggtttcac ggcggggccg    420
agagcgcgcc cagttgccgt cgccgccgcc gcctcctcct cttctccggc gaccgatggc    480
gtggcgccgg tgccaccccg ctccaatcac tcggtcataa agcgtcacac actatcagtt    540
tttgttggtg atgaaagtgg gatgatcaat cgaattgctg gggtttttgc tagaagagga    600
tataacatcg agtcattggc tgttgggttg aacaaggata aagcattatt tacaatagtt    660
gtgtcaggaa cagacaaaat attgaaccag gttgtagagc aactaaacaa acttgttaat    720
gtaataaagg ttgatgactt atcaatggaa ccacaagttg aaagagaact tatgcttata    780
aaagtaaatg cagagcggga aaagctacct gagataatgg gtttggttcg cattttcaaa    840
gcagaagtgg ttgatctttc agaccataca ctaactattg aggtaatatc tgtggtgtgt    900
cttcgctcga agattactga tgttgtcttt cttatggttc tttgtggtta tgttaaaggt    960
aactggagat cctggaaaga tggttgcaat acagaagact ctgagcaaat atgggatcag   1020
agaaattgct agaactggca agatagcttt acgccgtgaa agaatgggag aaactgctcc   1080
attttggagg ttctctgcag cttcttatcc tgatctcgaa atggcaatac cttcaaattt   1140
ccagcaaaac actggtgcga gggcaatcga tcagaataca gaaggatctt caggggggtga  1200
tgtttatcca gtggaatctt atgaaagctt ctcatcaagt caaattctgg atgctcattg   1260
gggtgttatg actgatggtg atccaacagg gttttgttca catactctat caattcttgt   1320
gaatgatgtc cctggagttc tcaatgttgt aacaggtgtt ttctccagaa ggggctacaa   1380
tattcagagt cttgctgttg gtccagctgc aaaagaagga acttctcgca tcactactgt   1440
tgttcctgga actgatgaat ccattgccaa gctagtacat caactgtaca agctcattga   1500
tgttcatgag gtccaggatt ttactcactt accatttgtt ggtagagagt taatgatcat   1560
aaaggttgct gcaaatgcta cagcccgaag ggatgtctta gatattgctc agatttttga   1620
ggcacagaaa gttgacatat ctgatcacac aattacacta ctgctcaccg gagacattga   1680
```

```
cagaatggtt agattgcaaa agatgctgga gcaatatggt atctgtgagg ttgcacgaac   1740

aggacgggtt gctctgctcc gtgagtctgg agttgactcc aaataccttc gtgggttttc   1800

cctccctctg taattctcca tctgcggatc gacatagcac tccacaattc aggtcgcacg   1860

gccattttga ggaatcattc aaatattcta gggtgagaac tgtagacaca ctatattgtt   1920

ggggttgcta cgttctatgc tattaagctt cttgcttatg caagtatata tcacgcagca   1980

cctgggcaga aaccatatcc ggtccaatat tttcattgca caggtagtat acgtgtccta   2040

gttgaaggaa aggcagtata tctgtctctt atacacatct                         2080
```

```
<210> SEQ ID NO 30
<211> LENGTH: 528
<212> TYPE: DNA
<213> ORGANISM: Sorghum halepense

<400> SEQUENCE: 30

acaatataca gagccttgct gttggcccag ctgagaagga aggcatttca cgtattacaa     60

cagttgttcc tggtactgtt gaatccattg agaagttagt tcagcagctt tacaagcttg    120

ttgatgtgca tgaagttcat gacattaccc cctcaccttt tgctgaaagg gaactgatgc    180

ttattaaggt ttctgtaaac actgctgctc ggagggaaat cctagatatt gccgaaatct    240

tccgagcaaa acctgttgat gtttctgacc atacagtaac gcttcagctt actggagatt    300

ttgacaagat ggttgcacta caaaggttat tggagccata tggcatctgc gaggtcgcca    360

gaactggacg agtggcactg gtccgcgaat cgaaggtcga ctccaagtac ctccgcggct    420

actctcttcc attgtaacct ggcatttgtg atggtgatgg cctgatgaag agcttggttg    480

gttgttatag agcagaccat ctggcgctgg gttgtgttgt gcagttac                 528
```

```
<210> SEQ ID NO 31
<211> LENGTH: 2559
<212> TYPE: DNA
<213> ORGANISM: Sorghum halepense

<400> SEQUENCE: 31

cgccgcgccc atcaggtgct cagcggcgcc acccgccacg ctgacggtga cggctccccc     60

ggccaccccg ctccggccgt ggggccccac cgatccccgc aagggcgccg acatcctcgt    120

cgaggctctt gagcgctgcg gcgtccgcga cgtcttcgcc taccccggcg gcgcgtccat    180

ggagatccac caggcactca cccgttcccc cgtcatcgcc aaccacctct tccgccacga    240

gcaaggggag gccttcgccg cctctggctt cgcgcgctcc tcgggccgcg tcggcgtctg    300

cgtcgccacc tccggccccg gcgccaccaa cctagtctcc gcgctcgccg acgcgctgct    360

cgactccgtc cccatggtcg ccatcacggg acaggtgccg cggcgcatga ttggcaccga    420

cgccttccag gagacgccca tcgtcgaggt cacccgctcc atcaccaaac acaactatct    480

ggtccttgac gtcgacgaca tcccccgcgt cgtgcaggag gctttcttcc tcgcctcctc    540

tggtcgcccg ggaccggtgc ttgtcgacat ccccaaggac atccagcagc agatggccgt    600

gccggtctgg gacacgccca tgagtctgcc tgggtacatt gcgcgccttc ccaagcctcc    660

tgcgactgaa ttgcttgagc aggtgctgcg tcttgttggt gaatcaaggc gccctgttct    720

ttatgttggt ggtggctgcg cagcatctgg cgaggagttg cgccgctttg tggagatgac    780

tggaatccca gtcacaacta ctcttatggg ccttggcaac ttccccggcg acgacccact    840

gtctctgcgc atgcttggta tgcatggcac ggtgtatgca aattatgcag tggataaggc    900
```

agatcttttg cttgcatttg gtgtgcggtt tgatgatcgt gtgacaggga agattgaggc 960
ttttgcaagc agggctaaga ttgtgcacat tgatattgat cccgctgaga ttggcaagaa 1020
caagcagcca catgtgtcca tctgtgcaga cgttaagctt gctttgcagg gcatgaatgc 1080
tcttctggaa ggaagcacat caaagaagag ctttgacttt ggctcatggc aagctgagtt 1140
ggatcagcag aagagagagt tccccttgg gtataaaact tttgatgacg agatccagcc 1200
acaatatgct attcaggttc ttgatgagct gacaaaaggg gaggccatca ttgccacagg 1260
tgttgggcag caccagatgt gggcggcaca gtactacact tacaagcggc caaggcagtg 1320
gttgtcttca gctggtcttg ggctatggg atttggtttg ccggctgctg ctggcgctgc 1380
tgtggccaac ccaggtatca ctgttgttga catcgacgga gatggtagct tcctcatgaa 1440
cattcaggag ctagctatga tccgaattga gaacctccca gtgaaggtct ttgtgctaaa 1500
caaccagcac ctggggatgg tggtgcagtg ggaggacagg ttctataagg ccaatagagc 1560
acacacatac ttgggaaacc cagagaatga aagtgagata tatccagatt tcgtgacaat 1620
tgccaaaggg ttcaacattc cagcagtccg tgtgacaaag aagagcgaag tccatgcagc 1680
aatcaagaag atgcttgaga ctccagggcc atacctcttg gatataatcg tcccgcacca 1740
ggagcatgtg ttgcctatga tccctagtgg tggggctttc aaggatatga tcctggatgg 1800
tgatggcagg actgtgtatt gatctaaatt tcagcatgca catctccctg cctttctttg 1860
acatgcatat gagctggtac aagggtgatg tgttatttat gtgatgttct cctgtgttct 1920
atctttttgt aagccgtcag ctatctatag tgtgcttgtt tgatgtactc tgttatggta 1980
atcttaagta gtttcctacc ttgtagtggt gtagtctgtt gtttcgtgct ggcatatctg 2040
tcatcagagg tcatgtaagt gccttttgct acagataaat aaggaaataa gcattgctat 2100
gcagtggttc tgaattggct tctgttacca aatttaggtg ttcaactggt ccttgctttt 2160
gttttagctc ttttttcttt gtttgtttat tttgttgtta attccaactc aacataatgt 2220
gtatgtcatg tggggccgtg cgtatacaag acgccggcgt gccagagacg tgcgcggcag 2280
agcgcggtga ccgcgcgcag atccaggggg atcaggccca gcatggctga gttatctctt 2340
aggcttagtt gctgttttat ttcccttaat cttaggaggt ttgttgggcc tgaggccaat 2400
atattgtact cggtgaacaa ttagatggat taagtagaaa gttatcccta atcgtatctc 2460
tctctcccaa tatcgttaag cctgcggcgg aggggtaaac ctcgccggag aagacggatc 2520
gtggctacga actacgtagc cgaggtcctg ctacccagg 2559

<210> SEQ ID NO 32
<211> LENGTH: 1043
<212> TYPE: DNA
<213> ORGANISM: Sorghum halepense

<400> SEQUENCE: 32
caggttcttg atgagctgac aaaaggggag gccatcattg ccacaggtgt tgggcagcac 60
cagatgtggg cggcacagta ctacacttac aagcggccaa ggcagtggtt gtcttcagct 120
ggtcttgggg ctatgggatt tggtttgccg gctgctgctg gcgctgctgt ggccaaccca 180
ggtatcactg ttgttgacat cgacggagat ggtagcttcc tcatgaacat tcaggagcta 240
gctatgatcc gaattgagaa cctcccagtg aaggtctttg tgctaaacaa ccagcacctg 300
gggatggtgg tgcagtggga ggacaggttc tataaggcca atagagcaca cacatacttg 360
ggaaacccag agaatgaaag tgagatatat ccagatttcg tgacaattgc caaagggttc 420
aacattccag cagtccgtgt gacaaagaag agcgaagtcc atgcagcaat caagaagatg 480

-continued cttgagactc cagggccata cctcttggat ataatcgtcc cgcaccagga gcatgtgttg 540
cctatgatcc ctagtggtgg ggctttcaag gatatgatcc tggatggtga tggcaggact 600
gtgtattgat ctaaatttca gcatgcacat ctccctgcct ttctttgaca tgcatatgag 660
ctggtacaag ggtgatgtgt tatttatgtg atgttctcct gtgttctatc tttttgtaag 720
ccgtcagcta tctatagtgt gcttgtttga tgtactctgt tatggtaatc ttaagtagtt 780
tcctaccttg tagtggtgta gtctgttgtt tcgtgctggc atatctgtca tcagaggtca 840
tgtaagtgcc ttttgctaca gataaataag gaaataagca ttgctatgca gtggttctga 900
attggcttct gttaccaaat ttaggtgttc aactggtcct tgcttttgtt ttagctcttt 960
ttttcttgtt tgtttatttt gttgttaatt ccaactcaac ataatgtgta tgtcatgtgg 1020
ggccgtgcgt atacaagacg ccg 1043

<210> SEQ ID NO 33
<211> LENGTH: 1248
<212> TYPE: DNA
<213> ORGANISM: Sorghum halepense

<400> SEQUENCE: 33
cactaccgct gcgcccaagg cgaggcgccg ggcgcacctc ctggccgcac ggcgcgccct 60
cgccgcgccc atcaggtgct cagcggcgcc acccgccacg ctgacggtga cggctccccc 120
ggccaccccg ctccggccgt ggggccccac cgatccccgc aagggcgccg acatcctcgt 180
cgaggctctt gagcgctgcg gcgtccgcga cgtcttcgcc taccccggcg gcgcgtccat 240
ggagatccac caggcactca cccgttcccc cgtcatcgcc aaccacctct tccgccacga 300
gcaaggggag gccttcgccg cctctggctt cgcgcgctcc tcgggccgcg tcggcgtctg 360
cgtcgccacc tccggccccg gcgccaccaa cctagtctcc gcgcttgccg acgcgctgct 420
cgactccgtc cccatggtcg ccatcacggg acaggtgccg cgacgcatga ttggcaccga 480
cgccttccag gagacgccca tcgtcgaggt cacccgctcc atcaccaaac ataactacct 540
ggtcctcgac gtcgacgaca tcccccgcgt cgtgcaggag gctttcttcc tcgcctcttc 600
tggtcgcccg ggaccggtgc ttgtcgacat ccccaaggac atccagcagc agatggccgt 660
gccggtctgg gacacgccca tgagtctgcc tgggtacatt gcgcgccttc ccaagcctcc 720
tgcgactgaa ttgcttgagc aggtgctgcg tcttgttggt gaatcaaggc gccctgttct 780
ttatgttggt ggtggctgcg cagcatctgg cgaggagttg cgccgctttg tggagatgac 840
tggaatccca gtcacaacta ctcttatggg ccttggcaac ttccccggtg acgacccact 900
gtctctgcgc atgcttggta tgcatggcac ggtgtatgca aattatgcag tggataaggc 960
agatcttttg cttgcatttg gtgtgcggtt tgatgatcgt gtgacaggga agattgaggc 1020
ttttgcaagc agggctaaga ttgtgcacat tgatattgat cccgctgaga ttggcaagaa 1080
caagcagcca catgtgtcca tctgtgcaga cgttaagctt gctttgcagg gcatgaatgc 1140
tcttctggaa ggaagcacat caaagaagag ctttgacttt ggctcatggc aagctgagtt 1200
ggatcagcag aagagagagt tccccttgg gtataaaact tttgatga 1248

<210> SEQ ID NO 34
<211> LENGTH: 1542
<212> TYPE: DNA
<213> ORGANISM: Sorghum halepense

<400> SEQUENCE: 34

```
atgctaaaag tgtaatattt tcactcatac aaatggagaa gctttcagga tcaatagtca     60

acagataaaa catgtttatt ttcactcaaa taaacaaaga gtaatcttcc atgtctattg    120

aattattact aaagtgatgt aaactttaat acaacttaaa cctttatttt tcttctcaag    180

ttcagttcta tcaatatcaa ttgaaaaaac tattctctgt tatatgctat tttagtcctt    240

tccttccagg aacctaggga ataactaatg catgtccatg aaaaacagcg aagttgcatc    300

cttataagtg ttgtaaatag ttcgatcgtg tggcaaaggc aaaatgctat taagcatatg    360

caactaatta tttgttatta acagcgttta ctgcactttc tcactgatgt gcctcatgta    420

ttttccttaa tttgtagggt cataaagcgt cacacactat cagtttttgt tggtgatgaa    480

agtgggatga tcaatcgaat tgctggggtt tttgctagaa gaggatataa catcgagtca    540

ttggctgttg ggttgaacaa ggataaagca ttatttacaa tagttgtgtc aggaacagac    600

aaaatattga accaggttgt agagcaacta aacaaacttg ttaatgtaat aaaggttagt    660

cattttcctg tgccatttgg cttatagaat gattgataac taatatgctg tgaaactcat    720

tgcttgttgt tttgttctta ttattctgtt caatggtgta tcttctactc atagcttaat    780

atttggatta ataaacaggt tgatgactta tcaatggaac cacaagttga aagagaactt    840

atgcttataa aagtaaatgc agagcgggaa aagctacctg aggtacagac atactcatct    900

ttcaaaatgt atctgcacct tcttggcctg taactcaaac tgaacattaa atgtggatca    960

tttttttgta tagagccata ggaaatatgg aaattaacaa tagggacatt acagatcagg   1020

tctgtggacc tggcactact aaactttgtt gcttggctga catctctagt tgtgaataca   1080

gataatgggt ttggttcgca ttttcaaagc agaagtggtt gatctttcag accatacact   1140

aactattgag gtaatatctg tggtgtgtct tcgctagaag attactgatg ttgtctttct   1200

tatggttctt tgtggttatg ttaaaggtaa ctggagatcc tggaaagatg gttgcaatac   1260

agaagactct gagcaaatat gggatcagag aaattgctag aactggcaag gtcattcttg   1320

ttcagaaaat agtgaaaata tatcctgatc ttgttcttta ctagacctaa catttgtctt   1380

atagatagct ttacgccgtg aaagaatggg agaaactgct ccattttgga ggttctctgc   1440

agcttcttat cctgatctcg aaatggcaat accttcaaat ttccagcaaa acactggtgc   1500

gagggcaatc gatcagaata cagaaggatc ttcaggggta ag                      1542
```

<210> SEQ ID NO 35
<211> LENGTH: 1537
<212> TYPE: DNA
<213> ORGANISM: Sorghum halepense

<400> SEQUENCE: 35

```
gatttatgaa tgatgtttgc tttagcttct ctcactgtta cgatgttttt caactgatat     60

ttccctagtt ctatgcttcc tattgattag cttcatgtgg tcaattggtt catctccttg    120

aattggtttt agttggtgct cattctgttg aattgggtac taagtagtaa gtacaactcc    180

atttgtcttt ctgaggatac ttcttactgc tattgatagt ttagtaacat tagtccttcc    240

aatgtgaacc ctgtatgtgt gtacatgcac atgttgtcat ttatatattt tcctatttgc    300

acatatctga cattgcagtc aaatagcatg aatgcattac ttaatttgtt ttttggactc    360

ttttaagtat tttggcagta tcattaatta ttaaagtaag aaaatactcg cacattcttt    420

ttcttattgg tgtaatgttt tctgaaaata ccttttatca tcctcacact gttagtttga    480

gtttgaatga gtttatttat atgtatttct ctgcttctac ccagggtgat gtttatccag    540

tggaatctta tgaaagcttc tcatcaagtc aaattctgga tgctcattgg ggtgttatga    600
```

ctgatggtga tgtacggtct tgtgttctaa tgactttgaa ctgtttggtg ctagctagag 660
atgaaccaca tctagttgta ctcatttcac tagaagctat tgtgttgtta gaagttaaaa 720
gacatgaccg catgagtagc cagaatccaa attcgagact agattatata taactaaatt 780
gtggttcata gtgaagaggg ttttgtacct atttataaga cataactaaa ttcgagacat 840
gattgcaact aaatgtacct atttataaac taaactagca atttcttgtt gcttcagcca 900
acagggtttt gttcacatac tctatcaatt cttgtgaatg atgtccctgg agttctcaat 960
gttgtaacag gtgttttctc cagaaggggc tacaatattc aggttgttca aaccaatttt 1020
gtattttatg ctccctttat ttcggtaatt gcataatcca atccttgcta aacagtaacc 1080
atcacttttg cagagtcttg ctgttggtcc agctgcaaaa gaaggaactt ctcgcatcac 1140
tactgttgtt cctggaactg atgaatccat tgccaagcta gtacatcaac tgtacaagct 1200
cattgatgtt catgaggtaa aaattaacat gcagtttgca tgattgttat agaagtgctg 1260
aaagtcattt tggttttctc aggtccagga ttttactcac ttaccatttg ttggtagaga 1320
gttaatgatc ataaaggttg ctgcaaatgc tacagcccga agggatgtct tagatattgc 1380
tcagattttt gaggcacaga aagttgacat atctgatcac acaattacac tactggtaac 1440
tatcattgaa acaatgttta cttgagcact tacctcatgt agcactctaa tattcttcta 1500
aaattatgat aatttcatct acttgtataa aatcctt 1537

<210> SEQ ID NO 36
<211> LENGTH: 365
<212> TYPE: DNA
<213> ORGANISM: Sorghum halepense

<400> SEQUENCE: 36
tgtcaccaga ttttacactg aaaaccttat tcgatgtttt gcacacggtc ctcaccattg 60
tgttgcacac atgacaggtc gccagaactg gacgagtggc actggtccgc gaatcgaagg 120
tcgactccaa gtacctccgc ggctactctc ttccattgta acctggcatt tgtgatggtg 180
atggcctgat gaagagcttg gttggttgtt atagagcaga ccatctggcg ctgggttgtg 240
ttgtgcagtt acaggacttg tttctttcat gtcgtgaact ccctcgcctg cgtgtccaat 300
aatgttctcc ccggtaatat gcgtgttgag gttgcatgtg tatcccaacg actgtcagaa 360
taaga 365

<210> SEQ ID NO 37
<211> LENGTH: 5166
<212> TYPE: DNA
<213> ORGANISM: Sorghum halepense

<400> SEQUENCE: 37
actagttatt gacaagtgca tacttgtcag agccttgctg ttggcccagc tgagaaggaa 60
ggcatttcac gtattacaac agttgttcct ggtactgttg aatccattga gaagttagtt 120
cagcagcttt acaagcttgt tgatgtgcat gaagtaagct gcatgtaact cctaccaaaa 180
tcatttgtgt ttgcaaattt attatgttaa ctaacaaaaa catgcgattc ctgcaggttc 240
atgacattac cccctcacct tttgctgaaa gggaactgat gcttattaag gtttctgtaa 300
acactgctgc tcggagggaa atcctagata ttgccgaaat cttccgagca aaacctgttg 360
atgtttctga ccatacagta acgcttcagg ttggcatcct aacaatttgt gtgtttctcc 420
cagatttcca tcagtgcctt tgccaacact gatgatacta gagccagttt tagaaaaagc 480

-continued

```
gctgtgcaca ctgcacagcc acaaattaga tcacattgct tttgttgatt ttctgttgca    540
tagtaccact tgtggttaca ataacaacat catacccata tagaaacact gaatgtttga    600
caccagtact attttttcat gctgcttcat ctaactgctc caagctatta gctattgcaa    660
aactcttgca taatggatcc cttattgatg attgcagctt actggagatt ttgacaagat    720
ggttgcacta caaaggttat tggagccata tggcatctgc gaggtatatt gcttgtcact    780
cacatcatct taagtgtgaa aaggcaattt ttgggtcctt tgggatgaac ggacagtcgg    840
atactttttt atttgacgcc agcagttgtt ttgttttctt ctgtagttta aaacacagcc    900
tgacaacctc ctgaagatta cttgtgattg tgaaacagaa tataagcaat tgtgcacaat    960
gccacatggt taagtagtcc taaataaaac tattcaaaag taacctgtga tgttctgtcc   1020
gcagccaatt gtcaccagat tttacactga aaaccttatt cgatgttttg cacacggtcc   1080
tcaccattgt gttgcacaca tgacaggtcg ccagaactgg acgagtggca ctggtccgcg   1140
aatcgaaggt cgactccaag tacctccgcg gctactctct tccattgtaa cctggcattt   1200
gtgatggtga tggcctgatg aagagcttgg ttggttgtta tagagcagac catctggcgc   1260
tgggttgtgt tgtgcagtta caggacttgt ttctttcatg tcgtgaactc cctcgcctgc   1320
gtgtccaata atgttctccc cggtaatatg cgtgttgagg ttgcatgtgt atcccaacga   1380
ctgtcagaat aagatgcata tacctgtttg cttcagcgga gagagatgcc aatcgtttga   1440
aacgcgtcaa tagtggtatg ctctggttgg gacttgggac ttgggaggct gccggcggca   1500
ggccagtcct ggcttgcacg aaaaaaaaaa agatccctcg ctgtgcttgg gtcgccaggt   1560
ttcagggctt tttctcaact ctgcagcttg agaaattttc tccaggggtc agagttttta   1620
cctcgatcga ggtcattccg caggggttga gtttttttta gtttatataa atatatgttt   1680
atacagttat actacttgat acggtgaggc agcctggcgc atgctgcgct gagggcgcat   1740
ctctcctacg aggctgctaa aacggtacgg atattttttt agctgtatat cgaatttgtt   1800
tagagaagtt tagatttatc tgtatttaag tctgaatatt taacatttga tgttgtatcc   1860
atatatgagt atttaaatca tatatttatg atgttccaat catatttcat ccgtcatagt   1920
taatattatt tatattcaaa tctaaatcct catagaaata taaaaataaa tataatatcg   1980
gttatatccg ttcgtatttc atcccctatt ggttactgga ctgttgtgtg gctgatctga   2040
gcactgagct tgccaattga ttgacacctt ggctaataag tcatagttga gaataatgtt   2100
cgctaattta ttatgagaga aaaatactac taaataataa ataatgggag attctacgaa   2160
taagctcaag ccaacggagc tacgcctttg cttgcctatg cgctacgagg agcctctcgt   2220
gagtcatacg cacctacacg tgaccgtgct actcgagcca agttggacgt gccgcaggac   2280
actgccaccg ccatctatgg tctagggctg cgggtcgcgg agaggctaat gggggtggcc   2340
gttgcacgcg acgaaacaaa cgggcgcggg ccaggccaac gttactgggc ttccgaccga   2400
ctccagaggc cctatcccac caatgcaatg cagcccagga gcggagacgg aggaaggcgt   2460
ggcacccgac ccgattccgg gtaggaaggt acggcgaggt aagcgaagaa gcatccagac   2520
tctcgcagtc tcgctcgagg ggcaggggcg cagggcaggg ccgggcaggg ggcgggcggc   2580
gatccgaatc caatcgccgg gagggaggaa gcaaccggcg gcggtagagg cggagggatg   2640
acgcgcggga agcagaagat cgacgcgcag cggcgtaacg cggagcggaa ccagaaatcc   2700
aaggggtccc agctcgaggc ccgcgccgtc ggcctcaagg tcgtctgccc catctgcaag   2760
gtaaataagc cggagccccg ctctccgatc gctagccatc gcctggactg gaacctgccg   2820
ggtttgcctc ggcagtagat ccggccaatc tgtccaattt tgccgtatcc gtgcttgcct   2880
```

-continued

```
actgcatcac agcatacgga gcatttcaat agtgtctact gcatcacagc gcacggacca   2940
aagttgttca acttctggcc gggcctgctc tgcagagtat ccatccatct agcgcctcac   3000
tttatctgga aacaaaaatt ttgccagtaa attgaaatgt tcctgctgca tatcatcagt   3060
actattgctc taacctcctt taatcagcca gtttgttgta ggccaatcgt tgacacatgt   3120
tgttccagcg tactcatatt gttgccttgg gggtttgggg ccgggtaata gtgatactgt   3180
cacggcccct cacctcagcc agcccaagga agcccatcta cagaggaaga gcacaagggc   3240
ccgtgcaagg aatgtccgcg ccctcggccc agaatgggtc tgtaatcgct gtgtgctggc   3300
tagtgagtag ataaggagag gaagtgagga ggattggcat catctatctt gtaacagact   3360
aaaccctagt aagaacgccg gcctcgttgg tccttggcga aggaactcat ggttgcgatc   3420
ccagtgggtc gctaacagat actaggcatc ctgactagaa tgagagattg ggagtactcg   3480
aagtggattc tactggccag tgtgtctgac actttaccac accgcagtta aagctagtgc   3540
tacaaagaag tggccacata accttctcct agcatgattt gatctcacgt gtaaaagact   3600
tccatcacat ttttcccaaa agtagagcca atatttcaga aagaattcct gttgtgcaac   3660
cttcgtctaa acacatggtt tagctgtact ctttcattac ccaatgcttt cttcatatga   3720
taactcaaaa ggttactgca gcatattggc tctagtcttc tgtattttct ggattccttt   3780
taaatcggga gtaaagtcgt gggttcatta tgtggatgcc ctacttttta cctggctagt   3840
tgcatttgag gaacatacct gctcacctgg tgttgctatt tccataggta caattggcaa   3900
atgaaaaaca gctgaccgat cactacggat caaagcatcc aaaggagaaa cctccaagca   3960
catcgaccac ggaataacca tgactggtgg tgatgcagga acatagatcc tgcttggctg   4020
gtttgaggat ctttaagtct gatccatggc ctggagttgg atcttaaagt cggctatact   4080
ctgtagtgtg tcttatttcc tcttgtttca ggcaacaccc ttgatacgag tgtgcatttc   4140
tgctagtatg ttctgtgatc gtactgccga tgtatctcca aactgtatgt gatcgcccgt   4200
ggcattggga tgatgcgaaa aaaaattatg atcataacta tgttcaaatg tttgtggctt   4260
tttacaacat ggcttatgca cgtgcgttcc ctagccctaa tggccgccaa ataggccacc   4320
acggcaccac ccctggtgtt tgatcggtgc cgtgcttcag ttgtatccgg atgaatgaag   4380
tgaggaacat gagctggtcg atcccaatca agtaaaaggc ttgtctgacg atgctatcag   4440
gccttcttaa acggctaatg ctgttagcat cagtgaactg gtatcgtggc aaaatcgcta   4500
tccccatcga caggccaaga gcatttgcac gtcaccaatg ccataaataa ctcatgctgt   4560
aatatttgga ggaaataaaa cgtgcttata tatattcttc ttctcatttt tacaaagtta   4620
ctttagtttt gtacttgacg agtatgaaaa aggggctagg agcattaggg gcactctatg   4680
ctgtatttag aaaggtcaac atataatttc gttgcaaggg ttagttggta aattcacagt   4740
ttgccacatg gcatggtctc attcccctag ccacccaaaa tatatggata atagccgata   4800
cagtagctgt cagccatagt tatctggtga agtatatcac ggatgatgac ggacgttttt   4860
cttttggaga ggctgcagtc ttttattcga agatatttgg tcaacgttgg aatgctagct   4920
ttgatctggc tgtacaacaa ggctttatta gccgaatgtc agctattcag caatgttttt   4980
ctttcacaac aaatcagcta atagtatttt tatcataatt tattagtcaa acgaacatac   5040
gctaacaagg taccactagt gagagctata ggacgctgat ggagaaggag aacaagacaa   5100
ggtacacgaa gatgttgttc agttccaaaa aaaaattgta aaatggacac tgtaacactt   5160
ttattt                                                              5166
```

<210> SEQ ID NO 38
<211> LENGTH: 1544
<212> TYPE: DNA
<213> ORGANISM: Sorghum halepense

<400> SEQUENCE: 38
atgctaaaag tgtaatattt tcactcatac aaatggagaa gctttcagga tcaatagtca 60
acagataaaa catgtttatt ttcactcaaa taaacaaaga gtaatcttcc atgtctattg 120
aatttttact aaagtgatgt aaactttaat acaacttaaa cctttatttt tcttctcaag 180
ttcagttcta tcaatatcaa ttgaaaaaac tattctctgt tatatgctat tttagtcctt 240
tccttccagg aacctaggga ataactacat gtccatgaaa aacagcgaag ttgcatgctt 300
ataagtgttg taaatagttc gatcctgtgg caaaggcaaa atgctatgct attaagcata 360
tgcaactaat tatttgttat taacagcgtt tactgcactt tctcactgat gtgcctcatg 420
aattttcctt aatttgtagg gtcataaagc gtcacacact atcagttttt gttggtgatg 480
aaagtgggat gatcaatcga attgctgggg tttttgctag aagaggatat aacatcgagt 540
cattggctgt tgggttgaac aaggataaag cattatttac aatagttgtg tcaggaacag 600
acaaaatatt gaaccaggtt gtagagcaac taaacaaact tgttaatgta ataaaggtta 660
gtcattttcc tgtgccattt ggcttataga atgattgata actaatatgc tgtgaaactc 720
attgcttgtt gttttgttct tattattctg ttcaatggtg tatcttctac tcatagctta 780
atatttggat taataaacag gttgatgact tatcaatgga accacaagtt gaaagagaac 840
ttatgcttat aaaagtaaat gcagagcggg aaaagctacc tgaggtacag acatactcat 900
ctttcaaaat gtatctgcac cttcttggcc tgtaactcaa actgaacatt aaatgtggat 960
catttttttg tatagagcca taggaaatat ggaaattaac aatagggaca ttacagatca 1020
ggtctgtgga cctggcacta ctaaactttg ttgcttggct gacatctcta gttgtgaata 1080
cagataatgg gtttggttcg cattttcaaa gcagaagtgg ttgatctttc agaccataca 1140
ctaactattg aggtaatatc tgtggtgtgt cttcgctcga agattactga tgttgtcttt 1200
cttatggttc tttgtggtta tgttaaaggt aactggagat cctggaaaga tggttgcaat 1260
acagaagact ctgagcaaat atgggatcag agaaattgct agaactggca aggtcattct 1320
tgttcagaaa atagtgaaaa tatatcctga tcttgttctt tactagacct aacatttgtc 1380
ttatagatag ctttacgccg tgaaagaatg ggagaaactg ctccattttg gaggttctct 1440
gcagcttctt atcctgatct cgaaatggca ataccttcaa atttccagca aaacactggt 1500
gcgagggcaa tcgatcagaa tacagaagga tcttcagggg taag 1544

<210> SEQ ID NO 39
<211> LENGTH: 1770
<212> TYPE: DNA
<213> ORGANISM: Sorghum halepense

<400> SEQUENCE: 39
tctgtttcta ttttcttctt ctgatggatg aggcggctcg ggtttctggc gccaaatgca 60
gggtgcggcg ccacacgatt tcggtgttcg tcggggacga gagcggcatg atcaaccgca 120
tcgccggggt cttcgccagg agaggctaca acatcgagtc gctcgccgtg ggctcaaca 180 aggacaaggc cctcttcacc attgtcgtct ccgggaccga cagggtgctc aaccaagtca 240
tcgagcagct caataagctt gtcaacgtcc ttagtgtgag tccgccttgt caaaatttag 300
caaaactcac gcgaatccat acttgatttt gatgcccccg gtttgagcac ttggtgacaa 360

```
ttcactagta cagtgagatt ttgttccatg agtttagctc gcccgaatct tctgtccttt    420
ttattctgtt aggatcgtcg tttccacttt cgtggagcat cttttgtgta gctagacaga    480
gcatgcgtaa ctttttttctt tcctgattta gtcattatca tgttcgaagt attcttttcc    540
cttttcccct agaatcgctg ccagcctgac agtcatgtca acgtcaggga catactcctt    600
tctaggggat acctcaaatg caacatcatt attatacgcc ctgtatcatg tttatgcaat    660
gcactttctg tttgtgcacc tgtgccgtgt atggtaagca ctgttgctct ggttaatcat    720
ttgatgaaaa aaataagata ctcaacttca ttattctgac tatgtggtag tacttattta    780
gttcaatttt aatgctaccc tgtacatgtc tatatcctat aacctaaagc agcctttcag    840
ttaggagtta ttctgagttt tctttgttct tgcgatttga agatgctgat ttcttgggga    900
aaagatttat tgttctctct gaacgtacta tgcagataat acattgcttt actttccttc    960
tgaattctta gccagaaaaa cttcatggat taccattcct tcactgtttg cgtcaactaa   1020
acatttagat ggttttaact accatgatat tttctctctg aaaattatct actgctactg   1080
ttttgttcct aacttgcact aagagtaata ccaataaatt cttatttatt ttttgtttgg   1140
atctgatcaa ttacaggttg aagatctatc taaagaacct caggttgaaa gagagctgat   1200
gcttataaaa ctaaacgttg aacctgatca gcgccctgag gtatgatgta gcgttgagtt   1260
agtctttgta atccaaaact tcaattagca tcctgtaccc acgattctca attgcatggt   1320
gatccttaca acggtgcttc ttgtcatgac tgacaggtca tggttttagt tgatattttc   1380
agagcaaaag ttgttgatat atctgagaaa acacttacca tagaggtaaa aactcaatct   1440
ctaactagtg tacatatttt gattggtatc cattttcctg tactgaactg tatgtttaat   1500
gggcacttca ccaatgttag gtagctggag atcctggcaa aattgctgca gtgcagcgga   1560
atctaaggaa attcggaatc aaagaaattt gcaggacagg aaaagtaatt tctaatgttc   1620
tttccttgca tggacacata tttttttctt gtaatgctaa tttaatgccc tatcttctta   1680
gattgctttg agacgtgaaa agattggtgc aacagcccgt ttctggcaat tttctgctgc   1740
ttcttaccca gaccttatag aggcattgcc                                    1770
```

<210> SEQ ID NO 40
<211> LENGTH: 18174
<212> TYPE: DNA
<213> ORGANISM: Sorghum halepense

<400> SEQUENCE: 40

```
tagcgatgcc gtgatagtca tggcagtcag ggtgcttact cggatgctca agcggcggtt     60
agtggtcact gaaatggtcc tttgggtaca tatatggcgt ggtcacaggg cggtgaacac    120
tgcgactgac ccgcccctca cgtagaaagc taaaaacatc tctcatcttt aactcaggaa    180
atagcggata aacgttgcca tattctcaac aaattgtcag aaactaatct aggttaggct    240
acccttgata tacaatttga taaggagcga actgtgcccg attcacacac tcaacccaca    300
aaaatggggg ttgacggggg agagtatgcc ggaatcccac ccaccatccc tctaaagggc    360
taccctgtta ggggagataa cccacaacga ccatgaggac accacgatga gcaccacgtc    420
ttcacacacc agccatgcca gcggcggcgg ggacgaccac aaccacgacg actccgccgt    480
cgggcaggtc tccatcaaca cgcacggcac agatgatctc ctggacgaaa tagacggcct    540
gctggaaaac aatgcagagg aattcgtccg ctcctacgtg cagaaaggcg gccaataaac    600
gccatgaccc cgccccgggt actcacccgc agaatcaccg ggattgaaac cgagtacggc    660
```

-continued

```
atcacctaca ccgccgacgg acaacggcga ctgagtcccg atgacatcgc ccgctacctt    720
tttcgctcag tggtggaccg ctacggcagc tccaacatct tcacctccaa cggctcacgc    780
ctctaccttg atgtgggctc ccacccagag ttcgccaccg cagaatgcga cagcctcatt    840
caactactca ccatggacaa agcaggcgac cgcattctgg acaacctcgc ccaacacgcc    900
gaaacaaccc tggccactga aggcactgcc gcagccgccg acggccacgt ctacctacta    960
aaaaacaacg tggattcctt cggcaactcc tacggctgcc acgaaaacta cctggtcaca   1020
cgccaaacgg tagtcaaaac tctaggccgc catctcctgc cgttcttgat tacccgccaa   1080
ctcatcagcg gcgctggcaa aatttaccac cccatccccg gaagccccag cgagcactac   1140
ggcctaggtt tttgcatgtc acaacgcgcg gaccacgtct gggagggcgt ttcttcagcc   1200
accacgcgat cccgtcccat catcaacact cgcgacgaac ctcacgcgga ctcccaccac   1260
taccgtcgcc tacacatcat cgttggggat tcctccatgg ccgaacccac cttcgccctc   1320
aaaatcggag caaccctcct cgtgctggaa atgatcgaag cagacatgcc gctgcccagc   1380
cttgaactcg ccgacgagac caccgccatt cgcgatatcg cccgtgacac caccggcacc   1440
tgcctggtca agctccgaaa cggcaccacc atcaccgcag gcgaaataca gcgcgcctac   1500
tgcgacgcag cacatacatg gatgcaacaa cgccccacag acaccaacac cgataccctc   1560
agcagcgtcg tggacctctg gacacgcacc cttgatgcca ttgacaccca agacttttcc   1620
cacgttgatc gcgatatcga ttgggtgatc aaacactccc tgattcgccg ctaccaagaa   1680
cgctacggat tcgaccttga ccaccccaaa ctctcccaaa ttgatctgat gtaccacgac   1740
atccgaccgg gcaggggact agcatccatc ctcgaatcca agggcctgat caaccgctgg   1800
accaccgatg acgccatcgc ccacgccacg gaacacgcgc cggacaccac ccgagcgcac   1860
ctccgcggcc gcttcatcac cgccgcacat gagactaata ctcccttttc cgtggactgg   1920
atgcgcctga aaatcaccgc accagaaccc cagcttgtgg aactgggcga ccccttcgcg   1980
gccgtcgata cccgtgtcga cgaactcatt aaccacatgc ataaaggaca caacagtggc   2040
gaaaaatgaa ttccacgaac gcctgatcaa cctcacgttc gccttcctcc acgccaacgc   2100
cacaggccgc agatacatca ctgcagaatg gattcgcacc aacgttgcag gctaccaaga   2160
ccgcactgac gcagccttcc aacgcatgtt cgcccgcgac cgcagcattc tcgccaaagt   2220
cggcgtcccc atcgaaacca tcgcacaagc cacacttgac gacgcacccg gctaccgact   2280
caacccacac aactactacc tccccgaagt cagcttcact cctgacgagg cagctgtcct   2340
cgcactcgcc ggcgacaaag gactcaacca cgaactcgct gcgttcgccc ggtccgggtg   2400
gacaaaactc gcagcagcag gcgcctcaac cgtcacagcc caagacagcg ccccggtgat   2460
gttcaacaac gtcaccgacc tggtgtact cactgcacaa tccctagata ccatcctcaa    2520
ggcccaccgc aaccaccacc gcattcactt cgactacacg ccacacaaaa acgctgaacc   2580
cacgcgccgg gtgatggacc cttggggcat tgttaaccat caggaccgtt ggtaccttgt   2640
gggttttgac atcgaacgcg atgctccgcg aaccttccgc atcacccgcg ttagcaatat   2700
agatattgtt ggccgggcca tacatctcgc cccggaacac acaccattac aggagcttgt   2760
tgcagattcc ctgcgcagcc gcaaagtgct tatcgacgcc acgattactg ccgaaccagg   2820
caccgctggt gagctcacct cccgcgcgag ccaccgcgat catgatacgt atgtgctcac   2880
cggcgtggat cgagactggc tggtgcgaac agctgcggca tatgcgccgc atgcgctggt   2940
ggtggagcct gcagatgttc gcgatgatgt gattgctcaa cttcgttccc tgctggaggt   3000
gaccccacgt gactgctaaa gccgaccgcc tcgccgaggt ggtgcacatg ctaaatctgc   3060
```

tgccgtattt tgaggcgcat ccaggcatat ccttgatgga ggcatccaaa gatttgggcc 3120
gcagccccaa ggaattgatg gatgacctca acagcctgtg gtgttgcgga ctaccagggc 3180
tttttcctgg cgacctcgtg gacctggatc atacgtacaa gtcggtgaaa gtcaccaatg 3240
cccaaggcat ggataagcct ttgcgtctca cccacacaga ggctggggcg ctgctgctgg 3300
cgctggagtc cttagagaac cttcctggac taaccaaccg tgaagtcgtg caaagtgccg 3360
ctgcgaagct acgcggcatc atgggggatg aaactacggc cgtggtggac tctatcgtcg 3420
ccgacacagt tgttgagcac acctcaccgc ttttggacgc aattcgccgc agtcttgatc 3480
acggcctgat gctgaggttt acctattatt cggcgcgcag cgattcctcc aaccagcgca 3540
ccgtccaccc ggcgcgggtg ttcagcgtca agggagacac gtacctcgca gcctgggacg 3600
atgaggcgca ggcccaccgc accttcaagg tggatcgcat gagtgatgtt gaggtgttgg 3660 ataccccccag tactccgcac gctgaggaca tgaagtttga tgaagacgac ccgttcgcct 3720
tcggtaagga aacagacact gtgtctttag agatccaccc agatgtgctg tggcttgcgg 3780
attatgtgcc cttggaactg ggggagaccg gccccgatgg gtgggttgcg gccaccatgc 3840
cgatgggttc acccgcttgg gtggtgcgtt tcgccatagg acaagcgggc agagttcggg 3900
ttactgcccc cgaagaggtc acccgcacca ttgctgcaca agcggaggcg gcgttgggcg 3960
cgtattctaa acgacgtagt atgagtggtg aataacgtca ccgtctgttg agaggacatc 4020
atgccgaatc ttggccctac tgagctgatt atcattgctg ttgttttgat tttgctgttc 4080
ggttcgaaaa aacttccaga tgcggctcga tccataggcc gttctatgcg catcttcaag 4140
tctgaggtga aagaactaaa caatgatgac caggtgacag ccgccaccga accccgtcag 4200
attgagcagt cccagcccca gcaagcaccc caagctcaga ctgacaccca gcacaatact 4260
tctgcttagc ctatgttggt gtgatgagta cgtctgatac gactaaaaaa cgcctcggcc 4320
gggtaaagcg agaaaagaaa ccggacgacg gcagcatgtc gctggtggag cacattcaag 4380
agcttcgcct gcgcctgctc atttcgcttg ctgcattggc cgtaggcacc atcgttgggt 4440
ttatctggta ccaacagagc ctgtttggcc tacccaccct tggtgacatt cttcgcggcc 4500
cctactgcaa ccttccagac accgcacggg cagacctttc tgccgatggt gagtgcaagc 4560
tgctggccac cgggcccttc gacatgttca tgctgcgttt gaaagtcggt gccttggcag 4620
gttccgtgtt tgcgtcccct gtgtggctcg cacaagtctg gtttttttatc actccagggt 4680 taaagaaaaa tgaacaacgc tggacattct ctttcgttgc cattgcggtg atgcttttttg 4740 tcttcggcgc tattttggcg tactttgtgg tggcgtacgg cctggagttt cttctcacca 4800
ttggtgatga aacccaagtc gcagcactca gcggtacgca gtactacaag ttcctcctcg 4860
cgctgcttct catttcggc gtgagttttg aggtgccgct gatcctagcc atgctcaaca 4920
tagtcggcct ggttagttac cagcagttga aggaaaagcg ccgcctgatt attttcctgt 4980
tgtttgtctt cgccgctttc atgacaccag gccaagaccc ggtgtccatg gcggtgctag 5040
ccacggcatt gacactactc gttgaatgcg ccatccaatt cgcccgcatc aacgacaaac 5100
gcaaaaaccg tcaacgccca gaatggttgg acgtggacga tgacaaggca tcatcaatcg 5160
agccaacccc cgttgatact gctccgactc ccacgccaca gcgcaccgac ctgacacaac 5220
gcccgcccac cgattttgac gacgtgctat aagctgctta aacaaatgcc ccgacacgcg 5280
gtagcgttag gggcatgagt tttaccgcgc ccgtcggcac acatcttgct gagttctgcg 5340
accgcctgga ttttcccctc gacgactttc aaatcgaagg ctgccaagcc gtcgaagcag 5400

-continued

```
atcatggtgt cctcgtgtgc gcacccaccg gcgcgggaaa aaccattgtt ggcgaattcg   5460
cggtttccct ggcactatcg cgcggcacaa agtgcttcta caccacgccg atcaaagcac   5520
tcagcaacca gaaataccac gacctcgtcg aggctcacgg tgacgatgcc gtcggcctgc   5580
tcacaggcga tgtttccatc aacggttccg cagatattgt tgtcatgacc acggaagttc   5640
tgcgcaacat gatctacgca gaatccccgg ccctggaacg cctcacccat gtcgtcatgg   5700
acgagatcca cttcctcgcc gacgcttccc gcggccccgt gtgggaagaa gtcatcctca   5760
accttgccga aagtgtcaac atcatcggct tgtccgccac cgtcagtaat tccgaagaat   5820
tcggagcgtg gctgactacc gtccgcggcg acaccactgt tatcgtctca gaacaacgcc   5880
ccgttccact tgaccaatgg atgctggtca accgcaccct actcccgctt tttcaaccgg   5940
gaagcaccga gcatgtcaac aaaaaactcg aagcaaaagt ccacaagcta gaatccggca   6000
gcatcagtac ccagtcctac gacaaaaacc agcaggcacg tttccgatcc cgcagccgca   6060
acggcaacca acccggcagg tcccaccgct ccggcatcag ccgcccggcc gaccgtttcc   6120
gcccactcgg caggccagag gtcatccaga ttctgcaggc acactccatg ctgcccgcca   6180
ttacctttat tttttcccgc gcgggctgcg acgccgccct tctgcaatgc cttcgctccc   6240
gactcaccct caccacccag gacgaagcca acaccatcgc cagcatcatc gatgctggtg   6300
tcgccgacat ccccgccgca gaccttgaaa tactccgttt caaacaatgg cgcgccgctc   6360
tcatgcgcgg attcgccgcc caccacgcgg gaatgctccc agctttccgg cacatcgttg   6420
aagaactctt cgtcaaagga ctcgtccgcg ccgtctttgc taccgaaacc ctagccctcg   6480
gcatcaacat gccggcacgc acagttgtgc tggaaaaact cgtcaaattt aatggcgaat   6540
cccacgctga actcacccca ggccaataca cccaactcac cggccgcgca ggacgtcgcg   6600
gcatcgacac catcggcaac gcagtggtgc aatggtcacc cgcaatggaa ccgcaagcgg   6660
tggccggctt ggcgtcgaca cgcacctacc cgctcatctc caccttcacc cccggataca   6720
acatggccgt caacctcgtt ggatcgatgg ggcgggaaaa agctcgtgac ctactggagc   6780
attccttcgc acagttccaa atcgatcgca gattgggagg ctcggcagtt cgcaaccggc   6840
aaacccaggc cgacatcgag gcctacctca aggcggccca ttgcgaaagg ggagatttca   6900
ccgtatacgc ccggttgcgg gaaaacatta gggagctgga acatgagcag gcgaggttgc   6960
gcaaaggtga acttcctagc caggttgccg actcactgtc gagccttgat cctggggaca   7020
tcatcgccgt gccatctggg cgtcacgctg ggtgggtcgt tgtcgttgac cctggcaccc   7080
acggcacgag aggtcaacgg cctcgccccc ttgtcatgac tccggatcgg acggtgattc   7140
gtctggggca tcaggatatt gacgcccccg ttacgcgagt agccggcgtg aaagtcccgc   7200
gccatttcca ccccgaaaac caggccgatc gtcgctgcct cggcaaggcc ttcgatcggg   7260
tacttgaggg gctggggagg ccagtggtga agccgcgtcg tgctgcggtg gatgctgagc   7320
tttccgacca gatcaccgag ctgcgctccc agatgaaggc tcatccctgc cactcctgcc   7380
ctgatcgcga gtcccatgcg cgtttcgctg aacgtgccat gagacttcgc cgtcgcagtg   7440
agagggaatt gacgaaagca cgcgcgaagg cgacgtcgat tgccacccag tttgagcgaa   7500
ttgtgctggt actggaggct ttgggatacc tcggtacgag tggggatact gtcacggacg   7560
ctggccggat gctttcgggg atctattccg aactcgactt ggtgacggct gaggcaattc   7620
ggcgaggcgt ctttgacggc ctggattgtc cgcagttggc ggcggtgttg tcgaccatcg   7680
ttcacgagtc gcggccgggg gaccggggcc accttcatcg catgcccgat gggaagagcg   7740
aagcggcgga gtcacaactg cgtgcggtcc gagccgaaat tggtctgctc gagcgtgacc   7800
```

accgcattga gcgtccccga gatctcgaca ttggttttgc cgaggccagc tatgcatggg 7860
ctgccggtgc cggtctggac accgtactcg acgacatgag tgctggtgat tttgtgcgcc 7920
gggtgcgtca ggtgtgcgat ctagctggac agattgccca tgccggggtt ggggagaatc 7980
tggcccacac ttgtcgtcaa gtggtgggtg ccatgcagcg tggggttgtc accatggacc 8040
gcgaagaaga ctgattcgtg cgcccactaa caagggggat gtgcggcccg gtagcctgag 8100
gtcatggctg tggctatacg tgtcattcca tgtctggacg ttaaggatgg gcgggtcgtt 8160
aaaggggtta acttcgtcgg tctgcgcgat gccggtgatc ccgtggagct agcggcggaa 8220
tacgggcggc tcggtgccga cgaggtgact ttcctcgaca tttctgcctc aacagagggg 8280
cgcgccacca ctcgcgagat ggtgacacgg tgcgctgaga cagttttcgt gcccctcact 8340
gtaggtggtg gggtgcgcgg ggtcgacgac gtcgatgtcc tgctgagggc gggagctgac 8400
aaagttggtg tcaacaccgc agcgattgct catcccggga tgatcgacga ggtcgctgac 8460
cggtttggca atcaggtcat cgtgttgtct gtcgatgccc gtcgcgaacc agatcggcca 8520
tccggttttg ggtgacgac ccatggtggc acccgttcgg cagggttgga cgccgttgag 8580
tgggcttgcc aagccgtgga gcgtggggca ggtgagattc tgctcaattc gatggacgcc 8640
gatggtacgg ctgatggctt cgatattgag atgatcgagg cagtgagagc agctgtcgac 8700
gtccccctca tcgcttcagg tggagctgga aaggttgccg atttcgtcga ggcggcgcgc 8760
gccggagttg acgcggtgct cgccgcgtca gtttttcact atcacaccct gacgatcgcg 8820
cagatcaagg acggcctgcg tcatgccggc tttgaggtcc gctgagcgaa cacgtactgc 8880
acgcctagcc gatgtggtag tcataactta tggactgcct tttctgctca atcgctgcgg 8940
gagacatccc agcgacgatc attgactcgg acgacgcctc agtcgcattc ctcgacatcg 9000
agcctttcca ggatggccac actctcgtca tcccgcgtag gcacgttaca agcgttctcg 9060
acgatgatgg tgagctcgga cgtatcagcc cgatggtcac gaaggtggct cgtcgcctcg 9120
tggactctct gggggcttct ggagtcaatg tcgtctcaaa cgccggtgag gttgccggtc 9180
agagtgtcca tcatctgcac gtgcatgtca ttccccggta cgaccgtgag ccgggcatca 9240
acgccattcg gtcggccatg cctcgtcgcc ctattgagga ggttgcggcc atggtgactg 9300
gggaatcgaa tcgcaaatag ctcataatgt gagacgtttg tccgaaactg ttgacggtta 9360
gtcgtgcaca caaggatcag tggcatgaac gaccagcttc ttgttattgg ctagtgtcct 9420
gatcctcccg gacagcacga cctgcccgat atctctgcct gggtgcgtca gttacagcgg 9480
atgaaaaacc tatgcactca catggtgaag aaacgcccga ggaagaaatc tccccccgca 9540
gcaggtcatc cagcgcgttg gtgctttggc accccaagac accgtgctcg gcatggtgcg 9600
ccagcggcag aacctgttct tttgattgtc ggttctttca catggatctg cactccgacc 9660
ccttaccaga cttcgtcaag cttgctgaag cattggggtg cgctgttttc cgggtcgcag 9720
accgggcatg gtcgacgaga cgatcacagc tgccaacacg atcaatgacc gcccggtcgt 9780
ggtggaattc atcatccgca ctgacgccat ggtctggccg atggtggctt tcggagccag 9840
taatgatgaa atcacgatcg cccgagatat ggctccggac tggggtgacg ttggagacga 9900
cgttgctccc ggcgacgagg acagcaacga tgatgaggcc gggaagatga gttgaccaga 9960
cgcgtactgt cggtgtcgcc gactgacgat cccagtgaga cccggatgac gatcggagtg 10020
gacgccgtct ccgcccaggc ccttgaacaa attatcaagc aacttaacaa actcattgag 10080
attcataaga tcgccgaacc agagccgagc acggtcaccc gtgagctcat cctggtcaaa 10140

-continued gtgcgttcca acgtcgaaaa ccgttcaaag atcatcgaca ccgttgctct acgtcgtgcc 10200
aaggccgtcg acgcctcact ggaatcgctg acgatcgagg ccaccgggtg acgtgagaag 10260
ctggatgtgt tattgcaggt gctggaacac ttcggaattg tcgaacttgt tcaatccgga 10320
caagtggccc tcaaccgtgg tgtggctgtt ctcggggcga aacgccccgg gtgacgttcc 10380
ctagatccca agacaaccca gacccccaac aaggagagaa atacgctatg gcaaagatct 10440
actacgacga tgacgccgat ctgtccatca tccaaaaccg tcaggttgcc gtcatcggtt 10500
acggttccca aggtcatgct cacgctctca acctgcgcga ctccggtgtc gatgtgcgtg 10560
tcggtctgcg tgacggctcc tcgtctatcg ccaaggctga ggctcagggg ctgcgggtgc 10620
tgtccatcga ggatgcctgc gaagaggccg acttaattat ggtgctcgtt cccgaccaaa 10680
accagcgcca gctctatgct gagcacattg ccccgcacct caaggacggt gacgctctct 10740
tcttcgctca cggcttcaac gtccacttcg gctacatcaa agctccccag ggcgtcgacg 10800
tctgtatggt tgccccgaag ggtcccggtc acatcgtgcg tcgggagtac tctgatggtc 10860
gcggagtccc ggtgctggtg tgcgtcgagc aggatgcctc tggcatcgcc tgggacctca 10920
cgaggtctta cgccaaggcc ctcggcggtt tgcgcgccgg cggcattgaa acgagcttcc 10980
gtgaggagac cgagaccgat cttttcggtg agcaagcggt gctgtgcggt ggcctgtccc 11040
acctcatcca ggccggtttt gagactctcg ttaccgccgg ttaccagccg gagatggcct 11100
attttgaggt ttgtcacgag atgaagatga tcgtcgacct catcatcgaa ggcggtatct 11160
ccaagctgcg ttggtcaatt tccgatactg ctgagtatgg cgactacgtg tctggcccgc 11220
gtgtgatcga cgaccacgtc aaaaagaata tgaaggcggt cctagacgac atccaaaatg 11280
gcgccttcgc taagcgtttc atcgccgatc aggatgccgg tgctccacag tccaagaaat 11340
ttcgcgaggg tgaggcaaag catccgatcg aggccaccgg taaagagctt cgcaagatgt 11400
actcctggct ggcagctgct gatgacgact acaccgaagg cagcgtggct cgttgagcct 11460
gctggcctga cgttgagggc ccgtaggtac cgcgggccct caattctgta tcctctgcct 11520
cgtcagcctc gagcagatag ccgacaggca acgatggccg ccatgtcgga ggcaagctga 11580
atctcggtgg cgtgcacctt cgggtgggtc agccaggcca gcctggtggt atcgacggtg 11640
ccattgatgt cgtggggagg aaaaccatgg ctggggggca tatcgtcgat gacgacgagg 11700
cctccgaccg agaccgcctt gagaatctcg tcaacatcgt gcgctctcgc tactcggatc 11760
ggtaccgaga gcaggccgaa ggggccgtga tcgagcaggt catcccaggt gccctcgatg 11820
acctcgatat cgaggtcagc caagacctcg cgagctcggg cgcagaccgt gggatctggt 11880
tcgtaactga caaccctggt gcgttttcgt gcccccagtc gtagccaggc agctcctgcc 11940
ccagaccccg tttcgcactc cccaatggcg ccatgtaccc cggccgccag ggtagccatg 12000
aatcggccgg tctcattgcg ggtggtggtg aaatagccca tctccagtgc gttatggaga 12060
gctttcgtca ccggttcagg gatctcggga atgggtaaca cggggccatt ctgccagtcg 12120
gtatcttcga actttttgtg agggcggtta gctggtagtt ggttgggtca gatgcgttgg 12180
gcaatgtctc gcccgatctc gctggtcgtt cgagcggggc cggaagccct agtggcattg 12240
tccgccgaga cagcctcgcg gacgcgggct gcatcctcag ggcggtcaag gtgatctagc 12300
agcaatgcta tcgacaggat cgctgccgtc gggtcagcct taccagtgcc agcaatgtca 12360
ggcgctgagc cgtgcaccgg ctcaaacatc gacgggaatt cgccggaggt attgatattg 12420
gcgctagggg cgagcccgac gccaccggtc accgctgagg caaggtcggt gatgatgtca 12480
ccgatgaggt tgtcggtgac gatgacgtcg aatcgctggg ggtctcgtac cagagcgatc 12540

-continued

```
gtgacagcgt cgacgtgcaa gtaggtcgac gtgcaagtag tcagtggtga cactcgggaa  12600
ctcttgaaca acttcgtcga cgatccgacg ccacaaggtt ccggcattga cgagcacgtt  12660
gtgcttgtgg atcagggcga aatggccgcg ctccaaataa aactgacggc acctctgtcg  12720
agtcaggggt agcaccgaca gcgtcgagca cgatggcgac ttcctgggca atctcggcca  12780
gagtggagtt gtcaagaacc tctcccgtgg ccttccaatg tgcggcgcca aggtggtact  12840
cgtgggtggc aaaagcatca gatccgacgg tctgctccag cacgcggagt gcctgctcgg  12900
tgacttcggg gccaattccg tcgccgccga tgacagcggg ttgcgttacg tcgtcggtca  12960
taggtgaacc atactcagca cgtccacgat atgatccgtc gattcaaaaa atggaacgaa  13020
tggctcggcg tgggtgtaat gtgtggctat gagtttgcgc tttgcttctg ctgacgatct  13080
gacgtggtcc tccgacgagc ggatcgcgct ggaacatgcc aatccacgat ttggtgcggt  13140
ccttgccgac catatggctg ttgctacctg gcaggccggt gaaggctgga gagacgacgc  13200
cgtggtcaac taccacggac ttgatatcaa tcctggcagc gctgtgctgc attatgccca  13260
ggagattttc gagggcctga aggcttaccg ccacgctgac ggttctatct ggctcttccg  13320
ccctgatcag aacggtgagc gttttgttcg gtcggccgag cgtctcgccc tgcccacgct  13380
gcgagtcgaa gacttcgtta ctgcttgtat gcgcttggtt gaggtcgact cccgttgggt  13440
ccctgagccc ggtgagggtg gagagaagtc cctctacctg cggccgttca tgatcgccta  13500
ccaggatttc ctcggtcttg ccgcggcaag taccgtgctg ttttccgtta ttggttctcc  13560
cgttggcgct tactttgtca gcggggtgaa accgctgcgg ctcctcgtcg agcgtcgtca  13620
agctcgaacg gcccccggcg gtaccggtga ggcgaagtgc ggtggcaatt acgcagcttc  13680
gctgcgttcc cagatcgatg ccaagacccg tggctgcaac gaggtgctct ttgtcgatgc  13740
agttgaacat cgctggatcg aggaactggg tggtatgaac ttcatggcca tcagcaagga  13800
cggtcagctc gtcacccccg agttagctgg caccatccta cgtggcgtga ctcgcagatc  13860
cattctggaa gttgccccgg acctcggtct tgaaccagtg gagcgcaaga tcgatgttga  13920
cgagctcctt gatggcgttc gctctggcga gttcccggaa gtcttcgcct gcggtaccgc  13980
cgcggttgtc acaccgatcg gctctttcct agatggagat accgacgtga aggtctctga  14040
gcccaccgga aagaccacga tggagatccg tcgccgtctg ctggatatcc agttcggacg  14100
cgctgaggac acccgtggct ggttgaagcg agtctgctga cggcgtcgac gtccattggg  14160
gccggcccca atgatatgtt cacgactggg ctacgacggt gtcgatgaca atgtcttgcg  14220
gctggaaggt ttgcccgacg gtgaacgcgt tggtcatggc atcctcggcc cgcgcaatgg  14280
agtcgggggt gtcggtgagc agggtggcca atggctggcc tgtgacaacg cggtcgccgg  14340
ggcgaactct taacatgatg ccagccgcag cttgcaccgg atcctctttg cgggcgcgtc  14400
cggcacccaa acgccaggca gctaggccaa cggacatggc atcaatcccg gtgatgacgc  14460
cagcctcggt ggcgacgatg tcctgggtgt ggtgggccat cggtagtgga gcgtcagggt  14520
cgccgccctg ggcacgaacc atgttgcgcc agacatccat tgcctggcca ctggcgagta  14580
catcggccgg gtcgatgccg tccaatccag ccaccttcat catgtgacgg gccaaggcga  14640
cggtgagctc gacgacgtcg gcaggacctc cgccggctaa cacctcgagg gattcggcaa  14700
cctcgatgcc gttaccgcag gcgtaaccca gtgggacgtc catgtgggtc agtagggcgg  14760
tggtacgcac ccccggcggct tcacctagct cgacgagacg gctggcgagt tcgcgggcgt  14820
ccttatctgt cttcatgaag gcacccgagc cggtcttgac atcgaggacg aggctgtcgg  14880
```

tgccctcggc gatcttcttg ctcatgatgg acgaagcgat cagcgggatg gactcgacgg 14940
tgccggtaac gtcgcgcagg gcgtagagct tcttgtcagc aggggctagt cccgggcccg 15000
ctgcgcagat gacagcgccg actttctcga gctgggcgac catctcgtca tgagagagat 15060
ccgcccgcca tccgggaatg gcctccatct tgtcgagggt gcctccggtg tggcccaggc 15120
cacgcccaga cagctgtggg acggcagcac cgcatgcggc caccagggga gccagcggca 15180
aggtaatttt gtcgcccacg ccgccagtgg agtgcttgtc gacggtgggg cgggatagcc 15240
caacgaagga catccgctcg cccgactcga tcatggccgt cgtccaggct gacagctcag 15300
cgtcgtcgag cccctggaag tacaccgcca tcgccatggc agacatctgc tcgtcggcga 15360
cgatgtcgtc ggtgtaggcg cggataagcc atgcgatttg gtcggagttg agagcctggc 15420
cttcgcgctt agcgcggata aggtcgacga cggaataggt gctggtcatg gcgcaagtat 15480
gacagggctt acccttctcc agtgcgtgga tgccccggtt atgtcgcgtt atgtcgttag 15540
tcttaactca tgcgtattgc ccggtttgtc accgctggtt ccgaccctgc cttcgggatc 15600
gtagagcttg ctgccgatca tggagatcat cccgagacca tcgccgttat cacgggggac 15660
ccagtggcgg caccggttca atacactggt gcccgtcacg accttgccga tgcgcgactg 15720
ctgtctccgg tgattccgcg atcgaagatc attggggttg gtcgcaacta cgccgatcac 15780
gccagcgagc tgggcaatga ggttccccac caaccgcttc tatttgttaa gccgaatacc 15840
tcggttatcg gccctgacga acccattgtg cgaccgactg cgtcctccaa cctgcactac 15900
gagggggagc tggccatcgt tatcggacgg atctgtaagg acgtgccaga ggacagagct 15960
caggaagtca tctttgggtt caccgttgcc aatgacgtca ctgcccgcga tctgcaagat 16020
tctgacggtc actgggttcg cgccaagggt gctgacacct tctgcccgct ggggccatgg 16080
atggttaccc acttctccat tgcggaagcg tctcactgcc agatcgtgac tcgactggac 16140
ggtagggaag ttcagcacgg taataccgac cagatggtcc actccatccc caagctcatc 16200
tcctatatct cctcgttcat gaccttgttg ccgggcgatg tcatcctcac gggtaccccc 16260
gctgaggtcg ggccgatgga actcggacag cgcgtcgagg ttgaaattga ggggatcggg 16320
acgctaacga acactgtcgt ggaggcctga tggcggctcg tgccctgtcc cgccgtgcga 16380
cggtgactga ccccgagcca cgggtcgact acacccgggt tctcgttgat tcgagtgctg 16440
gcccgggtcc cggactgctg gggctcatcg ggttgctgtt ggggtatgcc gtcgtcgttc 16500
cggggctgct atacgccttc cttggcgtcg gttggctcct cgagcgtacc gacggggaag 16560
gattcagcgc ctattacacg cgagcagccg ggtatcacac cgtcgggggg ctcatagcca 16620
cacatgtggc tctagccagc ctgatcgtcg tggtgcttgt gctcgcccgc taccttaacc 16680
atcgtgtgcc gcgatgggtg gcttcggtac aaccaggaat tcgctggaga ttcgggttgt 16740
tggtgggcct tgtcgctgtc gtggtgctca acctcacgca gttactggta cgaggagggg 16800
ccaacgccca ttacatcgtt ccccggcact ggtgggcgtg gttgttggca atcatcataa 16860
cttcgccgtt ccaagcgatc gccgaggaga tgttctttcg cggctacctc atgaacgtca 16920
tctctggact gtcggtgaac ctgccggaaa aagccgggcg ctggacgtca gtagtcgtct 16980
ccgcactggt ttttgccctt atgcatggca cgcaaaacgc gtggcttttc gcggatcgat 17040
tcgcctttgg tttgctcgcc ggttggctcg tcatcgttac aggaggcctc gaggctggcg 17100
tggcggctca cgtcgtcaac aaccttttcg ccttcggtta tgcagtcttc ctgagagggg 17160
tgtcgcaggc ccgcggcatg accgcgatga gttgggtgga cgccgcgtgg gacattggtg 17220
gcttcttggc gatcgctctt gccggatggt ggatcggaag tctcatgaga gtggcccgac 17280
ggacacccgc gtgacaagga gtttcgtcct gatttgcaaa gttggtggat gggccattaa 17340
agtttctcgt cgttgcgcca ccgaggttca tcacggtgga atgacattgg ggtatggggt 17400
aattggcagc ccgactgatt ctggttcagt tagtccaggt tcgagtcctg gtaccccagc 17460
gcgggaaacc aaatccgtga agttgcacag atagcggatg gattgctaaa gtttcccagc 17520
ccggtttgga aacgagtcgg gggacaatcg aagaaggttc tcaagaccga gctcgacggt 17580
cattgataac ctcatggccc cgtagtgcag cggcctagca cgcggccctc tcaaggctga 17640
aacggcggtt cgaatccgct cggggctacc catagtagat ggcccggatc tagcaggatc 17700
cgggccatgg cagcattttg acgagatgcc atcccccaag acgcgaggaa ttaccctctc 17760
acacctctgg tcactttggg cagcactgtg atcctcattg cgcggaccgg cgcagcacct 17820
ccgataagcg ctctcccgcc gcgacgacgg caggagcgtg aatacgtccc ggctgacggg 17880
tgagacgctc gatcggtcct gacaccgata tagccgcaat gaccttccct gagggagagc 17940
gcactggggc cgagaccgat gccacaccgg cctcacgctc accgacagat tgagaccagc 18000
cgcgcttgcg cacggccgcc aaggtgactt cggagaaggc agagtggctc aagccacggc 18060
ggatcttgtc aacgtcttcc catgccagca ggatctgagc ggctgaaccg gcatccatcg 18120
acaacaccga cccgaccgga atggtgtcgt gaagaccggt gggacgctca gcag 18174

<210> SEQ ID NO 41
<211> LENGTH: 569
<212> TYPE: DNA
<213> ORGANISM: Sorghum halepense

<400> SEQUENCE: 41
gagagctgat gcttataaaa ctaaatgttg aacctgatca gcgccctgag gtatgatgta 60
gtctttgtaa tccaaaactt caattagcat cctgtacaca tgattctcaa ttgcatggtg 120
atccttacaa cggtgcttct tgtcatgact gacaggtcat ggttttagtt gatattttca 180
gagcaaaagt tgttgatata tctgagaaaa cacttaccat agaggtaaaa actcaatctc 240
taactagtgt acatattttg attggtatcc attttcctgt actgaactgt atgtttaatg 300
ggcatttcac caatgttagg tagctggaga tcctggcaaa attgctgcag tgcagcggaa 360
tctaaggaaa ttcggaatca aagaaatttg caggacagga aaagtaattt ctaatgttct 420
ttccttgcat ggacacataa tttttttctg taatgctaat ttaatgccct atcttcttag 480
attgctttga gacgtgaaaa gattggtgca acagcccgtt tctggcaatt ttctgctgct 540
tcttacccag accttataga ggcattgcc 569

<210> SEQ ID NO 42
<211> LENGTH: 5166
<212> TYPE: DNA
<213> ORGANISM: Sorghum halepense

<400> SEQUENCE: 42
actagttatt gacaagtgca tacttgtcag agccttgctg ttggcccagc tgagaaggaa 60
ggcatttcac gtattacaac agttgttcct ggtactgttg aatccattga gaagttagtt 120
cagcagcttt acaagcttgt tgatgtgcat gaagtaagct gcatgtaact cctaccaaaa 180
tcatttgtgt ttgcaaattt attatgttaa ctaacaaaaa catgcgattc ctgcaggttc 240
atgacattac cccctcacct tttgctgaaa gggaactgat gcttattaag gtttctgtaa 300
acactgctgc tcggagggaa atcctagata ttgccgaaat cttccgagca aaacctgttg 360

```
atgtttctga ccatacagta acgcttcagg ttggcatcct aacaatttgt gtgtttctcc    420
cagatttcca tcagtgcctt tgccaacact gatgatacta gagccagttt tagaaaaagc    480
gctgtgcaca ctgcacagcc acaaattaga tcacattgct tttgttgatt ttctgttgca    540
tagtaccact tgtggttaca ataacaacat catacccata tagaaacact gaatgtttga    600
caccagtact atttttttcat gctgcttcat ctaactgctc caagctatta gctattgcaa    660
aactcttgca taatggatcc cttattgatg attgcagctt actggagatt ttgacaagat    720
ggttgcacta caaaggttat tggagccata tggcatctgc gaggtatatt gcttgtcact    780
cacatcatct taagtgtgaa aaggcaattt ttgggtcctt tgggatgaac ggacagtcgg    840
atactttttt atttgacgcc agcagttgtt ttgttttctt ctgtagttta aaacacagcc    900
tgacaacctc ctgaagatta cttgtgattg tgaaacagaa tataagcaat tgtgcacaat    960
gccacatggt taagtagtcc taaataaaac tattcaaaag taacctgtga tgttctgtcc   1020
gcagccaatt gtcaccagat tttacactga aaaccttatt cgatgttttg cacacggtcc   1080
tcaccattgt gttgcacaca tgacaggtcg ccagaactgg acgagtggca ctggtccgcg   1140
aatcgaaggt cgactccaag tacctccgcg gctactctct tccattgtaa cctggcattt   1200
gtgatggtga tggcctgatg aagagcttgg ttggttgtta tagagcagac catctggcgc   1260
tgggttgtgt tgtgcagtta caggacttgt ttctttcatg tcgtgaactc cctcgcctgc   1320
gtgtccaata atgttctccc cggtaatatg cgtgttgagg ttgcatgtgt atcccaacga   1380
ctgtcagaat aagatgcata tacctgtttg cttcagcgga gagagatgcc aatcgtttga   1440
aacgcgtcaa tagtggtatg ctctggttgg gacttgggac ttgggaggct gccggcggca   1500
ggccagtcct ggcttgcacg aaaaaaaaaa agatccctcg ctgtgcttgg gtcgccaggt   1560
ttcagggctt tttctcaact ctgcagcttg agaaattttc tccaggggtc agagttttta   1620
cctcgatcga ggtcattccg caggggttga gttttttttta gtttatataa atatatgttt   1680
atacagttat actacttgat acggtgaggc agcctggcgc atgctgcgct gagggcgcat   1740
ctctcctacg aggctgctaa aacggtacgg atattttttt agctgtatat cgaatttgtt   1800
tagagaagtt tagatttatc tgtatttaag tctgaatatt taacatttga tgttgtatcc   1860
atatatgagt atttaaatca tatatttatg atgttccaat catatttcat ccgtcatagt   1920
taatattatt tatattcaaa tctaaatcct catagaaata taaaaataaa tataatatcg   1980
gttatatccg ttcgtatttc atcccctatt ggttactgga ctgttgtgtg gctgatctga   2040
gcactgagct tgccaattga ttgacacctt ggctaataag tcatagttga gaataatgtt   2100
cgctaattta ttatgagaga aaaatactac taaataataa ataatgggag attctacgaa   2160
taagctcaag ccaacggagc tacgcctttg cttgcctatg cgctacgagg agcctctcgt   2220
gagtcatacg cacctacacg tgaccgtgct actcgagcca agttggacgt gccgcaggac   2280
actgccaccg ccatctatgg tctagggctg cgggtcgcgg agaggctaat gggggtggcc   2340
gttgcacgcg acgaaacaaa cgggcgcggg ccaggccaac gttactgggc ttccgaccga   2400
ctccagaggc cctatcccac caatgcaatg cagcccagga gcggagacgg aggaaggcgt   2460
ggcacccgac ccgattccgg gtaggaaggt acggcgaggt aagcgaagaa gcatccagac   2520
tctcgcagtc tcgctcgagg ggcaggggcg cagggcaggg ccgggcaggg ggcgggcggc   2580
gatccgaatc caatcgccgg gagggaggaa gcaaccggcg gcggtagagg cggagggatg   2640
acgcgcggga agcagaagat cgacgcgcag cggcgtaacg cggagcggaa ccagaaatcc   2700
aaggggtccc agctcgaggc ccgcgccgtc ggcctcaagg tcgtctgccc catctgcaag   2760
```

-continued gtaaataagc cggagccccg ctctccgatc gctagccatc gcctggactg gaacctgccg 2820
ggtttgcctc ggcagtagat ccggccaatc tgtccaattt tgccgtatcc gtgcttgcct 2880
actgcatcac agcatacgga gcatttcaat agtgtctact gcatcacagc gcacggacca 2940
aagttgttca acttctggcc gggcctgctc tgcagagtat ccatccatct agcgcctcac 3000
tttatctgga aacaaaaatt ttgccagtaa attgaaatgt tcctgctgca tatcatcagt 3060
actattgctc taacctcctt taatcagcca gtttgttgta ggccaatcgt tgacacatgt 3120
tgttccagcg tactcatatt gttgccttgg gggtttgggg ccgggtaata gtgatactgt 3180
cacggcccct cacctcagcc agcccaagga agcccatcta cagaggaaga gcacaagggc 3240
ccgtgcaagg aatgtccgcg ccctcggccc agaatgggtc tgtaatcgct gtgtgctggc 3300
tagtgagtag ataaggagag gaagtgagga ggattggcat catctatctt gtaacagact 3360
aaaccctagt aagaacgccg gcctcgttgg tccttggcga aggaactcat ggttgcgatc 3420
ccagtgggtc gctaacagat actaggcatc ctgactagaa tgagagattg ggagtactcg 3480
aagtggattc tactggccag tgtgtctgac actttaccac accgcagtta aagctagtgc 3540
tacaaagaag tggccacata accttctcct agcatgattt gatctcacgt gtaaaagact 3600
tccatcacat ttttcccaaa agtagagcca atatttcaga aagaattcct gttgtgcaac 3660
cttcgtctaa acacatggtt tagctgtact ctttcattac ccaatgcttt cttcatatga 3720
taactcaaaa ggttactgca gcatattggc tctagtcttc tgtattttct ggattccttt 3780
taaatcggga gtaaagtcgt gggttcatta tgtggatgcc ctacttttta cctggctagt 3840
tgcatttgag gaacatacct gctcacctgg tgttgctatt tccataggta caattggcaa 3900
atgaaaaaca gctgaccgat cactacggat caaagcatcc aaaggagaaa cctccaagca 3960
catcgaccac ggaataacca tgactggtgg tgatgcagga acatagatcc tgcttggctg 4020
gtttgaggat ctttaagtct gatccatggc ctggagttgg atcttaaagt cggctatact 4080
ctgtagtgtg tcttatttcc tcttgtttca ggcaacaccc ttgatacgag tgtgcatttc 4140
tgctagtatg ttctgtgatc gtactgccga tgtatctcca aactgtatgt gatcgcccgt 4200
ggcattggga tgatgcgaaa aaaaattatg atcataacta tgttcaaatg tttgtggctt 4260
tttacaacat ggcttatgca cgtgcgttcc ctagccctaa tggccgccaa ataggccacc 4320
acggcaccac ccctggtgtt tgatcggtgc cgtgcttcag ttgtatccgg atgaatgaag 4380
tgaggaacat gagctggtcg atcccaatca agtaaaaggc ttgtctgacg atgctatcag 4440
gccttcttaa acggctaatg ctgttagcat cagtgaactg gtatcgtggc aaaatcgcta 4500
tccccatcga caggccaaga gcatttgcac gtcaccaatg ccataaataa ctcatgctgt 4560
aatatttga ggaaataaaa cgtgcttata tatattcttc ttctcatttt tacaaagtta 4620
ctttagtttt gtacttgacg agtatgaaaa aggggctagg agcattaggg gcactctatg 4680
ctgtatttag aaaggtcaac atataatttc gttgcaaggg ttagttggta aattcacagt 4740
ttgccacatg gcatggtctc attcccctag ccacccaaaa tatatggata atagccgata 4800
cagtagctgt cagccatagt tatctggtga agtatatcac ggatgatgac ggacgttttt 4860
cttttggaga ggctgcagtc ttttattcga agatatttgg tcaacgttgg aatgctagct 4920
ttgatctggc tgtacaacaa ggctttatta gccgaatgtc agctattcag caatgttttt 4980
ctttcacaac aaatcagcta atagtatttt tatcataatt tattagtcaa acgaacatac 5040
gctaacaagg taccactagt gagagctata ggacgctgat ggagaaggag aacaagacaa 5100
ggtacacgaa gatgttgttc agttccaaaa aaaaattgta aaatggacac tgtaacactt 5160
ttattt 5166

<210> SEQ ID NO 43
<211> LENGTH: 1770
<212> TYPE: DNA
<213> ORGANISM: Sorghum halepense

<400> SEQUENCE: 43
tctgtttcta ttttcttctt ctgatggatg aggcggctcg ggtttctggc gccaaatgca 60
gggtgcggcg ccacacgatt tcggtgttcg tcggggacga gagcggcatg atcaaccgca 120
tcgccggggt cttcgccagg agaggctaca acatcgagtc gctcgccgtg ggctcaaca 180 aggacaaggc cctcttcacc attgtcgtct ccgggaccga cagggtgctc aaccaagtca 240
tcgagcagct caataagctt gtcaacgtcc ttagtgtgag tccgccttgt caaaatttag 300
caaaactcac gcgaatccat acttgatttt gatgcccccg gtttgagcac ttggtgacaa 360
ttcactagta cagtgagatt ttgttccatg agtttagctc gcccgaatct tctgtccttt 420
ttattctgtt aggatcgtcg tttccacttt cgtggagcat cttttgtgta gctagacaga 480
gcatgcgtaa ctttttcttt tcctgattta gtcattatca tgttcgaagt attcttttcc 540
cttttcccct agaatcgctg ccagcctgac agtcatgtca acgtcaggga catactcctt 600
tctaggggat acctcaaatg caacatcatt attatacgcc ctgtatcatg tttatgcaat 660
gcactttctg tttgtgcacc tgtgccgtgt atggtaagca ctgttgctct ggttaatcat 720
ttgatgaaaa aaataagata ctcaacttca ttattctgac tatgtggtag tacttattta 780
gttcaatttt aatgctaccc tgtacatgtc tatatcctat aacctaaagc agcctttcag 840
ttaggagtta ttctgagttt tctttgttct tgcgatttga agatgctgat ttcttgggga 900
aaagatttat tgttctctct gaacgtacta tgcagataat acattgcttt actttccttc 960
tgaattctta gccagaaaaa cttcatggat taccattcct tcactgtttg cgtcaactaa 1020
acatttagat ggttttaact accatgatat tttctctctg aaaattatct actgctactg 1080
ttttgttcct aacttgcact aagagtaata ccaataaatt cttatttatt ttttgtttgg 1140
atctgatcaa ttacaggttg aagatctatc taaagaacct caggttgaaa gagagctgat 1200
gcttataaaa ctaaacgttg aacctgatca gcgccctgag gtatgatgta gcgttgagtt 1260
agtctttgta atccaaaact tcaattagca tcctgtaccc acgattctca attgcatggt 1320
gatccttaca acggtgcttc ttgtcatgac tgacaggtca tggttttagt tgatattttc 1380
agagcaaaag ttgttgatat atctgagaaa acacttacca tagaggtaaa aactcaatct 1440
ctaactagtg tacatatttt gattggtatc cattttcctg tactgaactg tatgtttaat 1500
gggcacttca ccaatgttag gtagctggag atcctggcaa aattgctgca gtgcagcgga 1560
atctaaggaa attcggaatc aaagaaattt gcaggacagg aaaagtaatt tctaatgttc 1620
tttccttgca tggacacata tttttttct gtaatgctaa tttaatgccc tatcttctta 1680
gattgctttg agacgtgaaa agattggtgc aacagcccgt ttctggcaat tttctgctgc 1740
ttcttaccca gaccttatag aggcattgcc 1770

<210> SEQ ID NO 44
<211> LENGTH: 3709
<212> TYPE: DNA
<213> ORGANISM: Sorghum halepense

<400> SEQUENCE: 44

-continued

```
tgaaaaacat actgataacc gtaactacag aaaaccacac ctatctgact atccaaaacc     60
acaacttcca caggaatatc tcacctgtcc actgtcccct gaatcataat ccttgtagag    120
caccacgcaa ttatctctga agtcataata cacctaaacc ctaaacccta atctatgatg    180
ctaacagcac aggacaggac acaatcatat tcataaccag gcttaaaacc ctacatggga    240
tttgttcaaa agccaaatct acagatgatt cctatggttt aattcaatgt atgaatctga    300
ctaaccacgt tgaaatcact gcagcaccaa aattctcatg gcaatcacaa tgtcgtattc    360
tatccaggtt agttgctctt gtttttttta acacctatca catcgaatgt ttagacacat    420
gcatgaagta ctaaatataa attatttatg aaactaaaaa cacacctaga gaataatttg    480
cgagacgaaa cttttaagcc taactagttt atgattggac attaattgtc aaataaaacg    540
aaaatactat aggacatgtt aaactttaac gtctcttacc aacacccccct tatctttata    600
aggaacaata aacaaaattt gccccactgt tctagatcac ctaataatat ccccagctaa    660
aaacaataaa ggtttcctag aattaagaca agcatgactg ttcctccagg agggtttgga    720
acattgttgc agtcttgcag atacgggcga agggtgagaa acagagcgga gggctggagg    780
tgacctcggt agtcgacgcc ggagttgagc ttgacaacga cggggcggcc cctgatggac    840
ttgaggaagt ccgatggcgt cttcaccatc gcgccggcgc ccgaggcggg cctgtcgctg    900
ccgccgccgc tgctcatctt gcgcgctgtg cccccggcgg tgttcctgtg ttgcggatcg    960
cgggtgggcc aggtggatgc gagtgcgacc cgtttggact ccggccggag cggccggatc   1020
cctggtcggt gtcagtgccg tttactctgg gccccacgtg tcagtaccgt ctgtagatga   1080
caacaacccg tcgtccacag tcatgtccaa tatatccttt cttctttttt tttcgattcg   1140
gatatctatc ttcctttttt ttccaaaaat cttcttgacg caccagcgcg cacgtttgtg   1200
gtaaacgccg acacgtcggt cccacgttga tagaccccac cgaccagtga gtagcgtgta   1260
cgtattcggg ggtgacggac gtgtcgccgt cgtcttgcta gtcccattcc catctgagcc   1320
acacatctct gaacaaaaaa aggagggagg cctccacgca catccccctc cgtgccaccc   1380
gccccaaacc ctcgcgccgc ctccgagaca gccgccgcaa ccatggccac cgccgccgcc   1440
gccgctgccg ccgcgctagc cggcgccact accgctgcgc ccaaggcgag gcgccgggcg   1500
cacctcctgg ccgcacggcg cgccctcgcc gcgcccatca ggtgctcagc ggcgccaccc   1560
gccacgctga cggtgacggc tcccccggcc accccgctcc ggccgtgggg ccccaccgat   1620
ccccgcaagg gcgccgacat cctcgtcgag gctcttgagc gctgcggcgt ccgcgacgtc   1680
ttcgcctacc ccggcggcgc gtccatggag atccaccagg cactcacccg ttcccccgtc   1740
atcgccaacc acctcttccg ccacgagcaa ggggaggcct tcgccgcctc tggcttcgcg   1800
cgctcctcgg gccgcgtcgg cgtctgcgtc gccacctccg gccccggcgc caccaaccta   1860
gtctccgcgc tcgccgacgc gctgctcgac tccgtcccca tggtcgccat cacgggacag   1920
gtgccgcggc gcatgattgg caccgacgcc ttccaggaga cgcccatcgt cgaggtcacc   1980
cgctccatca ccaaacacaa ctacctggtc ctcgacgtcg acgacatccc ccgcgtcgtt   2040
caggaggctt tcttcctcgc ttcctctggt cgcccgggac cggtgcttgt cgacatcccc   2100
aaggacatcc agcagcagat ggcggtgccg gtctgggaca cgcccatgag tctgcctggg   2160
tacattgcgc gccttcccaa gcctcctgcg actgaattgc ttgagcaggt gctgcgtctt   2220
gttggtgaat caaggcgccc tgttctttat gttggtggtg gctgcgcagc atctggcgag   2280
gagttgcgcc gctttgtgga gatgactgga atcccagtca caactactct tatgggcctt   2340
```

```
ggcaacttcc ccggcgacga cccactgtct ctgcgcatgc ttggtatgca tggcacggtg   2400
tatgcaaatt atgcagtgga taaggcagat cttttgcttg catttggtgt gcggtttgat   2460
gatcgtgtga cagggaagat tgaggctttt gcaagcaggg ctaagattgt gcacattgat   2520
attgatcccg ctgagattgg caagaacaag cagccacatg tgtccatctg tgcagacgtt   2580
aagcttgctt tgcagggcat gaatgctctt ctggaaggaa gcacatcaaa gaagagcttt   2640
gactttggct catggcaagc tgagttggat cagcagaaga gagagttccc ccttgggtat   2700
aaaacttttg atgacgagat ccagccacaa tatgctattc aggttcttga tgagctgaca   2760
aaaggggagg ccatcattgc cacaggtgtt gggcagcacc agatgtgggc ggcacagtac   2820
tacacttaca agcggccaag gcagtggttg tcttcagctg gtcttggggc tatgggattt   2880
ggtttgccgg ctgctgctgg cgctgctgtg gccaacccag gtatcactgt tgttgacatc   2940
gacggagatg gtagcttcct catgaacatt caggagctag ctatgatccg aattgagaac   3000
ctcccagtga aggtctttgt gctaaacaac cagcacctgg ggatggtggt gcagtgggag   3060
gacaggttct ataaggccaa tagagcacac acatacttgg gaaacccaga gaatgaaagt   3120
gagatatatc cagatttcgt gacaattgcc aaagggttca acattccagc agtccgtgtg   3180
acaaagaaga gcgaagtcca tgcagcaatc aagaagatgc ttgagactcc agggccatac   3240
ctcttggata taatcgtccc gcaccaggag catgtgttgc ctatgatccc tagtggtggg   3300
gctttcaagg atatgatcct ggatggtgat ggcaggactg tgtattgatc taaatttcag   3360
catgcacatc tccctgcctt tctttgacat gcatatgagc tggtacaagg gtgatgtgtt   3420
atttatgtga tgttctcctg tgttctatct ttttgtaagc cgtcagctat ctatagtgtg   3480
cttgtttgat gtactctgtt atggtaatct taagtagttt cctaccttgt agtggtgtag   3540
tctgttgttt cgtgctggca tatctgtcat cagaggtcat gtaagtgcct tttgctacag   3600
ataaataagg aaataagcat tgctatgcag tggttctgaa ttggcttctg ttaccaaatt   3660
taggtgttca actggtcctt gcttttgttt tagctctttt tttcttgtt              3709
```

<210> SEQ ID NO 45
<211> LENGTH: 2004
<212> TYPE: DNA
<213> ORGANISM: Sorghum halepense

<400> SEQUENCE: 45

```
atattattca attataaact aattagattt aaaaattcat cttgtgattt atggataaac     60
tgtgtaatta gtttttattt tcgtccatat ctaatgtttc atgcatatgc tctatgattt    120
aatgtgacaa agttttttttg tttcgggaga aaaaggtgat gcggagccgc cagtcctaga    180
ttgggaaatc aaccacctca tccgtccgcg tgtgcgcgtt gacacaaaag tccctctctc    240
cctccgaaaa cccccgccgc ggcgttccgt tccccctccg gcatctccgg tatccatcct    300
ttcgccatga acgctgctgc aatcatctcc cgacttggcc tcgccacctc agggcctggg    360
gccgggtccc acgcggactg ccggccgccg acgccggcgg tgggtttcac ggcggggccg    420
agagcgcgcc cagttgccgt cgccgccgcc gcctcctcct cttctccggc gaccgatggc    480
gtggcgccgg tgccaccccg ctccaatcac tcggtcataa agcgtcacac actatcagtt    540
tttgttggtg atgaaagtgg gatgatcaat cgaattgctg gggtttttgc tagaagagga    600
tataacatcg agtcattggc tgttgggttg aacaaggata aagcattatt tacaatagtt    660
gtgtcaggaa cagacaaaat attgaaccag gttgtagagc aactaaacaa acttgttaat    720
gtaataaagg ttgatgactt atcaatggaa ccacaagttg aaagagaact tatgcttata    780
```

```
aaagtaaatg cagagcggga aaagctacct gagataatgg gtttggttcg cattttcaaa    840
gcagaagtgg ttgatctttc agaccataca ctaactattg aggtaactgg agatcctgga    900
aagatggttg caatacagaa gactctgagc aaatatggga tcagagaaat tgctagaact    960
ggcaagatag ctttacgccg tgaaagaatg ggagaaactg ctccattttg gaggttctct   1020
gcagcttctt atcctgatct cgaaatggca ataccttcaa atttccagca aaacactggt   1080
gcgagggcaa tcgatcagaa tacagaagga tcttcagggg gtgatgttta tccagtggaa   1140
tcttatgaaa gcttctcatc aagtcaaatt ctggatgctc attggggtgt tatgactgat   1200
ggtgatccaa cagggttttg ttcacatact ctatcaattc ttgtgaatga tgtccctgga   1260
gttctcaatg ttgtaacagg tgttttctcc agaaggggct acaatattca gagtcttgct   1320
gttggtccag ctgcaaaaga aggaacttct cgcatcacta ctgttgttcc tggaactgat   1380
gaatccattg ccaagctagt acatcaactg tacaagctca ttgatgttca tgaggtccag   1440
gattttactc acttaccatt tgttggtaga gagttaatga tcataaaggt tgctgcaaat   1500
gctacagccc gaagggatgt cttagatatt gctcagattt ttgaggcaca gaaagttgac   1560
atatctgatc acacaattac actactgctc accggagaca ttgacagaat ggttagattg   1620
caaaagatgc tggagcaata tggtatctgt gaggttgcac gaacaggacg ggttgctctg   1680
ctccgtgagt ctggagttga ctccaaatac cttcgtgggt tttccctccc tctgtaattc   1740
tccatctgcg gatcgacata gcactccaca attcaggtcg cacggccatt ttgaggaatc   1800
attcaaatat tctagggtga gaactgtaga cacactatat tgttggggtt gctacgttct   1860
atgctattaa gcttcttgct tatgcaagta tatatcacgc agcacctggg cagaaaccat   1920
atccggtcca atattttcat tgcacaggta gtatacgtgt cctagttgaa ggaaaggcag   1980
tatatctgtc tcttatacac atct                                          2004
```

<210> SEQ ID NO 46
<211> LENGTH: 1285
<212> TYPE: DNA
<213> ORGANISM: Sorghum halepense

<400> SEQUENCE: 46

```
atagagccat aggaaatatg gaaattaaca acaggggaca ttacagatca ggtctgtgga     60
cctggcacta ctaaactttg ttgcttggct gacatctcta gttgtgaata cagataatgg    120
gtttggttcg cattttcaaa gcagaagtgg ttgatctttc agaccataca ctaactattg    180
aggtaactgg agatcctgga aagatggttg caatacagaa gactctgagc aaatatggga    240
tcagagaaat tgctagaact ggcaagatag ctttacgccg tgaaagaatg ggagaaactg    300
ctccattttg gaggttctct gcagcttctt atcctgatct cgaaatggca ataccttcaa    360
atttccagca aaacactggt gcgagggcaa tcgatcagaa tacagaagga tcttcagggg    420
gtgatgttta tccagtggaa tcttatgaaa gcttctcatc aagtcaaatt ctggatgctc    480
attggggtgt tatgactgat ggtgatccaa cagggttttg ttcacatact ctatcaattc    540
ttgtgaatga tgtccctgga gttctcaatg ttgtaacagg tgttttctcc agaaggggct    600
acaatattca gagtcttgct gttggtccag ctgcaaaaga aggaacttct cgcatcacta    660
ctgttgttcc tggaactgat gaatccattg ccaagctagt acatcaactg tacaagctca    720
ttgatgttca tgaggtccag gattttactc acttaccatt tgttggtaga gagttaatga    780
tcataaaggt tgctgcaaat gctacagccc gaagggatgt cttagatatt gctcagattt    840
```

-continued

```
ttgaggcaca gaaagttgac atatctgatc acacaattac actactgctc accggagaca    900

ttgacagaat ggttagattg caaaagatgc tggagcaata tggtatctgt gaggttgcac    960

gaacaggacg ggttgctctg ctccgtgagt ctggagttga ctccaaatac cttcgtgggt   1020

tttccctccc tctgtaattc tccatctgcg gatcgacata gcactccaca attcaggtcg   1080

cacggccatt ttgaggaatc attcaaatat tctagggtga gaactgtaga cacactatat   1140

tgttggggtt gctacgttct atgctattaa gcttcttgct tatgcaagta tatatcacgc   1200

agcacctggg cagaaaccat atccggtcca atattttcat tgcacaggta gtatacgtgt   1260

cctagttgaa ggaaaggcag tatat                                         1285
```

<210> SEQ ID NO 47
<211> LENGTH: 562
<212> TYPE: DNA
<213> ORGANISM: Sorghum halepense

<400> SEQUENCE: 47

```
caacaaggac aaggccctct tcaccattgt cgtctccggg accgacaggg tgctcaacca     60

agtcatcgag cagctcaata agcttgtcaa cgtccttagt gttgaagatc tatctaaaga    120

acctcaggtt gaaagagagc tgatgcttat aaaactaaac gttgaacctg atcagcgccc    180

tgaggtcatg gttttagttg atattttcag agcaaaagtt gttgatatat ctgagaaaac    240

acttaccata gaggtagctg gagatcctgg caaaattgct gcagtgcagc ggaatctaag    300

gaaattcgga atcaaagaaa tttgcaggac aggaaaaatt gctttgagac gtgaaaagat    360

tggtgcaaca gcccgtttct ggcaattttc tgctgcttct tacccagacc ttatagaggc    420

attgccgaaa aaatccaatt acatctgtaa ataggacagt gaatggaagt tttgatcaac    480

catccaatgc tgggggtgat gtctatcctg tggaatctta tgagacctta tcagcaaacc    540

atgtacttga tgctcattgg gg                                             562
```

<210> SEQ ID NO 48
<211> LENGTH: 1294
<212> TYPE: DNA
<213> ORGANISM: Sorghum halepense

<400> SEQUENCE: 48

```
aaatccaatt acatctgtaa ataggacagt gaatggaagt tttgatcaac catccaatgc     60

tggggtatgt aaccttttac ttttaaaact ttctagaatt tttttttctt atatcatgtc    120

ctgctctgtt tataatttta cacttagttt tggtcgaatg atgcatataa ccaatttgag    180

gtggatacat taaagaaaaa aaacctgtga tttcagtaat gcctattcac ttgaaccaac    240

tgcgggtgag cttctatgtt aacagataaa ggtaccaata atcactggct gtatttaagt    300

aattacctgc agtgatgctg gcatattagt tttctgagtc taataagttt gaacaattac    360

ctcgagcctt gagaggggtt agttcaccaa agtcaataca tttataaatg cacggtaatg    420

cagaatggtc ttatgaataa tcaactggta actgaatgta catatagtat ttgcacatat    480

gaaacagtag tactgatgga cgagtcgtgc agtaccatga cacctggtac attgaacttg    540

tgtgaactgt atatatttac tattgtgtta atgggaatgt attgttgggt gatacccaca    600

catagtgcac aaacatacat aaatagtatt aacagggatt gcagtcttag tcgtagtcca    660

cgtttgctca atatgtagtt tggactaata ctaataccat taatggttac agcatgctag    720

ttgtttagac ttccatcgaa tgcatttgat acaatattac agtctacaca ctattcctgg    780

ctcttataac acgtgttgtt ttgactttgg aactgtccag ggtgatgtct atcctgtgga    840
```

atcttatgag accttatcag caaaccatgt acttgatgct cattggggtg ttctggatga 900
tgatgatgat gtaagtatag agatttccat catgtgattt gcatttagtg ctacatggac 960
attgctggtt tgctctgcgc ataattgcat cctgaatcta attataatgt gactggagtg 1020
tgttttcatt tacacttcca ttatgtttgc aagaagtcaa tttgtaggca aagcctatct 1080
agctttaaga aacggtaata atgcttaacc tgcatgttta tgtatattgt tgttatcttg 1140
cagctgctaa tcccagtatt gattttgtgt ggtacaggta actggacttc gctcacatac 1200
cctctccatt cttgtgaatg actgtcctgg tgtcctcaac attgtaacag gagtctttgc 1260
tcgcaggggc tacaatatac aggttttctt tgtc 1294

<210> SEQ ID NO 49
<211> LENGTH: 1543
<212> TYPE: DNA
<213> ORGANISM: Sorghum halepense

<400> SEQUENCE: 49
gacaatgatt tatgaatgat gtttgcttta gcttctctca ctgttacgat gtttttcaac 60
tgatatttcc ctagttctat gcttcctatt gattagcttc atgtggtcaa ttggttcatc 120
tccttgaatt ggttttagtt ggtgctcatt ctgttgaatt gggtactaag tagtaagtac 180
aactccattt gtctttctga ggatacttct tactgctatt gatagtttag taacattagt 240
ccttccaatg tgaaccctgt atgtgtgtac atgcacatgt tgtcatttat atattttcct 300
atttgcacat atctgacatt gcagtcaaat agcatgaatg cattacttaa tttgtttttt 360
ggactctttt aagtattttg gcagtatcat taattattaa agtaagaaaa tactcgcaca 420
ttctttttct tattggtgta atgttttctg aaaatacctt ttatcatcct cacactgtta 480
gtttgagttt gaatgagttt atttttatgt gtttctctgc ttctacccag ggtgatgttt 540
atccagtgga atcttatgaa agcttctcat caagtcaaat tctggatgct cattggggtg 600
ttatgactga tggtgatgta cggtcttgtg ttctaatgac tttgaactgt ttggtgctag 660
ctagagatga accacatcta gttgtactca tttcactaga agctattgtg ttgttagaag 720
ttaaaagaca tgaccgcatg agtagccaga atccaaattc gagactagat tatatataac 780
taaattgtgg ttcatagtga agagggtttt gtacctattt ataagacata actaaattcg 840
agacatgact gcaactaaat gtacctattt ataaactaaa ctagcaattt cttgttgctt 900
cagccaacag ggttttgttc acatactcta tcaattcttg tgaatgatgt ccctggagtt 960
ctcaatgttg taacaggtgt tttctccaga aggggctaca atattcaggt tgttcaaacc 1020
aattttgtat tttatgctcc ctttatttcg gtaattgcat aatccaatcc ttgctaaaca 1080
gtaaccatca cttttgcaga gtcttgctgt tggtccagct gcaaaagaag gaacttctcg 1140
catcactact gttgttcctg gaactgatga atccattgcc aagctagtac atcaactgta 1200
caagctcatt gatgttcatg aggtaaaaat taacatgcag tttgcatgat tgttatagaa 1260
gtgctgaaag tcattttggt tttctcaggt ccaggatttt actcacttac catttgttgg 1320
tagagagtta atgatcataa aggttgctgc aaatgctaca gcccgaaggg atgtcttaga 1380
tattgctcag atttttgagg cacagaaagt tgacatatct gatcacacaa ttacactact 1440
ggtaactatc attgaaacaa tgtttacttg agcacttacc tcatgtagca ctctaatatt 1500
cttctaaaat tatgataatt tcatctactt gtataaaatc ctt 1543

<210> SEQ ID NO 50

<211> LENGTH: 761
<212> TYPE: DNA
<213> ORGANISM: Sorghum halepense

<400> SEQUENCE: 50
acctcggccc ccgctgccgt gtcggcggtc gcccccgcgg ccgccgccgc cagggacaag 60
taagcggccc ccccttgccc gccgaaatgc tgcctcctta cttctcaatc tctctcgcgg 120
gcgcgcggga ctcgggttgt tttggttgtg cacgcgccgc ttttgtctgt ttctattttc 180
ttcttctgat ggatgaggcg gctcgggttt ctggcgccaa atgcagggtg cggcgccaca 240
cgatttcggt gttcgtcggg gacgagagcg gcatgatcaa ccgcatcgcc ggggtcttcg 300
ccaggagagg ctacaacatc gagtcgctcg ccgtggggct caacaaggac aaggccctct 360
tcaccattgt cgtctccggg accgacaggg tgctcaacca agtcatcgag cagctcaata 420
agcttgtcaa cgtccttagt gtgagtccgc cttgtcaaaa tttagcaaaa ctcacgcgaa 480
tccatacttg attttgatgc ccccggtttg agcacttggt gacaattcac tagtacagtg 540
agattttgtt ccatgagttt agctcgcccg aatcttctgt cctttttatt ctgttatagg 600
atcgtttcca ctttcgtgga gcatcttttg tgtagctaga cagagcatgc gtaacttttt 660
tctttcctga tttagtcatt atcatcttcg aagtattctt ttccctttc ccctagaatc 720 gctgccagcc tgacagtcat gtcaacgtca gggacatact c 761

<210> SEQ ID NO 51
<211> LENGTH: 1537
<212> TYPE: DNA
<213> ORGANISM: Sorghum halepense

<400> SEQUENCE: 51
gatttatgaa tgatgtttgc tttagcttct ctcactgtta cgatgttttt caactgatat 60
ttccctagtt ctatgcttcc tattgattag cttcatgtgg tcaattggtt catctccttg 120
aattggtttt agttggtgct cattctgttg aattgggtac taagtagtaa gtacaactcc 180
atttgtcttt ctgaggatac ttcttactgc tattgatagt ttagtaacat tagtccttcc 240
aatgtgaacc ctgtatgtgt gtacatgcac atgttgtcat ttatatattt tcctatttgc 300
acatatctga cattgcagtc aaatagcatg aatgcattac ttaatttgtt ttttggactc 360
ttttaagtat tttggcagta tcattaatta ttaaagtaag aaaatactcg cacattcttt 420
ttcttattgg tgtaatgttt tctgaaaata ccttttatca tcctcacact gttagtttga 480
gtttgaatga gtttatttat atgtatttct ctgcttctac ccagggtgat gtttatccag 540
tggaatctta tgaaagcttc tcatcaagtc aaattctgga tgctcattgg ggtgttatga 600
ctgatggtga tgtacggtct tgtgttctaa tgactttgaa ctgtttggtg ctagctagag 660
atgaaccaca tctagttgta ctcatttcac tagaagctat tgtgttgtta gaagttaaaa 720
gacatgaccg catgagtagc cagaatccaa attcgagact agattatata taactaaatt 780
gtggttcata gtgaagaggg ttttgtacct atttataaga cataactaaa ttcgagacat 840
gattgcaact aaatgtacct atttataaac taaactagca atttcttgtt gcttcagcca 900
acagggtttt gttcacatac tctatcaatt cttgtgaatg atgtccctgg agttctcaat 960
gttgtaacag gtgttttctc cagaaggggc tacaatattc aggttgttca aaccaatttt 1020
gtattttatg ctccctttat ttcggtaatt gcataatcca atccttgcta aacagtaacc 1080
atcacttttg cagagtcttg ctgttggtcc agctgcaaaa gaaggaactt ctcgcatcac 1140
tactgttgtt cctggaactg atgaatccat tgccaagcta gtacatcaac tgtacaagct 1200

```
cattgatgtt catgaggtaa aaattaacat gcagtttgca tgattgttat agaagtgctg   1260

aaagtcattt tggttttctc aggtccagga ttttactcac ttaccatttg ttggtagaga   1320

gttaatgatc ataaaggttg ctgcaaatgc tacagcccga agggatgtct tagatattgc   1380

tcagattttt gaggcacaga aagttgacat atctgatcac acaattacac tactggtaac   1440

tatcattgaa acaatgttta cttgagcact tacctcatgt agcactctaa tattcttcta   1500

aaattatgat aatttcatct acttgtataa aatcctt                            1537
```

<210> SEQ ID NO 52
<211> LENGTH: 1770
<212> TYPE: DNA
<213> ORGANISM: Sorghum halepense

<400> SEQUENCE: 52

```
tctgtttcta ttttcttctt ctgatggatg aggcggctcg ggtttctggc gccaaatgca     60

gggtgcggcg ccacacgatt tcggtgttcg tcggggacga gagcggcatg atcaaccgca    120

tcgccggggt cttcgccagg agaggctaca acatcgagtc gctcgccgtg gggctcaaca    180

aggacaaggc cctcttcacc attgtcgtct ccgggaccga cagggtgctc aaccaagtca    240

tcgagcagct caataagctt gtcaacgtcc ttagtgtgag tccgccttgt caaaatttag    300

caaaactcac gcgaatccat acttgatttt gatgcccccg gtttgagcac ttggtgacaa    360

ttcactagta cagtgagatt ttgttccatg agtttagctc gcccgaatct tctgtccttt    420

ttattctgtt aggatcgtcg tttccacttt cgtggagcat cttttgtgta gctagacaga    480

gcatgcgtaa cttttttctt tcctgattta gtcattatca tgttcgaagt attcttttcc    540

cttttcccct agaatcgctg ccagcctgac agtcatgtca acgtcaggga catactcctt    600

tctaggggat acctcaaatg caacatcatt attatacgcc ctgtatcatg tttatgcaat    660

gcactttctg tttgtgcacc tgtgccgtgt atggtaagca ctgttgctct ggttaatcat    720

ttgatgaaaa aaataagata ctcaacttca ttattctgac tatgtggtag tacttattta    780

gttcaatttt aatgctaccc tgtacatgtc tatatcctat aacctaaagc agcctttcag    840

ttaggagtta ttctgagttt tctttgttct tgcgatttga agatgctgat ttcttgggga    900

aaagatttat tgttctctct gaacgtacta tgcagataat acattgcttt actttccttc    960

tgaattctta gccagaaaaa cttcatggat taccattcct tcactgtttg cgtcaactaa   1020

acatttagat ggttttaact accatgatat tttctctctg aaaattatct actgctactg   1080

ttttgttcct aacttgcact aagagtaata ccaataaatt cttatttatt ttttgtttgg   1140

atctgatcaa ttacaggttg aagatctatc taaagaacct caggttgaaa gagagctgat   1200

gcttataaaa ctaaacgttg aacctgatca gcgccctgag gtatgatgta gcgttgagtt   1260

agtctttgta atccaaaact tcaattagca tcctgtaccc acgattctca attgcatggt   1320

gatccttaca acggtgcttc ttgtcatgac tgacaggtca tggttttagt tgatattttc   1380

agagcaaaag ttgttgatat atctgagaaa acacttacca tagaggtaaa aactcaatct   1440

ctaactagtg tacatatttt gattggtatc cattttcctg tactgaactg tatgtttaat   1500

gggcacttca ccaatgttag gtagctggag atcctggcaa aattgctgca gtgcagcgga   1560

atctaaggaa attcggaatc aaagaaattt gcaggacagg aaaagtaatt tctaatgttc   1620

tttccttgca tggacacata tttttttct gtaatgctaa tttaatgccc tatcttctta   1680

gattgctttg agacgtgaaa agattggtgc aacagcccgt ttctggcaat tttctgctgc   1740
```

ttcttaccca gaccttatag aggcattgcc 1770

<210> SEQ ID NO 53
<211> LENGTH: 1543
<212> TYPE: DNA
<213> ORGANISM: Sorghum halepense

<400> SEQUENCE: 53
gacaatgatt tatgaatgat gtttgcttta gcttctctca ctgttacgat gtttttcaac 60
tgatatttcc ctagttctat gcttcctatt gattagcttc atgtggtcaa ttggttcatc 120
tccttgaatt ggttttagtt ggtgctcatt ctgttgaatt gggtactaag tagtaagtac 180
aactccattt gtctttctga ggatacttct tactgctatt gatagtttag taacattagt 240
ccttccaatg tgaaccctgt atgtgtgtac atgcacatgt tgtcatttat atattttcct 300
atttgcacat atctgacatt gcagtcaaat agcatgaatg cattacttaa tttgtttttt 360
ggactctttt aagtattttg gcagtatcat taattattaa agtaagaaaa tactcgcaca 420
ttctttttct tattggtgta atgttttctg aaaatacctt ttatcatcct cacactgtta 480
gtttgagttt gaatgagttt atttttatgt gtttctctgc ttctacccag ggtgatgttt 540
atccagtgga atcttatgaa agcttctcat caagtcaaat tctggatgct cattggggtg 600
ttatgactga tggtgatgta cggtcttgtg ttctaatgac tttgaactgt ttggtgctag 660
ctagagatga accacatcta gttgtactca tttcactaga agctattgtg ttgttagaag 720
ttaaaagaca tgaccgcatg agtagccaga atccaaattc gagactagat tatatataac 780
taaattgtgg ttcatagtga agagggtttt gtacctattt ataagacata actaaattcg 840
agacatgact gcaactaaat gtacctattt ataaactaaa ctagcaattt cttgttgctt 900
cagccaacag ggttttgttc acatactcta tcaattcttg tgaatgatgt ccctggagtt 960
ctcaatgttg taacaggtgt tttctccaga aggggctaca atattcaggt tgttcaaacc 1020
aattttgtat tttatgctcc ctttatttcg gtaattgcat aatccaatcc ttgctaaaca 1080
gtaaccatca cttttgcaga gtcttgctgt tggtccagct gcaaaagaag gaacttctcg 1140
catcactact gttgttcctg gaactgatga atccattgcc aagctagtac atcaactgta 1200
caagctcatt gatgttcatg aggtaaaaat taacatgcag tttgcatgat tgttatagaa 1260
gtgctgaaag tcattttggt tttctcaggt ccaggatttt actcacttac catttgttgg 1320
tagagagtta atgatcataa aggttgctgc aaatgctaca gcccgaaggg atgtcttaga 1380
tattgctcag atttttgagg cacagaaagt tgacatatct gatcacacaa ttacactact 1440
ggtaactatc attgaaacaa tgtttacttg agcacttacc tcatgtagca ctctaatatt 1500
cttctaaaat tatgataatt tcatctactt gtataaaatc ctt 1543

<210> SEQ ID NO 54
<211> LENGTH: 1413
<212> TYPE: DNA
<213> ORGANISM: Sorghum halepense
<220> FEATURE:
<221> NAME/KEY: unsure
<222> LOCATION: (1)..(1413)
<223> OTHER INFORMATION: unsure at all n locations

<400> SEQUENCE: 54
aatccttggg acagtagaaa caccatatgg ttcaccattg actttatcat gccgttatga 60
tcctaccatt aagtaacata gtatattgat gtcaaaaagt aaaataaggt tatcttctaa 120
aatttttagt aaatttccat tgtagaagac tgcttcaaaa tttatagttt ttttctttgg 180

```
cttggccaat gatttttccc ctttgttttt gattaatagt atgcattcat atttgtacta    240
atttctttaa taaaaatatt tccttggtgc catgattagt gagcaataac cttgttggca    300
tatgcagctc accggagaca ttgacagaat ggttagattg caaaagatgc tggagcaata    360
tggtatctgt gaggtttgta tttctaactc acatttatgt ctaccattag cccattacat    420
gcatgatccg tgagcaaatt tgtccaagtt ttctatgtct ggaggagttt atcctatgct    480
aaagtgtgat gtgatttggt gcttgaaaat atattgcaat aactacctgt actctttgcc    540
cgtgccttgt gcaggttgca cgaacaggac gggttgctct gctccgtgag tctggagttg    600
actccaaata ccttcgtggg ttttccctcc ctctgtaatt ctccatctgc ggatcgacat    660
agcactccac aattcaggtc gcacggccat tttgaggaat cattcaaata ttctagggtg    720
agaactgtag acacactata ttgttggggt tgctacgttc tatgctatta agcttcttgc    780
ttatgcaagt atatatcacg cagcacctgg gcagaaacca tatccggtcc aatattttca    840
ttgcacaggt agtatacgtg tcctagttga aggaaaggca gtatatattc tttttgaact    900
taaaggcagt atatattcag aaaaaccata ttgctcaaac taatgtgctg attggtttgg    960
ggtttttggg ccgcgatcag gttgcaccat gaatagggcc ttgtttagtt cccaacaaat   1020
tttgtaaaat tttttagatt tccggtcaca tatcgaattt atggatatat atggagcatt   1080
aaatatagat caaaaaataa ctaattacac agtttattaa tttacaagat gaatttttttg  1140
agcctcttta gttcatgatt ggataaatatn nnnnnnnnnn aaatgaaagt gttacagtat  1200
ttattttgca cataattttg gaactagacg aggactagat tcccttgctt gggtttagtt   1260
gggctggtct gcagtcgatg gtaccgtgaa tggatactgg cccatttaat cttgaatacc   1320
actccctcac tcgacgatgt caggtccaat tcctcgcacg agtgcacaga ccgctgccct   1380
tgaacagccg cgactccctg ggccttgggg acg                                1413
```

<210> SEQ ID NO 55
<211> LENGTH: 940
<212> TYPE: DNA
<213> ORGANISM: Sorghum halepense

<400> SEQUENCE: 55

```
tgtgtggtac aggcaactgg acttcgctcg cataccctct ccattcttgt gaatgactgt     60
cctggtgtcc tcaacattgt aacaggagtc tttgctcgca ggggctacaa tatacaggtt    120
ttctttgtcg aaaagctctt cttgttgaat atagtgccag actagttatt gacaagtgca    180
tacttgtcag agccttgctg ttggcccagc tgagaaggaa ggcatttcgc gtattacaac    240
agttgttcct ggtactgttg aatccattga gaagttagtt cagcagcttt acaagcttgt    300
tgatgtgcat gaagtaagct gcatgtaact cctaccaaaa tcatttgtgt ttgcaaattt    360
attatgttaa ctaacaaaaa catgcgattc ctgcaggttc atgacattac cccctcacct    420
tttgctgaaa gggaactgat gcttattaag gtttctgtaa acactgctgc tcggagggaa    480
atcctagata ttgccgaaat cttccgagca aaacctgttg atgtttctga ccatacagta    540
acgcttcagg ttggcatcct aacaatttgt gtgtttctcc cagatttcca tcagtgcctt    600
tgccaacact gatgatacta gagccagttt tagaaaaagc gctgtgcaca ctgcacagcc    660
acaaattaga tcacattgct tttgttgatt ttctgttgca tagtaccgct tgtggttaca    720
ataacaacat catacccata tagaaacact gaatgtttga caccagtact attttttcat    780
gctgcttcat ctaactgctc caagctatta gctattgcaa aactcttgca taatggatcc    840
```

```
cttattgatg attgcagctt actggagatt ttgacaagat ggttgcacta caaaggttat    900

tggagccata tggcatctgc gaggtatatt gcttgtcact                          940


<210> SEQ ID NO 56
<211> LENGTH: 569
<212> TYPE: DNA
<213> ORGANISM: Sorghum halepense

<400> SEQUENCE: 56

gagagctgat gcttataaaa ctaaatgttg aacctgatca gcgccctgag gtatgatgta     60

gtctttgtaa tccaaaactt caattagcat cctgtacaca tgattctcaa ttgcatggtg    120

atccttacaa cggtgcttct tgtcatgact gacaggtcat ggttttagtt gatattttca    180

gagcaaaagt tgttgatata tctgagaaaa cacttaccat agaggtaaaa actcaatctc    240

taactagtgt acatatttg attggtatcc attttcctgt actgaactgt atgtttaatg    300

ggcatttcac caatgttagg tagctggaga tcctggcaaa attgctgcag tgcagcggaa    360

tctaaggaaa ttcggaatca aagaaatttg caggacagga aaagtaattt ctaatgttct    420

ttccttgcat ggacacataa tttttttctg taatgctaat ttaatgccct atcttcttag    480

attgctttga gacgtgaaaa gattggtgca acagcccgtt tctggcaatt ttctgctgct    540

tcttacccag accttataga ggcattgcc                                      569


<210> SEQ ID NO 57
<211> LENGTH: 654
<212> TYPE: DNA
<213> ORGANISM: Sorghum halepense

<400> SEQUENCE: 57

attatggagc aggtgaccaa acagctcaat aagattattc cagtaatcaa ggtggtagag     60

ctggacacgg actcaacagt ggcgcgtgcc atcatgctgg taaaggtggc tgccaacaat    120

accaacaggc cgcaggttgt cgacgccgtc aatattttcc gcgcccgagt ggttgatgtg    180

gcgcaagagt ctgtagtggt agaggccact ggcaccccgg gaaagctggc tgcactgctc    240

gatgtcttgg agccattcgg tgtgctcgag ctggttcagt cgggagatgt tgctttgggc    300

cgcggcccca aagcaatggc ccttccacgc aaataaatct cactatgtga gcaaactgtc    360

ccgcataatg gtatagtgct gggtgggacg ttgtttcatt gaactttcaa acgcaacaga    420

attgaggact acaacatggc tattgaaacc ttctacgacg acgatgcaga cctgtctatc    480

attcagggtc gcaaggtagc cgtcattggt tatggctcgc aagggcatgc gcatgcgcag    540

aacctgcgtg attccggcgt tgaggtcgta attggcctgc gcgatggatc taagtctgtg    600

cctaaggcgg aagaagcggg atttgaggtc aagaccgtgg cagaggctgc caag          654


<210> SEQ ID NO 58
<211> LENGTH: 5166
<212> TYPE: DNA
<213> ORGANISM: Sorghum halepense

<400> SEQUENCE: 58

actagttatt gacaagtgca tacttgtcag agccttgctg ttggcccagc tgagaaggaa     60

ggcatttcac gtattacaac agttgttcct ggtactgttg aatccattga gaagttagtt    120

cagcagcttt acaagcttgt tgatgtgcat gaagtaagct gcatgtaact cctaccaaaa    180

tcatttgtgt ttgcaaattt attatgttaa ctaacaaaaa catgcgattc ctgcaggttc    240

atgacattac cccctcacct tttgctgaaa gggaactgat gcttattaag gtttctgtaa    300
```

```
acactgctgc tcggagggaa atcctagata ttgccgaaat cttccgagca aaacctgttg    360
atgtttctga ccatacagta acgcttcagg ttggcatcct aacaatttgt gtgtttctcc    420
cagatttcca tcagtgcctt tgccaacact gatgatacta gagccagttt tagaaaaagc    480
gctgtgcaca ctgcacagcc acaaattaga tcacattgct tttgttgatt ttctgttgca    540
tagtaccact tgtggttaca ataacaacat catacccata tagaaacact gaatgtttga    600
caccagtact atttttttcat gctgcttcat ctaactgctc caagctatta gctattgcaa    660
aactcttgca taatggatcc cttattgatg attgcagctt actggagatt ttgacaagat    720
ggttgcacta caaaggttat tggagccata tggcatctgc gaggtatatt gcttgtcact    780
cacatcatct taagtgtgaa aaggcaattt ttgggtcctt tgggatgaac ggacagtcgg    840
atactttttt atttgacgcc agcagttgtt ttgttttctt ctgtagttta aaacacagcc    900
tgacaacctc ctgaagatta cttgtgattg tgaaacagaa tataagcaat tgtgcacaat    960
gccacatggt taagtagtcc taaataaaac tattcaaaag taacctgtga tgttctgtcc   1020
gcagccaatt gtcaccagat tttacactga aaaccttatt cgatgttttg cacacggtcc   1080
tcaccattgt gttgcacaca tgacaggtcg ccagaactgg acgagtggca ctggtccgcg   1140
aatcgaaggt cgactccaag tacctccgcg gctactctct tccattgtaa cctggcattt   1200
gtgatggtga tggcctgatg aagagcttgg ttggttgtta tagagcagac catctggcgc   1260
tgggttgtgt tgtgcagtta caggacttgt ttctttcatg tcgtgaactc cctcgcctgc   1320
gtgtccaata atgttctccc cggtaatatg cgtgttgagg ttgcatgtgt atcccaacga   1380
ctgtcagaat aagatgcata tacctgtttg cttcagcgga gagagatgcc aatcgtttga   1440
aacgcgtcaa tagtggtatg ctctggttgg gacttgggac ttgggaggct gccggcggca   1500
ggccagtcct ggcttgcacg aaaaaaaaaa agatccctcg ctgtgcttgg gtcgccaggt   1560
ttcagggctt tttctcaact ctgcagcttg agaaattttc tccaggggtc agagttttta   1620
cctcgatcga ggtcattccg caggggttga gtttttttta gtttatataa atatatgttt   1680
atacagttat actacttgat acggtgaggc agcctggcgc atgctgcgct gagggcgcat   1740
ctctcctacg aggctgctaa aacggtacgg atattttttt agctgtatat cgaatttgtt   1800
tagagaagtt tagatttatc tgtatttaag tctgaatatt taacatttga tgttgtatcc   1860
atatatgagt atttaaatca tatatttatg atgttccaat catatttcat ccgtcatagt   1920
taatattatt tatattcaaa tctaaatcct catagaaata taaaaataaa tataatatcg   1980
gttatatccg ttcgtatttc atcccctatt ggttactgga ctgttgtgtg gctgatctga   2040
gcactgagct tgccaattga ttgacacctt ggctaataag tcatagttga gaataatgtt   2100
cgctaattta ttatgagaga aaaatactac taaataataa ataatgggag attctacgaa   2160
taagctcaag ccaacggagc tacgcctttg cttgcctatg cgctacgagg agcctctcgt   2220
gagtcatacg cacctacacg tgaccgtgct actcgagcca agttggacgt gccgcaggac   2280
actgccaccg ccatctatgg tctagggctg cgggtcgcgg agaggctaat gggggtggcc   2340
gttgcacgcg acgaaacaaa cgggcgcggg ccaggccaac gttactgggc ttccgaccga   2400
ctccagaggc cctatcccac caatgcaatg cagcccagga gcggagacgg aggaaggcgt   2460
ggcacccgac ccgattccgg gtaggaaggt acggcgaggt aagcgaagaa gcatccagac   2520
tctcgcagtc tcgctcgagg ggcaggggcg cagggcaggg ccgggcaggg ggcgggcggc   2580
gatccgaatc caatcgccgg gagggaggaa gcaaccggcg gcggtagagg cggagggatg   2640
```

-continued acgcgcggga agcagaagat cgacgcgcag cggcgtaacg cggagcggaa ccagaaatcc 2700
aaggggtccc agctcgaggc ccgcgccgtc ggcctcaagg tcgtctgccc catctgcaag 2760
gtaaataagc cggagccccg ctctccgatc gctagccatc gcctggactg gaacctgccg 2820
ggtttgcctc ggcagtagat ccggccaatc tgtccaattt tgccgtatcc gtgcttgcct 2880
actgcatcac agcatacgga gcatttcaat agtgtctact gcatcacagc gcacggacca 2940
aagttgttca acttctggcc gggcctgctc tgcagagtat ccatccatct agcgcctcac 3000
tttatctgga aacaaaaatt ttgccagtaa attgaaatgt tcctgctgca tatcatcagt 3060
actattgctc taacctcctt taatcagcca gtttgttgta ggccaatcgt tgacacatgt 3120
tgttccagcg tactcatatt gttgccttgg gggtttgggg ccgggtaata gtgatactgt 3180
cacggcccct cacctcagcc agcccaagga agcccatcta cagaggaaga gcacaagggc 3240
ccgtgcaagg aatgtccgcg ccctcggccc agaatgggtc tgtaatcgct gtgtgctggc 3300
tagtgagtag ataaggagag gaagtgagga ggattggcat catctatctt gtaacagact 3360
aaaccctagt aagaacgccg gcctcgttgg tccttggcga aggaactcat ggttgcgatc 3420
ccagtgggtc gctaacagat actaggcatc ctgactagaa tgagagattg ggagtactcg 3480
aagtggattc tactggccag tgtgtctgac actttaccac accgcagtta aagctagtgc 3540
tacaaagaag tggccacata accttctcct agcatgattt gatctcacgt gtaaaagact 3600
tccatcacat ttttcccaaa agtagagcca atatttcaga aagaattcct gttgtgcaac 3660
cttcgtctaa acacatggtt tagctgtact ctttcattac ccaatgcttt cttcatatga 3720
taactcaaaa ggttactgca gcatattggc tctagtcttc tgtattttct ggattccttt 3780
taaatcggga gtaaagtcgt gggttcatta tgtggatgcc ctacttttta cctggctagt 3840
tgcatttgag gaacatacct gctcacctgg tgttgctatt tccataggta caattggcaa 3900
atgaaaaaca gctgaccgat cactacggat caaagcatcc aaaggagaaa cctccaagca 3960
catcgaccac ggaataacca tgactggtgg tgatgcagga acatagatcc tgcttggctg 4020
gtttgaggat ctttaagtct gatccatggc ctggagttgg atcttaaagt cggctatact 4080
ctgtagtgtg tcttatttcc tcttgtttca ggcaacaccc ttgatacgag tgtgcatttc 4140
tgctagtatg ttctgtgatc gtactgccga tgtatctcca aactgtatgt gatcgcccgt 4200
ggcattggga tgatgcgaaa aaaaattatg atcataacta tgttcaaatg tttgtggctt 4260
tttacaacat ggcttatgca cgtgcgttcc ctagccctaa tggccgccaa ataggccacc 4320
acggcaccac ccctggtgtt tgatcggtgc cgtgcttcag ttgtatccgg atgaatgaag 4380
tgaggaacat gagctggtcg atcccaatca agtaaaaggc ttgtctgacg atgctatcag 4440
gccttcttaa acggctaatg ctgttagcat cagtgaactg gtatcgtggc aaaatcgcta 4500
tccccatcga caggccaaga gcatttgcac gtcaccaatg ccataaataa ctcatgctgt 4560
aatattttga ggaaataaaa cgtgcttata tatattcttc ttctcatttt tacaaagtta 4620
ctttagtttt gtacttgacg agtatgaaaa aggggctagg agcattaggg gcactctatg 4680
ctgtatttag aaaggtcaac atataatttc gttgcaaggg ttagttggta aattcacagt 4740
ttgccacatg gcatggtctc attcccctag ccacccaaaa tatatggata atagccgata 4800
cagtagctgt cagccatagt tatctggtga agtatatcac ggatgatgac ggacgttttt 4860
cttttggaga ggctgcagtc ttttattcga agatatttgg tcaacgttgg aatgctagct 4920
ttgatctggc tgtacaacaa ggctttatta gccgaatgtc agctattcag caatgttttt 4980
ctttcacaac aaatcagcta atagtatttt tatcataatt tattagtcaa acgaacatac 5040
gctaacaagg taccactagt gagagctata ggacgctgat ggagaaggag aacaagacaa 5100
ggtacacgaa gatgttgttc agttccaaaa aaaaattgta aaatggacac tgtaacactt 5160
ttattt 5166

<210> SEQ ID NO 59
<211> LENGTH: 1770
<212> TYPE: DNA
<213> ORGANISM: Sorghum halepense

<400> SEQUENCE: 59
tctgtttcta ttttcttctt ctgatggatg aggcggctcg ggtttctggc gccaaatgca 60
gggtgcggcg ccacacgatt tcggtgttcg tcggggacga gagcggcatg atcaaccgca 120
tcgccggggt cttcgccagg agaggctaca acatcgagtc gctcgccgtg gggctcaaca 180
aggacaaggc cctcttcacc attgtcgtct ccgggaccga cagggtgctc aaccaagtca 240
tcgagcagct caataagctt gtcaacgtcc ttagtgtgag tccgccttgt caaaatttag 300
caaaactcac gcgaatccat acttgatttt gatgccccg gtttgagcac ttggtgacaa 360
ttcactagta cagtgagatt ttgttccatg agtttagctc gcccgaatct tctgtccttt 420
ttattctgtt aggatcgtcg tttccacttt cgtggagcat cttttgtgta gctagacaga 480
gcatgcgtaa cttttttctt tcctgattta gtcattatca tgttcgaagt attcttttcc 540
cttttcccct agaatcgctg ccagcctgac agtcatgtca acgtcaggga catactcctt 600
tctaggggat acctcaaatg caacatcatt attatacgcc ctgtatcatg tttatgcaat 660
gcactttctg tttgtgcacc tgtgccgtgt atggtaagca ctgttgctct ggttaatcat 720
ttgatgaaaa aaataagata ctcaacttca ttattctgac tatgtggtag tacttattta 780
gttcaatttt aatgctaccc tgtacatgtc tatatcctat aacctaaagc agcctttcag 840
ttaggagtta ttctgagttt tctttgttct tgcgatttga agatgctgat ttcttgggga 900
aaagatttat tgttctctct gaacgtacta tgcagataat acattgcttt actttccttc 960
tgaattctta gccagaaaaa cttcatggat taccattcct tcactgtttg cgtcaactaa 1020
acatttagat ggttttaact accatgatat tttctctctg aaaattatct actgctactg 1080
ttttgttcct aacttgcact aagagtaata ccaataaatt cttatttatt ttttgtttgg 1140
atctgatcaa ttacaggttg aagatctatc taaagaacct caggttgaaa gagagctgat 1200
gcttataaaa ctaaacgttg aacctgatca gcgccctgag gtatgatgta gcgttgagtt 1260
agtctttgta atccaaaact tcaattagca tcctgtaccc acgattctca attgcatggt 1320
gatccttaca acggtgcttc ttgtcatgac tgacaggtca tggttttagt tgatattttc 1380
agagcaaaag ttgttgatat atctgagaaa acacttacca tagaggtaaa aactcaatct 1440
ctaactagtg tacatatttt gattggtatc cattttcctg tactgaactg tatgtttaat 1500
gggcacttca ccaatgttag gtagctggag atcctggcaa aattgctgca gtgcagcgga 1560
atctaaggaa attcggaatc aaagaaattt gcaggacagg aaaagtaatt tctaatgttc 1620
tttccttgca tggacacata tttttttct gtaatgctaa tttaatgccc tatcttctta 1680
gattgctttg agacgtgaaa agattggtgc aacagcccgt ttctggcaat tttctgctgc 1740
ttcttaccca gaccttatag aggcattgcc 1770

<210> SEQ ID NO 60
<211> LENGTH: 1274
<212> TYPE: DNA

<213> ORGANISM: Sorghum halepense

<400> SEQUENCE: 60

```
tacaaacacg tccactttca gcatttgatc ttaggcattc taccagttcc tctaacaaag     60
cttccagaca tgttattcca ttgaaggctc gttcattcac acaatcttca cttgggggct    120
gttctggttc tggggaccag gagattgtga tagctatggg aagcaatgag ggtgatagag    180
tgagtacatt tgacagggca ttgcagatga tgaaaacctc aggtgtcagc gtcaccaggc    240
atgcctgcct ttatgagact gcccctgctt atgtggccga tcagccgcgg ttcctgaact    300
ctgccgttcg gggcacgact aggctgggac cgcatgagct gcttaagaag ctcaaggaaa    360
ttgagaagga tattgggcgc actggtggaa taagatgatg ctatcgaaac aagctggcac    420
tctctctcga agtccagtgg cggattcttt gaattatggg ataaactcgg gggtgaatct    480
atgattggaa cagaaggtat taaaagggta ttacccattg gaaattgtct gcttgattgg    540
tctgatagaa gtctcatcat ggggatcctc aatctgacac cagacagctt tagtgatgga    600
ggaaagtttc aaccagtgga agctgccatt gctcaggcca agctattaat ctcagagggt    660
gcagacatca ttgatattgg tgctcaatct accaggccct ttgcaaggag gttatctcca    720
catgaagagc ttgagaggtt ggttcctgtt ctggatgtga ttacaaaaat tcctgagatg    780
gagggcaagt taatctcagt ggatacattc tatgcagaag ttgccagtga agctgtgaaa    840
agaggagctc acatgatcaa cgatgtatcc ggtggacagc ttgatccaag aatttttaaa    900
gttgcagctg aactgggaat tccatatgtt gcaatgcaca tgaggggaga tccgtcaact    960
atgcaaagcg aacaaaattt acagtatgat aatgtctgca aggaagttgc ttctgagcta   1020
tacaaaaggt gagagaagca gagttatctg ggattccatt gtggaggtta gttcttgatc   1080
ctggcattgg cttctccaag aaatctggac ataaccttga agtaattatg ggattggaat   1140
ccattaggag ggagatggga aaaatgagta taggtgcttc acatgtgcca atattactag   1200
gaccctcaag gaaaagtttt tgggtgaaat atgcaaccgt accaatccag ttgagagaga   1260
tgttgttact gcta                                                      1274
```

<210> SEQ ID NO 61
<211> LENGTH: 1020
<212> TYPE: DNA
<213> ORGANISM: Sorghum halepense

<400> SEQUENCE: 61

```
gcccgagacc tatcgatcta gatatacttc tttatggtaa ctccgagatt aatagtgaga     60
ctctgattgt gcctcatgaa cgcatccatg agaggccttt gttttagcac ctcttgttga    120
ccttctaggt acatctggtg acgatggtat tgaaacaagt tggcactctc tctcaaagtg    180
cagtggcggt ttctttgaat tatggaataa acttgggggt gagtctatga ttggaacaga    240
aagcattaaa agggtattac ctgttgggga tcgtttgttg gattggtgcg agaggaccct    300
tgtcatgggg atcctcaatc tgacaccaga cagctttagt gatggaggaa agtttcaacc    360
agtggaagct gccattgctc aggccaagct attaatctca gagggtgcag acatcattga    420
tattggtgct caatctacca ggccctttgc aaggaggtta tctccacatg aagagcttga    480
gaggttggtt cctgttctgg atgtgattac aaaaattcct gagatggagg gcaagttaat    540
ctcagtggat acattctatg cagaagttgc cagtgaagct gtgaaaagag gagctcacat    600
gatcaacgat gtatccggtg gacagcttga tccaagaatt tttaaagttg cagctgaact    660
gggaattcca tatgttgcaa tgcacatgag gggagatccg tcaactatgc aaagcgaaca    720
```

aaatttacag tatgataatg tctgcaagga agttgcttct gagctataca aaaggtgaga 780
gaagcagagt tatctgggat tccattgtgg aggttagttc ttgatcctgg cattggcttc 840
tccaagaaat ctggacataa ccttgaagta attatgggat tggaatccat taggagggag 900
atgggaaaaa tgagtatagg tgcttcacat gtgccaatat tactaggacc ctcaaggaaa 960
agtttttggg tgaaatatgc aaccgtacca atccagttga gagagatgtt gttactgcta 1020

<210> SEQ ID NO 62
<211> LENGTH: 8604
<212> TYPE: DNA
<213> ORGANISM: Sorghum halepense

<400> SEQUENCE: 62
ctgatcttac tcatcctcca agatccttga ccagagcttc cagacatgtt gttccattca 60
aggcccgttt gtctacgcaa tgctcacttg agggccgttc agttgaccaa gagattgtga 120
ttgctatggg aagtaatgtg ggggatagag tcagtacatt caacagggca ttgcagctga 180
tgaaaagctc aggcgtgaac atcactaggc atgcctgtct ttatgagact gcccctgctt 240
atgtgactga tcagccacgg tttcttaact ctgccattcg gggcacaact aggctcgggc 300
cacatgagct tcttaaaatg ctaaaagaaa ttgagaaggg tattggccgc actggtggaa 360
taaggtatgg cccgagacct atcgatctag atatacttct ttatggtaac tccgagatta 420
atagtgagac tctaattgtg ccacatgagc gcatccatga gaggtcattt gttttagcac 480
ctcttgttga ccttctaggt gcatctggtg acgatggtat tgaaacaagt tggcactctc 540
tctcaaagtg cagtggcggt ttctttgaat tatggaataa acttgggggt gagtctatga 600
ttggaacaga aagcattaaa agggtattac ctgttgggga tcgtttgttg gattggtgcg 660
agaggaccct tgtcatgggg gtccttaatt tgacaccaga cagctttagt gatggaggta 720
agtttcaaca agtggaagct gccatttctc aggctaagtt attaatctca gaaggtgcag 780
atatcattga tattggtgct caatctacca ggccctttgc aaatagatta tctccaaacg 840
aggagcttga gaggttggtt cctgttctgg atgtgattac aaaaattcct gagatggagg 900
gcaagttaat ctcagtggat acattctatg cagaagttgc cagtgaagct gtgaaaagag 960
gagctcacat gatcaacgat gtatccggtg gacagcttga tccaagaatt tttaaagttg 1020
cagctgaact gggaattcca tatgttgcaa tgcacatgag gggagatccg tcaactatgc 1080
aaagcgaaca aaatttacag tatgataatg tctgcaagga agttgctttg gagctataca 1140
cacaggtgag agaagcagag ttatctggga ttccattgtg gaggttagtt cttgatcctg 1200
gcattggctt ctccaagaaa tctggacata accttgaagt aattatggga ttggaatcca 1260
ttaggaggga gatgggaaaa atgagtatag gtgcttcaca tgtgccaata ttactgggac 1320
cttcaaggaa aagatttttg ggcgaaatat gcaatcgtgc caatccagtt gagagagatg 1380
ttgccactgt tgcagctgtg acagctggaa ttttgaatgg agccaacata gtaagggtcc 1440
ataatgctgg atatggtgca gatgctgcaa aggtttgtga tgcattgcgt aagggaagaa 1500
gttgcaaaaa ctgaactatc tgatcaaaca gataccaaac tccagttata tacaagaaaa 1560
aggtgaggtc agatagtact ctgctgctaa atgggattgt cattgtgaag tatcattgct 1620
gtaatgaacc agagataatg ttttttcttg tgtcatcatt ttttctaaaa tcttcaatgg 1680
atcatgggtt caacttagat tattcgaaag agcagccaag gaataaggtc gcagaagctg 1740
ctagtgaagt tgcaaatact tcttttggtc ctatttagat gattttgctg aacttttttt 1800

-continued ctaatttaat aatatcagaa ggactctgac attttaggat ttgaaattgt caagttctac 1860
tagtctgatt tatctgtatc tcttctagtt cagacatatt tgattgattg ggcttacacc 1920
agctttccta cttctccctg tagcttcatc ttttgtacct tgatgtaccc aataaggaaa 1980
tcttatatac aacaaatgcc atatgatatg caaagtctca acaatttgtc tatgattttt 2040
ttcctgaggg tttatcttcc acttataaca tctactgttt gctgctaaat attttttagg 2100
cgcttcccat gtaggtttat tttcattctg aattgctgtt atttgcattt ctcactctta 2160
gcaaacttca ttggcacctc ctagtctttg ctgtcttcat ccattgaagg aatttcaaga 2220
acttttgtgc agatgactgg tcatcaatat ggatattgcc catgatatca actcacactt 2280
ttgaggattc tttttccttc ttttcttttg aaagttactg tttttttatc tgattgataa 2340
cacttgctaa tttcgtgcaa aaacatttgg gggaaataca aagcctcatg tgatttgtgc 2400
gtggttgtca ttgacacata atttttacta tttcaagtat gaattattca ctgagtaatg 2460
aaaagggaat gtacaaagtt cagttaacag aatataatat taattgttat cgcgtctgtg 2520
tggtatatct tcttctggtt tctttggcat attgccacag tggaaaattg atttcagatt 2580
caactggaat ctatcatctc gtaaaggccg tggctggttt cctgaggggc atctttcaac 2640
agaagtcgat tgggacacaa caggcatgca cttgagatta gatgtacgaa gactaggttg 2700
cttatccctg atgagatcat gagagtaaga aaattcttat aattgcaaat atcatttact 2760
gttgagaatg gccattgcca ctatgactcc aaaatagacc acatcctgct tctatatgtt 2820
gctaatgaac tttaaataaa cggcaaagaa aaaaattctt tcatgaagag aatgcagata 2880
taacatgatg agggagcctg aagaaaattt gcagtgtgga ggttttagcc aaatggacgt 2940
gggatgctag actgacaacg ttttgtacac tttgattcta catatcctct agtaattcat 3000
agtctacttt gatttgtaaa tgctgaagct gtactactct tcttgattta cattcagatt 3060
tgccacttgc tgtgtcttct ctgaaacaac cctagcgttg acacggaggt acaaagatca 3120
gcatataaat agatgtagct gactaactgt gacagctgac aacgaatcat gtgtgcctgc 3180
taagttttct gaaacacatg actaatttat taaaacaccc ttttatgtac actataagat 3240
acggctgaac tctgctcctg ttctagtata ctgtaagatt tcagtgagac agatatggca 3300
aaactttaca aagccgtata catgcatgag agagagctaa tagaacctga catatatata 3360
gatgtttgat gcattttttt tcatgcttac acttaattta tctaacttgt aatttccact 3420
ttttctcaat ttgtaatgtg gtgctatgtt gagatgtatt ccttcgtaga gaaagtcctt 3480
agatctcagg ggaaaaaact ctcgactgct gaattctttt ttcatgtttc aaaaaaaaag 3540
aaaagaaaag aagtcagtta cttcttctat ctaatgtcat gatgcaaagt caaattaata 3600
tttcgtcctg aaacgatgac cattgcccat ctttcagaag agctccatgc tgcaagttca 3660
gactagtcca aacaacggtg aagggtaaag aagtcttcag atatgtctca ccacatagtt 3720
taacagaaca gctctggagt acttttttaa gccacatcaa gaatcgatgt taaacgatac 3780
tcgagttcat gtgaacaaat gcttccaagt tcatgtctca gttggccttg cgtgtgaatt 3840
gcaggaagac atggcaacag gcagacaaaa catatggtgt gcagagtttg cctgatccag 3900
tgatgtgaac actcggcctc ttatcctgtt ccctgtcata tattccggtt acgacctccc 3960
caggtcagta cttctctgca gcatttctca cctcttattt tccttatcct ttcttttgaa 4020
agtaccagat gtcaagatat attctttcat ggtgaatgaa ataaagtcag ttctaacgtc 4080
ttacaatttg gaatggggga gtaacttgtt gtgctatcag tttatcaaag aattctactt 4140
tcctgagtga acttaattat agttgtacat tacatcagga catgtactgg gtgctagctt 4200

-continued

```
aaaaaaaaga ttaacacctc gttcttatgc taaaaaaacc caaaaatgac atcaagatca   4260
catcattctg gaattctgca tagcgaaata tatgcattag agtatagcac cagtgctttc   4320
tactcataaa agtagacttg tatgttttca atcaataata caatgagggc ttatgttttc   4380
ataaactcct tgacatggtt ctgctctact gcactttatg tgatacaaat catatgtttt   4440
ttttagaaag ggcggcaaaa ggtttgcctt attagacgag gaaaaaacaa aaagaaagga   4500
aaaccaaact agaagagtag tccccctatt atggttccca tctcgatcac accgaaccaa   4560
cctatgtata acttagagga tttagagggg ggcataacgg ggaggctaca aacaggaaac   4620
caaccaaagc aagctaaaga tccttaaaaa aactaatcta gatgccaact gaaactgttg   4680
tatgttctcc ttgcaaagag ccgctacttg ttgtggttgt gacaccttgt gttgaaagat   4740
tcttttgtta cgttccttcc atatgttcca ccagaaataa atcataatgt catcgaaggt   4800
tttcctttgt tctttggcga tctccctacg gcatttacgc cagtaattgt acaaggaccc   4860
caacatactt actgagtcca atactgacaa tcaaaaccat cttttgataa tatccccaaa   4920
catcctttgc agagatgtat ttgggtttcc ggttcagtgt tgcatagaac attttatttt   4980
aaggataaca tgtgaaatgc atatatgctt gtcatgctac actagttgtt agacatgaca   5040
aaaagttact tggtcaggaa acaccggagc ggaacacctg tgccacttcc ttgtaataca   5100
cacaggacca caacttcatt atgtagaaac gaatagtggt gagtgctgcc aggaaaatca   5160
tctcccacta tgtacacgtt aagcatctta ttgttccctt tccattacta catcacataa   5220
acccaatatt tgaatcacac agtggccatt aattcgtaca taggccaaat taggcctaca   5280
tgatctgttt atgtagaaac gaattccttg agcagattgc tacatatggg tctcatctca   5340
tctcacgcta tgctgcatgc gtttgggttc tcatcgctga agatagtagt gatctgggtg   5400
tcatctcctt tgccccttgc cggtagtac tctgcaggga tgtagtacct gccttgttgc   5460
accggaaagc caccaccata gccgccgtac tcggctacgt aaggtgatgc ttcgtacctg   5520
acgccatgca tgtccatggg gtggttcgcc ttcgcccagt gctcactgtg catgtggtgg   5580
ccaccatggc cgtacccgtc atgtactgtg cgtaccacgg tggccgccgg ggtctctgcc   5640
ggctttgcct ccttgttctc cggcgccggc gcctcagctt gtacggcctc ctctacttct   5700
gctgctgctg ctgctggagg aggagcggcg tcggctgctg gcgggtcggc gggaggtggt   5760
ggggccgcct gggcctcccc ttcggcttca gcgtcggcag ggggaggcgg ctgagcctcg   5820
gctgcggcgg tggcggtggc ggcggggtcg gtgtgagaga agatggtggg gactctcttg   5880
gtcttcctga tggccttgac gagcctctca ggatcggcca tccccaccac cgtgatcttg   5940
tgggttgctt gatctatgta tacttcgcta acacctgcac agtgcaggtt cattccatta   6000
ttaacttgta agatgtcatg taatgctatt gtaatcttgt tagagtatca tatcatgctc   6060
gtgacaagct agtcgagctg gatatctgaa tgattaatgg atggagtcaa aagaaattgt   6120
tagttttgag gttcgaattg gctttaccat caatggcact cagggtcttc ctgatcttgt   6180
tcccgcagcc attgcagtcc atccttacat ggagctccgt tattcgtggt gtctgcagtt   6240
ttaacgcaag cagattagca cagccaccat acaaacaaac aaacaaaaca aaaacattga   6300
aaaacgtatc cttttggaga ttaattccat tatattcagt cacaaaagac acaatgcagg   6360
attattgata ttgtccatac agacacacca gacatcatgc atgaatctaa actattcctc   6420
aattcactag catgcgaagg aaaaaaaaat gcaacaagag cttgagttat gaagattcca   6480
caaacctcca gtgttgtagt catgattgaa gctgcaaaga gttcgagcta gcagggaatg   6540
```

```
aactcttgtg aagaccttag cacagggcag gtttggtgtt gtgtcactga ccatgcaaat   6600
gagttgcatt ttatatcgca attgcttgtg cggggggtgg ttttgggatg gaatatttac   6660
tggtcgattt gtgtgggtca cccaaagaat caccggaaag cgaaaagagc gtcccctagc   6720
tagctagatg gctccatctt ggcatgacct ccgtttcttt tccatggagt cgcagtcatg   6780
caagtggcct ttccgatcga gttgtttaca agttgtactg tgccacgcct tggtttttat   6840
ctgtcatcca ccactgtatg cttgtagagt tttttttct cgaaaacaca aaagatttgc    6900
gtatcattgt gttaagcaga agagtttaaa caaacataca acacacttta gtgaagcacc   6960
gagggagatc gacctaaaat agccgaagct gaaccatcct agctagtata catgtataga   7020
gtgtttggcc ttttttatgt acatgctctt attgtgttgt attttatttt tcctgttgtc   7080
caaagttctg gctacattcc ttgcttcatg tttgcacttt ggaatagcac ttacagcagt   7140
gctagcatca gtttgcagtg gaatcaagct caaagcactc gggctcaaga agtgcttcgt   7200
atgcgattgg cttttccatt cacaaccggg gattccattt tcttcattat tctccatttt   7260
ggagccagct ttggttaaaa atttggcata ctctgattgg agtgctgatg ggaatatccc   7320
ttgtagccgg ccagagagaa gatagaaagg atgaaaagat gatagatgga ggctcctttg   7380
ttcaaaagag gagctctttt gagaggtgga ggatatccac tcctagtgaa tcctcttagg   7440
taaagcaaag tatttatgtt tgtgcaacct tgattgtatc tcatctatct atattcttat   7500
ctgctatgta cacagtatgg aaattttgtg gttctctgtg ctctagttct tgtagattct   7560
ctgccagttg gatgttaaca tcttttagat tattgaaggc aagtgcaatg ttgtttttat   7620
ataattgaat ccaataatac tgaaaaagaa aataaatgat acttcgtaaa ttgcatttat   7680
ccccaaacca tgacgatgat actaattttg tgtcaaactt agttaatttt ttaaaaggtt   7740
cgggacttgc gtattttata agttctcgtg agataagatg ctttaattat tggccacatg   7800
tttcttatac ggataggccg gcaaagatga atgattattg ccgagaatgc tgacggcatg   7860
tactgctatc aggagatgag gcctgactgt gtttattctt ggattgagct cttcacctga   7920
gcagtcactt ttgtggcttc tttttcatgt cgagaaaaat ctttcatctt aatttggtgt   7980
caacgccatg gttgtacgta agtttttgtc accgggggtt ctattattga aacgggcctt   8040
ttctatagaa atggtacgta gcgctggacg acgttgatga tgcatgcaaa ggcaaaagag   8100
tacccatctg tgtatgctta tatctttttt aaaaaaataa tagtgtatga ttatatctgt   8160
gcacacgcac acaaaaagtt ctggaaaaag ttgtactact ttgggccttc tatagttcca   8220
tcacattttt tgtcatctat gtaaggggtc atttggatcc tttttcattt agaggaatta   8280
aaatctactt aataaattag gctatttggt ttgaaatttg acatttcatc attttctaaa   8340
gttcacatat gaatctatct taaattcata gggtgtgaga tggaatttga ttctatagat   8400
cattattcta tgtttctact ttgcaaccta tagcacgctc ttcgactcac tcctctgtgg   8460
tagaaataca atacataagt atctctctcg tgtagccaac cataatttgt aaatacagtc   8520
catatacaac catattaact taattaatat gtgtttaaat tacgattatt aaaataaatt   8580
gaattctaag gatccaaata gggc                                          8604
```

<210> SEQ ID NO 63
<211> LENGTH: 220
<212> TYPE: DNA
<213> ORGANISM: Sorghum halepense

<400> SEQUENCE: 63

```
ctgatcttac tcatcctcca agatccttga ccagagcttc cagacatgtt gttccattca     60
```

aggcccgttt gtctacgcaa tgctcacttg agggccgttc agttgaccaa gagattgtga 120
ttgctatggg aagtaatgtg ggtgatagag tcagtacatt caacagggca ttgcagctga 180
tgaaaagctc aggcgtgaac atcactaggc atgcctgtct 220

<210> SEQ ID NO 64
<211> LENGTH: 263
<212> TYPE: DNA
<213> ORGANISM: Sorghum halepense

<400> SEQUENCE: 64
tcactaggca tgcctgtctt tatgagactg cccctgctta tgtgactgat cagccacggt 60
ttcttaactc tgccattcgg ggcacaacta ggctcgggcc acatgagctt cttaaaatgc 120
taaaagaaat tgagaagggt attggacgca ctggtggaat aaggtatggc ccgagaccta 180
tcgatctaga catacttctt tatggtaact ccgagattaa tagtgagact ctaattgtgc 240
cacatgagcg catccatgag agg 263

<210> SEQ ID NO 65
<211> LENGTH: 2163
<212> TYPE: DNA
<213> ORGANISM: Sorghum halepense

<400> SEQUENCE: 65
caactactag ccttctttga ttctgaagta tatatgctca acgatgctcc tccatcctaa 60
ggggtcactt aggaagatgt tttcatctgc tactgctacg agctactatt atggaggagt 120
aatacaaaca cgtccacttt caggtactgt tccgacttct gctattcagg ttatctatat 180
ttcccaatca agcccatgtc caactcataa ccacttgtat aatttttttt tcacagcatt 240
tgatcttagg cattctacca gttcctctaa caaagcttcc agacatgtta ttccattgaa 300
ggctcgttca ttcacacaat cttcacttgg gggctgttct ggttctgggg accaggagat 360
tgtggtagct atgggaagca atgtgggtga tagagtgagt acatttgaca gggcattgca 420
gatgatgaag acctcaggtg tcaacatcac cagacatgcc tgcctttatg agactgcccc 480
tgcttatgtg accgatcagc cgctgttcct gaactctgcc gttcggggca cgactaggct 540
gggaccgcat gagctgctta agaagctcaa ggaaattgag aaggatattg gcactggtgg 600
aataaggtat ggccctagac caattgatct agacatactt ctgtatggca attctcagat 660
tactaccgag actctgattg tgcctcatga acgcatccat gagaggcctt ttgttttagc 720
acctcttgtt gaccttctgg gtacatccgc agatgatgct atcgaaacaa gctggcactc 780
tctctcgaag tccagtggcg ggttctttga attgtgggat aaactcgggg gtgaatctat 840
gattggaaca gaaggtatta aaagggtatt acccattgga aatcgtctgc ttgattggtc 900
tgagagaact ctcatcatgg ggatcctcaa tctgacacca gacagcttta gtgatggagg 960
aaagtttcaa ccaatggaag ctgccattgc tcaggccaag ctattaatct cagagggtgc 1020
agacatcatt gatattggtg ctcaatctac caggcccttt gcaaggaggt tatctccaca 1080
tgaagagctt gagaggttgg ttcctgttct ggatgaggtc acaaaaaattc ctgagatgga 1140 gggaaggttg ctctcagtag atacattcta cgcagaagtc gccactgaag ctgtaaaaag 1200
aggagttcat atgatcaacg atgtatccgg tggacaactt gacccgagaa ttcttaaagt 1260
tgcagctgaa ctgggtgttc catatgttat catgcacatg aggggagatc catcaactat 1320
gcaaagtgaa aagaatttac agtatggtga cgtctgcaag gaagttgctt ctgagctata 1380

-continued taaaatgttg agagaagcag agctatctgg gattccactg tggaggatag tcattgatcc 1440
tggcattggt ttctccaaga acaccggaca taaccttgaa ataattaagg gcttggaatc 1500
cattaggagg gagataggta aaatgagtat aggtgcatca catgtgccaa tattactagg 1560
accctcaagg aaaagttttt tgggtgaaat atgcaaccgt accgatccag ttgagagaga 1620
tgttgttact gctatagctg tggcagatgg tattataaat ggtgctaaca tagtaagggt 1680
tcataatgtt ggatatagtg cagatgctgt aaagtactgt tcagcatcgc gaaagggtag 1740
aagattgaat tacctggttg aatagatact gatctccaat ttgtacaaga aaatggtggt 1800
gcatggaatc ctcatatcac accactgtgg agtatcatat tataagcatt aatatataaa 1860
tcagagaata gagttgatgt tttccttgtg tcatctccta tctatgatct tccatggatc 1920
gtgggttgaa ttcatgttac ttggaatgag ggtgggtagg gtgggggggt aaggtttcaa 1980
tagctgctac tgcatttttt tccatcaaat atcatcaaaa tgatttttac atttcagtaa 2040
ttcaaattga caagtctgat ttccttgtaa cttctctatt tcagatttat tggatagatt 2100
ggagtatacc tgcttgcttg tatatatttg tactttgaca tagccaatga ggaaatatca 2160
tgt 2163

<210> SEQ ID NO 66
<211> LENGTH: 1917
<212> TYPE: DNA
<213> ORGANISM: Sorghum halepense

<400> SEQUENCE: 66
gtacaactca gttgatcaag ctgtgaagcg tgctaaagag atgatagatg agggtgtaga 60
cattatagac gttggaggta tctcaacacg accaggtcat aaagaagtat cgcttaaaga 120
agagatgaat cgtgtattac ctgtggttga gtctatcgtt aaatatgatg tgcaaatttc 180
ggttgataca tttcgaagtg aagttgcaga agcttgtctt aaacttggtg tttcaatgat 240
taatgatcag tgggcaggcc tatttgattc gaatatgttt aatgtggtat ctaagtacgg 300
tgctgaaatt gtacttatgc ataatggtga tggttataga gatgaacctg ttgttgaaga 360
gatgcttgta tcattacttg cacaagcgaa taaggctgaa ttggccggta taccacataa 420
taaaatctgg ttagatcctg gaataggttt tgctaaaaca cgagaagaag aaaatgaggt 480
aatggcaaga ttagatgaat tggtagcgac cgactatcca gttttacttg caacaagtcg 540
aaaaagatac attaaagaaa tgatgaatca agaatcttct tcttcggata gagacgaggc 600
aactgcagct acaacggctt atggtataat gaaaggcgtt cgtggggttc gagttcataa 660
tgtattatta aatacgcgac tagcccaaag tatggatttt ctaaaggaga atgaatatga 720
acgacatcat ctttcttaat ggaatgcgtt tttatggtta tcatggagtt ttagctgcag 780
aaaacgatat tggacaaatt tttgttgttg atatcacttt aaaggttgat cttagttatg 840
caggtcaatc agatgatgta aaagatactg taaattatgg agaggtttat aaagatgtaa 900
agtctattgt tgaaggtcca cgttcatgct taattgagca tctggctgaa cgtattgcaa 960
aacatataaa ttcacactat aatcgtgtaa tggaaacgaa agttagaatc actaaagaaa 1020
acccacctat tcctggtcat tacgatggtg ttgggattga aatagtgagg gagaatgact 1080
aaatggttaa agcttattta ggattaggga gcaatattgg aaatagagaa ctacaactca 1140
atgaggctat taaaatactt catgactatc aaggtattca agtaactcaa gtttctcata 1200
tttatgagac tgaaccagtg ggatatacta atcaaccgaa attcttaaac ttgtgcattg 1260
agatagagac tgaattgaat ccacaatctt tgttaaaatg ttgtttaaca acggaacaac 1320

```
aacttcatcg taaaagagaa atacgttggg ggcctagaac tttagatata gatatactac   1380
tgtttggtga tcaaattatt gaacaagata atttatcagt gccgcaccct agaatgaaag   1440
aacgttcgtt tgttcttatc ccgttaaatg atatagccac caaacaaata gaaccgattt   1500
ctaataaaag tatcggacaa ctagtagtac ctgataatag tgtgaaaaaa tataaggaat   1560
aataaagcat agtaatatgg ttttgaaact tttaattaaa gaaatttata tattgctaat   1620
caataagttt ataagggttg caactattcg atgaaaatat aaattacttt attacatttg   1680
ggtagtaaag taaatgactt agctttgaca gaaatctcgc ccgtattagt tttaaacatg   1740
acaccttcaa cacctatgat gtcacctaag tcagccattt tccaaatgtt aaattgatca   1800
tctccaactt gatcttttct tacataaatt tgaatctgac ctttcaagtc ttgaatatgt   1860
gcaaatcccg ctttaccttt accacgttta gtcataagac gacctgcaat tgacacg      1917
```

<210> SEQ ID NO 67
<211> LENGTH: 1511
<212> TYPE: DNA
<213> ORGANISM: Sorghum halepense

<400> SEQUENCE: 67

```
gacgcggtgc aggcgggcgc cgaggagatc gtgctgcagc ccatcaagga gatctccggc     60
accgtcaagc tgcccgggtc caagtcgctg tccaaccgga tcctcctgct cgccgccctg    120
tccgagggga caacagtggt tgataacctg ttgaacagtg aggatgttca ctacatgctt    180
ggggccttga acactcttgg gctctctgtc gaagcagaca aagttgccaa aagagctgtt    240
gttgttggct gtggtggaaa attcccagtt gaggacgcta aagaggaagt gcagctcttc    300
ttggggaatg ctggaactgc aatgcggcca ttgacagcag ctgttactgc tgctggtgga    360
aatgcaactt acgtgcttga tggagtacca agaatgaggg agagacccat tggtgacttg    420
gttgtcggat tgaagcagct tggtgcggac gttgattgtt tccttggcac tgactgccca    480
cccgttcgta tcaatgggat tggagggcta cctggcggca aggttaagct ctctggctcc    540
atcagcagtc agtacttgag tgccttgctg atggctgctc ctttggctct tggtgatgtg    600
gagattgaaa tcattgataa attaatctcc attccctatg ttgaaatgac attgagattg    660
atggagcgtt ttggcgtgaa agcagagcat tctgatagct gggacagatt ctacattaag    720
ggaggtcaaa aatacaagtc ccccaaaaat gcctatgttg aaggtgatgc ctcaagtgca    780
agctatttct tggctggtgc tgcaattact ggagggactg tgactgttga aggttgtggc    840
accaccagtt tgcagggtga tgtgaagttt gctgaggtac tggagatgat gggagcaaag    900
gttacatgga ccgagactag cgtaactgtt actggtccac cacgacagcc atttgggagg    960
aaacacctca aggctattga tgttaacatg aacaaaatgc ctgatgttgc catgactctt   1020
gctgtggttg ccctctttgc cgatggccca acagctatca gagacgtggc gtcctggaga   1080
gtaaaggaga ccgagaggat ggttgccatc cggacggagc taaccaagct gggagcatct   1140
gttgaggaag ggccggacaa ctgcatcatc acaccgccag agaagctgaa cgtgacggcg   1200
atcgacacat acgacgacca caggatggcc atggccttct cccttgccgc ctgtgcggag   1260
gtccccgtca cgatccggga ccctgggtgc acccggaaga ccttccccga ctacttcgat   1320
gtgctgagca cgttcgtcaa gaactaagcg tgtgatatac taccacacag cgggattgca   1380
gtgatcttgc tgggcatgtg cggaggaaat acattttttt tgttctcttt tccgggataa   1440
gttttgagcc tgtaatatta gttgctcgta gcatgtttct atgacagatc ttgagtctct   1500
```

tatacacatc t 1511

<210> SEQ ID NO 68
<211> LENGTH: 2730
<212> TYPE: DNA
<213> ORGANISM: Sorghum halepense

<400> SEQUENCE: 68
cagccatttg ggaggaaaca cctcaaggct attgatgtta acatgaacaa aatgcctgat 60
gttgccatga ctcttgctgt ggttgccctc tttgccgatg gcccaacagc tatcagagac 120
ggtaaaacat tctcagccct gctaccatgc ctattctaca tgacaagatt cacacagagt 180
aacattcaag acatggttct ggttacgcac cactaatagc tattgctctt cgacagtggc 240
gtcctggaga gtaaaggaga ccgagaggat ggttgcgatc cggacggagc taaccaaggt 300
aaaagtgaca tactcctact tcacaagtct catgttgtgt tttcatagct ctctgcctct 360
tgctcttgcc tgcggtcgct tcatcctcaa atgttgctgc ttgtgtttcc gccagctggg 420
agcatctgtt gaggaagggc cggactactg catcataaca cccccagaga agctgaacgt 480
gacggcgatc gacacatacg acgaccacag gatggccatg gccttctccc ttgccgcctg 540
tgcggaggtc cccgtcacga tccgggaccc tgggtgcacc cggaagacct tccccgacta 600
cttcgatgtg ctgagcacgt tcgtcaagaa ctaagcgtgt gatatactac cacgcagcgg 660
gattgaagtg atcttgctag gcatgtgcgg aggaaataca ttttttttgt tctctttccc 720
gggataagtt ttgagcctgt aatattagtt gttcgtagca tgtttctatg acagatcttg 780
agtgtgtatt gtacacaaat tcgtatccag agtggttcat tggaacaata ataagaataa 840
taaattacct ttcagcggtt atcaagtttg ccattacaat tttggagatg acggcatcag 900
ccattcacca atttagcata tcttcacgtt aggatttttt tatttatttt taatcctttt 960
atattttaat aaaaacacct cctagaaatt ttttgcagta ataccctcca catgcaattt 1020
tttgcaccct cttgtcacgc cacatgcatt ggcatagatc ctagtgcttc atatattgtt 1080
tgcttgtctt ataagccata ttttttatta gtattttgtt ataataaatt agcaaacggt 1140
attttcatga gtgaccgtat aatttttaag cttaaggagt gaccgtgtaa ttttttagct 1200
tcatatacta agtgacctgc atatactaag taaccgtgta ttttttttag cctcacatga 1260
acatatcctg agaaacccag atgtaaaacc atgaaatacg ttattcaaaa aatacccaaa 1320
caaactcgtt caactattaa catctagtga aacagcccag atgtaaaacc acgaaatacg 1380
ttattcaaag tcccaaagaa actacccaca caaactattt caactattaa catcagtgaa 1440
acaggcaact gcagttcatc cgataacatc tgctgaaaag gcagcgaaac ataagattct 1500
agatttatca cgtgatgaaa agctatgcat tagggggatc atccattaac catttttcca 1560
ttcatgcact aacatccatt gaaacaggct acatccatat cgtgccacaa aacctcaata 1620
agactttaac tctgatgcaa atagcttatc gatcaggagg gaattcctct gttacaccaa 1680
gttctctcac tagaaactga aaacatcctg ttcatcatta tatgataaag tgctggctac 1740
cacattacgc atcgctgata gtcacctcaa cctccacacc tggttcaatg gtgatcgagg 1800
tgatctgctt gaccacgtct ggtgtactga tgagatcaat caccctcttg tgaatcctca 1860
tctcaaagcg atcccaggtg ttggtacctg aaatagtcaa gacaattatc aataattgca 1920
tcaagaataa tccatataca aagtgaagtc caaaaagaaa acctggcacg aggataacaa 1980
gaaacatcaa gaattgaagt tgtcggatga agtaacatgc tggcatcagt tttaaaaagc 2040
tcgattttga tacatcaagt atcagtgtaa acatattgca tcatcatctg ctcagcatgt 2100

```
tgacatctcc tgtactaatc ttcaagatat aggggcattt aatgcagcaa aatgacaggc   2160

catactaaaa tttgcatagc accacaggac ttgaggccaa caaaatgcag atcacatcaa   2220

taaaaagaag cgtggaatat cactcaaaag ttaactagaa aagtttattt aactgaaaat   2280

gttcgaacag tgaaagcatt gaatggacca accatcagtt ttaaaaagct cgaatttgta   2340

agtcctcaga gaaaatctca ggattaactt gtttggcatc atatggttag cccatcacaa   2400

acagcaagcc caacacatta actcaggtga actagactga ctgggcaggg tcctgaaaga   2460

aagtacatgc taggcatttt gcactaaact ttctaggata tagaaggctc ttaagggtag   2520

caagaaggaa tcaatggcac atccaataac taaagaaaag actatgtatg gttagcccat   2580

cacaaacagc aagcccaaca cattaactca tgtgaactag actgactggg cagggtcctg   2640

aaagaaagta catgctagac attttgcact aaactttcta ggatatagaa ggctcttaag   2700

ggtatcaaga aggaatcaat ggcacatcca                                    2730
```

<210> SEQ ID NO 69
<211> LENGTH: 943
<212> TYPE: DNA
<213> ORGANISM: Sorghum halepense

<400> SEQUENCE: 69

```
gaatatatgc accgtaggca aaaattgttg cagggtagaa agctagtaat gagtattgac     60

tgtgtaaatt acttaaatca gttgggatat ggccattcta ttggagtcaa gaacgctaac    120

caaaatagcc aagcaatgcc tatttagtag tcacctaatt atacagaggg aagaaccatg    180

tagactgttg atatcaccag aagtcgcatc ctcttgaatc ttgaaacttg gcttacaaga    240

gacagtctag gtagcaggac tttagctact tggcaattgg catggatacc tttttgtttt    300

ttccaggaaa aggtacttga ttggtttttt gtgccccgtc tgtgatgtgt gaacctgctc    360

ttttattgct ttagaagggc gtatccatgt ttcccaacat gcctccctta gttcattgta    420

ctgacatcag ttcataactt catatgttca taagcgtttt ccctaaacta aaccttcttt    480

tgctttgcaa tcaataggtc ccccaaaaat gcctatgttg aaggtgatgc ctcaagtgca    540

agctatttct tggctggtgc tgcaattact ggagggactg tgactgttga aggttgtggc    600

accaccagtt tgcaggtaaa actttgctgc aatgctaact gcttttgcct ttttggtttc    660

agcactactc tctgagtcac taaataacat aatcatctgt agacatactc cagtgagtgg    720

atattcatgt aataataata actagttaaa cataccaacc taaacagtcc tgtaaaattc    780

agtccttaca ctgtctccat ttcgttatta acttgctgaa taccacaggg tgatgtgaaa    840

tttgctgagg tactggagat gatgggagca aaggttacgt ggaccgagac tagcgttact    900

gttactggcc caccacggca gccatttggg aggaaacacc tca                      943
```

<210> SEQ ID NO 70
<211> LENGTH: 1279
<212> TYPE: DNA
<213> ORGANISM: Sorghum halepense

<400> SEQUENCE: 70

```
ttaccactgt tacattgtac aggttaagct ctctggctcc atcagcagtc agtacttgag     60

tgccttgctg atggctgctc ctttggctct tggggatgtg gagattgaaa tcattgataa    120

attaatctcc attccctatg tcgaaatgac attgagattg atggaacgtt ttggcgtgaa    180

agcagagcat tctgatagct gggacagatt ctacattaag ggaggtcaaa aatacaagta    240
```

-continued

```
agctttgtaa tttatttcac aatgatgtca acgattcagt tttcagtttt ccaaacagat    300

gcatccatat ttgaatatat gcaccgtagg caaaaatcat tgcagggtag aaaactagta    360

atgagtattg actctgtaaa ttacttaatc agttgggata tggccagtct attggagtca    420

agaacgctaa ccaaaatagc caagcaatgc ttatttagta gccacctaat tatacagagg    480

gaacaaccat gtagactgtt gatatcacca gaagtcgcat cctcttgaaa cttggcttat    540

aagagacagt ctaggtagca ggactttagc tacttggcaa ttggcatgga tacctttttt    600

ttttcaggac aaggcacttg attggttttt tgccccgtct gtgatgtgtg aacctgctcc    660

tctattgctt tagaaggaca atatccatgt tgttttttta gataaagttc catgttgtta    720

cccaacatgc atcccttagt tcattgtact gaaatcagtt catatgttca ttagctgttt    780

ccctaaacta gaccttcttt tgctttgcaa tcaataggtc ccccaaaaat gcctatgttg    840

aaggtgatgc ctcaagtgca agctatttct tggctggtgc tgcaattact ggagggactg    900

tgactgttga aggttgtggc accaccagtt tgcaggtaaa actttgctgc aatgctgatt    960

gcttttgcct ttttttggtt tcggcattac tctacaagcc accatcacta aataacataa   1020

tcatctgtaa atgtcaaata gacatacttc agtgagtgga tattcatgta ataataacta   1080

gttaaacata ccaacctaaa cagtcctgta aaatacgctc cttacactgt ctccgtttcc   1140

ttaataattt gctgaatacg gcagggtgat gtgaagtttg ctgaggtact ggagatgatg   1200

ggagcaaagg ttacatggac cgagactagc gtaactgtta ctggcccacc acgacagcca   1260

tttgggagga aacacctca                                                1279
```

```
<210> SEQ ID NO 71
<211> LENGTH: 1835
<212> TYPE: DNA
<213> ORGANISM: Sorghum halepense

<400> SEQUENCE: 71
```

```
gcgtggtccc cttggcggcg gcggcggcac ccgcggtgca ggcaggcgcc gaggagatcg     60

tgctgcagcc catcaaggag atctccggca ccgtcaagct gcccgggtcc aagtcgctgt    120

ccaaccggat cctcctgctc gccgccctgt ccgaggtaag tggggacggt cctccctccc    180

tccctccctc cctctcttct tggccaactg gaatttggtt gtggccgtgt ggagatgaga    240

ttttacaggg ggtttgctgc tgccctgttt cagtgttttt cttgtccaat aataccacga    300

attatcggtg tagtccatct cacgatcaga tgcactacat acctagctcc ctagtttgtc    360

tagtaattgt ttgtattcgg cttaggatga tcaatcttca accaacacag taaaatcaac    420

ttgtaaatac taaataataa acaatatata tataaaaggt gggtgtcgcc ctatgcccct    480

atcggcctac tcattcttgt ggggaatggc atgctctctc ttggtagttg gtggatggtg    540

aactctgctg tgaaatttag gtacatgata aaaaaaagaa ccacccaggg gccagagcct    600

cttaccctgc tgttaacaaa ctggatgtca aaaatgttca atttatcatt gactactaat    660

tctggatgta gttgttagtt gttcgagcaa tgagatggac ctcactaatt tgttaatttg    720

tttagtagcc agtgctccct gccacttatt caggttaagg tgatcaatgt gtgaacacga    780

aacaggggga ttcttgctat gctggagtat tgattcttag gatgccatgc tatccctttg    840

ctgttttgtg gcctctgcta tgaaatttgg gtgcaataaa ctagccctga agggttgatc    900

ttatgctgtc atcatgatga aagatggagt attgatgatc ctttacgttg tttttaacaa    960

atttggtcac aaaactagca ttgattacta cttcttaatg aggattttta aaaaaaactt   1020

gttaataaag aaaaaaaata gcttcttgtt tgttaattgt gttttttaa tctttgatca   1080
```

```
ggggacaaca gtggttgata acctgttgaa cagtgaggat gttcactaca tgcttggggc   1140
cttgaacact cttgggctct ctgtcgaagc agacaaagtt gccaaaagag ctgttgttgt   1200
tggctgtggt ggaaagttcc cagttgagga cgctaaagag gaagtgcagc tcttcttggg   1260
gaatgctgga actgcaatgc ggccattgac agcagctgtt actgctgctg gtggaaatgc   1320
aacgtatgct tttaccccta cagtatttgt tgaagttagt aggaagtcca tgggtatgtg   1380
tcgtggctta tggggcattg gtttttcaac ttcagttacg tgcttgatgg agtaccaaga   1440
atgagggaga gacccatcgg cgacttggtt gtcggattga agcagcttgg tgcggacgtt   1500
gattgtttcc ttggcactga ctgcccaccc gttcgtatca atggaattgg agggctacct   1560
ggcggcaagg ttagttacta agggctacat gctacattct tctgtaaatg gtatcaacta   1620
ttctcgagct tttgcatttg taaggaaaac atagattgat ctgactaacc tgcaaatggt   1680
catccctaac tagcaaacca tgtttccatt aagctcaatg aagtaatgct tggcatgtct   1740
ttagcaaatc ttctcggggc atttcctgtt ttctagtcta atattatatg tttttagcat   1800
gaattaactc ttaccactgt tacattgtac aggtt                              1835
```

<210> SEQ ID NO 72
<211> LENGTH: 5316
<212> TYPE: DNA
<213> ORGANISM: Sorghum halepense

<400> SEQUENCE: 72

```
ggcgggcgcc gaggagatcg tgctgcagcc catcaaggag atctccggca ccgtcaagct     60
gcccgggtcc aagtcgctgt ccaaccggat cctcctgctc gccgccctgt ccgaggtaag    120
tggggacggc cctccctccc tctcttcttg gccaactgga atttggttgt ggccgtgtgg    180
agatgagatt ttacaggggg tttgctgctg ccctgtttca gtgtttttct tgttcgataa    240
taccacgaat tctcggtgta gtccatctca cgatcagatg cactacatac ctagctccct    300
agtttgtcta ctaattgttt gtattcggct taggatgatc aatcttcaac caacacagta    360
aaatcaactt gtaaatacta aaaaatatat aaaaatggtg ggtgtcgccc tatgccccta    420
tcggcctact cattcttgtg gggaatggca tgctctctct tggtagttgg tggatggtga    480
actctgctgt gaaatttagg tacatgataa aaaaaaacca cccaggggcc agggcctctt    540
accctgctgt taacaaactg gatgtcaaaa atgttcaatt tgtcattgac tactaattct    600
ggatgtagtt gttagttgtt cgagcgatga gatggacctc actaatttgt taatttgttt    660
agtagccagt gctccctgcc acttattcag gttaaggtga tcaatgtgtg aacacgaaac    720
agggggattc ttgctatgcc ggagtattga ttcttaggat gccatgctat ccctttgctg    780
ttttgtggcc tctgctatga aatttgggtg caataaacta gccctgaagg gttgatctta    840
tgctgtcatc atgatgaaag atagagtatt gatgatcctt tacgttgttt ttaacaaatt    900
cggtcacaaa gctagcattg attacttctt aatgaggatt tttaaaaaaa cttgttaata    960
aagaaaaaaa tagcttcttg tttgttaatt gtattttttt taatctttga tcaggggaca   1020
acagtggttg ataacctgtt gaacagtgag gatgttcact acatgcttgg ggccttgaac   1080
actcttgggc tctctgtcga agcagacaaa gttgccaaaa gagctgttgt tgttggctgt   1140
ggtggaaaat tcccagttga ggacgctaaa gaggaagtgc agctcttctt ggggaatgct   1200
ggaactgcaa tgcggccatt gacagcagct gttactgctg ctggtggaaa tgcaacgtat   1260
gctttttacc ctacagtatt tgttgaagtt agtaggaagt ccatgggtat gtgtcgtggc   1320
```

-continued

```
ttatggggca ttggtttttc aacttcagtt acgtgcttga tggagtacca agaatgaggg   1380
agagacccat tggtgacttg gttgtcggat tgaagcagct tggtgcggac gttgattgtt   1440
tccttggcac tgactgccca cccgttcgta tcaatgggat tggagggcta cctggcggca   1500
aggttagtta ctaagggcta catgctacat tcttctgtaa atggtatcaa ctattctcga   1560
gcttttgcat ttgtaaggaa aacatagatt gatctgacta acctgcaaat ggtcatccct   1620
aactagcaaa ccatgtttcc attaagctca atgaagtaat gcttggcatg tctttagcaa   1680
atcttctcgg ggcatttcct gttttctagt ctaataatat atgtttttag catgaattaa   1740
ctattaccac tgttacattg tacaggttaa gctctctggc tccatcagca gtcagtactt   1800
gagtgccttg ctgatggctg ctcctttggc tcttggtgat gtggagattg aaatcattga   1860
taaattaatc tccattccct atgttgaaat gacattgaga ttgatggagc gttttggcgt   1920
gaaagcagag cattctgata gctgggacag attctacatt aagggaggtc aaaaatacaa   1980
gtaagctttg taatttattt cacaatgatg tcaacgattc agttttcagt tttccaaaca   2040
gatgcatcca tatttgaata tatgcaccgt aggcaaaaat cattgcatgg tagaaaacta   2100
gtaatgagta ttgactgtgt aaattactta atcagttggg atatggccag tctattggag   2160
tcaagaacgc taaccaaaat agccaagcaa tgcctattta gtagtcatct aattatacag   2220
agggaacaac catgtagact gttgatatca ccagaagtcg catcctcttg aaacttggct   2280
tataagagac agtctaggta gcaggacttt agctacttgg caattggcat ggataccttt   2340
ttttcaggaa aaggcacttg attggttttt tgtgccccgt ctgtgatgtg tgaacctgct   2400
cctctattgc tttagaagga caatatccat gttgttaccc aacatgcatc ccttagttca   2460
tttactgaaa tcagttcata tgttcattag ctgtttccct aaactagacc ttcttttgct   2520
ttgcaatcaa taggtccccc aaaaatgcct atgttgaagg tgatgcctca agtgcaagct   2580
atttcttggc tggtgctgca attactggag ggactgtgac tgttgaaggt tgtggcacca   2640
ccagtttgca ggtaaaactt tgctgcaatg ctgattgctt ttgccttttt ttggtttcgg   2700
cattactcta caagtcacca tcactaaata acataatcat ctgtaaatgt caaatagaca   2760
tacttcagtg agtggatatt catgtaataa taactagtta aacataccaa cctaaacagt   2820
cctgtaaaat acgctcctta cactgtctcc gtttccttaa taatttgctg aatacggcag   2880
ggtgatgtga agtttgctga ggtactggag atgatgggag caaaggttac atggaccgag   2940
actagcgtaa ctgttactgg tccaccacga cagccatttg ggaggaaaca cctcaaggct   3000
attgatgtta acatgaacaa aatgcctgat gttgccatga ctcttgctgt ggttgccctc   3060
tttgccgatg gcccaacagc tatcagagac ggtaaaacat tctcagccct gctaccatgc   3120
ctattctaca tgacaagatt cacagtaaca ttcaagacat ggttctggtt acgcgccact   3180
aatagctatt gctcttcgac agtggcgtcc tggagagtaa aggagaccga gaggatggtt   3240
gccatccgga cggagctaac caaggtaaaa ttgacatact cctacttcac aagtctcatg   3300
ttgtgttttc atagctctct gcctcttgct cttgcctgcg gtcgcttcat cctcaaatgt   3360
tgctgcttgt gtttccacca gctgggagca tctgttgagg aagggccgga caactgcatc   3420
atcacaccgc cagagaagct gaacgtgacg gcgatcgaca catacgacga ccacaggatg   3480
gccatggcct tctcccttgc cgcctgtgcg gaggtccccg tcacgatccg ggaccctggg   3540
tgcacccgga agaccttccc cgactacttc gatgtgctga gcacgttcgt caagaactaa   3600
gcgtgtgata tactaccaca cagcgggatt gcagtgatct tgctgggcat gtgcggagga   3660
aatacatttt tttttgttct cttttccggg ataagttttg agcctgtaat attagttgct   3720
```

```
cgtagcatgt ttctatgaca gatcttgagt gtattgtacg tccaaattcg taccctgagt   3780
ggttcattgg aacaataata agaataataa attacgtttc agcggttatt ttggagatga   3840
tggcatcagc tattcaccaa tttagcatat cttcacgtta ggattttttt atttattttt   3900
aatcctttat attttaaaaa acctcctaga aatttttgc agtaataccc tcttgatcac    3960
gccacatcca attttttaca gtaataccct cttgatcacg ccacatgggc acagatagtg   4020
cttcatatat tgtttgcttg tcttataaga ttttctcaca ataaatcagc aaacataaga   4080
ttttttcaca ataaactgac tgtaattttt tagcttcata tgctaagtga ccatcacata   4140
ctaagtgacc gtgtattttt ttagcctcac atgaacatat cctgagaaac ccagatgtaa   4200
aaccatgaaa gacgttattc aaagcctcaa agaaaatacc cacacaaact cgttcaacta   4260
ttaacatcta gtgaaacagc ccagatgtaa aaccacgtaa tacgttattc aaagtctcaa   4320
agaaactacc cacacaaact cgttcaacta ttaacatcta gtgaaacagg caactccagt   4380
tcatccgata acatctgctg aaaaggcagc gaaacatcaa gaatctagat ttatcacgtg   4440
atgaaaagca atgcattagg gggatcatcc attaaccatt ttccattcat gcactaacat   4500
ccattgaaac aggctacatc catatcgtgc cacaaaacct cgataagact taattctgat   4560
gcaaatagct tatcgatcag gagggaattc ttctgttaca ccaagttctc tcactagaaa   4620
ctgaaaacat cctgttcatc attatatgat aaggtgctgg ctaccacatt acgcgtcgct   4680
gatagtcacc tcaacctcca cacctggttc aatggtgatc gaggtgatct gcttgaccac   4740
gtctggtgta ctgatgagat caatcaccct cttgtgaatc ctcatctcaa agcgatccca   4800
ggtgttggta cctgaaatag tcaagacaat tatcaataat tgcatcaaga ataatccata   4860
tacaaagtga aatccaaaaa gaaatcctgg cacgaggata acaagaaaca tcaagaattg   4920
aagttgtagg atgaagtaac atgctggcat cagttttaaa aagctcgatt ttgatacatc   4980
aagtatcagt gtaaacatat tgcatcatca tctgctcagc atgttgacat atctcctata   5040
ctaatcttca agatataggg gcattgaatg cagcaaaatg acaggccata ctaaaatttg   5100
catagcacca caggactcaa ggccaacaaa atgcagatca catcaataaa aagaagtgtg   5160
gaacatcact caaaagttaa ctggaaaagt ttattgaact gaaaacgttt gaacagtgaa   5220
agcattgaat ggaccaacca tcagttttaa aaagctcgaa tttgtaagtc ctcagagaaa   5280
atctcaggat taacttgttt ggcatcatat ggttag                             5316
```

```
<210> SEQ ID NO 73
<211> LENGTH: 8582
<212> TYPE: DNA
<213> ORGANISM: Sorghum halepense
<220> FEATURE:
<221> NAME/KEY: unsure
<222> LOCATION: (1)..(8582)
<223> OTHER INFORMATION: unsure at all n locations

<400> SEQUENCE: 73

tcacctcgtt ccctcaagac tcaagaacag ccatgggcct acaagtccgt cgtcaatctg     60
ggccgagcgg gttttgctgc gtacagagtt ctattgcttc cttgtccagc ccatagttgc    120
tagctatgtc ccctagcaag aacgaagcca acaacccaat ttcaaaaaaa aaaaaaaacg    180
aagccaacta cccaatgctg accattaccc acatgacaca tgtataaggt cattcttaat    240
ggaagtttca tgacacggtt ttcaatatat ccatatttta aaaatagtgc atagaagttt    300
nnnnnnnnnn nnnnnnatat taaatagggt gccacataag cagaattgct gacttggcag    360
```

-continued

```
ggtcattaaa tgaaggagtt tcatcagata agagaggagt ttcatcccca tgaaacttat    420
gtgactcggt tacctagttt atagtcttgg taactgtacc ataaaactat gcattgagac    480
tggcctactc acataaaact cttatcgtct ctctcttcat taatatagcg ccacatcagc    540
atatttaata tgtatgaaac tctaatgaaa ctcccattaa aattagccta agacgtcatc    600
cagcacgatt gttacgtgcc tataaggagc ttaattatat cattaatatt tattgctaat    660
aactcctcca tcctcttccc tctacgttag gttcaacgtt gacgtgcttg tgtattgcag    720
attattgcac ttgctcttta tgtgtacgat ggcatggttt ggtgcagtga caccaaatca    780
gttctttgac aagtctaaag gcttcaattt tctactaggc gggcaaccaa ccattgtatc    840
attacacaaa gtggagtcat agggtgagtt gggttgtact tgtcccttgg tgttggtaca    900
gtatatggtt gccttttggc ttgtcagcac ttaggacaat ggttagtgat gtattttcta    960
aagtactcct tgagattctt catcagaaac aacgtgaagt tagcctctag ctccaccttt   1020
ttgtgcagca gagttttaat tttgaagctg ataggctgtt tggcaacacg gagctagagc   1080
aaagctaaaa aaacagaagt agaacaattc catacactct ctaaggcttg caaaagataa   1140
aactggtaga tgttttgtgt ttgatcgatt agattttgtt gatcaggcgc acccttacat   1200
ttacagtgtg agaatggtct tatatctgat cgaagatata gttaatacaa attaataaaa   1260
acctgcgcga atctccaaac cctactctgc tcaactcgga acgaggaagc cgtcttgaca   1320
aaccggctta ggcatcgttt ggttcgtgag gaagcatgtc ttgaaacaat tccaaccaag   1380
aatgtttaac taatttatat agccttagat catctgaaac aattcctggg tggtggaatt   1440
ctctccaacc aaacgagcct ccgcgcatga taggtcagtt ctgagccttg atctatgata   1500
tggacaaacc aagcaactac ttggacacca gcaggcaaaa gcaaaggtgg aaagtaacga   1560
agaagacccg cgaaaaacaa gtgctaacgg aggccggaag ggcggcacgt acgagtgcgg   1620
tgcaccgtgc tgcattcgtg cacacctgtg gaaaaggaaa gcgaaagaaa accaacacag   1680
gcaactcagg cccgatgcgc ccacctacta cccccctccc catgggtctc tctggctgtc   1740
gcgcccagat ctgccactcg gcggcggcgc tgcagcgagt cgcgtcgtgc tcgtgtcgcg   1800
ggggttggtg gcagtaggag caccccggcg cgtgagcacg ctctcaccgg cccgcaggcc   1860
gcagcccgct tctatttctt cctccccacc cgaccccgtg caggtggcac tggcagtcag   1920
tccacgccac caaccgcgga ggcgaaccaa accaaccgcg cgcccaggcc gcccgccctc   1980
cccccaccct accaacccgc gtcgtcgtcn ngggcgcgcg ggcgccgcgt ggtccccttg   2040
gcggcggcgg cggcacccgc ggtgcaggcg ggcgccgagg agatcgtgct gcagcccatc   2100
aaggagatct ccggcaccgt caagctgccc gggtccaagt cgctgtccaa ccggatcctc   2160
ctgctcgccg ccctgtccga ggtaagtggg gacggccctc cctccctccc tccctctctt   2220
cttggccaac tggaatttgg gtgtggccgt gtggagatga gattttacag gggtttgct    2280
gctgccctgt ttcagtgttt ttcttgttcg ataataccac gaattctcgg tgtagtccat   2340
ctcacgatca gatgcactac atacctagct ccctagtttg tctactaatt gtttgtattc   2400
ggcttaggat gatcaatctt caaccaacac agtaaaatca acttgtaaat actaaaaaat   2460
atataaaaat ggtgggtgtc gccctatgcc cctatcggcc tactcattct tgtggggaat   2520
ggcatgctct ctcttggtag ttggtggatg gtgaactctg ctgtgaaatt taggtacatg   2580
ataaaaaaaa accacccagg ggccagggcc tcttaccctg ctgttaacaa actggatgtc   2640
aaaaatgttc aatttgtcat tgactactaa ttctggatgt agttgttagt tgttcgagcg   2700
atgagatgga cctcactaat ttgttaattt gtttagtagc cagtgctccc tgccacttat   2760
```

```
tcaggttaag gtgatcaatg tgtgaacacg aaacaggggg attcttgcta tgccggagta   2820
ttgattctta ggatgccatg ctatcccttt gctgttttgt ggcctctgct atgaaatttg   2880
ggtgcaataa actagccctg aagggttgat cttatgctgt catcatgatg aaagatagag   2940
tattgatgat cctttacgtt gtttttaaca aattcggtca caaagctagc attgattact   3000
tcttaatgag gatttttaaa aaaacttgtt aataaagaaa aaaatagctt cttgtttgtt   3060
aattgtattt tttttaatct ttgatcaggg gacaacagtg gttgataacc tgttgaacag   3120
tgaggatgtt cactacatgc ttggggcctt gaacactctt gggctctctg tcgaagcaga   3180
caaagttgcc aaaagagctg ttgttgttgg ctgtggtgga aaattcccag ttgaggacgc   3240
taaagaggaa gtgcagctct tcttggggaa tgctggaact gcaatgcggc cattgacagc   3300
agctgttact gctgctggtg gaaatgcaac gtatgctttt taccctacag tatttgttga   3360
agttagtagg aagtccatgg gtatgtgtcg tggcttatgg ggcattggtt tttcaacttc   3420
agttacgtgc ttgatggagt accaagaatg agggagagac ccattggtga cttggttgtc   3480
ggattgaagc agcttggtgc ggacgttgat tgtttccttg gcactgactg cccacccgtt   3540
cgtatcaatg ggattggagg gctacctggc ggcaaggtta gttactaagg gctacatgct   3600
acattcttct gtaaatggta tcaactattc tcgagctttt gcatttgtaa ggaaaacata   3660
gattgatctg aataacctgc aaatggtcat ccctaactag caaaccatgt tagcattaag   3720
ctcaatgaag taatgcttgg catgtcttta gcaaatcttc tcggggcatt tcctgttttc   3780
tagtctaata atatatgttt ttagcatgaa ttaactatta ccactgttac attgtacagg   3840
ttaagctctc tggctccatc agcagtcagt acttgagtgc cttgctgatg gctgctcctt   3900
tggctcttgg tgatgtggag attgaaatca ttgataaatt aatctccatt ccctatgttg   3960
aaatgacatt gagattgatg gagcgttttg gcgtgaaagc agagcattct gatagctggg   4020
acagattcta cattaaggga ggtcaaaaat acaagtaagc tttgtaattt atttcacaat   4080
gatgtcaacg attcagtttt cagttttcca aacagatgca tccatatttg aatatatgca   4140
ccgtaggcaa aaatcattgc atggtagaaa actagtaatg agtattgact gtgtaaatta   4200
cttaatcagt tgggatatgg ccagtctatt ggagtcaaga acgctaacca aaatagccaa   4260
gcaatgccta tttagtagtc atctaattat acagagggaa caaccatgta gactgttgat   4320
atcaccagaa gtcgcatcct cttgaaactt ggcttataag agacagtcta ggtagcagga   4380
ctttagctac ttggcaattg gcatggatac cttttttca ggaaaaggca cttgattggt   4440
tttttgtgcc ccgtctgtga tgtgtgaacc tgctcctcta ttgctttaga aggacaatat   4500
ccatgttgtt acccaacatg catcccttag ttcatttact gaaatcagtt catatgttca   4560
ttagctgttt ccctaaacta gaccttcttt tgctttgcaa tcaataggtc ccccaaaaat   4620
gcctatgttg aaggtgatgc ctcaagtgca agctatttct tggctggtgc tgcaattact   4680
ggagggactg tgactgttga aggttgtggc accaccagtt tgcaggtaaa actttgctgc   4740
aatgctgatt gcttttgcct ttttttggtt tcggcattac tctacaagtc accatcacta   4800
aataacataa tcatctgtaa atgtcaaata gacatacttc agtgagtgga tattcatgta   4860
ataataacta gttaaacata ccaacctaaa cagtcctgta aaatacgctc cttacactgt   4920
ctccgtttcc ttaataattt gctgaatacg gcagggtgat gtgaagtttg ctgaggtact   4980
ggagatgatg ggagcaaagg ttacatggac cgagactagc gtaactgtta ctggtccacc   5040
acgacagcca tttgggagga aacacctcaa ggctattgat gttaacatga acaaaatgcc   5100
```

```
tgatgttgcc atgactcttg ctgtggttgc cctctttgcc gatggcccaa cagctatcag   5160
agacggtaaa acattctcag ccctgctacc atgcctattc tacatgacaa gattcacagt   5220
aacattcaag acatggttct ggttacgcgc cactaatagc tattgctctt cgacagtggc   5280
gtcctggaga gtaaaggaga ccgagaggat ggttgccatc cggacggagc taaccaaggt   5340
aaaattgaca tactcctact tcacaagtct catgttgtgt tttcatagct ctctgcctct   5400
tgctcttgcc tgcggtcgct tcatcctcaa atgttgctgc ttgtgtttcc accagctggg   5460
agcatctgtt gaggaagggc cggacaactg catcatcaca ccgccagaga agctgaacgt   5520
gacggcgatc gacacatacg acgaccacag gatggccatg gccttctccc ttgccgcctg   5580
tgcggaggtc cccgtcacga tccgggaccc tgggtgcacc cggaagacct tccccgacta   5640
cttcgatgtg ctgagcacgt tcgtcaagaa ctaagcgtgt gatatactac cacacagcgg   5700
gattgcagtg atcttgctgg gcatgtgcgg agnnaataca tttttttttg ttctcttttc   5760
cgggataagt tttgagcctg taatattagt tgctcgtagc nnnnntctat gacagatctt   5820
gagtgtattg tacgtccaaa ttcgtaccct gagtggttca ttggaacaat aataagaata   5880
ataaattacg tttcagcggt tattttggag atgatggnnt cagctattca ccaatttagc   5940
atatcttcac gttaggattt ttttatttat ttttaatcct ttatatttta aaaaacctcc   6000
tagaaatttt ttgcagtaat accnnnnnnn nnnnnnnnna tccaattttt tacagtaata   6060
ccctcttgat nnnnnnacat gggcacagat agtgcttcat atattgtttg cttgtcttat   6120
aagattttct cacaataaat cagcaaacat aagattttnn nnnaataaac tgactgtaat   6180
tttttagctt catatgctaa gtgaccatca catactaagt gaccgtgtat ttttttagcc   6240
tcacatgaac atatcctgag aaacccagat gtaaaaccat gaaagacgtt attcaaagcc   6300
tcaaagaaaa tacccacaca aannnnnnnn nnnnnnnnnn tctagtgaaa cagcccagat   6360
gtaaaaccac gtaatacgtt attcaaagtc tcaaagaaac taccnnnnnn nnnnnnnnnn   6420
nnnnnnnnnn tctagtgaaa caggcaactc cagttcatcc gataacatct gctgaaaagg   6480
cagcgaaaca tcaagaatct agatttatca cgtgatgaan nnnnnnnnnn nnnnnnnnnn   6540
nnnnnnnnnn nnnnnnnnnn nnnnnnnnnn nnnnnnnnnn nnnnnnnnnn nnnncatatc   6600
gtgccacaaa acctcgataa gacttaattc tgatgcaaat agcttatcga tcaggaggga   6660
attcttctgt tacaccaagt tctctcacta gaaactgaaa acatcctgtt catcattata   6720
tgataaggtg ctggctacca cattacgcgt cgctgatagt cacctcaacc tccacacctg   6780
gttcaatggt gatcgaggtg atctgcttga ccacgtctgg tgtactgatg agatcaatca   6840
ccctcttgtg aatcctcatc tcaaagcgat cccaggtgtt ggtacctgaa atagtcaaga   6900
caattatcaa taattgcatc aagaataatc catatacaaa gtgaaatccn nnnnnnnnnc   6960
ctggcacgag gataacaaga aacatcnnnn nntgaagttg taggatgaag taannnnnnn   7020
nnnnnnnnnn nnnnnnnnnn nattttgata catcaagtat cagtgtaaac atattgcatc   7080
atcatctgct cagcatgttg acatatctcc tatactaatc ttcaagatat aggggcattg   7140
aatgcagcaa aatgacaggc catactaaaa tttgcatagc accacaggac tcanggccaa   7200
caaaatgcag atcacnnnnn nnnnnnnnnn nnnnnnnnnn nnnnnnnnng ttaactggaa   7260
aagtttattg aactgaaaac gtttgaacag tgaaagcatt gaatggacca accnnnnnnn   7320
nnnnnnnnnn nnnatttgta agtcctcaga gaaaatctca ggattaactt gtttggcatc   7380
atatggttag tccatcacaa acagcaagcc gaacacatnn nctcaggtga actagactga   7440
tgactgggcg ggtcctgaaa gaaagtacat gctaggcatt ttgcactaaa ctttctagga   7500
```

```
tatagaaggc tcttaagggt agcaagaagg aataatggca nnnnnnntaa ctaaagaaaa   7560
agactatgta tgcccaaaat tggtcacaat atttagacta ctctgggcat agcctattcc   7620
agactgctgc atgccaaann nnnnnnnnnn nnnnnnnnnn nnnnnnntta acagccaatg   7680
ttaaactgct ctatgatcaa gcagtaagta aatcaatttt agctgaaann nngcaataac   7740
tagaatgtca ctaannnnnn nnnnnnnnnn nnnnnnnnnn nnnnnnnnnn nnnnnnnata   7800
gacttcaatg acgtaatctc agcagcatct cctaattaac nnnnnnnnnn nnnnnnnnnn   7860
nnnnnnnnnn nncaccaaga tctcactcta agagtatgac accacacaaa tgctcttatc   7920
ccaagagtat tgatacacat gaatacagca tgttccataa atgaagatga aattttcccg   7980
gagacaatat gctaagcatc agttttaaan nnnnnnnnnn nntggacatc agagaccccg   8040
aaagatctca gtctatgtat aagtnnnnnn nnatctgctc agcataccat cgcatcccac   8100
agctctacat atcgatcaca ccaaacgatt cgagacctat atttatgaac gtgactacgt   8160
gaggcgatga gggagagagg tcaccttcgc cacagggaga cttcctggtg gtgatgtgga   8220
gcaccttggt aggcatccgc acggggccct tgatcttcag ctccttgccc ttggcaccct   8280
tcaccagatc gccgcagact gcgcaacgaa acgcgaggta agttcttgga ttccaacccg   8340
atgccgcagg aacgaacaaa ggaaatggca tccaccgtca cgcaatggag cacggaagac   8400
tgatagcagc cttacctttc tcgaggttct tgacgctcct ggaggagagc gtgatgcgga   8460
tcctgtgctg cggatccatc aggcccgcct cgaacccggc cttgcccgac ttcatcggcg   8520
gcgcgtacgc cacatccgcc gccgccatgg tacgtcggag taggggagct ggggagggag   8580
gg                                                                  8582
```

<210> SEQ ID NO 74
<211> LENGTH: 6239
<212> TYPE: DNA
<213> ORGANISM: Sorghum halepense
<220> FEATURE:
<221> NAME/KEY: unsure
<222> LOCATION: (1)..(6239)
<223> OTHER INFORMATION: unsure at all n locations

<400> SEQUENCE: 74

```
tttttccaaa tcagagtaca gatgattgat aaagtcataa tgtatgtttc gttatcgatg     60
ggcactatca cttatcagcg accgaagact ttcagcctag attttaaaca actgagctat    120
ggtcatcagt tcggaaccac ctgcaggata tcacttgttt caggttaaac aacgtgatga    180
ctgatggatt gcggcacaat gatattgatc atggacgtgt ttatagactc ctaaaacgac    240
gggtgtgttc acnnnnnnnn nnnnnnnnnn nnnnnnnnnn nnnnnnnnnn nnnnnnnnnn    300
nnnnnnnnnn nnnnnnnnnn nnnnnnnnnn nnnnnnnnnn nnnnnnnnnn nnnnnnnnnn    360
nnnnnnnnnn nnnnnnnnnn nnnnnnnnnn nnnnnnaaaa aaaaagaacg aagccaacta    420
cccaatgctg accattaccc acatgacaca tgtataaggc cattcttaat ggaagtttca    480
tgacacagtt tccaatatat acatatttta aaaacagtgc atagaagttt catggggatg    540
aaactctctc tacggtcagt ctcaatacat gtttcatgag agtgtcatgc atattaaata    600
gggtgccaca taagcagaat tgctgacttg tcagagtcat taaataaagg agtttcatca    660
gatgagagag gagtttcatc tccatgaaac ttatgtgact cggttaccta gtttatagtc    720
ttggtaactg taccataaaa ctatacattg agactgacct actcacataa aactcttatc    780
gtctctctct ttattaacat agcgccacat cagcatattt aatatgtatg aaactctaat    840
```

-continued

```
gaaacctcca ttaaaactag cctaaggcgt catccagcaa gattgttatg tgcctataag    900
gagcttaatt atatcattaa tatttattgc taataactcc tccatcctct tccctctatg    960
ttaggttcaa cgcgacgtgc ttgtgtattg cagattattg tacttgctct ttatgtgtac   1020
gatggcatgg tttggtgcac tgacaccaaa tcagttcttt gacaagttta aaggcttcaa   1080
ttttctacta gccgggcaac caaccattgt atcattacac aaagtggagt catagggtga   1140
gttggtttgt acttgtccct tggtgttggg tacagtatat ggttgccttt tggcttgtca   1200
acacttagga caatggttag tgatgtattt tctagagtac tccttgagat tcttcatcag   1260
aaacaacatg aagttagcct ctagctctac ctttttgtgc agcagagttt taattttgaa   1320
gcttaggggc tgtttggcaa cacggagcta gagcaaagct aaaaaacaga agtagaacaa   1380
ttccatacac tctctaaggc ttgcaaaaaa taaaactggt agatctgttt tgtgtttgat   1440
agattagatt ttgttgatca ggcgcaccct tacatttaca gtgtgagaat ggtcttatat   1500
ctgactgaag atagttaata caaattaata aaaacctgcg cgaatctcca aaccctactc   1560
tactcaactc ggaacgagga agccgtcttg acaaaccggc ttaggcatcg tttggttcgt   1620
gaggaagcat gtcttgaaac aattcccacc aagaatgttt aactaattta tatagcctta   1680
gatcatctga aacaattcct gatcctgggt ggtggaattc tctccaacca aacgagctct   1740
tagccacgac gagaccgcac atgataggtc acttctgagc cttgacctat gacatggaca   1800
aaccaagcaa ctacttagga caccgtcagg taaaagcaaa ggtggaaagt aacgaagacg   1860
acctgcgaga aacaagtgct aacggaggcc ggaagggcgt cacgtacgag tgcggtgcac   1920
cgtgctgcat tcgtgtgcac acacacgtac acctgtggaa aaggaaaccg aaagaaaacc   1980
aacacaggca actcaggccc gatgcggcca cctactaccc cccctcccca tgggtctctc   2040
tcgctctcgc gcccagatct gccactcggc ggcgccgctg cagcgagtcg cgtcgtgctc   2100
gtgtcgcggg ggttggtggc agtaggagca ccccggtgcg tgagcacgct caccggcccg   2160
cagcccgctt ctatttcttc ctcctcccca cccgaccccg tgcaggtggc agtcagtcca   2220
cgccaccaac cgcggaggcg aaccaaacca accgcgcgcc caggccgccc gccctccccc   2280
caccctacca acccgcgtcg tcgtcggcaa tggcggccat ggcgaccaag gccaccgtgt   2340
cgctggacct cgccgtggga ccgcgccacc accaccgccc gagctcggcg gcgcgcgcgt   2400
ccgcccgccc cgccgccgcc gccgccgccg tacgcgggct gagggcgcgc gggcgccgcg   2460
tggtcccctt ggcggcggcg gcggcacccg cggtgcaggc gggcgccgag gagatcgtgc   2520
tgcagcccat caaggagatc tccggcaccg tcaagctgcc cgggtccaag tcgctgtcca   2580
accggatcct cctgctcgcc gccctgtccg aggtaagtgg ggacggccct ccctccctct   2640
cttcttggcc aactggaatt tggttgtggc cgtgtggaga tgagatttta caggggggttt   2700
gctgctgccc tgtttcagtg tttttcttgt tcgataatac cacgaattct cggtgtagtc   2760
catctcacga tcagatgcac tacataccta gctccctagt ttgtctagta attgtttgta   2820
ttcggcttag gatgatcaat cttcaaccaa tacagtaaaa tcaacttgta aatactaata   2880
tatataaggt gggtgtcgcc ctatgctcct actgtcggcc tactcattct tgtggggaat   2940
ggcatgctct ctctcttggt agttcgtgga tggtgaaatc tgctgtgaaa tttaggtaca   3000
tgataaaaaa aaggattcct aaaaaaaaag aaccacccag gggccagggc ctcttaccct   3060
gctgttaaca aactggatgt aaaaaatgtt caatttgtca ttgactacta attctggatg   3120
tagttgttag ttgttcgagc aatgagatgg acctcactaa tttgttaatt tgtttagtag   3180
ccagtgctcc ctgccactta ttcaggttaa ggtgatcaat gtgtgaacac gaaacagggg   3240
```

-continued

```
gattcttgct atgccggagt attgattctt aggatgccat gctattcctt tgctgttttg   3300
tggcctctgc tatgaaattt gggtgcaata aactagccct gaagggttga tcttatgctg   3360
tcatcatgat gaaagatgga gtattgatga tcctttacgt tgtttttaac aaatttggtc   3420
acaaaactag cattgattac ttcttaatga ggatttttaa aaaaaacttg ttaataaaga   3480
aaaaaatagc ttcttgtttg ttaattgtgt ttttttaatc tttgatcagg ggacaacagt   3540
ggttgataat ctgttgaaca gtgaggatgt tcactacatg cttggggcct tgaacactct   3600
tgggctctct gtcgaagcag acaaagttgc caaaagagct gttgttgttg gctgtggtgg   3660
aaagttccca gttgaggacg ctaaagagga agtgcagctc ttcttgggga atgctggaac   3720
tgcaatgcgg ccattgacag cagctgttac tgctgctggt ggaaatgcaa cgtatgcttt   3780
ttaccctaca gtatttgttg aagttagtag gaagtccatg ggtatgtgtc gtggcttatg   3840
gggcattggt ttttcaactt cagttacgtg cttgatggag taccaagaat gagggagaga   3900
cccattggtg acttggttgt cggattgaag cagcttggtg cggacgttga ttgtttcctt   3960
ggcactgact gcccacccgt tcgtatcaat ggaattggag ggctacctgg cggcaaggtt   4020
agttactaag ggctacatgc tacattcttc tgtaaatggt ataaactatt ctcgagcttt   4080
tgcatttgta aggaaaacat agattgatct gactaacctg caaatggtca tccctaacta   4140
gcaaaccatg tttccattaa gctcaatgaa gtaatgcttg gcatgtcttt agcaaatctt   4200
ctcggggcat ttcctgtttt ctagtctaat aatatatgtt tttagcatga attaactctt   4260
accactgtta cattgtacag gttaagctct ctggctccat cagcagtcag tacttgagtg   4320
ccttgctgat ggctgctcct ttggctcttg ggatgtgga gattgaaatc attgataaat   4380
taatctccat tccctatgtc gaaatgacat tgagattgat ggagcgtttt ggcgtgaaag   4440
cagagcattc tgatagctgg gacagattct acattaaggg aggtcaaaaa tacaagtaag   4500
ctttgtaatt tatttcactt tgatgtaaac gattcagttt tcagttttcc aaacagatgc   4560
atccatattt gaatatatgc accgtaggca aaaattgttg cagggtagaa agctagtaat   4620
gagtattgac tgtgtaaatt acttaaatca gttgggatat ggccattcta ttggagtcaa   4680
gaacgctaac caaaatagcc aagcaatgcc tatttagtag tcacctaatt atacagaggg   4740
aagaaccatg tagactgttg atatcaccag aagtcgcatc ctcttgaatc ttgaaacttg   4800
gcttacaaga gacagtctag gtagcaggac tttagctact tggcaattgg catggatacc   4860
tttttgtttt ttccaggaaa aggtacttga ttggtttttt gtgccccgtc tgtgatgtgt   4920
gaacctgctc ttttattgct ttagaagggc gtatccatgt ttcccaacat gcctccctta   4980
gttcattgta ctgacatcag ttcatatgtt cataagcgtt ttccctaaac taaaccttct   5040
tttgctttgc aatcaatagg tcccccaaaa atgcctatgt tgaaggtgat gcctcaagtg   5100
caagctattt cttggctggt gctgcaatta ctggagggac tgtgactgtt gaaggttgtg   5160
gcaccaccag tttgcaggta aaactttgct gcaatgctaa ctgcttttgc ctttttggtt   5220
tcagcactac tctctgagtc actaaataac ataatcatct gtagacatac tccagtgagt   5280
ggatattcat gtaataataa taactagtta aacataccaa cctaaacagt cctgtaaaat   5340
tcagtcctta cactgtctcc atttcgttat taacttgctg aataccacag ggtgatgtga   5400
aatttgctga ggtactggag atgatgggag caaaggttac gtggaccgag actagcgtta   5460
ctgttactgg cccaccacgg cagccatttg ggaggaaaca cctcaaggct attgatgtta   5520
acatgaacaa aatgcctgat gttgccatga ctcttgctgt ggttgccctc tttgccgatg   5580
```

gcccaacagc tatcagagac ggtaaaacat tctcagccct gctaccatgc ctattctaca 5640
tgacaagatt cacacagagt aacattcaag aaatggttct gattacgcgc cactaatagc 5700
tattgctctt cgacagtggc gtcctggaga gtaaaggaga ccgagaggat ggttgcgatc 5760
cggacggagc taaccaaggt aaaagtgaca tactcctact tcacaagtct catgttgtgt 5820
tttcatagct ctctgcctct tgctcttgcc tgctgtcgct tcatcctcaa atgttgctgc 5880
ttgtgtttcc gccagctggg agcttctgtt gaggaagggc cggactactg catcatcaca 5940
cccccagaga agctgaacgt gacggcgatc gacacatacg acgaccacag gatggccatg 6000
gccttctccc ttgccgcctg tgcggaggtc cccgtcacga tccgggaccc tgggtgcacc 6060
cggaagacct tccccgacta cttcgatgtg ctgagcacgt tcgtcaagaa ctaagcgtgt 6120
gatatactac cacgcagcgg gattgaagtg atcttgctag gcatgcgcgg aggaaataca 6180 tttttttgt tctcttttcc gggataagtt ttgagcctgt aatattagtt gctcgtagc 6239

<210> SEQ ID NO 75
<211> LENGTH: 1723
<212> TYPE: DNA
<213> ORGANISM: Sorghum halepense

<400> SEQUENCE: 75
gccgccgccc ctctcctccc actcggcagt cgagacctgt gacgagcgca gacgacgcga 60
gacgagacga cgaggagggg agagagagag agcaggccgg tccgtcatcc gttggttcgg 120
gaatggcggc gcaggcggtg gtgccggcga tgcagtgcca ggtcggagtg aaggcggcgg 180
cgggcgcccg ggcgaggccg gcggcggcgc gagacaggtg tggggcgtca ggagtaggac 240
cggccgcggc ggcgcctcgc cggggttcaa ggtcatggcc gtcagcacgg gcagcaccgg 300
ggtggtgccg cgcctcgagc agctgctcaa catggacacc acgccctaca ccgacaagat 360
catcgccgag tacatctggg tcggaggatc tggaatcgac atcagaagca aatcaaggac 420
aatttcaaaa ccggtggagg atccctcaga actaccgaaa tggaactatg atgggtcaag 480
cacagggcaa gccccgggag aagacagtga agtcattcta tacccccagg ctatcttcaa 540
ggacccattc cgaggtggca acaacatttt ggttatctgt gatacctaca cgccacaggg 600
cgaacccctt cctactaaca aacggcacag ggctgcgcaa atttttagtg acccaaaggt 660
cgttgaacaa gtgccatggt ttggcataga gcaagagtac actttgctcc agaaagatgt 720
gaattggcct cttggttggc ctgttggagg ctaccctggt ccccagggtc cctactactg 780
tgctgtagga gcagacaaat catttggccg tgacatatca gatgctcact acaaggcttg 840
cctttatgct ggaattaaca ttagtggaac aaacggggag gtcatgcctg gtcagtggga 900
gtaccaagtt ggacctagtg ttggcattga agcaggagat cacatatgga tttcaagata 960
cattctcgag agaatcacag agcaagctgg ggttgtcctt acccttgatc caaaaccaat 1020
tcagggtgac tggaatggag ctggctgcca cacaaattac agcacaaaga ccatgcgtga 1080
agatggagga tttgaagata tcaagagagc aatcctgaat ctttctctgc gccatgattt 1140
gcatattagt gcatacggag aaggaaatga aagaagattg acagggaagc atgagaccgc 1200
tagcatcgag accttctcat ggggtgtggc aaaccgtggc tgctctgttc gtgtggggcg 1260
agataccgag gcaaaaggga aaggttacct agaagaccgt cgcccggcat caaacatgga 1320
cccatacatt gtgacggggc tactggctga aacaacaatt ctctggcaac caacccttga 1380
agcagaggtt cttgccgcca agaagctggc gctgaaggta tgaagcagtt gaaggatgtc 1440
tcaggcacga ataaacaggc ccacaacaaa attgattctg ctgttcactg gccttggtcc 1500

```
cgcaactctg ctcggcgcca ctctgtacaa aattaattac cattctggac cacattgtct   1560

ttgattcatc ggttacggtt gttacatttt gcttggacac catcacacca tgtttggact   1620

tggcctgtac ttcttgtagc aatttttgtg tgaagtgaag ttcgaattgg gcttcactct   1680

cggtcagggc caggagccca ggatctgtct cttatacaca tct                     1723
```

<210> SEQ ID NO 76
<211> LENGTH: 3101
<212> TYPE: DNA
<213> ORGANISM: Sorghum halepense

<400> SEQUENCE: 76

```
tttttactcc actataatcg gaactctata aatataaatc aaatcaacca cttctagcaa     60

taaagctgcg tcgcctggaa tttaatattt cccacaccaa ccgcttcacg tccgagtcca    120

catctaactg acaggtggcc tctaacagac aggtcccgca tgtcagactt gggggctgca    180

cgccttcccg gtacactgtg gtcctcttct cgcacctacc gcgtcgagga aataaccgaa    240

tataatatac gcggaactcc aaaggtaata ttcgtactaa tcctatattg ccgtggtatt    300

tgtacgtata aagcgtatac gtatacgtat tttattggga tcaactctca aagagcggag    360

ccggctggac gccaacttgt ttcccatcct tgtccttggt cgtcgccaat atatagccgc    420

cctcatcccg gccgatccct tcgtctcaat cccacaccac cacctcctcc ctcttcttcc    480

tcctttgggt ccttcccagc cgccgccggc catggcctcc ctcaccgacc tcgtcaacct    540

cagcctctcg gacaccaccg agaagatcat cgccgagtac atatggtacg ccgcgcgttt    600

ccctgttctt tatctgcacg caacgctctc tctttttgcc tcgctagtca gaaagaatcg    660

atcttgcttg gtgcccggtc gccttctcat ggcgtctccc catccggaac aggatttgga    720

gaggggtttt gggagaccgc ctcatgccgt gtcgcatctc ttgttttatt ttggtgatca    780

gtcaagcggg gaggttttat ttgttgattc ttcttcaagt aaaaatctgt tattttggct    840

cgtttatttg cccatgaata tctggcttca gtttcggata tgctcggaga gagctggaga    900

gatgcgcagt accettctga cttttgtttg tcctgctgcg ggaggatctc cccagcggca    960

gtctctggct ctctgctcac cgggtccctc accggccacc gcaccgctta tatggtgtta   1020

tgactgtatc actggcgacc gccagatgaa tctgttgtct agaagatcta atcgcatgtc   1080

ttacgcgtta attgattccc ctggtgccag tattattagt actttttaaa aaaaaaaaac   1140

aacagtattg ttagtactca aaagatgcaa gtttttgttg ttgttactac aaacgcgtct   1200

tggattgctc tgctccgagg aatatggtga gcagttgttc agtctgttag gcgatttgac   1260

cccatcttaa cgcatgcctt ttttttggtt gcaggatcgg tggatctggc atggatctca   1320

ggagcaaagc cagggtaaga taaaaagatt cccagcacta ggaggggacg gtatcccggg   1380

atactgtttg tggtggctcg tcactactca cttatcctat cacttatctc tgaagtcacc   1440

atccgctgag ctgttctttg gcttatatac aagagctctg ctcaccacta ccactgcaat   1500

tgattttttt ttctcttctg ttctatttcg taaaaattat actgatctcg ttgtggttgg   1560

tgctggtgca gaccctctcc ggcccggtga ccgatcccag caagctgccc aagtggaact   1620

acgacggctc cagcaccggc caggcccccg gcgaggacag tgaggtcatc ctgtagtaag   1680

tgtcatggca tgccaagctt tggatgcatt cttttgtttg tttgtttgtt ttactagcaa   1740

acgtggaacg atccttatct cttgggcatg tgccaccctg tagcccgcag gctatcttca   1800

aggacccatt ccggaggggc aacaacatcc ttgtaagttt tcacttttat catccaagtg   1860
```

gcaaccatac gtttccgtgt tatataatgc tacagttcat tggtccaact cagatcagtt 1920
catctttgtg aggaaaaaaa agtgtgtatt gtttcatcaa gtaaataaac taaaagttgt 1980
atgtactgtt taaataaatt agattttttt ttaaaatatg cctgatgtat aggttggact 2040
atcttgatgc agcactaaag gttcctgatg caatttctct actctgaatc tttgtccagt 2100
tatgcagaat tgcctgatcc aatttttcta ctctgaatct tgtccagtta tgcagtattg 2160
caaattgtat ataacatgat gacttggtgt tatgagcttt gatattcttt tttttgtagt 2220
taggtttgag tatccagtgt accaaaccat ggtttaggaa tccaattggt cgattcattt 2280
tcttgtctaa taataatagg gaccactctt aggcgttcaa tgaattcgtt tgacttgcag 2340
gtcatgtgcg attgctacac cccagctggc gagccaattc ccaccaacaa gaggcacaac 2400
gccgccaaga tcttcagcaa ccctgaggtc gccgctgagg agccctggta tgcaaatctc 2460
cccttgtata tttgtgatga aagccaaaac gatctgtctt tgtatgattg attgaccatg 2520
gttgtccttg caaatggtag gtacggtatt gagcaggagt acaccctcct tcagaaggac 2580
accaactggc cccttgggtg gcctcttggt ggcttccctg gccctcaggt acaacacacg 2640
atggcttcgc taatttgctt tgcttgctta agacatgctt catcgattcg gtcctacatt 2700
tgttgaagtg tcacctaaat gatgttcaac gtccatgttt agggtccgta ctactgtgga 2760
gttggtgcgg acaagtcatt cgggcgtgat atagttgatg cccactacaa ggcttgcatt 2820
tatgcaggca tcaacatcag tggcatcaac ggagaggtca tgccagggca ggtgagatac 2880
tactactaca ctaggcaact tcttttgtaa ccctcaagct accatgtttc tgaccatggc 2940
aaacattgtg gttggttcca gtgggaattc caagttggac cgtccgtcgg catttcttca 3000
ggcgatcagg tctgggttgc tcggtacatt cttgaggtat gacatcacat cttctcagct 3060
ctatatgtat atactatgtt gatcaaatat agcgccatct t 3101

<210> SEQ ID NO 77
<211> LENGTH: 5258
<212> TYPE: DNA
<213> ORGANISM: Sorghum halepense

<400> SEQUENCE: 77
aattgaatcc gccgagagcg accaatgctc ggtgctcgcc gtgctgctgc attccgtggt 60
gacgcgccgg ttgctttgct gaaggtctcg actgccgagt gggaggagag gggcggtggc 120
cggtccgtca gcgtcatccg ttggttcggg aatggcggcg caggcggtgg tgccggcgat 180
gcagtgccag gtcggagtga aggcggcggc gggcgctcgg gcgaggccgg cggcggcggg 240
cggcagggtg tggggcgtca ggagtaggac cggccgcggc ggcgcctcgc cggggttcaa 300
ggtcatggcc gtcagcacgg gcagcaccgg ggtggtgccg cgcctcgagc agctgctcaa 360
tatggacacc acgccctaca ccgacaagat catcgccgag tacatctggt acgtgcgtac 420
cgtagcgatt tgcctttttt tttacaagct aataaaatag cattggaacc actaaagacc 480
atcacttccg aagcttttgt gggtgctgat tcgtctctgc tttccagttc ctgctcccca 540
cttagataac aatgtgcacc ggatactctt gtgagcaaac ttacaaaata tatatattct 600
aaaatgagat cactcaacat tgtgtagggt cggaggatct ggaatcgaca tcagaagcaa 660
atcaagggtg agcattcaac gtcaccatcc caccatcgtc tgcatctcct ttattggaca 720
ctttggacag ttcccagtct ttagggaatg aatcaatgag cacagggccc ttttccaatt 780
tgcatatcgc ttttacttgg ctatattcaa aataaatctt aatgcctgtg tttcagacaa 840
tttcaaaacc ggtggaggat ccctcagaac taccgaaatg gaactatgat gggtcaagca 900

-continued

```
cagggcaagc cccgggagaa gacagtgaag tcattctata gtaagaggga aattacaata    960
tatgtgctct tttatatgca agcattttac tgttacattt ctcatgtttc tctttctgtt   1020
ttcagccccc aggctatctt caaggaccca tttcgaggtg gcaacaacat tttggtactt   1080
cccatgccaa ccgaatcaga ccttcgtata cacgttttta gctttttttgt gccatcccac   1140
ataaacttga ataaaaaagg gctaaaagaa tagcagttac tagttactag aatgctactg   1200
ccttttcacc tagtccttta gctgtaatgc gttatttgat tcattgtagt tgtggcatat   1260
tcctcttgga ttgaatggca cattgtcacc tgaatgcatt ggcaaacttg atgaacttta   1320
actagcatgt gcatgacagc acgctgataa atataaaatt tggcttctca ggttatctgt   1380
gatacctaca cgccacaggg cgaacccctt cctactaaca aacggcacag ggctgcgcaa   1440
atttttagtg acccaaaggt cgttgaacaa gtgccatggt aattatgact taatcacatg   1500
cgccatataa attataatgc aaatctcact attattttct cattgccttc acggaatgtt   1560
gaaagttgaa aacacttgtt gtgtcatttt ccttccaggt ttggcataga gcaagagtac   1620
actttgctcc agaaagatgt gaattggcct cttggttggc ctgttggagg ctaccctggt   1680
ccccaggtat tatgttaaat aagaagaaaa aaattggttt gtcatgccat atgatgttgc   1740
tctgttggaa tacatgtctt gtattggctt aatgagcaca attttgaaaa gtgtattttt   1800
gtgtggcaaa ctatggcagg gtccctacta ctgtgctgta ggagcagaca aatcatttgg   1860
ccgtgacata tcagatgctc actacaaggc ttgcctttat gctggaatta acattagtgg   1920
aacaaacggg gaggtcatgc ctggtcaggt atggttatga acttatgata cttctataca   1980
tttgtatttg tattttcttt ttctgaatca gtgcggtata ccaccaccat tccgcccctc   2040
atttctcttc ttgcaaagga aaatataaaa ttgtttatca ggcagaagca gaacttcata   2100
aaccttatct gtgcagtggg agtaccaagt tggacctagt gttggcattg aagcaggaga   2160
tcacatatgg atttcaagat acattctcga ggtacctcaa acaataatta aggatttccc   2220
ccatatcgtg tcattttatt tctttttctt cttcataatt attagagcat acagtatttt   2280
acaagttcag caccttattg tagtaaggca tttatgatta cacacagcaa catatcacga   2340
ttgaattagg catttgagaa taattttctc ctggtgaaaa attatatttc attttatctg   2400
tattgttcaa aatatgaggc ctgaagccca tgatttcaac ctttagttaa taccaatttt   2460
tacatcacca taaacacttc taaatattgt cctactcacc tttatcagag aatcacagag   2520
caagctgggg ttgtccttac ccttgatcca aaaccaattc aggtatgtcc atcagtaagt   2580
tgtttcgaat cattacaatg taataggatt aaagtaatct taacatatag caatactgta   2640
ttggtgacag ggtgactgga atggagctgg ctgccacaca aattacaggt tacagtcttt   2700
tatgataatg cttcatttcc ttccgttgtt tgttcatggt aattttgtca ttaacggaca   2760
gacaccagaa tgcctatagc agtataattt accatatgct gactgctgag tgttaaagga   2820
aaaaagtttg ttctaatgtt ctagaaaggg agtagaagtg aagtattagt atatcattaa   2880
taaattgttg tctagtgtga ttggatccag atgattgtcc attcgcttct attaattact   2940
aactttcgtt atttaatatt tttctcaaca catttgacac actgggactg acagacagtc   3000
tgaattcctt gcgaatgtag cacaaagacc atgcgtgaag atggaggatt tgaagatatc   3060
aagagagcaa tcctgaatct ttctctgcgc catgatttgc atattagtgc atacggagaa   3120
ggaaatgaaa gaagattgac agggaagcat gagaccgcta gcatcgagac cttctcatgg   3180
gtatagatgg atcacctttc attatttttt gcgagtctgc tgaatattgt ttatttgtaa   3240
```

gttgtaccaa tgaaacattt tcatttatca gggtgtggca aaccgtggct gctctgttcg 3300
tgtggggcga gataccgagg caaaagggaa aggtacatgt tcttgcagtg ttccctgaaa 3360
ttgcttacag ttggaactca caaaatacac cccacgccct agtaaataaa taaataccac 3420
agtgacatat aatttccccc taacttcgca tcatcttttt gagttggtgt agcttctaac 3480
tggggtcgta cgattgcact ctatatgaat gaccctataa tgtgcttggt ttccagttcc 3540
ttggggatga ttttgagtaa atctgtccag atacaccctc attcgctcag ggcatcagta 3600
attttctatc ttgcatcttg tcagatgatt tttgacataa ctctaactcc ctactcttaa 3660
agcaagtgct gcactgctgc aaaatccatg catttgaatt taataacttg aattacaaat 3720
ccagatccac ttaccctttt caccttgttg tctccaacag gttacctaga agaccgtcgc 3780
ccggcatcaa acatggaccc atacattgtg acggggctac tggctgaaac aacaattctc 3840
tggcaaccaa cccttgaagc agaggttctt gctgccaaga agctggcgct gaaggtatga 3900
agcagttgaa ggatgtctca ggcacgaata aacaggccca caacaaaatt gattctgctg 3960
ttcactggcc ttggtcccgc aactctgctc ggcgccactc tgtacaaatt aattaccatt 4020
ctggaccaca ttgtctttga ttcatcggtt acggttgtta cattttgctt ggacaccatc 4080
acaccatgtt tggacttggc ctgtacttct tgtagcaatt tttgtgtgaa gtgaagttcg 4140
aattgggctt cactctcggt cagggccagg agcccaggat tcaacattgc aaccggaaaa 4200
aagttcaatt tatctctccc aaccttttga cctctattaa ctttttaaag aaaaattaaa 4260
aaatatatct aaaaaatgta aaaataaatt taaaatcatc caaatatttc tacataaaaa 4320
attaaatatc ataaaatcta gtttaatcat catcatcatc acactataaa agagcgagtt 4380
tttttgagag gcttctccct ctataataac cgtttagtct agatggcgtg ctatatgagc 4440
ccagagatca atggtgatct aacatgtaaa atgtaagact cctcttcaac caagattcct 4500
tctagacctc gaaaaaggaa aataataaaa atctaaacac acgtgtaaga cttcaatgcc 4560
catatgagcc aagttatcat gttcgaggac tgatgccaat gcaagccaaa aaggactttg 4620
actctcacac gatccaaaat actaatgcaa aatgtattta tacaagccaa aaatattaat 4680
gttaaacatg tttggactcg ataattgctc agtacaagta tatgtgtggc catatctttg 4740
agtccaccca tatataaaga tattctattt ctatatttaa ataatgtcta tgatatatac 4800
gaattgatat atcgagaatt caattaatat tctcattgta tataaaatat ttttcacaaa 4860
catgtgtgta ttgcgcgagc atatttgcta gtcttaggga attcaaagag aaattatttt 4920
gtcttagaaa aatatgatag cagttttagg tttttaccac cgtagtatat ctacacgagc 4980
ggagagctcc ctggagccag tacaataagt taaaaaactg ggagaggcca tgctcatact 5040
tgggtctagg agacaagcta gggttaaaat ttgagagcct tgtagcttat aatcgccaaa 5100
aatgcatttc atggaccttt tacttaatta tgatgggagg tgggagaaaa ttaggaaaag 5160
agagagaatc accgggagag agaggatgag gattcggtag attttttat gttggtctac 5220 ttatagaaat gttcactata gcatctccag tgttaggc 5258

<210> SEQ ID NO 78
<211> LENGTH: 1431
<212> TYPE: DNA
<213> ORGANISM: Sorghum halepense

<400> SEQUENCE: 78
ttgatcaaat atagcgccat cttaaccaag catgatttgc accacttatg ttatgtgcta 60
ataacaatcg gtgctccttt ccttcacaga ggatcaccga gatcgccggt gtggtgttga 120

```
cattcgaccc aaaacccatc cctggtgact ggaacggtgc cggcgcacac accaactaca    180
gcaccaagtc catgaggaac gagggcgggt acgaggtgat caaggccgcc atcgagaagc    240
tgaagctgcg gcacaaggag cacatcgcgg cctacggcga gggcaacgag cgccgcctca    300
ccggcaggca cgagaccgcc gacatcaaca ccttcagctg ggtacgcccc ccattccttc    360
ctactgtgct gctgctgctg catcgtggag aatcggcgaa cccgtgtgcc aactgttgtc    420
tgttgtctgc ggtgcaggga gtggcaaacc gtggcgcgtc agtgcgcgtg ggccgggaga    480
cggagcagaa cggcaagggc tacttcgagg accgccggcc ggcgtccaac atggacccat    540
acgtggtgac ctccatgatt gccgacacca ccatcctctg gaagccctga agcggaaggt    600
ttcctccatc cagctcgctg tctcgtgtcg gtttgttccg cggcagtgtc ccggccgttg    660
cattgcaggg tcccgtccag cgatttgcgc aacaattgtt ccttcccgtt ccgtttgctt    720
atactactct actactgcaa tttagctaga atttgggtca ggtcgtggtg tgccaaaaca    780
aaacacataa aaactttgac gcttcccact tccattccat gccgtccgtc cgcttgggtg    840
atctcctcct accttcttct tcttcttgtg taatcctcca ataatggccg taccacactt    900
gtggtacctt tcagtacttg ctgcatcctc atgcattgca ttgtataagt ggtcgctttc    960
ctacgcgctc caatgtctgt ggctttcctg atgcgataag ggagggaatg gttagtgggt   1020
ggcagcatta ttgtcatcgt cgcccatcgg ccgatcggat ggcctctttt aggtcagatt   1080
ctgaacgaac gatttgtctt ttcctggaaa attcagcaac accggtcgtt ttacagtaat   1140
tttcgctcca ccagcttatc actgttgatc tcggctcctt gcccatcgcc catcggcgca   1200
tgggatgaat agattagtct gttttggtca gattctgaac ggacgatttg tcttttcccc   1260
cgggaaaatt gaaaattcag caccaccgag gtgtttgatt ttcggtggat gaacctatca   1320
ctcttgatcg gttgaggtgt cactcgacac agcttaatgc ttggctgcta caagcgaatc   1380
catcaaacat aacgaggccc taaaccatgg gactgtttgg ttctggctcc t            1431
```

<210> SEQ ID NO 79
<211> LENGTH: 266
<212> TYPE: DNA
<213> ORGANISM: Sorghum halepense

<400> SEQUENCE: 79

```
ctcgccgggg ttcaaggtca tggccatcag cacgggcagc accggggtgg tgccgcgcct     60
cgagcagctg ctcaatatgg acaccacgcc ctacaccgac aagatcatcg ccgagtacat    120
ctggtacgtg cgtaccgtag cgatttgcct ttttttata caagctaata aaatagcatt    180
ggaaccacta aagaccatca cttctgaagc ttttgtgggt gctgattcgt ctctgctttc    240
cagttcctgc tccccactta gataac                                         266
```

<210> SEQ ID NO 80
<211> LENGTH: 1143
<212> TYPE: DNA
<213> ORGANISM: Sorghum halepense

<400> SEQUENCE: 80

```
ggatgttgtc ggattcactt caatgtatgt gttgtggtgt ggattgaagt ggaatttagt     60
tcaaatttca atccaatcca cctcaataca tgtggattga tgtgaatccg actaaacaag    120
gcctaagatg cgatgtgaat ggtttctgat gctggtgtct ctgcatcagg gcgtggcgaa    180
ccgcggcgcg tccatccgcg tgggccgcga cacggagagg gagggcaagg gatacttcga    240
```

```
ggaccgcagg ccggcatcca acatggaccc ctacgtcgtc accggcatga tcgccgagac    300

caccatcctg tggaacggaa actgataaac tcacggttgt tcctcttctg cacaacgcta    360

ctacgcctgc aatgcgcgca tccgctctga tgtcatgtca gtttggtttt gcgatttcgg    420

ttccccgtcg tggggtgtcc taaaattttt tacttcggtc tccggtgtac tgcttggaaa    480

gtctgaataa cggctgcaat ggattttgct ttcgtcatag gggtacctag ctacctttag    540

ctgttctttc ctgtttattg gatatgtata atgtaatgta atactactac tacgtgattt    600

tatatgaaaa gaaccattgt cgtcttgttc gcgatcacaa gtacggtggt tccattccaa    660

ttccatgctg tccacccttt ccattgtcag actcagacgc agcaccactg tcacactgtg    720

ggattttgaa gtagaagcac gacacttatc ctggggccaa caaattaaat ctgagatatc    780

ccgtctctgt cttgtgtgag ttgtgaccac cgaggcaccc aaggaatacg atacgatgcc    840

gtgcggctct ttaatcttca gccccttctt tttaccaatt gtcgatgaaa cgcacacctg    900

ctgccaatgt ggcgcctttt acctttacta catgaaagtg gttgaaagga aacggagggt    960

cttccggttc cgcatctggg actagcaaat ccaggtctta tccagggcga cgctggcgaa   1020

gaaatagcag atcgtgcagc aatatattgt gcagcaccga gcagcaacca gacagcagct   1080

attttccttg gaagcaacca gacagtatac gatagctcga ctttgtctcg gtctcctggt   1140

att                                                                 1143
```

<210> SEQ ID NO 81
<211> LENGTH: 346
<212> TYPE: DNA
<213> ORGANISM: Sorghum halepense

<400> SEQUENCE: 81

```
ttgatcaaat atagcgccat cttaaccaag catgatttgc accacttatg ttatgtggta     60

ataacaatcg gtgctccttt ccttcacaga ggatcaccga gatcgccggt gtggtgttga    120

cattcgaccc aaagcccatc cctggtgact ggaacggtgc cggcgcacac accaactaca    180

gcaccaagtc catgaggaac gagggcgggt acgaggtgat caagaccgcc atcgagaagc    240

tgaagctgcg gcacaaggag cacatcgcgg cctacggcga gggcaacgag cgccgcctca    300

ccggcaggca cgagaccgcc gacatcaaca ccttcagctg ggtacg                   346
```

<210> SEQ ID NO 82
<211> LENGTH: 246
<212> TYPE: DNA
<213> ORGANISM: Sorghum halepense

<400> SEQUENCE: 82

```
gttgtctcca acaggttacc tagaagaccg tcgcccggca tcaaacatgg acccatacat     60

tgtgacgggg ctactggctg aaacaacaat tctctggcaa ccaacccttg aagcggaggt    120

tcttgccgcc aagaagctgg cgctgaaggt atgaagcagt tgaaggatgt ttcaggcacg    180

aataaacagg cccacaacaa aattgattct gctgttcact ggccttggtc ccgcgactct    240

gctcgg                                                               246
```

<210> SEQ ID NO 83
<211> LENGTH: 2468
<212> TYPE: DNA
<213> ORGANISM: Sorghum halepense

<400> SEQUENCE: 83

```
agttcctgct ccccacttag ataacaatgt gcaccggata ctcttgtgag caaacttaca     60
```

```
aaatatatat attctaaaat gagatcactc aacattgtgt agggtcggag gatctggaat    120
cgacatcaga agcaaatcaa gggtgagcat tcaacgtcac catcccacca tcgtctgcat    180
ctcctttatt ggacactttg gacagttccc agtctttagg gaatgaatca atgagcacag    240
ggccctttc caatttgcat atcgctttta cttggctata ttcaaaataa atcttaatgc    300
ctgtgtttca gacaatttca aaaccggtgg aggatccctc agaactaccg aaatggaact    360
atgatgggtc aagcacaggg caagccccgg gagaagacag tgaagtcatt ctatagtaag    420
agggaaatta caatatatgt gctcttttat atgcaagcac tttactgtta catttgtgat    480
gtttctcttt ctgttttcag cccccaggct atcttcaagg acccattccg aggtggcaac    540
aacattttgg tacttaccat gccaaccgaa tcagaccttc atatacacgt ttttagcttt    600
tttgtgccat cccgcataaa cttgaataaa agggctaaaa gaatagcagt tactagttac    660
tagaatgcta ctgccttttc aactagtcct ttagctgtaa tgtgttattt gattctgttg    720
tagttgtggc atattcctct tggattgaat gacacattgt caccttaatg cattggcaaa    780
cttgatgaac tttaactagc atgtgcatga cagcacgctg ataaatataa aatttggctt    840
ctcaggttat ctgtgatacc tacacgccac agggcgaacc ccttcctact aacaaacggc    900
acagggcttc gcaaattttt agtgacccaa aggtcgttga acaagtgcca tggtaattat    960
gagttaatca catgcgccat ataaattata atgcaaatct cactattatt ttctcattgc   1020
cttcacggaa tgttgaaagt tgaaaacact tgttgtgtca ttttccttcc aggtttggca   1080
tagagcaaga gtacactttg ctccagaaag atgtgaattg gcctcttggt tggcctgttg   1140
gaggctaccc tggtccccag gtattatgtt aaataagaag aaaaaaattg gtttgtcatg   1200
ccatatgatg ttgctttgtt ggaatacatg tcttgtattg gcttaatgag cacaattttg   1260
aaaaatgtat ttttgtgtgg caaactatgg cagggtccct actactgtgc tgtaggagca   1320
gacaaatcat ttggccgtga catatcagat gctcactaca aggcttgcct ttatgctgga   1380
attaacatta gtggaacaaa cggggaggtc atgcctggtc aggtatggtt atgaacttat   1440
gatacttcta tacattagta tttgtatttt ctttttctga atcagtgcgg tataccacca   1500
ccattccgcc cctcatttct cttcttgcaa aggaaaatat aaaattgttt atcaggcaga   1560
agcagaactt cataaacctt atctgtgcag tgggagtacc aagttggacc tagtgttggc   1620
attgaagcag gagatcacat atggatttca agatacattc tcgaggtacc tcaaacaata   1680
attaaggatt tcccccatat cgtgtcattt tatttctttt tcttcttcat aattattaga   1740
gcatacagta ttttacaagt tcagcacctt attgtagtaa ggcatttatg attacacaca   1800
gcaacatatc acgactgaat taggcatttg agaataattt tctcctggtg aaaaattata   1860
tttcatttta tatgtattgt tcaaaatatg aggcctgaag cccatgattt caacctttag   1920
ttaataccaa tttttacatc accataaaca cttctaaata ttgtcctact cacctttatc   1980
agagaatcac agagcaagct ggggttgtcc ttacccttga tccaaaacca attcaggtat   2040
gtccaccagt aagttggttc gaatcattat agtgtaatag gattaaagta atcttaacat   2100
atagcaatac tgtattggtg acagggtgac tggaacggag ctggctgcca cacaaattac   2160
aggttacagt cttttatgat aatgcttcat ttccttccgt tgtttgttca tggtaatttt   2220
gtcattaacg gacagacacc agaatgccta tagcagtata atttaccata tgctgactgc   2280
tgagtgttaa aggaaaaaag tttgttctaa tgttctagaa agggagtaga agtgaagtat   2340
tagtatatca ttaataaatt gttgtctagt gtgattggat ccagatgatt gtccattcgc   2400
```

```
ttctattaat tactaacttt cgttatttaa tatttttctc aacacatttg acacactggg   2460

actgacag                                                            2468


<210> SEQ ID NO 84
<211> LENGTH: 1483
<212> TYPE: DNA
<213> ORGANISM: Sorghum halepense

<400> SEQUENCE: 84

atactgatct cgttgtggtt ggtgctggtg cagaccctct ccggcccggt gaccgatccc     60

agcaagctgc ccaagtggaa ctacgacggc tccagcaccg gccaggcccc cggcgaggac    120

agtgaggtca tcctgtagta agtgtcatga catgccaagc tttggatgca ttcttttgtt    180

tgtttgtttg ttttactagc aaacatggaa cgatccttat ctctttggca tgtgccaccc    240

tgtagcccgc aggctatctt caaggaccca ttccggaggg gcaacaacat ccttgtaagt    300

tttcactttt atcatccaag tggcaacgat acgtttccgt gttatataat gctacagttc    360

attggtccaa ctcagatcag ttcatctttg tgaggaaaaa aaagtgtgta ttgtttcatc    420

aagtaaataa actaaaagtt gtatgtactg tttaaataaa ttagattttt ttaaaaatat    480

gcctgatgta taggttggac tatcttgatg cagcactaaa ggttcctgat gcaatttctc    540

tactctgaat ctttgtccag ttatgcagaa ttgcctgatc catttttttct actctgaatc    600

ttgtccagtt atgcagtatt gcaaattgta tataacatga tgacttggtg ttatgagctt    660

tgatattctt ttttttgtag ttaggtttga gtatccagtg taccaaacca tggtttagga    720

atccaattgg tcgattcatt ttcttgtcta ataataatag ggaccactct taggcgttca    780

atgaattcgt ttgacttgca ggtcatgtgc gattgctaca ccccagctgg cgagccaatt    840

cccaccaaca agaggcacaa cgccgccaag atcttcagca accctgaggt cgccgctgag    900

gagccctggt atgcaaatct ccccttgtat atttgtgatg aaagccaaaa cgatctgtct    960

ttgtatgatt gattgaccat ggttgtcctt gcaaatggta ggtacggtat tgagcaggag   1020

tacaccctcc ttcagaagga caccaactgg ccccttgggt ggcctcttgg tggcttccct   1080

ggccctcagg tacaacacac gatggcttcg ctaatttgct tgcttgctta agacatgctt   1140

catcgattcg gtcctacatt tgttgaagtg tcacctaaat gatgttcaac gtccatgttt   1200

agggtccgta ctactgtgga gttggtgcgg acaagtcatt cgggcgtgat atagttgatg   1260

cccactacaa ggcttgcatt tatgcaggca tcaacatcag tggcatcaac ggagaggtca   1320

tgccagggca ggtgagatac tactactaca ctaggcaact tcttttgtaa ccctcaagct   1380

accatgtttc tgaccatggc aaacattgtg gttggttcca gtgggaattc caagttggac   1440

cgtccgtcgg catttcttca ggcgatcagg tctgggttgc tcg                     1483


<210> SEQ ID NO 85
<211> LENGTH: 2314
<212> TYPE: DNA
<213> ORGANISM: Sorghum halepense
<220> FEATURE:
<221> NAME/KEY: unsure
<222> LOCATION: (1)..(2314)
<223> OTHER INFORMATION: unsure at all n locations

<400> SEQUENCE: 85

tggaggatcc ctcagaacta ccgaaatgga actatgatgg gtcaagcaca gggcaagccc     60

cgggagaaga cagtgaagtc attctatagt aagagggaaa ttacaatata tgtgctcttt    120

tatatgcaag cactttactg ttacatttgt gatgtttctc tttctgtttt cagcccccag    180
```

gctatctnna tcttcaagga cccattccga ggtggcaaca acattttggt acttaccatg 240
ccaaccgaat cagaccttca tatacacgtt tttagctttt ttgtgccatc ccgcataaac 300
ttgaataaaa gggctaaaag aatagcagtt actagttact agaatgctac tgccttttca 360
actagtcctt tagctgtaat gtgttatttg attctattgt agttgtggca tattcctctt 420
ggattgaatg gcacattgtc acctgacggc aaacttgatg aactttaact agcatgtgca 480
tgacagcacg ctgataaata taaaatttgg cttctcaggt tatctgtgat acctacacgc 540
cacagggcga accccttcct actaacaaac ggcacagggc tgcgcaaatt tttagtgacc 600
caaaggtcgt tgaacaagtg ccatggtaat tatgacttaa tcacatgcgc catataaatt 660
ataatgcaaa tctcactatt attttctcat tgccttcacg gaatgttgaa agttgaaaac 720
acttgttgtg tcattttcct tccaggtttg gcatagagca agagtacact ttgctccaga 780
aagatgtgaa ttggcctctt ggttggcctg ttggaggcta ccctggtccc caggtattat 840
gttaaataag aagaaaaaaa ttggtttgtc atgccatatg atgttgctct gttggaatac 900
atgtcttgta ttggcttaat gagcacaatt ttgaaaagtg tatttttgtg tggcaaacta 960
tggcagggtc cctactactg tgctgtagga gcagacaaat catttggccg tgacatatca 1020
gatgctcact acaaggcttg cctttatgct ggaattaaca ttagtggaac aaacggggag 1080
gtcatgcctg gtcaggtatg gttatgaact tatgatactt ctatacattt gtatttgtat 1140
tttctttttc tgaatcagtg cggtatacca ccaccattcc gcccctcatt tctcttcttg 1200
caaaggaaaa tataaaattg tttatcaggc agaagcagaa cttcataaac cttatctgtg 1260
cagtgggagt accaagttgg acctagtgtt ggcattgaag caggagatca catatggatt 1320
tcaagataca ttctcgaggt acctcaaaca ataattaagg atttccccca tatcgtgtca 1380
ttttatttct ttttcttctt cataattatt agagcataca gtattttaca agttcagcac 1440
cttattgtag taaggcattt atgattacac acagcaacat atcacgattg aattaggcat 1500
ttgagaataa ttttctcctg gtgaaaaatt atatttcatt ttatctgtat tgttcaaaat 1560
atgaggcctg aagcccatga tttcaacctt tagttaatac caatttttac nnnnnnnnnn 1620
nnnnnnnnnn nnnnnnnnnn nnnnnnnnnn nnnnnnnnnn nnnnnnnnnn ncagtaagtt 1680
gtttcgaatc attacaatgt aataggatta aagtaatctt aacatatagc aatactgtat 1740
tggtgacagg gtgactggaa tggagctggc tgccacacaa attacaggtt acagtctttt 1800
atgataatgc ttcatttcct tccgttgttt gttcatggta attttgtcat taacggacag 1860
acaccagaat gcctatagca gtataattta ccatatgctg actgctgagt gttaaaggaa 1920
aaaagtttgt tctaatgttc tagaaaggga gtagaagtga agtattagta tatcattaat 1980
aaattgttgt ctagtgtgat tggatccaga tgattgtcca ttcgcttcta ttaattacta 2040
actttcgtta tttaatattt ttctcaacac atttgacaca ctgggactga cagacagtct 2100
gaattccttg cgaatgtagc acaaagacca tgcgtgaaga tggaggattt gaagatatca 2160
agagagcaat cctgaatctt tctctgcgcc atgatttgca tattagtgca tacggagaag 2220
gaaatgaaag aagattgaca gggaagcatg agaccgctag catcgagacc ttctcatggg 2280
tatagatgga tcacctttca ttattttttg cgag 2314

<210> SEQ ID NO 86
<211> LENGTH: 1000
<212> TYPE: DNA
<213> ORGANISM: Sorghum halepense
<220> FEATURE:

<221> NAME/KEY: unsure
<222> LOCATION: (1)..(1000)
<223> OTHER INFORMATION: unsure at all n locations

<400> SEQUENCE: 86
gttatgactg tatcactggc caccgccaga tgaatctgtt gtctagaaga tctaatcgca 60
tgtcttacgc gttaattgat tcccctggtg ccagtattat tagtactttt ttttaaaaaa 120
aacaacagta tttgttagta ctcaaaagat gcaagttttt gttgttgtta ctacaaacac 180
gtcttggatt gctctgctcc gaggaatatg gcgagcagtt gttcagtctg ttaggcgatt 240
tgaccccatc ttaacgcatg cctttttttt tggttgcagg atcnnnnnnn nnnnnnnnnn 300
nnnnnnnnnn nnnnnnnnnn nnnnnnnnnn nnnnnnnnnn nnnnnnnnnn nnnnnctgca 360
attgattttt tttctcttct gttttatttc gtaaaaatta tactgatctc gttgtggttg 420
gtgctggtgc agaccctctc cggcccggtg accgatccca gcaagctgcc caagtggaac 480
tacgacggct ccagcaccgg ccaggccccc ggcgaggaca gtgaggtcat cctgtagtaa 540
gtgtcatgac atgccaagct ttggatgcat tcttttgttt gtttgtttgt tttactagca 600
aacatggaac gatccttatc tctttggcat gtgccaccct gtagcccgca ggctatcttc 660
aaggacccat tccggagggg caacaacatc cttgtaagtt ttcactttta tcatccaagt 720
ggcaaccata cgtttccgtg ttatataatg ctacagttca ttggtccaac tcagatcagt 780
tcatctttgt gaggaaaaaa agtgtgtatt gtttcatcaa gtaaataaac taaaagttgt 840
atgtactgtt taaataaatt agattttttt aaaaatatgc ctgatgtata ggttggacta 900
tcttgatgca gcactaaagg ttcctgatgc aatttctcta ctctgaatct ttgtccagtt 960
atgcagaatt gcctgatcca ttttttctac tctgaatctt 1000

<210> SEQ ID NO 87
<211> LENGTH: 5308
<212> TYPE: DNA
<213> ORGANISM: Sorghum halepense

<400> SEQUENCE: 87
agtgacatat aatttccccc taacttcgca tcatcttttt gagttggtgt agcttctaac 60
tggggtcgta cgattgcact ctatatgaat ggccctataa tgtgcttggt ttcccgttcc 120
ttggggatga ttttgagtaa atctgtccag atacaccctc attcgctcat ggcatcagta 180
attttctatt ttgcatcttg tcagatgatt tttgacataa cgcaactctc tactcttaaa 240
gcaagtgctg cactgctgca aaatccatgc atttgaattt agtaacttga attacaaatc 300
cagagacact taccctttc accttgttgt ctccaacagg ttacctagaa gaccgtcgcc 360
cggcatcaaa catggaccca tacattgtga cggggctact ggctgaaaca acaattctct 420
ggcaaccaac ccttgaagcg gaggttcttg ccgccaagaa gctggcgctg aaggtatgaa 480
gcagttgaag gatgtttcag gcacgaataa acaggcccac aacaaaattg attctgctgt 540
tcactggcct tggtcccgcg actctgctcg gcgccactct gtacaaaatt aattaccatt 600
ctggaccaca ttgtctttga ttcatcggtt acggttgtta cattttgctt ggacaccatc 660
acaccatgtt tggacttggc ctgtacttct tgtagcaatt tttgtgggaa gtgaagttcg 720
aattgggctt cactctcggt cagggccagg agcccaggat tcaacattgc aaccggaaaa 780
aagtttaatt tatctctccc agccttttga tctctattaa ctttttaaag aaaaaattaa 840
aaatatatct aaaaattata aaaataaatt taaaatcatc caaatatttc tacataaaaa 900
ataatgcaaa atatcataaa atctagttta atcatcatca tcatcacact ataaaagaat 960

-continued

```
gagttttttt gagaggcttc tccctatgta ataaccgttt aatctagaca ccgtgctata   1020
tgagccctct atcaatggtg atcaaaatgt tagactcctc ttcaaccaag attccttcta   1080
gacctcaaaa aatgaaaata ataaaaattt aaacacaagt gagatgtaag acttcaatgc   1140
ccatatgagc caagttatca tgttcgagga ctccgacgtg aatgcaagcc aaaaaggact   1200
ttgactctca cgatccaaaa tactaatgca aaatgtattt atacaagcca aaaatattaa   1260
tgttaaacat atttgaactt gatttaaaaa atattaatgt gtaacatgtt tggactcgat   1320
aattgctcag taaagatatt ctatttctat atttaaataa atgtctatgg tatatacgaa   1380
ctgatatatc gagcattcaa ttaatattct cattgtatat gaaatatttt tcgcaaacat   1440
gtgtgtgttg cgcaagcata tttgctagtc ttaggaaatt caaagagaaa ttattttgtc   1500
ttagaaaaat atgatactag tttcaggttt ttaccaccgt agtatatcta cacgagcgga   1560
gagcttgccg gagccagtac aataagttaa aaactgggag aggccatgct cgtacctagg   1620
tcgaggagat aagctagggt taaaatttga tagccttgta gcttataatc gccaaaaata   1680
catttcgtgg accttttact taattatgat gggaggtggg agaaaattag gataagagag   1740
aaaatcacag ggagagagat gaggatgagg attgggtaga tttttttttt tttatgttgg   1800
tctacttata gaaatgttca ctatagcatc tccagtgtta ggcacaagcg aaccggaaaa   1860
agcaacattc gagcatttga gcgctgagtg tcagaacgaa aatcataatt tgcagatggg   1920
ttgaaccaag ggaaggaaaa agagaaccgg gaacaatgga gcattcggac gctcggtgtc   1980
aaaacaaaaa tcatagtttg cagatgagtc aaaccgaggg ataaaaaatt gtttgttgat   2040
gcatcgcctc tcatcactct cctactctca agagcgccac tcagataaag tttttttttt   2100
aattccattc aggtgcatca gtcgatgtgc acattagagg caacgagctg tgcttttgtt   2160
cgattgtact tgtacggttc aacatagcgt tggagatatt ctcatagacg acagtttctt   2220
attatgatgt cttgtactct gtggtttcta cattcagact gcccttgtaa actactattc   2280
gtgtatcaat gccgtgccag ccgctcagcc cgcgcggcac agcggctgcc ggtgcaagaa   2340
actgcagcat cacacggcag aggacagggt aattaaccca acaatgcctc ccacagccac   2400
ggctggcatg tcggcagcac gccaccgata tagcaacctt tttaacggtg ctttttttggg   2460
ccacttcaac gacgatttga cgtacgaccg gctgccattt cgtgtgcgtg gatcagcata   2520
gcgccatagc acattagcac ctatcaacga gagaagcaaa tcatgcaagg gcaggggcac   2580
agagctagaa agcaagagag caagagcaac agaagcacta tatatatttt acaaagacgg   2640
caggggtgct tgtacaatac tacaatccag cgatgaaaac acacgactaa caacataatt   2700
gactacacaa ggatgaagga ttaaggacag tgtcctatgg tttggtgggg tgcctgtgct   2760
tgggcttcgc tgtcggcgga gagccagcat gcatggccac gccgctgtag tccgcgctgt   2820
agatcagccc tgcctccgcg tcctcgccct gatccgccgt ccaacccgcc ttggcctcct   2880
cctcctcctc cttgggcttc ttcacctcca tagccacttc ctgcaggcca tggacggata   2940
ctgtgtgtca agttctctgt ctgcacattg ctgaagatgt taactgaacc ccaaaaacaa   3000
tgcatcctat atgaagactg aaaacaggca gacaacggct ggattcagac ttccaggcac   3060
tcggtttttc tttctttgca gataacaaaa tgggacttcg atcaacaggt tcttagtgat   3120
tgatttatga actatgtatg gggtaagaac tgacctcaga cttcaacagg tgcttgctct   3180
gatgctggta attgtaccct gatgactggc cgagttctct gcctttgcga cctagaacca   3240
gcgccggatg cctgccgagg gaagacggag gagaggatga agaagcatct gcagctgcaa   3300
```

gagtggctag aagaaggatt gaaacaagta ctacacagga tgccttcatc atgctgctgt 3360
attgggctat tgccattgtt gtcgatgttg gcaacacgag aagagcaaag caggctcctc 3420
tctccgaggc tctcttgggg tattatatac aaaaataatt tgggacggct gcaggacccc 3480
aaatgcacga cggtgtctag agtttgacac atttgcagat tagacctgta tttatgaaaa 3540
gttagatgat tagtatgatt cagattagta ccatctataa gtaccacttt gcaacacatg 3600
gagaaaccag gggcagtttt agcataatga gccttagttt gtggaccatt acgtcacatg 3660
tgagagtgaa taagcaattg cgttaggagg aataggagtg tacaattatt aggtacctag 3720
ggaggggcac gggcaacccc gaagtttggc gatttgctga atgccttttt gaatggcttt 3780
tctttgtttc tttttttctc tacgggctct cgtgagaata catagatccc tactactaaa 3840
tctgccaaac taaagaggac cccatgaccc agacaggcaa catactgcgc agcacacaca 3900
catgatgctg ctccatcggt cgactgaact gatcaatgtt gtctctcgtc tgcactaccg 3960
tttaccggcc tgatgggatg ggcaatgtcc tcgcagtgac actgacaccc catgcatcag 4020
ggttctttca tgctcatggt ctgggtggat gcatcatgca tcatgcctgc agtgaaattc 4080
cttgtgttgt gttgtgtgta tgctgcgtgc acctcaatat accaaggttg taggagacct 4140
atctatgcca atagaagaga gagatagtga ctcttgacag aggatgaatg ttcagataga 4200
aaaagcaatg gtcatcaaac tgaagtttga gctaatttgc aggaccaggc tgtgtaaaaa 4260
aatttgaaat gaatttagaa tcgattagat ttaaaaatta tttcgaaaaa cacttttgca 4320
gaatctcaac atctcctggc ccctcttggg cctcaccgtg acccccatgc ctcagggttc 4380
tttcacgttc atggctcatg ttgtgggtgg atgcgtcatg ccttcagtat ttagtgtatt 4440
accatatgct gcatgcatct caatatatgt atcaagactg tagttatagc ctcgtaggag 4500
accctatcta tgccaaacag aaaagagatc cagtgactcg ttgcaaagag ataaatgttg 4560
agaccaacga agcaatggcc atcaagtctg aagtttgagc cgatttgcag gacaaggctg 4620
ataataacca accactaacc actctgattt atttggtccg tgtctaacgt tgggaaggca 4680
agctccaaat gcgtatcttt ctgtgggggg cttgtgctgc agattcgttg tacacttggc 4740
acttggcagc atgtggtttc aggcatgttc ttgtattctg aaagctgaga cacctcatta 4800
attaatagag tatttggtta ttattatagt tcctgattag agccgtctgg tgcgagtgtc 4860
tgccagaatg gggggctcga gacaacgagg tcaagctcag agaggtttct tttatcagac 4920
cttgtcctct ttgtctcttg ctaataagct gttggtcacg gaaacgtcaa gttttatata 4980
tgggctcggt gtatatagta gtactaatat ggaagtgtgt accgacatgc atgcggccta 5040
aaataacatg ccaccagcag cggatagcat cgtcgtctct tgcattgcga gtcagtctgt 5100
accagtgcca gttcttttcc ccgtttccgc tgcatttgct cttattagtt gtagttgggt 5160
tcacaaatca caacagaaat cagagtgatc atctgatcac aatgtttgtc aacagaaaac 5220
gtactgtgtg ccaactgcca agtgctatat ataatcgtat atagaaccaa tgatgcacgc 5280
ctaattttgg gggaaattat atgtcact 5308

<210> SEQ ID NO 88
<211> LENGTH: 3346
<212> TYPE: DNA
<213> ORGANISM: Sorghum halepense

<400> SEQUENCE: 88
gtctttgtat gattgattga ccatggttgt ccttgcaaat ggtaggtacg gtattgagca 60
ggagtacacc ctccttcaga aggacaccaa ctggcccctt gggtggcctc ttggtggctt 120

-continued

```
ccctggccct caggtacaac acacgatggc ttcgctaatt tgctttgctt gcttaagaca    180
tgcttcatcg attcggtcct acatttgttg aagtgtcacc taaatgatgt tcaacgtcca    240
tgtttagggt ccgtactact gtggagttgg tgcggacaag tcattcgggc gtgatatagt    300
tgatgcccac tacaaggctt gcatttatgc aggcatcaac atcagtggca tcaacggaga    360
ggtcatgcca gggcaggtga gatactacta ctacactagg caacttcttt tgtaaccctc    420
aagctaccat gtttctgacc atggcaaaca ttgtggttgg ttccagtggg aattccaagt    480
tggaccgtcc gtcggcattt cttcaggcga tcaggtctgg gttgctcggt acattcttga    540
ggtatgacat cacatcttct cagctctata tgtatatact atgttgatca aatatagcgc    600
catcttaacc aagcatgatt tgcaccactt atgttatgtg gtaataacaa tcggtgctcc    660
tttccttcac agaggatcac cgagatcgcc ggtgtggtgt tgacattcga cccaaaaccc    720
atccctggtg actggaacgg tgccggcgca cacaccaact acagcaccaa gtccatgagg    780
aacgagggcg ggtacgaggt gatcaaggcc gccatcgaga agctgaagct gcggcacaag    840
gagcacatcg cggcctacgg cgagggcaac gagcgccgcc tcaccggcag gcacgagacc    900
gccgacatca acaccttcag ctgggtacgc cccccattcc ttcctactgt gctgctgctg    960
ctgcatcgtg gagaatcggc gaacccgtgt gccaactgtt gtctgttgtc tgtgcggtgc   1020
agggagtggc aaaccgtggc gcgtcagtgc gcgtgggccg ggagacggag cagaacggca   1080
agggctactt cgaggaccgc cggccggcgt ccaacatgga cccatacgtg gtgacctcca   1140
tgatcgccga caccaccatc ctctggaagc cctgaagcgg aagctttcct ccatccagct   1200
cgccgtctcg tgtcggtttg ttccgcggca gtgtcccggc cgttgcattg cagggtcccg   1260
tccagcgatt tgcgcaacaa ttgttccttc ccgttccgtt tgcttatact actctactac   1320
tgcaatttag ctagaatttg ggtcaggtcg tggtgtgcca aaacaaaaca cataaaaact   1380
ttgacgcttc ccacttccat tccatgccgt ccgtccgctt gggtgatctc ctcctacctt   1440
cttcttcttc ttgtgtaatc ctccaataat ggccgtacca cacttgtggt acctttcagt   1500
acttgctgca tcctcatgca ttgcattgta taagtggtcg ctttcctacg cgctccaatg   1560
tctgtggctt tcctgatgcg ataagggagg gaatggttag tgggtggcag cattattgtc   1620
atcgtcgccc atcggccgat cggatggcct cttttaggtc agattctgaa cgaacgattt   1680
gtcttttcct ggaaaattca gcaacaccgg tcgttttaca gtaattttcg ctccaccagc   1740
ttatcactgt tgatcgtcgg ctcgttgccc atcgcccatc ggcgcatggg atgaataaat   1800
tagtctgttt tggtcagatt ctgaacggac gatttgtctt ttcccccggg aaaattgaaa   1860
attcagcacc accgaggtgt ttgattttcg gtggatgaac ctatcactct tgatcggttg   1920
aggtgtcact cgacacagct taatgctcgg ctgttagagc aactccagca gggcccctac   1980
tcaagcccta atagctaaat atgagtgccc aggctaaaaa cattactcca gcagggctcc   2040
tattccagac cccatatttg gctgggcacc catatttctc cctcggaccc cattcctgtt   2100
ggcccaacag gacagccccc atccttcatc gcatgtccta gccccagcgt atgctccctc   2160
tctctcttcc cttgcacgtg catcacaccc taccgtaact ggctcgatgc tctaattgta   2220
tccctatcca aatgaagaag aaagaggaaa aagaaaaaga caatgacgag taggtccagt   2280
ctgtcattct ctctggaata ggtttagggg ctcaaattta ggtgctactg ttggagttga   2340
agcaaaaaag tagagcccca agaaatagga ggagcaccca aattaaaaat aggagcttag   2400
ttttggggta ctgctggagt tgctcttagc aagcgaatcc ataaacataa cgaggccctc   2460
```

```
aaccaaggga ctgtttggtt ctggctcctc cagaaatggc ttacggtggg ccctgccaaa   2520
gagtgggctc tgccaaagag taggagctcg aaattttcgt ctcggatcgt ggggccacat   2580
ccgtacatgt tgctacagga gccaccaagc actgcacggc cccctccctc tctcgggccg   2640
attggccgga tcgaatactt ctccatgttg attcgtctga tcggatcatc tggtccaaca   2700
gcaggtacta gcagagtgca tgccgagaga gagagagaga gaaagagaga gagagaggat   2760
gggcattgct ttcttgacgt tgattcacat cgttgacctg tgggcattgg tgaccacggc   2820
accttcacca actccggcga catggcacgg ccacaacaac gcaaccactc ggcttgagga   2880
atggcgacgc catcttcttc tctccaatct ggtcagtcaa gccctgacag cggccggccc   2940
gccatggcaa gcattccacg cagtgtctct cagcccagca cgtctctcca agctcaactt   3000
tgtttatgca gcgtctcaac ttccaacagc attttggtgt tcttccaagt caaaaatatt   3060
acatacaagt acagtggcaa cggtgcagat tggttccact agtcttcttg gtctagtgac   3120
ccaatggcat ggttaaggcc agccatcctt ttgctgccgg aaagggctga ttggccggca   3180
tgatcggtcc atcgccatgg atccattgag agaaagaaac aaatcagcaa gcaccacttc   3240
gtgacgcgaa aagcaatcac ggctcactgc cttgtactag gtgccgccct gtgttagcga   3300
ttggagtatc tccctataaa ctactcctac tctgtttcct aggaat                  3346
```

```
<210> SEQ ID NO 89
<211> LENGTH: 3126
<212> TYPE: DNA
<213> ORGANISM: Sorghum halepense

<400> SEQUENCE: 89
```

```
gtatacattt cagtatgcat tttattgcct aggatatctg tgcaggagag aacatttttg     60
tatgaaaaaa tggaaaggga atatagtgca caaaagataa atggtcaaca tgtttttttg    120
ggacaaactg gaaagaaaaa ggtggcctgc caggaggtga caagtagcct ccccggcgat    180
gttcaaattg gaagctgaca gttgactaaa tttgccattt acttttgtat gactatatga    240
ataaattgct gatttatttt tctttcacag tggttacatg gcgcctgagt gcttccatgg    300
gagtagcatc tcagtgaagt ctgatgtttt tagctttgga gtcttgattt tggagataat    360
aagtggaagg aaagttgcca ctagtttccg tcgatacaaa agatcggaca atctgatggc    420
ttacgtaagt aatctcttgt acaaaagaat gttgagtaac tgtaccacct gctttcaagg    480
ctatcaggct aaatgatcta cttttgaaac aggcttggcg actttgggaa gatggaaact    540
gtaagcagct catcgacaac tctctaagtg ttgaggaaca taacagtgag tcagaaataa    600
tcaggtgcat tcagattgcg ctcctatgtg ttcaggccaa cccagaggac aggcctgaca    660
tggtagaggt tgtcaggatg ctaagcatca agggcaccca gctggacaat cctaggcaac    720
ctgcttattt cgatgaactc atcgtggcaa caacaagcaa ccataccagc actcggtacc    780
tcacagctat gcatgtgtat ccagcttaat agatagtatc tgaataatgc atagcagact    840
gttcccatca ggtagcatgt ttgcatatat ttgactgcaa ccttttcatg gtttgctctt    900
tatgtcactc gagtcaaacc aaccgcttat ccatgaggtt tgtacatagt gatcagaaaa    960
tgaagttgtc attcctaact ggaggataga tctacagtta ttttagtgac tccagtttcc   1020
ttaacaaatt taggctatcc ataaggcctt atagtctatt actcagaaca gggttgtatg   1080
caattcctag caaaaggaaa gatactaatt tcctgcaagg ttgatttgta aacagatcat   1140
tcaaaagcct ataaattcct aatctgatga agcaaaatca gattatccat tcataagaaa   1200
gatttcacac ctcccaaaga tgaattgctt gatgcgaaaa tcagagaacg tcctctgaac   1260
```

acaagaacgt gcacatatgc tgatatgctt ctgcacctat cttcacctca gcttgttggc 1320
ctttctcaga acgtcttcaa tggccggtga catcactagc tcccatctga tgtggaagcg 1380
tgtggtttgg tatctacgaa caaatcaggg agttccggaa tccaaaatca ttttttata 1440 ttaaggcctt gtttacttcc actccaaaac ccaaaaattt tcaagattcc ccgtcacatc 1500
gaatctttgg tcgcatgcat gaagcattaa atatagatga aaataaaagc taactgcaca 1560
gtttatctgt aatttgtgag atgaatcttt tgagcctagt tactacgtga ttggacaacg 1620
tttgtcaaat aaaaacgaaa gtgctagagt gtaaaaattc aaaaaaaaaa ttggatcctg 1680
agaggttgaa cctcatgaaa agtttccttc gtgtatcaaa ttcctatgtt tttctatgct 1740
aaatccaaat gctcgattta tagttcccta tgtttctttc gatccataag attcaagatg 1800
ttagagcatt ctatccctta gaccttgaat attgtcggat tcacctcgat ccacatatgt 1860
tggtgtggat tgaagtggaa tttagttcaa atttcaatcc aatccacctc aatacatgtg 1920
gattgatgtg aatccgacta tatctgaaca atctgaacaa ggcctaagat gcgatgtgaa 1980
tggtttctga tgctggtgtc tctgcatcag ggcgtggcga accgcggcgc gtccatccgc 2040
gtgggccgcg acacggagag ggagggcaag ggatacttcg aggaccgcag gccggcatcc 2100
aacatggacc cctacgtcgt caccggcatg atcgccgaga ccaccatcct gtggaacgga 2160
aactgataaa cccacggttg ttcctcttct gcacaacgct actacgcctg caatgcgcgc 2220
atccgctctg atgtcatgtc agtttggttt tgcgatttcg gttccccgtc gtggggtgtc 2280
ctaaaatttt ttacttcggt ctccggtgta ctgcttggaa agtctgaata acggctgcaa 2340
atggattttg ctttcgtcat aggggtacct agctaccttt agctgttctt tcctgtttat 2400
tggatatgta taatgtaatg taatactact actacgtgat tttatatgaa aagaatcatt 2460
gtcgttttgt tcgcgatcac aagtacggtg gttccattcc aattccatgc tgtccaccct 2520
ttccattgtc agactcagac gcagcaccac tgtcacactg tgggattttg aagtagaagc 2580
acgacactta tcctggggcc aacaaattaa actctgagat atcccgtctc tgtcttgtgt 2640
gagttgtgac caccgaggca cccaaggaat acgatacgat gccgtgcggc tctttaatct 2700
tcagcccctt ctttttacca attgtcgatg aaacgcacac ctgctgccaa tgtggcgcct 2760
tttaccttta ctacatgaaa gtggttgaaa ggaaacggag ggtcttccgg ttccgcatct 2820
gggactagca aatccaggtc ttatccaggg cgacgctggc gaagaaatag cagatcgtgc 2880
agcaatatat tgtgcagcac cgagcagcaa ccagacagca gctattttcc ttggaagcaa 2940
ccagacagta tacgatagct cgactttgtc tcggtctcct ggtattgggc ttcgtcctag 3000
ctttcgccag ctcggcccaa cacacgtgat gggtcccgaa tgggtttgca tgcctctgaa 3060
ggatcaggcc catttaatag ctatattagc tgctgccgta aaagagaaaa agcctatttt 3120
tccttt 3126

<210> SEQ ID NO 90
<211> LENGTH: 1131
<212> TYPE: DNA
<213> ORGANISM: Sorghum halepense

<400> SEQUENCE: 90
tcgagctcta cggcgacgtc gtgctccggt acgtcagcta cccggacgac gcggacgcgt 60
ccttcctgcc ggggttcgtg ggcgtgagca gccccggcgc ggcggactac gggctgagga 120
ggttcgacca catcgtcggc aacgtgccgg agctggcgcc ggcggccgcc tacttcgctg 180
gcttcacggg gttccacgag ttcgccgagt tcacggcgga ggacgtgggc accacggaga 240
gcgggctcaa ctcgatggtg ctcgccaaca acgcggagaa cgtgctgctc ccactcaacg 300
agccggtgca cggcaccaag cgccgcagcc agatacagac gttcttggac caccacggcg 360
gccccggcgt gcagcacatg gcgctggcca gcgacgacgt gctcagaacg ctgagggaga 420
tgcaggcgcg ctcggccatg ggcggcttcg agttcatggc gcctccggcg cccgaatact 480
atgacggcgt gaggcggcgc gccggggacg tgctcacgga ggcgcagatt aaggagtgtc 540
aggaactagg ggtgctggtg gacagagatg accagggcgt gctgctccag atcttcacca 600
agccagtggg ggacaagcca acgttgttct tggagatcat tcaaaggatc gggtgcatgg 660
agaaggatga gaaggggcaa gaataccaga agggtggctg tggcgggttt ggcaagggaa 720
acttctccca gctgttcaaa tccattgagg attatgagaa gtcccttgaa gctaagcaag 780
ctgcagcagc tcagggaccc tagaacagag cttgaagaca agagactgtt gcggcacatt 840
gtatcatgga acaaaaataa taataatgtt cttgtaacac ttgacatgca aatgtttgtg 900
ttgtatatga agagacgatg ctatgatggg tgtaatagat ggtagagagg gtacaaccct 960
aataagtatt aatgatgcat tatttgcgta tctgttgtgc aagtttgcat gaaaacaaag 1020
agggtcagta tgaggcataa ttaatctgtc cctgggattc ttgtaatcac ctgatgctat 1080
ttttgtttat gatgagaagg cagttgtcct tgacttccaa aaggtaatcc t 1131

<210> SEQ ID NO 91
<211> LENGTH: 4147
<212> TYPE: DNA
<213> ORGANISM: Sorghum halepense
<220> FEATURE:
<221> NAME/KEY: unsure
<222> LOCATION: (1)..(4147)
<223> OTHER INFORMATION: unsure at all n locations

<400> SEQUENCE: 91
ctcgcggtgc gcgccgtcgc gctccgcgtg gccgacgcgg aggacgcctt ccgcgccagc 60
gtcgcggccg gcgcgcgccc ggcgttcgag cccgtcgagc tcggcctcgg cttccgcctc 120
gccgaggtcg agctctacgg cgacgtcgtg ctccggtacg tcagctaccc ggacgacgcg 180
gacgcgtcct tcctgccggg gttcgtgggc gtgagcagcc ccggcgcggc ggactacggg 240
ctgaggaggt tcgaccacat cgtcggcaac gtgccggagc tggcgccggc ggccgcctac 300
ttcgctggct tcacggggtt ccacgagttc gccgagttca cggcggagga cgtgggcacc 360
acggagagcg ggctcaactc gatggtgctc gccaacaacg cggagaacgt gctgctccca 420
ctcaacgagc cggtgcacgg caccaagcgc cgcagccaga tacagacgtt cttggaccac 480
cacggcggcc ccggcgtgca gcacatggcg ctggccagcg acgacgtgct cagaacgctg 540
agggagatgc aggcgcgctc ggccatgggc ggcttcgagt tcatggcgcc tccggcgccc 600
gaatactatg acggcgtgag gcggcgcgcc ggggacgtgc tcacggaggc gcagattaag 660
gagtgtcagg aactaggggt gctggtggac agagatgacc agggcgtgct gctccagatc 720
ttcaccaagc cagtggggga caagtaaaaa acttctgctt ctttcaccat tttgcagtgc 780
atgatgcatg tagaattgca aaggaacaat ttcaggatag gtactcagct aattcaggat 840
tgcgggcata tagaatatac agtataaagg tataaaactc cctttttgtg cttccatgca 900
tgatttgcgt ctttatgaag atcgtgacag caaaaagagg accctttttg catcctgtga 960
atcatattcg agcgcccaag tcccaactga ttacatgatg cacaataatc catcatcatc 1020
gttggtactc tgcacttaat tttgaagatt ttagctcagg attctagtgt caacgccatg 1080

-continued

```
gttattttat ttccttgacc tctatgcaat ccaaaatcta attggatcag ctatgtcatt   1140
caggccaacg ttgttcttgg agatcattca aaggatcggg tgcatggaga aggatgagaa   1200
ggggcaagaa taccagaagg gtggctgtgg cgggtttggc aagggaaact tctcccagct   1260
gttcaaatcc attgaggatt atgagaagtc ccttgaagct aagcaagctg cagcagctca   1320
gggaccctag aacagagctt gaagacaaga gactgttgcg gcacattgta tcatggaaca   1380
aaaataataa taatgttctt gtaacacttg acatgcaaat gtttgtgttg tatatgaaga   1440
gacgatgcta tgatgggtgt aatagatggt agagagggta caaccctaat aagtattaat   1500
gatgcattat ttgcgtatct gttgtgcaag tttgcatgaa aacaaagagg gtcagtatga   1560
ggcataatta atctgtccct gggattcttg taatcacctg atgctatttt tgtttatgat   1620
gagaaggcag ttgtccttga cttctgccga aaaggtaatc ctgcggcaag aatataacaa   1680
attgcgcatt cattccagta acctgaaaga agcagaagtt aaacagaaaa atacagaata   1740
agggcatcta agacatctta ttggatgtat caggcattca cgtgttcatc ttgagttctg   1800
tgacctagaa tagcacaaca tggacctgac aaaggcttgt tcaggtaaca acttaaacgt   1860
acagaaatca ctgtccaggg atattaatat tattacatat atgctgcaga attaaagaat   1920
tgcaatgcat caatataata tgctgtagat ctgttccata tatctgatgc cagtattcgt   1980
atactatgct gtagattatt atatgcatca ataccagata acttaatcac aactcaaaat   2040
ccaacacttc aaatcacttg gatggaaaga tcataaatgc atataatggt tggaatgcat   2100
ggctgtagtt gtacttaaag aattaaagaa ctgctcatca cgtccttgat agcagcacac   2160
cttattctca tgaggaaaat agcctggaga acatgtaagc atggcagccc tgcaacacat   2220
cgagcagtgg ggcggtctgt gaagcctcag agacatcacg gtccctccat ttctgcatca   2280
tcccttcggc atctggtgca acctggtgct gcagcactga agcagccagc ggtccgatca   2340
aattgagtct agttgcggca gagaacacat ccctcattgt cacaaacatg taagcccgct   2400
gcgctgtctc actgtcgaat ccaactagcc cacatatcaa cccaaatata gacgcgtggt   2460
gaaatgacac gctcttggaa ccaaggaatg tccgccggag atcctgcagt gcttgacttt   2520
cagtgaagac agacgcagct accctcagca gagccgagcc ctgagatatg gatgccttcc   2580
ttgcaacctc gttcgtcaat gtggcttcca gcaactgatc cagtttgacc catgccgctg   2640
catcagggga cttgctagca cagtatacga acggaagcaa caggctgcca gtgttgtcca   2700
ggacctggat gacaaacaac ttcaagtcgt cctggttgtt taccatgcga gattgcatag   2760
cagcttcaag gccataggaa tgtgcaaaac caccggttgg gagaatggag tccagaatct   2820
gccactgggt ccattgcaaa ctcggattca cgcccactgc attggaaggc acttcctcca   2880
tttcgcaatc tgctgtgtgg aacagtcgtg atttcttcga aactgggcta tcggactcca   2940
ttagcatcaa cagagtggat ggaacagtct ccagtactga aaacggcaaa attgcagtaa   3000
ggttagattt caaccccaca aaaacaacac attgcccaga aaactccgga gatttacaca   3060
caagtatcta caaagtatct cggctctaac gctcctcaca tggatcacat cttccattga   3120
ctcgttctcg ttcagtggcg actgacgact gaacaactca agatagaggc atagagctct   3180
cagctaagca ttgcatcgaa caccctgggg tcgtcagtca tctagcatga aagaaccctt   3240
tgcactaact tggccaagaa ttaacaggca cctacctaag cttttcaaca aatatagaac   3300
gtttggaacc aactgagcaa gtgaatttgg cgagtacctg agttgcttgg acagaactgt   3360
ttactccaag aagaggcaga aggtcgtcag ggagcggttg cgactggcta cggctagctc   3420
```

gccttacagg tctccaggga acaagaagtt gctgcgccga tccaccggcc acgaagtccc 3480
tccctcgagt tcaaatacgg gggttgacca tttgacgctc cgcgcgagag cgagcggcgg 3540
tgccgccgcg gatcatcaga gaggagagga cggggaaact tttttctttt tcttttttcc 3600
cgagcacgca ataataaagg gcgacccaac ccaactcgcc cttgttagag catcttcaag 3660
ggattttgca aatgaatttt gtatttgatg ttgtctgcaa agtcctaaac tcatttacaa 3720
agtctaaaaa tagtctaact tcaagggact ttgcatttag acttgnnnaa cccaaagtgt 3780
ggaccccacc ctcgaatttt tttttcatcg atcgcgcccg cacgtttttt ttccttcgcg 3840
ccattttgac gtacgtcgtg cgtgccagtc gccgtccagg ccaggtcgcc gccaattgcc 3900
gtccagccta ggtcttcgcg ccagtcgccg cccagcccaa gccgtgttcg tcgttcgtcg 3960
ccgtcgtcgt tcgcgtcagt tcggctccgt ccacctccgt cctcctccga gggaaggtcc 4020
ccgcgagaga aggtccacct ctgttcccgc gccgtggccg tggctgcgag ggaaggtccg 4080
tgcggggtgg ggggccgggg ggacggagtc cgacgnnnnn ggccgaaatt gtagatgcaa 4140
agtggtg 4147

<210> SEQ ID NO 92
<211> LENGTH: 2894
<212> TYPE: DNA
<213> ORGANISM: Sorghum halepense
<220> FEATURE:
<221> NAME/KEY: unsure
<222> LOCATION: (1)..(2894)
<223> OTHER INFORMATION: unsure at all n locations

<400> SEQUENCE: 92
catcgttggt actctgcact taattttgaa gattttagct caggattcta gtgtcaacgc 60
catggttatt ttatttcctt gacctctatg caatccaaaa tctaattgga tcagctatgt 120
cattcaggcc aacgttgttc ttggagatca ttcaaaggat cgggtgcatg gagaaggatg 180
agaaggggca agaataccag aagggtggct gtggcgggtt tggcaaggga aacttctccc 240
agctgttcaa atccattgag gattatgaga agtcccttga agctaagcaa gctgcagcag 300
ctcagggacc ctagaacaga gcttgaagac aagagactgt tgcggcacat tgtatcatgg 360
aacaaaaata ataataatgt tcttgtaaca cttgacatgc aaatgtttgt gttgtatatg 420
aagagacgat gctatgatgg gtgtaataga tggtagagag ggtacaaccc taataagtat 480
taatgatgca ttatttgcgt atctgttgtg caagtttgca tgaaaacaaa gagggtcagt 540
atgaggcata attaatctgt ccctgggatt cttgtaatca cctgatgcta tttttgttta 600
tgatgagaag gcagttgtcc ttgacttctg ccgaaaaggt aatcctgcgg caagaatata 660
acaaattgcg cattcattcc agtaacctga aagaagcaga agttaaacag aaaaatacag 720
aataagggca tctaagacat cttattggat gtatcaggca ttcacgtgtt catcttgagt 780
tctgtgacct agaatagcac aacatggacc tgacaaaggc ttgttcaggt aacaacttaa 840
acgtacagaa atcactgtcc agggatatta atattattac atatatgctg cagaattaaa 900
gaattgcaat gcatcaatat aatatgctgt agatctgttc catatatctg atgccagtat 960
tcgtatacta tgctgtagat tattatatgc atcaatacca gataacttaa tcacaactca 1020
aaatccaaca cttcaaatca cttggatgga aagatcataa atgcatataa tggttggaat 1080
gcatggctgt agttgtactt aaagaattaa agaactgctc atcacgtcct tgataccagc 1140
acaccttatt ctcatgagga aaatagcctg gagaacatgt aagcatggca gccctgcaac 1200
acatcgagca gtggggcggt ctgtgaagcc tcagagacat cacggtccct ccatttctgc 1260
atcatccctt cggcatctgg tgcaacctgg tgctgcagca ctgaagcagc cagcggtccg 1320
atcaaattga gtctagttgc ggcagagaac acatccctca ttgtcacaaa catgtaagcc 1380
cgctgcgctg tctcactgtc gaatccaact agcccacata tcaacccaaa tatagacgcg 1440
tggtgaaatg acacgctctt ggaaccaagg aatgtccgcc ggagatcctg cagtgcttga 1500
ctttcagtga agacagacgc agctaccctc agcagagccg agccctgaga tatggatgcc 1560
ttccttgcaa cctcgttcgt caatgtggct tccagcaact gatccagttt gacccatgcc 1620
gctgcatcag gggacttgct agcacagtat acgaacggaa gcaacaggct gccagtgttg 1680
tccaggacct ggatgacaaa caacttcaag tcgtcctggt tgtttaccat gcgagattgc 1740
atagcagctt caaggccata ggaatgtgca aaaccaccgg ttgggagaat ggagtccaga 1800
atctgccact gggtccattg caaactcgga ttcacgccca ctgcattgga aggcacttcc 1860
tccatttcgc aatctgctgt gtggaacagt cgtgatttct tcgaaactgg gctatcggac 1920
tccattagca tcaacagagt ggatggaaca gtctccagta ctgaaaacgg caaaattgca 1980
gtaaggttag atttcaaccc cacaaaaaca acacattgcc cagaaaactc cggagattta 2040
cacacaagta tctacaaagt atctcggctc taacgctcct cacatggatc acatcttcca 2100
ttgactcgtt ctcgttcagt ggcgactgac gactgaacaa ctcaagatag aggcatagag 2160
ctctcagcta agcattgcat cgaacaccct ggggtcgtca gtcatctagc atgaaagaac 2220
cctttgcact aacttggcca agaattaaca ggcacctacc taagcttttc aacaaatata 2280
gaacgtttgg aaccaactga gcaagtgaat ttggcgagta cctgagttgc ttggacagaa 2340
ctgtttactc caagaagagg cagaaggtcg tcagggagcg gttgcgactg gctacggcta 2400
gctcgcctta caggtctcca gggaacaaga agttgctgcg ccgatccacc ggccacgaag 2460
tccctccctc gagttcaaat acgggggttg accatttgac gctccgcgcg agagcgagcg 2520
gcggtgccgc cgcggatcat cagagaggag aggacgggga aacttttttc tttttctttt 2580
ttcccgagca cgcaataata aagggcgacc caacccaact cgcccttgtt agttgtcaaa 2640 ttttttttggt tttagttacg gtagtgtttt tgtttttatt taacaattat tatctaatta 2700
taaannaatt agatttaaaa gattcatatt ataatttaca gtatgtaatt agtttttgct 2760
tttaatgtat ttaatacttt atgtatatgt cgcacgattt gatataacag aaatcttaaa 2820
aagtttttga ctttttggcg aactaaacaa gggccttgtt tagttccgaa aagatttcga 2880
atttcggtac tgta 2894

<210> SEQ ID NO 93
<211> LENGTH: 675
<212> TYPE: DNA
<213> ORGANISM: Sorghum halepense

<400> SEQUENCE: 93
aaaaggctgt tggtgcccta gggccggtca gcaacttcat cagcttcaca tcactacaag 60
ctatgaagga gccactcacc aacaaacacc agaagacaaa tcacatccgc aaccacagaa 120
ttttctgtcc acgtggcccc atcaccaccc tttatttacc ccgtcagtca tccctcatcc 180
cagggtcact caccggtcag ccaagcgcac ctgcaactgc aaagctgcgg aggccgccac 240
gccgccacgc cctccgagag ccaagcacaa tgcccccgac ccccaccaca gccgccgcaa 300
ccggcgccgc cgtggcggcg gcatcagcgg agcaggcggc gttccgcctc gtgggccacc 360
gcaacttcct ccgcgtgaac ccgcgctccg accgcttcca cacgctcgcg ttccaccacg 420
tggagctctg gtgcgccgac gcggcctccg ccgcgggccg cttctccttc gggctcggcg 480
cgccgctcgc cgcgcggtcc gacctctcaa cggggaacac agcgcacgcg tccctgctgc 540
tccgctcggg cgccctcgct ttcctcttca cggcgcccta cgcgcacggc gccgacgccg 600
ccacggcctc gctgccctcc ttctccgccg ccgaggcgcg gcgcttcgcg gccgaccacg 660
gcctcgcggt gcgcg 675

<210> SEQ ID NO 94
<211> LENGTH: 436
<212> TYPE: DNA
<213> ORGANISM: Sorghum halepense

<400> SEQUENCE: 94
cggcggcctc gcggtgcgcg ccgtcgctgt ccgtgtctcc gacgccgccg aggcgttccg 60
cgccagcgtc gccgcgggtg cgcgcccggc cttcgccccc gccgagctcg gccacggctt 120
cgtgtttgcc gaagtcgagc tctacggaga cgccgtcctt cgtttcgtga gctacccgga 180
cgacacgggc ggcgtggcct tcctccccgg gttcgagaac gtcgcaaact catcagcgtg 240
cccggcgccg gactacggac tcaaccggtt cgaccacatc gtcggcggcg tgccggacct 300
ggctccggtc gccgcgtaca tcgccggctt cacgggcttc cacgaattcg acagggtcaa 360
cggcgacgaa ataggcacgg ccgagagctc gctcaacggc ctggtgctgg cggacagctc 420
ggagaaggtg ctcctc 436

<210> SEQ ID NO 95
<211> LENGTH: 710
<212> TYPE: DNA
<213> ORGANISM: Sorghum halepense

<400> SEQUENCE: 95
cggcctcggc ttccgcctcg ccgaggtcga gctctacggc gacgtcgtgc tccggtacgt 60
cagctacccg gacgacgcgg acgcgtcctt cctgccgggg ttcgtgggcg tgagcagccc 120
cggcgcggcg gactacgggc tgaggaggtt cgaccacatc gtcggcaacg tgccggagct 180
ggcgccggcg gccgcctact tcgctggctt cacggggttc cacgagttcg ccgagttcac 240
ggcggaggac gtgggcacca cggagagcgg gctcaactcg atggtgctcg ccaacaacgc 300
ggagaacgtg ctgctcccac tcaacgagcc ggtgcacggc accaagcgcc gcagccagat 360
acagacgttc ttggaccacc acggcggccc cggcgtgcag cacatggcgc tggccagcga 420
cgacgtgctc agaacgctga gggagatgca ggcgcgctcg gccatgggcg gcttcgagtt 480
catggcgcct ccggcgcccg aatactatga cggcgtgagg cggcgcgccg gggacgtgct 540
cacggaggcg cagattaagg agtgtcagga actaggggtg ctggtggaca gagatgacca 600
gggcgtgctg ctccagatct tcaccaagcc agtgggggac aagtaaaaaa cttctgcttc 660
tttcaccatt ttgcagtgca tgatgcatgt agaattgcaa aggaacaatt 710

<210> SEQ ID NO 96
<211> LENGTH: 583
<212> TYPE: DNA
<213> ORGANISM: Sorghum halepense

<400> SEQUENCE: 96
taaacaaaag gctgttggtg ccctagggcc ggtcagcaac ttcatcagct tcacatcact 60
acaagctatg aaggagccac tcaccaacaa acaccagaag acaaatcaca tccgcaacca 120
cagaattttc tgtccacgtg gccccatcac caccctttat ttaccccgtc agtcatccct 180

```
catcccaggg tcactcaccg gtcagccaag caaacctgca actgcaaagc tgcggaggcc    240
gccacgccgc cacgccctcc gagagccaag cacaatgccc ccgaccccca ccacagccgc    300
cgcaaccggc gccgccgtgg cggcggcatc agcggagcag gcggcgttcc gcctcgtggg    360
ccaccgcaac ttcctccgcg tgaacccgcg ctccgaccgc ttccacacgc tcgcgttcca    420
ccacgtggag ctctggtgcg ccgacgcggc ctccgccgcg ggccgcttct ccttcgggct    480
cggcgcgccg ctcgccgcgc ggtccgacct ctcaacgggg aacacagcgc acgcgtccct    540
gctgctccgc tcgggcgccc tcgctttcct cttcacggcg ccc                      583
```

<210> SEQ ID NO 97
<211> LENGTH: 2563
<212> TYPE: DNA
<213> ORGANISM: Sorghum halepense

<400> SEQUENCE: 97

```
ctaaattgcc cttgcccgca cgtcccttag cccaccgcct ggactcgtct cgcccgcggc     60
cgatttcctg catccgctcg ccgcgccgca atccggaggc cggaggagac tgcgctcagt    120
cgagcactac ctggggccca gcatcctcgc gaccatctcc ggcacggcgt ccgccctctg    180
cagccccggt gtccctgcga ccgtcgctgc tgtcctactt cgccactggc cactttgccc    240
ggcgacgagc accacagaac actagtagtc tgcctgtgct tattggttga agcggagctg    300
accacacttc atcaacagtt gcttcaacat ggacactggc tgcctctcat ctatgaacat    360
tactggagct agccaagcaa gaccttttgc gggacaactt cctcagagat gttttgcgac    420
tactcaccat tcgagctttt ccgtgagaaa tcttgtctta aggaataaag gaaggagatc    480
acaccgtaga catgctgcct tgcaggttgt ctgcaaggat tttccaagac ctccactaga    540
aagcacaata aactatttgg aagctgggca gctctcttcg ttttttagaa acagcgaacg    600
ccccagtaaa ccgttgcagg tcgtgattgc tggtgcagga ttggctggtc tatcaacggc    660
gaagtatctg gcagatgctg gccataaacc catattgctt gaggcaagag atgttttggg    720
cggaaaggta gctgcttgga aggatgaaga tggggattgg tacgagactg ggcttcatat    780
ctttttttgga gcttatccca acattcagaa tctgtttggt gagcttggaa ttgaggatcg    840
tttgcagtgg aaagaacact ccatgatatt tgccatgcca aacaagccag gagaattcag    900
ccggtttgat ttcccagaaa ctttgccagc acctgtaaac ggaatatggg ccatactgag    960
aaacaatgaa atgcttacct ggccagagaa ggtgaagttt gcaattggac ttctgccagc   1020
aatggtgggt ggtcaacctt atgttgaagc tcaagatggc ttaaccgttt cagaatggat   1080
gaaaaagcag ggtgttcctg atcgggtgaa cgatgaggtt tttattgcaa tgtccaaggc   1140
actcaatttc ataaatcctg atgagctatc catgcagtgc attttgattg ctttgaacag   1200
atttcttcag gagaagcatg gttccaaaat ggcattcttg gatggtaatc cacctgaaag   1260
gctatgcatg cctattgttg atcacattcg gtctaggggt ggagaggtcc gcttgaattc   1320
tcgtattaag aagatagagc tgaatcctga tggaactgta aaacacttcg cacttagcga   1380
tggaactcaa ataactggag atgcttatgt ttgtgcagca ccagttgata tcttcaagct   1440
tcttgtacct caagagtgga gtgaaattac ttacttcaag aagctggaga agttggtggg   1500
agttcctgtt atcaatgttc atatatggtt tgacagaaaa ctgaaaaaca catatgacca   1560
tcttcttttc agcaggagtt cacttttaag tgtctatgca gacatgtcag taacctgcaa   1620
ggaatactat gatccaaacc gttcaatgct ggagttggtc ttcgctcctg cagacgaatg   1680
```

-continued

```
gattggtcga agtgacactg aaatcattga tgcaactatg gaagagctag ccaagttatt   1740

tcctgatgaa attgctaccg accagagtaa agcaaagatt cttaagtatc atattgtgaa   1800

gacaccgaga tcggtttaca aaactgtccc aaactgtgaa ccttgccgac ctctccaaag   1860

gtcaccgatc gagggtttct atctggctgg tgattacaca aagcagaaat acttggcttc   1920

catggaaggt gcagttttat ccgggaagct ttgcgcccag tctatagtgc aggattatag   1980

caggcttgct ctcaggagcc agaaaagcct acaatccgaa gaagttcccg tcccatctta   2040

gttttagtta gtttagctat cgtcatcccc actgggtgcc atcttatcgc ctatttcatg   2100

ggaacccacc aaatggtcat gttggcgaca cctgttatgg tcctttgaca attctttaga   2160

gttgaattgt gactgtagtt gatatcatat tctgaaaaag cgatatatat gtaaaaagga   2220

cctgcatagc aattgttaga cctttgggaa agcaaaaggc gataaagaga tctcagagag   2280

atacttgtgt tgtagccctt tcaggtggtg gttccaatca atcggttaaa tcatcccacc   2340

acataggaag atttgtccat tctgcttgag gtaagcttag caaacctttg gtggcccctg   2400

ctccctgaac tttatcagga gagctgctgt agcagtcact ggccacattt ctcttgtctg   2460

tttgtactgg actattatat aggagtgttt atgagtatct ggcaacttgc atccagcaat   2520

ggctggatgt gtgcctctga tgttacatct acctgaatga agt                     2563
```

<210> SEQ ID NO 98
<211> LENGTH: 2817
<212> TYPE: DNA
<213> ORGANISM: Sorghum halepense

<400> SEQUENCE: 98

```
tctaggacgg gtatggagca ggctgcgatt gttgggcgca gtggtctgat agaaactgtg     60

gcgtagggac tggacgagat agtgtagacc tagaggggcg gcgctgcttg tttaatctga    120

ggtggtggtg ctataaagtt atctagaact tgctcgtgat catgctaatt ttttttcttc    180

tgtgcctcgt taattaatcc atcaattgtt ctcagcatag agtggcttca ttagtattta    240

gcaacctgga ttactcacga tactctgaag gacttcatga actgtgggtc taatggctcc    300

tcttgaattt gcagtagtct gcctgtgcct attagttgaa gcggagctga ccacacttca    360

tcaacagttg cttcaacatg gacactggct gcctctcatc tatgaacatt actggagcta    420

gccaagcaag accttttgcg ggacaacttc ctcagagatg ttttgcgact actcaccatt    480

cgagcttttc cgtgagaaat cttgtcttaa ggaataaagg aaggagatca caccgtagac    540

atgctgcctt gcaggttaat ccttttgttt ttcacttttt ccatgctttc actgtgtttc    600

ttgtgaaacc ataattgatt gccttttctg caggttgtct gcaaggattt tccaagacct    660

ccactagaaa gcacaataaa ctatttggaa gctgggcagc tctcttcgtt ttttagaaac    720

agcgaacgcc ccagtaaacc gttgcaggtc gtgattgctg gtgcaggtct gacgaaattc    780

atgattaatg ttttcacaaa tgttattttc ctttgtaagt tggggatttt cgagggaaac    840

actaattggc tgttagcttt attaatttgt tatgttactt ttgcaggatt ggctggtcta    900

tcaacggcga agtatctggc agatgctggc cataaaccca tattgcttga ggcaagagat    960

gttttgggcg gaaaggtctg atagatactt gcatgactgt ttgccactct ctgaattgct   1020

ctcatttact gttttcatca tctgttcctt tatgattctt ttttgtatgc attgatagat   1080

agctgcttgg aaggatgaag atggggattg gtacgagact gggcttcata tcttttgtaa   1140

gtttcagttc tggtcctcaa ggttctcttc atgatatttg atgttcctga ttatttctat   1200

tagaaaaaat acagttagta tgatggtttc tacacatatt aacaaactgt tacttgttaa   1260
```

-continued aaaaatgttg aggcacacca tcacacaaac tcctaaagca ctattttctt gtatcatgct 1320
tttttatttt cctaatgtcg caggagtttc tttcaagaat aatttgtaaa tatctgtgca 1380
aaatcattat tgcgaaaggg attttgttaa gttactagta gtgacaaaat agcccgaaaa 1440
gtttgcagac tactaaaaca tacagcagca catgtttcaa tgtcacataa accatgttaa 1500
cccatgggct atcatatcca taatgccata gtcgaatata tgttcttctg ttcacatgag 1560
cagttgagca ctggattgct actattcctt cctagcgtat atgacactta ttgtgtacgt 1620
gtatgtaacc atgtattttg gatttttggt ttaagttgga gcttatccca acattcagaa 1680
tctgtttggt gagcttggaa ttgaggatcg tttgcagtgg aaagagcact ccatgatatt 1740
tgccatgcca aacaagccag gagaattcag ccggtttgat ttcccagaaa ctttgccagc 1800
acctgtaaac ggtaagatta taaacaattt ggagttagcg caacaggttc tctcattttg 1860
ctaaaatatg gacattatta gggggtttat taatggcaat aatacatcat taccattgtg 1920
cttaactctg ctaatcgatg ccatactatg attcactatt gtgcttttaa caggaatatg 1980
ggccatactg agaaacaatg aaatgcttac ctggccagag aaggtgaagt ttgcaattgg 2040
acttctgcca gcaatggtgg gtggtcagcc ttatgttgaa gctcaagatg gcttaaccgt 2100
ttcagaatgg atgaaaaagc aggtacgagt taaatgtgtt gattatacta gtctctgtgt 2160
agaaaacagt ttgccgtctc atcaatatta gagagcttgt agtttgccag taattttcct 2220
ttcttgtcat atcttctgga aggagcatag ttagatccat aaacggaaat gcttcatatg 2280
ctcaagttct tatcttatat tttgttgtaa accccttttct atgcaaagtt aggctgagca 2340
atgatttttt ttttgggtgc tacctgatat acacatacag tgttcttcag atttggtttt 2400
acttttgcca tttggaatac ggatggacgg atggtaatat atccttctat tgtttatggt 2460
ctcatgtggt gcctgataca attatttgat cagcacaggg tgttcctgat cgggtgaacg 2520
atgaggtttt tattgcaatg tccaaggcac tcaatttcat aaatcctgat gagctatcca 2580
tgcagtgcat tttgattgct ttgaacagat ttcttcaggt atagctgctg ttgctttatt 2640
taattgtgca ctatattaat tgcctgttct gtttagagaa atagcctaca tatatcgatt 2700
cttattttct tgtctatatt cttattttta cttgagaaaa tgctaatatg tacttgcaac 2760
gttaatatac cttttgagtc tttgaaaaga ttactttggc cttgtttact tccaccc 2817

<210> SEQ ID NO 99
<211> LENGTH: 916
<212> TYPE: DNA
<213> ORGANISM: Sorghum halepense

<400> SEQUENCE: 99
ggggcgtcta gcgccttgca cgggtgaccc actgacactt ctcattcagt aacaggctgt 60
ggaaatgggg aatttcttag ggctcttggg ctctgaaggc atcggtaatt tgtaattggt 120
ctaggacggg tatggatcag gctgcgattg ttgggcgcag tggtctgata gaaactgtgg 180
cgtagggact ggacgagata gtgtagaacc tagaggggcg atgctgcttg tttaatctga 240
ggtggtggtg ctataaagtt atctagaact tgctcgtgat catgctaatt ttttttcttc 300
tgtgcctcgt taattaatcc atcaattgtt ctcagcatag agtggcttcg ttagtattta 360
gtaacctgga tcagtttact cacgataatc tgaaggactt catgaactgt gggtctaatg 420
gctcctcttg aatttgcagt agtctgcctg tgcttattgg ttgaagtgga gctgaccaca 480
cttcatcaac agttgcttca acatggacac tggctgcctc tcatctatga acattactgg 540
agctagccaa gcaagacctt ttgcgggaca acttcctcag agatgttttg cgactactca 600
ccattcgagc ttttccgtga gaaatcttgt cttaaggaat aaaggaagga gatcacaccg 660
tagacatgct gccttgcagg ttaatccttt tgtttttcac tttttccatg ctttcactgt 720
gtttcttgtg aaaccataat ggattgcctt ttctgcaggt tgtctgcaag gattttccaa 780
gacctccact agaaagcaca ataaactatt tggaagctgg gcagctctct tcgtttttta 840
gaaacagcga acgccccagt aaaccgttgc aggtcgtgat tgctggtgca ggtctgacga 900
aattcatgat taatgt 916

<210> SEQ ID NO 100
<211> LENGTH: 722
<212> TYPE: DNA
<213> ORGANISM: Sorghum halepense

<400> SEQUENCE: 100
gatgccatac tatgattcac tattgtgctt ttaacaggaa tatgggccat actgagaaac 60
aatgaaatgc ttacctggcc agagaaggtg aagtttgcaa ttggacttct gccagcaatg 120
gtgggtggtc aaccttatgt tgaagctcaa gatggcttaa ccgtttcaga atggatgaaa 180
aagcaggtac gagttaaatg tgttgattat actagtctct gtgtagaaaa cagtttgccg 240
tctcatcaat attagagagc ttgtagtttg ccagtaattt tcccctttct tgtcatatct 300
tctggaagga gcatagttag atccataaac ggaaatgctt catatgctca agttcttatc 360
ttatattttg ttgtaaaccc ctttctgtgc aaagttaggc tgagcaatga tttttttggg 420
tgctacctga tatacacata cagtgttttt cagatttggt tttacttttg ccatttggaa 480
tacggatgga cggatggtaa tacatccttc tattgtttat ggtctcatgt ggtgcctgat 540
acaattattt gatcagcaca gggtgttcct gatcgggtga acgatgaggt ttttattgca 600
atgtccaagg cactcaattt cataaatcct gatgagctat ccatgcagtg cattttgatt 660
gctttgaaca gatttcttca ggtatagctg ctgttgcttt atttaattgt gcactatatt 720
aa 722

<210> SEQ ID NO 101
<211> LENGTH: 376
<212> TYPE: DNA
<213> ORGANISM: Sorghum halepense

<400> SEQUENCE: 101
agcttggaat tgaggatcgt ttgcagtggg aagaacactc catgatattt gccatgccaa 60
acaagccagg agaattcagc cgattagacg gtaagactat aaacaatttg gagttagtgc 120
aacaggtact cattttgcta atatatatta tttaggaggt ttattagtgg caataataac 180
actacatctt tactgttgag cttaactctg ctaattggtg ccatactatg attcactatt 240
gtgcatttgt gcttttaaca gggatatagg ccactgagaa acaatgaaat gcttacctgg 300
ctggagaagg tgaagtttgc actgacttct tccagcaatg gttggtggcc aacctgaagc 360
tcaagatggc ttaact 376

<210> SEQ ID NO 102
<211> LENGTH: 647
<212> TYPE: DNA
<213> ORGANISM: Sorghum halepense

<400> SEQUENCE: 102
ttgtgtaaat gcgcaggaga agcatggttc caaaatggca ttcttggatg gtaatccacc 60
tgaaaggcta tgcatgccta ttgttgatca cattcggtct aggggtggag aggtccgctt 120
gaattctcgt attaagaaga tagagctgaa tcctgatgga actgtaaaac acttcacact 180
tagcgatgga actcaaataa ctggagatgc ttatgtttgt gcagcaccag gtgtgatttg 240
tttcaataaa gaataaacct tgtttcctgt gcagctattc aatttaactg actagtcttt 300
gtatttagtt gatatcttca agcttcttgt acctcaagag tggagtgaaa ttacttactt 360
caagaagctg gagaagttgg tgggagttcc tgttatcaat gttcatatat ggttagttga 420
ttgaaatatt tggttctgaa ttggaaatga cttgattccc ttgtctggtt atgcttgttc 480
ctcaagacat tcctgaagct tcgctgagaa tttctgttgt tttgaatacc tcaggtttga 540
cagaaaactg aaaaacacat atgaccatct tcttttcagc aggtatctct cctagctgta 600
gttcatgcat tttttgtgca gtaaatcttg attatgatta tttatca 647

<210> SEQ ID NO 103
<211> LENGTH: 2934
<212> TYPE: DNA
<213> ORGANISM: Sorghum halepense
<220> FEATURE:
<221> NAME/KEY: unsure
<222> LOCATION: (1)..(2934)
<223> OTHER INFORMATION: unsure at all n locations

<400> SEQUENCE: 103
catgattggg caataattac cacaaacaaa nnnaagtgct acagtgtcat gaaatttttc 60
acttcaggaa ctaaacaagg cctttgtgta aatgcgcagg agaagcatgg ttccaaaatg 120
gcattcttgg atggtaatcc acctgaaagg ctatgcatgc ctattgttga tcacattcgg 180
tctaggggtg gagaggtccg cttgaattct cgtattaaga agatagagct gaatcctgat 240
ggaactgtaa aacacttcgc acttagcgat ggaactcaaa taactggaga tgcttatgtt 300
tgtgcagcac caggtgtgat ttgtttcaat aaagaataaa ccttgtttcc tgtgcagcta 360
ttcaatttaa ctgactagtc tttgtattta gttgatatct tcaagcttct tgtacctcaa 420
gagtggagtg aaattactta cttcaagaag ctggagaagt tggtgggagt tcctgttatc 480
aatgttcata tatggttagt tgattgaaat atttggttct gaattggaaa tgacttgatt 540
cccttgtctg gttatgcttg ttcctcaaga cattcctgaa gcttcgctga gaatttctgt 600
tgttttgaat acctcaggtt tgacagaaaa ctgaaaaaca catatgacca tcttcttttc 660
agcaggtatc tctcctagct gtagttcatg catttttttgt gcagtaaatc ttgtttatga 720
ttatttatca agatatttta tgtgctattc tggttgcgct atcgttcatg tttgaatgtc 780
catgttcagt attaaatact gtatgccttg tttgttttct tttcaggagt tcacttttaa 840
gtgtctatgc agacatgtca gtaacctgca aggtactaac ttgaggagct tatcatcatt 900
ccataattgc tagcatacta tatcttcatt gtttctaggg cctcagagac cttcacatgt 960
gtcatacaat atccacctga aatttacttt attaactata tgtgatttag aaggaattca 1020
ttattaagtg gaaatataaa tatcttgtgt gttatgaatt ttagtcatgt gcgcacatac 1080
atgtattaag tgtaggactt caatcattgg tgaacatgtc tgtatgaatc acaatatgtt 1140
tggtagcaaa tgacatgggc gcacactcac ctgtttcttt ccttctgttt ttctaattct 1200
ttacaggaat actatgatcc aaaccgttca atgctggagt tggtcttcgc tcctgcagac 1260
gaatggattg gtcgaagtga cactgaaatc attgatgcaa ctatggaaga gctagccaag 1320
ttatttcctg atgaaattgc taccgaccag agtaaagcaa agattcttaa gtatcatatt 1380
gtgaagacac cgaggtgagg atacttgcca aagacccttc ctgatagata gtcataagta 1440
gctcaagctc tgatagtttt atgtgttgtt tccttatgtt cgtattatgg cttgctttga 1500
cagatcggtt tacaaaactg tcccaaactg tgaaccttgc cgacctctcc aaaggtcacc 1560
ggtcgagggt ttctatctgg ctggtgatta cacaaagcag aaatacttgg cttccatgga 1620
aggtgcagtt ttatccggga agctttgcgc ccagtctata gtgcaggtaa atactcacca 1680
tggtactggt tgtacataac ggcaccagat tgctgtgttg tgttgttgaa tttatttcag 1740
tatgatacat gttttgcgtc taatgaatta aaatttactg ctttcaggat tatagcaggc 1800
ttgctctcag gagccagaaa agcctacaat ccgaagaagt tcccgtccca tcttagtttt 1860
agttagttta gctatcgtca tccccactgg gtgccatctt atcgcctatt tcatgggaac 1920
ccaccaaatg gtcatgttgg cgacacctgt tatggtcctt tgacaattct ttagagttga 1980
attgtgactg tagttgatat catattcaga aaaagcgata tatatgtaaa aaggacctgc 2040
atagcaattg ttagaccttt gggaaagcaa aaggcgacaa agagatctca gagagatact 2100
tgtgttctag ccctttcagg tggtggttcc tatcaatcgg ttaattcatc ccaccacata 2160
ggaagatttg tccattctgc ttggtgcccc ctgctccctg aactttatca ggagagctgc 2220
tgtagcagtc actggccaca tttctcttgt ctgtttgtac tggactatta tataggagtg 2280
tttatgagta tctggcaact tggcatccag caatggctgg atgtgtgcct ctgatgttac 2340
atctacctga atgaagtaat gtaactggac caagaaagca tcagaacaat aatacctttt 2400
ctcgttagat ttgtattgcc aaagaattat ttgttgactg tttaggatat actcctagta 2460
gtctgtagtg cgcctacaag acgacgacga tgtgcaaaaa gctcaagccc ctgctaggct 2520
cggcagagga gcgggtggaa aatactcgta gccaggaaag ggaaagcaag cccatatgct 2580
acttgcatgg gccgtgcagc agcatgggcc caaccttact cctgtccgac ttgctttagc 2640
aaccgtgcct agtacagtac gagtttccca catgggtcag gaacttcggg aacataggac 2700
atagctcatt tcgaattgaa cgtatttttt tactatcttg atgagagaaa tataatggtg 2760
aaatccattt aacatcttga caaactttat aaagtagata ttttttttaac gaataggagg 2820 ggttttagat ccttactaaa aataacaaat aattttggtt gtcaacacaa ctccttctaa 2880
atccttgcaa ctccctgctg agcacacggt tatcatcatc tgcaccatgt gttc 2934

<210> SEQ ID NO 104
<211> LENGTH: 3891
<212> TYPE: DNA
<213> ORGANISM: Sorghum halepense

<400> SEQUENCE: 104
atactggata ccgtggaaac gtagagcact agagcgcacc aggcaccaaa aggcggcatc 60
ctccaccacc acatgtccgg ccacatcggt ctcgtctcgt cgtgcggtgc gcttgtccct 120
ttccaccgcc ccaaccaaat gaggaggagg tctttcccaa ttgggctccc ccgcctccac 180
gacactgcct ccgcctcgcc aagtccgccg cctccattcc tctcctctcc ccctcctccg 240
gtgagtactt ctctctctct ctcgccaacc ggagtccctt gctgatgcac actgcgtttc 300
tgtttaatct cgcggccagc gctcgatccg gttccgtatg ggggatgggg gcgtctagcg 360
ccttgcacgg tgactaactg acacttctca tttagtaaca caggttgtgg aaatggggga 420
tttcttaggg cttttaggct ttgaaggcat aggaaatttg taatttgtcc aggactggca 480
tgtagcaggc tgcgattatt gggcgcagtg gacaatgcta tgatggaaac tgtggcatag 540
ggactggacg agatagtgta gagtggagag cctagagggg agatgctgct tgtttaatct 600

-continued

```
gagatggtgg tgctacgaaa ttgtctagaa cgaggtccgg gtcatgcctt tttttttttg    660
acggtcaacg gaggcgttcc ccacctgatt ttattatggt tggcccaaaa acggcctttc    720
agttaagccg agttacaaag tttacaaaag acagagttac aattatcatg ccatttttgt    780
ttctgtctcg ttaacccatc aattgttctc agcatagaat aacttcatta gtatttagca    840
acctggatca atttactcat gatactttta agtcttaaga cgtatacata tgggaaaagg    900
cttcatgaac tgtgggtcta atggctcctc ttgaatttgc agtagtctta gtctgcctgt    960
gcctattggc tgaaccagag ctgaccccac tttatcaaga gttgcctcaa catggacact   1020
gactgcctgt catctatgaa cattactgga gctagccaag caagaccttt tgcgggacaa   1080
cttcctcctc agatgttttg cgagtagtca ccatgcgagc tttgccgtga aaaatcttgt   1140
cttaaagagt aaaggaaggc gatcacacca tagacatgct gccttgcagg tcgatctttt   1200
tgtttttcac cttttccatg ttttcactgt gtttcttgtg aaatcataat ttattgcctt   1260
tttctgcagg ttgtccgcaa ggatttttcca agacctccac tagaaagcat tatttggaag   1320
ctgggcagtt tagaaacagc gaacgcccga gtaaaccgtt gcaggttgtg attgctggtg   1380
caggtctgat gtaattcatg attaatgttt tcacagacgt tattttcctt tgtaagttgg   1440
ggaactttga gggaaactct aattgtctgt tagctttatt aatctgtgat gttacttttg   1500
caggattgtc tggtcaacgg cgaaatatct ggcagatgct agccataaac ccatattgct   1560
tgaggcaaga gatgttttgg gcggaaaggt tggatagata cttgcatgac tgtttaccac   1620
tctttgaatt gctctcatgc accgttttca tcatttgttc cttttatgat tttgtattgc   1680
attgataggt agctgcttgg aaggatgaag atggagattg gtatgagact gggcttcgta   1740
tcttttgtaa gttacagtgg tcctcgaggt tctcttcatg atatttgatg ttcttgatta   1800
tttctattag gaaaaataca gttaatatga tggctttggc ctgagttcat ccattttggg   1860
tgaatgaagc cggatagact atctatcctt tatctaaaaa aacacaatcg cacaaacgtc   1920
taaaccactc tttccttgta tcatgctttt ttaattttcc tagtgtcgta gaagtttctt   1980
tcaaggacaa tttgtaaata tctgtgcaaa atcactattg agaaagggac tttgttaagt   2040
tactagtagt gacaaaatag cctgaaaatt tttggactac taagacatac aacagcacat   2100
gttcaatgtc acaaaccatc ttgacccatg gaccatccta tgacagagct gcctgaaaat   2160
ttccagacta ctagacatac agctgcctga catcactgca gccgggcgac gcgtccgctc   2220
ccaccgctct catacgacag aggcgctgac gcggcagtgc ccgcgggcga gcaacacatg   2280
gtcgtggacg gaggcccatg tgagcaagtt gggccacttg ccggtgggat catgccgagg   2340
aaggactgcg cctttcgtat ttgcggtgcc cattggtgtc gcggtcagcg ggccgcgttc   2400
acgtggtgca tgacgcggtg cggttgcatc cttgtgatcg cgagagcagc ggcacgctag   2460
gccgctagcg ctagcttacg cggggtctcg ctggggtttt gccgttttgc ttcgcttttc   2520
cttgtgcggt ggctgcggct gcgggctggg caggtagttt gctctgggaa acctggtggc   2580
tactgatggc gtgggggtat acctgcgcgg gaccagtttt tcggtggaaa gtggtgggtt   2640
agggagacgt gcggagaagg cagtggtact agtatccgaa atgtgaccgg gcaagttttg   2700
tctggtgtcg tccccacgtg gcatgacgtg gctccgcctt tctgctccta accggcgcca   2760
tctcctagag atgaccttcc ttctggtgct cctctgttct cggccccagc cgagccgagc   2820
cgatctctac tgcttcgaag agttcctaac tggtcactct aatattaaaa taggaaatag   2880
cttgactatt aacaataact ttatttgaac tcttaccacc agtgtataaa attttatata   2940
```

gatttacaac gcgaagttgg tagcattact atattcctaa taaaaatact ttcataatat 3000
ttaagtatct tggttaacta tatatttttg tagatgtcgc cagtcaataa tttaatacaa 3060
cagagttttc tttttagtga aactcatatt tgtagttaga ggaaatacga aacagttaac 3120
tatagtaatt ttattttcta gcaagcatat aacatgtaat tggttaaaag tttccaaata 3180
tgtagaaaaa agccttaagt tatatttaag tcttcaataa attaatagga cataagaaat 3240
gtaaatatga cttatgaaca aaagatacga tagctagtga atatgtggca gtgtttcttc 3300
ttttacactg caataatctc ctgcattttc cgaaaaaaata atcttaggtt aaaaaataaa 3360
atctatgacg tacacgaaag tttgtctcct ctcacacgtg acatggcttg atttttccgc 3420
cactatatct ttattaaatc tctcatacgg tacatcattc tgagtgtgac gtgtgactcg 3480
tcttgttcct cctcctcctc ctatttaggc aactcccgac ggatctattg cctccccctg 3540
ccatgctact ccgttggccg ccatgaatga cgaccgggga agcttatccc ccctcttatc 3600
gagcccgaac tggctgccaa gcgacagccc gaggctgagc tccacctcct ccatctcctc 3660
ccgcagctgc cccggtctct gctccggtag cggcgcgtct cccttgccaa tcccgcacag 3720
caagtccctc gaaaaaaccc tccatcgcgc gcgcaagctt gtctcaggga gtctcaggga 3780
gcaagcttga gactccctga gacaaacttg cgcgcgcgat ggagggtttt tcaaggggcc 3840
tgctgtgccg gattggtaag ggagacgtgc cgccaccgga gcagaggcca g 3891

<210> SEQ ID NO 105
<211> LENGTH: 3832
<212> TYPE: DNA
<213> ORGANISM: Sorghum halepense

<400> SEQUENCE: 105
tattttatgt gctattctgg ttgcgctatc gttcatgttt gaatgtccat gttcagtatt 60
aaatactgta tgccttgttt gttttctttt caggagttca cttttaagtg tctatgcaga 120
catgtcagta acctgcaagg tactaacttg aggagcttat catcattccg taattgctag 180
catactatat cttcattgtt tctagggcct cagagacctt cacatgtgtc atacaatatc 240
cacctgaaat ttactttatt aactatatgt gatttagaag gaattcatta ttaagtggaa 300
atataaatat cttgtgtgtt atgaatttta gtcatgtgta ggacttcaat cattggtgaa 360
catgtctgta tgaatcacaa tatgtttggt agcaaatgac atgggcgcac actcacctgt 420
ttctttcctt ctgtttttct aattctttac aggaatacta tgatccaaac cgttcaatgc 480
tggagttggt cttcgctcct gcagacgaat ggattggtcg aagtgacact gaaatcattg 540
atgcaactat ggaagagcta gccaagttat ttcctgatga aattgctacc gaccagagta 600
aagcaaagat tcttaagtat catattgtga agacaccgag gtgaggatac ttgccaaaga 660
cccttcctga tagatagtca taagtagctc aagctctgat agttttatgt gttgtttcct 720
tatgttcgta ttatggcttg ctttgacaga tcggtttaca aaactgtccc aaactgtgaa 780
ccttgccgac ctctccaaag gtcaccgatc gagggtttct atctggctgg tgattacaca 840
aagcagaaat acttggcttc catggaaggt gcagttttat ccgggaagct ttgcgcccag 900
tctatagtgc aggtaaatac tcaccatggt actggttgta cataaaggca ccagattgct 960
atgttgtgtt gttgaattta tttcagtatg atacatgttt tgcgtctaat gaattaacat 1020
ttactgcttt caggattata gcaggcttgc tctcaggagc cagaaaagcc tacactccga 1080
acaagttccc gtcccatctt agttttagtt agtttagcta tcgtcatccc cactgggtgc 1140
catcttatcg cctatttcat gggaacccac caattggtca tgttggcgac acctgttatg 1200

```
gtcctttgac aattctttag agttgaattg tgactgtagt tgatatcata ttcagaaaaa   1260
gcgatatata tgtaaaaagg acctgcatag caattgttag acctttggga aagcaaaagg   1320
cgataaagag atctcagaga gatacttgtg ttgtagccct ttcaggtggt ggttcctatc   1380
aatcggttaa ttcatcccac cacataggaa gatttgtcca ttctgcttgg tggcccctgc   1440
tccctgaact ttatcaggag agctgctgta gcagtcactg gccacatttc tcttgtctgt   1500
ttgtactgga ctattatata ggagtgttta tgagtatctg gcaacttgca tccagcaatg   1560
gctggatgtg tgcctctgat gttacagcta cctgaatgaa gtaatgtaac tggaccaaga   1620
aagcatcaga acaataatac cttttctcgt tagatttgta ttgccaaaga attatttgtt   1680
gactgtttag gatatactcg tagtatgtag tgcgctagta tgtagtgcgc ctacaagcga   1740
cgacgatgtg caaaaagctc aaacccctgc taggctcggc agaggatagg gtggaaaata   1800
gtcgtaccca ggaaaggtaa agcgagccca tatgctactt gcatgggccg agaagcagcc   1860
cacgatttcg atgagagaaa cgagatggtg aaatttattt aacatcttga caataaaatg   1920
gatagtgttt tttaacgaat aggaggggtt tcagatcctt actgaaaaca atgaatattt   1980
ttggttgaca acacaagatc ccttctaaat ccttgcaatt ccctgctgag cacatgttta   2040
tcatcatctg caccatgtgt tgtagccttg ctcaagtcca tcttagatca tcacatttat   2100
tacccatcag gctaatatat aggtttcggc tcaattgacc aattttagac ttcataagac   2160
tgactctgta accactgatc cggcctacct ttatggatcg aataatcaac caactatcaa   2220
atcatgagtc tacccggccc tttcctcccg ttcctaattc atgcgtcgag gcctaaatta   2280
aacgagacac agtggagtgt gtggcccaat tagtcagcaa ctgggatcca tccgctcgct   2340
tccccgtcgc gcacgtacgt cctgactcga tcctcaggtg atccggtacg tgcgtgcgtt   2400
gcgagttgcg acgtcctccc agctcccgcc cgcccgagtc acgtggcgcc ggacccggac   2460
gcgcgcggcc gccgatactc gccggccggc cggccggccg acggaccgag accacacgat   2520
aggtttgtcg tagtacactt acactttcgc ggattctggc tgtgcgcacg gcccggccgc   2580
acattgggcg ccgccgcgtg atttgatcca tcgattcttg cgcagttgcg gttcccggat   2640
cgtccgtggg aagaaccgga cgcctagttc atggcggcgg cgaccagggt gatcggatcc   2700
aagccatcgg actgcttcca gttccaagac cctagcacct ggtacgtcct acatttccta   2760
tccccagccg gccatggcca ctatcccatc agcatgcaga tcggttgcgg atttgttttg   2820
tttctagttg cagcgccgcc atagttacag tttcttaatt gctccgttgt cttcaggcta   2880
taatctgatc aaagtttcca tgcatctagg atcgatgatc agtagtagta gtagttaatt   2940
atcgatccta attccataac caatttgtat cataaataga tccggtttcg ttcctgtttt   3000
caggtttttt tcttcatgtt cagataacac ggttttttgt tttctgaaaa ccttagtgca   3060
gagtgcagac aacaacaaca acaacaaaaa ttaaccactg atctttggta tctcccctgt   3120
acatcttggc gctcttgcag gacttgcata acggagcttg caagcgatgt ggtcgtccaa   3180
gtaggagaca cgtccttcca cctgcacaag gtatttgctt tccgagatta atcccagtgt   3240
tcatcacatt ctcatttctc aacgctagaa atgccgaaat gcccacacat ttgccccacg   3300
gaatgaatta aagttccact acatgaatct atgcatcgat gcttttagac ttgtcagata   3360
acttgtaagt ttcgaatatg cacgtttttc atgtgctgac aacgtgcact aaatgccatc   3420
tgcatcattt agactcagtt gatcagccgt agcggcacgc tgaagaagct tgtgaacgag   3480
tccaccggcg acgacgacag caaaccgtgc accgtgcgtc tggacgacgt ccccggcggg   3540
```

gcggaggcgt tcctgctggc ggccaggttc tgctacgacg tcgagacgga gctgaacgcg 3600
ggcaacgtcg tgccgctgcg gtgcgcggcg gagcacctcg ccatgaccga ggactacggc 3660
gaagggaacc tggtggagca ggcggagtcg ttcctgtccg aggtgctggc cggctgggac 3720
gacacggtgc gcgcgctgaa cgcgtgcgat gacgccgtgc tccctgccgc cgaggacctg 3780
ctcatcgtgc cgcggtgcat cgactcgctg gcggacaagg cctgcgccga cc 3832

<210> SEQ ID NO 106
<211> LENGTH: 1623
<212> TYPE: DNA
<213> ORGANISM: Sorghum halepense

<400> SEQUENCE: 106
ggcgctggcc acgcggcacg gcgtcgggga cgtgcttgtc acggaggccc gcgcccgccc 60
cggcggcaac atcaccaccg tcgagcgccc cgaggaaggg tacctctggg aggagggtcc 120
caacagcttc cagccatccg accccgttct ctccatggcc gtggacagcg ggctgaagga 180
tgacctggtt tttggggatc ccaacgcgcc acggttcgtg ctgtgggagg ggaagctgag 240
gcccgtgcca tccaagcccg ccgacctccc gttcttcgat ctcatgagca tccctggcaa 300
gctcagggcc ggtctcggcg cgcttggcat ccgcccgcct cctccaggcc gcgaggagtc 360
agtggaggag tttgtgcgcc gcaacctcgg tgctgaggtc tttgagcgcc taattgagcc 420
tttctgctca ggtgtctatg ctggtgatcc ttccaagctc agtatgaagg ctgcatttgg 480
gaaggtgtgg cggttagaag aagctggagg tagtattatt ggtggaacca tcaagacgat 540
tcaggagagg ggcaagaatc caaaaccacc gagggatccc cgccttccga agccaaaagg 600
gcagacagtt gcatctttca ggaagggtct tgccatgctt ccaaatgcca tcacatcaag 660
cttgggtagt aaagtcaaac tatcatggaa actcacgagc attacaaaat cagatggcaa 720
ggggtatgtt ttggagtatg aaacaccaga aggggttgtt ttggtgcagg ctaaaagtgt 780
tatcatgacc attccatcat atgttgctag cgacattttg cgtccacttt caggtgatgc 840
tgcagatgct ctatcaagat tctattatcc accagttgct gctgtaacgg tttcgtatcc 900
aaaggaagca attagaaaag aatgcttaat tgatggggaa ctccagggtt ttggccagtt 960
gcatccacgt agtcaaggag ttgagacatt aggaacaata tacagctcat cactctttcc 1020
aaatcgtgct cctgctggta gggtgttact tctaaactac ataggaggtg ctacaaacac 1080
aggaattgtt tccaagactg aaagtgagct ggtagaagca gttgaccgtg acctccgaaa 1140
aatgcttata aatcctacag cagtggatcc tttagtcctt ggtgtccgag tttggccaca 1200
agccatacct cagttcctgg taggacatct tgatcttctg gaggccgcaa aatctgccct 1260
ggaccaaggt ggctatgatg ggctgttcct aggagggaac tatgttgcag gagttgccct 1320
gggcagatgc attgagggcg catatgagag tgccgcgcaa atatatgact tcttgaccaa 1380
gtatgcctac aagtgatgga agtggagcgc tgcttgttaa ttgttatgtt gcatagatga 1440
ggtgagacca ggagtagtaa aaggcgttac gagtattttt cattcttatt tgtaaattgc 1500
acttctgttt tttttcctgt cagtaattag ttagatttta gttatgtagg agattgttgt 1560
gttcactgcc ctacaaaaga atttttattt tgcattcgtt tatgagagct gtgcagactt 1620
att 1623

<210> SEQ ID NO 107
<211> LENGTH: 1110
<212> TYPE: DNA
<213> ORGANISM: Sorghum halepense

<400> SEQUENCE: 107
atccttattt atgcgttagt acaatatagg tggatagctc catgttgtca tttaaaaata 60
ccaaatatac agctgaaggt ctttatttca tatacatgga tggggaatgt gcacctaccc 120
tttgcacaat gttgatacta actagggcat tgtcattctt tccatcctta tttatgctgt 180
tagtacaata taggtggata gctccatgtt gtcatttgaa aataccaaat gtacagctga 240
aggcatagaa attccatgaa gcatggttta tagagcatgt tagtgtgcat gttcattgcg 300
acttggttgc aaactagtaa cgattgtaat attagatctc tgatcaagga ttattctatt 360
cattactcac ctttattcaa ttctgtacat ttcttcattt acagcttggg tagtaaagtc 420
aaactatcat ggaaactcac gagcattaca aaatcagatg gcaaggggta tgttttggag 480
tatgaaacac cagaaggggt tgttttggtg caggctaaaa gtgttatcat gaccattcca 540
tcatatgttg ctagcgacat tttgcgtcca ctttcagtaa gtatagaata atcaattttc 600
atgttttcat aaactggagt attttagctt cttgataccc taaaataacg ttttttttgg 660
gaaaattacc agtcaggggt ggggtttgca cttgttaagt ggttgatgat ttctgccatt 720
ctgtggtcaa catctccatt gacatttact aaactactgc aaggctagca aaattctaaa 780
ccttgtcttc attgacatct gaatgactgt tgtagtgttg ttatcttcca agtggatcat 840
ttgtgtgaaa aaaattgcgg aaagttatgg tttttgtttt tcgtactaat aatgatgata 900
gtaaatgctg agcttgcaaa catgtcaata gtgtggtgga ggtcctttgg ttgggaggct 960
gcccaccggc agaccggggc tcaaatcctg ggttgcatga aaaaaggtcc ctagctgtgt 1020
aactgtctac agagatatat gtgctgcagg cacgtcctgg gcagctagct tttggggcct 1080
tttcttgacc ctgcaggaaa tttcttatgt 1110

<210> SEQ ID NO 108
<211> LENGTH: 2939
<212> TYPE: DNA
<213> ORGANISM: Sorghum halepense

<400> SEQUENCE: 108
catgggtgcg agcttgtcca ccagtgcggg cagcgacaag catggctcac acgtgttcat 60
cgtcgccgac aggcagggcc cgacacatat gccgctggtg gtgtgcaggc aagctcctcc 120
cagctgaagc atcacgggca agcttgtgcc ctgttcggtt ctggccccat cagcacacac 180
ataggtgagc tcgtcacgta gccggtgtgt gtgtgtgggg gaagacaagg gcagcggcca 240
gcatggtgga tgaggaggga gagtgcggca gggctggccc tggaggggga ggtggtggca 300
tgacagctag tgagggaggc acggtggccg ggggtggggc aaaggtgagg cagaggcaga 360
ggcatggcgg ttggcggagt ggaggcatga cggacggcga cgtggaggcg ctcgatggag 420
gtggcgatgc acaacccaca tccaggtgga gcagggtggt ggagcctagc ggaggtgagc 480
ttaaaagggc ctggacctag gcaggcatat taaaaaaata cacatatgtg gacccaactt 540
gaactttgaa aattgtgtta tagatagact gttggacagg taatttgtat ttttgactgt 600
gtggtacatg gactccggta tagagagctt gcttactata ttgttgtggg tgcccttagt 660
gaaactacat ttgtgtttat tgaacaaaag tttcttcaat agatttgtgt tcaaaacgct 720
tttaaggtag tgctgacttt gtagcaatta acaatatagt gttatggata ttaatggtca 780
aaatctccta gaaaatatgt cttacattga tggactgagg gagtatcatt tacatgttac 840
taggatctgt tggtattctt cctcatttga gcatgaactt tgtcattacc ctctgcaggg 900

-continued tgatgctgca gatgctctat caagattcta ttatccacca gttgctgctg taacggtttc 960
gtatccaaag gaagcaatta gaaaagaatg cttaattgat ggggaactcc agggttttgg 1020
ccagttgcat ccacgtagtc aaggagttga gacattaggt atttcttgca atggccaaat 1080
cttaaagctc caaacattat aagtttcttt cttttccagc ttgcttttat tctagcatta 1140
actttatttt atttttgggt ttaatccaag atagagattg tggtataaca gtattattgg 1200
taatatcctt ttgtaggaac aatatacagc tcatcactct ttccaaatcg tgctcctgct 1260
ggtagggtgt tacttctaaa ctacatagga ggtgctacaa acacaggaat tgtttccaag 1320
gttagcaata ctctgccaaa gctattgccg tgtttttatg attatgatgt gtttatatat 1380
ctttttagtg cccttcttta tgaatagaac ttttagtacc aataatatgt tctttaatta 1440
tcactataaa cactaactgc actcaaatca tggaaaattt gagctgctag ttatgtagta 1500
tgatttaaat agtctttatt tggttgccta ttattggctg tatgtttatg atcccatctc 1560
attttcagac tgaaagtgag ctggtagaag cagttgaccg tgacctccga aaaatgctta 1620
taaatcctac agcagtggat cctttagtcc ttggtgtccg agtttggcca caagccatac 1680
ctcagttcct ggtaggacat cttgatcttc tggaggccgc aaaatctgcc ctggaccaag 1740
gtggctatga tgggctgttc ctaggaggga actatgttgc aggagttgcc ctgggcagat 1800
gcattgaggg cgcatatgag agtgccgcgc aaatatatga cttcttgacc aagtatgcct 1860
acaagtgatg gaagtggagc gctgcttgtt aattgttatg ttgcatagat gaggtgagac 1920
caggagtagt aaaaggcgtt acgagtattt ttcattctta tttgtaaatt gcacttctgt 1980 ttttttcct gtcagtaatt agttagattt tagttatgta ggagattgtt gtgttcactg 2040
ccctacaaaa gaatttttat tttgcattcg tttatgagag ctgtgcagac ttatgtaacg 2100
ttttactgta agtatcaaca aaatcaaata ctattctgca agagctaaca taatgtgcaa 2160
ctgagattgc cttgaatgat tatcttgctt ctgcgtgaat aaaaaacctt gtgagtagac 2220
atgcaaatct tgtcaatgtt tttactctga gtaatactaa ttgctactac tatttgatat 2280
ggaacatatt tatttgaggg aatacagtag gggaaacccc ctactgtggt agtatatata 2340
tatattaaca tataaaagag ttagcaaagc tgtacaacaa accccatcaa gggtaaatgg 2400
ctcaaaaaac acccccaagg gtaaaactag aaaacttcac agcaggctga gtctaggaat 2460
taaatctgtg aaggtgtgct ttatattatg tacaaaacat gttttccaag actgaaagga 2520
agcttgattt cctctgaaga tttatttatt tctttgtttc catatctccc atgttgcact 2580
attgaagact tccataaaga attgatgttg acattctgct tttgctttct ggattgtatc 2640
aaagaagttg atgacatgat cccaagagat cccaataaaa ttccaacgcc tagtactgaa 2700
tgggcattca aaaaacagat gatatgtggt cccttctaga tttagattgc atagcacaca 2760
aatgtagttg tcctcttcaa tattgtggtc tcttctagat atggaacaca agggaggggg 2820
agggggtgca ttaaggcctt gtttagttta ccccaaaaac caaaaaaatt tcaaatttca 2880
agatttcccg tcatatttca agatttcccg tcatatcgtc atatcgaatc ttgcgacac 2939

<210> SEQ ID NO 109
<211> LENGTH: 363
<212> TYPE: DNA
<213> ORGANISM: Sorghum halepense

<400> SEQUENCE: 109
tcccagccca cctgcgccgt tccagtgggc catccctaac tccaagccca accgcactac 60
ccacatctcg tcgcgtcatc cactccgccg cacacgcgct gctcgcagct cgcagggata 120

```
tggtcgccgc cgccgccatg gccaccgctg catcggcggc cgcgccgcta ctcaacggga    180
cccgaaggcc tacgcggctc cgccgtcgcg gactccgcgt gcgctgcgct gctgtggcgg    240
gcggcgcggc cgaggcaccg gcctccatgg gcgcgcggct gtccgcggac tgcgtcgtgg    300
tgggcggcgg gatcagtggc ctctgcaccg cgcaggcgct ggccacgcgg cacggcgtcg    360
ggg                                                                   363
```

<210> SEQ ID NO 110
<211> LENGTH: 6802
<212> TYPE: DNA
<213> ORGANISM: Sorghum halepense

<400> SEQUENCE: 110

```
gtggtgggcg gcggcatcag tggcctctgc accgcgcagg cgctggccac gcggcacggc     60
gtcggggacg tgcttgtcac ggaggcccgc gcccgccccg gcggcaacat caccaccgtc    120
gagcgccccg aggaagggta cctctgggag gagggtccca acagcttcca gccatccgac    180
cccgttctct ccatggccgt acgcacctct ctcgctggcg ccccggcgtc ttctgatcag    240
actgttgcgg aggcgtgaaa ttgaaatgct caatggattg tatgcgcgcg cgcaggtgga    300
cagcgggctg aaggatgacc tggtttttgg ggatcccaac gcgccacggt tcgtgctgtg    360
ggaggggaag ctgaggcccg tgccatccaa gcccgccgac ctcccgttct tcgatctcat    420
gagcatccct ggcaagctca gggccggtct cggcgcgctt ggcatccgcc cgcctcctcc    480
agttcgtgct ctccccatgc cgcattctta aatcttgtac gttttgattg ttctattgcc    540
aatggggctg agcgtttccg gcgaaggttt cagggccgcg aggagtcagt ggaggagttt    600
gtgcgccgca acctcggtgc tgaggtcttt gagcgcctaa ttgagccttt ctgctcaggt    660
gcttattgca gtgtgctatt gctgtttgtt ctgatctgct acttgcagcg gttagccgat    720
tatattaaga atttaaacat ttctatgtaa acctaaggtg tctatgctgg tgatccttcc    780
aagctcagta tgaaggctgc atttgggaag gtgtggcggt tagaagaagc tggaggtagt    840
attattggtg gaaccatcaa gacgattcag gagaggggca agaatccaaa accaccgagg    900
gatccgtaag agactgattc attttctttt tattccacta attggctgtt ctgtcatatt    960
gatttgtttt aacctctttt agccgccttc cgaagccaaa agggcagaca gttgcatctt   1020
tcaggaaggg tcttgccatg cttccaaatg ccatcacatc aaggtttgtt cttattgttt   1080
tgtatattta ctaacaaaca tgtccatgtg ttgcaatgaa atgtacatct tgttacgttg   1140
tcgcttggac gacttgcagc tcagatatat atatgcaacg atcgtgtcat ctttccaata   1200
cgtctttgaa tctgactccg taataacgtg gctagatgca tgctgttcta actcatatta   1260
gcatgggttg taaatccggg tcataggtgc acgagggtaa aatatgatgg acggaagaat   1320
cctttgtgct tttaatattg gtaggtactc cagtatgtag atatttattc atgtagcaaa   1380
tcagttacgg atatgaggca tgtggactgt tcagatagat tgatgcctta ggtcaaactt   1440
gtttgcgtaa ttactatcat acaatgtcgt gttataactc ttcatttcat atacatggat   1500
ggggaatgcg cacctactct ttgcacaatt ttgatactaa ctagtgcatt gtcattcttt   1560
ctatccttat ttatgctgtt agtacaatat aggtggatag ctccatgttg tcatttaaaa   1620
ataccaaata tacagctgaa ggtctttatt tcatatacat ggatggggaa tgtgcaccta   1680
ccctttgcac aatgttgata ctaactaggg cattgtcatt ctttccatcc ttatttatgc   1740
tgttagtaca atataggtgg atagctccat gttgtcattt gaaaatacca aatgtacagc   1800
```

-continued

```
tgaaggcata gaaattccat gaagcatggt ttatagagca tgttagtgtg catgttcatt   1860
gcgacttggt tgcaaactag taacgattgt aatattagat ctctgatcaa ggattattct   1920
attcattact cacctttatt caattctgta catttcttca tttacagctt gggtagtaaa   1980
gtcaaactat catggaaact cacgagcatt acaaaatcag atggcaaggg gtatgttttg   2040
gagtatgaaa caccagaagg ggttgttttg gtgcaggcta aaagtgttat catgaccatt   2100
ccatcatatg ttgctagcga cattttgcgt ccactttcag taagtataga ataatcaatt   2160
ttcatgtttt cataaactgg agtattttag cttcttgata ccctaaaata acgttttttt   2220
tgggaaaatt accagtcagg ggtggggttt gcacttgtta agtggttgat gatttctgcc   2280
attctgtggt caacatctcc attgacattt actaaactac tgcaaggcta gcaaaattct   2340
aaaccttgtc ttcattgaca tctgaatgac tgttgtagtg ttgttatctt ccaagtggat   2400
catttgtgtg aaaaaaattg cggaaagtta tggtttttgt ttttcgtact aataatgatg   2460
atagtaaatg ctgagcttgg aaacatgtca atagtgtggt ggaggtcctt tggttgggag   2520
gctgcccacc ggcagaccgg ggctcaaatc ctgggttgca tgaaaaaagg tccctagctg   2580
tgtaactgtc tacagagata tatgtgctgc aggcacgtcc tgggcagcta gcttttgggg   2640
ccttttcttg accctgcagg aaatttctta tgtgatatac ctcgagggag gtcaatcccc   2700
caagggttga gtaaagagct tggatagaac tagagaagat tttatgaaca gactaattga   2760
agtggactgg accatttctt atgctgtcaa tatttgtagg ctttaaaatg acaattcaaa   2820
tatacaagaa aatttttatg ctcttaaatt tatgccgtgt tccttataaa atggcctcag   2880
tgatcagttc gtacaattaa tcatcttaag agaacaattt ccagctagat aattattatg   2940
attaaaaaag aaaacagaga gaagaaatag taccaggaca gactaattat caaggagacc   3000
caaccattgg ttgggatggt gctctaagtg cattgttgat aggttgttgc tgtgatgctt   3060
caataatctg gatatccttt tcccccctata tagtttacta tgatactatc tatattacat   3120
tgccttatat ccagttcaat ttggtccaag tccttcagag gatggtaaaa cgtcagctta   3180
catccaatcc caatcctttt tctttgacta tattctgtat atggctgtaa agacacttat   3240
ttgtttgtcc atatgagtat aggaccatgt tccacagaat gtcttgcgag gagtacccat   3300
gccattatcc tcaaggtccc gaaaataagc tgtagaaaaa ctctggaact aactagacct   3360
agacagttcc tggtggggct ggaaaaataa ctgaacagtt tagttaaatc acattgacat   3420
gcagatttga actgaaaaat aaaatctgaa ctaactagtg aagttcatac aatatttaaa   3480
atgatggtgc cagttgaccc attatagtta ttgctagcta ctggcgacat ttaaattcct   3540
tactctatgt ggcatggcaa cctagttggt tactactcaa gtactctgtc catcaatgta   3600
agatctagtt tgaaaagagt atagcttgca agttttgacc aatataagat gttcacctag   3660
gaagagagga gaggattttt tttttgtttt gaaataaaag acaggactac aggaggcacc   3720
cctggtgcca acactactgt cgtaaggcct ggaaaggaaa gatatgtacc acccttaagg   3780
ggatttaccc atcaaaggac agccctgcga tgttgcagta tatcctcttt tgtcaagaag   3840
gccacctgct ggaccgtttt atgggcgttg tcgaagatcc tcctattcct ctccttccac   3900
aagttccata gaatggggcg ttgcaagcat ggcctggcta ctggcgtggg tttcagtcac   3960
cgctgctacg tggggttgag cttcgcctcc agccattcat gggtgcgagc ttgtccacca   4020
gtgcgggcag cgacaagcat ggctcacacg tgttcatcgt cgccgacagg cagggcccga   4080
cacatatgcc gctggtggtg tgcaggcaag ctcctcccag ctgaagcatc acgggcaagc   4140
ttgtgccctg ttcggttctg gccccatcag cacacacata ggtgagctcg tcacgtagcc   4200
```

```
ggtgtgtgtg tgtgggggaa gacaagggca gcggccagca tggtggatga ggagggagag   4260

tgcggcaggg ctggccctgg agggggaggt ggtggcatga cagctagtga gggaggcacg   4320

gtggccgggg gtggggcaaa ggtgaggcag aggcagaggc atggcggttg gcggagtgga   4380

ggcatgacgg acggcgacat ggaggcgctc gatggaggtg gcgatgcaca acccacagcc   4440

aggtggagca gggtggtgga gcctagcgga ggtgagctta aaagggcctg gacctaggca   4500

ggcatattaa aaaaatacac atatgtggac ccaacttgaa ctttgaaaat tgtgttatag   4560

atagactgtt ggacaggtaa tttgtatttt tgactgtgtg gtacatggac tccggtatag   4620

agagcttgct tactatattg ttgtgggtgc ccttagtgaa actacatttg tgtttattga   4680

acaaaagttt cttcaataga tttgtgttcg aaacgctttt aaggtagtgc tgactttgta   4740

gcaattaaca atatagtgtt atggatatta atggtcaaaa tctcctagaa aatatgtctt   4800

acattgatgg actgagggag tatcaattac atgttactag gatctgttgg tattcttcct   4860

catttgagca tgaactttgt cattaccctc tgcagggtga tgctgcagat gctctatcaa   4920

gattctatta tccaccagtt gctgctgtaa cggtttcgta tccaaaggaa gcaattagaa   4980

aagaatgctt aattgatggg gaactccagg gttttggcca gttgcatcca cgtagtcaag   5040

gagttgagac attaggtatt tcttgcaatg gccaaatctt aaagctccaa acattataag   5100

tttctttctt ttccagcttg cttttatcct agcattaact ttattttatt tttgggttta   5160

atccaagata gagattgtgg tataacagta ttattggtaa tatccttttg taggaacaat   5220

atacagctca tcactctttc caaatcgtgc tcctgctggt agggtgttac ttctaaacta   5280

cataggaggt gctacaaaca caggaattgt ttccaaggtt agcaatactc tgccaaagct   5340

attgccgtgt ttttatgatt atgatgtgtt tatatatctt tttagtgccc ttctttatga   5400

atagaacttt tagtaccaat aatatgttct ttaattatca ctataaacac taactgcact   5460

caaatcatgg aaaatttgag ctgctagtta tgtagtatga tttaaatagt ctttatttgg   5520

ttgcctatta ttggctgtat gtttatgatc ccatctcatt ttcagactga aagtgagctg   5580

gtagaagcag ttgaccgtga cctccgaaaa atgcttataa atcctacagc agtggatcct   5640

ttagtccttg gtgtccgagt ttggccacaa gccatacctc agttcctggt aggacatctt   5700

gatcttctgg aggccgcaaa atctgccctg gaccaaggtg gctatgatgg gctgttccta   5760

ggagggaact atgttgcagg agttgccctg ggcagatgca ttgagggcgc atatgagagt   5820

gccgcgcaaa tatatgactt cttgaccaag tatgcctaca agtgatggaa gtggagcgct   5880

gcttgttaat tgttatgttg catagatgag gtgagaccag gagtagtaaa aggcgttacg   5940

agtatttttc attcttattt gtaaattgca cttctgtttt tttttcctgt cagtaattag   6000

ttagatttta gttatgtagg agattgttgt gttcactgcc ctacaaaaga atttttattt   6060

tgcattcgtt tatgagagct gtgcagactt atgtaacgtt ttactgtaag tatcaacaaa   6120

atcaaatact attctgcaag agctaacata atgtgcaact gagattgcct tgaatgatta   6180

tcttgcttct gcgtgaataa aaaaccttgt gagtagacat gcaaatcttg tcaatgtttt   6240

tactctgagt aatactaatt gctactacta tttgatatgg aacatattta tttgagggaa   6300

tacagtaggg gaaacccccct actgtggtag tatatatata ttaacatata aaagagttag   6360

caaagctgta caacaaaccc catcaagggt aaatggctca aaaaacaccc ccaagggtaa   6420

aactagaaaa cttcacagca ggctgagtct aggaattaaa tctgtgaagg tgtgctttat   6480

attatgtaca aaacatgttt tccaagactg aaaggaagct tgatttcctc tgaagattta   6540
```

tttatttctt tgtttccata tctcccatgt tgcactattg aagacttcca taaagaattg 6600
atgttgacat tctgcttttg ctttctggat tgtatcaaag aagttgatga catgatccca 6660
agagatccca ataaaattcc aacgcctagt actgaatggg cattcaaaaa acagatgata 6720
tgtggtccct tctagattta gattgcatag cacacaaatg tagttgtcct cttcaatatt 6780
gtggtctctt ctagatatgg aa 6802

<210> SEQ ID NO 111
<211> LENGTH: 1366
<212> TYPE: DNA
<213> ORGANISM: Sorghum halepense

<400> SEQUENCE: 111
ctggccacgc ggcacggcgt cggggacgtg cttgtcacgg aggcccgcgc ccgccccggc 60
ggcaacatca ccaccgtcga gcgccccgag gaagggtacc tctgggagga gggtcccaac 120
agcttccagc catccgaccc cgttctctcc atggccgtac gcacctctcg ctggcgcccc 180
ggcgtcttct gatcagactg ttgcggaggc gtgaaattga aatgctcaat ggattgtatg 240
cgcgcgcgca ggtggacagc gggctgaagg atgacctggt ttttggggac cccaacgcgc 300
cacggttcgt gctgtgggag gggaagctga ggcccgtgcc atccaagccc gccgacctcc 360
cgttcttcga tctcatgagc atccctggca agctcagggc cggtctcggc gcgcttggca 420
tccgcccgcc tcctccagtt cgtgctctcc ccatgccgca ttcttaaatc ttgtacgttt 480
tgattgttct attgccaatg ggctgagcg tttccggcga aggtttcagg gccgcgagga 540
gtcagtggag gagtttgtgc gccgcaacct cggtgctgag gtctttgagc gcctaattga 600
gcctttctgc tcaggtgctt attgcagtgt gctattgctg tttgttctga tctgctactt 660
gcagcggtta gccgattata ttaagaattt aaacatttct atgtaaacct aaggtgtcta 720
tgctggtgat ccttccaagc tcagtatgaa ggctgcattt gggaaggtgt ggcggttaga 780
agaagctgga ggtagtatta ttggtggaac catcaagacg attcaggaga ggggcaagaa 840
tccaaaacca ccgagggatc cgtaagagac tgattcattt tctttttatt ccactaattg 900
gctgttctgt catattgatt tgttttaacc tcttttagcc gccttccgaa gccaaaaggg 960
cagacagttg catctttcag gaagggtctt gccatgcttc caaatgccat cacatcaagg 1020
tttgttctta ttgttttgta tatttactaa caaacatgtc catgtgttgc aatgaaatgt 1080
acatcttgtt acgttgtcgc ttggacgact tgcagctcag atatatatat gcaacgatcg 1140
tgtcatcttt ccaatacgtc tttgaatctg actccgtaat aacgtggcta gatgcatgct 1200
gttctaactc atattagcat gggttgtaaa tccgggtcat aggtgcacga gggtaaaata 1260
tgatggacgg aagaatcctt tgtgctttta atattggtag gtactccagt atgtagatat 1320
ttattcatgt agcaaatcag ttacggatat gaggcatgtg gactgt 1366

<210> SEQ ID NO 112
<211> LENGTH: 1417
<212> TYPE: DNA
<213> ORGANISM: Sorghum halepense

<400> SEQUENCE: 112
ggtgaattgg aggccagtag actgatagat gatctcggtc tacaagacaa acagcagtat 60
cctaactccc aacacaagcg ttacattgtc aaagatggag caccagcact gattccttcg 120
gatcccattt cgctgatgaa aagcagtgtt ctttctacaa aatcaaagat tgcgttattt 180
tttgaaccat ttctctacaa gaaagctaac acaagaaacc ctggaaaagt atctgatgag 240
catttgagtg agagtgttgg gagcttcttt gaacgccact tcggaagaga agttgttgac 300
tatcttattg atccatttgt agctggaaca agtgcaggag atccagagtc actatctatt 360
tgtcatgcat tcccagcact gtggaatttg gaaagaaaat atggttcagt tgttgttggt 420
gccatcttgt ctaagctaac agctaaaggt gatccagtaa agacaagacg tgattcatca 480
gcgaaaagaa ggaatagacg cgtgtcgttt tcatttcatg gtggaatgca gtcactaata 540
aatgcacttc acaatgaagt tggagatgat aatgtgaagc ttggtacaga agtgttgtca 600
ttggcgtgta cattagatgg agcccctgca ccaggcgggt ggtcaatttc tgatgattcg 660
aaggatgcta gtggcaagga ccttgctaaa aaccaaacct ttgatgctgt tataatgaca 720
gctccattgt caaatgtcca gaggatgaag ttcacaaaag gtggagctcc ttttgttcta 780
gactttcttc ctaaggtgga ttatctacca ctatctctca tggtgaccgc ttttaagaag 840
gatgatgtca agaaacctct ggaaggattt ggcgtcttaa taccctacaa ggaacagcaa 900
aaacatggtc taaaaaccct tgggactctc ttctcctcaa tgatgttccc agatcgagct 960
cctgacgacc aatatttata tacaacattt gttgggggta gccacaatag agatcttgct 1020
ggagctccaa cgtctattct gaaacaactt gtgacctctg accttaaaaa actcttaggc 1080
gtacaggggc aaccaacttt tgtcaagcat atatactggg gaaatgcttt tcctttgtat 1140
ggtcatgatt acaattctgt attggaagct atagaaaaga tggagaaaaa tcttccaggg 1200
ttcttctacg caggaaataa caaggatggg cttgctgttg ggagtgttat agcttcagga 1260
agcaaggctg ctgaccttgc aatctcgtat cttgaatctc acaccaagca taataattta 1320
cattgaaagc atctgaccta tcctctagca gttgccggca aatttcctca gttcatgtac 1380
aacagaaact gttttgttgc agtctcagaa catcttc 1417

<210> SEQ ID NO 113
<211> LENGTH: 625
<212> TYPE: DNA
<213> ORGANISM: Sorghum halepense

<400> SEQUENCE: 113
acccaagcta aatgaatcac atcaaatgga atcagtcagc attcaaaata gcattgtctc 60
tgtatcacaa aagaatgagg attttgagtg tggaacaagc attgaatgct gcagaactgt 120
aagtgttaaa acactgaatg tgctctggta gaagcatcaa atgaaaagaa ttgccccact 180
gttcactgtg gtgctctgga gttactacct cacttgaagt ctgatgaaca tctgacggaa 240
aaaataatct agacatgtca actgaagtta gaaatgtatc actgccatcc agcaatttgg 300
atatccaacg tacgttatat ctggatagtt ctgttggaaa agttgaagtc cctcatcaac 360
aagaagcacg tgaaattgaa aatagtggaa acaactgtca aagtgacagg gttgaatttg 420
ctgttcatgg caaaagaata atcattgtgg gagcgggccc tgctggttta accgctgctc 480
gccatttgca acgtcaaggt tttcagtca ctattcttga ggcacgagaa aggattggcg 540
gccgtgttta tacagatcgc acatcacttt cggttcctgt agatttgggt cgctagcatt 600
attacagggg tgaggctgat atagc 625

<210> SEQ ID NO 114
<211> LENGTH: 3683
<212> TYPE: DNA
<213> ORGANISM: Sorghum halepense

<400> SEQUENCE: 114

```
caaggtccaa aacatctaac aattcgtctc acaatttaca accaatctat gcaatgaaaa     60
tttttggat ataaactaaa caaggcaagt tgtgacttgt gaagcctgaa gtctggcagc    120
gtcgccgcga gtcccaggct ttcagcgata ccagccgtgc gaaacggcgt gcgagaccca    180
ccgaaaaggc acattttgac cttggcaaac catttcgact acagacttca aaggtcccgc    240
gagacggcga caagtccacc ctccatccct tccccacctc catctctagg ctctagcgac    300
tccgatccgc gcacaaggca acaagcaaat ccccatccaa ttccaagccc caactcaaat    360
gctcgctcgg actgccacgg tctcctccac ttcgccccac tcccatcctt atcgccccac    420
ctccgctcgc agtctccgcc tacgtccggt cctcgcgatg gcgggctccg acgactcccg    480
cgcagctccc gccaggtcgg tcgccgtcgt cggcgccggg gtcaggtgag cgagcgctct    540
ttccctttcc gaccctcggg cgtgagaggg ttttggtgcg tgtttgttgc ctttgaggcg    600
tttgatgaaa tggtgctggg gtgggggtgc tctgtgcctt tgtgcagcgg gctcgtggcg    660
gcgtacaggc tcaggaagag cggcgtgaat gtgacggtgt tcgaggcggc cgacagggcg    720
ggaggaaaga tacggaccaa ttccgagggc gggtttctct gggatgaagg agcgaacacc    780
atggtgagcg catttcagtt ctgcctacaa tttgacggct tcgattgtgt tgtgccattc    840
tgcatagctg cttgcatctg cgtgacttgg attgtgccat tagtcaggag tcagtaagat    900
ggcccaactg aacagcctgc taactgtttg cattagcatc tagtgctaat tgccacgttg    960
tcctgaaaac aagtattacg gtggtgattg tggatctctc cttgttttgt gtgtagattg   1020
gttttaaggc cagcagtagc ggcggagctg gcaaaaatcc acgcttaggg ccagcctaat   1080
gcctaagcaa tctataatgg acccacatac cgatagttca caaaagcaac ggatacaatg   1140
cataatttag aagatatctc tattcaacgt acatttatgc aacaaacatg ataaaaatat   1200
gatgttgtac aaaataagta tctaattata gatcattatt tgattcatcc atgcctatca   1260
tatcatctat atttgcaagt gaacttgaac ctatacacga aatttgaaca tttaaaatca   1320
ctaggggaaa caatataaaa ctacactttg ttggtgaaca aaaatggata accgggaaca   1380
taacatactg gagaataaaa tggagtattg gtccttttca ttgtgtaatt ctagtagaag   1440
cctacaaatg gcagcataaa taattcatgg attcaatttg ttcaattgaa aatttgaaat   1500
agagaggatt ggacctgagc gtagagcttg tctggttgga gaaatcagga ggaaatgagg   1560
aatgaaacac tgagctgctt cattacttgt ttggctcctg cttgcggcac tgtggcagta   1620
ctcctctgca tctcctgcac tgctggacca ggtgactggc accactggac ccactcaatt   1680
gcagcctcat tgggcatcag tggagctggc gtcaaggtct ggcctctagg cgccgtgtct   1740
aggttgggct ggcactatta aaggtccagc cacgccgccg ctagggttag ctggcgcccg   1800
gctagtggga gtgaccaggg gagggagtgc gagggccgag gaagagggca gaggacaatt   1860
tttggacgca aggccgtctg gctgacatgc acctgggcaa accatgaggc ggcctatctg   1920
cttgaattag tttgtgactt gatggcttgg cctataactg atggacttct attgctatgc   1980
taggccacgc ctcaggctca gaccaattta taggaaacct gactaggcat agaattaatg   2040
atggtataag aggttttgga ccacgcctag ggccgtcgcc ctagtggccc taggcgtgta   2100
tccgccaacg gccagcagat aagttgatga ggttacttat tttttttcc ttgcagacag   2160
aaggtgaatt ggaggccagt agactgatag atgatctcgg tctacaagac aaacagcagt   2220
atgtatgtgc aaatgttgcc cacgaagcat tccttgtttt tttgatgatg tcttgatctg   2280
tttccatttc atttagctga tggttcaata tctgtttcag cctaactccc aacacaagcg   2340
ttacattgtc aaagatggag caccagcact ggtaaaaggg ctttgatgta atcatgtgtg   2400
```

tctctctttt cttcctgtat tctgcctcac ctttgaatat cctgcctttt gttctcataa 2460
gattccttcg gatcccattt cgctgatgaa aagcagtgtt ctttctacaa aatcaaaggt 2520
acattcagcc actgaataca aactgtcgat aacaaaatat catagcattg ctagtatcaa 2580
ttcttaccgc cattaattga agtagttact ttgagttaac tacttgataa attattatat 2640
tcctccgttt tttcccttca agctatgcat ttatgatttg tggtgatttt tgtcattttg 2700
ttttaactga attatgtttt atttttggct ctttgtagat tgcgttattt tttgaaccat 2760
ttctctacaa gaaagctaac acaagaaacc ctggaaaagt atctgatgag catttgagtg 2820
agaggtgaac cttcatactc tttgtgtctt gcattgatat gaaatttaaa attggaatca 2880
catatcaata tatcatacta gtattatttt ctttaagtaa gtcttgagct ataccttata 2940
cctattgttt cctcagtgtt ctcaaattct gaatatcaat atattaaggt atcccatata 3000
ttatacacca ttgcagtgtt ttcttttgag tgtggaaata atagaattac catgtcaaca 3060
ttttcagtgt tgggagcttc tttgaacgcc acttcggaag agaagtgagt ttctggaagg 3120
aactatggat aatcaagtga ctgaaagtta acagcttcag tcaacatcag aatgagccat 3180
ggctaagaac atctaaattt cttacaggtt gttgactatc ttattgatcc atttgtagct 3240
ggaacaagtg caggagatcc agagtcacta tctgtgagtt actatgctct ttcccatttt 3300
ttgcatttat ggattttaga tatgcatatt gcttcatatt ttcacagtaa attgtttata 3360
taactaattg tgcataatag tacatgttcc tgattctgtt tttagcgcaa aaagtcgcca 3420
gcctttctga tcagtcaggt cttatcatta acttctatgt tggtttgagt aattgtttgt 3480
tttgtgcaga tttgtcatgc attcccagca ctgtggaatt tggaaagaaa gtaagtcgca 3540
tgccaattgt cttgctcatt gctttagatt gtttttatta cccttttcaa tatggttttg 3600
tcctgttcat attgttcctt ttgctatctt gtttctttcc gtgcattctt atgttaacac 3660
cagcatacgg ttgtacaata tta 3683

<210> SEQ ID NO 115
<211> LENGTH: 3719
<212> TYPE: DNA
<213> ORGANISM: Sorghum halepense

<400> SEQUENCE: 115
ttagatttta gcactttgtt gttacaaata tggttagacc ttaccctttt tgttgaatta 60
tgttcatttg taatttataa tattttctct aaccatgttg cttcatgcct gtgctcccag 120
atatggttca gttgttgttg gtgccatctt gtctaagcta acagctaaag gtgatccagt 180
aaagacaaga cgtgattcat cagcgaaaag aaggaataga cgcgtgtcgt tttcatttca 240
tggtggaatg caggtattcc tccattgttt ttttttcaa gaagaatccc ttgattgaaa 300
tccttttaat tgttttatta ctatcaaaga ttttaattgg gagcccttgg atttttcatc 360
agctctaata attttgttgg tgccatttag aaatggtgag ttcagatttc agaccgtgca 420
agttctttgt ttgttcaact caaggacaca aggacattac ttcacaatga gtatcacttc 480
caagtctcac aacccagaaa agctgttagt gtgtggttat ggtttaacaa gtctcaccat 540
ccatatctag ctctagtgac cctgttacat cctaccataa tcattgtttg tagagttgat 600
acatgcttat tagcttgtga agatacatgt gttttgagca aataaattga agtgaaaata 660
tgtattttta agcaaatgat aagttttaga cattgcagat agtttgcatg gaagcaatga 720
tgactcctga atatactcat ctatcatgag aaatacaaac aaatctagat tttgatactt 780

-continued

```
accttggccc cttatccctt acccactcta tggaatgcat gttttatagc agtgcaatat    840
acatactgtc tgtcatttat gttgttaaag ttgttatatg ttttcttttc tggttgagta    900
agtttaaaag ttctgtgtta tttcagtcac taataaatgc acttcacaat gaagttggag    960
atgataatgt gaagcttggt acagaagtgt tgtcattggc gtgtacatta gatggagccc   1020
ctgcaccagg cgggtggtca atttctgatg attcgaagga tgctagtggc aaggaccttg   1080
ctaaaaacca aacctttgat gctgttataa tgacagtaag aactactaac ctgcatctgt   1140
cttttagagt tttggtctct ggtcaatgat ctggcaaatt ggttgccatt gatctgtaga   1200
gtttaccagc ttggtaatgt tctcagtcag gattttataa acatctgaac aataatattt   1260
gcctttttat ttttttcctt taggctccat tgtcaaatgt ccagaggatg aagttcacaa   1320
aaggtggagc tccttttgtt ctagactttc ttcctaaggt caggttagga tcaacctttt   1380
aggttaagaa acacagcaat tgacattatt gttcttgcaa gatagtatat acaactttac   1440
aagtatgagt ttcactgctt tcattataca catttcattt ttagtctttt ttcaaattat   1500
gcaggtggat tatctaccac tatctctcat ggtgaccgct tttaagaagg aagatgtcaa   1560
gaaacctctg gaaggatttg gcgtcttaat accctacaag gaacagcaaa aacatggtct   1620
aaaaaccctt ggtaggtcac ctcagccttt tttgggctct tttcagtttg caattcttgt   1680
tattttgagc catgaattaa atagcataga gcagcttgcc tcgtacttca cactttggtt   1740
tgcctgagta ttctgttcct catctttaca tgtgccaatg tttatcatgt agggactctc   1800
ttctcctcaa tgatgttccc agatcgagct cctgacgacc aatatttata tacaacattt   1860
gttgggggta gccacaatag agatcttgct ggagctccaa cgtataaatc ttatttcgat   1920
gatttatgtt gtttcctcat ttttaaacta ggtcattctt atagtttacg taaacaggtc   1980
tattctgaaa caacttgtga cctctgacct taaaaaactc ttaggcgtac aggggcaacc   2040
aacttttgtc aagtaagtac acaaacttag tttctaattg taggtatttt tattttcctt   2100
tcttgcactg gcattgttgt ctgccatctt ttagagagtc taaggtttgt gcaaatcttt   2160
tgaccacatg gtcatgtttt tctgttttca ttttttggtg gtactcaggc atatatactg   2220
gggaaatgct tttcctttgt atggtcatga ttacaattct gtattggaag ctatagaaaa   2280
gatggagaaa aatcttccag ggttcttcta cgcaggtaag ccactaaatg cacccttgtt   2340
taaaacaaat gttggatata tgaagttatg aactatgccc cttgtttagt gccttactga   2400
ttaccacaac atttgtgcaa catgtcaatc agctatgatt ttatgatttc ccatgacaac   2460
tcgctttcct tttcttcaga aatgaattct cgtacaaaac aaaacatata attaatattt   2520
ttatatagtt agtgaaccat agtagtaacc ccaaattttg gtgttatagg ttgaaaagtt   2580
taattggact ttattgtctt gtaggaaata acaaggatgg gcttgctgtt gggagtgtta   2640
tagcttcagg aagcaaggct gctgaccttg caatctcgta tcttgaatct cacaccaagc   2700
ataataattt acattgaaag catctgacct atcctctagc agttgccggc aaatttcctc   2760
agttcatgta caacagaaac tgttttgttg cagtctcaga acatcttcgc tccttcaggt   2820
attaaccctt cgtcgaacat ccaccagaaa tgtagcggga aaatgaggtt taaaactatt   2880
ctggtagtcg acatgctctt tttccctcac aagtagccca tgacacttgc tgttggaaat   2940
aaatttaaat ttgttaaatt gtttgagaat acatgtgtga ctttagcagc agagtctttg   3000
tttgagaata catgcatgaa gtattctcaa acaaagacct tacagatgag tgatgacata   3060
ccccattgac caaaggtcga tacctcgatc tcgatggatc acggttcgca ggtcagcttg   3120
tggccaaact gaaagtctgg tgagaatcca ggtaaaagat acgcctgtac gacatgcgtg   3180
```

```
ctcctctgtt gtgtgcataa tcatgatgtt cctctccttt catctttggc cccctctttt   3240

tggcgtctag agcactccat aaccacaagt ggattacatg atgcttgaag cttgggtttg   3300

gttcatacac gcactattta tccatcatta gttttgtata gtttcggaaa ggtgtcttca   3360

tctcaaagtg cactcggctt cagtcaggac gggaaacatg caatgcaagg catggttgtg   3420

agcgaggcag tgcaactgca aaacagcaaa aggatcttgc tgcttggaag ttggaactat   3480

acatggtttg gctccttgtg aggaaaacaa tgagagacac atttgcttgg ccttgggagc   3540

tttaaggcac aagcaaacct gagtagcgca ctccttgtcc tttgggagcc tttatgtcgt   3600

tcgttgtctt ttttctttc ttttcttttc tttttgggc acatccttcc tagtacagta   3660

gtactgggtg tatgggcatt tgagcatgca tggtggccac tgaccttaaa ggagcacat    3719
```

<210> SEQ ID NO 116
<211> LENGTH: 461
<212> TYPE: DNA
<213> ORGANISM: Sorghum halepense

<400> SEQUENCE: 116

```
gcttcctcgg agaccagcct gaacttgctt ccgaaaccaa agttgctccg agaaacggca     60

agaaggtcgc cgtggtcggc tctggtcctt ccggcattgc atgcgccgga gaacttgcgc    120

gcaacggctt tgacgtcacg gtctttgaag cattcttcac cggtggcggc gtattggtat    180

atggcattcc agaattccgt cttccaaagg ctgttgttaa gcgcgagatt gacggcctca    240

aagaccttgg cgtgaagttt gagtacaact cagttgtagg tcgcattact gatgctgacg    300

aacttttcga gaagggcttc gatgccatct acatcgcaac cggcgccggc ctgccaaaac    360

ttctgaacat cccaggtgag aatctcccca atgtcttttt cgcaaacgag tatctcaccc    420

gcgttaacct catgaaggcc aacaacttcc ctgagtatga c                        461
```

<210> SEQ ID NO 117
<211> LENGTH: 6501
<212> TYPE: DNA
<213> ORGANISM: Sorghum halepense

<400> SEQUENCE: 117

```
catcctacgc cgccaccgcc cctctttcac ccccggcggc aggcggctct cgccgccgcc     60

gccgcctcga ggccgtcctc ccctagtcgc aggtatgccc ccgccactcg cgccgtgacg    120

cccccgctgc gaaccccgct caccgccctc ctcccgcccg cagctccggc gccgacctcg    180

ccgcctcgcc ggcccgcctc ggtccaccgc cgtgtcacgg acacggctcc ccggaaagcc    240

cagcctttgc ctgcgacgag catctgtcag gtatgcctgc ccctctctcc ccttcctgcc    300

gcacgaaacc gaccacccca aaccctaata taagcatttt gtatcggatc tgacccagtt    360

gcgttacaag tttatacatg tatattgtac ctactgacaa ttttgttttt gctaaaatta    420

tcgggtgtac acacccatgt cctataccag cttcacagtg ccaggggaga tggaggacac    480

cttggctagt ataaggaaga agttgaagaa gcggaagaaa ggcaaggata gtaatgactt    540

cggtgcagtg gctgaatgtg gacctgaggt tccgacattg gttcaacagg aagatgtaca    600

tggtgttgtt gatataggtg atggtgatgc tgatgagaag agcaatttag atgtcgtgaa    660

actggagggg agtgatgttt ctgggaattg tgctcagggt ttggataatc tgggattgaa    720

agactccttg tcagtgctgt ttgcaagatc tggtcggaag tcacggcagg tctcagagga    780

ggcagaaggc atggaagttt cttgtttgca tgatggggat ggtcttaaca agggatctgg    840
```

-continued

```
tttggcccca gacacggctt ccaagggcac taaaaggaga aggcggcgga caaaggaaga    900
gatgaagaat gcttgtgtac aggatcggaa agcctcattg cctcggaaag caaaggcgaa    960
ggcaaatggt agcaagtcca ctagacacta taaggttggt gctggtcctg ggcaagcttt   1020
gggaggattg tcttctgttt ttaatgaact tgaagagaat gctgcagatg atggattatt   1080
tcaccgatca tcagctgaag agcttctaca agatgtggaa gccagcaaag tactaaatga   1140
tggatcaata aactctttca atggggtcac tgatcacttt gaaatctcag cttgggcaag   1200
caatcaccct gggctggaat cttattcagg aaatcttgat gaaaaaatat cttgcacagc   1260
agcaaatgca accaacgttg gcgtttctga tgcacacaca tgttcccaaa cgctagggaa   1320
ggaaagcagc gatgatgttg actgttctca aggcaagtca ccaacatcaa ccataaaaag   1380
gaaaactgct ctaaaaccaa aacaggtgcc tgggaaatct gttcgacgaa aagaggcagt   1440
attatctgtt gatgctgata ataaaccaac tgagactaca gaaattattg aagcaaatac   1500
tactatggtt attgaggaaa atttggatca gctgcctgtt atggggccca aggattcttg   1560
ttcttcgcat gacattgtag gaaataatcc tatgtgtcta ggtgcagaca tggcagcatc   1620
tgtgaaagat gtggatatag ttgatgtggc agcaccacta gattatgaag acaaggagaa   1680
tgcatgtgca tcaaaggtga aactgaagcg tgtcacacga ggctccaaaa aacgcaagca   1740
tggtgacatg gcatatgagg gcgatgttga ctgggaaact ctaatgcaag agcaggggct   1800
gttctcaaat ccctcagcag gttttccaga tcagtcaata aaaacaaaag atcaaattaa   1860
aacttcagaa gtttatgagg gtggaggaga tactggtgtt gccgcagtac gtgctggcct   1920
aaaggcaaag actattacac cgattgagaa gataaagttc aaggaagttt tgaagcgcaa   1980
gggtggcctt caggagtacc tagagtgcag gtaggttaat gcttccttac catattagta   2040
tcaaatttct gtgcttggtg gcattaaccc tgcatcatga ttttcctata tctgtttctt   2100
tttgtattcc aggaacatga tactaagtcg ctggagcaag gatgttaaac atttattgga   2160
tcttgcagac tgtggtgttt cagatgttcc tttgaaagat gagttgccgc atcaagctct   2220
tactcgtgat gtgtttttat tcttagacca atatgtaagt tgagttgcca ttagttttca   2280
ttattttcca gaattgcctt accaaattaa gccatcaact tccaaattaa gcattgcacg   2340
tctttgatga ctttctgaaa atcattgagc atatgtttca cttttacatg cagccagctt   2400
atagatctca aatttactac taaccttatt accttgttaa agatttttctt ttagttacta   2460
tgttttgctg aattagaaag cgcccgaatg attgcaccct atatgtcatc aattttcagg   2520
gctacataaa tgctggagtt gcgtcagata aggtggcaaa ggggcacgat gacactctgt   2580
atgaggttgt tgaagtaccc aagctaaatg aatcacatca aatggaatca gtcagcattc   2640
aaaattgcat tgtctctgta tcacaaaaga atgaggattt tgagtgtgga acaagcattg   2700
aatgctgcag aactgtaggt gttaaaaaca ctgaatgtgc tctggtagaa gcatcaaatg   2760
aaaagaattg ccccactgtt cactgtggtg ccctggagtt actacctcac ttgaagtctg   2820
atgaacatct gacggaaaaa aataatctag acatgtcaac tgaagttaga aatgcatcac   2880
tgccatccag caatttggat atccaacgta cgttatatct ggatagttct gttggaaaag   2940
ttgacgtccc tcatcaacaa gaagcacgtg aaattgaaaa tagtggaaac aactgtcaaa   3000
gtgacagggt tgaatttgct gttcatggca aaagaataat cattgtggga gcgggccctg   3060
ctggtttaac tgctgctcgc catttgcaac gtcaaggttt ttcagtcact gttcttgagg   3120
cacgagaaag gattggcggc cgtgtttata cagatcgcac atcactttcg gttcctgtag   3180
atttgggtgc tagcattatt acaggggtgg aggctgatat agctactgaa agacgggctg   3240
```

-continued

```
atccatcctc tttgatttgt tctcagcttg gtcttgaact tactacgttg aatagtgctt   3300
gccctctgta tgatgtagta actggtgaca aggttcctga ttctgtggat gaagatttag   3360
aagccgaata caatggcctt cttgaagagc tggcgctgct ttttgcgcaa aatggtgaca   3420
gtgcaattgg tttatccctg gaggatggac tggagtatgc tctcaggaag catcgtgcaa   3480
ctcaacctat ggattctgtg gagcaggatg gccacttgag atttatgaca aattctggag   3540
ctgtagacat ttccgtaagt gcttcaacag gaaaggatat agatcattgt ggaaagaatg   3600
ataagataga tgtcctcagc cctattgaga gaaggcttat gaattggcac tttgcacatt   3660
tagagtatgg ttgtgctgca acgctgaaat ctttatccct tccatactgg aaccaggatg   3720
atgtatatgg aggattcgga ggtgctcatt gcatgatcaa aggtggctat gacactgttc   3780
tacggaatct tgctaaagga cttgatatta ggttaaacca tgttgtaact gaagtactgt   3840
atggacctga ggagttaggt gctagctgta aggatgggag atatgtcaag gtttccactt   3900
caactggaag tgaacttact ggagatgctg tgttaataac tgttcctctt ggttgcttga   3960
aagcagagac aattaaattt tcaccttcct tgccagactg gaaagtatct tctataaacc   4020
ggcttgggtt tggtcttcta aacaagatag tattggagtt ccctgaggta ttttgggatg   4080
ataatgtgga ttactttggt gcaactgcag aagaaacaga tttaagagga cagtgtttta   4140
tgttttggaa tctcagaaag acagttgggg ctccagttct gatagctcta cttgttggga   4200
aggctgctat agatggacaa agcatcagtt ctggcgatca tgttaacaat gctatggtgg   4260
ttctccgaaa gctttttagg aatgcttctg taccagatcc agttgcatcc gttgtgacaa   4320
attggggact tgatcccttt agtagaggtg cttactctta tgttgcagtt ggagcatcag   4380
ggcgagatta tgatattctt ggaaggccag ttgaaaattg cttattcttt gcgggtgaag   4440
caacatgcaa agagcatcca gatactgttg gtggtgcaat tttgagtggt ttgcgagaag   4500
ctgttcgcat cattgactta ctgaacactg gcaatgacta tattgctgag gtggaagcgc   4560
tacagactta ccaaatgcag tcagacagtg aaagaaatga agttagggac atgtcaaata   4620
gacttgaagc atgtgaactt tctactgctc taagtaagaa ctcatctgat gcaatgtatc   4680
caattgttag caaggaatct ttgctgcaag aaatgttctt cagtgcaaag acaacatcag   4740
ggcgcctaca tttggctaag gagttattga agcttcctac agatgttctt aaatcatttg   4800
ctgggtctaa agaaggatta catacgctaa actcttggat acttgtaagt tgattaatga   4860
gttgtttctt taagcattac ataacactgg tacttttcct atattgaagt tcttcatgtt   4920
tgcattttga ttttggcagg attcacttgg gaaaaatgct actcaactac tgcggcactg   4980
tgtgcgtttg cttgtgcttg tttccactga tctggtagct gtacgtttat caggtctgtg   5040
caaagctcag tatctccatg tccctttaaa tggcgtgaga gaatgtctct tgacatgatt   5100
ttcatgttcc tcccttccag ccttatcttt ggaagggtac aaaaccatag gttaggttat   5160
cacattctta ttaggaatct aatttacctt accaatttag caaaaccctt cctattgtac   5220
tttttatgta tttgtttatt cactaggtcg atcaaaggag aacaaataaa caaatatctg   5280
acattactga gagaagagta tccgagtgca ctactacatt gatctatgtt tgttataact   5340
agagcgtgcc gtggatgttt gtataagtta tttgtcattg tagcctggtg acaaacctga   5400
ttcttttttc aacttcatgc aggaattggg aagactgtaa aggaaaaggt ttgtgtgcac   5460
acaagccgag atattcgtgc tatagctcgg cagttggtca gtgtgtggat tgaagttttt   5520
cgtagagaaa aggatagaaa tggtggactc aaattgttgc gtcgaatacc atcaattgaa   5580
```

-continued

```
ttgagtaaga ccaagagtaa ggatctgcaa tcagtaaagc ctgccttacg tgtgccaaat   5640
gaaactttgg acaataataa agtagtttcc cagcgccagc gtacaagatt cgcaagtagt   5700
cagtcaccgc caaagacaaa caagaagtat gagaacaagg aaatgaaatt ggaaactgtg   5760
acagctgctt tgtctgatgg caagttgctt tcccaaaagc aacaacatgg tattgaatct   5820
aaggtggagt gtggcattcc tatgtccgag gaagaagctg ctgcatttgc tgctgccgag   5880
gctgctcgag ttgctgccat agcagctgca caggtctgtg actaaaattt tcttttgatt   5940
aagatttgtc caactaatca ggttttaata tttaccattg accatcctta tcgtctctga   6000
taagaacatt atccataaaa agctgagaaa gattgttatc tgcctctcta tattagagca   6060
gtttcattac ctgacaccac agagttggct gtttatattt tcacaatttc attacctgcc   6120
actgcggaca tggaaattta tgctagttta gtcgttatta agaaggtggt cctagctcag   6180
ttggttgagg gtatgcccaa tttcagttcc tcatcgaagt gaattttcgt gcctattttc   6240
ttaatattac aaagccaacc ttgttcctcg taggttgctt tagttttttt atttaagcgt   6300
tgtttatctg tttcaaaatt cggggcgtgt attttttgtt agacttgttg catactacat   6360
ggtgtgttat tgtgtaccgt gtagctctga atgcaaaact acagagacat tttcattttt   6420
tttccttatt tataatacaa tctgttcccc ttctttctgt tcatttatta ccaagtgaag   6480
cacttatctc cagtattttt a                                             6501
```

<210> SEQ ID NO 118
<211> LENGTH: 6709
<212> TYPE: DNA
<213> ORGANISM: Sorghum halepense

<400> SEQUENCE: 118

```
aggcggctct cgccgccgcc gccgcctcga ggccgtcctc ccctagtcgc aggtatgccc     60
ccgccactcg cgccgtgacg cccccgctgc gaaccccgct caccgccctc ctcccgcccg    120
cagctccggc gccgacctcg ccgcctcgcc gccccgcctc ggtccaccgc cgtgtcacgg    180
acacggctcc ccggaaagcc cagcctttgc ctgcgacgag catctgtcag gtatgcctgc    240
ccctctctcc ccttcctgcc gcacgaaacc gaccacccca aaccctaata taagcatttt    300
gtatcggatc tgacccagtt gcgttacaag tttatacatg tatattgtac ctactgacaa    360
ttttgttttt gctaaaatta tcgggtgtac acacccatgt cctataccag ctccacagtg    420
ccaggggaga tggaggacac cttggctagt ataaggaaga agttgaagaa gcggaagaaa    480
ggcaaggagg gtaatgactt tggtgcagtg gctgaatgtg gacctgaggt tccgacattg    540
gttcaacagg aagatgtaca gggtgttgtt gatataggtg atgctgatgc tgatgagaag    600
agcaatttag atgtcgtgaa actggagggg agtgatgttt ctgggaattg tgctcagggt    660
ttggataatc tggggttgaa agactccttg tcagtgctgt ttgcaagatc tggtcggaag    720
tcacggcagg tctcagagga ggtagaaggc atggaagttt cttgtttgca tgatggggat    780
ggtcttaaca agggatctgg tttggcccca gacacggctt ccaagggcac taaaaggaga    840
aggcggcgga caaaggaaga gatgaagaat gcttgtgtac aggatcggaa agcctcattg    900
cctcggaaag caaaggcgaa ggcaaatggt agcaagtcca ctagacacta taaggttggt    960
gctggtcctg ggcaagcttt gggaggattg tcttctgttt ttaatgaact tgaagagaat   1020
gctgcagatg atggattatt tcaccgatca tcagctgaag agcttctacg agatgtggaa   1080
gccagcaaag tactaaatga tggatcaata aactctttca atggggtcac tgatcacttt   1140
gaaatctcag cttgggcaag caatcaccct gggctggaat cttattcagg aaatcttgat   1200
```

gaaaaaacat cttgcacagc agcaaatgca accaacgttg gcgtttctga tgcacacaca 1260
tgttcccaaa cgctagggaa ggaaagcagc gatgatgttg attgttctca aggcaagtca 1320
ccaacatcaa ccataaaaag gaaaactgct ctaaaaccaa aacaggtgcc tgggaaatct 1380
gttcgacgaa aagaggcagt attatctgtt gatgctgata ataaaccaac tgagactaca 1440
gaaattattg aagcaaatac tactatggtt attgaggaaa atttggatca gctgcctgtt 1500
atggggccca aggattcttg ttcttcgcat gacattgtag gaaataatcc tgtgtgtcta 1560
ggtgcagaca tggcagcacc tgtgaaagat gtggatatag ttgatgtggc agcaccacta 1620
gattatgaag acaaggagaa tgcatgtgca tcaaaggtga aactgaagcg tgtcacacga 1680
ggctccaaaa aacgcaaaca tggtgacatg gcatatgagg gcgatgttga ctgggaaact 1740
ctaatgcaag agcaggggct gttctcaaat ccctcagcag gttttccaga tcagtcaata 1800
aaaacaaaag atcaaattaa aacttcagaa gtttatgagg gtggaggaga tactggtgtt 1860
gccgcagtac gtgctggcct aaaggcaaag actattacac cgattgagaa gataaagttc 1920
aaggaagttt tgaagcgcaa gggtggcctt caggagtacc tagagtgcag gtaggttaat 1980
gcttccttac catattagta tcaaatttct gtgcttggtg gcattaaccc tgcatcatga 2040
ttttcctata tctgtttctt tttgtattcc aggaacatga tactaagtcg ctggagcaag 2100
gatgttaaac atttattgga tcttgcagac tgtggtgttt cagatgttcc tttgaaagat 2160
gagttgccgc atcaagcact tactcgtgat gtgtttttat tcttagacca atatgtaagt 2220
tgagttgcca ttagttttca ttattttcca gaattgcctt accaaattaa gccatcaact 2280
tccaaattaa gcattgcacg tctttgatga ctttctgaaa atcattgagc atatgtttcc 2340
cttttacatg cagccagctt atagatctca aatttactac taaccttatt accttgttaa 2400
agattttctt ttagttacta tgtttttctg aattagaaag cgcccgaatg attgcaccct 2460
atatgtcatc aattttcagg gctacataaa tgctggaatt gcgtcagata aggtggcaaa 2520
ggggcacgat gacactctgt atgaggttgt tgaagtaccc aagctaaatg aatcacatca 2580
aatggaatca gtcagcattc aaaatagcat tgtctctgta tcacaaaaga atgaggattt 2640
tgagtgtgga acaagcattg aatgctgcag aactgtaagt gttaaaaaca ctgaatgtgc 2700
tctggtagaa gcatcaaatg aaaagaattg ccccactgtt cactgtggtg ctctggagtt 2760
actacctcac ttgaagtctg atgaacatct gacggaaaaa aataatctag acatgtcaac 2820
tgaagttaga aatgtatcac tgccatccag caatttggat atccaacgta cgttatatct 2880
ggatagttct gttggaaaag ttgaagtccc tcatcaacaa gaagcacgtg aaattgaaaa 2940
tagtggaaac aactgtcaaa gtgacagggt tgaatttgct gttcatggca aaagaataat 3000
cattgtggga gcgggccctg ctggtttaac tgctgctcgc catttgcaac gtcaaggttt 3060
ttcagtcact gttcttgagg cacgagaaag gattggcggc cgtgtttata cagatcgcac 3120
atcactttcg gttcctgtag atttgggtgc tagcattatt acaggggtgg aggctgatat 3180
agctactgaa agacgggctg atccatcctc tttgatttgt tctcagcttg gtcttgaact 3240
tactacgttg aatagtgctt gccctctgta tgatgtagta actggtgaca aggttcctga 3300
ttctgtggat gaagatttag aagccgaata caatggcctt cttgaagagc tggcgctgct 3360
ttttgcgcaa aatggtgaca gtgcaattgg tttatccctg gaggatggac tggagtatgc 3420
tctcaggaag catcgtgcaa ctcaacctat ggattctgtg gagcaggatg gccacttgag 3480
atttatgaca aattctggag ctgtagacat ttccgtaagt gcttcaacag gaaaggatat 3540

```
agatcattgt ggaaagaatg ataagataga tgtcctcagc cctattgaga gaaggcttat   3600
gaattggcac tttgcacatt tagagtatgg ttgtgctgca acgctgaaat ctttatccct   3660
tccatactgg aaccaggatg atgtatatgg aggattcgga ggtgctcatt gcatgatcaa   3720
aggtggctat gacactgttc tacggaatct tgctaaagga cttgatatta ggttaaacca   3780
tgttgtaact gaagtactgt atggacctga ggagttaggt gctagctgta aggatgggag   3840
atatgtcaag gtttccactt caactggaag tgaatttact ggagatgctg tgttaataac   3900
tgttcctctt ggttgcttga aagcagagac aattaaattt tcaccttcct tgccagactg   3960
gaaagtatct tctataaacc ggcttgggtt tggtcttcta aacaagatag tattggagtt   4020
ccctgaggta ttttgggatg ataatgtgga ttactttggt gcaactgcag aagaaacaga   4080
tttaagagga cagtgtttta tgttttggaa tctcagaaag acagttgggg ctccagttct   4140
gatagctcta cttgttggga aggctgctat agatggacaa agcatcagtt ctggcgatca   4200
tgttaacaat gctatggtgg ttctccgaaa gctttttagg aatgcttctg taccagatcc   4260
agttgcatcc gttgtgacaa attggggact tgatcccttt agtagaggtg cttactctta   4320
tgttgcagtt ggagcatcag ggcgagatta tgatattctt ggaaggccag ttgaaaattg   4380
cttattcttt gcgggtgaag caacatgcaa agagcatcca gatactgttg gtggtgcaat   4440
tttgagtggt ttgcgagaag ctgttcgcat cattgactta ctgaacactg gcaatgacta   4500
tattgctgag gtggaagcgc tacagactta ccaaatgcag tcagacagtg aaagaaatga   4560
agttagggac atgtcaaata gacttgaagc atgtgaactt tctactgctc taagtaagaa   4620
ctcatctgat gcaatgtatc caattgttag caaggaatct ttgctgcaag aaatgttctt   4680
cagtgcaaag acaacatcag ggcgcctaca tttggctaag gagttattga agcttcctac   4740
agatgttctt aaatcatttg ctgggtctaa agaaggatta catacgctaa actcttggat   4800
acttgtaagt tgattaatga gttgtttctt taagcattac ataacactgg tacttttcct   4860
atattgaagt tcttcatgtt tgcattttga ttttggcagg attcacttgg gaaaaatgct   4920
actcaactac tgcggcactg tgtgcgtttg cttgtgcttg tttccactga tctggtagct   4980
gtacgtttat caggtctgtg caaagctcag tatctccatg tccctttaaa tggcgttaga   5040
gaatgtctct tgacatgatt ttcatgttcc tcccttccag ccttatcttt ggaagggtac   5100
aaaaccatag gttaggttat cacattctta tttaggaatc taatttacct taccaattta   5160
gcaaagccct tcctattgta ctttttatgt atttgtttat tcactaggtc gatcaaagga   5220
gaactactga gtatctgagt gcactactac attgatctat gtttgttata actagagcgt   5280
gccgtggatg tttgtataag ttatttgtca ttgtagcctg gtgacaaacc tgattcttct   5340
tttttcaact tcatgcagga attgggaaga ctgtaaagga aaaggtttgt gtgcacacaa   5400
gccgagatat tcgtgctata gctcggcagt tggtcagtgt gtggattgaa gtttttcgta   5460
gagaaaagga tagaaatggt ggactcaaat tgctgcgtcg aataccatca attgaattga   5520
gtaagaccaa gagtaaggat ctgcaatcag taaagcctgc cttacgtgtg ccaaatgaaa   5580
ctttggacaa taataaagta gtttcccagc gccagcgtac aagattcgca agtagtcagt   5640
caccgccaaa gacaaacaag aagtatgaga acaaggaaat gaaattggaa actgtgacag   5700
ctgctttgtc tgatggcaag ttgctttccc aaaagcaaca acatggtatt gaatctaagg   5760
tggagtgtgg cattcctatg tccgaggaag aagctgctgc atttgctgct gccgaggctg   5820
ctcgagttgc tgccatagca gctgcacagg tctgtgacta aaattttctt ttgattaaga   5880
tttgtccaac taatcaggtt ttaatattta ccattgacca tccttatcgt ctctgataag   5940
```

aacattatcc ataaaaagct gagaaagatt gttatctgcc tctctatatt agagcagttt 6000
cattacctga caccacagag ttggctgttt atattttcac aatttcatta cctgccactg 6060
cggacatgga aatttatgct agtttagtcg ttattaagaa ggtggtccta gctcagttgg 6120
ttgagggtat gcccaatttc agttcctcat cgaagttaat ttttgtgcct attttcttaa 6180
tattacaaag ccaaccttgt tcctcgtagg ttgctttagt tttttattt aagcgttgtt 6240 tatctgtttc aaaattcggg gcgtgtattt tttgttagac ttgttgcata ctacatggtg 6300
tgttattgtg taccgtgtag ctctgaatgc aaaactacag agacattttc attttttttcc 6360 ttatttataa tacaatctgt tccccttctt tctgttcatt tattaccaag tgaagcactt 6420
atctccagta tttttaaaag gatatccttt ttaaaatgaa ctagtttggt catttccatg 6480
ttattttctt gaatttataa tctccttatt ttgtgcatgt ttttgggaca taccttgcat 6540
gcaactatta gagcaagtat atttatcact gttgatcgaa tatatcacta aaaatggaaa 6600
ttttaaaatt aaacatggaa attggaggtt tagaaatttc aaacttgtaa gcagttttaa 6660
ctgactagtt tattgtttag attcagtaac tgagataatc aatagaaat 6709

<210> SEQ ID NO 119
<211> LENGTH: 6631
<212> TYPE: DNA
<213> ORGANISM: Sorghum halepense

<400> SEQUENCE: 119
tctcacaatt tacaaccaat ctatgcaatg aaaatttttt ggatataaac taaacaaggc 60
ctaagttgtg acttgtgaag cctgaaggct ggcagcgtcg ccgcgagtct caggctttca 120
gcgataccag ccgtgcgaaa cggcgtgcga gacccaccga aaaggcacat tttgaccttg 180
gcaaaccatt tcgactacag acttcaaagg tcccgcgaga cggcgacaag tccaccctcc 240
atcccttccc cacctccatc tctaggctct agcgactccg atccgtgcac aaggcaacaa 300
gcaaatcccc atccagttcc aagccccaac tcaaatgctc gctcggactg ccacggtctc 360
ctccacttcg ccccactccc atccttatcg ccccacctcc gctcgcagtc tccgcctacg 420
tccggtcctc gcgatggcgg gctccgacga ctcccgcgca gctcccgcca ggtcggtcgc 480
cgtcgtcggc gccggggtca ggtgagcgag cgctctttcc ctttccgacc ctcgggcgtg 540
agagggtttt ggtgcgtgtt tgttgccttt gaggcgtttg atgaaatggt gctggggtgg 600
gggtgctctg tgcctttgtg cagcgggctc gtggcggcgt acaggctcag gaagagcggt 660
gtgaatgtga cggtgttcga ggcggccgac agggcgggag gaaagatacg gaccaattcc 720
gagggcgggt ttctctggga tgaaggagcg aacaccatgg tgagcgcatt tcagttctgc 780
ctacaatttg acggcttcga ttgtgttgtg ccattctgca tagctgcttg catctgcgtg 840
acttggattg tgccattagt caggagtcag taagatggcc caactgaaca gcctgctaac 900
tgtttgcatt agcatctagt gctaattgcc acgttgtcct gaaaacaagt attacggtgg 960
tgattgtggt tctctccttg ttttgtgtgt agattggttt taaggccagc agtagcggcg 1020
gagctggcaa aaatccacgc ttagggccag cctaatgcct aagcaatcta taatggaccc 1080
acataccgat agttcacaaa agcaacggat acaatgcata atttagaaga tatctctatt 1140
caacatacat ttatgcaaca aacatgataa aaatatgatg ttgtacaaaa taagtatcta 1200
attatagatc attatttgat tcatccatgc ctatcatatc atctatattt gcaagtgaac 1260
ttgaacctat acacgaaatt tgaacattta aaatcactag ggaaacaat ataaaactac 1320

-continued

```
actttgttgg tgaacaaaaa tggataaccg ggaacataac atactggaga ataaaatgga   1380
gtattggtcc ttttcattgt gtaattctag tagaagccta caaatggcag cataaataat   1440
tcatggattc aatttgttca attgaaaatt tgaaatagag aggattggac ctgagcatag   1500
agcttgtctg gttggagaaa tcaggaggaa atgaggaatg aaacactgag ctgcttcttt   1560
acttgtttgg ctcctgcttg cggcactgtg gcattactcc tctgcatctc ctgcactgct   1620
ggaccaggtg actggcacca ctggacccac tcaattgcag cctcactggg catcagtgga   1680
gctggcgtca aggtctggcc tctaggcgcc gtgtctaggt tgggctggca ctattaaagg   1740
tccagccacg ccgccgctag ggttagctgg cgcccggcta gtgggagtga ccaggggagg   1800
gagtgtgagg gccgaggaag agggcagagg acaatttttg gacgcaaggc cgtctggctg   1860
acatgcacct gggcaaacca tgaggcggcc tatctgcttg aattagtttg tgacttgatg   1920
gcttggccta taactgatgg acttctattg ctatgctagg ccacgcctca ggctcagacc   1980
aatttatagg aaacctgact aggcatagaa ttaatgatgg tataagaggt tttggaccac   2040
gcctagggcc gtcgccctag tggccctagg cgtgtatccg ccaacggcca gcagataagt   2100
tgatgaggtt acttattttt ttttccttgc agacagaagg tgaattggag gccagtagac   2160
tgatagatga tctcggtcta caagacaaac agcagtatgt atgtgcaaat gttgcccacg   2220
aagcattcct tgtttttttg atgatgtctt gatctgtttc catttcattt agctgatggt   2280
tcaatatctg tttcagccta actcccaaca caagcgttac attgtcaaag atggagcacc   2340
agcactggta aaagggcttt gatgtaatca tgtgtgtctc tcttttcttc ctgtattctg   2400
cctcaccttt gaatatcctg ccttttgttc tcataagatt ccttcggatc ccatttcgct   2460
gatgaaaagc agtgttcttt ctacaaaatc aaaggtacat tcagccactg aatacaaact   2520
gtcgataaca aaatatcata gcattgctag tatcaattct taccgccatt aattgaagta   2580
gttactttga gttaactact tgataaatta ttatattcct ccgtttttc ccttcaagct   2640
atgcatttat gatttgtggt gatttttgtc attttgtttt aactgaatta tgttttattt   2700
ttggctcttt gtagattgcg ttattttttg aaccatttct ctacaagaaa gctaacacaa   2760
gaaaccctgg aaaagtatct gatgagcatt tgagtgagag gtgaaccttc atactctttg   2820
tgtcttgcat tgatatgaaa tttaaaattg gaatcacata tcaatatatc atactagtat   2880
tattttcttt aagtaagtct tgagctatac cttataccta ttgtttcctc agtgttctca   2940
aattctgaat atcaatatat taaggtatcc catatattat acaccattgc agtgtttcct   3000
tttgagtgtg gaaataatag aattaccatg tcaacatttt cagtgttggg agcttctttg   3060
aacgccactt cggaagagaa gtgagtttct ggaaggaact atggataatc aagtgactga   3120
aagttaacag cttcagtcaa catcagaatg agccgtggct aagaacatct aaatttctta   3180
caggttgttg actatcttat tgatccattt gtagctggaa caagtgcagg agatccagag   3240
tcactatctg tgagttacta tgctctttcc catttttgc atttatggat tttagatatg   3300
catattgctt catattttca cagtaaattg tttatataac taattgtgca taatagtaca   3360
tgttcctgat tctgttttta gcgcaaaaag tcgccagcct ttctgatcag tcaggtctta   3420
tcattaactt ctatgttggt ttgagtaatt gtttgttttg tgcagatttg tcatgcattc   3480
ccagcactgt ggaatttgga aagaaagtaa gtcgcatgcc aattgtcttg ctcattgctt   3540
tagattgttt ttattaccct tttcaatatg gttttgtcct gttcatattg ttccttttgc   3600
tatcttgttt ctttccgtgc attcttatgt taacaccagc atacggttgt acaatattat   3660
catatcagtt tgaaactgtt gagatctttc aagtcagcat tttattatat caccatcaat   3720
```

cttagtgtct catgtctttc ttgaagtagc tactttacct ttttgatttt ctgttaagag 3780
tttcatgaat tgggcattgg caaatgaacc cctgtttatg ctgcattgct gcttcctgtt 3840
ttcaccatat tcgtcttcct tttcttttta tcatcttttc tgataaccta gtgctatttt 3900
tccttgaaat ttagatttta gcactttgtt gttacaaata tggttagacc ttaccctttt 3960
tgttgaatta tgttcatttg taatttataa tattttctct aaccatgttg cttcatgcct 4020
gtgctcccag atatggttca gttgttgttg gtgccatctt gtctaagcta acagctaaag 4080
gtgatccagt aaagacaaga cgtgattcat cagcgaaaag aaggaataga cgcgtgtcgt 4140
tttcatttca tggtggaatg caggtattcc tccattgttt tttttcaag aagaatccct 4200
tgattgaaat ccttttaatt gttttattac tatcaaagat tttaattggg agcccttgga 4260
tttttcatca gctctaataa ttttgttggt gccatttaga aatggtgagt tcagatttca 4320
gaccgtgcaa gttctttgtt tgttcaactc aaggacacaa ggacattact tcacaatgag 4380
tatcacttcc aagtctcaca acccagaaaa gctgttagtg tgtggttatg gtttaacaag 4440
tctcaccatc catatctagc tctagtgacc ctgttacatc ctaccataat cattgtttgt 4500
agagttgata catgcttatt agcttgtgaa gatacatgtg ttttgagcaa ataaattgaa 4560
gtgaaaatat gtatttttaa gcaaatgata agttttagac attgcagata gtttgcatgg 4620
aagcaatgat gactcctgaa tatactcatc tatcatgaga aatacaaaca aatctagatt 4680
ttgatactta ccttggcccc ttatccctta cccactctat ggaatgcatg ttttatagca 4740
gtgcaatata catactgtct gtcatttatg ttgttaaagt tgttatatgt tttcttttct 4800
ggttgagtaa gtttaaaagt tctgtgttat ttcagtcact aataaatgca cttcacaatg 4860
aagttggaga tgataatgtg aagcttggta cagaagtgtt gtcattggcg tgtacattag 4920
atggagcccc tgcaccaggc gggtggtcaa tttctgatga ttcgaaggat gctagtggca 4980
aggaccttgc taaaaaccaa acctttgatg ctgttataat gacagtaaga actactaacc 5040
tgcatctgtc ttttagagtt ttggtctctg gtcaatgatc tggcaaattg gttgccattg 5100
atctgtagag tttaccagct tggtaatgtt ctcagtcagg attttataaa catctgaaca 5160
ataatatttg ccttttttatt tttttccttt aggctccatt gtcaaatgtc cagaggatga 5220
agttcacaaa aggtggagct ccttttgttc tagactttct tcctaaggtc aggttaggat 5280
caacctttta ggttaagaaa cacagcaatt gacattattg ttcttgcaag atagtatata 5340
caactttaca attatgagtt tcactgcttt cattatacac atttcatttt tagtcttttt 5400
tcaaattatg caggtggatt atctaccact atctctcatg gtgaccgctt ttaagaagga 5460
tgatgtcaag aaacctctgg aaggatttgg cgtcttaata ccctacaagg aacagcaaaa 5520
acatggtcta aaaacccttg gtaggtcacc tcagcctttt ttgggctctt ttcagtttgc 5580
aattcttgtt attttgagcc atgaattaaa tagcatagag cagcttgcct cgtacttcac 5640
actttggttt gcctgagtat tctgttcctc atctttacat gtgccaatgt ttatcatgta 5700
gggactctct tctcctcaat gatgttccca gatcgagctc ctgacgacca atatttatat 5760
acaacatttg ttgggggtag ccacaataga gatcttgctg gagctccaac gtataaatct 5820
tatttcgatg atttatgttg tttcctcatt tttaaactag gtcattctta tagtttacgt 5880
aaacaggtct attctgaaac aacttgtgac ctctgacctt aaaaaactct taggcgtaca 5940
ggggcaacca acttttgtca agtaagtaca caaacttagt ttctaattgt aggtattttt 6000
attttccttt cttgcactgg cattgttgtc tgccatcttt tagagagtct aaggtttgtg 6060
caaatctttt gaccacatgg tcatgttttt ctgttttcat tttttggtgg tactcaggca 6120
tatatactgg ggaaatgctt ttcctttgta tggtcatgat tacaattctg tattggaagc 6180
tatagaaaag atggagaaaa atcttccagg gttcttctac gcaggtaagc cactaaatgc 6240
acccttgttt aaaacaaatg ttggatatat gaagttatga actatgcccc ttgtttagtg 6300
ccttactgat taccacaaca tttgtgcaac atgtcaatca gctatgattt tatgatttcc 6360
catgacaact cgctttcctt ttcttcagaa atgaattctc gtacaaaaca aaacatataa 6420
ttaatatttt tatatagtta gtgaaccata gtagtaaccc caaattttgg tgttataggt 6480
tgaaaagttt aactggactt tattgtcttg taggaaataa caaggatggg cttgctgttg 6540
ggagtgttat agcttcagga agcaaggctg ctgaccttgc aatctcgtat cttgaatctc 6600
acaccaagca taataattta cattgaaagc a 6631

<210> SEQ ID NO 120
<211> LENGTH: 1932
<212> TYPE: DNA
<213> ORGANISM: Sorghum halepense

<400> SEQUENCE: 120
cgagcgccgt ggcgagcgta gggctggact ggacgagggc agcccaatag tggtcggcaa 60
cctcgtcgac ctctgatccc atctggtggg tggtgtgtgc attgtccgtg gtcacagcga 120
tgacgctata ccgagccgcc gacgggcgcg tggcatgcgg tgttccagca aaaagcgtgt 180
tggtttcgtg aagaggtcat cgtgccggta tagttttcga ggcctgccgc agcaggcgtg 240
ccaacttagc tcagtcggta gagcgacgct ctcgtaaagc gtaggtcacg ggttcgattc 300
ccgtagttgg ctccacgttc ccagagcatt gctgacaagg taccgcagtg gtccgctcaa 360
tcccgatttg cgaccgctcg tcccacgagg tcaaacttcg gatcgaacag gggcgacgct 420
cagctcgtca gaggcgccag gtacgatcaa ctcaccacga ttcatcgatc acggtccggc 480
catgagttcg gtccgtccag cggaattgca aggggacgca tgtacgacag catcatcatt 540
ggcgcgggtc tagccggact cacggctgct gaagagctcg cctccgcagg acactcggtg 600
gtggtcctgg aggcccgagc ccgggtaggc ggccgcttag aaaacgctga gttatccaac 660
ggacaggtcg ttgaactggg tggccagtgg gtgggagaag ggcatgagga acttcgctcc 720
ctcctctcct cacaagggtt agaactggtt gattcgaccg acggcgacgt cgttgtcaag 780
gccaggggca gggtctctca cgtcacaagt ttgtccgagc cgtccgctca ttccctcagc 840
cccttcgaat tggctgacct cggccagggc ctgctgaggt tccgtcgtct ggccgatcgt 900
gttgctaata acaagggctg ggcggcggct aatgccacct ggttgaacca gtcgttgagc 960
caatggacag cctcgaatgt tcgtaccgag gccggtcgtg gctacatcac gaacctcttc 1020
cgtcaagcct tcggtgtgtc tgccaatgac actcctctct tcaacggtct ggctaaggcc 1080
aacgccggtg tggacttgga atccctcgtc gccgtcaacg gtggccttaa gcagcagcgc 1140
gttaagggcg gggttgctca ggttacccgc aacctcgctg agcctctcgg tgacgatctt 1200
aaactctcca gcccggtccg atccgttcat agtgacgacg acggcgttac cgtcaccact 1260
actgatggca cgcagtatca gggacgtagc gtcatcgtca ccgtgccgcc gcggctactt 1320
aaggacatga cattcgagcc agcgctgcct gctgagcgtc tcgagatggc cgacaaggtg 1380
ccagctggca atgtcatcaa ggcctacctc gtttatgaca gcccatggtg gcgcacctct 1440
ggtgcttccg gccagatggg tgctgacgag ggcgctgtcc gcgtcatttt tgatgcctca 1500
gacgacgaga ccggcaaggg aatcctcatg ggcttcttcg agggcgccga ggcttccggc 1560
tacgggaaac tttcgatcgg tctgcgtcaa cgtgcctttg aagaggtcgt cgagtcggcc 1620
ttcggcaagg cccccagctc gccgatcgag taccttgatc gcgactggct cgctgagcct 1680
tacaccggcg gatgccacgg agcccacttc gctcccagtt tgtggacgac tacggggccg 1740
atccttgccg agccgctggg ccgggtgctc ttcgcggggg ctgagtacgc ctcttctttc 1800
aacggttata tggagggcgc actgcgcgct gctgctcgcg ctgctcagga ggtcctcgac 1860
ctgctctgag ccaagacgat cagccactga cttcttctgc ggcgaaccgt gccacgaggc 1920
cagcgtcaga gg 1932

<210> SEQ ID NO 121
<211> LENGTH: 30
<212> TYPE: DNA
<213> ORGANISM: Sorghum halepense

<400> SEQUENCE: 121
ggagaatact attttctgga gcttaatccc 30

<210> SEQ ID NO 122
<211> LENGTH: 30
<212> TYPE: DNA
<213> ORGANISM: Sorghum halepense

<400> SEQUENCE: 122
gggaaagtga aggagataac ttttaaagcc 30

<210> SEQ ID NO 123
<211> LENGTH: 30
<212> TYPE: DNA
<213> ORGANISM: Sorghum halepense

<400> SEQUENCE: 123
ggatagcatg gaagatttag tctctgcccc 30

<210> SEQ ID NO 124
<211> LENGTH: 30
<212> TYPE: DNA
<213> ORGANISM: Sorghum halepense

<400> SEQUENCE: 124
ggtgaaactc aagttggatt gtgatgggcc 30

<210> SEQ ID NO 125
<211> LENGTH: 30
<212> TYPE: DNA
<213> ORGANISM: Sorghum halepense

<400> SEQUENCE: 125
ggtcgcttgg atcttggaga tgtcaacacc 30

<210> SEQ ID NO 126
<211> LENGTH: 30
<212> TYPE: DNA
<213> ORGANISM: Sorghum halepense

<400> SEQUENCE: 126
ggcttatgga agcattggta tatccaaacc 30

<210> SEQ ID NO 127
<211> LENGTH: 30
<212> TYPE: DNA

<213> ORGANISM: Sorghum halepense

<400> SEQUENCE: 127
ggcttatgga agcattggta tatccaaacc 30

<210> SEQ ID NO 128
<211> LENGTH: 30
<212> TYPE: DNA
<213> ORGANISM: Sorghum halepense

<400> SEQUENCE: 128
ggaggatcca atgcttcgcc atgtggaacc 30

<210> SEQ ID NO 129
<211> LENGTH: 30
<212> TYPE: DNA
<213> ORGANISM: Sorghum halepense

<400> SEQUENCE: 129
ggtctcaggg cttaaaaacc tcgtctatcc 30

<210> SEQ ID NO 130
<211> LENGTH: 30
<212> TYPE: DNA
<213> ORGANISM: Sorghum halepense

<400> SEQUENCE: 130
ggagaatact attttctgga gcttaatccc 30

<210> SEQ ID NO 131
<211> LENGTH: 30
<212> TYPE: DNA
<213> ORGANISM: Sorghum halepense

<400> SEQUENCE: 131
gggcgaatac tattttttgg agcttaatcc 30

<210> SEQ ID NO 132
<211> LENGTH: 30
<212> TYPE: DNA
<213> ORGANISM: Sorghum halepense

<400> SEQUENCE: 132
ggaggatcca atgcttcgcc atgtggaacc 30

<210> SEQ ID NO 133
<211> LENGTH: 30
<212> TYPE: DNA
<213> ORGANISM: Sorghum halepense

<400> SEQUENCE: 133
ggaaggttac aatgaagtaa aatacacccc 30

<210> SEQ ID NO 134
<211> LENGTH: 30
<212> TYPE: DNA
<213> ORGANISM: Sorghum halepense

<400> SEQUENCE: 134
ggtaatattg acaatgaagt aggacgcgcc 30

<210> SEQ ID NO 135
<211> LENGTH: 30

<212> TYPE: DNA
<213> ORGANISM: Sorghum halepense

<400> SEQUENCE: 135
ggagaatact attttctgga gcttaatccc 30

<210> SEQ ID NO 136
<211> LENGTH: 30
<212> TYPE: DNA
<213> ORGANISM: Sorghum halepense

<400> SEQUENCE: 136
ggtgaaactc aagttggatt gtgatgggcc 30

<210> SEQ ID NO 137
<211> LENGTH: 30
<212> TYPE: DNA
<213> ORGANISM: Sorghum halepense

<400> SEQUENCE: 137
ggaacatgaa gctgtccacg ccagaattcc 30

<210> SEQ ID NO 138
<211> LENGTH: 30
<212> TYPE: DNA
<213> ORGANISM: Sorghum halepense

<400> SEQUENCE: 138
ggaagtggtg cgattgccag tgcatattcc 30

<210> SEQ ID NO 139
<211> LENGTH: 30
<212> TYPE: DNA
<213> ORGANISM: Sorghum halepense

<400> SEQUENCE: 139
ggtcaggtgt ggttcccaga ttctgcagcc 30

<210> SEQ ID NO 140
<211> LENGTH: 30
<212> TYPE: DNA
<213> ORGANISM: Sorghum halepense

<400> SEQUENCE: 140
ggtgtgctgg tcgctaacaa tgggatggcc 30

<210> SEQ ID NO 141
<211> LENGTH: 30
<212> TYPE: DNA
<213> ORGANISM: Sorghum halepense

<400> SEQUENCE: 141
ggtcgcttgg atcttggaga tgtcaacacc 30

<210> SEQ ID NO 142
<211> LENGTH: 30
<212> TYPE: DNA
<213> ORGANISM: Sorghum halepense

<400> SEQUENCE: 142
ggttggatcc aacccaaccc acccaacccc 30

<210> SEQ ID NO 143

<211> LENGTH: 30
<212> TYPE: DNA
<213> ORGANISM: Sorghum halepense

<400> SEQUENCE: 143
ggatagcatg gaagatttag tctctgcccc 30

<210> SEQ ID NO 144
<211> LENGTH: 30
<212> TYPE: DNA
<213> ORGANISM: Sorghum halepense

<400> SEQUENCE: 144
ggtgaaactc aagttggatt gtgatgggcc 30

<210> SEQ ID NO 145
<211> LENGTH: 30
<212> TYPE: DNA
<213> ORGANISM: Sorghum halepense

<400> SEQUENCE: 145
ggtcgcttgg atcttggaga tgtcaacacc 30

<210> SEQ ID NO 146
<211> LENGTH: 30
<212> TYPE: DNA
<213> ORGANISM: Sorghum halepense

<400> SEQUENCE: 146
ggtgtgctgg tcgctaacaa tgggatggcc 30

<210> SEQ ID NO 147
<211> LENGTH: 30
<212> TYPE: DNA
<213> ORGANISM: Sorghum halepense

<400> SEQUENCE: 147
ggcgctgctg cctggccggc tggctcagcc 30

<210> SEQ ID NO 148
<211> LENGTH: 30
<212> TYPE: DNA
<213> ORGANISM: Sorghum halepense

<400> SEQUENCE: 148
ggattggact ggggacgccc cccagcggcc 30

<210> SEQ ID NO 149
<211> LENGTH: 30
<212> TYPE: DNA
<213> ORGANISM: Sorghum halepense

<400> SEQUENCE: 149
ggtgtgctgg tcgctaacaa tgggatggcc 30

<210> SEQ ID NO 150
<211> LENGTH: 30
<212> TYPE: DNA
<213> ORGANISM: Sorghum halepense

<400> SEQUENCE: 150
ggcgctgctg cctggccggc tggctcagcc 30

<210> SEQ ID NO 151
<211> LENGTH: 30
<212> TYPE: DNA
<213> ORGANISM: Sorghum halepense

<400> SEQUENCE: 151
ggattggact ggggacgccc cccagcggcc 30

<210> SEQ ID NO 152
<211> LENGTH: 30
<212> TYPE: DNA
<213> ORGANISM: Sorghum halepense

<400> SEQUENCE: 152
gggagagtgg atttggggtt gtttcaaccc 30

<210> SEQ ID NO 153
<211> LENGTH: 30
<212> TYPE: DNA
<213> ORGANISM: Sorghum halepense

<400> SEQUENCE: 153
ggttcattcc ccggtcaagg gtgagcatcc 30

<210> SEQ ID NO 154
<211> LENGTH: 30
<212> TYPE: DNA
<213> ORGANISM: Sorghum halepense

<400> SEQUENCE: 154
gggccttggc aacttccccg gcgacgaccc 30

<210> SEQ ID NO 155
<211> LENGTH: 30
<212> TYPE: DNA
<213> ORGANISM: Sorghum halepense

<400> SEQUENCE: 155
gggtgatgtg ttatttatgt gatgttctcc 30

<210> SEQ ID NO 156
<211> LENGTH: 30
<212> TYPE: DNA
<213> ORGANISM: Sorghum halepense

<400> SEQUENCE: 156
gggccttggc aacttccccg gcgacgaccc 30

<210> SEQ ID NO 157
<211> LENGTH: 30
<212> TYPE: DNA
<213> ORGANISM: Sorghum halepense

<400> SEQUENCE: 157
gggtgatgtg ttatttatgt gatgttctcc 30

<210> SEQ ID NO 158
<211> LENGTH: 30
<212> TYPE: DNA
<213> ORGANISM: Sorghum halepense

<400> SEQUENCE: 158
gggtgatgtg ttatttatgt gatgttctcc 30

<210> SEQ ID NO 159
<211> LENGTH: 30
<212> TYPE: DNA
<213> ORGANISM: Sorghum halepense

<400> SEQUENCE: 159
gggccttggc aacttccccg gtgacgaccc 30

<210> SEQ ID NO 160
<211> LENGTH: 30
<212> TYPE: DNA
<213> ORGANISM: Sorghum halepense

<400> SEQUENCE: 160
ggagcggaga cggaggaagg cgtggcaccc 30

<210> SEQ ID NO 161
<211> LENGTH: 30
<212> TYPE: DNA
<213> ORGANISM: Sorghum halepense

<400> SEQUENCE: 161
ggccgccaaa taggccacca cggcaccacc 30

<210> SEQ ID NO 162
<211> LENGTH: 30
<212> TYPE: DNA
<213> ORGANISM: Sorghum halepense

<400> SEQUENCE: 162
ggccaagagc atttgcacgt caccaatgcc 30

<210> SEQ ID NO 163
<211> LENGTH: 30
<212> TYPE: DNA
<213> ORGANISM: Sorghum halepense

<400> SEQUENCE: 163
ggataatagc cgatacagta gctgtcagcc 30

<210> SEQ ID NO 164
<211> LENGTH: 30
<212> TYPE: DNA
<213> ORGANISM: Sorghum halepense

<400> SEQUENCE: 164
gggcggtgaa cactgcgact gacccgcccc 30

<210> SEQ ID NO 165
<211> LENGTH: 30
<212> TYPE: DNA
<213> ORGANISM: Sorghum halepense

<400> SEQUENCE: 165
ggactggatg cgcctgaaaa tcaccgcacc 30

<210> SEQ ID NO 166
<211> LENGTH: 30
<212> TYPE: DNA
<213> ORGANISM: Sorghum halepense

<400> SEQUENCE: 166
ggcgtcccca tcgaaaccat cgcacaagcc 30

<210> SEQ ID NO 167
<211> LENGTH: 30
<212> TYPE: DNA
<213> ORGANISM: Sorghum halepense

<400> SEQUENCE: 167
gggtgatgga cccttggggc attgttaacc 30

<210> SEQ ID NO 168
<211> LENGTH: 30
<212> TYPE: DNA
<213> ORGANISM: Sorghum halepense

<400> SEQUENCE: 168
ggaggcatcc aaagatttgg gccgcagccc 30

<210> SEQ ID NO 169
<211> LENGTH: 30
<212> TYPE: DNA
<213> ORGANISM: Sorghum halepense

<400> SEQUENCE: 169
ggacaagcgg gcagagttcg ggttactgcc 30

<210> SEQ ID NO 170
<211> LENGTH: 30
<212> TYPE: DNA
<213> ORGANISM: Sorghum halepense

<400> SEQUENCE: 170
ggccgaccgt ttccgcccac tcggcaggcc 30

<210> SEQ ID NO 171
<211> LENGTH: 30
<212> TYPE: DNA
<213> ORGANISM: Sorghum halepense

<400> SEQUENCE: 171
ggccgcgcag gacgtcgcgg catcgacacc 30

<210> SEQ ID NO 172
<211> LENGTH: 30
<212> TYPE: DNA
<213> ORGANISM: Sorghum halepense

<400> SEQUENCE: 172
ggttgccgac tcactgtcga gccttgatcc 30

<210> SEQ ID NO 173
<211> LENGTH: 30
<212> TYPE: DNA
<213> ORGANISM: Sorghum halepense

<400> SEQUENCE: 173
ggaccgcgaa gaagactgat tcgtgcgccc 30

<210> SEQ ID NO 174
<211> LENGTH: 30
<212> TYPE: DNA
<213> ORGANISM: Sorghum halepense

<400> SEQUENCE: 174
ggtgtcaaca ccgcagcgat tgctcatccc 30

<210> SEQ ID NO 175
<211> LENGTH: 30
<212> TYPE: DNA
<213> ORGANISM: Sorghum halepense

<400> SEQUENCE: 175
ggttttgggg tgacgaccca tggtggcacc 30

<210> SEQ ID NO 176
<211> LENGTH: 30
<212> TYPE: DNA
<213> ORGANISM: Sorghum halepense

<400> SEQUENCE: 176
gggcatcaac gccattcggt cggccatgcc 30

<210> SEQ ID NO 177
<211> LENGTH: 30
<212> TYPE: DNA
<213> ORGANISM: Sorghum halepense

<400> SEQUENCE: 177
ggacagcacg acctgcccga tatctctgcc 30

<210> SEQ ID NO 178
<211> LENGTH: 30
<212> TYPE: DNA
<213> ORGANISM: Sorghum halepense

<400> SEQUENCE: 178
gggtgcgtca gttacagcgg atgaaaaacc 30

<210> SEQ ID NO 179
<211> LENGTH: 30
<212> TYPE: DNA
<213> ORGANISM: Sorghum halepense

<400> SEQUENCE: 179
ggtgaagaaa cgcccgagga agaaatctcc 30

<210> SEQ ID NO 180
<211> LENGTH: 30
<212> TYPE: DNA
<213> ORGANISM: Sorghum halepense

<400> SEQUENCE: 180
ggagccagta atgatgaaat cacgatcgcc 30

<210> SEQ ID NO 181
<211> LENGTH: 30
<212> TYPE: DNA
<213> ORGANISM: Sorghum halepense

<400> SEQUENCE: 181
ggcgacgagg acagcaacga tgatgaggcc 30

<210> SEQ ID NO 182
<211> LENGTH: 30
<212> TYPE: DNA
<213> ORGANISM: Sorghum halepense

<400> SEQUENCE: 182
gggtgacgtt ccctagatcc caagacaacc 30

<210> SEQ ID NO 183
<211> LENGTH: 30
<212> TYPE: DNA
<213> ORGANISM: Sorghum halepense

<400> SEQUENCE: 183
ggcattgaaa cgagcttccg tgaggagacc 30

<210> SEQ ID NO 184
<211> LENGTH: 30
<212> TYPE: DNA
<213> ORGANISM: Sorghum halepense

<400> SEQUENCE: 184
ggtatctcca agctgcgttg gtcaatttcc 30

<210> SEQ ID NO 185
<211> LENGTH: 30
<212> TYPE: DNA
<213> ORGANISM: Sorghum halepense

<400> SEQUENCE: 185
ggtgccattg atgtcgtggg gaggaaaacc 30

<210> SEQ ID NO 186
<211> LENGTH: 30
<212> TYPE: DNA
<213> ORGANISM: Sorghum halepense

<400> SEQUENCE: 186
ggggggcata tcgtcgatga cgacgaggcc 30

<210> SEQ ID NO 187
<211> LENGTH: 30
<212> TYPE: DNA
<213> ORGANISM: Sorghum halepense

<400> SEQUENCE: 187
ggccgcgctc caaataaaac tgacggcacc 30

<210> SEQ ID NO 188
<211> LENGTH: 30
<212> TYPE: DNA
<213> ORGANISM: Sorghum halepense

<400> SEQUENCE: 188
ggccagagtg gagttgtcaa gaacctctcc 30

<210> SEQ ID NO 189
<211> LENGTH: 30
<212> TYPE: DNA
<213> ORGANISM: Sorghum halepense

<400> SEQUENCE: 189
ggtcaactac cacggacttg atatcaatcc 30

<210> SEQ ID NO 190
<211> LENGTH: 30
<212> TYPE: DNA
<213> ORGANISM: Sorghum halepense

<400> SEQUENCE: 190
ggccgttcat gatcgcctac caggatttcc 30

<210> SEQ ID NO 191
<211> LENGTH: 30
<212> TYPE: DNA
<213> ORGANISM: Sorghum halepense

<400> SEQUENCE: 191
ggtggcaatt acgcagcttc gctgcgttcc 30

<210> SEQ ID NO 192
<211> LENGTH: 30
<212> TYPE: DNA
<213> ORGANISM: Sorghum halepense

<400> SEQUENCE: 192
ggagataccg acgtgaaggt ctctgagccc 30

<210> SEQ ID NO 193
<211> LENGTH: 30
<212> TYPE: DNA
<213> ORGANISM: Sorghum halepense

<400> SEQUENCE: 193
ggacatggca tcaatcccgg tgatgacgcc 30

<210> SEQ ID NO 194
<211> LENGTH: 30
<212> TYPE: DNA
<213> ORGANISM: Sorghum halepense

<400> SEQUENCE: 194
gggcttaccc ttctccagtg cgtggatgcc 30

<210> SEQ ID NO 195
<211> LENGTH: 30
<212> TYPE: DNA
<213> ORGANISM: Sorghum halepense

<400> SEQUENCE: 195
gggttcaccg ttgccaatga cgtcactgcc 30

<210> SEQ ID NO 196
<211> LENGTH: 30
<212> TYPE: DNA
<213> ORGANISM: Sorghum halepense

<400> SEQUENCE: 196
gggtgctgac accttctgcc cgctggggcc 30

<210> SEQ ID NO 197
<211> LENGTH: 30
<212> TYPE: DNA
<213> ORGANISM: Sorghum halepense

<400> SEQUENCE: 197
gggtatcaca ccgtcggggg gctcatagcc 30

<210> SEQ ID NO 198
<211> LENGTH: 30
<212> TYPE: DNA
<213> ORGANISM: Sorghum halepense

<400> SEQUENCE: 198
ggactgtcgg tgaacctgcc ggaaaaagcc 30

<210> SEQ ID NO 199
<211> LENGTH: 30
<212> TYPE: DNA
<213> ORGANISM: Sorghum halepense

<400> SEQUENCE: 199
ggcatgaccg cgatgagttg ggtggacgcc 30

<210> SEQ ID NO 200
<211> LENGTH: 30
<212> TYPE: DNA
<213> ORGANISM: Sorghum halepense

<400> SEQUENCE: 200
gggggacaat cgaagaaggt tctcaagacc 30

<210> SEQ ID NO 201
<211> LENGTH: 30
<212> TYPE: DNA
<213> ORGANISM: Sorghum halepense

<400> SEQUENCE: 201
ggtcctgaca ccgatatagc cgcaatgacc 30

<210> SEQ ID NO 202
<211> LENGTH: 30
<212> TYPE: DNA
<213> ORGANISM: Sorghum halepense

<400> SEQUENCE: 202
ggagcggaga cggaggaagg cgtggcaccc 30

<210> SEQ ID NO 203
<211> LENGTH: 30
<212> TYPE: DNA
<213> ORGANISM: Sorghum halepense

<400> SEQUENCE: 203
ggccgccaaa taggccacca cggcaccacc 30

<210> SEQ ID NO 204
<211> LENGTH: 30
<212> TYPE: DNA
<213> ORGANISM: Sorghum halepense

<400> SEQUENCE: 204
ggccaagagc atttgcacgt caccaatgcc 30

<210> SEQ ID NO 205
<211> LENGTH: 30
<212> TYPE: DNA
<213> ORGANISM: Sorghum halepense

<400> SEQUENCE: 205
ggataatagc cgatacagta gctgtcagcc 30

<210> SEQ ID NO 206
<211> LENGTH: 30
<212> TYPE: DNA

<213> ORGANISM: Sorghum halepense

<400> SEQUENCE: 206
ggtcggtgtc agtgccgttt actctgggcc 30

<210> SEQ ID NO 207
<211> LENGTH: 30
<212> TYPE: DNA
<213> ORGANISM: Sorghum halepense

<400> SEQUENCE: 207
ggagggaggc ctccacgcac atccccctcc 30

<210> SEQ ID NO 208
<211> LENGTH: 30
<212> TYPE: DNA
<213> ORGANISM: Sorghum halepense

<400> SEQUENCE: 208
gggcgcacct cctggccgca cggcgcgccc 30

<210> SEQ ID NO 209
<211> LENGTH: 30
<212> TYPE: DNA
<213> ORGANISM: Sorghum halepense

<400> SEQUENCE: 209
gggccttggc aacttccccg gcgacgaccc 30

<210> SEQ ID NO 210
<211> LENGTH: 30
<212> TYPE: DNA
<213> ORGANISM: Sorghum halepense

<400> SEQUENCE: 210
gggtgatgtg ttatttatgt gatgttctcc 30

<210> SEQ ID NO 211
<211> LENGTH: 30
<212> TYPE: DNA
<213> ORGANISM: Sorghum halepense

<400> SEQUENCE: 211
ggttacagca tgctagttgt ttagacttcc 30

<210> SEQ ID NO 212
<211> LENGTH: 30
<212> TYPE: DNA
<213> ORGANISM: Sorghum halepense

<400> SEQUENCE: 212
ggcccccgct gccgtgtcgg cggtcgcccc 30

<210> SEQ ID NO 213
<211> LENGTH: 30
<212> TYPE: DNA
<213> ORGANISM: Sorghum halepense

<400> SEQUENCE: 213
ggtgaccaaa cagctcaata agattattcc 30

<210> SEQ ID NO 214
<211> LENGTH: 30

<212> TYPE: DNA
<213> ORGANISM: Sorghum halepense

<400> SEQUENCE: 214
ggagcggaga cggaggaagg cgtggcaccc 30

<210> SEQ ID NO 215
<211> LENGTH: 30
<212> TYPE: DNA
<213> ORGANISM: Sorghum halepense

<400> SEQUENCE: 215
ggccgccaaa taggccacca cggcaccacc 30

<210> SEQ ID NO 216
<211> LENGTH: 30
<212> TYPE: DNA
<213> ORGANISM: Sorghum halepense

<400> SEQUENCE: 216
ggccaagagc atttgcacgt caccaatgcc 30

<210> SEQ ID NO 217
<211> LENGTH: 30
<212> TYPE: DNA
<213> ORGANISM: Sorghum halepense

<400> SEQUENCE: 217
ggataatagc cgatacagta gctgtcagcc 30

<210> SEQ ID NO 218
<211> LENGTH: 30
<212> TYPE: DNA
<213> ORGANISM: Sorghum halepense

<400> SEQUENCE: 218
ggaacagaag gtattaaaag ggtattaccc 30

<210> SEQ ID NO 219
<211> LENGTH: 30
<212> TYPE: DNA
<213> ORGANISM: Sorghum halepense

<400> SEQUENCE: 219
ggtctgatag aagtctcatc atggggatcc 30

<210> SEQ ID NO 220
<211> LENGTH: 30
<212> TYPE: DNA
<213> ORGANISM: Sorghum halepense

<400> SEQUENCE: 220
ggaggaaagt ttcaaccagt ggaagctgcc 30

<210> SEQ ID NO 221
<211> LENGTH: 30
<212> TYPE: DNA
<213> ORGANISM: Sorghum halepense

<400> SEQUENCE: 221
ggtgagagaa gcagagttat ctgggattcc 30

<210> SEQ ID NO 222

<211> LENGTH: 30
<212> TYPE: DNA
<213> ORGANISM: Sorghum halepense

<400> SEQUENCE: 222
ggaggaaagt ttcaaccagt ggaagctgcc 30

<210> SEQ ID NO 223
<211> LENGTH: 30
<212> TYPE: DNA
<213> ORGANISM: Sorghum halepense

<400> SEQUENCE: 223
ggtgagagaa gcagagttat ctgggattcc 30

<210> SEQ ID NO 224
<211> LENGTH: 30
<212> TYPE: DNA
<213> ORGANISM: Sorghum halepense

<400> SEQUENCE: 224
ggtcatttgt tttagcacct cttgttgacc 30

<210> SEQ ID NO 225
<211> LENGTH: 30
<212> TYPE: DNA
<213> ORGANISM: Sorghum halepense

<400> SEQUENCE: 225
ggaggtaagt ttcaacaagt ggaagctgcc 30

<210> SEQ ID NO 226
<211> LENGTH: 30
<212> TYPE: DNA
<213> ORGANISM: Sorghum halepense

<400> SEQUENCE: 226
ggtgagagaa gcagagttat ctgggattcc 30

<210> SEQ ID NO 227
<211> LENGTH: 30
<212> TYPE: DNA
<213> ORGANISM: Sorghum halepense

<400> SEQUENCE: 227
ggcacctcct agtctttgct gtcttcatcc 30

<210> SEQ ID NO 228
<211> LENGTH: 30
<212> TYPE: DNA
<213> ORGANISM: Sorghum halepense

<400> SEQUENCE: 228
gggtgctagc ttaaaaaaaa gattaacacc 30

<210> SEQ ID NO 229
<211> LENGTH: 30
<212> TYPE: DNA
<213> ORGANISM: Sorghum halepense

<400> SEQUENCE: 229
ggcatttacg ccagtaattg tacaaggacc 30

<210> SEQ ID NO 230
<211> LENGTH: 30
<212> TYPE: DNA
<213> ORGANISM: Sorghum halepense

<400> SEQUENCE: 230
ggcgccggcg cctcagcttg tacggcctcc 30

<210> SEQ ID NO 231
<211> LENGTH: 30
<212> TYPE: DNA
<213> ORGANISM: Sorghum halepense

<400> SEQUENCE: 231
ggcactcagg gtcttcctga tcttgttccc 30

<210> SEQ ID NO 232
<211> LENGTH: 30
<212> TYPE: DNA
<213> ORGANISM: Sorghum halepense

<400> SEQUENCE: 232
ggagtgctga tgggaatatc ccttgtagcc 30

<210> SEQ ID NO 233
<211> LENGTH: 30
<212> TYPE: DNA
<213> ORGANISM: Sorghum halepense

<400> SEQUENCE: 233
ggaacagaag gtattaaaag ggtattaccc 30

<210> SEQ ID NO 234
<211> LENGTH: 30
<212> TYPE: DNA
<213> ORGANISM: Sorghum halepense

<400> SEQUENCE: 234
ggtctgagag aactctcatc atggggatcc 30

<210> SEQ ID NO 235
<211> LENGTH: 30
<212> TYPE: DNA
<213> ORGANISM: Sorghum halepense

<400> SEQUENCE: 235
ggaggaaagt ttcaaccaat ggaagctgcc 30

<210> SEQ ID NO 236
<211> LENGTH: 30
<212> TYPE: DNA
<213> ORGANISM: Sorghum halepense

<400> SEQUENCE: 236
ggaaaagttt tttgggtgaa atatgcaacc 30

<210> SEQ ID NO 237
<211> LENGTH: 30
<212> TYPE: DNA
<213> ORGANISM: Sorghum halepense

<400> SEQUENCE: 237
gggctctctg tcgaagcaga caaagttgcc 30

-continued

<210> SEQ ID NO 238
<211> LENGTH: 30
<212> TYPE: DNA
<213> ORGANISM: Sorghum halepense

<400> SEQUENCE: 238
ggctccatca gcagtcagta cttgagtgcc 30

<210> SEQ ID NO 239
<211> LENGTH: 30
<212> TYPE: DNA
<213> ORGANISM: Sorghum halepense

<400> SEQUENCE: 239
ggtcaaaaat acaagtcccc caaaaatgcc 30

<210> SEQ ID NO 240
<211> LENGTH: 30
<212> TYPE: DNA
<213> ORGANISM: Sorghum halepense

<400> SEQUENCE: 240
ggctattgat gttaacatga acaaaatgcc 30

<210> SEQ ID NO 241
<211> LENGTH: 30
<212> TYPE: DNA
<213> ORGANISM: Sorghum halepense

<400> SEQUENCE: 241
ggcccaacag ctatcagaga cgtggcgtcc 30

<210> SEQ ID NO 242
<211> LENGTH: 30
<212> TYPE: DNA
<213> ORGANISM: Sorghum halepense

<400> SEQUENCE: 242
ggctattgat gttaacatga acaaaatgcc 30

<210> SEQ ID NO 243
<211> LENGTH: 30
<212> TYPE: DNA
<213> ORGANISM: Sorghum halepense

<400> SEQUENCE: 243
ggggcattta atgcagcaaa atgacaggcc 30

<210> SEQ ID NO 244
<211> LENGTH: 30
<212> TYPE: DNA
<213> ORGANISM: Sorghum halepense

<400> SEQUENCE: 244
ggaaaaggta cttgattggt tttttgtgcc 30

<210> SEQ ID NO 245
<211> LENGTH: 30
<212> TYPE: DNA
<213> ORGANISM: Sorghum halepense

<400> SEQUENCE: 245
ggaccgagac tagcgttact gttactggcc 30

<210> SEQ ID NO 246
<211> LENGTH: 30
<212> TYPE: DNA
<213> ORGANISM: Sorghum halepense

<400> SEQUENCE: 246
ggacaaggca cttgattggt tttttgcccc 30

<210> SEQ ID NO 247
<211> LENGTH: 30
<212> TYPE: DNA
<213> ORGANISM: Sorghum halepense

<400> SEQUENCE: 247
ggcaggcgcc gaggagatcg tgctgcagcc 30

<210> SEQ ID NO 248
<211> LENGTH: 30
<212> TYPE: DNA
<213> ORGANISM: Sorghum halepense

<400> SEQUENCE: 248
ggtgggtgtc gccctatgcc cctatcggcc 30

<210> SEQ ID NO 249
<211> LENGTH: 30
<212> TYPE: DNA
<213> ORGANISM: Sorghum halepense

<400> SEQUENCE: 249
gggctctctg tcgaagcaga caaagttgcc 30

<210> SEQ ID NO 250
<211> LENGTH: 30
<212> TYPE: DNA
<213> ORGANISM: Sorghum halepense

<400> SEQUENCE: 250
ggtcatccct aactagcaaa ccatgtttcc 30

<210> SEQ ID NO 251
<211> LENGTH: 30
<212> TYPE: DNA
<213> ORGANISM: Sorghum halepense

<400> SEQUENCE: 251
ggcgggcgcc gaggagatcg tgctgcagcc 30

<210> SEQ ID NO 252
<211> LENGTH: 30
<212> TYPE: DNA
<213> ORGANISM: Sorghum halepense

<400> SEQUENCE: 252
ggtgggtgtc gccctatgcc cctatcggcc 30

<210> SEQ ID NO 253
<211> LENGTH: 30
<212> TYPE: DNA
<213> ORGANISM: Sorghum halepense

<400> SEQUENCE: 253
gggctctctg tcgaagcaga caaagttgcc 30

<210> SEQ ID NO 254
<211> LENGTH: 30
<212> TYPE: DNA
<213> ORGANISM: Sorghum halepense

<400> SEQUENCE: 254
ggtcatccct aactagcaaa ccatgtttcc 30

<210> SEQ ID NO 255
<211> LENGTH: 30
<212> TYPE: DNA
<213> ORGANISM: Sorghum halepense

<400> SEQUENCE: 255
ggctccatca gcagtcagta cttgagtgcc 30

<210> SEQ ID NO 256
<211> LENGTH: 30
<212> TYPE: DNA
<213> ORGANISM: Sorghum halepense

<400> SEQUENCE: 256
ggctattgat gttaacatga acaaaatgcc 30

<210> SEQ ID NO 257
<211> LENGTH: 30
<212> TYPE: DNA
<213> ORGANISM: Sorghum halepense

<400> SEQUENCE: 257
ggggcattga atgcagcaaa atgacaggcc 30

<210> SEQ ID NO 258
<211> LENGTH: 30
<212> TYPE: DNA
<213> ORGANISM: Sorghum halepense

<400> SEQUENCE: 258
ggcgggcgcc gaggagatcg tgctgcagcc 30

<210> SEQ ID NO 259
<211> LENGTH: 30
<212> TYPE: DNA
<213> ORGANISM: Sorghum halepense

<400> SEQUENCE: 259
ggtgggtgtc gccctatgcc cctatcggcc 30

<210> SEQ ID NO 260
<211> LENGTH: 30
<212> TYPE: DNA
<213> ORGANISM: Sorghum halepense

<400> SEQUENCE: 260
gggctctctg tcgaagcaga caaagttgcc 30

<210> SEQ ID NO 261
<211> LENGTH: 30
<212> TYPE: DNA
<213> ORGANISM: Sorghum halepense

<400> SEQUENCE: 261
ggctccatca gcagtcagta cttgagtgcc 30

<210> SEQ ID NO 262
<211> LENGTH: 30
<212> TYPE: DNA
<213> ORGANISM: Sorghum halepense

<400> SEQUENCE: 262
ggctattgat gttaacatga acaaaatgcc 30

<210> SEQ ID NO 263
<211> LENGTH: 30
<212> TYPE: DNA
<213> ORGANISM: Sorghum halepense

<400> SEQUENCE: 263
ggggcattga atgcagcaaa atgacaggcc 30

<210> SEQ ID NO 264
<211> LENGTH: 30
<212> TYPE: DNA
<213> ORGANISM: Sorghum halepense

<400> SEQUENCE: 264
ggtgaactag actgatgact gggcgggtcc 30

<210> SEQ ID NO 265
<211> LENGTH: 30
<212> TYPE: DNA
<213> ORGANISM: Sorghum halepense

<400> SEQUENCE: 265
ggatccatca ggcccgcctc gaacccggcc 30

<210> SEQ ID NO 266
<211> LENGTH: 30
<212> TYPE: DNA
<213> ORGANISM: Sorghum halepense

<400> SEQUENCE: 266
ggcgggcgcc gaggagatcg tgctgcagcc 30

<210> SEQ ID NO 267
<211> LENGTH: 30
<212> TYPE: DNA
<213> ORGANISM: Sorghum halepense

<400> SEQUENCE: 267
gggctctctg tcgaagcaga caaagttgcc 30

<210> SEQ ID NO 268
<211> LENGTH: 30
<212> TYPE: DNA
<213> ORGANISM: Sorghum halepense

<400> SEQUENCE: 268
ggtcatccct aactagcaaa ccatgtttcc 30

<210> SEQ ID NO 269
<211> LENGTH: 30
<212> TYPE: DNA
<213> ORGANISM: Sorghum halepense

<400> SEQUENCE: 269
ggctccatca gcagtcagta cttgagtgcc 30

<210> SEQ ID NO 270
<211> LENGTH: 30
<212> TYPE: DNA
<213> ORGANISM: Sorghum halepense

<400> SEQUENCE: 270
ggaaaaggta cttgattggt tttttgtgcc 30

<210> SEQ ID NO 271
<211> LENGTH: 30
<212> TYPE: DNA
<213> ORGANISM: Sorghum halepense

<400> SEQUENCE: 271
ggaccgagac tagcgttact gttactggcc 30

<210> SEQ ID NO 272
<211> LENGTH: 30
<212> TYPE: DNA
<213> ORGANISM: Sorghum halepense

<400> SEQUENCE: 272
ggcgcctcgc cggggttcaa ggtcatggcc 30

<210> SEQ ID NO 273
<211> LENGTH: 30
<212> TYPE: DNA
<213> ORGANISM: Sorghum halepense

<400> SEQUENCE: 273
gggagaagac agtgaagtca ttctataccc 30

<210> SEQ ID NO 274
<211> LENGTH: 30
<212> TYPE: DNA
<213> ORGANISM: Sorghum halepense

<400> SEQUENCE: 274
ggcacagggc tgcgcaaatt tttagtgacc 30

<210> SEQ ID NO 275
<211> LENGTH: 30
<212> TYPE: DNA
<213> ORGANISM: Sorghum halepense

<400> SEQUENCE: 275
ggaactctat aaatataaat caaatcaacc 30

<210> SEQ ID NO 276
<211> LENGTH: 30
<212> TYPE: DNA
<213> ORGANISM: Sorghum halepense

<400> SEQUENCE: 276
ggatttggag aggggttttg ggagaccgcc 30

<210> SEQ ID NO 277
<211> LENGTH: 30
<212> TYPE: DNA
<213> ORGANISM: Sorghum halepense

<400> SEQUENCE: 277
ggcccggtga ccgatcccag caagctgccc 30

<210> SEQ ID NO 278
<211> LENGTH: 30
<212> TYPE: DNA
<213> ORGANISM: Sorghum halepense

<400> SEQUENCE: 278
ggtaggtacg gtattgagca ggagtacacc 30

<210> SEQ ID NO 279
<211> LENGTH: 30
<212> TYPE: DNA
<213> ORGANISM: Sorghum halepense

<400> SEQUENCE: 279
ggcaacttct tttgtaaccc tcaagctacc 30

<210> SEQ ID NO 280
<211> LENGTH: 30
<212> TYPE: DNA
<213> ORGANISM: Sorghum halepense

<400> SEQUENCE: 280
ggctgctctg ttcgtgtggg gcgagatacc 30

<210> SEQ ID NO 281
<211> LENGTH: 30
<212> TYPE: DNA
<213> ORGANISM: Sorghum halepense

<400> SEQUENCE: 281
ggaaaaaagt tcaatttatc tctcccaacc 30

<210> SEQ ID NO 282
<211> LENGTH: 30
<212> TYPE: DNA
<213> ORGANISM: Sorghum halepense

<400> SEQUENCE: 282
ggtgatctaa catgtaaaat gtaagactcc 30

<210> SEQ ID NO 283
<211> LENGTH: 30
<212> TYPE: DNA
<213> ORGANISM: Sorghum halepense

<400> SEQUENCE: 283
ggtgccggcg cacacaccaa ctacagcacc 30

<210> SEQ ID NO 284
<211> LENGTH: 30
<212> TYPE: DNA
<213> ORGANISM: Sorghum halepense

<400> SEQUENCE: 284
ggcaggcacg agaccgccga catcaacacc 30

<210> SEQ ID NO 285
<211> LENGTH: 30
<212> TYPE: DNA

<213> ORGANISM: Sorghum halepense

<400> SEQUENCE: 285
ggattgatgt gaatccgact aaacaaggcc 30

<210> SEQ ID NO 286
<211> LENGTH: 30
<212> TYPE: DNA
<213> ORGANISM: Sorghum halepense

<400> SEQUENCE: 286
ggggccaaca aattaaatct gagatatccc 30

<210> SEQ ID NO 287
<211> LENGTH: 30
<212> TYPE: DNA
<213> ORGANISM: Sorghum halepense

<400> SEQUENCE: 287
ggtgccggcg cacacaccaa ctacagcacc 30

<210> SEQ ID NO 288
<211> LENGTH: 30
<212> TYPE: DNA
<213> ORGANISM: Sorghum halepense

<400> SEQUENCE: 288
ggcaggcacg agaccgccga catcaacacc 30

<210> SEQ ID NO 289
<211> LENGTH: 30
<212> TYPE: DNA
<213> ORGANISM: Sorghum halepense

<400> SEQUENCE: 289
ggcccggtga ccgatcccag caagctgccc 30

<210> SEQ ID NO 290
<211> LENGTH: 30
<212> TYPE: DNA
<213> ORGANISM: Sorghum halepense

<400> SEQUENCE: 290
ggtaggtacg gtattgagca ggagtacacc 30

<210> SEQ ID NO 291
<211> LENGTH: 30
<212> TYPE: DNA
<213> ORGANISM: Sorghum halepense

<400> SEQUENCE: 291
ggcaacttct tttgtaaccc tcaagctacc 30

<210> SEQ ID NO 292
<211> LENGTH: 30
<212> TYPE: DNA
<213> ORGANISM: Sorghum halepense

<400> SEQUENCE: 292
ggcccggtga ccgatcccag caagctgccc 30

<210> SEQ ID NO 293
<211> LENGTH: 30

<212> TYPE: DNA
<213> ORGANISM: Sorghum halepense

<400> SEQUENCE: 293
ggccctataa tgtgcttggt ttcccgttcc 30

<210> SEQ ID NO 294
<211> LENGTH: 30
<212> TYPE: DNA
<213> ORGANISM: Sorghum halepense

<400> SEQUENCE: 294
ggaaaaaagt ttaatttatc tctcccagcc 30

<210> SEQ ID NO 295
<211> LENGTH: 30
<212> TYPE: DNA
<213> ORGANISM: Sorghum halepense

<400> SEQUENCE: 295
ggacagggta attaacccaa caatgcctcc 30

<210> SEQ ID NO 296
<211> LENGTH: 30
<212> TYPE: DNA
<213> ORGANISM: Sorghum halepense

<400> SEQUENCE: 296
ggacagtgtc ctatggtttg gtggggtgcc 30

<210> SEQ ID NO 297
<211> LENGTH: 30
<212> TYPE: DNA
<213> ORGANISM: Sorghum halepense

<400> SEQUENCE: 297
ggtgcttgct ctgatgctgg taattgtacc 30

<210> SEQ ID NO 298
<211> LENGTH: 30
<212> TYPE: DNA
<213> ORGANISM: Sorghum halepense

<400> SEQUENCE: 298
ggtctgggtg gatgcatcat gcatcatgcc 30

<210> SEQ ID NO 299
<211> LENGTH: 30
<212> TYPE: DNA
<213> ORGANISM: Sorghum halepense

<400> SEQUENCE: 299
ggctcatgtt gtgggtggat gcgtcatgcc 30

<210> SEQ ID NO 300
<211> LENGTH: 30
<212> TYPE: DNA
<213> ORGANISM: Sorghum halepense

<400> SEQUENCE: 300
ggtaggtacg gtattgagca ggagtacacc 30

<210> SEQ ID NO 301

<211> LENGTH: 30
<212> TYPE: DNA
<213> ORGANISM: Sorghum halepense

<400> SEQUENCE: 301
ggcaacttct tttgtaaccc tcaagctacc 30

<210> SEQ ID NO 302
<211> LENGTH: 30
<212> TYPE: DNA
<213> ORGANISM: Sorghum halepense

<400> SEQUENCE: 302
ggtgccggcg cacacaccaa ctacagcacc 30

<210> SEQ ID NO 303
<211> LENGTH: 30
<212> TYPE: DNA
<213> ORGANISM: Sorghum halepense

<400> SEQUENCE: 303
ggcaggcacg agaccgccga catcaacacc 30

<210> SEQ ID NO 304
<211> LENGTH: 30
<212> TYPE: DNA
<213> ORGANISM: Sorghum halepense

<400> SEQUENCE: 304
ggctgggcac ccatatttct ccctcggacc 30

<210> SEQ ID NO 305
<211> LENGTH: 30
<212> TYPE: DNA
<213> ORGANISM: Sorghum halepense

<400> SEQUENCE: 305
ggctcctcca gaaatggctt acggtgggcc 30

<210> SEQ ID NO 306
<211> LENGTH: 30
<212> TYPE: DNA
<213> ORGANISM: Sorghum halepense

<400> SEQUENCE: 306
ggagccacca agcactgcac ggccccctcc 30

<210> SEQ ID NO 307
<211> LENGTH: 30
<212> TYPE: DNA
<213> ORGANISM: Sorghum halepense

<400> SEQUENCE: 307
gggccgattg gccggatcga atacttctcc 30

<210> SEQ ID NO 308
<211> LENGTH: 30
<212> TYPE: DNA
<213> ORGANISM: Sorghum halepense

<400> SEQUENCE: 308
ggtcagtcaa gccctgacag cggccggccc 30

<210> SEQ ID NO 309
<211> LENGTH: 30
<212> TYPE: DNA
<213> ORGANISM: Sorghum halepense

<400> SEQUENCE: 309
ggcaagcatt ccacgcagtg tctctcagcc 30

<210> SEQ ID NO 310
<211> LENGTH: 30
<212> TYPE: DNA
<213> ORGANISM: Sorghum halepense

<400> SEQUENCE: 310
ggttccacta gtcttcttgg tctagtgacc 30

<210> SEQ ID NO 311
<211> LENGTH: 30
<212> TYPE: DNA
<213> ORGANISM: Sorghum halepense

<400> SEQUENCE: 311
ggggccaaca aattaaactc tgagatatcc 30

<210> SEQ ID NO 312
<211> LENGTH: 30
<212> TYPE: DNA
<213> ORGANISM: Sorghum halepense

<400> SEQUENCE: 312
gggtttgcat gcctctgaag gatcaggccc 30

<210> SEQ ID NO 313
<211> LENGTH: 30
<212> TYPE: DNA
<213> ORGANISM: Sorghum halepense

<400> SEQUENCE: 313
ggcaacgtgc cggagctggc gccggcggcc 30

<210> SEQ ID NO 314
<211> LENGTH: 30
<212> TYPE: DNA
<213> ORGANISM: Sorghum halepense

<400> SEQUENCE: 314
ggagaacgtg ctgctcccac tcaacgagcc 30

<210> SEQ ID NO 315
<211> LENGTH: 30
<212> TYPE: DNA
<213> ORGANISM: Sorghum halepense

<400> SEQUENCE: 315
ggccccggcg tgcagcacat ggcgctggcc 30

<210> SEQ ID NO 316
<211> LENGTH: 30
<212> TYPE: DNA
<213> ORGANISM: Sorghum halepense

<400> SEQUENCE: 316
ggcaacgtgc cggagctggc gccggcggcc 30

<210> SEQ ID NO 317
<211> LENGTH: 30
<212> TYPE: DNA
<213> ORGANISM: Sorghum halepense

<400> SEQUENCE: 317
ggagaacgtg ctgctcccac tcaacgagcc 30

<210> SEQ ID NO 318
<211> LENGTH: 30
<212> TYPE: DNA
<213> ORGANISM: Sorghum halepense

<400> SEQUENCE: 318
ggccccggcg tgcagcacat ggcgctggcc 30

<210> SEQ ID NO 319
<211> LENGTH: 30
<212> TYPE: DNA
<213> ORGANISM: Sorghum halepense

<400> SEQUENCE: 319
ggtctccagg gaacaagaag ttgctgcgcc 30

<210> SEQ ID NO 320
<211> LENGTH: 30
<212> TYPE: DNA
<213> ORGANISM: Sorghum halepense

<400> SEQUENCE: 320
ggccaggtcg ccgccaattg ccgtccagcc 30

<210> SEQ ID NO 321
<211> LENGTH: 30
<212> TYPE: DNA
<213> ORGANISM: Sorghum halepense

<400> SEQUENCE: 321
ggtctccagg gaacaagaag ttgctgcgcc 30

<210> SEQ ID NO 322
<211> LENGTH: 30
<212> TYPE: DNA
<213> ORGANISM: Sorghum halepense

<400> SEQUENCE: 322
gggcgccctc gctttcctct tcacggcgcc 30

<210> SEQ ID NO 323
<211> LENGTH: 30
<212> TYPE: DNA
<213> ORGANISM: Sorghum halepense

<400> SEQUENCE: 323
ggcgccgacg ccgccacggc ctcgctgccc 30

<210> SEQ ID NO 324
<211> LENGTH: 30
<212> TYPE: DNA
<213> ORGANISM: Sorghum halepense

<400> SEQUENCE: 324
ggagaacgtg ctgctcccac tcaacgagcc 30

<210> SEQ ID NO 325
<211> LENGTH: 30
<212> TYPE: DNA
<213> ORGANISM: Sorghum halepense

<400> SEQUENCE: 325
ggccccggcg tgcagcacat ggcgctggcc 30

<210> SEQ ID NO 326
<211> LENGTH: 30
<212> TYPE: DNA
<213> ORGANISM: Sorghum halepense

<400> SEQUENCE: 326
gggcgccctc gctttcctct tcacggcgcc 30

<210> SEQ ID NO 327
<211> LENGTH: 30
<212> TYPE: DNA
<213> ORGANISM: Sorghum halepense

<400> SEQUENCE: 327
gggcttcata tcttttttgg agcttatccc 30

<210> SEQ ID NO 328
<211> LENGTH: 30
<212> TYPE: DNA
<213> ORGANISM: Sorghum halepense

<400> SEQUENCE: 328
ggtttacaaa actgtcccaa actgtgaacc 30

<210> SEQ ID NO 329
<211> LENGTH: 30
<212> TYPE: DNA
<213> ORGANISM: Sorghum halepense

<400> SEQUENCE: 329
ggtggttcca atcaatcggt taaatcatcc 30

<210> SEQ ID NO 330
<211> LENGTH: 30
<212> TYPE: DNA
<213> ORGANISM: Sorghum halepense

<400> SEQUENCE: 330
ggggcgtcta gcgccttgca cgggtgaccc 30

<210> SEQ ID NO 331
<211> LENGTH: 30
<212> TYPE: DNA
<213> ORGANISM: Sorghum halepense

<400> SEQUENCE: 331
ggttgcgcta tcgttcatgt ttgaatgtcc 30

<210> SEQ ID NO 332
<211> LENGTH: 30
<212> TYPE: DNA
<213> ORGANISM: Sorghum halepense

<400> SEQUENCE: 332
ggtggttcct atcaatcggt taattcatcc 30

<210> SEQ ID NO 333
<211> LENGTH: 30
<212> TYPE: DNA
<213> ORGANISM: Sorghum halepense

<400> SEQUENCE: 333
ggaagatttg tccattctgc ttggtgcccc 30

<210> SEQ ID NO 334
<211> LENGTH: 30
<212> TYPE: DNA
<213> ORGANISM: Sorghum halepense

<400> SEQUENCE: 334
ggaccaagaa agcatcagaa caataatacc 30

<210> SEQ ID NO 335
<211> LENGTH: 30
<212> TYPE: DNA
<213> ORGANISM: Sorghum halepense

<400> SEQUENCE: 335
ggatatactc ctagtagtct gtagtgcgcc 30

<210> SEQ ID NO 336
<211> LENGTH: 30
<212> TYPE: DNA
<213> ORGANISM: Sorghum halepense

<400> SEQUENCE: 336
gggctccccc gcctccacga cactgcctcc 30

<210> SEQ ID NO 337
<211> LENGTH: 30
<212> TYPE: DNA
<213> ORGANISM: Sorghum halepense

<400> SEQUENCE: 337
ggtgctacga aattgtctag aacgaggtcc 30

<210> SEQ ID NO 338
<211> LENGTH: 30
<212> TYPE: DNA
<213> ORGANISM: Sorghum halepense

<400> SEQUENCE: 338
ggcttcatga actgtgggtc taatggctcc 30

<210> SEQ ID NO 339
<211> LENGTH: 30
<212> TYPE: DNA
<213> ORGANISM: Sorghum halepense

<400> SEQUENCE: 339
ggacggaggc ccatgtgagc aagttgggcc 30

<210> SEQ ID NO 340
<211> LENGTH: 30
<212> TYPE: DNA
<213> ORGANISM: Sorghum halepense

<400> SEQUENCE: 340
ggcagtggta ctagtatccg aaatgtgacc 30

<210> SEQ ID NO 341
<211> LENGTH: 30
<212> TYPE: DNA
<213> ORGANISM: Sorghum halepense

<400> SEQUENCE: 341
ggttaactat atatttttgt agatgtcgcc 30

<210> SEQ ID NO 342
<211> LENGTH: 30
<212> TYPE: DNA
<213> ORGANISM: Sorghum halepense

<400> SEQUENCE: 342
ggcaactccc gacggatcta ttgcctcccc 30

<210> SEQ ID NO 343
<211> LENGTH: 30
<212> TYPE: DNA
<213> ORGANISM: Sorghum halepense

<400> SEQUENCE: 343
ggggaagctt atcccccctc ttatcgagcc 30

<210> SEQ ID NO 344
<211> LENGTH: 30
<212> TYPE: DNA
<213> ORGANISM: Sorghum halepense

<400> SEQUENCE: 344
ggtctctgct ccggtagcgg cgcgtctccc 30

<210> SEQ ID NO 345
<211> LENGTH: 30
<212> TYPE: DNA
<213> ORGANISM: Sorghum halepense

<400> SEQUENCE: 345
ggttgcgcta tcgttcatgt ttgaatgtcc 30

<210> SEQ ID NO 346
<211> LENGTH: 30
<212> TYPE: DNA
<213> ORGANISM: Sorghum halepense

<400> SEQUENCE: 346
ggtggttcct atcaatcggt taattcatcc 30

<210> SEQ ID NO 347
<211> LENGTH: 30
<212> TYPE: DNA
<213> ORGANISM: Sorghum halepense

<400> SEQUENCE: 347
ggaagatttg tccattctgc ttggtggccc 30

<210> SEQ ID NO 348
<211> LENGTH: 30
<212> TYPE: DNA
<213> ORGANISM: Sorghum halepense

<400> SEQUENCE: 348
ggaccaagaa agcatcagaa caataatacc 30

<210> SEQ ID NO 349
<211> LENGTH: 30
<212> TYPE: DNA
<213> ORGANISM: Sorghum halepense

<400> SEQUENCE: 349
ggcctacctt tatggatcga ataatcaacc 30

<210> SEQ ID NO 350
<211> LENGTH: 30
<212> TYPE: DNA
<213> ORGANISM: Sorghum halepense

<400> SEQUENCE: 350
ggccggccgg ccggccgacg gaccgagacc 30

<210> SEQ ID NO 351
<211> LENGTH: 30
<212> TYPE: DNA
<213> ORGANISM: Sorghum halepense

<400> SEQUENCE: 351
ggcggcgacc agggtgatcg gatccaagcc 30

<210> SEQ ID NO 352
<211> LENGTH: 30
<212> TYPE: DNA
<213> ORGANISM: Sorghum halepense

<400> SEQUENCE: 352
ggcacgctga agaagcttgt gaacgagtcc 30

<210> SEQ ID NO 353
<211> LENGTH: 30
<212> TYPE: DNA
<213> ORGANISM: Sorghum halepense

<400> SEQUENCE: 353
ggcggcaaca tcaccaccgt cgagcgcccc 30

<210> SEQ ID NO 354
<211> LENGTH: 30
<212> TYPE: DNA
<213> ORGANISM: Sorghum halepense

<400> SEQUENCE: 354
gggccggtct cggcgcgctt ggcatccgcc 30

<210> SEQ ID NO 355
<211> LENGTH: 30
<212> TYPE: DNA
<213> ORGANISM: Sorghum halepense

<400> SEQUENCE: 355
ggaggtgcta caaacacagg aattgtttcc 30

<210> SEQ ID NO 356
<211> LENGTH: 30
<212> TYPE: DNA
<213> ORGANISM: Sorghum halepense

<400> SEQUENCE: 356
ggaggtgcta caaacacagg aattgtttcc 30

<210> SEQ ID NO 357
<211> LENGTH: 30
<212> TYPE: DNA
<213> ORGANISM: Sorghum halepense

<400> SEQUENCE: 357
ggttagcaat actctgccaa agctattgcc 30

<210> SEQ ID NO 358
<211> LENGTH: 30
<212> TYPE: DNA
<213> ORGANISM: Sorghum halepense

<400> SEQUENCE: 358
ggggacgtgc ttgtcacgga ggcccgcgcc 30

<210> SEQ ID NO 359
<211> LENGTH: 30
<212> TYPE: DNA
<213> ORGANISM: Sorghum halepense

<400> SEQUENCE: 359
gggccggtct cggcgcgctt ggcatccgcc 30

<210> SEQ ID NO 360
<211> LENGTH: 30
<212> TYPE: DNA
<213> ORGANISM: Sorghum halepense

<400> SEQUENCE: 360
ggaggtgcta caaacacagg aattgtttcc 30

<210> SEQ ID NO 361
<211> LENGTH: 30
<212> TYPE: DNA
<213> ORGANISM: Sorghum halepense

<400> SEQUENCE: 361
ggttagcaat actctgccaa agctattgcc 30

<210> SEQ ID NO 362
<211> LENGTH: 30
<212> TYPE: DNA
<213> ORGANISM: Sorghum halepense

<400> SEQUENCE: 362
gggccggtct cggcgcgctt ggcatccgcc 30

<210> SEQ ID NO 363
<211> LENGTH: 30
<212> TYPE: DNA
<213> ORGANISM: Sorghum halepense

<400> SEQUENCE: 363
ggtagaagca tcaaatgaaa agaattgccc 30

<210> SEQ ID NO 364
<211> LENGTH: 30
<212> TYPE: DNA

<213> ORGANISM: Sorghum halepense

<400> SEQUENCE: 364
ggatagttct gttggaaaag ttgaagtccc 30

<210> SEQ ID NO 365
<211> LENGTH: 30
<212> TYPE: DNA
<213> ORGANISM: Sorghum halepense

<400> SEQUENCE: 365
gggtttctct gggatgaagg agcgaacacc 30

<210> SEQ ID NO 366
<211> LENGTH: 30
<212> TYPE: DNA
<213> ORGANISM: Sorghum halepense

<400> SEQUENCE: 366
ggacattact tcacaatgag tatcacttcc 30

<210> SEQ ID NO 367
<211> LENGTH: 30
<212> TYPE: DNA
<213> ORGANISM: Sorghum halepense

<400> SEQUENCE: 367
ggatcacggt tcgcaggtca gcttgtggcc 30

<210> SEQ ID NO 368
<211> LENGTH: 30
<212> TYPE: DNA
<213> ORGANISM: Sorghum halepense

<400> SEQUENCE: 368
ggagaccagc ctgaacttgc ttccgaaacc 30

<210> SEQ ID NO 369
<211> LENGTH: 30
<212> TYPE: DNA
<213> ORGANISM: Sorghum halepense

<400> SEQUENCE: 369
ggtatatggc attccagaat tccgtcttcc 30

<210> SEQ ID NO 370
<211> LENGTH: 30
<212> TYPE: DNA
<213> ORGANISM: Sorghum halepense

<400> SEQUENCE: 370
ggtccaccgc cgtgtcacgg acacggctcc 30

<210> SEQ ID NO 371
<211> LENGTH: 30
<212> TYPE: DNA
<213> ORGANISM: Sorghum halepense

<400> SEQUENCE: 371
ggttattgag gaaaatttgg atcagctgcc 30

<210> SEQ ID NO 372
<211> LENGTH: 30

<212> TYPE: DNA
<213> ORGANISM: Sorghum halepense

<400> SEQUENCE: 372
ggtggcatta accctgcatc atgattttcc 30

<210> SEQ ID NO 373
<211> LENGTH: 30
<212> TYPE: DNA
<213> ORGANISM: Sorghum halepense

<400> SEQUENCE: 373
ggtagaagca tcaaatgaaa agaattgccc 30

<210> SEQ ID NO 374
<211> LENGTH: 30
<212> TYPE: DNA
<213> ORGANISM: Sorghum halepense

<400> SEQUENCE: 374
ggatagttct gttggaaaag ttgacgtccc 30

<210> SEQ ID NO 375
<211> LENGTH: 30
<212> TYPE: DNA
<213> ORGANISM: Sorghum halepense

<400> SEQUENCE: 375
ggtcctagct cagttggttg agggtatgcc 30

<210> SEQ ID NO 376
<211> LENGTH: 30
<212> TYPE: DNA
<213> ORGANISM: Sorghum halepense

<400> SEQUENCE: 376
ggctctcgcc gccgccgccg cctcgaggcc 30

<210> SEQ ID NO 377
<211> LENGTH: 30
<212> TYPE: DNA
<213> ORGANISM: Sorghum halepense

<400> SEQUENCE: 377
ggtccaccgc cgtgtcacgg acacggctcc 30

<210> SEQ ID NO 378
<211> LENGTH: 30
<212> TYPE: DNA
<213> ORGANISM: Sorghum halepense

<400> SEQUENCE: 378
ggttattgag gaaaatttgg atcagctgcc 30

<210> SEQ ID NO 379
<211> LENGTH: 30
<212> TYPE: DNA
<213> ORGANISM: Sorghum halepense

<400> SEQUENCE: 379
ggtggcatta accctgcatc atgattttcc 30

<210> SEQ ID NO 380

-continued

```
<211> LENGTH: 30
<212> TYPE: DNA
<213> ORGANISM: Sorghum halepense

<400> SEQUENCE: 380

ggtagaagca tcaaatgaaa agaattgccc                                        30


<210> SEQ ID NO 381
<211> LENGTH: 30
<212> TYPE: DNA
<213> ORGANISM: Sorghum halepense

<400> SEQUENCE: 381

ggatagttct gttggaaaag ttgaagtccc                                        30


<210> SEQ ID NO 382
<211> LENGTH: 30
<212> TYPE: DNA
<213> ORGANISM: Sorghum halepense

<400> SEQUENCE: 382

ggtcctagct cagttggttg agggtatgcc                                        30


<210> SEQ ID NO 383
<211> LENGTH: 30
<212> TYPE: DNA
<213> ORGANISM: Sorghum halepense

<400> SEQUENCE: 383

ggacattact tcacaatgag tatcacttcc                                        30


<210> SEQ ID NO 384
<211> LENGTH: 30
<212> TYPE: DNA
<213> ORGANISM: Sorghum halepense

<400> SEQUENCE: 384

ggactcacgg ctgctgaaga gctcgcctcc                                        30


<210> SEQ ID NO 385
<211> LENGTH: 30
<212> TYPE: DNA
<213> ORGANISM: Sorghum halepense

<400> SEQUENCE: 385

ggcggccgct tagaaaacgc tgagttatcc                                        30


<210> SEQ ID NO 386
<211> LENGTH: 30
<212> TYPE: DNA
<213> ORGANISM: Sorghum halepense

<400> SEQUENCE: 386

gggcggcggc taatgccacc tggttgaacc                                        30
```

METHODS AND COMPOSITIONS FOR WEED CONTROL

CROSS REFERENCE TO RELATED APPLICATIONS

This application is a U.S. National Stage Application of PCT/US2014/023409, filed on Mar. 11, 2014, which claims the benefit of U.S. Provisional Application No. 61/779,476, filed on Mar. 13, 2013, which is incorporated by reference in its entirety herein.

INCORPORATION OF SEQUENCE LISTING

A computer readable form of a sequence listing is filed with this application by electronic submission and is incorporated into this application by reference in its entirety. The sequence listing is contained in the file named P34106US01_SEQ.txt, which is 415,089 bytes in size (measured in operating system MS windows) and was created on Sep. 10, 2015.

FIELD OF THE INVENTION

The invention relates generally to the field of weed management. More specifically, the invention relates to control of *Sorghum* weed species and compositions containing polynucleotide molecules. The invention further provides methods and compositions useful for Johnsongrass control.

BACKGROUND OF THE INVENTION

Weeds are plants that compete with cultivated plants in an agronomic environment and cost farmers billions of dollars annually in crop losses and the expense of efforts to keep weeds under control. Weeds also serve as hosts for crop diseases and insect pests. Weeds are plants that are unwanted in any particular environment. The losses caused by weeds in agricultural production environments include decreases in crop yield, reduced crop quality, increased irrigation costs, increased harvesting costs, reduced land value, injury to livestock, and crop damage from insects and diseases harbored by the weeds. The principal means by which weeds cause these effects are: 1) competing with crop plants for water, nutrients, sunlight and other essentials for growth and development, 2) production of toxic or irritant chemicals that cause human or animal health problem, 3) production of immense quantities of seed or vegetative reproductive parts or both that contaminate agricultural products and perpetuate the species in agricultural lands, and 4) production on agricultural and nonagricultural lands of vast amounts of vegetation that must be disposed of Herbicide tolerant weeds are a problem with nearly all herbicides in use, there is a need to effectively manage these weeds. There are over 365 weed biotypes currently identified as being herbicide resistant to one or more herbicides by the Herbicide Resistance Action Committee (HRAC), the North American Herbicide Resistance Action Committee (NAHRAC), and the Weed Science Society of America (WSSA).

*Sorghum* weed species, especially, Johnsongrass (*Sorghum halepense*) shattercane (*Sorghum bicolor*) and sudangrass (*Sorghum Sudanese*) are difficult to control weeds that have been shown to develop tolerance to several classes of frequently used herbicides.

The present invention provides herbicidal compositions that comprise polynucleotide compositions useful for modulating gene expression in the *Sorghum* weed species, johnsongrass in particular, genes providing the production of herbicide target proteins, such as, acetyl-CoA carboxylase (ACCase), acetolactate synthase (ALS large subunit and ALS small subunit, also known as acetohydroxyacid synthase, AHAS), dihydropteroate synthetase (DHPS), 5-enolpyruvylshikimate-3-phosphate synthase (EPSPS), glutamine synthetase (GS2), 4-hydroxyphenyl-pyruvate-dioxygenase (HPPD), phytoene desaturase (PDS), protoporphyrinogen IX oxidase (PPDX) in plants for the purpose of enhancing control of johnsongrass in an agronomic environment and for the management of herbicide resistant johnsongrass.

SUMMARY OF THE INVENTION

The invention comprises a method of *Sorghum* species weed control, in particular johnsongrass (*Sorghum halepense*) plant control comprising an external application of a herbicidal composition to a *Sorghum halepense* plant or a part of the *Sorghum halepense* plant in need of control, said herbicidal composition comprising a polynucleotide, an organosilicone surfactant concentration of about 0.2 percent or greater, and an effective dose of a nonpolynucleotide herbicide, wherein the polynucleotide is at least 19 contiguous polynucleotides in length and essentially identical or essentially complementary to a segment of a *Sorghum halepense* gene polynucleotide selected from the group consisting of SEQ ID NO: 1-120, wherein said treated plant is more sensitive to said nonpolynucleotide herbicide relative to a similar plant treated with a herbicide composition not containing said polynucleotide.

In another aspect of the invention, the herbicide composition comprises a polynucleotide at least 19 contiguous polynucleotides in length and essentially identical or essentially complementary to a segment of a *Sorghum halepense* gene polynucleotide selected from the group consisting of SEQ ID NO: 1-25, and an organosilicone surfactant concentration of about 0.2 percent or greater, and a nonpolynucleotide herbicide selected from the group consisting of aryloxyphenoxypropionates, cyclohexanediones and phenylpyrazoline.

In another aspect of the invention, the herbicide composition comprises a polynucleotide at least 19 contiguous polynucleotides in length and essentially identical or essentially complementary to a segment of a *Sorghum halepense* gene polynucleotide selected from the group consisting of SEQ ID NO: 26-44, and an organosilicone surfactant concentration of about 0.2 percent or greater, and a nonpolynucleotide herbicide selected from the group consisting of sulfonylureas, imidazolinones, triazolopyrimidines, pyrimidinyl(thio)benzoates, and sulfonylaminocarbonyl-triazolinones.

In another aspect of the invention, the herbicide composition comprises a polynucleotide at least 19 contiguous polynucleotides in length and essentially identical or essentially complementary to a segment of a *Sorghum halepense* gene polynucleotide selected from the group consisting of SEQ ID NO: 45-59, and an organosilicone surfactant concentration of about 0.2 percent or greater, and a nonpolynucleotide herbicide selected from the group consisting of sulfonylureas, imidazolinones, triazolopyrimidines, pyrimidinyl(thio)benzoates, and sulfonylaminocarbonyl-triazolinones.

In another aspect of the invention, the herbicide composition comprises a polynucleotide at least 19 contiguous polynucleotides in length and essentially identical or essentially complementary to a segment of a *Sorghum halepense* gene polynucleotide selected from the group consisting of SEQ ID NO: 60-66, and an organosilicone surfactant concentration of about 0.2 percent or greater, and a nonpolynucleotide herbicide selected from the group consisting of sulfonamides and asulam.

In another aspect of the invention, the herbicide composition comprises a polynucleotide at least 19 contiguous polynucleotides in length and essentially identical or essentially complementary to a segment of a *Sorghum halepense* gene polynucleotide selected from the group consisting of SEQ ID NO: 67-74, and an organosilicone surfactant concentration of about 0.2 percent or greater, and a nonpolynucleotide herbicide selected from the group consisting of glyphosate.

In another aspect of the invention, the herbicide composition comprises a polynucleotide at least 19 contiguous polynucleotides in length and essentially identical or essentially complementary to a segment of a *Sorghum halepense* gene polynucleotide selected from the group consisting of SEQ ID NO: 75-89, and an organosilicone surfactant concentration of about 0.2 percent or greater, and a nonpolynucleotide herbicide selected from the group consisting of glufosinate.

In another aspect of the invention, the herbicide composition comprises a polynucleotide at least 19 contiguous polynucleotides in length and essentially identical or essentially complementary to a segment of a *Sorghum halepense* gene polynucleotide selected from the group consisting of SEQ ID NO: 90-96, and an organosilicone surfactant concentration of about 0.2 percent or greater, and a nonpolynucleotide herbicide selected from the group consisting of triketones, isoxazoles, and pyrazoles.

In another aspect of the invention, the herbicide composition comprises a polynucleotide at least 19 contiguous polynucleotides in length and essentially identical or essentially complementary to a segment of a *Sorghum halepense* gene polynucleotide selected from the group consisting of SEQ ID NO: 97-105, and an organosilicone surfactant concentration of about 0.2 percent or greater, and a nonpolynucleotide herbicide selected from the group consisting of pyridazinones, pyridinecarboxamides, beflubutamid, fluridone, flurochloridone and flurtamone.

In another aspect of the invention, the herbicide composition comprises a polynucleotide at least 19 contiguous polynucleotides in length and essentially identical or essentially complementary to a segment of a *Sorghum halepense* gene polynucleotide selected from the group consisting of SEQ ID NO: 106-120, and an organosilicone surfactant concentration of about 0.2 percent or greater, and a nonpolynucleotide herbicide selected from the group consisting of acifluorfen-Na, bifenox, chlomethoxyfen, fluoroglycofen-ethyl, fomesafen, halosafen, lactofen, oxyfluorfen, fluazolate, pyraflufen-ethyl, cinidon-ethyl, flumioxazin, flumiclorac-pentyl, fluthiacet-methyl, thidiazimin, oxadiazon, oxadiargyl, azafenidin, carfentrazone-ethyl, sulfentrazone, pentoxazone, benzfendizone, butafenacil, pyrazogyl, and profluazol.

The polynucleotide of the herbicide composition is at least 19 contiguous nucleotides, and at least 85 percent identical to a gene sequence selected from the group consisting of SEQ ID NO:1-120. The polynucleotide can also be sense or anti-sense ssDNA or ssRNA, dsRNA, or dsDNA, or dsDNA/RNA hybrids.

In another aspect of the invention, the herbicide composition comprises a polynucleotide at least 19 contiguous nucleotide in length or at least 85 percent homologous to polynucleotides selected from the group consisting of SEQ ID NO: 121-386. The polynucleotide can also be sense or anti-sense ssDNA or ssRNA, dsRNA, or dsDNA, or dsDNA/RNA hybrids.

In a further aspect of the invention, the polynucleotide molecule containing composition of the invention may be combined with other herbicidal compounds in a premix or tankmix to provide additional control of unwanted johnsongrass plants in a field of crop plants or combined with other agricultural chemicals to provide additional benefit to crop plants in a field treated with the herbicide composition of the invention.

DETAILED DESCRIPTION

The invention provides a method and herbicide compositions containing a polynucleotide that provide for regulation of herbicide target gene expression and enhanced control of weedy *Sorghum* plant species and important herbicide resistant *Sorghum* weed biotypes. Aspects of the method can be applied to manage johnsongrass plants in agronomic and other cultivated environments.

The following definitions and methods are provided to better define the present invention and to guide those of ordinary skill in the art in the practice of the present invention. Unless otherwise noted, terms are to be understood according to conventional usage by those of ordinary skill in the relevant art. Where a term is provided in the singular, the inventors also contemplate aspects of the invention described by the plural of that term.

Herbicide activity is often directed to known enzymes in a plant cell. These enzymes include acetyl-CoA carboxylase (ACCase), acetolactate synthase (ALS large subunit and ALS small subunit, also known as acetohydroxyacid synthase, AHAS), dihydropteroate synthetase (DHPS), 5-enolpyruvylshikimate-3-phosphate synthase (EPSPS), glutamine synthetase (GS2), 4-hydroxyphenyl-pyruvate-dioxygenase (HPPD), phytoene desaturase (PDS), and protoporphyrinogen IX oxidase (PPDX). Plant genes encode for these enzymes and the polynucleotides that provide for the expression of these enzymes have been isolated from johnsongrass (*Sorghum halepense*) in the invention. The genes that encode for these enzymes are herein referred to as herbicide target genes.

The Acetyl-CoA carboxylase (ACCase) enzyme catalyzes the biotin-dependent carboxylation of acetyl-CoA to produce malonyl-CoA, this is the first and the committed step in the biosynthesis of long-chain fatty acids. This enzyme is the target of many herbicides that include members of the chemical families of aryloxyphenoxypropionates, cyclohexanediones and phenylpyrazoline, that include, but are not limited to an aryloxyphenoxypropionate comprising clodinafop (Propanoic acid, 2-[4-[(5-chloro-3-fluoro-2-pyridinyl)oxy]phenoxy]-2-propynyl ester, (2R)), cyhalofop (butyl (2R)-2-[4-(4-cyano-2-fluorophenoxy)phenoxy]propionate), diclofop(methyl 2-[4-(2,4-dichlorophenoxy)phenoxy]propanoate), fenoxaprop (ethyl(R)-2-[4-(6-chloro-1,3-benzoxazol-2-yloxy)phenoxy]propionate), fluazifop (2R)-2-[4-[[5-(trifluoromethyl)-2-pyridinyl]oxy]phenoxy]propanoic acid), haloxyfop (2-[4-[[3-chloro-5-(trifluoromethyl)-2-pyridinyl]oxy]phenoxy]propanoic acid), propaquizafop (2-[[(1-methylethylidene)amino]oxy]ethyl(2R)-2-[4-[(6-chloro-2quinoxalinyl)oxy]phenoxy]propanoate) and quizalofop (2R)-2-[4-[(6-chloro-2-quinoxalinyl)oxy]phenoxy]propanoic acid; a cyclohexanedione comprising alloxydim (methyl 2,2-dimethyl-4,6-dioxo-5-[(1E)-1-[(2-propen-1-yloxy)imino]butyl]cyclohexanecarboxylate), butroxydim (2-[1-(ethoxyimino)propyl]-3-hydroxy-5-[2,4,6-trimethyl-3-(1-oxobutyl)phenyl]-2-cyclohexen-1-one), clethodim (2-[1-[[[(2E)-3-chloro-2-propen-1-yl]oxy]imino]propyl]-5-[2-(ethylthio)propyl]-3-hydroxy-2-cyclohexen-1-one), cycloxydim (2-[1-(ethoxyimino)butyl]-3-hydroxy-5-(tetrahydro-2H-thiopyran-3-yl)-2-cyclohexen-1-one), profoxydim (2-[1-[[2-(4-chlorophenoxy)propoxy]imino]butyl]-3-hydroxy-5-(tetrahydro-2H-thiopyran-3-yl)-2-cyclohexen-1-one), sethoxydim (2-[1-(ethoxyimino)butyl]-5-[2-(ethylthio)propyl]-3-hydroxy-2-cyclohexen-1-one), tepraloxydim (2-[1-[[[(2E)-3-chloro-2-propen-1-yl]oxy]imino]propyl]-3-hydroxy-5-(tetrahydro-2H-pyran-4-yl)-2-cyclohexen-1-one) and tralkoxydim (2-[1-(ethoxyimino)propyl]-3-hydroxy-5-(2,4,6-trimethylphenyl)-2-cyclohexen-1-one); a phenylpyrazoline comprising pinoxaden (8-(2,6-diethyl-4-methylphenyl)-1,2,4,5-tetrahydro-7-oxo-7H-pyrazolo[1,2-d][1,4,5]oxadiazepin-9-yl 2,2-dimethylpropanoate).

The ALS (acetolactate synthase, also known as acetohydroxyacid synthase, AHAS) enzyme catalyzes the first step in the synthesis of the branched-chain amino acids (valine, leucine, and isoleucine). This enzyme is the target of many herbicides that include members of the chemical families of Sulfonylureas, Imidazolinones, Triazolopyrimidines, Pyrimidinyl(thio)benzoates, and Sulfonylaminocarbonyl-triazolinones, amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flupyrsulfuron-methyl-Na, foramsulfuron, halosulfuron-methyl, imazosulfuron, iodosulfuron, metsulfuron-methyl, nicosulfuron, oxasulfuron, primisulfuron-methyl, prosulfuron, pyrazosulfuron-ethyl, rimsulfuron, sulfometuron-methyl, sulfosulfuron, thifensulfuron-methyl, triasulfuron, tribenuron-methyl, trifloxysulfuron, triflusulfuron-methyl, tritosulfuron, imazapic, imazamethabenz-methyl, imazamox, imazapyr, imazaquin, imazethapyr, cloransulam-methyl, diclosulam, florasulam, flumetsulam, metosulam, bispyribac-Na, pyribenzoxim, pyriftalid, pyrithiobac-Na, pyriminobac-methyl, flucarbazone-Na, and procarbazone-Na.

The dihydropteroate synthetase (DHPS) is an enzyme involved in folic acid synthesis which is needed for purine nucleotide biosynthesis. This enzyme is the target of herbicides that include the carbamate chemical family and sulfonamides and asulam.

The EPSPS (5-enolpyruvylshikimate-3-phosphate synthase) enzyme catalyzes the conversion of shikimate-3-phosphate into 5-enolpyruvyl-shikimate-3-phosphate, an intermediate in the biochemical pathway for creating three essential aromatic amino acids (tyrosine, phenylalanine, and tryptophan). The EPSPS enzyme is the target for the herbicide N-phosphonomethyl glycine also known as glyphosate.

The glutamine synthetase (GS2) enzyme is an essential enzyme in the metabolism of nitrogen by catalyzing the condensation of glutamate and ammonia to form glutamine. This enzyme is the target of phosphinic acids herbicides that include glufosinate-ammonium and bialaphos.

The 4-hydroxyphenyl-pyruvate-dioxygenase (HPPD) is an Fe-containing enzyme, that catalyzes the second reaction in the catabolism of tyrosine, the conversion of 4-hydroxyphenylpyruvate to homogentisate. This enzyme is the target of many herbicides that include members of the chemical families of Triketones, Isoxazoles, and Pyrazoles, includes but are not limited to Triketones, such as, mesotrione, tefuryltrione, tembotrione, and sulcotrione; Isoxazoles, such as, isoxachlortole, pyrasulfotole, and isoxaflutole; Pyrazoles, such as, benzofenap, pyrazolynate, topramezone and pyrazoxyfen. Additional HPPD inhibitors include benzobicyclon and bicyclopyrone, The phytoene desaturase (PDS) enzyme is an essential enzyme in the carotenoid biosynthesis pathway. This enzyme is the target of herbicides that include Pyridazinones, Pyridinecarboxamides, beflubutamid, fluridone, flurochloridone and flurtamone.

Protoporphyrinogen oxidase (PPDX) catalyses the oxidation of protoporphyrinogen IX to protoporphyrin IX during the synthesis of tetrapyrrole molecules. PPDX inhibitor herbicide, which include but is not limited to acifluorfen-Na, bifenox, chlomethoxyfen, fluoroglycofen-ethyl, fomesafen, halosafen, lactofen, oxyfluorfen, fluazolate, pyraflufen-ethyl, cinidon-ethyl, flumioxazin, flumiclorac-pentyl, fluthiacet-methyl, thidiazimin, oxadiazon, oxadiargyl, azafenidin, carfentrazone-ethyl, sulfentrazone, pentoxazone, benzfendizone, butafenacil, pyrazogyl, and profluazol.

As used herein "solution" refers to homogeneous mixtures and non-homogeneous mixtures such as suspensions, colloids, micelles, and emulsions.

Weedy plants are plants that compete with cultivated plants, those of particular importance include, but are not limited to important invasive and noxious weeds and herbicide resistant biotypes in crop production, such as, *Amaranthus* species—*A. albus, A. blitoides, A. hybridus, A. palmeri, A. powellii, A. retroflexus, A. spinosus, A. tuberculatus*, and *A. viridis; Ambrosia* species—*A. trifida, A. artemisifolia; Lolium* species—*L. multiflorum, L. rigidium, L perenne; Digitaria* species—*D. insularis; Euphorbia* species—*E. heterophylla; Kochia* species—*K. scoparia; Sorghum* species—*S. halepense; Conyza* species—*C. bonariensis, C. canadensis, C. sumatrensis; Chloris* species—*C. truncate; Echinochola* species—*E. colona, E. crus-galli; Eleusine* species—*E. indica; Poa* species—*P. annua; Plantago* species—*P. lanceolate; Avena* species—*A. fatua; Chenopodium* species—*C. album; Setaria* species—*S. viridis, Abutilon theophrasti, Ipomoea* species, *Sesbania*, species, *Cassia* species, *Sida* species, *Brachiaria*, species and *Solanum* species.

*Sorghum* weed species include, but are not limited to johnsongrass (*Sorghum halepense*), shattercane (*Sorghum biocolor*), and sudangrass (*Sorghum sudanese*). The polynucleotide molecules of the invention were isolated from johnsongrass and may be applicable in the method and compositions to provide control of the *sorghum* weed species other than johnsongrass where sufficient homology and complementarity of the molecules exist.

It is contemplated that the composition of the present invention will contain multiple polynucleotides and herbicides that include any one or more polynucleotides identical or complementary to a segment of the any one or more herbicide target gene sequences, and the corresponding nonpolynucleotide herbicides. Additionally, the composition may contain a pesticide, where the pesticide is selected from the group consisting of insecticides, fungicides, nematocides, bactericides, acaricides, growth regulators, chemosterilants, semiochemicals, repellents, attractants, pheromones, feeding stimulants, and biopesticides. Any one or more of these compounds can be added to the trigger oligonucleotide to form a multi-component pesticide giving an even broader spectrum of agricultural protection. Examples of such agricultural protectants with which compounds of this invention can be formulated are: insecticides such as abamectin, acephate, azinphos-methyl, bifenthrin, buprofezin, carbofuran, chlorfenapyr, chlorpyrifos, chlorpyrifos-methyl, cyfluthrin, beta-cyfluthrin, cyhalothrin, lambda-cyhalothrin, deltamethrin, diafenthiuron, diazinon, diflubenzuron, dimethoate, esfenvalerate, fenoxycarb, fenpropathrin, fenvalerate, fipronil, flucythrinate, tau-fluvalinate, fonophos, imidacloprid, isofenphos, malathion, metaldehyde, methamidophos, methidathion, methomyl, methoprene, methoxychlor, methyl 7-chloro-2,5-dihydro-2-[[N-(methoxycarbonyl)-N-[4-(trifluoromethoxy)phenyl] amino]carbonyl]indeno[1,2-e][1,3,4]oxadiazine-4a(3H)-carboxylate (DPX-JW062), monocrotophos, oxamyl, parathion, parathion-methyl, permethrin, phorate, phosalone, phosmet, phosphamidon, pirimicarb, profenofos, rotenone, sulprofos, tebufenozide, tefluthrin, terbufos, tetrachlorvinphos, thiodicarb, tralomethrin, trichlorfon and triflumuron; most preferably a glyphosate compound is formulated with a fungicide compound or combinations of fungicides, such as azoxystrobin, benomyl, blasticidin-S, Bordeaux mixture (tribasic copper sulfate), bromuconazole, captafol, captan, carbendazim, chloroneb, chlorothalonil, copper oxychloride, copper salts, cymoxanil, cyproconazole, cyprodinil (CGA 219417), diclomezine, dicloran, difenoconazole, dimethomorph, diniconazole, diniconazole-M, dodine, edifenphos, epoxiconazole (BAS 480F), famoxadone, fenarimol, fenbuconazole, fenpiclonil, fenpropidin, fenpropimorph, fluazinam, fluquinconazole, flusilazole, flutolanil, flutriafol, folpet, fosetyl-aluminum, furalaxyl, hexaconazole, ipconazole, iprobenfos, iprodione, isoprothiolane, kasugamycin, kresoxim-methyl, mancozeb, maneb, mepronil, metalaxyl, metconazole, S-methyl 7-benzothiazolecarbothioate (CGA 245704), myclobutanil, neo-asozin (ferric methanearsonate), oxadixyl, penconazole, pencycuron, probenazole, prochloraz, propiconazole, pyrifenox, pyroquilon, quinoxyfen, spiroxamine (KWG4168), sulfur, tebuconazole, tetraconazole, thiabendazole, thiophanate-methyl, thiram, triadimefon, triadimenol, tricyclazole, trifloxystrobin, triticonazole, validamycin and vinclozolin; combinations of fungicides are common for example, cyproconazole and azoxystrobin, difenoconazole, and metalaxyl-M, fludioxonil and metalaxyl-M, mancozeb and metalaxyl-M, copper hydroxide and metalaxyl-M, cyprodinil and fludioxonil, cyproconazole and propiconazole; commercially available fungicide formulations for control of Asian soybean rust disease include, but are not limited to Quadris® (Syngenta Corp), Bravo® (Syngenta Corp), Echo 720® (Sipcam Agro Inc), Headline® 2.09EC (BASF Corp), Tilt® 3.6EC (Syngenta Corp), PropiMax™ 3.6 EC (Dow AgroSciences), Bumper® 41.8EC (MakhteshimAgan), Folicur® 3.6F (Bayer CropScience), Laredo® 25EC (Dow AgroSciences), Laredo™ 25EW (Dow AgroSciences), Stratego® 2.08F (Bayer Corp), Domark™ 125SL (Sipcam Agro USA), and Pristine®38% WDG (BASF Corp) these can be combined with glyphosate compositions as described in the present invention to provide enhanced protection from soybean rust disease; nematocides such as aldoxycarb and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents such as *Bacillus thuringiensis, Bacillus thuringiensis* delta endotoxin, baculovirus, and entomopathogenic bacteria, virus and fungi.

Numerous nonpolynucleotide herbicides are available that can be added to the composition of the present invention, for example, members of the herbicide families that include but are not limited to amide herbicides, aromatic acid herbicides, arsenical herbicides, benzothiazole herbicides, benzoylcyclohexanedione herbicides, benzofuranyl alkylsulfonate herbicides, carbamate herbicides, cyclohexene oxime herbicides, cyclopropylisoxazole herbicides, dicarboximide herbicides, dinitroaniline herbicides, dinitrophenol herbicides, diphenyl ether herbicides, dithiocarbamate herbicides, halogenated aliphatic herbicides, imidazolinone herbicides, inorganic herbicides, nitrile herbicides, organophosphorus herbicides, oxadiazolone herbicides, oxazole herbicides, phenoxy herbicides, phenylenediamine herbicides, pyrazole herbicides, pyridazine herbicides, pyridazinone herbicides, pyridine herbicides, pyrimidinediamine herbicides, pyrimidinyloxybenzylamine herbicides, quaternary ammonium herbicides, thiocarbamate herbicides, thiocarbonate herbicides, thiourea herbicides, triazine herbicides, triazinone herbicides, triazole herbicides, triazolone herbicides, triazolopyrimidine herbicides, uracil herbicides, and urea herbicides. In particular, the rates of use of the added herbicides can be reduced in compositions comprising the polynucleotides of the invention. Use rate reductions of the additional added herbicides can be 10-25 percent, 26-50 percent, 51-75 percent or more can be achieved that enhance the activity of the polynucleotides and herbicide composition and is contemplated as an aspect of the invention.

An agronomic field in need of johnsongrass plant control is treated by application of the herbicide composition of the present invention directly to the surface of the growing plants, such as by a spray. For example, the method is applied to control johnsongrass in a field of crop plants by spraying the field with the composition. The composition can be provided as a tank mix, a sequential treatment of components (generally the polynucleotide containing composition followed by the herbicide), or a simultaneous treatment or mixing of one or more of the components of the composition from separate containers. Treatment of the field can occur as often as needed to provide weed control and the components of the composition can be adjusted to target specific johnsongrass herbicide target genes through utilization of specific polynucleotides or polynucleotide compositions identical or complementary to the gene sequences. The composition can be applied at effective use rates according to the time of application to the field, for example, preplant, at planting, post planting, post-harvest. The non-polynucleotide herbicides can be applied to a field at effective rates of 1 to 2000 g ai/ha (active ingredient per hectare) or more. The polynucleotides of the composition can be applied at rates of 1 to 30 grams per acre depending on the number of polynucleotide molecules as needed for effective johnsongrass control.

Crop plants in which johnsongrass weed control is needed include but are not limited to, i) corn, soybean, cotton, canola, sugar beet, alfalfa, sugarcane, rice, and wheat; ii) vegetable plants including, but not limited to, tomato, sweet pepper, hot pepper, melon, watermelon, cucumber, eggplant, cauliflower, broccoli, lettuce, spinach, onion, peas, carrots, sweet corn, Chinese cabbage, leek, fennel, pumpkin, squash or gourd, radish, Brussels sprouts, tomatillo, garden beans, dry beans, or okra; iii) culinary plants including, but not limited to, basil, parsley, coffee, or tea; or, iv) fruit plants including but not limited to apple, pear, cherry, peach, plum, apricot, banana, plantain, table grape, wine grape, citrus, avocado, mango, or berry; v) a tree grown for ornamental or commercial use, including, but not limited to, a fruit or nut tree; or, vi) an ornamental plant (e. g., an ornamental flowering plant or shrub or turf grass). The methods and compositions provided herein can also be applied to plants produced by a cutting, cloning, or grafting process (i. e., a plant not grown from a seed) include fruit trees and plants that include, but are not limited to, citrus, apples, avocados, tomatoes, eggplant, cucumber, melons, watermelons, and grapes as well as various ornamental plants. The crop plants can be transgenic and genetically engineered or genetically selected to be resistant to one or more of the nonpolynucleotide herbicides.

Polynucleotides

As used herein, the term "DNA", "DNA molecule", "DNA polynucleotide molecule" refers to a single-stranded DNA (ssDNA) or double-stranded DNA (dsDNA) molecule of genomic or synthetic origin, such as, a polymer of deoxyribonucleotide bases or a DNA polynucleotide molecule. As used herein, the term "DNA sequence", "DNA nucleotide sequence" or "DNA polynucleotide sequence" refers to the nucleotide sequence of a DNA molecule. As used herein, the term "RNA", "RNA molecule", "RNA polynucleotide molecule" refers to a single-stranded RNA (ssRNA) or double-stranded RNA (dsRNA) molecule of genomic or synthetic origin, such as, a polymer of ribonucleotide bases that comprise single or double stranded regions. Unless otherwise stated, nucleotide sequences in the text of this specification are given, when read from left to right, in the 5' to 3' direction. The nomenclature used herein is that required by Title 37 of the United States Code of Federal Regulations § 1.822 and set forth in the tables in WIPO Standard ST.25 (1998), Appendix 2, Tables 1 and 3.

As used herein, "polynucleotide" refers to a DNA or RNA molecule containing multiple nucleotides and generally refers both to "oligonucleotides" (a polynucleotide molecule of typically 50 or fewer nucleotides in length) and polynucleotides of 51 or more nucleotides. Embodiments of this invention include compositions including oligonucleotides having a length of 19-25 nucleotides (19-mers, 20-mers, 21-mers, 22-mers, 23-mers, 24-mers, or 25-mers), or medium-length polynucleotides having a length of 26 or more nucleotides (polynucleotides of 26, 27, 28, 29, 30, 46, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, or about 300 nucleotides), or long polynucleotides having a length greater than about 300 nucleotides (for example, polynucleotides of between about 300 to about 400 nucleotides, between about 400 to about 500 nucleotides, between about 500 to about 600 nucleotides, between about 600 to about 700 nucleotides, between about 700 to about 800 nucleotides, between about 800 to about 900 nucleotides, between about 900 to about 1000 nucleotides, between about 300 to about 500 nucleotides, between about 300 to about 600 nucleotides, between about 300 to about 700 nucleotides, between about 300 to about 800 nucleotides, between about 300 to about 900 nucleotides, or about 1000 nucleotides in length, or even greater than about 1000 nucleotides in length, for example up to the entire length of a herbicide target gene including coding or non-coding or both coding and non-coding portions of the target gene). A herbicide target gene comprises any polynucleotide molecule of the gene in a plant cell or fragment thereof for which the modulation of the expression of the herbicide target gene product is provided by the methods and compositions of the present invention. Where a polynucleotide is double-stranded, its length can be similarly described in terms of base pairs. Oligonucleotides and polynucleotides of the present invention can be made that are essentially identical or essentially complementary to adjacent genetic elements of a gene, for example, spanning the junction region of an intron and exon, the junction region of a promoter and a transcribed region, the junction region of a 5' leader and a coding sequence, the junction of a 3' untranslated region and a coding sequence.

Polynucleotide compositions used in the various embodiments of this invention include compositions including oligonucleotides or polynucleotides or a mixture of both, including RNA or DNA or RNA/DNA hybrids or chemically modified oligonucleotides or polynucleotides or a mixture thereof. In some embodiments, the polynucleotide may be a combination of ribonucleotides and deoxyribonucleotides, for example, synthetic polynucleotides consisting mainly of ribonucleotides but with one or more terminal deoxyribonucleotides or synthetic polynucleotides consisting mainly of deoxyribonucleotides but with one or more terminal dideoxyribonucleotides. In some embodiments, the polynucleotide includes non-canonical nucleotides such as inosine, thiouridine, or pseudouridine. In some embodiments, the polynucleotide includes chemically modified nucleotides. Examples of chemically modified oligonucleotides or polynucleotides are well known in the art; see, for example, US Patent Publication 20110171287, US Patent Publication 20110171176, and US Patent Publication 20110152353, US Patent Publication, 20110152346, US Patent Publication 20110160082, herein incorporated by reference. For example, including but not limited to the naturally occurring phosphodiester backbone of an oligonucleotide or polynucleotide can be partially or completely modified with phosphorothioate, phosphorodithioate, or methylphosphonate internucleotide linkage modifications, modified nucleoside bases or modified sugars can be used in oligonucleotide or polynucleotide synthesis, and oligonucleotides or polynucleotides can be labeled with a fluorescent moiety (for example, fluorescein or rhodamine) or other label (for example, biotin).

The polynucleotides can be single- or double-stranded RNA or single- or double-stranded DNA or double-stranded DNA/RNA hybrids or modified analogues thereof, and can be of oligonucleotide lengths or longer. In more specific embodiments of the invention the polynucleotides that provide single-stranded RNA in the plant cell are selected from the group consisting of (a) a single-stranded RNA molecule (ssRNA), (b) a single-stranded RNA molecule that self-hybridizes to form a double-stranded RNA molecule, (c) a double-stranded RNA molecule (dsRNA), (d) a single-stranded DNA molecule (ssDNA), (e) a single-stranded DNA molecule that self-hybridizes to form a double-stranded DNA molecule, and (f) a single-stranded DNA molecule including a modified Pol III gene that is transcribed to an RNA molecule, (g) a double-stranded DNA molecule (dsDNA), (h) a double-stranded DNA molecule including a modified Pol III gene that is transcribed to an RNA molecule, (i) a double-stranded, hybridized RNA/DNA molecule, or combinations thereof. In some embodiments these polynucleotides include chemically modified nucleotides or non-canonical nucleotides. In embodiments of the method the polynucleotides include double-stranded DNA formed by intramolecular hybridization, double-stranded DNA formed by intermolecular hybridization, double-stranded RNA formed by intramolecular hybridization, or double-stranded RNA formed by intermolecular hybridization. In one embodiment the polynucleotides include single-stranded DNA or single-stranded RNA that self-hybridizes to form a hairpin structure having an at least partially double-stranded structure including at least one segment that will hybridize to RNA transcribed from the gene targeted for suppression. Not intending to be bound by any mechanism, it is believed that such polynucleotides are or will produce single-stranded RNA with at least one segment that will hybridize to RNA transcribed from the gene targeted for suppression. In certain other embodiments the polynucleotides further includes a promoter, generally a promoter functional in a plant, for example, a pol II promoter, a pol III promoter, a pol IV promoter, or a pol V promoter.

The term "gene" refers to chromosomal DNA, plasmid DNA, cDNA, intron and exon DNA, artificial DNA polynucleotide, or other DNA that encodes a peptide, polypeptide, protein, or RNA transcript molecule, and the genetic elements flanking the coding sequence that are involved in the regulation of expression, such as, promoter regions, 5' leader regions, 3' untranslated regions. Any of the components of the herbicide target gene are potential targets for the oligonucleotides and polynucleotides of the present invention.

The polynucleotide molecules of the present invention are designed to modulate expression by inducing regulation or suppression of an endogenous herbicide target gene in a johnsongrass plant and are designed to have a nucleotide sequence essentially identical or essentially complementary to the nucleotide sequence of the gene or to the sequence of RNA transcribed from the target gene, which can be coding sequence or non-coding sequence. These effective polynucleotide molecules that modulate expression are referred to as "a trigger, or triggers". By "essentially identical" or "essentially complementary" is meant that the trigger polynucleotides (or at least one strand of a double-stranded polynucleotide or portion thereof, or a portion of a single strand polynucleotide) are designed to hybridize to the endogenous gene noncoding sequence (including promoters and regulatory elements of the gene) or to RNA transcribed (known as messenger RNA or an RNA transcript) from the endogenous gene to effect regulation or suppression of expression of the endogenous gene. Trigger molecules are identified by "tiling" the gene targets with partially overlapping probes or non-overlapping probes of antisense or sense polynucleotides that are essentially identical or essentially complementary to the nucleotide sequence of an endogenous gene. Multiple target sequences can be aligned and sequence regions with homology in common, according to the methods of the present invention, are identified as potential trigger molecules for the multiple targets. Multiple trigger molecules of various lengths, for example 19-25 nucleotides, 26-50 nucleotides, 51-100 nucleotides, 101-200 nucleotides, 201-300 nucleotides or more can be pooled into a few treatments in order to investigate polynucleotide molecules that cover a portion of a gene sequence (for example, a portion of a coding versus a portion of a noncoding region, or a 5' versus a 3' portion of a gene) or an entire gene sequence including coding and noncoding regions of a target gene. Polynucleotide molecules of the pooled trigger molecules can be divided into smaller pools or single molecules in order to identify trigger molecules that provide the desired effect.

The herbicide target gene RNA and DNA polynucleotide molecules are sequenced by any number of available methods and equipment. Some of the sequencing technologies are available commercially, such as the sequencing-by-hybridization platform from Affymetrix Inc. (Sunnyvale, Calif.) and the sequencing-by-synthesis platforms from 454 Life Sciences (Bradford, Conn.), Illumina/Solexa (Hayward, Calif.) and Helicos Biosciences (Cambridge, Mass.), and the sequencing-by-ligation platform from Applied Biosystems (Foster City, Calif.), as described below. In addition to the single molecule sequencing performed using sequencing-by-synthesis of Helicos Biosciences, other single molecule sequencing technologies are encompassed by the method of the invention and include the SMRT™ technology of Pacific Biosciences, the Ion Torrent™ technology, and nanopore sequencing being developed for example, by Oxford Nanopore Technologies.

Embodiments of single-stranded polynucleotides functional in this invention have sequence complementarity that need not be 100 percent, but is at least sufficient to permit hybridization to RNA transcribed from the herbicide target gene or DNA of the herbicide target gene to form a duplex to permit a gene silencing mechanism. Thus, in embodiments, a polynucleotide fragment is designed to be essentially identical to, or essentially complementary to, a sequence of 19 or more contiguous nucleotides in either DNA gene sequence or messenger RNA transcribed from the target gene. By "essentially identical" is meant having 100 percent sequence identity or at least about 83, 84, 85, 86, 87, 88, 89, 90, 91, 92, 93, 94, 95, 96, 97, 98, or 99 percent sequence identity when compared to the sequence of 19 or more contiguous nucleotides in either the target gene or RNA transcribed from the target gene; by "essentially complementary" is meant having 100 percent sequence complementarity or at least about 83, 84, 85, 86, 87, 88, 89, 90, 91, 92, 93, 94, 95, 96, 97, 98, or 99 percent sequence complementarity when compared to the sequence of 19 or more contiguous nucleotides in either the target gene or RNA transcribed from the target gene. In some embodiments of this invention polynucleotide molecules are designed to have 100 percent sequence identity with or complementarity to one allele or one family member of a given target gene (coding or non-coding sequence of a gene for of the present invention); in other embodiments the polynucleotide molecules are designed to have 100 percent sequence identity with or complementarity to multiple alleles or family members of a given target gene.

In certain embodiments, the polynucleotides used in the compositions that are essentially identical or essentially complementary to the target gene or transcript will comprise the predominant nucleic acid in the composition. Thus in certain embodiments, the polynucleotides that are essentially identical or essentially complementary to the target gene or transcript will comprise at least about 50%, 75%, 95%, 98% or 100% of the nucleic acids provided in the composition by either mass or molar concentration. However, in certain embodiments, the polynucleotides that are essentially identical or essentially complementary to the target gene or transcript can comprise at least about 1% to about 50%, about 10% to about 50%, about 20% to about 50%, or about 30% to about 50% of the nucleic acids provided in the composition by either mass or molar concentration. Also provided are compositions where the polynucleotides that are essentially identical or essentially complementary to the target gene or transcript can comprise at least about 1% to 100%, about 10% to 100%, about 20% to about 100%, about 30% to about 50%, or about 50% to a 100% of the nucleic acids provided in the composition by either mass or molar concentration.

"Identity" refers to the degree of similarity between two polynucleic acid or protein sequences. An alignment of the two sequences is performed by a suitable computer program. A widely used and accepted computer program for performing sequence alignments is CLUSTALW v1.6 (Thompson, et al. Nucl. Acids Res., 22: 4673-4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there are 100 matched amino acids between a 200 and a 400 amino acid protein, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

Trigger molecules for specific herbicide target gene family members can be identified from coding and/or non-coding sequences of gene families of a plant or multiple plants, by aligning and selecting 200-300 polynucleotide fragments from the least homologous regions amongst the aligned sequences and evaluated using topically applied polynucleotides (as sense or anti-sense ssDNA or ssRNA, dsRNA, or dsDNA) to determine their relative effectiveness in inducing the herbicidal phenotype. The effective segments are further subdivided into 50-60 polynucleotide fragments, prioritized by least homology, and reevaluated using topically applied polynucleotides. The effective 50-60 polynucleotide fragments are subdivided into 19-30 polynucleotide fragments, prioritized by least homology, and again evaluated for induction of the yield/quality phenotype. Once relative effectiveness is determined, the fragments are utilized singly, or again evaluated in combination with one or more other fragments to determine the trigger composition or mixture of trigger polynucleotides for providing the yield/quality phenotype.

Trigger molecules for broad activity against *Sorghum* weed species can be identified from coding and/or non-coding sequences of gene families of a plant or multiple plants, by aligning and selecting 200-300 polynucleotide fragments from the most homologous regions amongst the aligned sequences and evaluated using topically applied polynucleotides (as sense or anti-sense ssDNA or ssRNA, dsRNA, or dsDNA) to determine their relative effectiveness in inducing the yield/quality phenotype. The effective segments are subdivided into 50-60 polynucleotide fragments, prioritized by most homology, and reevaluated using topically applied polynucleotides. The effective 50-60 polynucleotide fragments are subdivided into 19-30 polynucleotide fragments, prioritized by most homology, and again evaluated for induction of the yield/quality phenotype. Once relative effectiveness is determined, the fragments may be utilized singly, or in combination with one or more other fragments to determine the trigger composition or mixture of trigger polynucleotides for providing the yield/quality phenotype.

Methods of making polynucleotides are well known in the art. Chemical synthesis, in vivo synthesis and in vitro synthesis methods and compositions are known in the art and include various viral elements, microbial cells, modified polymerases, and modified nucleotides. Commercial preparation of oligonucleotides often provides two deoxyribonucleotides on the 3' end of the sense strand. Long polynucleotide molecules can be synthesized from commercially available kits, for example, kits from Applied Biosystems/Ambion (Austin, Tex.) have DNA ligated on the 5' end in a microbial expression cassette that includes a bacterial T7 polymerase promoter that makes RNA strands that can be assembled into a dsRNA and kits provided by various manufacturers that include T7 RiboMax Express (Promega, Madison, Wis.), AmpliScribe T7-Flash (Epicentre, Madison, Wis.), and TranscriptAid T7 High Yield (Fermentas, Glen Burnie, Md.). dsRNA molecules can be produced from microbial expression cassettes in bacterial cells (Ongvarrasopone et al. ScienceAsia 33:35-39; Yin, Appl. Microbiol. Biotechnol 84:323-333, 2009; Liu et al., BMC Biotechnology 10:85, 2010) that have regulated or deficient RNase III enzyme activity or the use of various viral vectors to produce sufficient quantities of dsRNA. In some embodiments design parameters such as Reynolds score (Reynolds et al. Nature Biotechnology 22, 326-330 (2004) and Tuschl rules (Pei and Tuschl, Nature Methods 3(9): 670-676, 2006) are known in the art and are used in selecting polynucleotide sequences effective in gene silencing. In some embodiments random design or empirical selection of polynucleotide sequences is used in selecting polynucleotide sequences effective in gene silencing. In some embodiments the sequence of a polynucleotide is screened against the genomic DNA of the intended plant to minimize unintentional silencing of other genes.

The polynucleotide compositions of this invention are useful in compositions, such as solutions of polynucleotide molecules, at low concentrations, alone or in combination with other components either in the same solution or in separately applied solutions that provide a permeability-enhancing agent. While there is no upper limit on the concentrations and dosages of polynucleotide molecules that can useful in the methods of this invention, lower effective concentrations and dosages will generally be sought for efficiency. The concentrations can be adjusted in consideration of the volume of spray or treatment applied to plant leaves or other plant part surfaces, such as flower petals, stems, tubers, fruit, anthers, pollen, or seed. In one embodiment, a useful treatment for herbaceous plants using 25-mer oligonucleotide molecules is about 1 nanomole (nM) of oligonucleotide molecules per plant, for example, from about 0.05 to 1 nM per plant. Other embodiments for herbaceous plants include useful ranges of about 0.05 to about 100 nM, or about 0.1 to about 20 nM, or about 1 nM to about 10 nM of polynucleotides per plant. To illustrate embodiments of the invention, the factor 1×, when applied to oligonucleotide molecules is arbitrarily used to denote a treatment of 0.8 nM of polynucleotide molecule per plant; 10×, 8 nM of polynucleotide molecule per plant; and 100×, 80 nM of polynucleotide molecule per plant.

The polynucleotide compositions of this invention are useful in compositions, such as liquids that comprise polynucleotide molecules, alone or in combination with other components either in the same liquid or in separately applied liquids that provide a transfer agent. As used herein, a transfer agent is an agent that, when combined with a polynucleotide in a composition that is topically applied to a target plant surface, enables the polynucleotide to enter a plant cell. In certain embodiments, a transfer agent is an agent that conditions the surface of plant tissue, e. g., leaves, stems, roots, flowers, or fruits, to permeation by the polynucleotide molecules into plant cells. The transfer of polynucleotides into plant cells can be facilitated by the prior or contemporaneous application of a polynucleotide-transferring agent to the plant tissue. In some embodiments the transferring agent is applied subsequent to the application of the polynucleotide composition. The polynucleotide transfer agent enables a pathway for polynucleotides through cuticle wax barriers, stomata and/or cell wall or membrane barriers into plant cells. Suitable transfer agents to facilitate transfer of the polynucleotide into a plant cell include agents that increase permeability of the exterior of the plant or that increase permeability of plant cells to oligonucleotides or polynucleotides. Such agents to facilitate transfer of the composition into a plant cell include a chemical agent, or a physical agent, or combinations thereof. Chemical agents for conditioning or transfer include (a) surfactants, (b) an organic solvent or an aqueous solution or aqueous mixtures of organic solvents, (c) oxidizing agents, (d) acids, (e) bases, (f) oils, (g) enzymes, or combinations thereof. Embodiments of the method can optionally include an incubation step, a neutralization step (e.g., to neutralize an acid, base, or oxidizing agent, or to inactivate an enzyme), a rinsing step, or combinations thereof. Embodiments of agents or treatments for conditioning of a plant to permeation by polynucleotides include emulsions, reverse emulsions, liposomes, and other micellar-like compositions. Embodiments of agents or treatments for conditioning of a plant to permeation by polynucleotides include counter-ions or other molecules that are known to associate with nucleic acid molecules, e. g., inorganic ammonium ions, alkyl ammonium ions, lithium ions, polyamines such as spermine, spermidine, or putrescine, and other cations. Organic solvents useful in conditioning a plant to permeation by polynucleotides include DMSO, DMF, pyridine, N-pyrrolidine, hexamethylphosphoramide, acetonitrile, dioxane, polypropylene glycol, other solvents miscible with water or that will dissolve phosphonucleotides in non-aqueous systems (such as is used in synthetic reactions). Naturally derived or synthetic oils with or without surfactants or emulsifiers can be used, e. g., plant-sourced oils, crop oils, such as those listed in the $9^{th}$ Compendium of Herbicide Adjuvants, can be used, e. g., paraffinic oils, polyol fatty acid esters, or oils with short-chain molecules modified with amides or polyamines such as polyethyleneimine or N-pyrrolidine. Transfer agents include, but are not limited to, organosilicone preparations.

In certain embodiments, an organosilicone preparation that is commercially available as Silwet® L-77 surfactant having CAS Number 27306-78-1 and EPA Number: CAL-.REG.NO. 5905-50073-AA, and currently available from Momentive Performance Materials, Albany, N.Y. can be used to prepare a polynucleotide composition. In certain embodiments where a Silwet L-77 organosilicone preparation is used as a pre-spray treatment of plant leaves or other plant surfaces, freshly made concentrations in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) are efficacious in preparing a leaf or other plant surface for transfer of polynucleotide molecules into plant cells from a topical application on the surface. In certain embodiments of the methods and compositions provided herein, a composition that comprises a polynucleotide molecule and an organosilicone preparation comprising Silwet L-77 in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided.

In certain embodiments, any of the commercially available organosilicone preparations provided such as the following Breakthru S 321, Breakthru S 200 Cat #67674-67-3, Breakthru OE 441 Cat #68937-55-3, Breakthru S 278 Cat #27306-78-1, Breakthru S 243, Breakthru S 233 Cat #134180-76-0, available from manufacturer Evonik Goldschmidt (Germany), Silwet® HS 429, Silwet® HS 312, Silwet® HS 508, Silwet® HS 604 (Momentive Performance Materials, Albany, N.Y.) can be used as transfer agents in a polynucleotide composition. In certain embodiments where an organosilicone preparation is used as a pre-spray treatment of plant leaves or other surfaces, freshly made concentrations in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) are efficacious in preparing a leaf or other plant surface for transfer of polynucleotide molecules into plant cells from a topical application on the surface. In certain embodiments of the methods and compositions provided herein, a composition that comprises a polynucleotide molecule and an organosilicone preparation in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided.

Organosilicone preparations used in the methods and compositions provided herein can comprise one or more effective organosilicone compounds. As used herein, the phrase "effective organosilicone compound" is used to describe any organosilicone compound that is found in an organosilicone preparation that enables a polynucleotide to enter a plant cell. In certain embodiments, an effective organosilicone compound can enable a polynucleotide to enter a plant cell in a manner permitting a polynucleotide mediated suppression of a target gene expression in the plant cell. In general, effective organosilicone compounds include, but are not limited to, compounds that can comprise: i) a trisiloxane head group that is covalently linked to, ii) an alkyl linker including, but not limited to, an n-propyl linker, that is covalently linked to, iii) a poly glycol chain, that is covalently linked to, iv) a terminal group. Trisiloxane head groups of such effective organosilicone compounds include, but are not limited to, heptamethyltrisiloxane. Alkyl linkers can include, but are not limited to, an n-propyl linker. Poly glycol chains include, but are not limited to, polyethylene glycol or polypropylene glycol. Poly glycol chains can comprise a mixture that provides an average chain length "n" of about "7.5". In certain embodiments, the average chain length "n" can vary from about 5 to about 14. Terminal groups can include, but are not limited to, alkyl groups such as a methyl group. Effective organosilicone compounds are believed to include, but are not limited to, trisiloxane ethoxylate surfactants or polyalkylene oxide modified heptamethyl trisiloxane.

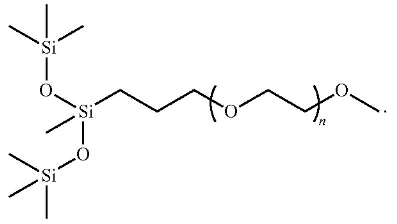

(Compound I: polyalkyleneoxide heptamethyltrisiloxane, average n = 7.5)

In certain embodiments, an organosilicone preparation that comprises an organosilicone compound comprising a trisiloxane head group is used in the methods and compositions provided herein. In certain embodiments, an organosilicone preparation that comprises an organosilicone compound comprising a heptamethyltrisiloxane head group is used in the methods and compositions provided herein. In certain embodiments, an organosilicone composition that comprises Compound I is used in the methods and compositions provided herein. In certain embodiments, an organosilicone composition that comprises Compound I is used in the methods and compositions provided herein. In certain embodiments of the methods and compositions provided herein, a composition that comprises a polynucleotide molecule and one or more effective organosilicone compound in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided.

Compositions of the present invention include but are not limited components that are one or more polynucleotides essentially identical to, or essentially complementary to herbicide target gene sequence (promoter, intron, exon, 5' untranslated region, 3' untranslated region), a transfer agent that provides for the polynucleotide to enter a plant cell, a herbicide that complements the action of the polynucleotide, one or more additional herbicides that further enhance the herbicide activity of the composition or provide an additional mode of action different from the complementing herbicide, various salts and stabilizing agents that enhance the utility of the composition as an admixture of the components of the composition.

In aspects of the invention, methods include one or more applications of a polynucleotide composition and one or more applications of a permeability-enhancing agent for conditioning of a plant to permeation by polynucleotides. When the agent for conditioning to permeation is an organosilicone composition or compound contained therein, embodiments of the polynucleotide molecules are double-stranded RNA oligonucleotides, single-stranded RNA oligonucleotides, double-stranded RNA polynucleotides, single-stranded RNA polynucleotides, double-stranded DNA oligonucleotides, single-stranded DNA oligonucleotides, double-stranded DNA polynucleotides, single-stranded DNA polynucleotides, chemically modified RNA or DNA oligonucleotides or polynucleotides or mixtures thereof.

In various embodiments, a johnsongrass herbicide target gene includes coding (protein-coding or translatable) sequence, non-coding (non-translatable) sequence, or both coding and non-coding sequence. Compositions of the invention can include polynucleotides and oligonucleotides designed to target multiple genes, or multiple segments of one or more genes. The target gene can include multiple consecutive segments of a target gene, multiple non-consecutive segments of a target gene, multiple alleles of a target gene, or multiple target genes from one or more species.

An aspect of the invention provides a method for modulating expression of an herbicide target gene in a johnsongrass plant including (a) conditioning of a plant to permeation by polynucleotides and (b) treatment of the plant with the polynucleotide molecules, wherein the polynucleotide molecules include at least one segment of 19 or more contiguous nucleotides cloned from or otherwise identified from the target gene in either anti-sense or sense orientation, whereby the polynucleotide molecules permeate the interior of the plant and induce modulation of the target gene. The conditioning and polynucleotide application can be performed separately or in a single step. When the conditioning and polynucleotide application are performed in separate steps, the conditioning can precede or can follow the polynucleotide application within minutes, hours, or days. In some embodiments more than one conditioning step or more than one polynucleotide molecule application can be performed on the same plant. In embodiments of the method, the segment can be cloned or identified from (a) coding (protein-encoding), (b) non-coding (promoter and other gene related molecules), or (c) both coding and non-coding parts of the target gene. Non-coding parts include DNA, such as promoter regions or the RNA transcribed by the DNA that provide RNA regulatory molecules, including but not limited to: introns, 5' or 3' untranslated regions, and microRNAs (miRNA), trans-acting siRNAs, natural anti-sense siRNAs, and other small RNAs with regulatory function or RNAs having structural or enzymatic function including but not limited to: ribozymes, ribosomal RNAs, t-RNAs, aptamers, and riboswitches.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1. Polynucleotides Related to the Herbicide Target Genes of Johnsongrass (*Sorghum halepense*)

Polynucleotides were isolated from johnsongrass and sequenced and those identified as noncoding or coding regions of herbicide target genes acetyl-CoA carboxylase (ACCase), acetolactate synthase (ALS large subunit and ALS small subunit, also known as acetohydroxyacid synthase, AHAS), dihydropteroate synthetase (DHPS), 5-enolpyruvylshikimate-3-phosphate synthase (EPSPS), glutamine synthetase (GS2), 4-hydroxyphenyl-pyruvate-dioxygenase (HPPD), phytoene desaturase (PDS), protoporphyrinogen IX oxidase (PPDX) were selected. These are shown as SEQ ID NO:1-120.

Polynucleotide molecules were extracted from johnsongrass tissues by methods standard in the field, for example, total RNA was extracted using Trizol Reagent (Invitrogen Corp, Carlsbad, Calif. Cat. No. 15596-018), following the manufacturer's protocol or modifications thereof by those skilled in the art of polynucleotide extraction that may enhance recover or purity of the extracted RNA. Briefly, starting with approximately 1 gram of ground plant tissue for extraction. Prealiquot 10 milliliters (mL) Trizol reagent to 15 mL conical tubes. Add ground powder to tubes and shake to homogenize. Incubate the homogenized samples for 5 minutes (min) at room temperature (RT) and then add 3 mL of chloroform. Shakes tubes vigorously by hand for 15-30 seconds (sec) and incubate at RT for 3 min. Centrifuge the tubes at 7,000 revolutions per minute (rpm) for 10 min at 4 degrees C. (centigrade). Transfer the aqueous phase to a new 1.5 mL tube and add 1 volume of cold isopropanol. Incubate the samples for 20-30 min at RT and centrifuge at 10,000 rpm for 10 min at 4 degrees C. Wash pellet with Sigma-grade 80 percent ethanol. Remove the supernatant and briefly air-dry the pellet. Dissolve the RNA pellet in approximately 200 microliters of Diethylpyrocarbonate (DEPC) treated water. Heat briefly at 65 C to dissolve pellet and vortex or pipet to resuspend RNA pellet. Adjust RNA concentration to 1-2 microgram/microliter. RNA was used to make cDNA libraries by standard methods that were then sequenced.

Genomic DNA (gDNA) was extracted using EZNA SP Plant DNA Mini kit (Omega Biotek, Norcross Ga., Cat # D5511) and Lysing Matrix E tubes (Q-Biogen, Cat #6914), following the manufacturer's protocol or modifications thereof by those skilled in the art of polynucleotide extraction that may enhance recover or purity of the extracted DNA. Briefly, aliquot ground tissue to a Lysing Matrix E tube on dry ice, add 800 μl Buffer SP1 to each sample, homogenize in a bead beater for 35-45 sec, incubate on ice for 45-60 sec, centrifuge at ≥14000 rpm for 1 min at RT, add 10 microliter RNase A to the lysate, incubate at 65° C. for 10 min, centrifuge for 1 min at RT, add 280 μl Buffer SP2 and vortex to mix, incubate the samples on ice for 5 min, centrifuge at ≥10,000 g for 10 min at RT, transfer the supernatant to a homogenizer column in a 2 ml collection tube, centrifuge at 10,000 g for 2 min at RT, transfer the cleared lysate into a 1.5 ml microfuge tube, add 1.5 volumes Buffer SP3 to the cleared lysate, vortex immediately to obtain a homogeneous mixture, transfer up to 650 μl supernatant to the Hi-Bind column, centrifuge at 10,000 g for 1 min, repeat, apply 100 μl 65° C. Elution Buffer to the column, centrifuge at 10,000 g for 5 min at RT.

Next-generation DNA sequencers, such as the 454-FLX (Roche, Branford, Conn.), the SOLiD (Applied Biosystems), and the Genome Analyzer (HiSeq2000, Illumina, San Diego, Calif.) are used to provide polynucleotide sequence from the DNA and RNA extracted from the plant tissues. Raw sequence data is assembled into contigs. The contig sequence is used to identify trigger molecules that can be applied to the plant to enable regulation of the gene expression. SEQ ID NO: 1-120 (summarized in Table 1) contains the target cDNA and gDNA sequence contigs from the various herbicide target genes of johnsongrass.

TABLE 1

Johnsongrass herbicide target gene sequences and fragments SEQ ID NO: 1-120.

| SEQ ID NO | GENE | TYPE |
|---|---|---|
| 1 | ACCase | cDNAContig |
| 2 | ACCase | cDNAContig |
| 3 | ACCase | gDNAContig |
| 4 | ACCase | gDNAContig |
| 5 | ACCase | gDNAContig |
| 6 | ACCase | gDNAContig |
| 7 | ACCase | gDNAContig |
| 8 | ACCase | gDNAContig |
| 9 | ACCase | gDNAContig |
| 10 | ACCase | gDNAContig |
| 11 | ACCase | gDNAContig |
| 12 | ACCase | gDNAContig |
| 13 | ACCase | gDNAContig |
| 14 | ACCase | gDNAContig |
| 15 | ACCase | gDNAContig |

TABLE 1-continued

Johnsongrass herbicide target gene sequences and fragments SEQ ID NO: 1-120.

| SEQ ID NO | GENE | TYPE |
|---|---|---|
| 16 | ACCase | gDNAContig |
| 17 | ACCase | gDNAContig |
| 18 | ACCase | gDNAContig |
| 19 | ACCase | gDNAContig |
| 20 | ACCase | gDNAContig |
| 21 | ACCase | gDNAContig |
| 22 | ACCase | gDNAContig |
| 23 | ACCase | gDNAContig |
| 24 | ACCase | gDNAContig |
| 25 | ACCase | gDNAContig |
| 26 | ALS | cDNAContig |
| 27 | ALS | cDNAContig |
| 28 | ALS | cDNAContig |
| 29 | ALS | cDNAContig |
| 30 | ALS | cDNAContig |
| 31 | ALS | gDNAContig |
| 32 | ALS | gDNAContig |
| 33 | ALS | gDNAContig |
| 34 | ALS | gDNAContig |
| 35 | ALS | gDNAContig |
| 36 | ALS | gDNAContig |
| 37 | ALS | gDNAContig |
| 38 | ALS | gDNAContig |
| 39 | ALS | gDNAContig |
| 40 | ALS | gDNAContig |
| 41 | ALS | gDNAContig |
| 42 | ALS | gDNAContig |
| 43 | ALS | gDNAContig |
| 44 | ALS | gDNAContig |
| 45 | ALS_small | cDNAContig |
| 46 | ALS_small | cDNAContig |
| 47 | ALS_small | cDNAContig |
| 48 | ALS_small | gDNAContig |
| 49 | ALS_small | gDNAContig |
| 50 | ALS_small | gDNAContig |
| 51 | ALS_small | gDNAContig |
| 52 | ALS_small | gDNAContig |
| 53 | ALS_small | gDNAContig |
| 54 | ALS_small | gDNAContig |
| 55 | ALS_small | gDNAContig |
| 56 | ALS_small | gDNAContig |
| 57 | ALS_small | gDNAContig |
| 58 | ALS_small | gDNAContig |
| 59 | ALS_small | gDNAContig |
| 60 | DHPS | cDNAContig |
| 61 | DHPS | cDNAContig |
| 62 | DHPS | gDNAContig |
| 63 | DHPS | gDNAContig |
| 64 | DHPS | gDNAContig |
| 65 | DHPS | gDNAContig |
| 66 | DHPS | gDNAContig |
| 67 | EPSPS | cDNAContig |
| 68 | EPSPS | gDNAContig |
| 69 | EPSPS | gDNAContig |
| 70 | EPSPS | gDNAContig |
| 71 | EPSPS | gDNAContig |
| 72 | EPSPS | gDNAContig |
| 73 | EPSPS | gDNAContig |
| 74 | EPSPS | gDNAContig |
| 75 | GS2 | cDNAContig |
| 76 | GS2 | gDNAContig |
| 77 | GS2 | gDNAContig |
| 78 | GS2 | gDNAContig |
| 79 | GS2 | gDNAContig |
| 80 | GS2 | gDNAContig |
| 81 | GS2 | gDNAContig |
| 82 | GS2 | gDNAContig |
| 83 | GS2 | gDNAContig |
| 84 | GS2 | gDNAContig |
| 85 | GS2 | gDNAContig |
| 86 | GS2 | gDNAContig |
| 87 | GS2 | gDNAContig |
| 88 | GS2 | gDNAContig |
| 89 | GS2 | gDNAContig |

TABLE 1-continued

Johnsongrass herbicide target gene sequences and fragments SEQ ID NO: 1-120.

| SEQ ID NO | GENE | TYPE |
|---|---|---|
| 90 | HPPD | cDNAContig |
| 91 | HPPD | gDNAContig |
| 92 | HPPD | gDNAContig |
| 93 | HPPD | gDNAContig |
| 94 | HPPD | gDNAContig |
| 95 | HPPD | gDNAContig |
| 96 | HPPD | gDNAContig |
| 97 | PDS | cDNAContig |
| 98 | PDS | gDNAContig |
| 99 | PDS | gDNAContig |
| 100 | PDS | gDNAContig |
| 101 | PDS | gDNAContig |
| 102 | PDS | gDNAContig |
| 103 | PDS | gDNAContig |
| 104 | PDS | gDNAContig |
| 105 | PDS | gDNAContig |
| 106 | PPOX | cDNAContig |
| 107 | PPOX | gDNAContig |
| 108 | PPOX | gDNAContig |
| 109 | PPOX | gDNAContig |
| 110 | PPOX | gDNAContig |
| 111 | PPOX | gDNAContig |
| 112 | PPOX | cDNAContig |
| 113 | PPOX | cDNAContig |
| 114 | PPOX | gDNAContig |
| 115 | PPOX | gDNAContig |
| 116 | PPOX | gDNAContig |
| 117 | PPOX | gDNAContig |
| 118 | PPOX | gDNAContig |
| 119 | PPOX | gDNAContig |
| 120 | PPOX | gDNAContig |

Example 2. Polynucleotides of the Invention Related to Trigger Molecules of the Johnsongrass Herbicide Target Genes The gene sequences and fragments of SEQ ID NO: 1-120 were selected into short polynucleotide lengths of 30 contiguous nucleotides as shown in Table 2, SEQ ID NO:121-386. These polynucleotides are tested to select an efficacious trigger to any of the herbicide target gene sequence regions. The trigger polynucleotides are constructed as sense or anti-sense ssDNA or ssRNA, dsRNA, or dsDNA, or dsDNA/RNA hybrids and combined with an organosilicone based transfer agent and nonpolynucleotide herbicide to provide a new herbicidal composition. The polynucleotides are combined into sets of two to three polynucleotides per set, using 4-8 nM of each polynucleotide. Each polynucleotide set is prepared with the organosilicone transfer agent and applied to a johnsongrass plant or to a field of crop plants containing johnsongrass plants in combination with a nonpolynucleotide herbicide that targets one or more of the enzymes of the herbicide target genes, or followed by the nonpolynucleotide herbicide treatment one to three days later. The effect is measured as stunting the growth and/or killing of the plant and is measured 8-14 days after treatment with the herbicidal composition. The most efficacious trigger sets are identified and the individual polynucleotides are tested in the same methods as the sets are and the most efficacious single polynucleotide is identified. By this method it is possible to identify one oligonucleotide or several oligonucleotides that effect plant sensitivity to non-polynucleotide herbicide.

It is contemplated that additional 19-30 polynucleotides can be selected from the sequences of SEQ ID NO: 1-120 that are specific for a herbicide target gene in johnsongrass or include activity against a few related weed species, for example, *Sorghum bicolor* and *Sorghum Sudanese*.

TABLE 2

Polynucleotides SEQ ID NO: 121-386.

| SEQ ID NO | SEQ | GENE |
|---|---|---|
| 121 | GGAGAATACTATTTTCTGGAGCTTAATCCC | ACCase |
| 122 | GGGAAAGTGAAGGAGATAACTTTTAAAGCC | ACCase |
| 123 | GGATAGCATGGAAGATTTAGTCTCTGCCCC | ACCase |
| 124 | GGTGAAACTCAAGTTGGATTGTGATGGGCC | ACCase |
| 125 | GGTCGCTTGGATCTTGGAGATGTCAACACC | ACCase |
| 126 | GGCTTATGGAAGCATTGGTATATCCAAACC | ACCase |
| 127 | GGCTTATGGAAGCATTGGTATATCCAAACC | ACCase |
| 128 | GGAGGATCCAATGCTTCGCCATGTGGAACC | ACCase |
| 129 | GGTCTCAGGGCTTAAAAACCTCGTCTATCC | ACCase |
| 130 | GGAGAATACTATTTTCTGGAGCTTAATCCC | ACCase |
| 131 | GGGCGAATACTATTTTTTGGAGCTTAATCC | ACCase |
| 132 | GGAGGATCCAATGCTTCGCCATGTGGAACC | ACCase |
| 133 | GGAAGGTTACAATGAAGTAAAATACACCCC | ACCase |
| 134 | GGTAATATTGACAATGAAGTAGGACGCGCC | ACCase |
| 135 | GGAGAATACTATTTTCTGGAGCTTAATCCC | ACCase |
| 136 | GGTGAAACTCAAGTTGGATTGTGATGGGCC | ACCase |
| 137 | GGAACATGAAGCTGTCCACGCCAGAATTCC | ACCase |
| 138 | GGAAGTGGTGCGATTGCCAGTGCATATTCC | ACCase |
| 139 | GGTCAGGTGTGGTTCCCAGATTCTGCAGCC | ACCase |
| 140 | GGTGTGCTGGTCGCTAACAATGGGATGGCC | ACCase |
| 141 | GGTCGCTTGGATCTTGGAGATGTCAACACC | ACCase |
| 142 | GGTTGGATCCAACCCAACCCACCCAACCCC | ACCase |
| 143 | GGATAGCATGGAAGATTTAGTCTCTGCCCC | ACCase |
| 144 | GGTGAAACTCAAGTTGGATTGTGATGGGCC | ACCase |
| 145 | GGTCGCTTGGATCTTGGAGATGTCAACACC | ACCase |
| 146 | GGTGTGCTGGTCGCTAACAATGGGATGGCC | ACCase |
| 147 | GGCGCTGCTGCCTGGCCGGCTGGCTCAGCC | ACCase |
| 148 | GGATTGGACTGGGGACGCCCCCCAGCGGCC | ACCase |
| 149 | GGTGTGCTGGTCGCTAACAATGGGATGGCC | ACCase |
| 150 | GGCGCTGCTGCCTGGCCGGCTGGCTCAGCC | ACCase |
| 151 | GGATTGGACTGGGGACGCCCCCCAGCGGCC | ACCase |
| 152 | GGGAGAGTGGATTTGGGGTTGTTTCAACCC | ACCase |
| 153 | GGTTCATTCCCCGGTCAAGGGTGAGCATCC | ACCase |
| 154 | GGGCCTTGGCAACTTCCCCGGCGACGACCC | ALS |
| 155 | GGGTGATGTGTTATTTATGTGATGTTCTCC | ALS |

TABLE 2-continued

Polynucleotides SEQ ID NO: 121-386.

| SEQ ID NO | SEQ | GENE |
|---|---|---|
| 156 | GGGCCTTGGCAACTTCCCCGGCGACGACCC | ALS |
| 157 | GGGTGATGTGTTATTTATGTGATGTTCTCC | ALS |
| 158 | GGGTGATGTGTTATTTATGTGATGTTCTCC | ALS |
| 159 | GGGCCTTGGCAACTTCCCCGGTGACGACCC | ALS |
| 160 | GGAGCGGAGACGGAGGAAGGCGTGGCACCC | ALS |
| 161 | GGCCGCCAAATAGGCCACCACGGCACCACC | ALS |
| 162 | GGCCAAGAGCATTTGCACGTCACCAATGCC | ALS |
| 163 | GGATAATAGCCGATACAGTAGCTGTCAGCC | ALS |
| 164 | GGGCGGTGAACACTGCGACTGACCCGCCCC | ALS |
| 165 | GGACTGGATGCGCCTGAAAATCACCGCACC | ALS |
| 166 | GGCGTCCCCATCGAAACCATCGCACAAGCC | ALS |
| 167 | GGGTGATGGACCCTTGGGGCATTGTTAACC | ALS |
| 168 | GGAGGCATCCAAAGATTTGGGCCGCAGCCC | ALS |
| 169 | GGACAAGCGGGCAGAGTTCGGGTTACTGCC | ALS |
| 170 | GGCCGACCGTTTCCGCCCACTCGGCAGGCC | ALS |
| 171 | GGCCGCGCAGGACGTCGCGGCATCGACACC | ALS |
| 172 | GGTTGCCGACTCACTGTCGAGCCTTGATCC | ALS |
| 173 | GGACCGCGAAGAAGACTGATTCGTGCGCCC | ALS |
| 174 | GGTGTCAACACCGCAGCGATTGCTCATCCC | ALS |
| 175 | GGTTTTGGGGTGACGACCCATGGTGGCACC | ALS |
| 176 | GGGCATCAACGCCATTCGGTCGGCCATGCC | ALS |
| 177 | GGACAGCACGACCTGCCCGATATCTCTGCC | ALS |
| 178 | GGGTGCGTCAGTTACAGCGGATGAAAAACC | ALS |
| 179 | GGTGAAGAAACGCCCGAGGAAGAAATCTCC | ALS |
| 180 | GGAGCCAGTAATGATGAAATCACGATCGCC | ALS |
| 181 | GGCGACGAGGACAGCAACGATGATGAGGCC | ALS |
| 182 | GGGTGACGTTCCCTAGATCCCAAGACAACC | ALS |
| 183 | GGCATTGAAACGAGCTTCCGTGAGGAGACC | ALS |
| 184 | GGTATCTCCAAGCTGCGTTGGTCAATTTCC | ALS |
| 185 | GGTGCCATTGATGTCGTGGGGAGGAAAACC | ALS |
| 186 | GGGGGGCATATCGTCGATGACGACGAGGCC | ALS |
| 187 | GGCCGCGCTCCAAATAAAACTGACGGCACC | ALS |
| 188 | GGCCAGAGTGGAGTTGTCAAGAACCTCTCC | ALS |
| 189 | GGTCAACTACCACGGACTTGATATCAATCC | ALS |
| 190 | GGCCGTTCATGATCGCCTACCAGGATTTCC | ALS |
| 191 | GGTGGCAATTACGCAGCTTCGCTGCGTTCC | ALS |
| 192 | GGAGATACCGACGTGAAGGTCTCTGAGCCC | ALS |
| 193 | GGACATGGCATCAATCCCGGTGATGACGCC | ALS |

TABLE 2-continued

Polynucleotides SEQ ID NO: 121-386.

| SEQ ID NO | SEQ | GENE |
|---|---|---|
| 194 | GGGCTTACCCTTCTCCAGTGCGTGGATGCC | ALS |
| 195 | GGGTTCACCGTTGCCAATGACGTCACTGCC | ALS |
| 196 | GGGTGCTGACACCTTCTGCCCGCTGGGGCC | ALS |
| 197 | GGGTATCACACCGTCGGGGGGCTCATAGCC | ALS |
| 198 | GGACTGTCGGTGAACCTGCCGGAAAAAGCC | ALS |
| 199 | GGCATGACCGCGATGAGTTGGGTGGACGCC | ALS |
| 200 | GGGGGACAATCGAAGAAGGTTCTCAAGACC | ALS |
| 201 | GGTCCTGACACCGATATAGCCGCAATGACC | ALS |
| 202 | GGAGCGGAGACGGAGGAAGGCGTGGCACCC | ALS |
| 203 | GGCCGCCAAATAGGCCACCACGGCACCACC | ALS |
| 204 | GGCCAAGAGCATTTGCACGTCACCAATGCC | ALS |
| 205 | GGATAATAGCCGATACAGTAGCTGTCAGCC | ALS |
| 206 | GGTCGGTGTCAGTGCCGTTTACTCTGGGCC | ALS |
| 207 | GGAGGGAGGCCTCCACGCACATCCCCCTCC | ALS |
| 208 | GGGCGCACCTCCTGGCCGCACGGCGCGCCC | ALS |
| 209 | GGGCCTTGGCAACTTCCCCGGCGACGACCC | ALS |
| 210 | GGGTGATGTGTTATTTATGTGATGTTCTCC | ALS |
| 211 | GGTTACAGCATGCTAGTTGTTTAGACTTCC | ALS_small |
| 212 | GGCCCCCGCTGCCGTGTCGGCGGTCGCCCC | ALS_small |
| 213 | GGTGACCAAACAGCTCAATAAGATTATTCC | ALS_small |
| 214 | GGAGCGGAGACGGAGGAAGGCGTGGCACCC | ALS_small |
| 215 | GGCCGCCAAATAGGCCACCACGGCACCACC | ALS_small |
| 216 | GGCCAAGAGCATTTGCACGTCACCAATGCC | ALS_small |
| 217 | GGATAATAGCCGATACAGTAGCTGTCAGCC | ALS_small |
| 218 | GGAACAGAAGGTATTAAAAGGGTATTACCC | DHPS |
| 219 | GGTCTGATAGAAGTCTCATCATGGGGATCC | DHPS |
| 220 | GGAGGAAAGTTTCAACCAGTGGAAGCTGCC | DHPS |
| 221 | GGTGAGAGAAGCAGAGTTATCTGGGATTCC | DHPS |
| 222 | GGAGGAAAGTTTCAACCAGTGGAAGCTGCC | DHPS |
| 223 | GGTGAGAGAAGCAGAGTTATCTGGGATTCC | DHPS |
| 224 | GGTCATTTGTTTTAGCACCTCTTGTTGACC | DHPS |
| 225 | GGAGGTAAGTTTCAACAAGTGGAAGCTGCC | DHPS |
| 226 | GGTGAGAGAAGCAGAGTTATCTGGGATTCC | DHPS |
| 227 | GGCACCTCCTAGTCTTTGCTGTCTTCATCC | DHPS |
| 228 | GGGTGCTAGCTTAAAAAAAAGATTAACACC | DHPS |
| 229 | GGCATTTACGCCAGTAATTGTACAAGGACC | DHPS |
| 230 | GGCGCCGGCGCCTCAGCTTGTACGGCCTCC | DHPS |

TABLE 2-continued

Polynucleotides SEQ ID NO: 121-386.

| SEQ ID NO | SEQ | GENE |
|---|---|---|
| 231 | GGCACTCAGGGTCTTCCTGATCTTGTTCCC | DHPS |
| 232 | GGAGTGCTGATGGGAATATCCCTTGTAGCC | DHPS |
| 233 | GGAACAGAAGGTATTAAAAGGGTATTACCC | DHPS |
| 234 | GGTCTGAGAGAACTCTCATCATGGGGATCC | DHPS |
| 235 | GGAGGAAAGTTTCAACCAATGGAAGCTGCC | DHPS |
| 236 | GGAAAAGTTTTTTGGGTGAAATATGCAACC | DHPS |
| 237 | GGGCTCTCTGTCGAAGCAGACAAAGTTGCC | EPSPS |
| 238 | GGCTCCATCAGCAGTCAGTACTTGAGTGCC | EPSPS |
| 239 | GGTCAAAAATACAAGTCCCCCAAAAATGCC | EPSPS |
| 240 | GGCTATTGATGTTAACATGAACAAAATGCC | EPSPS |
| 241 | GGCCCAACAGCTATCAGAGACGTGGCGTCC | EPSPS |
| 242 | GGCTATTGATGTTAACATGAACAAAATGCC | EPSPS |
| 243 | GGGGCATTTAATGCAGCAAAATGACAGGCC | EPSPS |
| 244 | GGAAAAGGTACTTGATTGGTTTTTTGTGCC | EPSPS |
| 245 | GGACCGAGACTAGCGTTACTGTTACTGGCC | EPSPS |
| 246 | GGACAAGGCACTTGATTGGTTTTTTGCCCC | EPSPS |
| 247 | GGCAGGCGCCGAGGAGATCGTGCTGCAGCC | EPSPS |
| 248 | GGTGGGTGTCGCCCTATGCCCCTATCGGCC | EPSPS |
| 249 | GGGCTCTCTGTCGAAGCAGACAAAGTTGCC | EPSPS |
| 250 | GGTCATCCCTAACTAGCAAACCATGTTTCC | EPSPS |
| 251 | GGCGGGCGCCGAGGAGATCGTGCTGCAGCC | EPSPS |
| 252 | GGTGGGTGTCGCCCTATGCCCCTATCGGCC | EPSPS |
| 253 | GGGCTCTCTGTCGAAGCAGACAAAGTTGCC | EPSPS |
| 254 | GGTCATCCCTAACTAGCAAACCATGTTTCC | EPSPS |
| 255 | GGCTCCATCAGCAGTCAGTACTTGAGTGCC | EPSPS |
| 256 | GGCTATTGATGTTAACATGAACAAAATGCC | EPSPS |
| 257 | GGGGCATTGAATGCAGCAAAATGACAGGCC | EPSPS |
| 258 | GGCGGGCGCCGAGGAGATCGTGCTGCAGCC | EPSPS |
| 259 | GGTGGGTGTCGCCCTATGCCCCTATCGGCC | EPSPS |
| 260 | GGGCTCTCTGTCGAAGCAGACAAAGTTGCC | EPSPS |
| 261 | GGCTCCATCAGCAGTCAGTACTTGAGTGCC | EPSPS |
| 262 | GGCTATTGATGTTAACATGAACAAAATGCC | EPSPS |
| 263 | GGGGCATTGAATGCAGCAAAATGACAGGCC | EPSPS |
| 264 | GGTGAACTAGACTGATGACTGGGCGGGTCC | EPSPS |
| 265 | GGATCCATCAGGCCCGCCTCGAACCCGGCC | EPSPS |
| 266 | GGCGGGCGCCGAGGAGATCGTGCTGCAGCC | EPSPS |
| 267 | GGGCTCTCTGTCGAAGCAGACAAAGTTGCC | EPSPS |
| 268 | GGTCATCCCTAACTAGCAAACCATGTTTCC | EPSPS |

TABLE 2-continued

Polynucleotides SEQ ID NO: 121-386.

| SEQ ID NO | SEQ | GENE |
|---|---|---|
| 269 | GGCTCCATCAGCAGTCAGTACTTGAGTGCC | EPSPS |
| 270 | GGAAAAGGTACTTGATTGGTTTTTTGTGCC | EPSPS |
| 271 | GGACCGAGACTAGCGTTACTGTTACTGGCC | EPSPS |
| 272 | GGCGCCTCGCCGGGGTTCAAGGTCATGGCC | GS2 |
| 273 | GGGAGAAGACAGTGAAGTCATTCTATACCC | GS2 |
| 274 | GGCACAGGGCTGCGCAAATTTTTAGTGACC | GS2 |
| 275 | GGAACTCTATAAATATAAATCAAATCAACC | GS2 |
| 276 | GGATTTGGAGAGGGGTTTTGGGAGACCGCC | GS2 |
| 277 | GGCCCGGTGACCGATCCCAGCAAGCTGCCC | GS2 |
| 278 | GGTAGGTACGGTATTGAGCAGGAGTACACC | GS2 |
| 279 | GGCAACTTCTTTTGTAACCCTCAAGCTACC | GS2 |
| 280 | GGCTGCTCTGTTCGTGTGGGGCGAGATACC | GS2 |
| 281 | GGAAAAAAGTTCAATTTATCTCTCCCAACC | GS2 |
| 282 | GGTGATCTAACATGTAAAATGTAAGACTCC | GS2 |
| 283 | GGTGCCGGCGCACACACCAACTACAGCACC | GS2 |
| 284 | GGCAGGCACGAGACCGCCGACATCAACACC | GS2 |
| 285 | GGATTGATGTGAATCCGACTAAACAAGGCC | GS2 |
| 286 | GGGGCCAACAAATTAAATCTGAGATATCCC | GS2 |
| 287 | GGTGCCGGCGCACACACCAACTACAGCACC | GS2 |
| 288 | GGCAGGCACGAGACCGCCGACATCAACACC | GS2 |
| 289 | GGCCCGGTGACCGATCCCAGCAAGCTGCCC | GS2 |
| 290 | GGTAGGTACGGTATTGAGCAGGAGTACACC | GS2 |
| 291 | GGCAACTTCTTTTGTAACCCTCAAGCTACC | GS2 |
| 292 | GGCCCGGTGACCGATCCCAGCAAGCTGCCC | GS2 |
| 293 | GGCCCTATAATGTGCTTGGTTTCCCGTTCC | GS2 |
| 294 | GGAAAAAAGTTTAATTTATCTCTCCCAGCC | GS2 |
| 295 | GGACAGGGTAATTAACCCAACAATGCCTCC | GS2 |
| 296 | GGACAGTGTCCTATGGTTTGGTGGGGTGCC | GS2 |
| 297 | GGTGCTTGCTCTGATGCTGGTAATTGTACC | GS2 |
| 298 | GGTCTGGGTGGATGCATCATGCATCATGCC | GS2 |
| 299 | GGCTCATGTTGTGGGTGGATGCGTCATGCC | GS2 |
| 300 | GGTAGGTACGGTATTGAGCAGGAGTACACC | GS2 |
| 301 | GGCAACTTCTTTTGTAACCCTCAAGCTACC | GS2 |
| 302 | GGTGCCGGCGCACACACCAACTACAGCACC | GS2 |
| 303 | GGCAGGCACGAGACCGCCGACATCAACACC | GS2 |
| 304 | GGCTGGGCACCCATATTTCTCCCTCGGACC | GS2 |
| 305 | GGCTCCTCCAGAAATGGCTTACGGTGGGCC | GS2 |

TABLE 2-continued

Polynucleotides SEQ ID NO: 121-386.

| SEQ ID NO | SEQ | GENE |
|---|---|---|
| 306 | GGAGCCACCAAGCACTGCACGGCCCCCTCC | GS2 |
| 307 | GGGCCGATTGGCCGGATCGAATACTTCTCC | GS2 |
| 308 | GGTCAGTCAAGCCCTGACAGCGGCCGGCCC | GS2 |
| 309 | GGCAAGCATTCCACGCAGTGTCTCTCAGCC | GS2 |
| 310 | GGTTCCACTAGTCTTCTTGGTCTAGTGACC | GS2 |
| 311 | GGGGCCAACAAATTAAACTCTGAGATATCC | GS2 |
| 312 | GGGTTTGCATGCCTCTGAAGGATCAGGCCC | GS2 |
| 313 | GGCAACGTGCCGGAGCTGGCGCCGGCGGCC | HPPD |
| 314 | GGAGAACGTGCTGCTCCCACTCAACGAGCC | HPPD |
| 315 | GGCCCCGGCGTGCAGCACATGGCGCTGGCC | HPPD |
| 316 | GGCAACGTGCCGGAGCTGGCGCCGGCGGCC | HPPD |
| 317 | GGAGAACGTGCTGCTCCCACTCAACGAGCC | HPPD |
| 318 | GGCCCCGGCGTGCAGCACATGGCGCTGGCC | HPPD |
| 319 | GGTCTCCAGGGAACAAGAAGTTGCTGCGCC | HPPD |
| 320 | GGCCAGGTCGCCGCCAATTGCCGTCCAGCC | HPPD |
| 321 | GGTCTCCAGGGAACAAGAAGTTGCTGCGCC | HPPD |
| 322 | GGGCGCCCTCGCTTTCCTCTTCACGGCGCC | HPPD |
| 323 | GGCGCCGACGCCGCCACGGCCTCGCTGCCC | HPPD |
| 324 | GGAGAACGTGCTGCTCCCACTCAACGAGCC | HPPD |
| 325 | GGCCCCGGCGTGCAGCACATGGCGCTGGCC | HPPD |
| 326 | GGGCGCCCTCGCTTTCCTCTTCACGGCGCC | HPPD |
| 327 | GGGCTTCATATCTTTTTTGGAGCTTATCCC | PDS |
| 328 | GGTTTACAAAACTGTCCCAAACTGTGAACC | PDS |
| 329 | GGTGGTTCCAATCAATCGGTTAAATCATCC | PDS |
| 330 | GGGGCGTCTAGCGCCTTGCACGGGTGACCC | PDS |
| 331 | GGTTGCGCTATCGTTCATGTTTGAATGTCC | PDS |
| 332 | GGTGGTTCCTATCAATCGGTTAATTCATCC | PDS |
| 333 | GGAAGATTTGTCCATTCTGCTTGGTGCCCC | PDS |
| 334 | GGACCAAGAAAGCATCAGAACAATAATACC | PDS |
| 335 | GGATATACTCCTAGTAGTCTGTAGTGCGCC | PDS |
| 336 | GGGCTCCCCCGCCTCCACGACACTGCCTCC | PDS |
| 337 | GGTGCTACGAAATTGTCTAGAACGAGGTCC | PDS |
| 338 | GGCTTCATGAACTGTGGGTCTAATGGCTCC | PDS |
| 339 | GGACGGAGGCCCATGTGAGCAAGTTGGGCC | PDS |
| 340 | GGCAGTGGTACTAGTATCCGAAATGTGACC | PDS |
| 341 | GGTTAACTATATATTTTTGTAGATGTCGCC | PDS |
| 342 | GGCAACTCCCGACGGATCTATTGCCTCCCC | PDS |
| 343 | GGGGAAGCTTATCCCCCCTCTTATCGAGCC | PDS |
| 344 | GGTCTCTGCTCCGGTAGCGGCGCGTCTCCC | PDS |
| 345 | GGTTGCGCTATCGTTCATGTTTGAATGTCC | PDS |
| 346 | GGTGGTTCCTATCAATCGGTTAATTCATCC | PDS |
| 347 | GGAAGATTTGTCCATTCTGCTTGGTGGCCC | PDS |
| 348 | GGACCAAGAAAGCATCAGAACAATAATACC | PDS |
| 349 | GGCCTACCTTTATGGATCGAATAATCAACC | PDS |
| 350 | GGCCGGCCGGCCGGCCGACGGACCGAGACC | PDS |
| 351 | GGCGGCGACCAGGGTGATCGGATCCAAGCC | PDS |
| 352 | GGCACGCTGAAGAAGCTTGTGAACGAGTCC | PDS |
| 353 | GGCGGCAACATCACCACCGTCGAGCGCCCC | PPOX |
| 354 | GGGCCGGTCTCGGCGCGCTTGGCATCCGCC | PPOX |
| 355 | GGAGGTGCTACAAACACAGGAATTGTTTCC | PPOX |
| 356 | GGAGGTGCTACAAACACAGGAATTGTTTCC | PPOX |
| 357 | GGTTAGCAATACTCTGCCAAAGCTATTGCC | PPOX |
| 358 | GGGGACGTGCTTGTCACGGAGGCCCGCGCC | PPOX |
| 359 | GGGCCGGTCTCGGCGCGCTTGGCATCCGCC | PPOX |
| 360 | GGAGGTGCTACAAACACAGGAATTGTTTCC | PPOX |
| 361 | GGTTAGCAATACTCTGCCAAAGCTATTGCC | PPOX |
| 362 | GGGCCGGTCTCGGCGCGCTTGGCATCCGCC | PPOX |
| 363 | GGTAGAAGCATCAAATGAAAAGAATTGCCC | PPOX |
| 364 | GGATAGTTCTGTTGGAAAAGTTGAAGTCCC | PPOX |
| 365 | GGGTTTCTCTGGGATGAAGGAGCGAACACC | PPOX |
| 366 | GGACATTACTTCACAATGAGTATCACTTCC | PPOX |
| 367 | GGATCACGGTTCGCAGGTCAGCTTGTGGCC | PPOX |
| 368 | GGAGACCAGCCTGAACTTGCTTCCGAAACC | PPOX |
| 369 | GGTATATGGCATTCCAGAATTCCGTCTTCC | PPOX |
| 370 | GGTCCACCGCCGTGTCACGGACACGGCTCC | PPOX |
| 371 | GGTTATTGAGGAAAATTTGGATCAGCTGCC | PPOX |
| 372 | GGTGGCATTAACCCTGCATCATGATTTTCC | PPOX |
| 373 | GGTAGAAGCATCAAATGAAAAGAATTGCCC | PPOX |
| 374 | GGATAGTTCTGTTGGAAAAGTTGACGTCCC | PPOX |
| 375 | GGTCCTAGCTCAGTTGGTTGAGGGTATGCC | PPOX |
| 376 | GGCTCTCGCCGCCGCCGCCGCCTCGAGGCC | PPOX |
| 377 | GGTCCACCGCCGTGTCACGGACACGGCTCC | PPOX |
| 378 | GGTTATTGAGGAAAATTTGGATCAGCTGCC | PPOX |
| 379 | GGTGGCATTAACCCTGCATCATGATTTTCC | PPOX |
| 380 | GGTAGAAGCATCAAATGAAAAGAATTGCCC | PPOX |

TABLE 2-continued

| Polynucleotides SEQ ID NO: 121-386. | | |
|---|---|---|
| SEQ ID NO | SEQ | GENE |
| 381 | GGATAGTTCTGTTGGAAAAGTTGAAGTCCC | PPOX |
| 382 | GGTCCTAGCTCAGTTGGTTGAGGGTATGCC | PPOX |
| 383 | GGACATTACTTCACAATGAGTATCACTTCC | PPOX |
| 384 | GGACTCACGGCTGCTGAAGAGCTCGCCTCC | PPOX |
| 385 | GGCGGCCGCTTAGAAAACGCTGAGTTATCC | PPOX |
| 386 | GGGCGGCGGCTAATGCCACCTGGTTGAACC | PPOX |

Example 3. Methods Used in the Invention Related to Treating Plants or Plant Parts with a Topical Mixture of the Trigger Molecules Johnsongrass plants are grown in the greenhouse (30/20 C day/night T; 14 hour photoperiod) in 4 inch square pots containing Sun Gro® Redi-Earth and 3.5 kg/cubic meter Osmocote® 14-14-14 fertilizer. When the plants at 5 to 10 cm in height are pre-treated with a mixture of single-strand antisense or double-strand polynucleotides (ssDNA ro dsRNA targeting one or more of the herbicide target gene sequences from SEQ ID NO: 1-120) at 16 nM, formulated in 10 millimolar sodium phosphate buffer (pH 6.8) containing 2% ammonium sulfate and 0.5% Silwet L-77. Plants are treated manually by pipetting 10 μL of polynucleotide solution on fully expanded mature leaves, for a total of 40 microliters of solution per plant. Twenty-four and forty-eight hours later, the plants are treated with and effective dose of the nonpolynucleotide herbicide corresponding to the herbicide target gene in which the polynucleotides have homology. Four replications of each treatment is conducted. Plant height is determined just before treatment and at intervals up to twelve days after herbicide treatments to determine effect of the polynucleotide and herbicide treatments.

Example 4. A Method to Control Johnsongrass in a Field

A method to control johnsongrass in a field comprises the use of trigger polynucleotides that can modulate the expression of one or more herbicide target genes in johnsongrass. In Table 2, an analysis of herbicide target gene sequences provided a collection of 30-mer polynucleotides that can be used in compositions to affect the growth or develop or sensitivity to a polynucleotide herbicide to control multiple weed species in a field. A composition containing 1 or 2 or 3 or 4 or more of the polynucleotides of Table 2 or fragments thereof would enable broad activity of the composition against the herbicide resistant johnsongrass species or multiple *Sorghum* weed species that occur in a field environment.

The method includes creating a composition that comprises components that include at least one polynucleotide of Table 2 or fragment thereof or any other effective gene expression modulating polynucleotide essentially identical or essentially complementary to SEQ ID NO:1-120, a transfer agent that mobilizes the polynucleotide into a plant cell and nonpolynucleotide herbicide. The polynucleotide of the composition includes a dsRNA, ssDNA or dsDNA or a combination thereof. A composition containing a polynucleotide can have a use rate of about 1 to 30 grams or more per acre depending on the size of the polynucleotide and the number of polynucleotides in the composition. The composition may include one or more additional herbicides as needed to provide effective multi-species weed control in addition to control of johnsongrass and related weed species. A field of crop plants in need of weed plant control is treated by spray application of the composition. The composition can be provided as a tank mix, a sequential treatment of components (generally the polynucleotide followed by the nonpolynucleotide herbicide), a simultaneous treatment or mixing of one or more of the components of the composition from separate containers or as a premix of all of the components of the herbicidal composition. Members of the nonpolynucleotide herbicide families include but are not limited to amide herbicides, aromatic acid herbicides, arsenical herbicides, benzothiazole herbicides, benzoylcyclohexanedione herbicides, benzofuranyl alkylsulfonate herbicides, carbamate herbicides, cyclohexene oxime herbicides, cyclopropylisoxazole herbicides, dicarboximide herbicides, dinitroaniline herbicides, dinitrophenol herbicides, diphenyl ether herbicides, dithiocarbamate herbicides, halogenated aliphatic herbicides, imidazolinone herbicides, inorganic herbicides, nitrile herbicides, organophosphorus herbicides, oxadiazolone herbicides, oxazole herbicides, phenoxy herbicides, phenylenediamine herbicides, pyrazole herbicides, pyridazine herbicides, pyridazinone herbicides, pyridine herbicides, pyrimidinediamine herbicides, pyrimidinyloxybenzylamine herbicides, quaternary ammonium herbicides, thiocarbamate herbicides, thiocarbonate herbicides, thiourea herbicides, triazine herbicides, triazinone herbicides, triazole herbicides, triazolone herbicides, triazolopyrimidine herbicides, uracil herbicides, and urea herbicides. Treatment of the plants in the field can occur as often as needed to provide weed control and the components of the composition can be adjusted to target specific weed species or weed families.

I claim:

1. A method of controlling a *Sorghum* species plant comprising: treating a *Sorghum* species plant or a part thereof in need of control with a first herbicidal composition comprising a double-stranded RNA (dsRNA) polynucleotide, an organosilicone surfactant in a concentration of about 0.2 percent or greater by weight, and an effective dose of a nonpolynucleotide herbicide, wherein said dsRNA polynucleotide is identical or complementary to at least 21 contiguous nucleotides of a *Sorghum* species gene polynucleotide selected from the group consisting of SEQ ID NOs: 26, 27, 30-36, 38-41, 43, 46-57, 59-66, 76, 79, 82, 84, 86, 87, 90, 93-120, 122-129, 131-133, 136, and 140-153, wherein said *Sorghum* species plant is more sensitive to said nonpolynucleotide herbicide, relative to a similar plant treated with a second herbicidal composition not containing said dsRNA polynucleotide.

2. The method of claim 1, wherein said *Sorghum* species plant is selected from the group consisting of *Sorghum* halepense, *Sorghum bicolor*, and *Sorghum sudanense.*

3. The method of claim 1, wherein (a) said *Sorghum* species gene polynucleotide is selected from the group consisting of SEQ ID NOs: 122-129, 131-133, 136, and 140-153, and said nonpolynucleotide herbicide is selected from the group consisting of aryloxyphenoxypropionates, cyclohexanediones, and phenylpyrazoline;

(b) said *Sorghum* species gene polynucleotide is selected from the group consisting of SEQ ID NOs: 26, 27, 30-36, 38-41, and 43, and said nonpolynucleotide herbicide is selected from the group consisting of sulfonylureas, imidazolinones, triazolopyrimidines, pyrimidinyl(thio)benzoates, and sulfonylaminocarbonyl-triazolinones;

(c) said *Sorghum* species gene polynucleotide is selected from the group consisting of SEQ ID NOs: 46-57 and 59 and said nonpolynucleotide herbicide is selected from the group consisting of sulfonylureas, imidazolinones, triazolopyrimidines, pyrimidinyl(thio)benzoates, and sulfonylaminocarbonyl-triazolinones;

(d) said *Sorghum* species gene polynucleotide is selected from the group consisting of SEQ ID NOs: 60-66 and said nonpolynucleotide herbicide is selected from the group consisting of sulfonamides and asulam;

(e) said *Sorghum* species gene polynucleotide is selected from the group consisting of SEQ ID NOs: 76, 79, 82, 84, 86, and 87 and said nonpolynucleotide herbicide is glufosinate;

(f) said *Sorghum* species gene polynucleotide is selected from the group consisting of SEQ ID NOs: 90 and 93-96 and said nonpolynucleotide herbicide is selected from the group consisting of triketones, isoxazoles, and pyrazoles;

(g) said *Sorghum* species gene polynucleotide is selected from the group consisting of SEQ ID NOs: 97-105 and said nonpolynucleotide herbicide is selected from the group consisting of pyridazinones, pyridinecarboxamides, beflubutamid, fluridone, flurochloridone, and flurtamone; or (h) said *Sorghum* species gene polynucleotide is selected from the group consisting of SEQ ID NOs: 106-120 and said nonpolynucleotide herbicide is selected from the group consisting of acifluorfen-Na, bifenox, chlomethoxyfen, fluoroglycofen-ethyl, fomesafen, halosafen, lactofen, oxyfluorfen, fluazolate, pyraflufen-ethyl, cinidon-ethyl, flumioxazin, flumiclorac-pentyl, fluthiacet-methyl, thidiazimin, oxadiazon, oxadiargyl, azafenidin, carfentrazone-ethyl, sulfentrazone, pentoxazone, benzfendizone, butafenacil, pyrazogyl, and profluazol.

4. The method of claim 1, wherein said dsRNA polynucleotide is at least 20 contiguous nucleotides in length.

5. The method of claim 1, wherein said dsRNA polynucleotide is selected from the group consisting of SEQ ID NOs: 154-159, 164-201, 208-210, 218-236, 275-279, 289-301, 313-318, and 322-386.

6. The method of claim 1, wherein said first herbicidal composition comprises any combination of two or more of said dsRNA polynucleotides and two or more of said nonpolynucleotide herbicides that inhibit the activity of two or more proteins selected from the group consisting of acetyl-CoA carboxylase (ACCase), acetolactate synthase (ALS) large subunit, ALS small subunit, 7,8-dihydropteroate synthase (DHPS), glutamine synthetase 2 (GS2), 4-hydroxyphenyl-pyruvate-dioxygenase (HPPD), phytoene desaturase (PDS), protoporphyrinogen IX oxidase (PPDX), and wherein said *Sorghum* species plant is more sensitive to said two or more nonpolynucleotide herbicides, relative to a similar plant treated with a herbicidal composition not containing said two or more dsRNA polynucleotides.

7. The method of claim 1, wherein said first herbicidal composition further comprises one or more herbicides selected from the group consisting of: 5-diarylpyrazole herbicides, 2-thiopyrimidine herbicides, 3-CF3-benzene herbicides, acetamide herbicides, amide herbicides, aminoacrylate herbicides, aminotriazine herbicides, aromatic acid herbicides, arsenical herbicides, arylaminopropionic acid herbicides, arylcarboxamide herbicides, arylcyclodione herbicides, aryloxyphenoxy-propionate herbicides, azolecarboxamide herbicides, azoloazinone herbicides, azolotriazine herbicides, benzamide herbicides, benzenesulfonamide herbicides, benzhydryl herbicides, benzimidazole herbicides, benzofuran herbicides, benzofuranyl alkylsulfonate herbicides, benzohydrazide herbicides, benzoic acid herbicides, benzophenylmethanone herbicides, benzothiadiazinone herbicides, benzothiazole herbicides, benzothiazoleacetate herbicides, benzoxazole herbicides, benzoylcyclohexanedione herbicides, benzyloxymethylisoxazole herbicides, benzylpyrazole herbicides, benzylpyridine herbicides, benzylpyrimidone herbicides, bipyridylium herbicides, carbamate herbicides, chloroacetamide herbicides, chloroacetamide herbicides, chlorocarbonic acid herbicides, cyclohexanedione herbicides, cyclohexene oxime herbicides, cyclopropylisoxazole herbicides, diarylether herbicides, dicarboximide herbicides, dihydropyrancarboxamide herbicides, diketo-epoxide herbicides, diketopiperazine herbicides, dinitroaniline herbicides, dinitrophenol herbicides, diphenylether herbicides, diphenylfuranone herbicides, dithiocarbamate herbicides, fluoroalkene herbicides, glyphosate herbicides, halogenated aliphatic herbicides, hydantocidin herbicides, hydroxypyrazole herbicides, imidazolinone herbicides, indazole herbicides, indenedione herbicides, inorganic herbicides, isoxazole herbicides, isoxazolesulfone herbicides, isoxazolidinone herbicides, nicotinohydrazide herbicides, nitrile herbicides, nitrile-amide herbicides, nitropyrazole herbicides, N-phenylphthalimide herbicides, organoarsenical herbicides, organophosphates herbicides, organophosphorus herbicides, oxabicycloheptane herbicides, oxadiazole herbicides, oxadiazolebenzamide herbicides, oxadiazolone herbicides, oxazole herbicides, oxazolidinedione herbicides, oxyacetamide herbicides, phenoxy herbicides, phenoxyalkyne herbicides, phenoxycarboxylic acid herbicides, phenoxypyridazinol herbicides, phenylalkanoate herbicides, phenylcarbamate herbicides, phenylenediamine herbicides, phenylethylurea herbicides, phenylimidazole herbicides, phenylisoxazole herbicides, phenylpyrazole herbicides, phenylpyrazoline herbicides, phenylpyridazine herbicides, phenylpyridine herbicides, phenylpyrrolidone herbicides, phosphinic acid herbicides, phosphonate herbicides, phosphoroamidate herbicides, phosphorodithioate herbicides, phthalamate herbicides, propionamide herbicides, pyrazole herbicides, pyrazole-arylether herbicides, pyrazolium herbicides, pyridazine herbicides, pyridazinone herbicides, pyridine herbicides, pyridinecarboxamide herbicides, pyridinecarboxylic acid herbicides, pyridinone herbicides, pyridyl-benzylamide herbicides, pyridyl-ether-carboxamide herbicides, pyrimidinecarboxylic acid herbicides, pyrimidinediamine herbicides, pyrimidinedione herbicides, pyrimidinedione herbicides, pyrimidinone herbicides, pyrimidinyl(thio)benzoate herbicides, pyriinidinyloxybenzylamine herbicides, pyrimidylmethanol herbicides, pyrrolidone herbicides, quaternary Ammonium herbicides, quinoline-carboxylic acid herbicides, quinoxaline herbicides, semicarbazone herbicides, sulfonamide herbicides, sulfonylamino-carbonyl-triazolinone herbicides, sulfonylurea herbicides, sulfonylurea herbicides, tetrazolinone herbicides, thiadiazole herbicides, thiatriazine herbicides, thienopyrimidine herbicides, thiocarbamate herbicides, thiocarbonate herbicides, thiourea herbicides, tolyltriazole herbicides, triazine herbicides, triazinedione herbicides, triazine-sulfonanilide herbicides, triazinone herbicides, triazole herbicides, triazolecarboxamide herbicides, triazoleimine herbicides, triazolinone herbicides, triazolone herbicides, triazolopyrimidine herbicides, triketone herbicides, uracil herbicides, and urea herbicides.

8. The method of claim 1, wherein said organosilicone surfactant is in a concentration of about 0.2 percent to about 2.0 percent by weight.

9. A herbicidal composition comprising an admixture of a dsRNA polynucleotide, an organosilicone surfactant in a concentration of about 0.2 percent or greater by weight, and an effective dose of a nonpolynucleotide herbicide, wherein said dsRNA polynucleotide is identical or complementary to at least 21 contiguous nucleotides of a *Sorghum* species gene polynucleotide selected from the group consisting of SEQ ID NOs: 26, 27, 30-36, 38-41, 43, 46-57, 59-66, 76, 79, 82, 84, 86, 87, 90, 93-120, 122-129, 131-133, 136, and 140-153, wherein a *Sorghum* species plant treated with said herbicidal composition is more sensitive to said nonpolynucleotide herbicide, relative to a similar plant treated with a herbicidal composition not containing said dsRNA polynucleotide.

10. The herbicidal composition of claim 9, wherein said dsRNA polynucleotide is selected from the group consisting of SEQ ID NOs: 154-159, 164-201, 208-210, 218-236, 275-279, 289-301, 313-318, and 322-386.

11. The herbicidal composition of claim 9, further comprising a pesticide, wherein said pesticide is selected from the group consisting of insecticides, fungicides, nematicides, bactericides, acaricides, growth regulators, chemosterilants, semiochemicals, repellents, attractants, pheromones, feeding stimulants, and biopesticides.

12. The herbicidal composition of claim 9, comprising a premix or a tankmix combination.

* * * * *